(12) United States Patent
Deng et al.

(10) Patent No.: US 10,570,408 B2
(45) Date of Patent: Feb. 25, 2020

(54) TRANSGENIC PLANTS WITH ENHANCED AGRONOMIC TRAITS

(71) Applicant: Monsanto Technology LLC, St. Louis, MO (US)

(72) Inventors: Molian Deng, Grover, MO (US); Zhidong Xie, Maryland Heights, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/732,622

(22) Filed: Dec. 5, 2017

(65) Prior Publication Data

US 2018/0245095 A1    Aug. 30, 2018

Related U.S. Application Data

(63) Continuation of application No. 14/998,728, filed on Feb. 8, 2016, now abandoned, which is a continuation of application No. 13/815,411, filed on Feb. 27, 2013, now abandoned, which is a continuation of application No. 12/218,251, filed on Jul. 10, 2008, now abandoned.

(60) Provisional application No. 60/958,909, filed on Jul. 10, 2007.

(51) Int. Cl.
*C12N 15/82* (2006.01)
*A01H 1/02* (2006.01)
*C12Q 1/6895* (2018.01)

(52) U.S. Cl.
CPC ........... *C12N 15/8261* (2013.01); *A01H 1/02* (2013.01); *C12N 15/8241* (2013.01); *C12Q 1/6895* (2013.01); *C12Q 2600/13* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 7,033,806 B2 * | 4/2006 | Lagarias | C12N 9/001 435/189 |
| 2003/0204874 A1 | 10/2003 | Kim et al. | |
| 2003/0233670 A1 | 12/2003 | Edgerton et al. | |
| 2004/0034888 A1 | 2/2004 | Liu et al. | |
| 2006/0236419 A1 | 10/2006 | La Rosa et al. | |
| 2007/0277269 A1 | 11/2007 | Alexandrov et al. | |
| 2011/0265221 A1 | 10/2011 | Abad et al. | |
| 2013/0283461 A1 | 10/2013 | Abad et al. | |
| 2016/0230183 A1 | 8/2016 | Abad et al. | |

FOREIGN PATENT DOCUMENTS

| | | |
|---|---|---|
| JP | 2003-310071 | 11/2003 |
| WO | WO-0250289 A1 | 6/2002 |
| WO | WO-2006076423 A2 | 7/2006 |
| WO | WO-2008070179 A2 | 6/2008 |
| WO | WO-2009009142 A3 | 1/2009 |

OTHER PUBLICATIONS

Whisstock J.C. et al. Prediction of protein function from protein sequence and structure. Q Rev Biophys. Aug. 2003;36(3):307-40. Review. (Year: 2003).*
Hill M.A. et al. Functional analysis of conserved histidines in ADP-glucose pyrophosphorylase from *Escherichia coli*. Biochem Biophys Res Commun. Mar. 17, 1998;244(2):573-7. (Year: 1998).*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 1998 (Year: 1998).*
"Alignment of SEQ ID No. 397 and four disclosed homologs", (Apr. 2, 2012), 1 pg.
"U.S. Appl. No. 12/218,251, Final Office Action dated Aug. 2, 2012", 19 pgs.
"U.S. Appl. No. 12/218,251, Non Final Office Action dated Dec. 1, 2011", 13 pgs.
"U.S. Appl. No. 12/218,251, Preliminary Amendment dated May 13, 2010", 9 pgs.
"U.S. Appl. No. 12/218,251, Response filed Apr. 2, 2012 to Non Final Office Action dated Dec. 1, 2011", 14 pgs.
"U.S. Appl. No. 12/218,251, Response filed Sep. 8, 2011 to Restriction Requirement dated Aug. 8, 2011", 10 pgs.
"U.S. Appl. No. 12/218,251, Restriction Requirement dated Aug. 8, 2011", 12 pgs.
"U.S. Appl. No. 12/218,251, Supplemental Preliminary Amendment dated Jun. 10, 2011", 20 pgs.
"U.S. Appl. No. 13/815,411, Final Office Action dated Nov. 6, 2015", 28 pgs.
"U.S. Appl. No. 13/815,411, Non Final Office Action dated Mar. 27, 2015", 25 pgs.
"U.S. Appl. No. 13/815,411, Preliminary Amendment filed Feb. 27, 2013", 9 pgs.

(Continued)

*Primary Examiner* — Cynthia E Collins

(74) *Attorney, Agent, or Firm* — Schwegman Lundberg & Woessner, P.A.

(57) ABSTRACT

This invention provides recombinant DNA constructs, transgenic plant nuclei and cells with such recombinant DNA construct for expression of proteins that are useful for imparting enhanced agronomic trait(s) to transgenic crop plants. This invention also provides transgenic plants and progeny seed comprising the transgenic plant cells where the plants are selected for having an enhanced trait selected from the group of traits consisting of enhanced water use efficiency, enhanced cold tolerance, increased yield, enhanced nitrogen use efficiency, enhanced seed protein and enhanced seed oil. Also disclosed are methods for manufacturing transgenic seed and plants with enhanced traits.

10 Claims, 7 Drawing Sheets

Specification includes a Sequence Listing.

(56) References Cited

OTHER PUBLICATIONS

"U.S. Appl. No. 13/815,411, Response filed Jul. 27, 2015 to Non Final Office Action dated Mar. 27, 2015", 10 pgs.
"U.S. Appl. No. 13/815,411, Response filed Dec. 9, 2014 to Restriction Requirement dated Oct. 10, 2014", 10 pgs.
"U.S. Appl. No. 13/815,411, Restriction Requirement dated Oct. 10, 2014", 12 pgs.
"U.S. Appl. No. 13/815,411, Supplemental Preliminary Amendment filed Jun. 21, 2013", 4 pgs.
"U.S. Appl. No. 14/998,728, Non Final Office Action dated Sep. 5, 2017", 29 pgs.
"U.S. Appl. No. 14/998,728, Response filed Aug. 22, 2017 to Restriction Requirment dated Jun. 22, 2017", 9 pgs.
"U.S. Appl. No. 14/998,728, Restriction Requirement dated Jun. 22, 2017", 12 pgs.
"European Application Serial No. 08780144.5, Extended European Search Report dated Dec. 23, 2010", 8 pgs.
"European Application Serial No. 11174743.2, Extended European Search Report dated Mar. 14, 2012", 8 Pgs.
"European Application Serial No. 11174743.2, Partial European Search Report dated Nov. 17, 2011", 5 pgs.
"European Application Serial. No. 12186820.2, European Search Report dated Jun. 21, 2013", 8 pgs.
"European Application Serial No. 12186820.2, Examination Notification Art. 94(3) dated Apr. 7, 2014", 4 pgs.
"European Application Serial No. 12186820.2, Examination Notification Art. 94(3) dated Oct. 29, 2014", 5 pgs.
"European Application Serial No. 12186820.2, Office Action dated Oct. 17, 2012", 1 pg.
"European Application Serial No. 12186820.2, Partial European Search Report dated Feb. 21, 2013", 5 pgs.
"European Application Serial No. 12186820.2, Response Dec. 18, 2012 to Office Action dated Oct. 17, 2012", 5 pgs.
"European Application Serial No. 12186820.2, Response filed Aug. 18, 2014 to Examination Notification Art. 94(3) dated Apr. 7, 2014", 3 pgs.
"European Application Serial No. 12794105.2, Response filed Jan. 24, 2014 to Extended European Search Report dated Jun. 21, 2013", 8 pgs.
"GenBank: AAQ81632.1", (Oct. 5, 2004).
"International Application Serial No. PCT/US2008/008557, International Search Report dated Feb. 6, 2009", 3 pgs.
"International Application Serial No. PCT/US2008/008557, Written Opinion dated Feb. 6, 2009", 5 pgs.
"Phytochromobilin synthase [*Zea mays*]", NCBI, GenBank, Sequence Accession No. AAT66259.1, (Sep. 17, 2004), 1 pg.
Bouche, N., et al., "*Arabidopsis* gene knockout: phenotypes wanted", Curr Opin Plant Biol., 4(2), (2001), 111-117.
Chen, S. L., et al., "Identification of genes subject to positive selection in uropathogenic strains of *Escherichia coli*: A comparative genomics approach", Proc. Natl. Acad. Sci. USA, 103(15), (Apr. 2006), 5977-5982.
Devi, S. R., et al., "A Novel High-Throughput Genetic Screen for Stress-Responsive Mutants of *Arabidopsis thaliana* Reveals New Loci Involving Stress Responses", The Plant Journal, 47(4), (2006), 652-663.
Falcon-Perez, et al., "Functional domain analysis of the yeast ABC transporter Ycf1 p by site-directed mutagenesis", J Biol Chem. 274(33), (Aug. 13, 1999), 23584-23590.
Fu, Yan, et al., "Types and Frequencies of Sequencing Errors in Methyl-Filtered and High C0t Maize Genome Survey Sequences", Plant Physiology, vol. 135, (Aug. 2004), pp. 2040-2045.
Gelhaye, E., et al., "The thioredoxin h system of higher plants", Plant Physiol Biochem, 42(4), (Apr. 2004), 265-271.
Greene, E. A., et al., "Spectrum of Chemically Induced Mutations From a Large-Scale Reverse-Genetic Screen in *Arabidopsis*", Genetics, 164, (Jun. 2003), 731-740.
Hill, Margaret A, et al., "Functional Analysis of Conserved Histidines in ADP-Glucose Pyrophosphorylase from *Escherichia coli*", Biochem Biophys Res Commun., 244(2), (Mar. 17, 1998), 573-577.

Israelsson, et al., "Cloning and overproduction of gibberellin 3-oxidase in hybrid aspen trees", Effects on gibberellin homeostasis and development. Plant Physiol. 135(1), 221-30.
Lamberg, A., et al., "Site-directed mutagenesis of the alpha subunit of human prolyl 4-hydroxylase. Identification of three histidine residues critical for catalytic activity", J Biol Chem. 270(17), (Apr. 28, 1995), 9926-9931.
Lu, C., et al., "A High-Throughput Screen for Genes from Castor that Boost Hydroxy Fatty Acid Accumulation in Seed Oils of Transgenic *Arabidoopsis*", The Plant Journal, 45(5),, (2006), 847-856.
Matsushita, Akane, et al., "AGF1, an AT-Hook Protein, Is Necessary for the Negative Feedback of AtGA3ox1 Encoding GA 3-Oxidase", Plant Physiology, American Society of Plant Biologists, v. 143, Mar. 2007, www.plantphysiol.org., 1152-1162.
McDowall, K. J., et al., "The ams-1 and rne-3071 Temperature-Sensitive Mutations in the ams Gene Are in Close Proximity to Each Other and Cause Substitutions within a Domain That Resembles a Product of the *Escherichia coli* mre Locus", Journal of Bacteriology, 175(13), (Jul. 1993), 4245-4249.
Renard, Michelle, et al., "Identification and Characterization of Thioredoxin h Isoforms Differentially Expressed in Germinating Seeds of the Model Legume Medicago truncatula", Plant Physiology, vol. 155, (Mar. 2011), 1113-1126.
Rhoads, David M, et al., "Regulation of the Cyanide-resistant Alternative Oxidase of Plant Mitochondria", Identification of the cysteine residue involved in alpha-keto acid stimulation and intersubunit disulfide bond formation. J. Biol. Chem., 273(46), (Nov. 13, 1998), 30750-30756.
Sahrawy, M., et al., "Intron position as an evolutionary marker of thioredoxins and thioredoxin domains", J Mol Evol, 42(4), (Apr. 1996), 422-431.
Skandalis, A., et al., "Enzymatic Properties of Rat DNA Polymerase Beta Mutants Obtained by Randomized Mutagenesis", Nucleic Acids Res., 29(11), (2001), 2418-2426.
Stoop, A. A., et al., "High-Density Mutagenesis by Combined DNA Shuffling and Phage Display to Assign Essential Amino Acid Residues in Protein-Protein Interactions: Application to Study Structure-Function of Plasminogen Activation Inhibitor 1 (PAI-1)", J. Mol. Biol., 301(5), (2000), 1135-47.
Takahashi, Y., et al., "A High-Throughput Screen of Cell-Death-Inducing Factors in Nicotiana Benthamiana Identifies a Novel MAPKK that Mediates INF1-induced Cell Death Signaling and non-Host Resistance to Pseudomonas Cichorii", The Plant Journall, 9(6), (2007), 1030-1040.
Wen, Tsui-Jung, et al., "Analyses of Mutants of Three Genes That Influence Root Hair Development in *Zea mays* (Gramineae) Suggest That Root Hairs are Dispensable", American Journal of Botany, vol. 81, No. 7, (Jul. 1994), pp. 833-842.
Whisstock, J C, et al., "Prediction of protein function from protein sequence and structure", Q Rev Biophys. 36(3), (2003), 307-340.
Yeh, T. C., et al., "A Dual Role for the Kinase-like Domain of the Tyrosine Kinase Tyk2 in Interferon-alpha Signaling", Proc Natl Acad Sci., USA, 97(16), (2000), 8991-8996.
Kohchi, Takayuki, et al., "The *Arabidopsis* HY2 Gene Encodes Phytochromobilin Synthase, a Ferredoxin-Dependent Biliverdin Reductase", The Plant Cell, vol. 13, (Feb. 2001), 425-436.
Sawers, Ruairidh J.H., et al., "Elongated mesocotyl1, a Phytochrome-Deficient Mutant of Maize", Plant Physiology, vol. 130, (Sep. 2002), 155-163.
Sawers, Ruairidh J.H., et al., "The Elm1 (ZmHy2) Gene of Maize Encodes a Phytochromobilin Synthase", Plant Physiology, vol. 136, (Sep. 2004), 2771-2781.
U.S. Appl. No. 12/218,251, filed Jul. 10, 2008, Thioredoxin Expressing Transgenic Plants With Enhanced Agronomic Traits.
U.S. Appl. No. 13/815,411, filed Feb. 27, 2013, Transgenic Plants With Enhanced Agronomic Traits.
U.S. Appl. No. 14/998,728, filed Feb. 8, 2016, Transgenic Plants With Enhanced Agronomic Traits.

* cited by examiner

```
SEQ ID NO: homolog SEQ ID NOs
4210       ----------------------------------------------------------------
4213       ----------------------------------------------------------------
23796      ------------------------------MASNIMQRCNVFMSERVKLHAAMLALQFGYAGFHIVS
5323       ------------------------------MSP-----------VPERTKLHIAMAVFQTGYAGNHVIM
9197       ----------------------------------MVHGRLCNRDGWILTAMVVTEFSNVGVNTLV
22010      ----------------------------------MVHGRLCNRDGWILTAMVVTEFSNVGVNTLV
2187       ----------------------------------------------------------------
26922      ----------------------------MAGAVSLWRREAVFLTAMLAGETSIVGLSTLF
12208      ----------------------------MAGAVSLWRREAVFLTAMLAGETSIVGLSTLF
27336      ----------------------------MAGAVSLWRREAVFLTAMLAGETSIVGLSTLF
19871      -------------------------MPIMAGTASPWRREAVFLTAMLVVETSVVGISTLF
11517      ----------------------------------------------------------------
8202       -------------------------MPIMAGTASPWRREAVFLTAMLVVETSVVGISTLF
6010       ----------------------------------------------------------------
16802      ----------------------------MARTVSLWRREAVFLTAMLATETGVVGISTLF
301        ----------------------------------------------------------------
2040       -------------------------------MTRKYFQREVLPVTALVIMECANVGLNTLF
6920       ----------------------------------------------------------------
5087       ----------------------MKKEMI---------EEVVIVGGLVMVQFVYAGNSLLM
5965       MEGLLSYRSNVLRNIMREREKDRKKMLISEIFSENEDEEVVIIGGLVMVQFVYAGNSLLM
3372       -----------------------------MAAVAMADGGGKKPYVVAVAIQAINTGTFVVS
consensus  -----------------------------xxxxxxxxxxxxxxxxxxxxxxxxxxxxxxx
30526

----------------------------------------------------------------
----------------------------------------------------------------
RAALNMGVSKVVFPVYRNILALMLIGPCAYFLEKKERPALTLSFLIQFFLLALCGITGQS
RFALNLGVSKLIFPLYRNIIALSVLAPSAFFLEKKERPRMTTSLLIQFFLLGLVGITLNQ
KAATSKGLSPFVVLVYSYTFGSLLLLPLTFFSFRSRSLPPLTFSILCNMGILGLIASAFQ
KAATSKGLSPFVVLVYSYTFGSLLLLPLTFFSFR--------------------SAFQ
------------------------------------------------------MYV
KVATSKGLNIYPFLSYSYLLASLLLLPSLFFTN----------SASILSKIGLLGFLGSMYV
KVATSKGLNIYPFLSYSYLLASLLLLPSLFFTNRSRSLPPLSASILSKIGLLGFLGSMYV
KVATSKGLNIYPFLSYSYLLASLLLLPSLFFTNRSRSLPPLSASILSKIGLLGFLGSMYV
KFATSKGLNIYPFLGYSYLLASLLLLPSLFFTNRSSSLPPLSVSILSKIGLLGFLGSMYV
------------------------------------------------------MYV
KFATSKGLNIYPFLGYSYLLASLLLLPSLFFTNRSSSLPPLSVSILSKIGLLGFLGSMYV
------------------------------------------------------MYV
KVATSKGLNLYAFLGYSYLLASLLLLPSLFFTDRSRSLPPLSLSILSKIGLLGLLGSMYV
----------------------------------------------------------------
KAATLQGMGFHVFIVYSYGLAALLLLPSLFFSYRSRTLPPMNFSILYKVVLLGLIGCCSN
----------------------------------------------------------------
SYLMSLGLGPFTIVIFSTFATFLILSPFAILFERKQWPKELSARLIGKLVLISFAGVTLF
SYLMSLSLGPLTIVIFSTFATFLILSPFAILFERKQWPDELSPRLIGKLVLISFAGVTLF
KAAFDSGMYTYIFVFYRLAAATALLVPIALINCACRRSQSTTSTPAQAMSCRLLFKLFLC
xxxxxxxxxxxxxxxxxxxxxxxxxxxxxxxxxxxxxxxxxxxxxxxxxxxxxxxxxxxx ----------------------------------------------------------------
----------------------------------------------------------------
RIL------------------------------------------SLR-IVLHIPTFA
GFY------------------------------------------IFG-LDNTSPTFA
ILG------------------------------------------YNG-IKYSSPTLS
ILG------------------------------------------YNG-IKYSSPTLS
```

Fig. 1A

```
ITG--------------------------------------------GIG-IEYSNPTLA
ITG--------------------------------------------GIG-IEYSNPTLA
ITG--------------------------------------------GIG-IEYSNPTLA
ITG--------------------------------------------GIG-IEYSNPTLA
ITG--------------------------------------------YIG-IEYSSPTLA
ITG--------------------------------------------YIG-IEYSSPTLA
ITG--------------------------------------------YIG-IEYSSPTLA
ITG--------------------------------------------YIG-IEYSSPTLA
ITG--------------------------------------------YIG-IEYSSPTLA
------------------------------------------------------------
IMG--------------------------------------------YTG-INYSSPTLA
------------------------------------------------------------
QSL--------------------------------------------FLEGIRLTSPAMA
QTL--------------------------------------------FLEGIRLTSPAMA
AFLGSAGLTLQALTKFVKKSCQEVGGFTSLLSSSLLQGKAEHLHPQVYHASLKQTSATVA
xxx--------------------------------------------xxx-ixxxxptxa ------------------------------------------------------------
------------------------------------------------------------
SAIQNSVPAITFIMAAALRLEKVHISRRDGLAKIIGTVACVSGATIITLYKGPPITHIWR
SATENAVPAVSFLMAALLGIEKVELKRRDGVAKVVGTFVSVAGSLAITLYKGP---TIYQ
SAMSNVNPAFTFILAVVFRMENISLGKKSSVAKVLGTILSIIGALVVTLYHGP-------
SAMSNVNPAFTFILAVVFRMENISLGKKSSVAKVLGTILSIIGALVVTLYHGP-------
SAIGNIVPALTFILAVIFRMEKVSFKERSSVAKVMGTILSLIGAFVVIFYHGPRVFVASS
SAIGNIVPALTFILAVIFRMEKVSFKERSSVAKVMGTILSLIGAFVVIFYHGPRVFVASS
SAIGNIVPALTFILAVIFRMEKVSFKERSSVAKVMGTILSLIGAFVVIFYHGPRVFVASS
SAIGNIVPALTFILAVIFRMEKVSFKERSSVAKVMGTILSLIGAFVVIFYHGPRVFVASS
SAINNITPALTFILAIIFRMEKVSFKERSSLAKLMGTILSLIGALVVIFYHGPRVFLASS
SAINNITPALTFILAIIFRMEKVSFKERSSLAKLMGTILSLIGALVVIFYHGPRVFLASS
SAINNITPALTFILAIIFRMEKVSFKERSSLAKLMGTILSLIGALVVIFYHGPRVFLASS
SAINNITPALTFILAIIFRMEKVSFKERSSLAKLMGTILSLIGALVVIFYHGPRVFLASS
SAISNITPALTFILAIIFRMEKVSFKERSSVAKVMGTILSLIGALVVVLYHGPRVFVASS
--------------------MEKASFKEKSSVAKMVGTIVSLVGALVVVLYHGPRVFTPSS
SAISNLTPAFTFLLAILFRMESVSFKRTSSVARMLGTIVSIGGAFIVTLYNGPVVINMSP
--------------------MERIYWRHFSSQAKAIGTIVSMAGAFVVILYKGPPILKIHS
TAMPNLAPGLIFFIAWIVRLEKMNMKCVYSKLKILGTLLCVFGALTMSLMHSASIIQDEK
TAMPNLAPGLIFFIAWMVRLEKMDMKCVYSKLKILGTLLCVFGALTMSLMHSASIIQDEK
SAATNSMPVVTFLLALVLRMETIKLRRRSGLGKLAGVALCLAGVLVIAFYVGPSIRPLAH
saxxnxxpxxxfxxaxxxrmexxxxxxxssxakxxgtxxsxxgaxxxxxyxgpxxxxxxx -----------FLPDSKHVTASEDDNWILGCLLLLASSVFWSCWMIMQVPISSSCPDHVLST
-----------FLPDSKHVTASEDDNWILGCLLLLASSVFWSCWMIMQVPISSSCPDHVLST
PNLEVTASYFKAFQGNDLSAKSENWTLGCIYLLGNCLAWSGWIVLQAPVLKRYPARLSVT
PSLRSMD----QPTNAGEAEEQNKNWTLGCVCLMGHCLCWSSWIVLQSPLLKRYPARYSFV
-------------------MLMSSHSDWIIGGGLLALQYILVSVSYLVMAHTMGRYPSAVVVT
-------------------MLMSSHSDWIIGGGLLALQYILVSVSYLVMAHTMGRYPSAVVVT
P-----PYLNFRQLSPPLSSSKSDWLIGGAILTIQGIFVSVSFILQTHIMREYPEAFTVS
P-----PYLNFRQLSPPLSSSKSDWLIGGAILTIQGIFVSVSFILQTHIMREYPEAFTVS
P-----PYLNFRQLSPPLSSSKSDWLIGGAILTIQGIFVSVSFILQTHIMREYPEAFTVS
P-----PYLNFRQLSPPLSSSKSDWLIGGAILTIQGIFVSVSFILQAHIMREYPEAFTVS
P-------PYVNFRQFSPPLSSSNSDWLIGGALLTMQGIFVSVSFILQAHIMSVYPAAFRVS
P-------PYVNFRQFSPPLSSSNSDWLIGGALLTMQGIFVSVSFILQAHIMSVYPAAFRVS
P-------PYVNFRQFSPPLSSSNSDWLIGGALLTMQGIFVSVSFILQAHIMSVYPAAFRVS
```

Fig. 1B

```
P-----PYVNFRQFSPPLSSSNSDWLIGGALLTMQGIFVSVSFILQAHIMSVYPAAFRVS
P-----PYINFRQLSPPLSSSNSDWLIGGALLTIRDIFVSVSFILQAKIMSTYPAAFTVS
P-----PFPQLRQLLLPLSSSNSDWIIGGCLLAIKDTLVPVAFILQAHIMKLYPAPFTVS
P-----S------ISLRSQSPNHDWIIGAAFLAVEYFMVPLWYIVQTQIMREYPSEFTVV
S------IS------YNTLQFSPNLNWILGGFLCAGDSLLSSMWYIYQVSVTKKYPAVIVIV
D---------------NASIFVFDRDRVVGCIYLLGAVFVLSTNVVLQASTLAEFPAPISLS
D---------------NASIFVFDRDRVVGCMYLLGAVFILSSNVVLQASTLAEFPAPISLS
HP------------VFAHKTQSVGNGAWIRGTFLLILSCTTWSLWITLQVPLLIEYPNKLMAT
x------xxxxxxxxxxxxxsxxxdwxxGxxxlxxxxxxxxsxxxxlqxxxxxxyPxxxxxx FWMCLFATIQSAMFALLKEP-DLQAWILPSPLQ-ISCSLYAG-IGIAVSFFIQSWCISER
FWMCLFATIQSAIFALLKEP-DLQAWILPSPLQ-ISCSLYAG-IGIAVSFFIQSWCISER
SFTCFFGVIQFLIIAAFFET-DLEHWKIHSGGE-LFTILYAGFVASGIAFSVQIWCIDRG
SYSCLFAVFQIVGISAYFER-DLESWKIKSGRE-MYALLYTGLVGSGMVFAIQIYVVERG
LVHNVCIAVVCAFVSLLAEKDNPKAWVIRFDIT-LITVVATGILNSGYY-VIHTWAVSHK
LVHNVCIAVVCAFVSLLAEKDNPKAWVIRFDIT-LITVVATGILNSGYY-VIHTWAVSHK
ILYILCISIVTSMIGLVVEKNNPSIWIIHFDIT-LFTIVTTGIITSVYY-VIHSWAIRHK
ILYILCISIVTSMIGLVVEKNNPSIWIIHFDIT-LFTIVTTGIITSVYY-VIHSWAIRHK
ILYILCISIVTSMIGLVVEKNNPSIWIIHFDIT-LFTIVTTGIITSVYY-VIHSWAIRHK
ILYILCISIVTSMIGLVVEKNNPSIWIIHFDIT-LFTIVTTGIITSVYY-VIHSWAIRHK
FLYTVCVSIVTSTIGLVVEKNNPSVWIIHFDIT-LITIVTMAIVTSVYY-VIHSWTVRHK
FLYTVCVSIVTSTIGLVVEKNNPSVWIIHFDIT-LITIVTMAIVTSVYY-VIHSWTVRHK
FLYTVCVSIVTSTIGLVVEKNNPSVWIIHFDIT-LITIVTMAIVTSVYY-VIHSWTVRHK
FLYTVCVSIVTSTIGLVVEKNNPSVWIIHFDIT-LITIVTMAIVTSVYY-VIHSWTVRHK
FLYIVSVSIVTSMIGLVVEKNNPSVWIIRFDIT-LITIVTMAIITSVYY-VIHSWTVRHK
FFYFLIASILTSLIGIVAEKNNPSIWIIHFDIT-LVCIVVGGIFNPGYY-AIHLWAVRNK
CYYSFGVSFWTGLATLFTEGSDLSAWKIKPNIA-LVSIVCSGLFGSCINNTIHTWALRIK
FFQVVFITIQTGVYALIVVR-DPSAWELKLDMG-LIVILYQAVAAIGIRYFLQTWSVQRA
AITALIGVLITMLVQLLQNQSGKVLTRSLISIGNLVGFSLLGGMVSGACVSFNGWAMKKR
AITSLIGVVITTMLQLLQNPNTKVVTRSLISISNLVGFSLLGGMVSGACVSFNGWAMKKR
AMQCLFSALQSFVVAVVVEK-DFTKWKLGLDIG-----LLAAFLGTGALMYLQAWCAEMS
xxxxxxxxxxxxxxxlxxexxxxxxwxixxxix-lxxxxxxxxxxsxxxxxixxwxxxxx GPLYCAMFNPLATVITALVAATFLEEKLYVGSLVGAIGVTVGLYIVLWGKAKDFDG-----
GPLYCAMFNPLATVITALVAATFLEEKLYVGSLVGAIGVTVGLYIVLWGKAKDFDG-----
GPVFVAVYQPVQTIAVAIMASIILGEQFYLGGIFGAILIIIGLYLVLWGKSEEKR------
GPLFVSAYLPLQTLLAALLATFALGEHLYLGGLIGAILIICGLYLVVMGKSGRR------
GPVYLSMFKPLSILIAAVSTFIFLGESLYLGSVMGGILISIGFYMVLWGKA---------
GPVYLSMFKPLSILIAAVSTFIFLGESLYLGSVMGGILISIGFYMVLWGKA---------
RPLYLAIFKPLSILIAVVMGTIFLNDSLYLGCLIGGILITLGFYVVMWGKA---------
RPLYLAIFKPLSILIAVVMGTIFLNDSLYLGCLIGGILITLGFYVVMWGKA---------
RPLYLAIFKPLSILIAVVMGTIFLNDSLYLGCLIGGILITLGFYVVMWGKA---------
GPLYLAIFKPLSILIAVVMGTIFLNDSLYLGCLIGGILITLGFYAVMWGKS---------
GPLYLAIFKPLSILIAVVMGAIFLNDSLYLGWY-------------------
GPLYLAIFKPLSILIAVVMGAIFLNDSLYLGWY-------------------
GPLYLAIFKPLSILIAVVMGAIFLNDSLYLGCLIGGILITLGFYAVMWGKA---------
GPLYLAIFKPLSILIAVVMGAIFLNDSLYLGCLIGGILITLGFYAVMWGKA---------
GPLYLAIFKPLSILIAVVMSAVFLNDSLYLGCLIGGLLITLGFYAVMWGKA---------
GPVYLAIFRPLSILIAVIMGAIFLGDSFYLGSLVGGILISLGFYTVMWGKA---------
GPLFVAMFKPLSIAIAVAMGVIFLHDSLYIGSLIGATVITTGFYTVMWGKAKEAAMVEDD
GPLFCAMFKPIGIIFTVFLGSIFLGDDFYLGSLIGAVIIVVGFYAVQWGKA---------
GPVMVSMFSPFATVISVGFSVLTLGESICLGSVGGMALMFMGLYLVLWAKG----------
GPVMVSMFSPIATVISVGLSVVTLGEPVRIGSVGGMALMFIGLYLVLWAKG----------

GPVFVVMWSPLAFIFTIFSSSFFLGEVVHLGSILGGILLVGGLYSVLWGKSNERKNMILP
```

Fig. 1C

```
gPxxxaxfxPlxxxixxxxxxxxfLxxxlylGxxxgxxlxxxgxyxvxwgkx---------

TKQELPQSNMVDDERSNRTDLEEPLLAEKSEYVAEIKMEG--------------------
TKQELPQSNMVDDERSNRTDLEEPLLAEKSEYVAEIKMEG--------------------
LGLLQAKSSMVPENQPDNMDQSATLIINSSNGIKPNTSSSLTQPLLLDTSYKTVNIPSPS
-------------------------KLFANSNT---------------------------
-----KEDKVDIIGAIESSPSHNAPLLDNFKS----------------------------
-----KEDKVDIIGAIESSPSHNAPLLDNFKS----------------------------
----NEEKNKLL---SFSGKEKTPLLLSGKNDQI--------------------------
----NEEKNKLL---SFSGKEKTPLLLSGKNDQI--------------------------
----NEEKNKLL---SFSGKEKTPLLLSGKNDQI--------------------------
----NEEKDKLL---SFSGKEKTPLLLSGKNEQV--------------------------
------------------------------------------------------------
------------------------------------------------------------
-----NEEKDQLS----FSE-KEKTPLLLNRKNDQV------------------------
-----NEEKDQLS----FSE-KEKTPLLLNRKNDQV------------------------
------NEEKDQLL----LVSGKERTPLLLNG----------------------------
----KEGKTQFL---SLS--EETPLLDENIDDRI--------------------------
NKANNEDATNEADHDSPLASQKAPLLESYKNDEHV-------------------------
----SEEKVEKGIENLETQSNVVPLLQNKV------------------------------
-----KEGFSQIESFECEFDAKKPLLS---------------------------------
-----KEGFSQIDSFESEYDPKKPLLS---------------------------------
VMPEKSQGQGDGDGATTQEKHGETNLTSQV------------------------------
------xxxxxxxxxxxxxxxxxxxxpllxxxxxxxx----------------------

-------*
-----*
DEPQP*
-----*
-----*
-----*
-----*
-------*
-------*
----------*
-------*
-----*
-----*
-----*
-----*
-----*
-------*
----------*
-------*
----------*
-------*
-----*
```

Fig. 1D

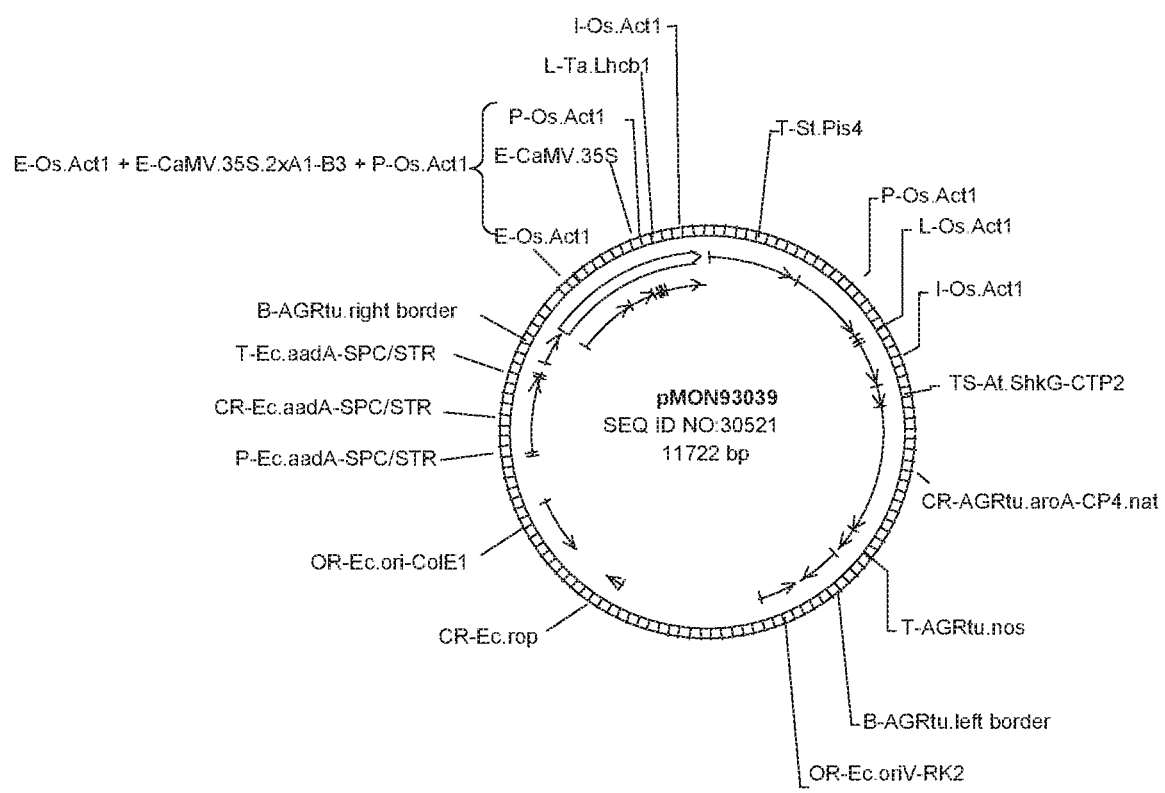
Fig. 2 Plasmid map of pMON93039

Fig. 3   Plasmid map of pMON82053
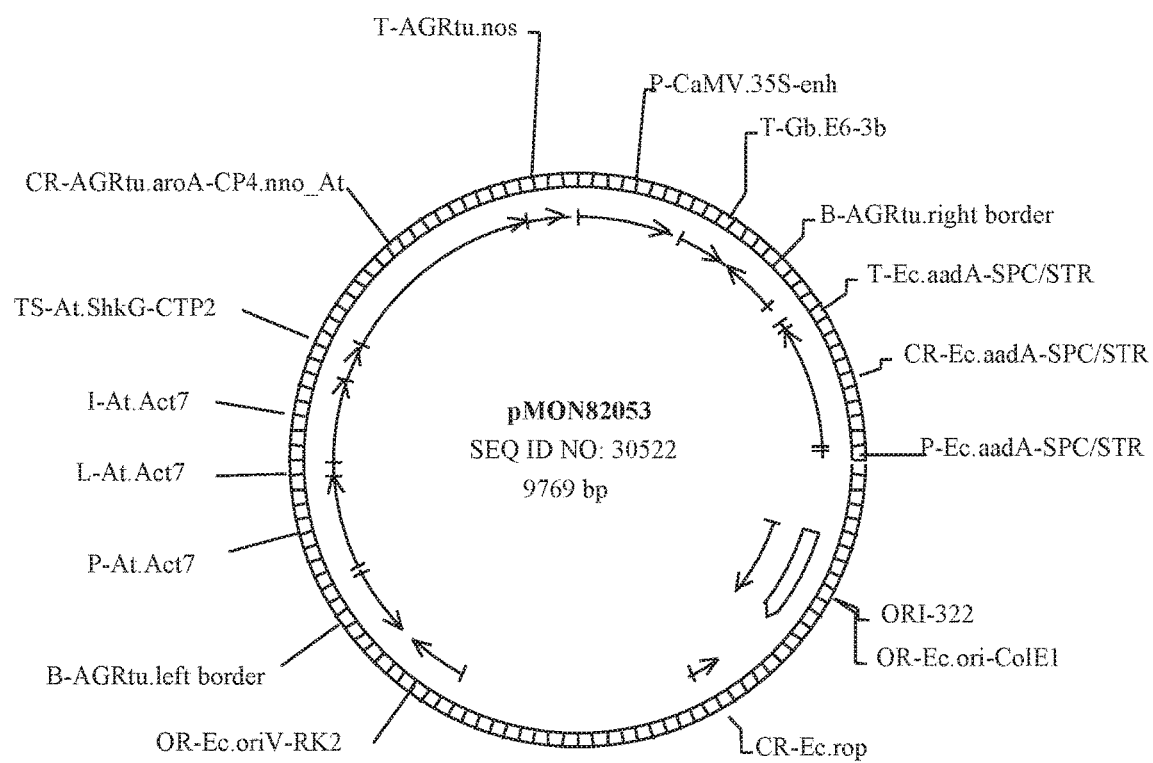

Fig. 4 Plasmid map of pMON99053
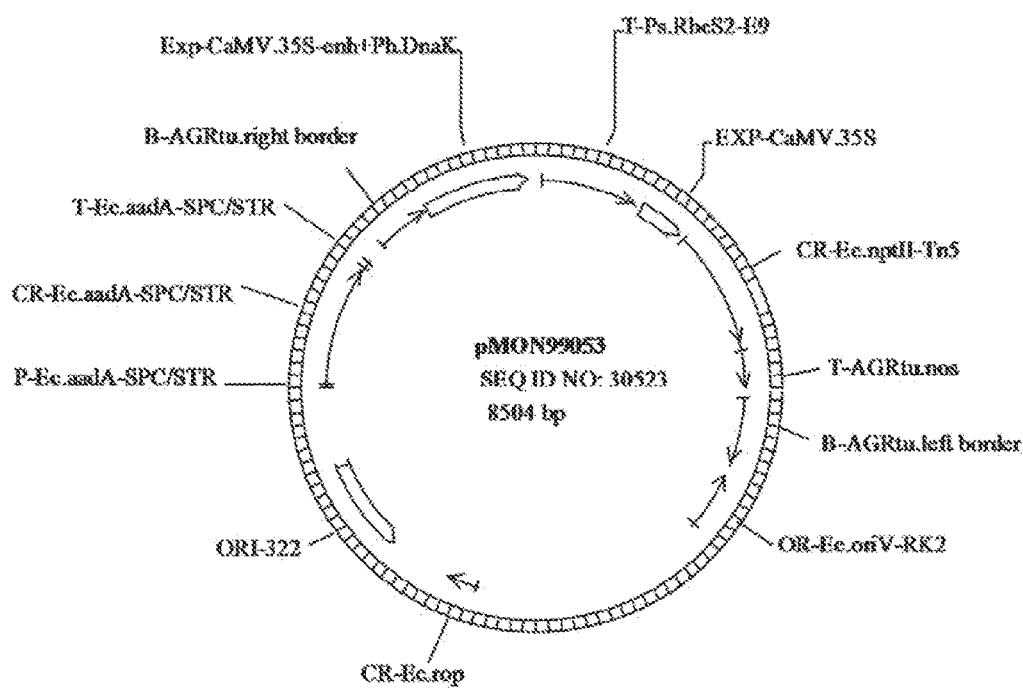

TRANSGENIC PLANTS WITH ENHANCED AGRONOMIC TRAITS

CROSS REFERENCE TO RELATED APPLICATIONS

This application is a continuation of U.S. application Ser. No. 14/998,728, filed Feb. 8, 2016, which application is a continuation of U.S. application Ser. No. 13/815,411, filed Feb. 27, 2013, which application is a continuation of U.S. application Ser. No. 12/218,251, filed Jul. 10, 2008, which application claims the benefit of priority under 35 USC § 119(e) of U.S. provisional application Ser. No. 60/958,909, filed Jul. 10, 2007, the contents of which are incorporated by reference in their entireties.

INCORPORATION OF SEQUENCE LISTING

Two copies of the sequence listing (Copy 1 Replacement Feb. 28, 2018 and Copy 2 Replacement Feb. 28, 2018) and a computer readable form (CRF) of the sequence listing, all on CD-Rs, each containing the text file named "3126.026US4.TXT", which is 105,787,392 bytes (measured in MS-WINDOWS), were created on Feb. 28, 2018 and are herein incorporated by reference.

INCORPORATION OF COMPUTER PROGRAM LISTING

Two copies of the Computer Program Listing (Copy 1 and Copy 2) and a computer readable form (CRF) containing folders hmmer-2.3.2 and 226pfamdir, all on CD-Rs are incorporated herein by reference in their entirety. Folder Hmmer-2.3.2 contains the source code and other associated file for implementing the HMMer software for Pfam analysis. Folder 226pfamDir contains 226 Pfam Hidden Markov Models. Both folders were created on CD-R on Dec. 5, 2017, having a total size of 19,449,856 bytes (measured in MS-WINDOWS).

FIELD OF THE INVENTION

Disclosed herein are recombinant DNA useful for providing enhanced traits to transgenic plants, seeds, pollen, plant cells and plant nucleui of such transgenic plants, methods of making and using such recombinant DNA, plants, seeds, pollen, plant cells and plant nuclei. Also disclosed are methods of producing hybrid seed comprising such recombinant DNA.

SUMMARY OF THE INVENTION

This invention employs recombinant DNA for expression of proteins that are useful for imparting enhanced agronomic traits to the transgenic plants. Recombinant DNA in this invention is provided in a construct comprising a promoter that is functional in plant cells and that is operably linked to a DNA segment that encodes a protein. In some embodiments of the invention, such protein defined by protein domains e.g. a "Pfam domain module" (as defined herein below) from the group of Pfam domain modules identified in Table 11. In other embodiments of the invention, e.g. where a Pfam domain module is not available, such protein is defined a consensus amino acid sequence of an encoded protein that is targeted for production e.g. a protein having amino acid sequence with at least 90% identity to a consensus amino acid sequence in the group of SEQ ID NO: 30526 through SEQ ID NO: 30550. In more specific embodiments of the invention the protein expressed in plant cells is a protein selected from the group of proteins identified in Table 2 and their homologs identified in Table 8.

Other aspects of the invention are specifically directed to plant cell nuclei and transgenic cells comprising the recombinant DNA construct of the invention, transgenic plants comprising a plurality of such plant cells, progeny transgenic seed, embryo and transgenic pollen from such plants. Such transgenic plants are selected from a population of transgenic plants regenerated from plant cells transformed with recombinant DNA construct and expressed the protein by screening transgenic plants in the population for an enhanced trait as compared to control plants that do not have the recombinant DNA construct, where the enhanced trait is selected from group of enhanced traits consisting of enhanced water use efficiency, enhanced cold tolerance, increased yield, enhanced nitrogen use efficiency, enhanced seed protein and enhanced seed oil.

In yet another aspect of the invention the plant cell nuclei, plant cells, transgenic plants, seeds, and pollen further comprise recombinant DNA expressing a protein that provides tolerance from exposure to an herbicide applied at levels that are lethal to a wild type plant cell. Such tolerance is especially useful not only as an advantageous trait in such plants but is also useful in a selection step in the methods of the invention. In aspects of the invention such herbicide is a glyphosate, dicamba, or glufosinate compound.

Yet other aspects of the invention provide transgenic plants which are homozygous for the recombinant DNA and transgenic seed of the invention from corn, soybean, cotton, canola, alfalfa, wheat or rice plants.

This invention also provides methods for manufacturing non-natural, transgenic seed that can be used to produce a crop of transgenic plants with an enhanced trait resulting from expression of stably-integrated, recombinant DNA construct provided by herein. More specifically the method comprises (a) screening a population of plants for an enhanced trait and a recombinant DNA construct of the invention, where individual plants in the population can exhibit the trait at a level less than, essentially the same as or greater than the level that the trait is exhibited in control plants which do not express the recombinant DNA, (b) selecting from the population one or more plants that exhibit the trait at a level greater than the level that said trait is exhibited in control plants, and (c) collecting seed from a selected plant. The method further comprises (d) verifying that the recombinant DNA construct is stably integrated in said selected plants, and (e) analyzing tissue of a selected plant to determine the production of a protein having the function of a protein selected from SEQ ID NO: 299 through SEQ ID NO: 30468. In one aspect of the invention the plants in the population further comprise DNA expressing a protein that provides tolerance to exposure to a herbicide applied at levels that are lethal to wild type plant cells and the selecting is affected by treating the population with the herbicide, e.g. a glyphosate, dicamba, or glufosinate compound. In another aspect of the invention the plants are selected by identifying plants with the enhanced trait. The methods are especially useful for manufacturing corn, soybean, cotton, canola, alfalfa, wheat or rice seed.

Another aspect of the invention provides a method of producing hybrid corn seed comprising acquiring hybrid corn seed from a herbicide tolerant corn plant which also has stably-integrated, recombinant DNA construct comprising a promoter that is (a) functional in plant cells and (b) is operably linked to DNA that encodes a protein provided by the invention. The methods further comprise producing corn plants from the hybrid corn seed, wherein a fraction of the plants produced from said hybrid corn seed is homozygous for said recombinant DNA, a fraction of the plants produced from said hybrid corn seed is hemizygous for the recombinant DNA construct, and a fraction of the plants produced from said hybrid corn seed has none of the recombinant DNA construct; selecting corn plants which are homozygous and hemizygous for the recombinant DNA construct by beating with an herbicide; collecting seed from herbicide-treated-surviving corn plants and planting the seed to produce further progeny corn plants; repeating the selecting and collecting steps at least once to produce an inbred corn line; and crossing the inbred corn line with a second corn line to produce hybrid seed.

BRIEF DESCRIPTION OF THE DRAWINGS

FIG. 1A-D is a consensus amino acid sequence of SEQ ID NO: 301 and its homologs.

FIGS. 2-4 are plasmid maps.

DETAILED DESCRIPTION OF THE INVENTION

In the attached sequence listing:

SEQ ID NO:1-298 are nucleotide sequences of the coding strand of DNA for "genes" used in the recombinant DNA imparting an enhanced trait in plant cells, i.e. each represents a coding sequence for a protein;

SEQ ID NO: 299-596 are amino acid sequences of the cognate protein of the "genes" with nucleotide coding sequences 1-298;

SEQ ID NO: 597-30468 are amino acid sequences of homologous proteins;

SEQ ID NO: 30469-30520 are nucleotide sequences of the elements in base plasmid vectors SEQ ID NO: 30521 is a nucleotide sequence of a base plasmid vector useful for corn transformation;

SEQ ID NO: 30522 is a nucleotide sequence of a base plasmid vector useful for soybean and canola transformation;

SEQ ID NO: 30523 is a nucleotide sequence of a base plasmid vector useful for cotton transformation;

SEQ ID NO: 30524 is a nucleotide sequence of a Sphas1 promoter from soybean;

SEQ ID NO: 30525 is a nucleotide sequence of a Sphas1 leader from soybean.

SEQ ID NO: 30526-30550 are consensus sequences.

Table 1 lists the protein SEQ ID NOs and their corresponding consensus SEQ ID NOs.

TABLE 1

| Gene ID | PEP SEQ ID NO | Consensus SEQ ID NO |
|---|---|---|
| PHE0006007__18714 | 301 | 30526 |
| PHE0006460__15962 | 453 | 30527 |
| PHE0006657__16192 | 334 | 30528 |
| PHE0006712__16273 | 415 | 30529 |
| PHE0006859__16873 | 376 | 30530 |
| PHE0006907__16797 | 594 | 30531 |
| PHE0006936__16828 | 348 | 30532 |
| PHE0006969__16871 | 428 | 30533 |
| PHE0007578__17852 | 446 | 30534 |
| PHE0007650__18175 | 358 | 30535 |
| PHE0008172__18471 | 397 | 30536 |
| PHE0008308__18841 | 392 | 30537 |
| PHE0008340__19155 | 410 | 30538 |

TABLE 1-continued

| Gene ID | PEP SEQ ID NO | Consensus SEQ ID NO |
|---|---|---|
| PHE0008422__18842 | 412 | 30539 |
| PHE0008698__24421 | 364 | 30540 |
| PHE0010197__21429 | 569 | 30541 |
| PHE0010201__21433 | 576 | 30542 |
| PHE0010201__21768 | 574 | 30543 |
| PHE0010223__21491 | 545 | 30544 |
| PHE0010397__21762 | 538 | 30545 |
| PHE0010398__21763 | 539 | 30546 |
| PHE0010615__22400 | 510 | 30547 |
| PHE0010838__22702 | 575 | 30548 |
| PHE0011447__23660 | 586 | 30549 |
| PHE0012170__24424 | 572 | 30550 |

As used herein a "plant cell" means a plant cell that is transformed with stably-integrated, non-natural, recombinant DNA construct, e.g. by *Agrobacterium*-mediated transformation or by bombardment using microparticles coated with recombinant DNA construct or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" means a plant whose genome has been altered by the stable integration of recombinant DNA construct. A transgenic plant includes a plant regenerated from an originally-transformed plant cell and progeny transgenic plants from later generations or crosses of a transformed plant.

As used herein "recombinant DNA" means DNA which has been a genetically engineered and constructed outside of a cell including DNA containing naturally occurring DNA or cDNA or synthetic DNA.

As used herein "consensus sequence" means an artificial sequence of amino acids in a conserved region of an alignment of amino acid sequences of homologous proteins, e.g. as determined by a CLUSTALW alignment of amino acid sequence of homolog proteins.

As used herein a "homolog" means a protein in a group of proteins that perform the same biological function, e.g. proteins that belong to the same Pfam protein family and that provide a common enhanced trait in transgenic plants of this invention. Homologs are expressed by homologous genes. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. Hence, a polynucleotide useful in the present invention may have any base sequence that has been changed from SEQ ID NO:1 through SEQ ID NO: 298 substitution in accordance with degeneracy of the genetic code. Homologs are proteins that, when optimally aligned, have at least 60% identity, more preferably about 70% or higher, more preferably at least 80% and even more preferably at least 90% identity over the full length of a protein identified as being associated with imparting an enhanced trait when expressed in plant cells. Homologs include proteins with an amino acid sequence that has at least 90% identity to a consensus amino acid sequence of proteins and homologs disclosed herein.

Homologs are identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit is a likely ortholog, when the reciprocal query's best hit is the query protein itself or a protein encoded by a duplicated gene after speciation. A further aspect of the invention comprises functional homolog proteins that differ in one or more amino acids from those of disclosed protein as the result of conservative amino acid substitutions, for example substitutions are among: acidic (negatively charged) amino acids such as aspartic acid and glutamic acid; basic (positively charged) amino acids such as arginine, histidine, and lysine; neutral polar amino acids such as glycine, serine, threonine, cysteine, tyrosine, asparagine, and glutamine; neutral nonpolar (hydrophobic) amino acids such as alanine, leucine, isoleucine, valine, proline, phenylalanine, tryptophan, and methionine; amino acids having aliphatic side chains such as glycine, alanine, valine, leucine, and isoleucine; amino acids having aliphatic-hydroxyl side chains such as serine and threonine; amino acids having amide-containing side chains such as asparagine and glutamine; amino acids having aromatic side chains such as phenylalanine, tyrosine, and tryptophan; amino acids having basic side chains such as lysine, arginine, and histidine; amino acids having sulfur-containing side chains such as cysteine and methionine; naturally conservative amino acids such as valine-leucine, valine-isoleucine, phenylalanine-tyrosine, lysine-arginine, alanine-valine, aspartic acid-glutamic acid, and asparagine-glutamine. A further aspect of the homologs encoded by DNA useful in the transgenic plants of the invention are those proteins that differ from a disclosed protein as the result of deletion or insertion of one or more amino acids in a native sequence.

"Percent identity" describes the extent to which the sequences of DNA or protein segments are invariant throughout a window of alignment of nucleotide or amino acid sequences. An "identity fraction" for a sequence aligned with a reference sequence is the number of identical components which are shared by the sequences, divided by a length of the window of alignment, wherein the length does not include gaps introduced by an alignment algorithm. "Percent identity" ("% identity") is the identity fraction times 100. The alignment algorithm is preferably a local alignment algorithm, such as BLASTp. As used herein, sequences are "aligned" when the alignment produced by BLASTp has a minimal e-value.

"Pfam" database is a large collection of multiple sequence alignments and hidden Markov models covering many common protein families, e.g. Pfam version 19.0 (December 2005) contains alignments and models for 8183 protein families and is based on the Swissprot 47.0 and SP-TrEMBL 30.0 protein sequence databases. See S. R. Eddy, "Profile Hidden Markov Models", *Bioinformatics* 14:755-763, 1998. The Pfam database is currently maintained and updated by the Pfam Consortium. The alignments represent some evolutionary conserved structure that has implications for the protein's function. Profile hidden Markov models (profile HMMs) built from the protein family alignments are useful for automatically recognizing that a new protein belongs to an existing protein family even if the homology by alignment appears to be low.

Protein domains are identified by querying the amino acid sequence of a protein against Hidden Markov Models which characterize protein family domains ("Pfam domains") using HMMER software, a current version of which is provided in the appended computer listing. A protein domain meeting the gathering cutoff for the alignment of a particular Pfam domain is considered to contain the Pfam domain.

A "Pfam domain module" is a representation of Pfam domains in a protein, in order from N terminus to C terminus. In a Pfam domain module individual Pfam domains are separated by double colons "::". The order and copy number of the Pfam domains from N to C terminus are attributes of a Pfam domain module. Although the copy number of repetitive domains is important, varying copy number often enables a similar function. Thus, a Pfam domain module with multiple copies of a domain should define an equivalent Pfam domain module with variance in the number of multiple copies. A Pfam domain module is not specific for distance between adjacent domains, but contemplates natural distances and variations in distance that provide equivalent function. The Pfam database contains both narrowly- and broadly-defined domains, leading to identification of overlapping domains on some proteins. A Pfam domain module is characterized by non-overlapping domains. Where there is overlap, the domain having a function that is more closely associated with the function of the protein (based on the E value of the Pfam match) is selected.

Once one DNA is identified as encoding a protein which imparts an enhanced trait when expressed in transgenic plants, other DNA encoding proteins with the same Pfam domain module are identified by querying the amino acid sequence of protein encoded by candidate DNA against the Hidden Markov Models which characterizes the Pfam domains using HMMER software. Candidate proteins meeting the same Pfam domain module are in the protein family and have cognate DNA that is useful in constructing recombinant DNA for the use in the plant cells of this invention. Hidden Markov Model databases for use with HMMER software in identifying DNA expressing protein with a common Pfam domain module for recombinant DNA in the plant cells of this invention are also included in the appended computer listing.

The HMMER software and Pfam databases are version 19.0 and were used to identify known domains in the proteins corresponding to amino acid sequence of SEQ ID NO: 299 through SEQ ID NO: 596. All DNA encoding proteins that have scores higher than the gathering cutoff disclosed in Table 14 by Pfam analysis disclosed herein can be used in recombinant DNA of the plant cells of this invention, e.g. for selecting transgenic plants having enhanced agronomic traits. The relevant Pfams modules for use in this invention, as more specifically disclosed below, are zf-CCCH, PALP, GAF::HisKA::HATPase_c, TPR_2::TPR_1::TPR_2::TPR_1::TPR_4::TPR_2::TPR_1, efhand::efhand, Spermine_synth, ELFV_dehydrog_N::ELFV_dehydrog, PFK, PAS_3::PAS_3::Pkinase, S1, GDC-P, SWIM, B12-binding::Radical_SAM, S1, LRR_1::LRR_1::LRR_1::LRR_1::LRR_1::LRR_1::LRR_1, Chloroa_b-bind, LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase, WD40::WD40, YABBY, Ldh_1_N::Ldh_1_C, Sina, Na_H_antiport_1, ParBc, YABBY, Histone, Fe_bilin_red, Tryp_alpha_amyl, Pyr_redox_2::Thioredoxin, E2F_TDP, CN_hydrolase, YDG_SRA::Pre-SET::SET, APC8::TPR_1::TPR_1::TPR_1, Ras, tRNA_anti::tRNA-synt_2, Auxin_inducible, PGI, S1, Chloroa_b-bind, Bac_globin, Glyco_hydro_17, MGS, Spermine_synth, LRRNT_2::LRR_1::LRR_1::LRR_1::LRR_1::LRR_1::Pkinase, Aa_trans, LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase_Tyr, Gln-synt_N::Gln-synt_C, SAP18, TPP_enzyme_N::TPP_enzyme_M::TPP_enzyme_C, zf-C3HC4, eIF-1a, RPE65, PBP, Pkinase, AA_permease, F-box::LRR_1::LRR_2, zf-CCCH::zf-CCCH, Lactamase_B::Flavodoxin_1::Flavin_Reduct, Bac_globin, DSPc, adh_short, Tim17, Oxidored_molyb::Mo-co_dimer::Cyt-b5::FAD_binding_6::NAD_binding_1, ubiquitin::ubiquitin::ubiquitin::ubiquitin, MBD, CXC::CXC, HSF_DNA-bind, Spermine_synth, AP2, Peptidase_S10, PALP, EIN3, Gln-synt_N::Gln-synt_C, 2OG-FeII_Oxy, Glyco_hydro_9, GDC-P, B3, PTPA, Acyltransferase, Isochorismatase, FMO-like, Molybdop_Fe4S4::Molybdopterin::Molydop_binding::Fer2_BFD, Lir1, Prismane, Fer2, DEAD::Helicase_C, Molybdop_Fe4S4::Molybdopterin::Molydop_binding::Fer2_BFD, KNOX1::KNOX2::ELK, Glyoxalase, Sad1_UNC, Bac_globin, VPS28, PP2C, Pkinase::efhand::efhand::efhand, LEA_3, Peptidase_S10, Pkinase, CBFD_N-FYB_HMF, Gln-synt_N::Gln-synt_C, Pyr_redox_2::Fer2_BFD::NIR_SIR_ferr:NIR_SIR, NUDIX::NUDIX, FAD_binding_3, GST_N::GST_C, SAM_decarbox, Acyltransferase, NTP_transferase, G-patch, 2OG-FeII_Oxy, Gln-synt_N::Gln-synt_C, AAA::Vps4_C, Histone, Pkinase, TPR_1, F-box::Kelch_1::Kelch_1, Spermine_synth, Bac_globin, Bac_globin, zf-UBR, Homeobox::HALZ, Whirly, NAD_binding_1, PTR2, EIN3, 4HBT, adh_short, 2OG-FeII_Oxy, P-II, Myb_DNA-binding::Myb_DNA-binding, DAGK_cat, AP2, MFS_1, Chloroa_b-bind, DUF716, zf-Dof, CCT, Homeobox::HALZ, Histone, 2OG-FeII_Oxy, Globin, Pyr_redox_2::Fer2_BFD::NIR_SIR_ferr:NIR_SIR, Whirly, PsbP, bZIP_1, LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase_Tyr, Phil, BURP, Sterol_desat, DSPc, SNF5, Acyltransferase, GATase_2::Asn_synthase, adh_short, Homeobox::START, Pkinase, ParBc, SOI1L, DNA_photolyase::FAD_binding_7, Pkinase_Tyr, NAD_Gly3P_dh_N::NAD_Gly3P_dh_C, Na_H_Exchanger, peroxidase, Oxidored_molyb::Mo-co_dimer::Cyt-b5::FAD_binding_6::NAD_binding_1, Hexokinase_1::Hexokinase_2, DUF716, S10_plectin, Thi4, p450, CCT, adh_short, PSI_PSAK, DUF640, Thioredoxin, Globin, Ank::Pkinase, DAGAT, RPE65, Ank::Pkinase, GSHPx, Gln-synt_N::Gln-synt_C, MtN3_slv::MtN3_slv, Allene_ox_cyc, IGPD, MBD, CorA, Response_reg, Histone, AAA, Ribosomal_L10e, Pkinase, DUF26::DUF26::Pkinase, p450, mTERF, AA_kinase, PBP, GUN4, Lactamase_B::Flavodoxin_1::Rubredoxin, C2, RRM_1::RRM_1, Histone, Alpha-amylase, HLH, Thioredoxin, Histone_HNS, Myb_DNA-binding::Myb_DNA-binding, Cytochrom_C552, AP2::AP2, MtN3_slv::MtN3_slv, SHMT, ParBc, Mit_rib_S27, Ribosomal_S2, KNOX1::KNOX2::ELK, MFS_1, Glyco_transf_5::Glycos_transf_1, Cellulase, Ribosomal_L10e, Spermine_synth, Glyco_hydro_2_N::Glyco_hydro_2::Glyco_hydro_2_C, TP_methylase, AP2::AP2, Histone, Response_reg::CCT, Histone_HNS, DUF1716, p450, GATA, Pkinase, Sugar_tr, Aa_trans, Pribosyltran, Ribosomal_L10e, HLH, PMSR, DnaJ::DnaJ_CXXCXGXG::DnaJ_C, DUF1005, Glyco_transf_5::Glycos_transf_1, Spermine_synth, S1::EIF_2_alpha, RGS, Na_sulph_symp, S1, MtN3_slv::MtN3_slv, Lactamase_B::Flavin_Reduct, LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase, Chloroa_b-bind, PTR2, Agglutinin, PLATZ, NPH3, Auxin_inducible, PTR2, GAF::HisKA::Response_reg, PsbQ, GSH_synth_ATP, GATase_2::Asn_synthase, PHP, FtsJ, DUF6::TPT, Proteasome, PsbW_2, Glyco_hydro_9, NAD_binding_2::6 PGD, S1::EIF_2_alpha, Homeobox::START::MEKHLA, S1, Isoamylase_N::Alpha-amylase, E2F_TDP, and Rieske::PaO, for which the databases are included in the appended computer listing.

As used herein "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions.

As used herein "operably linked" means the association of two or more DNA fragments in a DNA construct so that the function of one, e.g. protein-encoding DNA, is controlled by the other, e.g. a promoter.

As used herein "expressed" means produced, e.g. a protein is expressed in a plant cell when its cognate DNA is transcribed to mRNA that is translated to the protein.

As used herein a "control plant" means a plant that does not contain the recombinant DNA that expressed a protein that impart an enhanced trait. A control plant is to identify and select a transgenic plant that has an enhance trait. A suitable control plant can be a non-transgenic plant of the parental line used to generate a transgenic plant, i.e. devoid of recombinant DNA. A suitable control plant may in some cases be a progeny of a hemizygous transgenic plant line that is does not contain the recombinant DNA, known as a negative segregant.

As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil. In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre, tonnes per acre, tons per acre, kilo per hectare. For example, maize yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as tocopherol, protein and starch, or oil particular oil components as may be manifest by an alterations in the ratios of seed components.

A subset of the nucleic molecules of this invention includes fragments of the disclosed recombinant DNA consisting of oligonucleotides of at least 15, preferably at least 16 or 17, more preferably at least 18 or 19, and even more preferably at least 20 or more, consecutive nucleotides. Such oligonucleotides are fragments of the larger molecules having a sequence selected from the group consisting of SEQ ID NO:1 through SEQ ID NO: 298, and find use, for example as probes and primers for detection of the polynucleotides of the present invention.

In some embodiments of the invention a constitutively active mutant, e.g. SEQ ID NO: 203, is constructed to achieve the desired effect. In other embodiments of the invention, a dominant negative gene is constructed to adversely affect the normal, wild-type gene product within the same cell.

DNA constructs are assembled using methods well known to persons of ordinary skill in the art and typically comprise a promoter operably linked to DNA, the expression of which provides the enhanced agronomic trait. Other construct components may include additional regulatory elements, such as 5' leaders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as disclosed in U.S. Pat. Nos. 5,164,316 and 5,322,938. Useful promoters derived from plant genes are found in U.S. Pat. No. 5,641,876, which discloses a rice actin promoter, U.S. Pat. No. 7,151,204, which discloses a maize chloroplast aldolase promoter and a maize aldolase (FDA) promoter, and U.S. Patent Application Publication 2003/0131377 A1, which discloses a maize nicotianamine synthase promoter, all of which are incorporated herein by reference. These and numerous other promoters that function in plant cells are known to those skilled in the art and available for use in recombinant polynucleotides of the present invention to provide for expression of desired genes in transgenic plant cells.

In other aspects of the invention, preferential expression in plant green tissues is desired. Promoters of interest for such uses include those from genes such as *Arabidopsis thaliana* ribulose-1,5-bisphosphate carboxylase (Rubisco) small subunit (Fischhoff et al. (1992) *Plant Mol Biol*. 20:81-93), aldolase and pyruvate orthophosphate dikinase (PPDK) (Taniguchi et al. (2000) *Plant Cell Physiol*. 41(1): 42-48).

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects of the invention, sufficient expression in plant seed tissues is desired to affect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res*. 6(2):157-166), globulin 1 (Belanger et al (1991) *Genetics* 129:863-872), glutelin 1 (Russell (1997) supra), and peroxiredoxin antioxidant (Per1) (Stacy et al. (1996) *Plant Mol Biol*. 31(6):1205-1216).

Recombinant DNA constructs prepared in accordance with the invention will also generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1, 6-biphosphatase gene, a rice glutelin gene, a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3'), and 3' elements from the genes within the host plant.

Constructs and vectors may also include a transit peptide for targeting of a gene to a plant organelle, particularly to a chloroplast, leucoplast or other plastid organelle. For descriptions of the use of chloroplast transit peptides see U.S. Pat. Nos. 5,188,642 and 5,728,925, incorporated herein by reference. For description of the transit peptide region of an *Arabidopsis* EPSPS gene useful in the present invention, see Klee, H. J. et al (*MGG* (1987) 210:437-442).

Transgenic plants comprising or derived from plant cells of this invention transformed with recombinant DNA construct can be further enhanced with stacked traits, e.g. a crop plant having an enhanced trait resulting from expression of DNA disclosed herein in combination with herbicide and/or pest resistance traits. For example, genes of the current invention can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Patent Application publication 2003/0083480 A1 also for imparting glyphosate tolerance; dicamba monooxygenase disclosed in U.S. Patent Application publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in U.S. Patent Application Publication 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and U.S. Patent Application Publication 2002/0112260, all of said U.S. patents and patent application Publications are incorporated herein by reference. Molecules and methods for imparting insect/nematode/virus resistance are disclosed in U.S. Pat. Nos. 5,250,515; 5,880,275; 6,506,599; 5,986,175 and U.S. Patent Application Publication 2003/0150017 A1, all of which are incorporated herein by reference.

Plant Cell Transformation Methods

Numerous methods for transforming chromosomes in a plant cell nucleus with recombinant DNA are known in the art and are used in methods of preparing a transgenic plant cell nucleus cell, and plant. Two effective methods for such transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 6,384,301 (soybean), U.S. Pat. No. 7,026,528 (wheat) and U.S. Pat. No. 6,329,571 (rice), all of which are incorporated herein by reference. Transformation of plant material is practiced in tissue culture on a nutrient media, i.e. a mixture of nutrients that will allow cells to grow in vitro. Recipient cell targets include, but are not limited to, meristem cells, hypocotyls, calli, immature embryos and gametic cells such as microspores, pollen, sperm and egg cells. Callus may be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell nucleus can be prepared by crossing a first plant having cells with a transgenic nucleus with recombinant DNA with a second plant lacking the trangenci nucleus. For example, recombinant DNA can be introduced into a nucleus from a first plant line that is amenable to transformation to transgenic nucleus in cells that are grown into a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line In the practice of transformation DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047, all of which are incorporated herein by reference. Selectable markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue, and plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from the plant cells of this invention are grown to generate transgenic plants having an enhanced trait as compared to a control plant and produce transgenic seed and pollen of this invention. Such transgenic plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein have enhanced agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil.

Table 2 provides a list of protein encoding DNA ("genes") that are useful as DNA segment in a recombinant DNA construct for production of transgenic plants with enhanced agronomic trait, the elements of Table 2 are described by reference to:

"PEP SEQ ID NO" identifies an amino acid sequence from SEQ ID NO: 299 to 596.

"NUC SEQ ID NO" identifies a DNA sequence from SEQ ID NO:1 to 298.

"BV id" is a reference to the identifying number of base vectors in Table 3 used for construction of the transformation vectors of the recombinant DNA. Construction of plant transformation constructs is illustrated in Example 1.

"Gene Name" denotes a common name for protein encoded by the recombinant DNA.

"Annotation" refers to a description of the top hit protein obtained from an amino acid sequence query of each PEP SEQ ID NO to GenBank database of the National Center for Biotechnology Information (ncbi). More particularly, "gi" is the GenBank ID number for the top BLAST hit;

"% id" refers to the percentage of identically matched amino acid residues along the length of the portion of the sequences which is aligned by BLAST (–F T) between the sequence of interest provided herein and the hit sequence in GenBank.

TABLE 2

| NUC SEQ ID NO | PEP SEQ ID NO | Gene ID | BV ID | Gene Name | e-value | % id | GenBank ID | Annotation |
|---|---|---|---|---|---|---|---|---|
| 1 | 299 | PHE0007721_18998 | 21 | Corn Homeotic protein knotted-1 | 1.00E-152 | 77 | 123183 | gb|AAP76321.1| homeobox transcription factor KNOTTED1 [*Zea mays*] |
| 2 | 300 | PHE0007756_18009 | 33 | *Arabidopsis* 9-cis-epoxycarotenoid dioxygenase | 0 | 90 | 15231856 | dbj|BAB01336.1| 9-cis-epoxycarotenoid dioxygenase [*Arabidopsis thaliana*] |
| 3 | 301 | PHE0006007_18714 | 30 | *Arabidopsis* nodulin MtN21 family protein | 1.00E-105 | 86 | 79607902 | ref|NP_974371.2|unknown protein [*Arabidopsis thaliana*] |
| 4 | 302 | PHE0004988_15925 | 13 | *Arabidopsis* transport inhibitor response 1 | 0 | 100 | 18412567 | gb|AAN71945.1| transport inhibitor response TIR1, AtFBL1 protein [*Arabidopsis thaliana*] |
| 5 | 303 | PHE0007140_21771 | 30 | *Arabidopsis* nodulin MtN3 like protein-4 | 1.00E-121 | 92 | 18421965 | gb|AAM61405.1| MtN3 like [*Arabidopsis thaliana*] |
| 5 | 303 | PHE0007140_22049 | 13 | *Arabidopsis* nodulin MtN3 like protein-4 | 1.00E-121 | 92 | 18421965 | gb|AAM61405.1| MtN3 like [*Arabidopsis thaliana*] |
| 6 | 304 | PHE0006823_16403 | 13 | *Arabidopsis* class 2 non-symbiotic hemoglobin | 3.00E-85 | 100 | 15228313 | gb|AAM65188.1| Non symbiotic hemoglobin Hb2 [*Arabidopsis thaliana*] |
| 7 | 305 | PHE0007440_22555 | 18 | Corn putative GTP-binding protein Rab11 | 1.00E-107 | 91 | 115462975 | gb|AAS98506.1| GTP-binding protein Rab11 [*Oryza sativa* (japonica cultivar-group)] |
| 8 | 306 | PHE0000206_22432 | 9 | Corn CDPK kinase domain | 0 | 87 | 115450483 | sp|P53684|Calcium-dependent protein kinase, isoform 11 (CDPK 11) [*Oryza sativa* (japonica cultivar-group)] |
| 9 | 307 | PHE0000598_16824 | 9 | Corn B1 regulatory protein | 0 | 91 | 22195 | emb|CAA40544.1| regulatory protein [*Zea mays*] |
| 10 | 308 | PHE0007590_17883 | 8 | *E. coli* ribosomal protein S1 domain 3 | 7.00E-33 | 56 | 118740922 | ref|ZP_01588962.1| ribosomal protein S1 [*Enterobacter* sp. 638] |
| 11 | 309 | PHE0007588_17881 | 8 | *E. Coli* RNAse E S1 domain | 2.00E-45 | 98 | 52695516 | pdb|1SMX| the S1 domain of Rnase E from *E. Coli* (Native) |
| 12 | 310 | PHE0007592_17885 | 8 | Yeast pre-mRNA splicing factor RNA helicase S1 domain | 1.00E-40 | 98 | 6320850 | gb|AAB64546.1| pre-mRNA splicing factor RNA helicase [*Saccharomyces cerevisiae*] |
| 13 | 311 | PHE0007587_17880 | 8 | *E. coli* Polyribonucleotide nucleotidyltransferase | 7.00E-35 | 100 | 124525928 | ref|ZP_01697933.1| Polyribonucleotide nucleotidyltransferase [*Escherichia coli* B] |
| 14 | 312 | PHE0007624_17923 | 8 | *E. coli* translation initiation factor IF-1 | 8.00E-34 | 100 | 15800747 | ref|NP_286761.1| translation initiation factor IF-1 [*Escherichia coli* O157:H7 EDL933] |
| 15 | 313 | PHE0007591_17884 | 8 | *E. coli* ribosomal protein S1 domain 5 | 2.00E-20 | 51 | 118068082 | ref|ZP_01536336.1| ribosomal protein S1 [*Serratia proteamaculans* 568] |
| 16 | 314 | PHE0007623_17922 | 8 | *Arabidopsis* N-carbamoylputrescine amidohydrolase | 1.00E-172 | 100 | 18401429 | gb|AAM63266.1| putative nitrilase [*Arabidopsis thaliana*] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 17 | 315 | PHE0007583_17871 | 6 | Rice MtN3 homolog | 1.00E-130 | 100 | 125526770 | gb|EAY74884.1|hypothetical protein OsI_002731 [Oryza sativa (indica cultivar-group)] |
| 18 | 316 | PHE0006618_16146 | 13 | Corn putative ribosomal protein S10 | 4.00E-49 | 95 | 115442401 | dbj|BAB63622.1| putative 40S ribosomal protein S10 [Oryza sativa (japonica cultivar-group)] |
| 19 | 317 | PHE0006791_16374 | 9 | Arabidopsis GUN4_ARATH Tetrapyrrole-binding protein | 1.00E-120 | 83 | 15231674 | sp|Q9LX31|GUN4_ARATH Tetrapyrrole-binding protein, chloroplast precursor [Arabidopsis thaliana] |
| 20 | 318 | PHE0007620_17918 | 13 | Arabidopsis thylakoid ascorbate peroxidase | 0 | 96 | 15223971 | dbj|BAF01533.1| thylakoid-bound ascorbate peroxidase [Arabidopsis thaliana] |
| 21 | 319 | PHE0006659_16195 | 13 | Soy hypothetical protein | 1.00E-112 | 49 | 125540608 | gb|EAY87003.1|hypothetical protein OsI_008236 [Oryza sativa (indica cultivar-group)] |
| 22 | 320 | PHE0006662_16198 | 13 | Ralstonia metallidurans hypothetical protein | 1.00E-06 | 38 | 114582111 | ref|XP_001161638.1| hypothetical protein isoform 1 [Pan troglodytes] |
| 23 | 321 | PHE0006274_15867 | 13 | Corn Transcription factor E2Fb | 0 | 78 | 115487438 | gb|ABA96515.1| Transcription factor E2F[Oryza sativa (japonica cultivar-group)] |
| 24 | 322 | PHE0006637_16166 | 14 | Corn ABI1 homolog | 1.00E-145 | 78 | 115437928 | ref|NP_001043415.1 Os01g0583100 (Oryza sativa (japonica cultivar-group) |
| 25 | 323 | PHE0006926_16815 | 13 | Corn putative vacuolar protein sorting-associated protein | 1.00E-84 | 81 | 115440323 | dbj|BAB63580.1| putative vacuolar protein sorting 28 [Oryza sativa (japonica cultivar-group)] |
| 26 | 324 | PHE0006821_16402 | 13 | Corn 1-aminocyclopropane-1-carboxylate deaminase | 1.00E-176 | 79 | 115448975 | dbj|BAD16875.1| 1-aminocyclopropane-1-carboxylate deaminase [Oryza sativa (japonica cultivar-group)] |
| 27 | 325 | PHE0007687_18057 | 29 | Arabidopsis cytochrome P450 | 0 | 100 | 21536828 | gb|AAM61160.1| cytochrome P450 homolog (Arabidopsis thaliana) |
| 27 | 325 | PHE0007687_18200 | 13 | Arabidopsis cytochrome P450 | 0 | 100 | 21536828 | gb|AAM61160.1| cytochrome P450 homolog, [Arabidopsis thaliana] |
| 28 | 326 | PHE0007642_17999 | 29 | Arabidopsis Non-phototropic hypocotyl protein 1 | 0 | 94 | 15231245 | sp|O48963| Phototropin-1 (Root phototropism protein 1) [Arabidopsis thaliana] |
| 29 | 327 | PHE0007677_18052 | 29 | Arabidopsis oxidoreductase | 0 | 100 | 15239022 | ref|NP_196694.1|oxidoreductase [Arabidopsis thaliana] |
| 29 | 327 | PHE0007677_18179 | 13 | Arabidopsis oxidoreductase | 0 | 100 | 15239022 | ref|NP_196694.1|oxidoreductase [Arabidopsis thaliana] |
| 30 | 328 | PHE0007644_18001 | 29 | Arabidopsis receptor protein kinase | 0 | 88 | 15220455 | ref|NP_176918.1| protein serine/threonine kinase [Arabidopsis thaliana] |
| 30 | 328 | PHE0007644_18169 | 13 | Arabidopsis receptor protein kinase | 0 | 88 | 15220455 | ref|NP_176918.1| protein serine/threonine kinase [Arabidopsis thaliana] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 31 | 329 | PHE0007640_17992 | 29 | Soy magnesium transporter mrs2-1-like | 1.00E-165 | 80 | 92889086 | gb|ABE89684.1| Mg2+ transporter protein, CorA-like [Medicago truncatula] |
| 32 | 330 | PHE0007678_18053 | 29 | Arabidopsis acyl-CoA thioesterase | 1.00E-107 | 100 | 18399594 | ref|NP_564457.1| acyl-CoA thioesterase [Arabidopsis thaliana] |
| 32 | 330 | PHE0007678_18180 | 13 | Arabidopsis acyl-CoA thioesterase | 1.00E-107 | 100 | 18399594 | ref|NP_564457.1| acyl-CoA thioesterase [Arabidopsis thaliana] |
| 33 | 331 | PHE0007649_18006 | 29 | Arabidopsis putative ankyrin protein kinase | 0 | 99 | 42566072 | ref|NP_191542.2| protein kinase/threonine kinase/protein-tyrosine kinase [Arabidopsis thaliana] |
| 34 | 332 | PHE0006726_16298 | 25 | Arabidopsis putative ARP2/3 protein complex subunit p41 | 0 | 97 | 15224586 | gb|AAC20725.1| putative ARP2/3 protein complex subunit p41 [Arabidopsis thaliana] |
| 35 | 333 | PHE0006218_8776 | 25 | Arabidopsis thioredoxin-disulfide reductase | 0 | 85 | 18405775 | ref|NP_565954.1| disulfide oxidoreductase/thioredoxin-disulfide reductase (Arabidopsis thaliana) |
| 36 | 334 | PHE0006657_16192 | 13 | Corn putative ATP-binding protein | 2.00E-83 | 71 | 115462871 | gb|AAV31386.1| putative ATP-binding protein [Oryza sativa (japonica cultivar-group)] |
| 37 | 335 | PHE0002554_17876 | 13 | Corn Chlorophyll a/b-binding protein CP29 precursor | 1.00E-158 | 95 | 2326947 | emb|CAA90681.1| Chlorophyll a/b-binding protein CP29 precursor [Zea mays] |
| 37 | 335 | PHE0002554_23104 | 9 | Corn Chlorophyll a/b-binding protein CP29 precursor | 1.00E-158 | 95 | 2326947 | emb|CAA90681.1| Chlorophyll a/b-binding protein CP29 precursor [Zea mays] |
| 38 | 336 | PHE0006807_16388 | 13 | Corn transcription factor APRR9 like | 1.00E-140 | 64 | 115484281 | gb|ABG22372.1| CCT motif family protein (Oryza sativa (japonica cultivar-group)] |
| 39 | 337 | PHE0003359_8487 | 9 | Corn dw f4-like protein | 0 | 86 | 60677681 | dbj|BAD90972.1| cytochrome P450 [Oryza sativa (japonica cultivar-group)] |
| 40 | 338 | PHE0006542_15785 | 9 | Arabidopsis methionine sulfoxide reductase | 1.00E-149 | 100 | 15234942 | ref|NP_194243.1| protein-methionine-S-oxide reductase [Arabidopsis thaliana] |
| 41 | 339 | PHE0007622_17921 | 8 | Arabidopsis spermine synthase | 0 | 100 | 18419941 | gb|AAF01311.1| spermine synthase [Arabidopsis thaliana] |
| 42 | 340 | PHE0007630_17956 | 3 | Corn GA3ox1 | 1.00E-151 | 75 | 125544881 | gb|EAY91020.1| hypothetical protein OsL_012253 [Oryza sativa (indica cultivar-group)] |
| 43 | 341 | PHE0007593_17886 | 8 | Corn spermidine synthase | 1.00E-169 | 92 | 115471679 | dbj|BAD30581.1| spermidine synthase 1 [Oryza sativa (japonica cultivar-group)] |
| 44 | 342 | PHE0006475_15588 | 9 | Arabidopsis PsbQ_like | 9.00E-89 | 100 | 42571459 | ref|NP_973820.1| calcium ion binding (Arabidopsis thaliana) |
| 45 | 343 | PHE0007619_17915 | 13 | Soy methyl-CpG-binding domain-containing protein | 1.00E-44 | 43 | 18394229 | ref|NP_563971.1| MBD10; DNA binding [Arabidopsis thaliana] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 46 | 344 | PHE0006846_16447 | 13 | Soy cuticle protein | 0 | 70 | 9758349 | dbj|BAB08850.1| lipid transfer protein; glossy1 homolog [Arabidopsis thaliana] |
| 47 | 345 | PHE0007584_17874 | 13 | Arabidopsis methyl-CpG-binding domain-containing protein | 1.00E-124 | 65 | 18394229 | ref|NP_563971.1| MBD10; DNA binding [Arabidopsis thaliana] |
| 48 | 346 | PHE0003695_17913 | 17 | Arabidopsis Erecta | 0 | 95 | 15225286 | gb|AAC49302.1| ERECTA, receptor protein kinase [Arabidopsis thaliana] |
| 48 | 346 | PHE0011554_23650 | 32 | Arabidopsis Erecta | 0 | 95 | 15225286 | gb|AAC49302.1| ERECTA, receptor protein kinase [Arabidopsis thaliana] |
| 49 | 347 | PHE0003695_17879 | 8 | Arabidopsis Erecta | 0 | 95 | 15225286 | gb|AAK59615.1| receptor protein kinase, ERECTA [Arabidopsis thaliana] |
| 49 | 347 | PHE0003695_23448 | 22 | Arabidopsis Erecta | 0 | 95 | 15225286 | gb|AAK59615.1| receptor protein kinase, ERECTA [Arabidopsis thaliana] |
| 50 | 348 | PHE0006936_16828 | 29 | Soy GNS1/SUR4 membrane protein | 2.00E-91 | 66 | 92868497 | gb|ABE78502.1|GNS1/SUR4 membrane protein [Medicago truncatula] |
| 51 | 349 | PHE0007645_18002 | 29 | Soy DNA binding protein | 2.00E-26 | 32 | 21617964 | gb|AAM67014.1| DNA binding protein-like [Arabidopsis thaliana] |
| 52 | 350 | PHE0006784_16366 | 6 | Corn cysteine synthase | 1.00E-165 | 93 | 2829688 | emb|CAA59798.1| O-acetylserine (thiol) lyase; cysteine synthase [Zea mays] |
| 53 | 351 | PHE0006171_16491 | 13 | Sorghum bicolor Glyoxalase | 6.00E-91 | 86 | 115463027 | ref|NP_001055113.1|Os05g0295800 [Oryza sativa (japonica cultivar-group)] |
| 54 | 352 | PHE0006868_16682 | 13 | Arabidopsis ME01451 | 3.00E-05 | 100 | 21592593 | gb|AAM64542.1| unknown [Arabidopsis thaliana] |
| 55 | 353 | PHE0006906_16796 | 13 | Corn 20S proteasome subunit beta-6 | 1.00E-121 | 96 | 115480019 | dbj|BAA28276.1| beta 6 subunit of 20S proteasome [Oryza sativa (japonica cultivar-group)] |
| 56 | 354 | PHE0006649_16180 | 13 | Wheat putative DRE binding factor 2 | 5.00E-62 | 64 | 60547461 | gb|AAX23704.1|HvCBF7 [Hordeum vulgare subsp. vulgare] |
| 57 | 355 | PHE0006809_16390 | 13 | E. coli hydroxylamine reductase | 0 | 97 | 89107724 | ref|NP_415394.4| hydroxylamine reductase [Escherichia coli K12] |
| 58 | 356 | PHE0006918_16808 | 13 | Corn putative dihydropyrimidine dehydrogenase | 0 | 82 | 125571037 | gb|EAZ12552.1|hypothetical protein OsJ_002377 [Oryza sativa (japonica cultivar-group)] |
| 59 | 357 | PHE0007813_18219 | 6 | Rice MtN3 homolog | 1.00E-119 | 86 | 115445683 | dbj|BAD23335.1| putative NEC1 [Oryza sativa (japonica cultivar-group)] |
| 60 | 358 | PHE0007650_18175 | 13 | Arabidopsis Kin17 protein | 0 | 83 | 18405389 | AAD10649.1| Kin17 protein [Arabidopsis thaliana] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 61 | 359 | PHE0006825_16405 | 13 | E. coli cytochrome c nitrite reductase | 0 | 100 | 15834306 | ref|ZP_01699144.1| Nitrite reductase [Escherichia coli B] |
| 62 | 360 | PHE0006964_16864 | 9 | Corn asparaginyl-tRNA synthetase | 0 | 84 | 115436616 | dbj|BAB61140.1| putative asparagine-tRNA ligase [Oryza sativa (japonica cultivar-group)] |
| 62 | 360 | PHE0006964_16865 | 13 | Corn asparaginyl-tRNA synthetase | 0 | 84 | 115436616 | dbj|BAB61140.1| putative asparagine-tRNA ligase [Oryza sativa (japonica cultivar-group)] |
| 63 | 361 | PHE0008105_18407 | 13 | Yeast transcriptional activator HAP5 | 1.00E-116 | 88 | 6324934 | sp|Q02516| Transcriptional activator HAP5 [Saccharomyces cerevisiae] |
| 63 | 361 | PHE0008105_18733 | 30 | Yeast transcriptional activator HAP5 | 1.00E-116 | 88 | 6324934 | sp|Q02516| Transcriptional activator HAP5 [Saccharomyces cerevisiae] |
| 64 | 362 | PHE0006630_16159 | 13 | Corn malate dehydrogenase | 0 | 92 | 126888 | sp|P15719| MDHP_maize Malate dehydrogenase [NADP] |
| 65 | 363 | PHE0006966_16868 | 29 | Arabidopsis Cryptochrome 1 | 0 | 95 | 18413170 | ref|NP_567341.1|Cryptochrome 1 [Arabidopsis thaliana] |
| 66 | 364 | PHE0008698_24421 | 3 | Corn expressed protein | 9.00E-06 | 38 | 115484935 | gb|AAX96767.1| expressed protein [Oryza sativa (japonica cultivar-group)] |
| 67 | 365 | PHE0006608_16123 | 25 | Soy glutathione peroxidase | 2.00E-82 | 90 | 21068666 | emb|CAD31839.1|putative phospholipid hydroperoxide glutathione peroxidase [Cicer arietinum] |
| 68 | 366 | PHE0010462_21459 | na | Deinococcus radiodurans nudixhydrolase | 1.00E-155 | 86 | 15805358 | ref|NP_294052.1|MutT/nudix family protein [Deinococcus radiodurans R1] |
| 69 | 367 | PHE0009211_21774 | 30 | Arabidopsis PF02519-auxin inducible-3 | 5.00E-50 | 89 | 15236198 | ref|NP_195205.1|unknown protein [Arabidopsis thaliana] |
| 70 | 368 | PHE0006256_8775 | 27 | Arabidopsis 9-cis-epoxycarotenoid dioxygenase | 0 | 92 | 15231856 | dbj|BAB01336.1| 9-cis-epoxycarotenoid dioxygenase [Arabidopsis thaliana] |
| 71 | 369 | PHE0006989_16918 | 29 | Arabidopsis putative protein kinase | 0 | 79 | 15231840 | dbj|BAB01042.1| protein kinase [Arabidopsis thaliana] |
| 72 | 370 | PHE0007649_18166 | 13 | Arabidopsis putative ankyrin protein kinase | 0 | 100 | 42566072 | ref|NP_191542.2| protein kinase/serine/threonine kinase/tyrosine kinase [Arabidopsis thaliana] |
| 73 | 371 | PHE0006708_16264 | 29 | Soy DNA helicase 45 | 0 | 89 | 3097266 | emb|CAA76677.1| translation initiation factor [Pisum sativum] |
| 74 | 372 | PHE0001117_19094 | 4 | Corn transcription factor G1543-like | 1.00E-101 | 84 | 125527033 | gb|EAY75147.1|hypothetical protein OsI_002994 [Oryza sativa (indica cultivar-group)] |
| 74 | 372 | PHE0001117_19095 | 9 | Corn transcription factor G1543-like | 1.00E-101 | 84 | 125527033 | gb|EAY75147.1|hypothetical protein OsI_002994 [Oryza sativa (indica cultivar-group)] |
| 75 | 373 | PHE0006266_8814 | 9 | Corn phytochromobilin synthase | 1.00E-164 | 100 | 49472889 | gb|AAT66259.1| phytochromobilin synthase [Zea mays] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 75 | 373 | PHE0006266_15483 | 4 | corn phytochromobilin synthase | 1.00E-164 | 100 | 49472889 | gb|AAT66259.1| phytochromobilin synthase [Zea mays] |
| 76 | 374 | PHE0006795_16378 | 13 | E. coli pH-dependent sodium/proton antiporter | 1.00E-172 | 82 | 16128013 | ref|NP_414560.1| pH-dependent sodium/proton antiporter [Escherichia coli K12] |
| 77 | 375 | PHE0006956_16853 | 13 | Agrobacterium nitrate reductase | 0 | 98 | 15891062 | ref|NP_356734.1|hypothetical protein AGR_L_1895 [Agrobacterium tumefaciens str. C58] |
| 78 | 376 | PHE0006859_16873 | 9 | Corn bHLH protein family | 2.00E-31 | 92 | 115451023 | gb|EAZ25749.1| hypothetical protein OsJ_009232 [Oryza sativa (japonica cultivar-group)] |
| 79 | 377 | PHE0006824_16404 | 13 | Corn Nonlegume hemoglobin-like | 6.00E-86 | 98 | 3913789 | gb|AAA19576.1| haemoglobin apoprotein [Hordeum vulgare] |
| 80 | 378 | PHE0006812_16393 | 13 | Nostoc 2-on-2 hemoglobin | 1.00E-61 | 100 | 23130505 | ref|ZP_00112318.1| Truncated hemoglobins (Nostoc punctiforme PCC 73102) |
| 81 | 379 | PHE0006815_16396 | 13 | Rice Trb-like | 2.00E-98 | 100 | 115468746 | dbj|BAD32857.1| putative 2-on-2 hemoglobin [Oryza sativa (japonica cultivar-group)] |
| 82 | 380 | PHE0006806_16387 | 13 | Corn Trb-like | 7.00E-80 | 83 | 14165165 | gb|AAK55410.1|AF376063_12-on-2 hemoglobin [Hordeum vulgare] |
| 83 | 381 | PHE0006624_16153 | 13 | Corn putative cytosolic 6-phosphogluconate dehydrogenase | 0 | 98 | 3342802 | gb|AAC27703.1| putative cytosolic 6-phosphogluconate dehydrogenase [Zea mays] |
| 84 | 382 | PHE0005006_15823 | 13 | Corn chlorophyll a/b-binding apoprotein CP24 precursor | 1.00E-112 | 80 | 115458738 | gb|EAY94374.1| hypothetical protein OsI_015607 [Oryza sativa (indica cultivar-group)] |
| 85 | 383 | PHE0003991_16771 | 13 | Corn AfMONFEED000559 Protamine P1 | — | — | — | — |
| 86 | 384 | PHE0006683_16229 | 13 | Corn response regulator 4 | 1.00E-102 | 85 | 12060384 | dbj|BAB20579.1| response regulator 4 [Zea mays] |
| 87 | 385 | PHE0006884_16703 | 7 | Corn granule-bound starch synthase precursor | 0 | 89 | 33321047 | gb|AAQ06291.1| granule-bound starch synthase precursor [Zea mays] |
| 88 | 386 | PHE0006691_16237 | 3 | E. coli NAD(P)H-dependent glycerol-3-phosphate dehydrogenase | 0 | 100 | 15804152 | ref|NP_290191.1| NAD(PH-dependent glycerol-3-phosphate dehydrogenase [Escherichia coli O157:H7 EDL933] |
| 89 | 387 | PHE0006790_16372 | 9 | Arabidopsis chlorophyll A oxygenase | 0 | 95 | 15219408 | ref|NP_175088.1| chlorophyll a oxygenase [Arabidopsis thaliana] |
| 90 | 388 | PHE0009143_19932 | 30 | E. coli StpA | 2.00E-57 | 86 | 83569970 | ref|ZP_00921418.1| DNA-binding protein H-NS [Shigella dysenteriae 1012] |
| 91 | 389 | PHE0008406_18830 | 30 | Yeast general amino acid permease | 0 | 98 | 14318464 | sp|P43548| Yeast general amino acid permease AGP3 |
| 92 | 390 | PHE0008279_18708 | 30 | Corn hypothetical protein | 5.00E-25 | 73 | 115462095 | gb|EAY96551.1| hypothetical protein OsI_017784 [Oryza sativa (indica cultivar-group)] |
| 93 | 391 | PHE0009142_19931 | 30 | E. coli DNA-binding protein H-NS | 3.00E-45 | 72 | 15801465 | ref|NP_415753.1| global DNA-binding transcriptional dual |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 94 | 392 | PHE0008308_18841 | 30 | Corn hypothetical protein | 5.00E-41 | 89 | 125537055 | gb\|EAY83543.1\| hypothetical protein OsI_037502 [Oryza sativa (indica cultivar group)] |
| 95 | 393 | PHE0007639_17991 | 29 | Chlorella optimized beta glutamate dehydrogenase | 0 | 99 | 118546 | emb\|CAA41636.1\| glutamate dehydrogenase (NADP+) [Chlorella sorokiniana] |
| 96 | 394 | PHE0007646_18170 | 13 | Arabidopsis kelch repeat-containing F-box family protein | 0 | 94 | 116831441 | gb\|ABK28673.1\| unknown [Arabidopsis thaliana] |
| 97 | 395 | PHE0007765_18182 | 13 | Arabidopsis glutathione transferase | 1.00E-130 | 100 | 15218872 | ref\|NP_176178.1\| glutathione transferase [Arabidopsis thaliana] |
| 98 | 396 | PHE0008167_18465 | 5 | Arabidopsis protein kinase | 1.00E-163 | 95 | 15233846 | ref\|NP_194179.1\| protein kinase/serine/threonine kinase/protein-tyrosine kinase [Arabidopsis thaliana] |
| 99 | 397 | PHE0008172_18471 | 5 | Arabidopsis putative thioredoxin H | 2.00E-46 | 97 | 4895214 | gb\|AAD32800.1\| putative thioredoxin H [Arabidopsis thaliana] |
| 100 | 398 | PHE0008183_18479 | 5 | Arabidopsis receptor protein kinase | 0 | 98 | 15239123 | ref\|NP_201371.1\| protein serine/threonine kinase [Arabidopsis thaliana] |
| 101 | 399 | PHE0007585_17875 | 6 | Arabidopsis drought-induced protein (Di21) | 2.00E-42 | 87 | 469112 | emb\|CAA55322.1\| Di21 [Arabidopsis thaliana] |
| 101 | 399 | PHE0007585_23902 | 30 | Arabidopsis drought-induced protein (Di21) | 2.00E-42 | 87 | 469112 | emb\|CAA55322.1\| Di21 [Arabidopsis thaliana] |
| 102 | 400 | PHE0006804_16385 | 6 | Rice small subunit of U2 snRNP auxiliary factor | 1.00E-107 | 100 | 125553324 | gb\|EAY99033.1\| hypothetical protein OsI_020266 [Oryza sativa (indica cultivar-group)] |
| 103 | 401 | PHE0006703_15751 | 15 | Lactobacillus ATP-dependent phosphofructokinase with ctp | 1.00E-164 | 92 | 104773899 | ref\|YP_618879.1\| 6-phosphofructokinase [Lactobacillus delbrueckii subsp. bulgaricus ATCC 11842] |
| 104 | 402 | PHE0007410_17653 | 3 | Umbelopsis glycerol-3-phosphate O-acyltransferase | 1.00E-144 | 42 | 58264662 | ref\|XP_569487.1\| glycerol-3-phosphate O-acyltransferase [Cryptococcus neoformans var. neoformans JEC21] |
| 105 | 403 | PHE0006854_16456 | 2 | Corn kernel specific yabby | 1.00E-115 | 71 | 32330681 | gb\|AAP79887.1\| yabby10 protein [Zea mays] |
| 106 | 404 | PHE0007721_21293 | 19 | Corn homeobox transcription factor KNOTTED1 | 1.00E-152 | 77 | 123183 | gb\|AAP76321.1\| homeobox transcription factor KNOTTED1 [Zea mays] |
| 107 | 405 | PHE0006563_15990 | 13 | Wheat glutamine-dependent asparagine synthetase | 0 | 97 | 53680379 | gb\|AAU89392.1\| glutamine-dependent asparagine synthetase [Triticum aestivum] |
| 107 | 405 | PHE0006563_16140 | 9 | Wheat glutamine-dependent asparagine synthetase | 0 | 97 | 53680379 | gb\|AAU89392.1\| glutamine-dependent asparagine synthetase [Triticum aestivum] |
| 108 | 406 | PHE0006619_16147 | 13 | Corn Delta 1-pyrroline-5- | 0 | 84 | 2081612 | dbj\|BAA19916.1\| delta-pyrroline-5-carboxylate |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 109 | 407 | PHE0006813_16394 | 13 | carboxylate synthetase | 1.00E-67 | 93 | 16078221 | synthetase [Oryza sativa (japonica cultivar-group)] sp|O31607| Hemoglobin-like protein yjbI (Truncated BHb (trHbHb) [Bacillus Subtilis] |
| 110 | 408 | PHE0006688_16234 | 13 | Bacillus subtilis Hemoglobin-like protein TrHb | 1.00E-131 | 99 | 11467185 | sp|P16037| maize Chloroplast 30S ribosomal protein S2 |
| 111 | 409 | PHE0006635_16164 | 13 | Corn ribosomal protein S2 | 9.00E-86 | 100 | 15800822 | ref|NP_286838.1|methylglyoxal synthase [Escherichia coli O157:H7 EDL933] |
| 112 | 410 | PHE0008340_19155 | 30 | E. coli methylglyoxal synthase | 1.00E-178 | 78 | 92896427 | gb|ABE93200.1| conserved hypothetical protein [Medicago truncatula] |
| 113 | 411 | PHE0008416_18838 | 30 | Soy hypothetical protein | 0 | 58 | 115480880 | ref|NP_001064033.1|Os10g0110600 [Oryza sativa (japonica cultivar-group)] |
| 114 | 412 | PHE0008422_18842 | 30 | Corn putative oligopeptide transporter | 1.00E-121 | 55 | 115448163 | dbj|BAD08083.1| unknown protein (Oryza sativa (japonica cultivar-group)] |
| 115 | 413 | PHE0008599_19166 | 30 | Corn unknown protein | 0 | 95 | 16330244 | ref|NP_440972.1| glycogen operon protein; GlgX [Synechocystis sp. PCC 6803] |
| 116 | 414 | PHE0008375_18732 | 30 | Synechocystis glycogen operon protein | 6.00E-95 | 99 | 16077136 | sp|P37472| Hypoxanthine-guanine phosphoribosyl-transferase (HGPRTase) [Bacillus subtilis] |
| 117 | 415 | PHE0006712_16273 | 27 | Bacillus hypoxanthine-guanine phosphoribosyl transferase | 4.00E-92 | 100 | 15237778 | ref|NP_200700.1| unknown protein [Arabidopsis thaliana] |
| 117 | 415 | PHE0006712_16362 | 13 | Arabidopsis unknown function | 4.00E-92 | 100 | 15237778 | ref|NP_200700.1| unknown protein [Arabidopsis thaliana] |
| 117 | 415 | PHE0006712_16363 | 9 | Arabidopsis unknown function | 4.00E-92 | 100 | 15237778 | ref|NP_200700.1| unknown protein [Arabidopsis thaliana] |
| 117 | 415 | PHE0006712_16364 | 6 | Arabidopsis unknown function | 4.00E-92 | 100 | 15237778 | ref|NP_200700.1| unknown protein [Arabidopsis thaliana] |
| 118 | 416 | PHE0008394_18763 | 9 | Corn altered glutamine synthetase | 0 | 97 | 121341 | sp|P25462| Glutamine synthetase (Glutamate--ammonia ligase) (GS2) [Zea mays] |
| 119 | 417 | PHE0008395_18764 | 9 | Corn altered glutamine synthetase | 0 | 97 | 121341 | sp|P25462| Glutamine synthetase (Glutamate--ammonia ligase) (GS2) [Zea mays] |
| 120 | 418 | PHE0008444_18846 | 3 | Corn glutamine synthetase1 | 0 | 100 | 112490284 | dbj|BAA03430.1| glutamine synthetase [Zea mays] |
| 121 | 419 | PHE0006819_16400 | 13 | Synechocystis A-type flavoproteins | 0 | 100 | 16331685 | sp|Q55393| Diflavin flavoprotein A 1 (SsATF573) (NADH:oxygen oxidoreductase) [Synechocystis sp. PCC 6803] |
| 122 | 420 | PHE0007417_17663 | 15 | Corn EIL1 | 0 | 76 | 125543684 | gb|EAY89823.1| hypothetical protein OsI_011056 [Oryza sativa (indica cultivar-group)] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 123 | 421 | PHE0008443_18845 | 13 | Barley asparagine synthetase1 | 0 | 97 | 13925886 | gb|AAK49456.1| glutamine-dependent asparagine synthetase 1 [*Hordeum vulgare* subsp. *vulgare*] |
| 124 | 422 | PHE0006818_16399 | 13 | *E. coli* flavorubredoxin | 0 | 100 | 16130617 | ref|AP003277.1|flavorubredoxin oxidoreductase [*Escherichia coli* W3110] |
| 125 | 423 | PHE0006579_16031 | 13 | Corn thiazole biosynthetic enzyme | 0 | 97 | 2501189 | sp|Q41738| Thiazole biosynthetic enzyme 1-1, chloroplast precursor [*Zea mays*] |
| 126 | 424 | PHE0006808_16389 | 13 | Rice transcription factor APRR9 like | 0 | 97 | 115484281 | gb|ABG22372.1| CCT motif family protein [*Oryza sativa (japonica cultivar-group)*] |
| 127 | 425 | PHE0008160_18460 | 5 | *Arabidopsis* pyruvate decarboxylase | 0 | 100 | 15234062 | ref|NP_195033.1| pyruvate decarboxylase [*Arabidopsis thaliana*] |
| 128 | 426 | PHE0007571_17834 | 24 | Soy homoglutathione synthetase | 0 | 97 | 7799808 | emb|CAB91078.1| homoglutathione synthetase [*Glycine max*] |
| 129 | 427 | PHE0007586_17877 | 13 | *Arabidopsis* Chlorophyll a-b binding protein | 1.00E-151 | 96 | 15225630 | gb|AAD32843.1| putative chlorophyll a/b binding protein [*Arabidopsis thaliana*] |
| 130 | 428 | PHE0006969_16871 | 13 | Rice hypothetical protein | 4.00E-34 | 100 | 115451023 | gb|EAZ25749.1| hypothetical protein OsI_009232 [*Oryza sativa (japonica cultivar-group)*] |
| 131 | 429 | PHE0009729_21717 | 13 | *Arabidopsis* bHLH | 1.00E-91 | 89 | 30698765 | gb|AAO64014.1| putative homeodomain leucine zipper protein [*Arabidopsis thaliana*] |
| 132 | 430 | PHE0006424_15520 | 9 | photosystem II reaction center 6.1 KD protein | 3.00E-37 | 75 | 15224531 | gb|AAM64951.1| photosystem II reaction center 6.1 KD protein [*Arabidopsis thaliana*] |
| 133 | 431 | PHE0006392_15480 | 9 | Corn PsbP | 9.00E-99 | 84 | 115489108 | gb|ABA98969.2| Thylakoid lumenal 21.5 kDa protein [*Oryza sativa (japonica cultivar-group)*] |
| 134 | 432 | PHE0006589_16093 | 13 | *Arabidopsis* thioredoxin-like protein | 3.00E-84 | 100 | 42563272 | dbj|BAE99426.1| thioredoxin-like protein [*Arabidopsis thaliana*] |
| 135 | 433 | PHE0009258_21487 | 16 | *Arabidopsis* sodium proton exchanger1 | 0 | 87 | 15240448 | ref|NP_198067.1|NHX1 (NA+/H+ EXCHANGER); sodium:hydrogen antiporter [*Arabidopsis thaliana*] |
| 135 | 433 | PHE0009258_20132 | 34 | *Arabidopsis* sodium proton exchanger1 | 0 | 87 | 15240448 | ref|NP_198067.1|NHX1 (NA+/H+ EXCHANGER); sodium:hydrogen antiporter [*Arabidopsis thaliana*] |
| 136 | 434 | PHE0006680_16226 | 13 | Corn flavanone 3-hydroxylase | 1.00E-161 | 81 | 18057095 | gb|AAL58118.1| putative flavanone 3-hydroxylase [*Oryza sativa (japonica cultivar-group)*] |

TABLE 2-continued

| NUC SEQ ID NO | PEP SEQ ID NO | Gene ID | BV ID NO | Gene Name | e-value | % id | GenBank ID | Annotation |
|---|---|---|---|---|---|---|---|---|
| 137 | 435 | PHE0006481_16072 | 13 | Corn Os09g0570300 homolog | 1.00E−145 | 81 | 115480783 | ref|NP_001063985.1|Os09g0570300 [Oryza sativa (japonica cultivar-group)] |
| 138 | 436 | PHE0006269_8820 | 23 | Synechocystis conserved tetratricopeptide repeat protein | 0 | 96 | 16329708 | ref|NP_440436.1|hypothetical protein slr2048 [Synechocystis sp. PCC 6803] |
| 138 | 436 | PHE0006269_8821 | 9 | Synechocystis conserved tetratricopeptide repeat protein | 0 | 96 | 16329708 | ref|NP_440436.1|hypothetical protein slr2048 [Synechocystis sp. PCC 6803] |
| 139 | 437 | PHE0006783_16365 | 11 | Brassica napus amino acid permease 6 | 0 | 97 | 31455393 | emb|CAD92450.1|amino acid permease 6 [Brassica napus] |
| 140 | 438 | PHE0003151_18392 | 28 | Soy aintegumenta 2 | 1.00E−141 | 47 | 38492172 | gb|AAR22388.1| ANT-like protein [Nicotiana tabacum] |
| 141 | 439 | PHE0008272_18723 | 30 | Arabidopsis heat shock factor protein 5 | 0 | 88 | 15220611 | sp|Q9S7U5| Heat shock transcription factor 5) (HSTF 5) [Arabidopsis thaliana] |
| 142 | 440 | PHE0008277_18706 | 30 | Yeast chromatin structure remodeling complex protein SFH1 | 0 | 95 | 6323354 | sp|Q06168| Chromatin structure remodeling complex protein SFH1 [Saccharomyces cerevisiae] |
| 143 | 441 | PHE0008109_18411 | 30 | Yeast uncharacterized protein YOR154W precursor | 0 | 93 | 6324728 | sp|Q12232| Yeast uncharacterized protein YOR154W precursor |
| 143 | 441 | PHE0008109_18568 | 13 | Yeast uncharacterized protein YOR154W precursor | 0 | 93 | 6324728 | sp|Q12232| Yeast uncharacterized protein YOR154W precursor |
| 144 | 442 | PHE0008280_18826 | 30 | Sinorhizobium putative trehalose synthase | 0 | 93 | 16263847 | ref|NP_436639.1| putative trehalose synthase protein [Sinorhizobium meliloti 1021] |
| 145 | 443 | PHE0002424_15825 | 13 | Corn NADPH:protochlorophyllide oxidoreductase A | 1.00E−140 | 77 | 90398977 | gb|EAY96061.1| hypothetical protein OsI_017294 [Oryza sativa (indica cultivar group)] |
| 146 | 444 | PHE0006914_16804 | 13 | Corn 26S protease regulatory subunit 7 | 0 | 100 | 115466876 | dbj|BAD35266.1| 26S protease regulatory subunit 7 [Oryza sativa (japonica cultivar-group)] |
| 147 | 445 | PHE0006642_16172 | 14 | Rice ent-kaurene oxidase | 0 | 97 | 115468620 | dbj|BAD54598.1| ent-kaurene oxidase [Oryza sativa (japonica cultivar-group)] |
| 148 | 446 | PHE0007578_17852 | 29 | Arabidopsis unknown protein | 2.00E−71 | 100 | 18395285 | ref|NP_564202.1|unknown protein [Arabidopsis thaliana] |
| 149 | 447 | PHE0009926_21079 | 30 | Arabidopsis putative dual-specificity protein phosphatase | 1.00E−84 | 100 | 18397475 | gb|AAM62982.1| putative dual specificity protein phosphatase [Arabidopsis thaliana] |
| 150 | 448 | PHE0006206_19159 | 30 | Arabidopsis ubiquitin ligase SINAT5 | 0 | 97 | 15234306 | ref|NP_194517.1| ubiquitin-protein ligase/zinc ion binding [Arabidopsis thaliana] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 151 | 449 | PHE0008274_18705 | 30 | *Arabidopsis* putative BURP domain containing protein | 1.00E-154 | 95 | 15222103 | gb|AAD43166.1| Putative BURP domain containing protein [*Arabidopsis thaliana*] |
| 152 | 450 | PHE0009510_20526 | 30 | *Cucurbita* spermidine synthase | 1.00E-164 | 89 | 49425361 | gb|AAT66041.1| spermidine synthase [*Cucumis sativus*] |
| 153 | 451 | PHE0009937_21097 | 34 | *Cucurbita* spermidine synthase | 1.00E-164 | 89 | 49425361 | gb|AAT66041.1| spermidine synthase [*Cucumis sativus*] |
| 154 | 452 | PHE0009927_21080 | 30 | *Brassica* putative dual-specificity protein phosphatase | 4.00E-79 | 88 | 30679726 | dbj|BAC42108.1| putative dual-specificity protein phosphatase [*Arabidopsis thaliana*] |
| 155 | 453 | PHE0006460_15962 | 13 | *Arabidopsis* unknown protein | 0 | 86 | 18394658 | ref|NP_564064.1|unknown protein [*Arabidopsis thaliana*] |
| 156 | 454 | PHE0006445_15956 | 13 | *Arabidopsis* allene oxide cyclase | 1.00E-142 | 100 | 18404656 | emb|CAC83762.1| allene oxide cyclase [*Arabidopsis thaliana*] |
| 157 | 455 | PHE0006987_16893 | 13 | *Arabidopsis* calcineurin B-like protein 2 | 1.00E-125 | 99 | 15241101 | dbj|BAB09281.1| calcineurin B-like protein 2 [*Arabidopsis thaliana*] |
| 158 | 456 | PHE0004230_15865 | 13 | Corn E2F3 like | 0 | 72 | 115446539 | dbj|BAD73815.1| putative E2F homolog [*Oryza sativa (japonica cultivar-group)*] |
| 159 | 457 | PHE0006814_16395 | 13 | *Arabidopsis* 2-on-2 hemoglobin | 2.00E-99 | 100 | 18418064 | dbj|BAD42999.1| 2-on-2 hemoglobin (GLB3) [*Arabidopsis thaliana*] |
| 160 | 458 | PHE0002773_15881 | 13 | Rice glucose-1-phosphate adenylyltransferase large subunit 1 | 0 | 100 | 115465649 | ref|NP_001056424.1|Os05g0580000 [*Oryza sativa (japonica cultivar-group)*] |
| 161 | 459 | PHE0006060_15842 | 13 | Corn ubiquitin precursor | 0 | 86 | 60677681 | dbj|BAD90972.1|cytochrome P450 [*Oryza sativa (japonica cultivar-group)*] |
| 162 | 460 | PHE0006850_16451 | 2 | Corn kernel specific yabby | 4.00E-73 | 74 | 115454365 | dbj|BAF45803.1| YABBY2 protein [*Oryza sativa (japonica cultivar group)*] |
| 163 | 461 | PHE0008043_18199 | 2 | Corn homeobox-9 | 0 | 99 | 40950648 | gb|AAR97952.1| rolled leaf1 [*Zea mays*] |
| 164 | 462 | PHE0000125_18852 | 13 | Corn receiver domain (TOC1-like) 10 | 1.00E-171 | 73 | 51571875 | dbj|BAD38854.1| pseudo-response regulator 1 [*Oryza sativa (japonica cultivar-group)*] |
| 165 | 463 | PHE0008269_18720 | 30 | *Arabidopsis* protein kinase | 0 | 96 | 15222311 | ref|NP_172195.1|MAPKKK13; protein kinase/protein serine/threonine kinase/protein-tyrosine kinase [*Arabidopsis thaliana*] |
| 166 | 464 | PHE0008264_18712 | 30 | *Arabidopsis* ubiquitin-protein ligase | 0 | 97 | 42567081 | ref|NP_194117.3| ubiquitin-protein ligase/zinc ion binding [*Arabidopsis thaliana*] |
| 167 | 465 | PHE0002782_20059 | 8 | Corn phosphoglucose isomerase | 0 | 89 | 115479643 | dbj|BAD17509.1| putative glucose-6-phosphate isomerase [*Oryza sativa (japonica cultivar group)*] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 167 | 465 | PHE0002782_22452 | 13 | Corn phosphoglucose isomerase | 0 | 89 | 115479643 | dbj|BAD17509.1| putative glucose-6-phosphate isomerase [*Oryza sativa* (*japonica* cultivar-group)] |
| 168 | 466 | PHE0009438_20404 | 9 | Corn GNC | 8.00E-84 | 52 | 115445073 | dbj|BAD17612.1| zinc finger protein-like [*Oryza sativa* (*japonica* cultivar-group)] |
| 169 | 467 | PHE0009429_20392 | 13 | Rice sulphiredoxin | 6.00E-68 | 85 | 71905635 | gb|AAZ52795.1| sulfiredoxin-like protein [*Oryza sativa* (*japonica* cultivar-group)] |
| 170 | 468 | PHE0009440_20406 | 13 | Yeast sulphiredoxin | 3.00E-66 | 100 | 6322764 | sp|P36077|SRX1_YEAST Sulfiredoxin |
| 171 | 469 | PHE0008543_18945 | 13 | *Agrobacterium* siroheme synthase | 0 | 97 | 17937602 | ref|NP_534391.1| siroheme synthase [*Agrobacterium tumefaciens* str. C58] |
| 171 | 469 | PHE0008543_18946 | 20 | *Agrobacterium* siroheme synthase | 0 | 97 | 17937602 | ref|NP_534391.1| siroheme synthase [*Agrobacterium tumefaciens* str. C58] |
| 171 | 469 | PHE0008543_18947 | 10 | *Agrobacterium* siroheme synthase | 0 | 97 | 17937602 | ref|NP_534391.1| siroheme synthase [*Agrobacterium tumefaciens* str. C58] |
| 172 | 470 | PHE0006960_16857 | 8 | Rice nitrate reductase | 0 | 96 | 115448947 | dbj|BAD16843.1| putative nitrate reductase [*Oryza sativa* (*japonica* cultivar-group)] |
| 173 | 471 | PHE0009427_20389 | 13 | *Arabidopsis* imidazoleglycerol-phosphate dehydratase | 1.00E-118 | 88 | 30686639 | dbj|BAB01781.1| imidazoleglycerol-phosphate dehydratase [*Arabidopsis thaliana*] |
| 174 | 472 | PHE0006437_15906 | 13 | *Arabidopsis* putative protein kinase | 1.00E-170 | 95 | 22327062 | ref|NP_197926.2| protein kinase/protein serine/threonine kinase/protein-tyrosine kinase [*Arabidopsis thaliana*] |
| 175 | 473 | PHE0007409_17652 | 3 | Rice mono- or diacylglycerol acyltransferase | 0 | 99 | 115467862 | dbj|BAD33251.1| putative mono- or diacylglycerol acyltransferase (*Oryza sativa* (*japonica* cultivar-group)] |
| 176 | 474 | PHE0009426_20387 | 13 | Yeast histidinol phosphatase | 0 | 100 | 14318548 | dbj|BAA09264.1| histidinol phosphatase [*Saccharomyces cerevisiae*] |
| 177 | 475 | PHE0009430_20393 | 13 | Soy sulphiredoxin | 2.00E-45 | 74 | 85719364 | gb|ABC75369.1|ParB-like nuclease [*Medicago truncatula*] |
| 178 | 476 | PHE0007003_16906 | 13 | Rice putative phosphotyrosyl phosphatase activator | 1.00E-171 | 82 | 115467132 | dbj|BAD37240.1| putative phosphotyrosyl phosphatase activator [*Oryza sativa* (*japonica* cultivar-group)] |
| 179 | 477 | PHE0008378_18741 | 13 | Yeast general control protein | 1.00E-144 | 94 | 6320828 | sp|P03069| General control protein GCN4 (Amino acid biosynthesis regulatory |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| | | | | | | | | protein) [*Saccharomyces cerevisiae*] |
| 180 | 478 | PHE0008273_18725 | 30 | *Arabidopsis* nucleic acid binding protein | 0 | 95 | 30683900 | ref|NP_180412.2| nucleic acid binding [*Arabidopsis thaliana*] |
| 181 | 479 | PHE0008547_18953 | 20 | Corn ferredoxin | 1.00E-38 | 75 | 119961 | sp|P27789| Maize ferredoxin-5 (Ferredoxin V) |
| 182 | 480 | PHE0006922_16812 | 13 | Corn putative hexokinase I | 0 | 87 | 115439869 | gb|AAZ93623.1| hexokinase 6 [*Oryza sativa (japonica cultivar-group)*] |
| 183 | 481 | PHE0006920_16810 | 13 | Corn putative CAD ATPase | 0 | 88 | 115439215 | gb|AAP92128.1| putative ATPase ATP1 [*Oryza sativa (japonica cultivar-group)*] |
| 184 | 482 | PHE0008396_18765 | 9 | Corn altered glutamine synthetase2 | 0 | 97 | 121341 | sp|P25462| Maize glutamine synthetase (Glutamate-ammonia ligase) (GS2) |
| 185 | 483 | PHE0006957_16854 | 13 | Corn glutamine synthetase2 C299A/C364A double mutant | 0 | 97 | 121341 | sp|P25462| Maize glutamine synthetase (Glutamate-ammonia ligase) (GS2) |
| 186 | 484 | PHE0006404_15936 | 13 | *Arabidopsis* RNA-binding protein | 0 | 96 | 18423760 | ref|NP_568826.1| RNA binding protein [*Arabidopsis thaliana*] |
| 187 | 485 | PHE0006820_16401 | 13 | *Nostoc punctiforme* A-type flavoproteins | 0 | 97 | 23129576 | ref|ZP_00111402.1| Uncharacterized flavoproteins [*Nostoc punctiforme* PCC 73102] |
| 188 | 486 | PHE0006690_16236 | 13 | Corn putative high affinity nitrate transporter | 0 | 79 | 108794607 | gb|ABG20828.1| high affinity nitrate transporter NRT2.5 [*Hordeum vulgare* subsp. *vulgare*] |
| 189 | 487 | PHE0006395_15932 | 13 | *Arabidopsis* leucine-rich repeat protein | 0 | 100 | 18391461 | gb|AAW57412.1| plant intracellular Ras-group-related LRR protein 3 [*Arabidopsis thaliana*] |
| 190 | 488 | PHE0006759_16384 | 6 | *Arabidopsis* glycine hydroxymethyltransferase/serine hydroxymethyltransferase | 0 | 100 | 15235745 | ref|NP_195506.1| Serine hydroxymethyltransferase 1); glycine hydroxymethyltransferase [*Arabidopsis thaliana*] |
| 191 | 489 | PHE0006576_16028 | 13 | Corn tuber-specific and sucrose-responsive element binding factor | 1.00E-87 | 57 | 115469098 | dbj|BAD37513.1| putative tuber-specific and sucrose-responsive element binding factor [*Oryza sativa (japonica* cultivar-group)] |
| 192 | 490 | PHE0006979_16885 | 13 | *Arabidopsis* xylogen like protein 12 | 1.00E-103 | 100 | 18405294 | dbj|BAE73268.1| xylogen like protein 12 [*Arabidopsis thaliana*] |
| 193 | 491 | PHE0009786_21754 | 9 | *Arabidopsis* HFR1-delta N105 mutant | 1.00E-97 | 93 | 18378953 | sp|Q9FE22| Long hypocotyl in far-red 1 (bHLH-like protein HFR1); gb|AAK15282.1| basic helix-loop-helix FB1 protein [*Arabidopsis thaliana*] |
| 193 | 491 | PHE0009786_20911 | 30 | *Arabidopsis* HFR1-delta N105 mutant | 1.00E-97 | 93 | 18378953 | sp|Q9FE22| Long hypocotyl in far-red 1 (bHLH-like protein HFR1); gb|AAK10282.1| basic |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 194 | 492 | PHE0006572_16007 | 13 | Arabidopsis phosphoenolpyruvate carboxylase kinase 2 | 1.00E-160 | 100 | 18396914 | helix-loop-helix FB1 protein [Arabidopsis thaliana] ref|NP_566229.1|Phosphoenol pyruvate carboxylase kinase 2 [Arabidopsis thaliana] |
| 195 | 493 | PHE0006828_16408 | 13 | Arabidopsis de-etiolated 1 | 0 | 94 | 42566387 | ref|NP_192756.2|DET1 (De-etiolated 1) [Arabidopsis thaliana] |
| 196 | 494 | PHE0006588_16092 | 13 | Corn electron transporter/thiol-disulfide exchange intermediate | 9.00E-90 | 100 | 30693659 | ref|NP_175021.2| electron transporter/thiol-disulfide exchange intermediate [Arabidopsis thaliana] |
| 197 | 495 | PHE0006985_16891 | 13 | Corn putative nuclear protein NAP | 0 | 75 | 115450034 | dbj|BAD23003.1| putative nuclear protein NAP [Oryza sativa (japonica cultivar-group)] |
| 198 | 496 | PHE0006875_16688 | 13 | Rice putative Photosystem I reaction center subunit V | 6.00E-61 | 85 | 115479799 | dbj|BAD33396.1| putative photosystem I reaction center subunit V [Oryza sativa (japonica cultivar-group)] |
| 199 | 497 | PHE0006626_16155 | 13 | Corn (1-3,1-4)-beta-glucanase | 1.00E-134 | 72 | 18984 | emb|CAA36801.1| (1-3,1-4)-beta-D-glucanase; emb|CAB41401.1| lichenase [Hordeum vulgare subsp. vulgare] |
| 200 | 498 | PHE0006689_16235 | 13 | Corn amino acid transporter family protein | 0 | 84 | 115443611 | dbj|BAD08181.1| putative amino acid transport protein [Oryza sativa (japonica cultivar-group)] |
| 201 | 499 | PHE0006799_16382 | 9 | Rhodopseudomonas Mg-protoporphyrin IX monomethylester cyclase | 0 | 97 | 39934738 | ref|NP_947014.1| Mg-protoporphyrin IX monomethyl ester oxidative cyclase 66 kD subunit [Rhodopseudomonas palustris CGA009] |
| 202 | 500 | PHE0006959_16856 | 8 | nitrate reductase | 0 | 95 | 115476820 | dbj|BAD09558.1| nitrate reductase apoenzyme [Oryza sativa (japonica cultivar-group)] |
| 203 | 501 | PHE0011615_23861 | 31 | Arabidopsis activated YODA | 0 | 78 | 38049268 | gb|AAR10436.1| YDA [Arabidopsis thaliana] |
| 204 | 502 | PHE0006925_16814 | 13 | Corn translocase inner membrane-like protein | 2.00E-74 | 66 | 115473245 | dbj|BAC83874.1| translocase inner membrane-like protein [Oryza sativa (japonica cultivar-group)] |
| 205 | 503 | PHE0006713_16274 | 25 | Arabidopsis cell division cycle protein 23-like | 0 | 96 | 15228343 | emb|CAB51062.1| cell division cycle protein 23 homolog [Arabidopsis thaliana] |
| 206 | 504 | PHE0008447_18848 | 13 | Corn light regulated protein | 1.00E-23 | 63 | 77023866 | gb|ABA61130.1| light-induced protein 1 [Lolium perenne] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 207 | 505 | PHE0006674_16221 | 13 | Rice putative nitrate transporter NRT1-5 | 0 | 95 | 115441781 | dbj|BAD82445.1| putative nitrate transporter NRT1-5 [*Oryza sativa (japonica* cultivar-group)] |
| 208 | 506 | PHE0010613_22398 | 3 | Corn high oil DAG kinase-like | 1.00E-165 | 80 | 115450433 | gb|ABF93745.1| expressed protein [*Oryza sativa (japonica* cultivar-group)] |
| 208 | 506 | PHE0010613_22404 | 7 | Corn high oil DAG kinase-like | 1.00E-165 | 80 | 115450433 | gb|ABF93745.1| expressed protein [*Oryza sativa (japonica* cultivar-group)] |
| 209 | 507 | PHE0002720_22558 | 18 | Corn DNA J protein | 0 | 83 | 115463255 | gb|AAV43840.1| putative DnaJ protein [*Oryza sativa (japonica* cultivar-group)] |
| 210 | 508 | PHE0011760_24005 | 31 | *Arabidopsis* YODA | 0 | 83 | 15222512 | ref|NP_176557.1| YDA (YODA); protein kinase/ protein serine/threonine kinase/protein-tyrosine kinase [*Arabidopsis thaliana*] |
| 211 | 509 | PHE0010612_22397 | 3 | Corn high oil nucleic acid binding | 1.00E-165 | 77 | 115450431 | gb|ABF93744.1| D111/G-patch domain-containing protein [*Oryza sativa (japonica* cultivar-group)] |
| 211 | 509 | PHE0010612_22403 | 7 | Corn high oil nucleic acid binding | 1.00E-165 | 77 | 115450431 | gb|ABF93744.1| D111/G-patch domain-containing protein [*Oryza sativa (japonica* cultivar-group)] |
| 212 | 510 | PHE0010615_22400 | 3 | Corn high oil unknown protein | 1.00E-32 | 28 | 125581548 | gb|EAZ22479.1| hypothetical protein OsJ_005962 [*Oryza sativa (japonica* cultivar-group)] |
| 213 | 511 | PHE0007411_17654 | 3 | Rice putative tafazzin isoform | 0 | 97 | 57899656 | dbj|BAD87325.1| putative tafazzin isoform [*Oryza sativa (japonica* cultivar-group)] |
| 214 | 512 | PHE0010617_22402 | 3 | Corn high oil hydrolase-like protein | 5.00E-98 | 69 | 115447203 | dbj|BAD20134.1| isochorismatase hydrolase-like protein [*Oryza sativa (japonica* cultivar-group)] |
| 215 | 513 | PHE0010610_22395 | 3 | Corn high oil RING-finger protein | 9.00E-27 | 75 | 2894379 | emb|CAA74911.1| ring finger protein [*Hordeum vulgare* subsp. *vulgare*] |
| 216 | 514 | PHE0006883_16702 | 7 | Corn glucosyl transferase | 0 | 93 | 136757 | sp|P04713| Granule-bound starch synthase 1, (GBSS-I) emb|CAA27574.1| glucosyl transferase [*Zea mays*] |
| 217 | 515 | PHE0010636_22408 | 3 | Corn glucose 6-phosphate translocator | 0 | 89 | 2997589 | gb|AAC08524.1| glucose-6-phosphate/phosphate-translocator precursor [*Zea mays*] |
| 217 | 515 | PHE0010636_22410 | 7 | Corn glucose 6-phosphate translocator | 0 | 89 | 2997589 | gb|AAC08524.1| glucose-6-phosphate/phosphate-translocator precursor [*Zea mays*] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 218 | 516 | PHE0011082_23038 | 30 | Soy SAG13 like | 3.00E-98 | 66 | 15239327 | gb|AAO22710.1| putative short chain alcohol dehydrogenase [Arabidopsis thaliana] |
| 219 | 517 | PHE0009475_20462 | 15 | Arabidopsis gibberellin 20-oxidase | 0 | 100 | 15235072 | ref|NP_194272.1| gibberellin 20-oxidase/gibberellin 3-beta-dioxygenase [Arabidopsis thaliana] |
| 219 | 517 | PHE0009475_20468 | 2 | Arabidopsis gibberellin 20-oxidase | 0 | 100 | 15235072 | ref|NP_194272.1| gibberellin 20-oxidase/gibberellin 3-beta-dioxygenase [Arabidopsis thaliana] |
| 219 | 517 | PHE0009475_20899 | 1 | Arabidopsis gibberellin 20-oxidase | 0 | 100 | 15235072 | ref|NP_194272.1| gibberellin 20-oxidase/gibberellin 3-beta-dioxygenase [Arabidopsis thaliana] |
| 219 | 517 | PHE0009475_21740 | any | Arabidopsis gibberellin 20-oxidase | 0 | 100 | 15235072 | ref|NP_194272.1| gibberellin 20-oxidase/gibberellin 3-beta-dioxygenase [Arabidopsis thaliana] |
| 219 | 517 | PHE0009475_20469 | 30 | Arabidopsis gibberellin 20-oxidase | 0 | 100 | 15235072 | ref|NP_194272.1| gibberellin 20-oxidase/gibberellin 3-beta-dioxygenase [Arabidopsis thaliana] |
| 220 | 518 | PHE0007415_17661 | 7 | Corn EIL2 | 0 | 75 | 125543684 | gb|EAY89823.1|hypothetical protein OsI_011056 [Oryza sativa (indica cultivar-group)] |
| 221 | 519 | PHE0006614_16129 | 22 | Soy STN7-LHCII protein kinase | 0 | 72 | 15241093 | emb|CAB82763.1| (1-4)-beta-mannan endohydrolase-like protein [Arabidopsis thaliana] |
| 222 | 520 | PHE0010611_22396 | 3 | Corn high oil flavin containing monooxygenase | 0 | 77 | 116317828 | gb|EAY92887.1| hypothetical protein OsI_014120 [Oryza sativa (indica cultivar-group)] |
| 223 | 521 | PHE0011719_23946 | na | Arabidopsis 1-acylglycerol-3-phosphate O-acyltransferase | 0 | 99 | 18410774 | ref|NP_567052.1| 1-acylglycerol-3-phosphate O-acyltransferase [Arabidopsis thaliana] |
| 224 | 522 | PHE0006861_16463 | 29 | Arabidopsis unknown protein | 0 | 87 | 5734789 | gb|AAD50054.1| Hypothetical protein [Arabidopsis thaliana] |
| 225 | 523 | PHE0006568_16005 | 13 | Corn receptor-like protein kinase | 0 | 60 | 115472561 | dbj|BAC84489.1| putative serine/threonine-specific protein kinase [Oryza sativa (japonica cultivar-group)] |
| 226 | 524 | PHE0010652_22429 | 3 | Corn high oil tRNA methyltransferase | 1.00E-172 | 94 | 115469828 | dbj|BAD53799.1| putative FtsJ homolog 1 isoform b [Oryza sativa (japonica cultivar-group)] |
| 227 | 525 | PHE0008158_18448 | 7 | ZMEN1 | 7.00E-65 | 56 | 115437056 | dbj|BAD73580.1| zinc-binding protein-like [Oryza sativa (japonica cultivar-group)] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 228 | 526 | PHE0003316_20755 | 30 | E. coli beta-glucuronidase with intron 2 from potato light-inducible tissue-specific gene | 0 | 100 | 475169 | emb|CAA83649.1| beta-glucuronidase [synthetic construct] |
| 229 | 527 | PHE0009478_20470 | 2 | Corn gibberellin 20 oxidase | 1.00E-167 | 82 | 37359180 | gb|AAN73384.1| putative gibberellin 20 oxidase [Oryza rufipogon] |
| 229 | 527 | PHE0009478_20900 | 1 | Corn gibberellin 20 oxidase | 1.00E-167 | 82 | 37359180 | gb|AAN73384.1| putative gibberellin 20 oxidase [Oryza rufipogon] |
| 229 | 527 | PHE0009478_20471 | any | Corn gibberellin 20 oxidase | 1.00E-167 | 82 | 37359180 | gb|AAN73384.1| putative gibberellin 20 oxidase [Oryza rufipogon] |
| 230 | 528 | PHE0010395_21760 | 30 | Soy DUF716 | 3.00E-84 | 55 | 124365521 | gb|ABN09755.1| Proteinase inhibitor I4, serpin [Medicago truncatula] |
| 231 | 529 | PHE0010391_21753 | 30 | Soy Unknown protein | 7.00E-64 | 91 | 115463333 | gb|AAV43818.1| unknown protein [Oryza sativa (japonica cultivar-group)] |
| 232 | 530 | PHE0010396_21761 | 30 | Soy DUF716 | 2.00E-83 | 56 | 124365521 | gb|ABN09755.1|Proteinase inhibitor I4, serpin [Medicago truncatula] |
| 233 | 531 | PHE0009511_22422 | 26 | Cucurbita S-adenosylmethionine decarboxylase | 1.00E-147 | 73 | 21239731 | gb|AAM44307.1| S-adenosylmethionine decarboxylase [Citrofortunella mitis] |
| 234 | 532 | PHE0010614_22399 | 3 | Corn high oil SOUL-like protein | 2.00E-94 | 80 | 115435220 | dbj|BAA96146.1| putative heme binding protein 2 [Oryza sativa (japonica cultivar-group)] |
| 235 | 533 | PHE0011420_23634 | 3 | Corn unknown protein | 0 | 91 | 115464535 | ref|NP_001055867.1|Os05g0482600 [Oryza sativa (japonica cultivar-group)] |
| 236 | 534 | PHE0011454_23667 | 13 | Corn H2B2 | 3.00E-36 | 87 | 122044864 | sp|P05621| Wheat histone H2B.2 |
| 237 | 535 | PHE0011443_24001 | 13 | Corn H2B1 | 2.00E-39 | 77 | 1708107 | sp|P54348| Maize histone H2B.5 (H2B) |
| 238 | 536 | PHE0011452_23665 | 13 | Corn H3-2 | 3.00E-69 | 99 | 15232146 | sp|P69246| Maize hHistone H3.2 |
| 239 | 537 | PHE0010394_21758 | 30 | Soy Sin3 associated polypeptide | 2.00E-52 | 82 | 115443887 | dbj|BAD07609.1| putative P18 [Oryza sativa (japonica cultivar-group)] |
| 240 | 538 | PHE0010397_21762 | 30 | Soy unknown protein | 7.00E-17 | 57 | 82568700 | dbj|BAE48663.1|Pm52 [Prunus mume] |
| 241 | 539 | PHE0010398_21763 | 30 | Soy unknown protein | 1.00E-17 | 56 | 82568700 | dbj|BAE48663.1|Pm52 [Prunus mume] |
| 242 | 540 | PHE0010100_21467 | 20 | Klebsiella nitrite reductase | 0 | 90 | 585562 | gb|AAA25099.1| nitrite reductase [Klebsiella oxytoca] |
| 243 | 541 | PHE0011503_23734 | 1 | Corn ethylene receptor etr1 mutant | 0 | 91 | 38607373 | gb|AAR25566.1| ethylene receptor [Zea mays] |
| 243 | 541 | PHE0011503_23736 | 15 | Corn ethylene receptor etr1 mutant | 0 | 91 | 38607373 | gb|AAR25566.1| ethylene receptor [Zea mays] |
| 244 | 542 | PHE0010099_21319 | 13 | Klebsiella nitrate reductase large subunit | 0 | 87 | 18314343 | gb|AAA25100.2| nitrate reductase large subunit [Klebsiella oxytoca] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 244 | 542 | PHE0010099_21461 | 9 | Klebsiella nitrate reductase large subunit | 0 | 87 | 18314343 | gb|AAA25100.2| nitrate reductase large subunit [Klebsiella oxytoca] |
| 244 | 542 | PHE0010099_21466 | 20 | Klebsiella nitrate reductase large subunit | 0 | 87 | 18314343 | gb|AAA25100.2| nitrate reductase large subunit [Klebsiella oxytoca] |
| 245 | 543 | PHE0011269_23400 | 13 | Arabidopsis HIO2019A | 0 | 96 | 42562138 | gb|AAF97271.1| meristem L1 layer homeobox protein like (ATML1) from Arabidopsis thaliana gb|U37589 and contains Transposase PF|01527, Homeobox PF|00046, and START PF|01852 domains. |
| 246 | 544 | PHE0008393_18762 | 20 | Corn roothairless 1 | 0 | 95 | 34733383 | gb|AAQ81632.1| roothairless 1 [Zea mays] |
| 247 | 545 | PHE0010223_21491 | 3 | Corn sucrose transport protein 4 | 0 | 87 | 49066602 | gb|AAT51689.1| sucrose transport protein [Zea mays] |
| 248 | 546 | PHE0011613_23858 | 3 | Corn WRI1 | 1.00E-109 | 56 | 85815798 | dbj|BAE78578.1|aintegumenta-like [Oryza sativa (japonica cultivar-group)] |
| 248 | 546 | PHE0011613_23860 | 7 | Corn WRI1 | 1.00E-109 | 56 | 85815798 | dbj|BAE78578.1|aintegumenta-like protein [Oryza sativa (japonica cultivar-group)] |
| 249 | 547 | PHE0001582_22064 | 1 | Corn ethylene receptor ETR1 like | 0 | 93 | 10241927 | gb|AAR25568.1| ethylene receptor [Zea mays] |
| 250 | 548 | PHE0007444_22314 | 18 | Corn aminopropyl transferase | 0 | 94 | 74481421 | gb|AAW57523.1| spermidine synthase [Zea mays] |
| 251 | 549 | PHE0010543_22298 | 16 | Corn en-like protein FDR2 | 4.00E-92 | 94 | 115498267 | gb|ABI98712.1| terminal flower 1 [Zea mays] |
| 252 | 550 | PHE0010543_22323 | 12 | Cen-like protein FDR2 | 3.00E-83 | 94 | 115498267 | gb|ABI98712.1| terminal flower 1 [Zea mays] |
| 253 | 551 | PHE0011081_23033 | 30 | Arabidopsis SUC2 | 0 | 88 | 15239921 | ref|NP_199174.1|carbohydrate/sugar transporter [Arabidopsis thaliana] |
| 254 | 552 | PHE0011075_23026 | 30 | Wheat P-II | 3.00E-62 | 77 | 125550734 | gb|EAY96443.1| hypothetical protein OsI_017676 [Oryza sativa (indica cultivar-group)] |
| 255 | 553 | PHE0010100_21462 | 9 | Klebsiella Nitrite reductase | 0 | 90 | 585562 | sp|Q06458| Nitrite reductase [NAD(PH] large subunit [Klebsiella oxytoca] |
| 256 | 554 | PHE0009640_21775 | 30 | Arabidopsis ME10609 | 3.00E-53 | 100 | 15236188 | ref|NP_195203.1| unknown protein [Arabidopsis thaliana] |
| 257 | 555 | PHE0010092_21307 | 13 | Corn translation initiation factor 2 alpha subunit | 1.00E-158 | 84 | 115452457 | gb|ABF95443.1| Eukaryotic translation initiation factor 2 alpha subunit [Oryza sativa (japonica cultivar-group)] |
| 258 | 556 | PHE0004611_24123 | 13 | Arabidopsis putative peptide transporter | 0 | 89 | 12325237 | gb|AAG52567.1| putative peptide transporter [Arabidopsis thaliana] |
| 259 | 557 | PHE0010093_21308 | 13 | Corn translation initiation factor 2 alpha subunit | 1.00E-162 | 85 | 115452457 | gb|ABF95443.1| Eukaryotic translation initiation factor 2 alpha subunit [Oryza sativa (japonica cultivar-group)] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 260 | 558 | PHE0008605_23084 | 13 | Arabidopsis putative histone H2B | 4.00E-40 | 98 | 15226943 | gb|AAM62619.1| putative histone H2B [Arabidopsis thaliana] |
| 261 | 559 | PHE0009939_21100 | 16 | Arabidopsis glycine dehydrogenase | 0 | 98 | 15234036 | ref|NP_195027.1| glycine dehydrogenase [Arabidopsis thaliana] |
| 262 | 560 | PHE0009941_21105 | 8 | Corn Moc1-like | 1.00E-124 | 80 | 125540188 | gb|EAY86583.1| hypothetical protein OsI_007816 [Oryza sativa (indica cultivar-group)] |
| 263 | 561 | PHE0009951_21135 | 8 | Yeast QSR1-like | 1.00E-115 | 93 | 6323104 | sp|P41805| Yeast 60S ribosomal protein L10 (L9) (Ubiquinol-cytochrome C reductase complex subunit VI-requiring protein) |
| 264 | 562 | PHE0009943_21127 | 8 | Arabidopsis QSR1-like | 1.00E-127 | 100 | 18408550 | gb|AAM64974.1| 60S ribosomal protein L10 [Arabidopsis thaliana] |
| 265 | 563 | PHE0009948_21132 | 8 | Soy QSR1-like | 1.00E-120 | 93 | 92870109 | gb|ABE79479.1| Ribosomal protein L10E [Medicago truncatula] |
| 266 | 564 | PHE0011084_23040 | 30 | Soy SNG1_sinapoylglucose:malate sinapoyltransferase | 0 | 77 | 92896730 | gb|ABE93328.1|Peptidase S10, serine carboxypeptidase [Medicago truncatula] |
| 267 | 565 | PHE0008233_23042 | 30 | Soy Phi-1 protein | 1.00E-122 | 71 | 3759184 | dbj|BAA33810.1| phi-1 [Nicotiana tabacum] |
| 268 | 566 | PHE0010854_22730 | 13 | Soy regulator of G-protein signaling | 1.00E-160 | 58 | 22331342 | ref|NP_189238.2| Regulator of G-protein signaling 1 [Arabidopsis thaliana] |
| 269 | 567 | PHE0003797_23051 | 10 | Corn DNA-binding protein Dof2 | 1.00E-44 | 63 | 1061306 | emb|CAA56287.1| Dof2 [Zea mays] |
| 270 | 568 | PHE0010194_21769 | 30 | Arabidopsis putative endo-1,4-beta glucanase | 0 | 94 | 15255301 | emb|CAB80722.1| putative endo-1,4-beta glucanase [Arabidopsis thaliana] |
| 271 | 569 | PHE0010197_21429 | 13 | Corn putative DNA binding protein | 2.00E-25 | 72 | 115451027 | gb|ABF94221.1| bHLH family protein [Oryza sativa (japonica cultivar-group)] |
| 271 | 569 | PHE0010197_21454 | 5 | Corn putative DNA binding protein | 2.00E-25 | 72 | 115451027 | gb|ABF94221.1| bHLH family protein [Oryza sativa (japonica cultivar-group)] |
| 271 | 569 | PHE0010197_21455 | 16 | Corn putative DNA binding protein | 2.00E-25 | 72 | 115451027 | gb|ABF94221.1| bHLH family protein [Oryza sativa (japonica cultivar-group)] |
| 271 | 569 | PHE0010197_21456 | 20 | Corn putative DNA binding protein | 2.00E-25 | 72 | 115451027 | gb|ABF94221.1| bHLH family protein [Oryza sativa (japonica cultivar-group)] |
| 271 | 569 | PHE0010197_21770 | 30 | Corn putative DNA binding protein | 2.00E-25 | 72 | 115451027 | gb|ABF94221.1| bHLH family protein [Oryza sativa (japonica cultivar-group)] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 272 | 570 | PHE0011665_23899 | 30 | Arabidopsis chlorophyll a/b binding protein | 1.00E-146 | 96 | 15225630 | gb|AAM20369.1| putative chlorophyll a/b binding protein [Arabidopsis thaliana] |
| 273 | 571 | PHE0012178_24443 | 3 | Corn putative chain C, structure of the plant transcriptional regulator Pbf-2 | 4.00E-99 | 78 | 115444353 | dbj|BAD28032.1| putative chain C, structure of the plant transcriptional regulator Pbf-2 [Oryza sativa (japonica cultivar-group)] |
| 274 | 572 | PHE0012170_24424 | 3 | Arabidopsis AGROS-like | 7.00E-40 | 74 | 30689607 | gb|ABC96792.1| ARGOS-like [Arabidopsis thaliana] |
| 275 | 573 | PHE0011064_22994 | 4 | Corn LPA1 | 0 | 85 | 115436512 | dbj|BAD52962.1| unknown protein [Oryza sativa (japonica cultivar-group)] |
| 275 | 573 | PHE0011064_23000 | 8 | Corn LPA1 | 0 | 85 | 115436512 | dbj|BAD52962.1| unknown protein [Oryza sativa (japonica cultivar-group)] |
| 275 | 573 | PHE0011064_23002 | 18 | Corn LPA1 | 0 | 85 | 115436512 | dbj|BAD52962.1| unknown protein [Oryza sativa (japonica cultivar-group)] |
| 275 | 573 | PHE0011064_23003 | 9 | Corn LPA1 | 0 | 85 | 115436512 | dbj|BAD52962.1| unknown protein [Oryza sativa (japonica cultivar-group)] |
| 275 | 573 | PHE0011064_23004 | 10 | Corn LPA1 | 0 | 85 | 115436512 | dbj|BAD52962.1| unknown protein [Oryza sativa (japonica cultivar-group)] |
| 276 | 574 | PHE0010201_21768 | 30 | Soy DNA-binding protein | 9.00E-30 | 75 | 30689711 | ref|NP_849712.1| transcription regulator [Arabidopsis thaliana] |
| 277 | 575 | PHE0010838_22702 | 30 | Soy PIN1 | 3.00E-32 | 71 | 25140423 | gb|AAN71616.1| PIN-like protein [Gossypium hirsutum] |
| 278 | 576 | PHE0010201_21433 | 13 | Soy DNA-binding protein | 1.00E-29 | 75 | 30689711 | ref|NP_849712.1| transcription regulator [Arabidopsis thaliana] |
| 279 | 577 | PHE0011446_23659 | 13 | Corn histone H3-1 | 7.00E-59 | 87 | 166384 | gb|AAA32655.1| histone H3 (H3-1.1) |
| 280 | 578 | PHE0001424_22077 | 9 | Corn seed storage protein, 35K isoform AmA1 - | 1.00E-68 | 41 | 57233444 | gb|AAW48295.1| pore-forming toxin-like protein Hfr-2 [Triticum aestivum] |
| 281 | 579 | PHE0011445_23658 | 13 | Corn putative elicitor-responsive gene-3 | 3.00E-71 | 89 | 115447529 | dbj|BAD25356.1| putative elicitor-responsive gene-3 [Oryza sativa (japonica cultivar-group)] |
| 282 | 580 | PHE0010090_21297 | 21 | Corn receptor protein kinase CLAVATA1 | 0 | 79 | 115451705 | gb|ABF94768.1| Receptor protein kinase CLAVATA1 precursor, [Oryza sativa (japonica cultivar-group)] |
| 283 | 581 | PHE0012180_24445 | 7 | Corn regulatory protein viviparous-1 | 0 | 83 | 138603 | sp|P26307| Maize regulatory protein viviparous-1 |
| 284 | 582 | PHE0011083_23039 | 30 | Soy SAG13 like homolog | 8.00E-87 | 63 | 15239327 | ref|NP_196225.1| oxidoreductase; dbj|BAA98195.1| short chain alcohol dehydrogenase-like [Arabidopsis thaliana] |

TABLE 2-continued

| NUC SEQ ID NO | PEP SEQ ID NO | Gene ID | BV ID | Gene Name | e-value | % id | GenBank ID | Annotation |
|---|---|---|---|---|---|---|---|---|
| 285 | 583 | PHE0011085_23041 | 30 | Soy SNG1_sinapoylglucose:malate sinapoyltransferase | 1.00E-157 | 62 | 92896727 | gb|ABE93325.1|Peptidase S10, serine carboxypeptidase [*Medicago truncatula*] |
| 286 | 584 | PHE0012175_24440 | 3 | Corn TSO1_like | 0 | 62 | 115489476 | gb|ABA99828.1| Tesmin/TSO1-like CXC domain containing protein [*Oryza sativa* (*japonica* cultivar-group)] |
| 286 | 584 | PHE0012175_24448 | 7 | Corn TSO1_like | 0 | 62 | 115489476 | gb|ABA99828.1| Tesmin/TSO1-like CXC domain containing protein [*Oryza sativa* (*japonica* cultivar-group)] |
| 287 | 585 | PHE0012177_24442 | 3 | Corn P24_like | 1.00E-101 | 74 | 119638471 | gb|ABL85062.1| expressed protein [*Brachypodium sylvaticum*] |
| 288 | 586 | PHE0011447_23660 | 13 | Corn P0031D02.12 protein | 1.00E-71 | 80 | 115440763 | gb|EAY76322.1| hypothetical protein OsI_004169 [*Oryza sativa* (*indica* cultivar-group)] |
| 289 | 587 | PHE0010194_21426 | 13 | *Arabidopsis* putative endo-1,4-beta glucanase | 0 | 95 | 15235301 | emb|CAB80722.1| putative endo-1,4-beta glucanase [*Arabidopsis thaliana*] |
| 290 | 588 | PHE0011666_23900 | 30 | Soy SPDS | 1.00E-165 | 87 | 99083515 | gb|ABF66657.1| spermidine synthase [*Ammopiptanthus mongolicus*] |
| 291 | 589 | PHE0011448_24160 | 13 | Corn histone H4-2 | 2.00E-30 | 80 | 115479301 | ref|NP_001063244.1| Os09g0433500 [*Oryza sativa* (*japonica* cultivar-group)] |
| 292 | 590 | PHE0008324_18636 | 13 | *Arabidopsis* T27I1.4 protein | 0 | 86 | 15218372 | ref|NP_172473.1| unknown protein [*Arabidopsis thaliana*] |
| 293 | 591 | PHE0006971_16875 | 13 | Ceres82Rice unknown protein | 1.00E-124 | 84 | 125583584 | gb|EAZ24515.1| hypothetical protein OsI_007998 [*Oryza sativa* (*japonica* cultivar-group)] |
| 294 | 592 | PHE0009939_21147 | 20 | *Arabidopsis* glycine dehydrogenase | 0 | 98 | 15234036 | ref|NP_195027.1| glycine dehydrogenase [*Arabidopsis thaliana*] |
| 295 | 593 | PHE0009953_21137 | 9 | Corn dicarboxylate translocator 1 | 0 | 89 | 40363459 | dbj|BAD06219.1| plastidic 2-oxoglutarate/malate transporter [*Zea mays*] |
| 296 | 594 | PHE0006907_16797 | 13 | Corn DUF150_MON_ZM4 1251 | 5.00E-94 | 60 | 115458524 | ref|NP_001052862.1| Os04g0438300 [*Oryza sativa* (*japonica* cultivar-group)] |
| 297 | 595 | PHE0008557_18970 | 13 | Corn FAD_binding_6[1]::NAD_binding_1[1] ferredoxin-NADP reductase | 0 | 89 | 115455751 | dbj|BAA07479.1| root ferredoxin-NADP+ reductase [*Oryza sativa* (*japonica* cultivar-group)] |
| 298 | 596 | PHE0006443_15955 | 13 | *Arabidopsis* putative SET-domain protein | 0 | 98 | 15226918 | gb|AAL32813.1| putative SET-domain protein [*Arabidopsis thaliana*] |

Selection Methods for Transgenic Plants with Enhanced Agronomic Trait

Within a population of transgenic plants regenerated from plant cells transformed with the recombinant DNA many plants that survive to fertile transgenic plants that produce seeds and progeny plants will not exhibit an enhanced agronomic trait. Selection from the population is necessary to identify one or more transgenic plant cells that can provide plants with the enhanced trait. Transgenic plants having enhanced traits are selected from populations of plants regenerated or derived from plant cells transformed as described herein by evaluating the plants in a variety of assays to detect an enhanced trait, e.g. enhanced water use efficiency, enhanced cold tolerance, increased yield, enhanced nitrogen use efficiency, enhanced seed protein and enhanced seed oil. These assays also may take many forms including, but not limited to, direct screening for the trait in a greenhouse or field trial or by screening for a surrogate trait. Such analyses can be directed to detecting changes in the chemical composition, biomass, physiological properties, morphology of the plant. Changes in chemical compositions such as nutritional composition of grain can be detected by analysis of the seed composition and content of protein, free amino acids, oil, free fatty acids, starch or tocopherols. Changes in biomass characteristics can be made on greenhouse or field grown plants and can include plant height, stem diameter, root and shoot dry weights; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant with an enhanced agronomic trait to also appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, phenotypic characteristics of harvested grain may be evaluated, including number of kernels per row on the ear, number of rows of kernels on the ear, kernel abortion, kernel weight, kernel size, kernel density and physical grain quality. Although the plant cells and methods of this invention can be applied to any plant cell, plant, seed or pollen, e.g. any fruit, vegetable, grass, tree or ornamental plant, the various aspects of the invention are preferably applied to corn, soybean, cotton, canola, alfalfa, wheat and rice plants.

The following examples are included to demonstrate aspects of the invention, those of skill in the art should, in light of the present disclosure, appreciate that many changes can be made in the specific aspects which are disclosed and still obtain a like or similar results without departing from the spirit and scope of the invention.

Example 1. Plant Expression Constructs

This example illustrates the construction of plasmids for transferring recombinant DNA into plant cells which can be regenerated into transgenic plants of this invention A. Plant Expression Constructs for Corn Transformation A base corn transformation vector pMON93039, as set forth in SEQ ID NO: 30521, illustrated in Table 3 and FIG. 2, was fabricated for use in preparing recombinant DNA for *Agrobacterium*-mediated transformation into corn tissue.

TABLE 3

| Function | Name | Annotation | Coordinates of SEQ ID NO: 30521 |
|---|---|---|---|
| *Agrobacterium* T-DNA transfer | B-AGRtu.right border | Agro right border sequence, essential for transfer of T-DNA. | 11364-11720 |
| Gene of interest expression cassette | E-Os.Act1 | Upstream promoter region of the rice actin 1 gene | 19-775 |
| | E-CaMV.35S.2xA1-B3 | Duplicated 35S A1-B3 domain without TATA box | 788-1120 |
| | P-Os.Act1 | Promoter region of the rice actin 1 gene | 1125-1204 |
| | L-Ta.Lhcb1 | 5' untranslated leader of wheat major chlorophyll a/b binding protein | 1210-1270 |
| | I-Os.Act1 | First intron and flanking UTR exon sequences from the rice actin 1 gene | 1287-1766 |
| | T-St.Pis4 | 3' non-translated region of the potato proteinase inhibitor II gene which functions to direct polyadenylation of the mRNA | 1838-2780 |
| Plant selectable marker expression cassette | P-Os.Act1 | Promoter from the rice actin 1 gene | 2830-3670 |
| | L-Os.Act1 | First exon of the rice actin 1 gene | 3671-3750 |
| | I-Os.Act1 | First intron and flanking UTR exon sequences from the rice actin 1 gene | 3751-4228 |
| | TS-At.ShkG-CTP2 | Transit peptide region of *Arabidopsis* EPSPS | 4238-4465 |
| | CR-AGRtu.aroA-CP4.nat | Coding region for bacterial strain CP4 native aroA gene. | 4466-5833 |
| | T-AGRtu.nos | A 3' non-translated region of the nopaline synthase gene of *Agrobacterium tumefaciens* Ti plasmid which functions to direct polyadenylation of the mRNA. | 5849-6101 |

TABLE 3-continued

| Function | Name | Annotation | Coordinates of SEQ ID NO: 30521 |
|---|---|---|---|
| *Agrobacterium* T-DNA transfer | B-AGRtu.left border | Agro left border sequence, essential for transfer of T-DNA. | 6168-6609 |
| Maintenance in *E. coli* | OR-Ec.oriV-RK2 | The vegetative origin of replication from plasmid RK2. | 6696-7092 |
| | CR-Ec.rop | Coding region for repressor of primer from the ColE1 plasmid. Expression of this gene product interferes with primer binding at the origin of replication, keeping plasmid copy number low. | 8601-8792 |
| | OR-Ec.ori-ColE1 | The minimal origin of replication from the *E. coli* plasmid ColE1. | 9220-9808 |
| | P-Ec.aadA-SPC/STR | Promoter for Tn7 adenylyltransferase (AAD(3")) | 10339-10380 |
| | CR-Ec.aadA-SPC/STR | Coding region for Tn7 adenylyltransferase (AAD(3")) conferring spectinomycin and streptomycin resistance. | 10381-11169 |
| | T-Ec.aadA-SPC/STR | 3' UTR from the Tn7 adenylyltransferase (AAD(3")) gene of *E. coli*. | 11170-11227 |

Other base vectors similar to the one described above were also constructed as listed in Table 4. These base corn transformation vectors are also used for wheat and rice transformations. See Table 4 for a summary of base vectors and base vector ID's which are referenced in Table 2. Also see Table 5 for a summary of regulatory elements used in the gene expression cassettes for these base vectors and the SEQ ID NOs for these elements.

Primers for PCR amplification of protein coding nucleotides of recombinant DNA are designed at or near the start and stop codons of the coding sequence, in order to eliminate most of the 5' and 3' untranslated regions. Each recombinant DNA coding for a protein identified in Table 2 is amplified by PCR prior to insertion into the insertion site within the gene of interest expression cassette of one of the base vectors as referenced in Table 2.

TABLE 4

| Base Vector ID | |
|---|---|
| | Corn Base Vector |
| 1 | pMON92709 |
| 2 | pMON92713 |
| 3 | pMON92715 |
| 4 | pMON92716 |
| 5 | pMON92718 |
| 6 | pMON92719 |
| 7 | pMON92721 |
| 8 | pMON92722 |
| 9 | pMON92724 |
| 10 | pMON92729 |
| 11 | pMON93025 |
| 12 | pMON93026 |
| 13 | pMON93039 |
| 14 | pMON93043 |
| 15 | pMON94781 |
| 16 | pMON94830 |
| 17 | pMON99009 |
| 18 | pMON99048 |
| 19 | pMON99051 |
| 20 | pMON99052 |
| 21 | pMON100406 |
| | Soy And Canola Base Vector |
| 22 | pMON74537 |
| 23 | pMON74552 |
| 24 | pMON74553 |
| 25 | pMON82053 |
| 26 | pMON83145 |
| 27 | pMON92671 |
| 28 | pMON97027 |
| 29 | pMON99006 |
| 30 | pMON100407 |
| 31 | pMON102815 |
| 32 | pMON102819 |
| | Cotton Base Vector |
| 33 | pMON95549 |
| 34 | pMON99053 |

TABLE 5

| Base vector | Promoter | SEQ ID NO | Leader | SEQ ID NO | Intron | SEQ ID NO |
|---|---|---|---|---|---|---|
| pMON92709 | P-Os.GT1 | 30469 | L-Os.GT1 | 30493 | I-Zm.DnaK | 30516 |
| pMON92713 | P-Zm.P39486 | 30470 | L-Zm.39486 | 30494 | I-Zm.DnaK | 30516 |
| pMON92715 | P-Hv.Per1 | 30471 | L-Hv.Per1 | 30495 | I-Zm.DnaK | 30516 |
| pMON92716 | P-Zm.FDA | 30472 | L-Zm.FDA | 30496 | I-Zm.DnaK | 30516 |
| pMON92718 | P-Zm.CLK1 | 30473 | L-Zm.Cik1 | 30497 | I-Zm.Cik1 | 30517 |
| pMON92719 | P-Zm.RAB17 | 30474 | L-Zm.RAB17 | 30498 | I-Zm.DnaK | 30516 |
| pMON92721 | P-Zm.SzeinC1 | 30475 | L-Zm.SzeinC1 | 30499 | I-Zm.DnaK | 30516 |

TABLE 5-continued

| Base vector | Promoter | SEQ ID NO | Leader | SEQ ID NO | Intron | SEQ ID NO |
|---|---|---|---|---|---|---|
| pMON92722 | P-CaMV.35S-enh | 30476 | L-CaMV.35S | 30500 | I-Zm.DnaK | 30516 |
| pMON92724 | P-Zm.-636aldolase-0:1:2 + P-Zm.PPDK | 30477 | L-Zm.PPDK | 30501 | I-Zm.DnaK | 30516 |
| pMON92729 | P-Zm.PPDK | 30478 | L-Zm.PPDK | 30501 | I-Zm.DnaK | 30516 |
| pMON93025 | P-At.SUC2 | 30479 | L-At.SUC2 | 30502 | I-Zm.DnaK | 30516 |
| pMON93026 | P-Os.H1 | 30480 | L-Os.H1 | 30503 | I Zm.DnaK | 30516 |
| pMON93039 | E-Os.Act1 + E-CaMV.35S.2xA1-B3 + P-Os.Act1 | 30481 | L-Ta.Lhcb1 | 30504 | I-Os.Act1 | 30518 |
| pMON93043 | P-Zm.EM | 30482 | L-Zm.EM | 30505 | I-Zm.DnaK | 30516 |
| pMON94781 | P-Zm.Brittle-2 | 30483 | L-Zm.Brittle-2 | 30506 | I-Zm.DnaK | 30516 |
| pMON94830 | P-Os.Act16 | 30484 | L-Os.Act16 | 30507 | I-Os.Act16 | 30519 |
| pMON99009 | P-CaMV.35S-enh | 30476 | L-Ph.DnaK | 30508 | None | / |
| pMON99048 | P-Os.Act1 + E-CaMV.35S.2xA1-B3 | 30485 | L-Ta.Lhcb1 | 30504 | I-Os.Act1 | 30518 |
| pMON99051 | P-Zm.Kn1 | 30486 | L-Zm.Kn1 | 30509 | None | / |
| pMON99052 | P-Os.Rcc.3 | 30487 | L-Os.Rcc3 | 30510 | I-Zm.DnaK | 30516 |
| pMON100406 | P-Zm.Kn1 | 30486 | L-Zm.Kn1 | 30509 | I-Zm.DnaK | 30516 |
| pMON74537 | P-At.RbcS4 | 30488 | L-At.RbcS4 | 30511 | None | / |
| pMON74552 | P-CaMV.35S-enh | 30476 | None | / | None | / |
| pMON74553 | P-CaMV.35S-enh | 30476 | None | / | None | / |
| pMON82053 | P-CaMV.35S-enh | 30476 | None | / | None | / |
| pMON83145 | P-Gm.Hsp20 | 30489 | L-Gm.Hsp20 | 30512 | None | / |
| pMON92671 | P-At.SAMS3 | 30490 | L-At.SAMS3 | 30513 | I-At.SAMS3 | 30520 |
| pMON97027 | P-At.GRP7 | 30491 | L-At.GRP7 | 30514 | None | / |
| pMON99006 | P-CaMV.35S-enh | 30476 | None | / | None | / |
| pMON100407 | P-CaMV.35S-enh | 30476 | L-Ph.DnaK | 30508 | None | / |
| pMON102815 | P-At.Erecta | 30492 | L-At.Erecta | 30515 | None | / |
| pMON102819 | P-CaMV.35S-enh | 30476 | None | / | None | / |
| pMON95549 | P-At.SAMS3 | 30490 | L-At.SAMS3 | 30513 | I-At.SMAS3 | 30520 |
| pMON99053 | P-CaMV.35S-enh | 30476 | L-Ph.DnaK | 30508 | None | / |

For construct pMON94830, the L-Os.Act16 leader sequence (SEQ ID IN 30507) is interrupted by the I-Os.Act16 intron sequence (SEQ ID NO 30519) between nucleotide positions 3344 and 3861.

B. Plant Expression Constructs for Soy and Canola Transformation

Vectors for use in transformation of soybean and canola were also prepared. Elements of an exemplary common expression vector pMON82053 are shown in Table 6 below and FIG. 3. Another example of elements used in plant expression cassette for gene of interest such as PEP SEQ ID NOs 366 and 521 were the P-Gm.Sphas1 promoter (SEQ ID NO: 30524) and the L-Gm.Sphas1 leader (SEQ ID NO: 30525) sequences.

TABLE 6

| Function | Name | Annotation | Coordinates of SEQ ID NO: 30522 |
|---|---|---|---|
| Agrobacterium T-DNA transfer | B-AGRtu.left border | Agro left border sequence, essential for transfer of T-DNA. | 6144-6585 |
| Plant selectable marker expression cassette | P-At.Act7 | Promoter from the Arabidopsis actin 7 gene | 6624-7861 |
| | L-At.Act7 | 5'UTR of Arabidopsis Act7 gene | |
| | I-At.Act7 | Intron from the Arabidopsis actin7 gene | |
| | TS-At.ShkG-CTP2 | Transit peptide region of Arabidopsis EPSPS | 7864-8091 |
| | CR-AGRtu.aroA-CP4.nno_At | Synthetic CP4 coding region with dicot preferred codon usage. | 8092-9459 |
| | T-AGRtu.nos | A 3' non-translated region of the nopaline synthase gene of Agrobacterium tumefaciens Ti plasmid which functions to direct polyadenylation of the mRNA. | 9466-9718 |
| Gene of interest expression cassette | P-CaMV.35S-enh | Promoter for 35S RNA from CaMV containing a duplication of the −90 to −350 region. | 1-613 |
| | T-Gb.E6-3b | 3' untranslated region from the fiber protein E6 gene of sea-island cotton. | 688-1002 |
| Agrobacterium T-DNA transfer | B-AGRtu.right border | Agro right border sequence, essential for transfer of T-DNA. | 1033-1389 |
| Maintenance in E. coli | OR-Ec.oriV-RK2 | The vegetative origin of replication from plasmid RK2. | 5661-6057 |
| | CR-Ec.rop | Coding region for repressor of primer from the ColE1 plasmid. Expression of this gene product interferes with primer binding at the | 3961-4152 |

TABLE 6-continued

| Function | Name | Annotation | Coordinates of SEQ ID NO: 30522 |
|---|---|---|---|
| | OR-Ec.ori-ColE1 | origin of replication, keeping plasmid copy number low. The minimal origin of replication from the *E. coli* plasmid ColE1. | 2945-3533 |
| | P-Ec.aadA-SPC/STR | Promoter for Tn7 adenylyltransferase (AAD(3")) | 2373-2414 |
| | CR-Ec.aadA-SPC/STR | Coding region for Tn7 adenylyltransferase (AAD(3")) conferring spectinomycin and streptomycin resistance. | 1584-2372 |
| | T-Ec.aadA-SPC/STR | 3' UTR from the Tn7 adenylyltransferase (AAD(3")) gene of *E. coli*. | 1526-1583 |

Primers for PCR amplification of protein coding nucleotides of recombinant DNA are designed at or near the start and stop codons of the coding sequence, in order to eliminate most of the 5' and 3' untranslated regions. Each recombinant DNA coding for a protein identified in Table 2 is amplified by PCR prior to insertion into the insertion site within the gene of interest expression cassette of one of the base vectors as referenced in Table 2.

C. Cotton Transformation Vector

Plasmids for use in transformation of cotton were also prepared. Elements of an exemplary common expression vector pMON99053 are shown in Table 7 below and FIG. 4. Primers for PCR amplification of protein coding nucleotides of recombinant DNA are designed at or near the start and stop codons of the coding sequence, in order to eliminate most of the 5' and 3' untranslated regions. Each recombinant DNA coding for a protein identified in Table 2 is amplified by PCR prior to insertion into the insertion site within the gene of interest expression cassette of one of the base vectors as referenced in Table 2.

TABLE 7

| Function | Name | Annotation | Coordinates of SEQ ID NO: 30523 |
|---|---|---|---|
| *Agrobacterium* T-DNA transfer | B-AGRtu.right border | Agro right border sequence, essential for transfer of T-DNA. | 1-357 |
| Gene of interest expression cassette | Exp-CaMV.35S-enh + Ph.DnaK | Enhanced version of the 35S RNA promoter from CaMV plus the petunia hsp70 5' untranslated region | 388-1091 |
| | T-Ps.RbcS2-E9 | The 3' non-translated region of the pea RbcS2 gene which functions to direct polyadenylation of the mRNA. | 1165 1797 |
| Plant selectable marker expression cassette | Exp-CaMV.35S | Promoter and 5' untranslated region from the 35S RNA of CaMV | 1828-2151 |
| | CR-Ec.nptII-Tn5 | Coding region for neomycin phosphotransferase gene from transposon Tn5 which confers resistance to neomycin and kanamycin. | 2185-2979 |
| | T-AGRtu.nos | A 3' non-translated region of the nopaline synthase gene of *Agrobacterium tumefaciens* Ti plasmid which functions to direct polyadenylation of the mRNA. | 3011-3263 |
| *Agrobacterium* T-DNA transfer | B-AGRtu.left border | Agro left border sequence, essential for transfer of T-DNA. | 3309-3750 |
| Maintenance in *E. coli* | OR-Ec.oriV-RK2 | The vegetative origin of replication from plasmid RK2. | 3837-4233 |
| | CR-Ec.rop | Coding region for repressor of primer from the ColE1 plasmid. Expression of this gene product interferes with primer binding at the origin of replication, keeping plasmid copy number low. | 5742-5933 |
| | OR-Ec.ori-ColE1 | The minimal origin of replication from the *E. coli* plasmid ColE1. | 6361-6949 |

TABLE 7-continued

| Function | Name | Annotation | Coordinates of SEQ ID NO: 30523 |
|---|---|---|---|
| | P-Ec.aadA-SPC/STR | Promoter for Tn7 adenylyltransferase (AAD(3")) | 7480-7521 |
| | CR-Ec.aadA-SPC/STR | Coding region for Tn7 adenylyltransferase (AAD(3")) conferring spectinomycin and streptomycin resistance. | 7522-8310 |
| | T-Ec.aadA-SPC/STR | 3' UTR from the Tn7 adenylyltransferase (AAD(3")) gene of E. coli. | 8311-8368 |

Example 2. Corn Transformation

This example illustrates plant cell transformation methods useful in producing transgenic corn plant cells, plants, seeds and pollen of this invention and the production and identification of transgenic corn plants and seed with an enhanced trait, i.e. enhanced water use efficiency, enhanced cold tolerance, increased yield, enhanced nitrogen use efficiency, enhanced seed protein and enhanced seed oil. Plasmid vectors were prepared by cloning DNA identified in Table 2 in the identified base vectors for use in corn transformation of corn plant cells to produce transgenic corn plants and progeny plants, seed and pollen.

For *Agrobacterium*-mediated transformation of corn embryo cells corn plants of a readily transformable line are grown in the greenhouse and ears are harvested when the embryos are 1.5 to 2.0 mm in length. Ears are surface sterilized by spraying or soaking the ears in 80% ethanol, followed by air drying. Immature embryos are isolated from individual kernels on surface sterilized ears. Prior to inoculation of maize cells, *Agrobacterium* cells are grown overnight at room temperature. Immature maize embryo cells are inoculated with *Agrobacterium* shortly after excision, and incubated at room temperature with *Agrobacterium* for 5-20 minutes. Immature embryo plant cells are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing 100 mg/L paromomycin and subcultured at about two week intervals. Transformed plant cells are recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

For transformation by microprojectile bombardment maize immature embryos are isolated and cultured 3-4 days prior to bombardment. Prior to microprojectile bombardment, a suspension of gold particles is prepared onto which the desired recombinant DNA expression cassettes are precipitated. DNA is introduced into maize cells as described in U.S. Pat. Nos. 5,550,318 and 6,399,861 using the electric discharge particle acceleration gene delivery device. Following microprojectile bombardment, tissue is cultured in the dark at 27° C. Additional transformation methods and materials for making transgenic plants of this invention, for example, various media and recipient target cells, transformation of immature embryos and subsequence regeneration of fertile transgenic plants are disclosed in U.S. Pat. Nos. 6,194,636 and 6,232,526 and U.S. patent application Ser. No. 09/757,089, which are incorporated herein by reference.

To regenerate transgenic corn plants a callus of transgenic plant cells resulting from transformation and selection is placed on media to initiate shoot development into plantlets which are transferred to potting soil for initial growth in a growth chamber at 26° C. followed by a mist bench before transplanting to 5 inch pots where plants are grown to maturity. The regenerated plants are self-fertilized and seed is harvested for use in one or more methods to select seeds, seedlings or progeny second generation transgenic plants (R2 plants) or hybrids, e.g. by selecting transgenic plants exhibiting an enhanced trait as compared to a control plant.

Transgenic corn plant cells are transformed with recombinant DNA from each of the genes identified in Table 2. Progeny transgenic plants and seed of the transformed plant cells are screened for enhanced water use efficiency, enhanced cold tolerance, increased yield, enhanced nitrogen use efficiency, enhanced seed protein and enhanced seed oil as reported in Example 7.

Example 3. Soybean Transformation

This example illustrates plant transformation useful in producing the transgenic soybean plants of this invention and the production and identification of transgenic seed for transgenic soybean having enhanced water use efficiency, enhanced cold tolerance, increased yield, enhanced nitrogen use efficiency, enhanced seed protein and enhanced seed oil.

For *Agrobacterium* mediated transformation, soybean seeds are imbided overnight and the meristem explants excised. The explants are placed in a wounding vessel. Soybean explants and induced *Agrobacterium* cells from a strain containing plasmid DNA with the gene of interest cassette and a plant selectable marker cassette are mixed no later than 14 hours from the time of initiation of seed imbition, and wounded using sonication. Following wounding, explants are placed in co-culture for 2-5 days at which point they are transferred to selection media for 6-8 weeks to allow selection and growth of transgenic shoots. Resistant shoots are harvested approximately 6-8 weeks and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil. Additionally, a DNA construct can be transferred into the genome of a soybean cell by particle bombardment and the cell regenerated into a fertile soybean plant as described in U.S. Pat. No. 5,015,580, herein incorporated by reference.

Transgenic soybean plant cells are transformed with recombinant DNA from each of the genes identified in Table 2. Transgenic progeny plants and seed of the transformed plant cells are screened for enhanced water use efficiency, enhanced cold tolerance, increased yield, enhanced nitrogen use efficiency, enhanced seed protein and enhanced seed oil as reported in Example 7.

Example 4. Cotton Transgenic Plants with Enhanced Agronomic Traits

Cotton transformation is performed as generally described in WO00036911 and in U.S. Pat. No. 5,846,797. Transgenic cotton plants containing each of the recombinant DNA having a sequence of SEQ ID NO: 1 through SEQ ID NO: 298 are obtained by transforming with recombinant DNA from each of the genes identified in Table 1. Progeny transgenic plants are selected from a population of transgenic cotton events under specified growing conditions and are compared with control cotton plants. Control cotton plants are substantially the same cotton genotype but without the recombinant DNA, for example, either a parental cotton plant of the same genotype that was not transformed with the identical recombinant DNA or a negative isoline of the transformed plant. Additionally, a commercial cotton cultivar adapted to the geographical region and cultivation conditions, i.e. cotton variety ST474, cotton variety FM 958, and cotton variety Siokra L-23, are used to compare the relative performance of the transgenic cotton plants containing the recombinant DNA. The specified culture conditions are growing a first set of transgenic and control plants under "wet" conditions, i.e. irrigated in the range of 85 to 100 percent of evapotranspiration to provide leaf water potential of −14 to −18 bars, and growing a second set of transgenic and control plants under "dry" conditions, i.e. irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Enhanced water use efficiency is indicated by increased yield, improved relative water content, enhanced leaf water potential, increased biomass, enhanced leaf extension rates, and improved fiber parameters.

The transgenic cotton plants of this invention are identified from among the transgenic cotton plants by agronomic trait screening as having increased yield and enhanced water use efficiency.

Example 5. Canola Transformation

This example illustrates plant transformation useful in producing the transgenic canola plants of this invention and the production and identification of transgenic seed for transgenic canola having enhanced water use efficiency, enhanced cold tolerance, increased yield, enhanced nitrogen use efficiency, enhanced seed protein and enhanced seed oil.

Tissues from in vitro grown canola seedlings are prepared and inoculated with overnight-grown *Agrobacterium* cells containing plasmid DNA with the gene of interest cassette and a plant selectable marker cassette. Following co-cultivation with *Agrobacterium*, the infected tissues are allowed to grow on selection to promote growth of transgenic shoots, followed by growth of roots from the transgenic shoots. The selected plantlets are then transferred to the greenhouse and potted in soil. Molecular characterization are performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant Transgenic canola plant cells are transformed with recombinant DNA from each of the genes identified in Table 2. Transgenic progeny plants and seed of the transformed plant cells are screened for enhanced water use efficiency, enhanced cold tolerance, increased yield, enhanced nitrogen use efficiency, enhanced seed protein and enhanced seed oil as reported in Example 7.

Example 6. Homolog Identification

This example illustrates the identification of homologs of proteins encoded by the DNA identified in Table 2 which is used to provide transgenic seed and plants having enhanced agronomic traits. From the sequence of the homologs, homologous DNA sequence can be identified for preparing additional transgenic seeds and plants of this invention with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided herein as SEQ ID NO: 299 through SEQ ID NO: 596 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided herein as SEQ ID NO: 299 through SEQ ID NO: 596 using NCBI "blastp" program with E-value cutoff of 1e-4. Up to 1000 top hits were kept. A BLAST searchable database was constructed based on these hits, and is referred to as "SubDB". SubDB was queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs from a large number of distinct organisms were identified and are reported by amino acid sequences of SEQ ID NO: 597 through SEQ ID NO: 30468. These relationships of proteins of SEQ ID NO: 299 through 596 and homologs of SEQ ID NO: 597 through 30468 are identified in Table 8. The source organism for each homolog is found in the Sequence Listing.

TABLE 8

| PEP SEQ ID NO: | homolog SEQ ID NOs | | | | | | | | | | |
|---|---|---|---|---|---|---|---|---|---|---|---|
| 299: | 22505 | 17330 | 17332 | 3832 | 26661 | 24604 | 24601 | 26617 | 26553 | 26585 | 26591 | 26640 |
| | 26582 | 26471 | 26635 | 26572 | 26576 | 26556 | 26609 | 26423 | 25650 | 26551 | 2373 | 2405 |
| | 24690 | 25446 | 25450 | 26422 | 26473 | 25340 | 10489 | 21242 | 21238 | 21241 | 21279 | 24723 |
| | 24725 | 25494 | 25690 | 25164 | 16529 | 7978 | 10037 | 16615 | 16621 | 11055 | 12923 | 6955 |
| | 7874 | 7948 | 7839 | 8664 | 12144 | 14757 | 17096 | 14796 | 14828 | 26829 | 12171 | 21124 |
| | 23048 | 20000 | 23191 | 22333 | 20933 | 15625 | 22212 | 19851 | 28192 | 27896 | 22998 | 22992 |
| | 15629 | 28137 | 24133 | 22151 | 29931 | 985 | 2060 | 944 | 28955 | 28930 | 28990 | 29965 |
| | 15658 | 21486 | 21255 | 20071 | 19073 | 19014 | 18158 | 18127 | 18109 | 15620 | 2239 | 2233 |
| | 16398 | 14851 | 11657 | 12588 | 11744 | 14570 | 13748 | 13790 | 12143 | 12170 | 12173 | 12919 |
| | 15622 | 15628 | 15656 | 15604 | 16393 | 16394 | 16392 | 12916 | 11037 | 22432 | 8701 | 24656 |
| | 19135 | 19853 | 7817 | 18495 | 2869 | 8263 | 29437 | 29438 | 22440 | 22435 | 21711 | 22465 |
| | 21146 | 17031 | 19010 | 21907 | 27742 | 22415 | 5429 | 1188 | 5421 | 18365 | 23435 | 12382 |
| | 12090 | 12087 | 10571 | 18362 | 23640 | 15382 | 987 | 6445 | 6417 | 5413 | 8888 | 2538 |
| | 24892 | 15423 | 1089 | 1127 | 5417 | 21701 | 24630 | 24633 | 21702 | 21705 | 25589 | 25558 |
| | 21697 | 7438 | 22989 | 17339 | 1478 | 1506 | 1479 | 9199 | 25171 | 26307 | 1472 | 25424 |
| | 25418 | 5394 | 23942 | 8884 | 8887 | 12914 | 23541 | | | | | |
| 300: | 16906 | 20559 | 21806 | 5055 | 9056 | 13559 | 14510 | 4167 | 13364 | 13441 | 11165 | |
| | 3862 | 1913 | 6572 | 9353 | 29885 | 5672 | 23667 | 20433 | 11405 | 26215 | 8142 | 13983 |
| | 9317 | 1831 | 16167 | 26355 | 11049 | 12454 | 607 | 20163 | 21550 | 8941 | 3691 | 19336 |
| | 8960 | 11635 | 2500 | 12784 | 9832 | 13853 | 14431 | 6891 | 25892 | 24022 | 26873 | 8074 |
| | 10050 | 6314 | 15883 | 23231 | 829 | 4758 | 4754 | 28646 | 4717 | 20464 | 9858 | 7971 |
| | 12622 | 20501 | 4271 | 12195 | 9291 | 19503 | 21548 | 4124 | 10854 | 26029 | 12272 | 1775 |
| | 25590 | 22837 | 22812 | 22556 | 10678 | 16223 | 25625 | 21334 | 8456 | 22176 | 14327 | 14302 |
| | 17822 | 17624 | 16859 | 16850 | 17780 | 17619 | 17629 | 16852 | 10588 | 10650 | 1001 | 29219 |
| | 15690 | 20293 | 25766 | 12151 | 21485 | 14320 | 17504 | 15478 | 15477 | 15066 | 15835 | 30365 |
| | 30421 | 2696 | 20311 | 3417 | 19744 | 18488 | 3839 | 8782 | 17965 | 3743 | 3775 | 17509 |
| | 17514 | 7091 | 6457 | 12394 | 12411 | 4075 | 4077 | 17590 | 21909 | 28286 | 3388 | 16788 |
| | 15982 | 7848 | 29135 | 20349 | 19157 | 14248 | 29979 | 17396 | 17358 | 17398 | 17407 | 17324 |
| | 17410 | 17366 | 17403 | 17357 | 17368 | 17360 | 19996 | 19846 | 11904 | 23714 | 2173 | 22814 |
| | 22809 | 20197 | 29687 | 3983 | 24318 | 21492 | 20319 | 26103 | 28858 | 6802 | 20161 | 3448 |
| | 4055 | 12112 | 7750 | 12606 | 13406 | 12501 | 6292 | 9527 | 13807 | 3896 | 12598 | 5152 |
| | 5149 | 5155 | 368 | 10357 | 26816 | | | | | | | |
| 301: | 23796 | 2040 | 5965 | 5087 | 6920 | 4213 | 4210 | 3372 | 5323 | 16802 | 27336 | 6010 |
| | 8202 | 26922 | 2187 | 12208 | 19871 | 11517 | 22010 | 9197 | | | | |
| 302: | 23710 | 23757 | 13694 | 19592 | 23650 | 22298 | 8204 | 25706 | 24745 | 15742 | 30254 | 26637 |
| | 15339 | 21922 | 20145 | 25220 | 16474 | 13767 | 24177 | 23168 | 13704 | | | |
| 303: | 3118 | 4379 | 29540 | 19057 | 23492 | 24494 | 29662 | 25823 | 22886 | 22040 | 8636 | |
| 304: | 26286 | 15828 | 29381 | 9463 | 1447 | 21905 | 14853 | 28599 | 20781 | 27729 | 18418 | 27603 |
| | 25716 | 26765 | 16175 | 23282 | 13862 | 1876 | 2531 | 5158 | 2533 | 1911 | 11707 | 6224 |
| | 26059 | 22774 | 10047 | 19527 | 24245 | 14187 | 10461 | 29433 | 11856 | 11359 | 8254 | 1796 |
| | 13315 | 5545 | 10252 | 6191 | 13314 | 17203 | 23729 | 19203 | 6192 | 6228 | 29464 | 11849 |
| | 11846 | 6202 | 6193 | 27557 | 1797 | 10397 | 18417 | 9442 | 9470 | 9471 | 9441 | 2568 |
| | 1789 | 6233 | 6227 | 6222 | 2751 | 26484 | 19634 | 2753 | 2526 | 10548 | 2523 | 1794 |
| | 6151 | 4931 | 4935 | 5392 | 10581 | 10578 | 2167 | 28003 | 16045 | 2532 | 18805 | 25644 |
| | 25642 | 9834 | 12912 | 12907 | 15640 | 633 | 25781 | 4120 | 9293 | 11181 | 8741 | 3780 |
| | 18808 | 26630 | 26485 | 24195 | 4726 | 377 | 14947 | 2501 | 18997 | 20773 | 19301 | 16345 |
| | 18906 | 7189 | 15422 | 18210 | 21903 | 25270 | 24910 | 2503 | 10083 | 10113 | 10084 | |
| 305: | 18758 | 19672 | 29878 | 23393 | 24854 | 10271 | 27282 | 5416 | 23140 | 27083 | 2820 | 18194 |
| | 12159 | 9628 | 23204 | 13486 | 8110 | 12511 | 29407 | 1503 | 1698 | 28122 | 17599 | 5085 |
| | 4965 | 5960 | 13895 | 14534 | 22724 | 18476 | 18472 | 18083 | 6734 | 4997 | 23491 | 17752 |
| | 26978 | 29291 | 24877 | 24879 | 27070 | 7649 | 1949 | 21111 | 19488 | 21730 | 23945 | 21686 |
| | 27651 | 27650 | 25269 | 26607 | 2212 | 12263 | 12554 | 13918 | 14019 | 13994 | 24823 | |
| 306: | 4073 | 22555 | 4100 | 27267 | 26975 | 4996 | 15934 | 19811 | 15228 | 25434 | 15706 | 9550 |
| | 6935 | 23481 | 1480 | 1482 | 22482 | 23641 | 21374 | 10611 | 11281 | 1517 | 1518 | 20953 |
| | 27704 | 18146 | 5286 | 3202 | 20016 | 12556 | 8797 | 12122 | 11246 | 15875 | 7987 | 28966 |
| | 24975 | 15587 | 1524 | 1520 | 1525 | 22082 | 16220 | 12190 | 17779 | 13034 | 6068 | 14309 |
| | 1994 | 8624 | 24174 | 25476 | 7577 | 15375 | 9142 | 6515 | | | | |
| 307: | 16517 | 13655 | 16944 | 13657 | 7250 | 7253 | 12523 | 12555 | 12496 | 12558 | 12553 | 12525 |
| | 12447 | 12531 | 12529 | 11716 | 12499 | 12463 | 12453 | 11714 | 12577 | 12494 | 11711 | 21462 |
| | 12491 | 12601 | 12582 | 12580 | 21464 | 21465 | 21507 | 21503 | 16115 | 29908 | 3927 | 21531 |
| | 11721 | 12449 | 12456 | 12564 | 12574 | 12579 | 12597 | 4697 | 27420 | 29700 | 887 | 888 |
| | 29909 | 10124 | 10158 | 3563 | 3567 | 2220 | 19295 | 11183 | 6149 | 23835 | 18693 | 5946 |
| | 11374 | 7886 | 10617 | 22967 | 2516 | 25498 | 16862 | 19210 | 19213 | 20295 | 12609 | 20321 |
| | 19214 | 21959 | 21952 | 9615 | 9870 | 2134 | 24575 | 19069 | 12843 | 24557 | 21955 | 9616 |

TABLE 8-continued

| PEP SEQ ID NO: | homolog SEQ ID NOs | | | | | | | | | | |
|---|---|---|---|---|---|---|---|---|---|---|---|
| | 5341 | 17200 | 24499 | 19179 | 16766 | 27442 | 27444 | 27475 | 11328 | 16431 | 22721 | 27181 |
| | 5216 | 30264 | 17131 | 27106 | 28708 | 27417 | 27447 | 877 | 873 | 875 | 871 | 8082 |
| | 6820 | 25860 | 22904 | 13900 | 14638 | 15177 | 21498 | 16830 | 27002 | 26518 | 10906 | |
| 308: | 21299 | 5872 | 17817 | 22477 | 17074 | 5710 | 14819 | 10604 | 17874 | 1813 | 10959 | 10605 |
| | 15093 | 26425 | 26689 | 15978 | 7997 | 20445 | 27568 | 22238 | 24487 | 14436 | 8017 | 11460 |
| | 11177 | 23024 | 7463 | 17377 | 12864 | 16004 | 7043 | 10148 | 5131 | 17879 | 2644 | 4412 |
| | 30069 | 7754 | 23829 | 27906 | 18649 | 18440 | 12984 | 10731 | 1103 | 9112 | 16047 | 10098 |
| | 7912 | 16569 | 16562 | 6731 | 17991 | 27109 | 737 | 4745 | 1628 | 1918 | 8843 | 10143 |
| | 23669 | 15513 | 26808 | 624 | 8628 | 24803 | 29563 | 22820 | 5123 | 10502 | 15852 | 29463 |
| | 22220 | 10856 | 18502 | 23546 | 13041 | 11144 | 7740 | 22616 | 15720 | 20242 | 23531 | 5722 |
| | 20633 | 5177 | 20273 | 19174 | 27912 | 17072 | 2243 | 16163 | 25856 | 5049 | 6431 | 1557 |
| | 7243 | 920 | 10764 | 22406 | 29189 | 5927 | 25074 | 30314 | 11963 | 2240 | 3307 | 17229 |
| | 1852 | 25569 | 23447 | 28980 | 12872 | 29015 | 25605 | 11835 | 16360 | 5509 | 30059 | 20235 |
| | 4232 | 777 | 18344 | 30237 | 16693 | 10540 | 9369 | 8759 | 9835 | 6007 | 24894 | 10066 |
| | 18130 | 29536 | 17856 | 26868 | 3903 | 16811 | 18196 | 21620 | 26548 | 7365 | 15998 | 3435 |
| | 27303 | 23365 | 7429 | 11162 | 26510 | 12980 | 9574 | 23826 | 21579 | 5242 | 18786 | 14691 |
| | 24298 | 12247 | 3422 | 15077 | 5617 | 2735 | 26140 | 997 | 29968 | 12410 | 12430 | 10035 |
| | 14455 | 7492 | 23858 | 24253 | 17897 | 14804 | 22708 | 1951 | 3376 | 2209 | 19943 | 4307 |
| | 28095 | 17187 | 11974 | 15174 | 24900 | 18475 | 20119 | 16286 | 18268 | 17385 | 22117 | 27898 |
| | 8793 | 15872 | 15906 | 4708 | 21261 | 26796 | 17926 | 27187 | 29242 | 3511 | 15315 | 28909 |
| | 14450 | 15500 | 18402 | 15627 | 29217 | 28317 | 25837 | 1144 | 10601 | 28448 | 696 | 19865 |
| | 19308 | 28313 | 24999 | 21607 | 2359 | 23902 | 7170 | 26313 | 18751 | 16086 | 24401 | 23719 |
| | 26186 | 20994 | 6420 | 27239 | 24526 | 5823 | 15225 | 19802 | 25521 | 16776 | 22806 | |
| | 5296 | 9126 | 19695 | 20534 | 28027 | 27517 | 28414 | 17210 | 6379 | 15657 | 5267 | 30048 |
| | 12519 | 10872 | 7999 | 3409 | 15362 | 18419 | 9898 | 24104 | 13253 | 13534 | 12783 | 16649 |
| | 21079 | 7630 | 26772 | 22421 | 1477 | 28203 | 24992 | 8063 | 2672 | 9815 | 13717 | 30388 |
| | 28256 | 22915 | 19937 | 8726 | 10192 | 5739 | 848 | 22943 | 28147 | 3316 | 5705 | 29741 |
| | 13175 | 9919 | 22404 | 1054 | 27138 | 29191 | 24754 | 9604 | 14403 | 23630 | 10191 | 14456 |
| | 29106 | 21213 | 2964 | 12239 | 28568 | 17977 | 6904 | 14167 | 29917 | 25066 | 6760 | 11818 |
| | 10338 | 11895 | 9584 | 13160 | 28158 | 4901 | 13340 | 8682 | 19451 | 2848 | 22433 | 2436 |
| | 25490 | 10991 | 20029 | 19992 | 12490 | 12785 | 26327 | | | | | |
| 309: | 20952 | 3236 | 24334 | 17181 | 27703 | 2623 | 29914 | 6200 | 7062 | 3530 | 3554 | 23659 |
| | 25523 | 881 | 10869 | 12110 | 6449 | 24143 | 20219 | 18629 | 16735 | 28415 | 10036 | 20347 |
| | 20380 | 24855 | 4163 | 9382 | 18086 | 13740 | 12955 | 3770 | 21914 | 17308 | 26890 | 5621 |
| | 4316 | 22499 | 13629 | 7216 | 14424 | 1693 | 15401 | 20539 | 26693 | 4545 | 6048 | 10842 |
| | 24512 | 4305 | 18585 | 2506 | 19115 | 14873 | 12308 | 18961 | 24529 | 9057 | 20738 | 7334 |
| | 29837 | 22519 | 24768 | 3969 | 15041 | 24322 | 23592 | 29505 | 3601 | 11341 | 994 | 29145 |
| | 11268 | 22722 | 19591 | 4525 | 2445 | 29611 | 3707 | 4339 | 23545 | 23449 | 26341 | 20094 |
| | 26889 | 7940 | 9580 | 26304 | 16101 | 5572 | 635 | 10465 | 4954 | 10916 | 15869 | 8855 |
| | 6601 | 3351 | 23384 | 4094 | 29250 | 21718 | 17876 | 2598 | 28965 | 5077 | 21429 | 17490 | 6375 |
| | 25086 | 13446 | 13636 | 23483 | 22483 | 7618 | 2598 | 29424 | 27960 | 18996 | 2440 | 7224 |
| | 13322 | 7785 | 27104 | 8134 | 6761 | 3390 | 3119 | 13435 | 20599 | 17077 | 24289 | 23988 |
| | 18684 | 20468 | 22443 | 27060 | 22953 | 27019 | 17163 | 27831 | 3678 | 18733 | 1346 | 17225 |
| | 3681 | 5554 | 26543 | 26495 | 19458 | 25397 | 1456 | 21781 | 24859 | 9468 | 9688 | 8767 |
| | 27583 | 7360 | 22732 | 20947 | 14430 | 3682 | 8790 | 14166 | 5271 | 28857 | 4601 | 1785 |
| | 6220 | 8856 | 8812 | 14515 | 5548 | 17409 | 11560 | 19742 | 5005 | 1435 | 30386 | 18204 |
| | 11765 | 23599 | 25429 | 24305 | 3499 | 7990 | 5931 | 13351 | 3632 | 7908 | 14951 | 7389 |
| | 24053 | 1667 | 1034 | 21846 | 12920 | 10712 | 17253 | 14508 | 17438 | 17283 | 5056 | 15270 |
| | 6588 | 24518 | 25812 | 8928 | 19389 | 21797 | 1648 | 15618 | 22165 | | | |
| 310: | 27320 | 24987 | 3155 | 1338 | 1958 | 13881 | 9392 | 5380 | 13563 | 19750 | 8872 | 25913 |
| | 27110 | 26243 | 7854 | 7289 | 14448 | 28326 | 27162 | 12993 | 29870 | 16402 | 16956 | 13426 |
| | 7595 | 22122 | 24090 | 19304 | 11864 | 17988 | 24435 | 18484 | 5785 | 18625 | 19889 | 18382 |
| | 5708 | 21735 | 18955 | 9538 | 23623 | 5991 | 16978 | 9399 | 20682 | 16184 | 15467 | 13163 |
| | 12299 | 17857 | 17272 | 10117 | 9126 | 1908 | 20035 | 18868 | 1615 | 22344 | 21292 | 5575 |
| | 23780 | 14761 | 1271 | 2801 | 2661 | 28391 | 13388 | 947 | 29985 | 8245 | 4032 | 23900 |
| | 2123 | | | | | | | | | | | |
| 311: | 6221 | 29064 | 17247 | 6808 | 12617 | 7461 | 25019 | 27320 | 12138 | 11900 | 28785 | 24432 |
| | 20920 | 5932 | 28450 | 24155 | 15601 | 19264 | 24987 | 7778 | 9425 | 9977 | 3155 | 13839 |
| | 8427 | 13528 | 9037 | 22855 | 8895 | 10354 | 1338 | 26530 | 6364 | 28603 | 978 | 30171 |
| | 1958 | 13881 | 17361 | 1702 | 18189 | 20590 | 23012 | 27156 | 27060 | 13620 | 5486 | 27102 |
| | 9677 | 22229 | 9392 | 15962 | 3210 | 8742 | 24082 | 990 | 10488 | 5380 | 17512 | 6124 |
| | 6055 | 13719 | 17369 | 29156 | 12186 | 15574 | 8776 | 13563 | 6889 | 19750 | 20360 | 7363 |
| | 8872 | 28972 | 25913 | 25286 | 27110 | 16970 | 14626 | 19913 | 2952 | 10499 | 8629 | 9397 |
| | 7854 | 7289 | 25142 | 6264 | 25242 | 3113 | 14448 | 20014 | 28326 | 25736 | 851 | 26389 |
| | 29409 | 27162 | 3838 | 4400 | 21345 | 29155 | 19112 | 1496 | 12993 | 29870 | 26415 | 24607 |
| | 16710 | 29604 | 10623 | 23311 | 16956 | 3771 | 3699 | 26331 | 13426 | 28618 | 30342 | 10787 |
| | 22013 | 13395 | 26237 | 19387 | 22122 | 1749 | 7561 | 12534 | 7615 | 6209 | 14740 | 13822 |
| | 10582 | 29510 | 1198 | 29849 | 2778 | 3070 | 3166 | 17352 | 19559 | 9318 | 10204 | 19304 |
| | 11864 | 11889 | 20011 | 11452 | 13280 | 2476 | 24435 | 30405 | 5660 | 11638 | 18484 | 5785 |
| | 24573 | 13152 | 3500 | 14627 | 20999 | 5418 | 8515 | 13432 | 14110 | 18625 | 16324 | 19889 |
| | 23903 | 14217 | 18382 | 22486 | 11208 | 24088 | 18108 | 5708 | 21735 | 18955 | 1869 | 25143 |
| | 29060 | 2007 | 5397 | 18687 | 9538 | 12522 | 23623 | 5991 | 16978 | 19643 | 9399 | 28296 |
| | 9636 | 29475 | 29781 | 23052 | 2283 | 1872 | 2649 | 25655 | 16184 | 15467 | 27532 | |
| | 22123 | 13163 | 23406 | 23689 | 20203 | 25024 | 28677 | 26110 | 22300 | 16840 | 12299 | 13125 |
| | 22619 | 23418 | 17857 | 17272 | 1059 | 17654 | 18868 | 2175 | 1615 | 2433 | 22344 | 3860 |
| | 13709 | 5536 | 13550 | 10665 | 16641 | 9608 | 18406 | 26357 | 25798 | 10449 | 9776 | 23647 |
| | 12590 | 8900 | 3871 | 27728 | 25721 | 21292 | 23335 | 24835 | 5575 | 23780 | 14761 | 26853 |
| | 4020 | 1271 | 22742 | 23275 | 7890 | 9028 | 27304 | 8248 | 6207 | 23774 | 13864 | 6901 |

TABLE 8-continued

| PEP SEQ ID NO: | homolog SEQ ID NOs | | | | | | | | | | |
|---|---|---|---|---|---|---|---|---|---|---|---|
| | 12323 | 28812 | 5966 | 23795 | 779 | 8321 | 18640 | 15951 | 7688 | 14971 | 10176 | 28391 |
| | 13388 | 1939 | 18213 | 23163 | 9301 | 25502 | 7903 | 22199 | 947 | 14605 | 21289 | 21454 |
| | 22941 | 28142 | 19272 | 10044 | 22584 | 8166 | 13412 | 8832 | 24883 | 19366 | 29985 | 8245 |
| | 28021 | 18519 | 30379 | 9864 | 4032 | 8721 | 22066 | 14766 | 1086 | 24339 | 17531 | |
| 312: | 29436 | 14850 | 13477 | 2138 | 3208 | 3901 | 17105 | 2948 | 7829 | 14379 | 21505 | 29152 |
| | 6268 | 10681 | 7413 | 1697 | 1731 | 7698 | 8049 | 13604 | 29275 | 29284 | 9724 | 13742 |
| | 1912 | 21193 | 8715 | 7643 | 7828 | 6865 | 24632 | 20340 | 13530 | 7677 | 13192 | 7650 |
| | 2984 | 3158 | 979 | 13456 | 6629 | 12057 | 26973 | 23946 | 3277 | 12182 | 17057 | 2940 |
| | 27892 | 16501 | 6452 | 2036 | 11240 | 6210 | 22683 | 3338 | 29324 | 4421 | 21469 | 20398 |
| | 7304 | 3711 | 8803 | 17032 | 4068 | 13005 | 20760 | 28766 | 1534 | 5146 | 20442 | 11809 |
| | 25387 | 26506 | 13006 | 18535 | 7196 | 7064 | 7797 | 19077 | 5312 | 3279 | 8228 | 20792 |
| | 18218 | 17456 | 21741 | 28268 | 3449 | 1481 | 24411 | 24354 | 25922 | 1317 | 29360 | 20125 |
| | 30411 | 3217 | 23290 | 13664 | 3219 | 25611 | 15880 | 25305 | 24248 | 20131 | 7112 | 2860 |
| | 10646 | 5156 | 1470 | 1142 | 7481 | 27379 | 21217 | 6230 | 16593 | 24413 | 20460 | 13800 |
| | 16362 | 8125 | 29539 | 20075 | 11470 | 1373 | 26316 | 5280 | 7442 | 9227 | 24646 | 18094 |
| | 7327 | 7675 | 20848 | 17411 | 10319 | 5924 | 24410 | 6609 | 3336 | 26729 | 13018 | 1166 |
| | 30256 | 14697 | 2319 | 12709 | 15730 | 1236 | 20681 | 10163 | 8239 | 19379 | 2773 | 13935 |
| | 9389 | 23802 | 17412 | 25072 | 16369 | 18560 | 16294 | 18464 | 29689 | 24938 | 5940 | 29678 |
| | 23107 | 19130 | 20049 | 9432 | 5741 | 3798 | 7143 | 5470 | 18614 | 26706 | 20439 | |
| | 19245 | 18180 | 22739 | 29232 | 17824 | 7846 | 24483 | 6980 | 19439 | 28063 | 28034 | 28517 |
| | 25763 | 20531 | 15282 | 7841 | 21094 | 8144 | 23215 | 26615 | 21259 | 26797 | 24388 | 18397 |
| | 27274 | 2891 | 17860 | 21646 | 29940 | 13321 | 1420 | 9912 | 19499 | 21628 | 3982 | 29311 |
| | 7967 | 16916 | 7737 | 29790 | 1567 | 25570 | 914 | 5088 | 16568 | 8596 | 6487 | 4080 |
| | 17527 | 3796 | 28784 | 3642 | 28118 | 11444 | 3001 | 19749 | 15976 | 20597 | 22491 | 23919 |
| | 18063 | 1508 | 15331 | 27385 | 17740 | 20542 | 13927 | 23800 | 29486 | 7823 | 7753 | 11283 |
| | 24645 | 19328 | 16305 | 3555 | 7085 | 4166 | 1076 | 9070 | 13431 | 15843 | 29128 | 22802 |
| | 16427 | 27445 | 7383 | 15299 | 10655 | 29283 | 13136 | 6028 | 12296 | 11261 | 17252 | 8509 |
| | 7087 | 29978 | 13414 | 26066 | 14846 | 9161 | 1622 | 29281 | 29277 | 28982 | 28106 | 1945 |
| | 1948 | 3473 | 19244 | 22787 | 14026 | 7390 | 9284 | 1214 | 14000 | 26960 | 8568 | 8408 |
| | 26923 | 25805 | 7557 | 17660 | 28819 | 27080 | 1854 | 2004 | 20328 | 27090 | 21887 | 8492 |
| | 18262 | 16472 | 13196 | 19626 | 10568 | 1737 | 14022 | 24551 | 29274 | 5794 | 12100 | 22587 |
| | 16387 | 29535 | 4332 | | | | | | | | | |
| 313: | 17074 | 1813 | 10959 | 10605 | 26425 | 20445 | 24487 | 8017 | 11177 | 23024 | 17377 | 4412 |
| | 23829 | 27906 | 18440 | 12984 | 1103 | 9112 | 10098 | 7912 | 16569 | 6731 | 17991 | 27109 |
| | 15513 | 5123 | 29463 | 18502 | 23546 | 11144 | 7740 | 15720 | 23531 | 20633 | 5177 | 20273 |
| | 19174 | 17072 | 25856 | 6431 | 1557 | 7243 | 920 | 29189 | 5927 | 25074 | 3307 | 25569 |
| | 23447 | 12872 | 29015 | 25605 | 20235 | 18344 | 30237 | 16693 | 10540 | 9369 | 8759 | 6007 |
| | 24894 | 17856 | 3903 | 18196 | 7365 | 15998 | 3435 | 27303 | 23365 | 26510 | 12980 | 21579 |
| | 5242 | 14691 | 24298 | 12247 | 26140 | 997 | 12410 | 12430 | 14455 | 7492 | 17897 | 14804 |
| | 2209 | 19943 | 4307 | 28095 | 17187 | 24900 | 18475 | 16286 | 17385 | 22117 | 27898 | 8793 |
| | 15872 | 15906 | 26796 | 29242 | 3511 | 28909 | 14450 | 15500 | 28317 | 10601 | 28448 | 24999 |
| | 6679 | 2359 | 26313 | 18751 | 16086 | 24401 | 23719 | 26186 | 28878 | 24526 | 15225 | 16776 |
| | 22806 | 5296 | 22030 | 19695 | 27517 | 28414 | 17210 | 6379 | 30048 | 7999 | 3409 | 15362 |
| | 18419 | 24104 | 1477 | 2672 | 9815 | 13717 | 30388 | 28256 | 19937 | 8726 | 5739 | 3316 |
| | 23630 | 10191 | 14456 | 28568 | 17977 | 6904 | 11818 | 9584 | 13160 | 28158 | 8682 | 2436 |
| | 25490 | 10991 | 12785 | | | | | | | | | |
| 314: | 9654 | 9673 | 21777 | 15580 | 11528 | 13502 | 11533 | 23861 | 24407 | 28881 | 9929 | 15909 |
| | 2026 | 2024 | 7638 | 7707 | 18981 | 4927 | 13475 | 6598 | 27339 | 12683 | 27159 | 8136 |
| | 11205 | 14840 | 17413 | 8976 | 21085 | 5071 | 2448 | 10342 | 18420 | 21118 | 28447 | 1024 |
| | 3282 | 9796 | 8951 | 7939 | 21197 | 22681 | 27449 | 24935 | 6736 | 18000 | 11318 | 880 |
| | 17374 | 13543 | 10709 | 4698 | 5976 | 1821 | 30380 | 4667 | 8746 | 1571 | 1995 | 19769 |
| | 9883 | 27269 | 14225 | 28504 | 20918 | 24317 | 28199 | 29834 | 21756 | 6606 | 12161 | |
| | 16555 | 27422 | 20200 | 16342 | 10305 | 17133 | 15606 | 7528 | 12805 | 18973 | 5126 | 23875 |
| | 7430 | 19393 | 20409 | 26205 | 14250 | 20631 | 18778 | 5604 | 18595 | 7297 | 16963 | 15136 |
| | 15135 | 19183 | 12794 | 27123 | 20160 | 27325 | 8420 | 18843 | 3853 | 8018 | 7422 | 10462 |
| | 30217 | 1449 | 15623 | 24442 | 29425 | 30351 | 28856 | 5115 | 4153 | 9250 | 4081 | 7562 |
| | 19629 | 4705 | 17899 | 21080 | 7799 | 23958 | 28418 | 11541 | 4323 | 24962 | 4441 | 5928 |
| | 19504 | 22840 | 23320 | 16031 | 10320 | 15441 | 12039 | 6174 | 25674 | 29249 | 4442 | 20579 |
| | 19864 | 6356 | 22935 | 25802 | 2113 | 10844 | 20659 | 1874 | 28045 | 20108 | 13080 | 11030 |
| | 26034 | 20373 | 5727 | 27347 | 24097 | 13266 | 28543 | 2125 | 1297 | 3298 | 21535 | 26376 |
| | 19745 | 20768 | 10468 | 29066 | 26645 | 29554 | 20649 | 11031 | 2131 | 2254 | 4730 | 22057 |
| | 16885 | 8070 | 10596 | 14924 | 21006 | 28643 | 27597 | 3628 | 10128 | 24115 | 24861 | 12868 |
| | 4090 | 22353 | 2006 | 4106 | 679 | 20010 | 24600 | 27798 | 19820 | 12528 | 19062 | 8510 |
| | 27025 | 25014 | 27688 | 8284 | 3995 | 9618 | 18099 | 16934 | 4933 | 1952 | 13825 | 2931 |
| | 5249 | 12748 | 8512 | 9718 | 17730 | 27686 | 26250 | 14669 | 18570 | 17231 | 13642 | 19946 |
| | 9136 | 11816 | 2140 | 13857 | 11842 | 29791 | 8461 | 22782 | 8554 | 19208 | 18717 | 20751 |
| | 29893 | 13799 | 26993 | 622 | 8452 | 7662 | 27919 | 12893 | 7851 | 6094 | 8543 | 3579 |
| | 29612 | 8818 | 29889 | 5042 | 9234 | 3565 | 13553 | 30290 | 22431 | 4025 | 18277 | 10401 |
| | 23490 | 30353 | 26497 | 19487 | 18167 | 26040 | 16434 | 29150 | 12068 | 11858 | 9622 | 5826 |
| | 12216 | 14178 | 7205 | 5038 | 20245 | 30228 | 20272 | 6346 | 25653 | 21664 | 4904 | 10032 |
| | 29906 | 11628 | 7563 | 13947 | 16316 | 3321 | 11534 | | | | | |
| 315: | 3118 | 4379 | 29540 | 2230 | 27094 | 3912 | 25003 | 2178 | 21097 | 303 | 11912 | 6746 |
| | 5259 | 23092 | 8636 | 22040 | 13730 | 19057 | 8657 | 837 | 6085 | 7368 | 22651 | 23492 |
| | 29662 | 25823 | 22109 | 673 | 5141 | 29560 | 23755 | 2734 | 22886 | 23408 | 13219 | |
| 316: | 6564 | 7427 | 6336 | 20668 | 22550 | 26457 | 13359 | 16779 | 26477 | 19000 | 11179 | 17036 |
| | 3121 | 30118 | 27987 | 15803 | 14623 | 27522 | 26779 | 9522 | 5758 | 29784 | 11115 | 24890 |
| | 9393 | | | | | | | | | | | |

TABLE 8-continued

| PEP SEQ ID NO: | homolog SEQ ID NOs | | | | | | | | | | |
|---|---|---|---|---|---|---|---|---|---|---|---|
| 317: | 22698 | 12832 | 6510 | 17834 | 3265 | 3266 | 15773 | 10250 | 2204 | 30051 | 2238 | 8405 |
|  | 5904 | 17661 | 6167 | 4285 | 19376 | 6130 | 26175 | 5869 | 28747 | 5449 | 6624 | 7814 |
|  | 25438 | 21333 | 12669 | 24544 | 2355 | 16895 | 23343 | 16933 | 2968 | 9669 | 14563 | 7311 |
|  | 28933 | 17404 | 27009 | 12245 | 2219 | 21729 | 27869 | 23389 | 12413 | 20658 | 9323 | 7193 |
|  | 16576 | 8475 | 24849 | 10509 | | | | | | | | |
| 318: | 18449 | 21998 | 22263 | 19277 | 5755 | 4138 | 9752 | 21886 | 17107 | 20954 | 21871 | 21867 |
|  | 21863 | 21857 | 21855 | 21829 | 21827 | 21820 | 21795 | 21793 | 21792 | 21789 | 21785 | 21772 |
|  | 21771 | 21766 | 21765 | 21761 | 20959 | 20950 | 20946 | 20941 | 20919 | 20917 | 20914 | 20910 |
|  | 20905 | 20881 | 20877 | 20873 | 20868 | 20867 | 20831 | 20827 | 20825 | 20821 | 20820 | 20790 |
|  | 20787 | 20782 | 21824 | 21818 | 20785 | 21897 | 20637 | 20745 | 19572 | 20780 | 20608 | 19762 |
|  | 19717 | 19575 | 19571 | 20743 | 20710 | 20709 | 20708 | 20705 | 20679 | 20676 | 20674 | 20669 |
|  | 20641 | 20638 | 20636 | 20635 | 20605 | 20603 | 20600 | 20598 | 19756 | 19752 | 19721 | 19715 |
|  | 19712 | 19710 | 19694 | 19693 | 19691 | 19689 | 19687 | 19660 | 19657 | 19655 | 19654 | 19620 |
|  | 19616 | 19612 | 19609 | 19604 | 19567 | 19516 | 20741 | 20740 | 20667 | 19656 | 19759 | 20712 |
|  | 19753 | 19570 | 20746 | 19523 | 13571 | 25848 | 19519 | 18302 | 24610 | 22379 | 6469 | 17349 |
|  | 24271 | 7720 | 21370 | 6978 | 1196 | 24814 | 10106 | 5217 | 7616 | 24409 | 4076 | 6384 |
|  | 7983 | 24152 | 23262 | 24732 | 19225 | 13648 | 20811 | 1040 | 24592 | 9450 | 22410 | 19949 |
|  | 10476 | 13355 | 16531 | 19147 | 5456 | 11070 | 1883 | 20473 | 18871 | 4920 | 23294 | 23753 |
|  | 3891 | 14199 | 30174 | 26494 | 26403 | 26512 | 26413 | 12319 | 17214 | 27157 | 23022 | 13188 |
|  | 24085 | 18599 | 29112 | 4486 | 21763 | 11104 | 16652 | 7995 | 11615 | 6242 | 4565 | 29478 |
|  | 6514 | 751 | 29501 | 16056 | 18737 | 12351 | 23018 | 18292 | 4444 | 4445 | 3521 | 4448 |
|  | 17267 | 4418 | 11430 | 11427 | 8643 | 15491 | 13686 | 6088 | 25417 | 24759 | 11563 | 24750 |
|  | 24718 | 24753 | 13852 | 30117 | 15661 | 26934 | 28121 | 10590 | 26942 | 1316 | 1320 | 20034 |
|  | 15779 | 15535 | 30070 | 14860 | 28134 | 1625 | 2698 | 23360 | 24636 | 11118 | 11119 | 10752 |
|  | 22693 | 18670 | 22670 | 22700 | 22307 | 18243 | 29362 | 22720 | 11958 | 24449 | 1566 | 12619 |
|  | 10543 | 5772 | 22625 | 24323 | 5775 | 22034 | 6513 | 14730 | 2754 | 30114 | 17842 | 26470 |
|  | 10704 | 17770 | 30003 | 2442 | 8480 | 22913 | 19311 | 759 | 26087 | 11626 | 13701 | 13695 |
|  | 1133 | 24587 | 23737 | 28983 | 3745 | 12333 | 6905 | 22007 | 12137 | 23735 | 29010 | 29002 |
|  | 13707 | 22819 | 14237 | 4567 | 29009 | 12336 | 24589 | 22912 | 2145 | 29901 | 15075 | 14268 |
|  | 22966 | 29012 | 12338 | 27965 | 27967 | 16836 | 23001 | 6894 | 24717 | 14175 | 6896 | 18284 |
|  | 3719 | 3597 | 1208 | 28387 | 19098 | 18135 | 11462 | 11147 | 13685 | 11605 | 28136 | 27271 |
|  | 12387 | 6927 | 10747 | 29654 | 5321 | 26112 | 16485 | | | | | |
| 319: | 26025 | 18678 | 23145 | 13256 | 2599 | 3183 | 13467 | 25819 | 16238 | 13308 | 6705 | 1683 |
|  | 15932 | 20103 | 30009 | 21685 | 3348 | 10360 | 26570 | 15434 | 748 | 26368 | 14375 | 13242 |
|  | 23151 | 7201 | 17322 | 1161 | 6545 | 9836 | 10114 | 3229 | 25937 | 8839 | 7235 | 949 |
|  | 17714 | 739 | 5568 | 6916 | 2999 | 13445 | 18676 | 902 | 26933 | 4874 | 25186 | 19390 |
|  | 27280 | 18674 | 10718 | 23528 | 29206 | 8357 | 28616 | 12136 | 21610 | 22770 | 7991 | 29517 |
|  | 2812 | 7767 | 16949 | 2443 | 23899 | 30090 | 5231 | 23613 | 24635 | 17792 | 2197 | |
| 321: | 5713 | 5731 | 7666 | 23694 | 22911 | 18150 | 26649 | 2034 | 10177 | 30006 | 8001 | 4692 |
|  | 29033 | 14395 | 29544 | 19248 | 15443 | 10544 | 24797 | 10873 | 7935 | 29003 | 15255 | 4236 |
|  | 3050 | 19552 | 16592 | 11607 | 21180 | 26293 | 619 | 16587 | 5988 | 9434 | 13332 | 14583 |
|  | 23776 | | | | | | | | | | | |
| 322: | 28075 | 20429 | 25267 | 20452 | 5815 | 20569 | 12740 | 24463 | 12571 | 21240 | 28866 | 16145 |
|  | 7644 | 10890 | 4953 | 14249 | 1859 | 26961 | 28687 | 16646 | 13103 | 19372 | 1075 | 11012 |
|  | 28763 | 13279 | 16909 | 18634 | 14200 | 14252 | 15965 | 3957 | 14353 | 22537 | 27917 | 13290 |
|  | 24094 | 3042 | 24671 | 16559 | 8844 | 17230 | 26537 | 11160 | 4101 | 19149 | 14848 | 16476 |
|  | 19844 | 21324 | 25887 | 5879 | 25536 | 7634 | 22302 | 3583 | 5654 | 13582 | 8655 | 16714 |
|  | 18408 | 25134 | 25133 | 2085 | 9245 | 2169 | 25665 | 7734 | 7755 | 7733 | 7758 | 1434 |
|  | 1433 | 29679 | | | | | | | | | | |
| 323: | 26396 | 29158 | 4822 | 18244 | 12967 | 17134 | 11009 | 16725 | 8007 | 2954 | 8852 | 27845 |
|  | 2629 | 18814 | 10620 | 2865 | 8453 | 2299 | 15558 | 6294 | 2856 | 10541 | 15612 | 23099 |
|  | 28255 | 23798 | 22907 | 19283 | 14119 | 20596 | 6506 | 2591 | 2566 | 19934 | 27102 | 12576 |
|  | 19816 | 15649 | 20313 | | | | | | | | | |
| 324: | 4695 | 7074 | 23887 | 24207 | 15227 | 11280 | 12210 | 8914 | 8949 | 17044 | 27663 | 17180 |
|  | 23934 | 23176 | 23961 | 23927 | 27394 | 27343 | 28223 | 12241 | 26039 | 25285 | 25527 | 6322 |
|  | 8016 | 9270 | 29224 | 24488 | 28695 | 29408 | 14433 | 24132 | 8404 | 3641 | 14676 | 22027 |
|  | 4437 | 2493 | 7857 | 29733 | 5336 | 25833 | 17806 | 10942 | 20040 | 8399 | 946 | 10186 |
|  | 25139 | 16681 | 11108 | 8605 | 28765 | 30462 | 30451 | 10230 | 11253 | 29561 | 11973 | 9044 |
|  | 23566 | 6539 | 28864 | 8447 | 29005 | 24017 | 21967 | 4180 | 22319 | 4209 | 10735 | 18450 |
|  | 12851 | 26694 | 23680 | 19205 | 7685 | 11739 | 11644 | 19428 | 24159 | 19804 | 3474 | 25828 |
|  | 5463 | 5645 | 3079 | 6583 | 4887 | 21096 | 3694 | 11173 | 23896 | 23179 | 23966 | 23964 |
|  | 7714 | 21631 | 23889 | 23182 | 23185 | 23183 | 23935 | 17359 | 25599 | 5662 | 15746 | 2535 |
|  | 14447 | 11777 | 20276 | 10765 | 26312 | 12608 | 6708 | 5902 | 20403 | 9884 | 10697 | 22878 |
|  | 7423 | 20522 | 19966 | 5193 | 10888 | 3855 | 20278 | 5961 | 2105 | 21958 | 11736 | 15766 |
|  | 15662 | 9897 | 25980 | 20518 | 17889 | 9174 | 18487 | 7192 | 21168 | 18308 | 22258 | 5063 |
|  | 19649 | 5527 | 10969 | 10930 | 10821 | 21447 | 16001 | 11131 | 24448 | 20463 | 6646 | 5955 |
|  | 25911 | 10041 | 6833 | 12380 | 23924 | 4084 | 18274 | 6410 | 8977 | 11799 | 16364 | 19324 |
|  | 27752 | 9060 | 5578 | 5505 | 9725 | 2564 | 20300 | 8874 | 5198 | 23929 | 8495 | 17165 |
|  | 21496 | | | | | | | | | | | |
| 325: | 8611 | 9653 | 26340 | 19789 | 12546 | 28386 | 8352 | 23722 | 17235 | 25214 | 4644 | 11567 |
|  | 17882 | 18815 | 735 | 8786 | 21982 | 29719 | 19123 | 15025 | 1540 | 22947 | 4036 | 7410 |
|  | 24039 | 22052 | 2033 | 25780 | 20845 | 21131 | 691 | 9520 | 9519 | 9596 | 15571 | 10045 |
|  | 17616 | 3844 | 20503 | 6259 | 6256 | 10247 | 1982 | 23494 | 23476 | 20841 | 17362 | 28976 |
|  | 7855 | 24763 | 28796 | 26709 | 28664 | 16116 | 16110 | 16108 | 16105 | 16150 | 20118 | 11117 |
|  | 15068 | 10850 | 16042 | 15543 | 22735 | 3988 | 25929 | 8584 | | | | |
| 326: | 5173 | 5172 | 5168 | 5169 | 27559 | 25561 | 19375 | 19137 | 18295 | 18861 | 19386 | 2279 |
|  | 17868 | 23434 | 16705 | 19125 | 27453 | 8946 | 13210 | 24880 | 24875 | 18157 | 18159 | 15947 |
|  | 14260 | 14257 | 14254 | 15950 | 15944 | 10855 | 11632 | 28068 | 19547 | 1934 | 24077 | 830 |

TABLE 8-continued

| PEP SEQ ID NO: | homolog SEQ ID NOs | | | | | | | | | | |
|---|---|---|---|---|---|---|---|---|---|---|---|
| | 25657 | 25654 | 14069 | 17785 | 23074 | 6277 | 6628 | 6651 | 25105 | 26050 | 29300 | 12395 |
| | 8739 | 18551 | 6717 | 11421 | 11419 | 13511 | 20310 | 29056 | 16028 | 21964 | 7335 | 26976 |
| | 8151 | 4386 | 27197 | 12982 | 20558 | 14902 | | | | | | |
| 327: | 6523 | 2683 | 29664 | 3149 | 14631 | 26698 | 13673 | 25648 | 9595 | 7270 | 4370 | 4300 |
| | 5542 | 5514 | 12826 | 22624 | 12508 | 27027 | 27382 | 28234 | 28229 | 28231 | 19433 | 26539 |
| | 3935 | 20377 | 28506 | 21950 | 18357 | 27665 | 18383 | 28986 | | | | |
| 328: | 19276 | 1841 | 14664 | 18388 | 5957 | 14824 | 14760 | 7167 | 1035 | 18155 | 11169 | 16259 |
| | 26096 | 13766 | 7607 | 22092 | 22095 | 29366 | 9481 | 17141 | 22928 | 7514 | 22125 | 21071 |
| | 23933 | 7949 | 9348 | 21774 | | | | | | | | |
| 329: | 6168 | 16169 | 9899 | 16853 | 16513 | 7735 | 21101 | 28633 | 22355 | 25004 | 21037 | 27223 |
| | 2177 | 17270 | 22039 | 8241 | 21036 | 18249 | 14094 | 15487 | 24629 | 13783 | 23668 | 30074 |
| | 25464 | 8907 | 14778 | 4638 | 29988 | 23768 | 20567 | | | | | |
| 330: | 7943 | 16938 | 1020 | 19490 | 10414 | 28426 | 23340 | 13212 | 5437 | 23076 | 27780 | 9605 |
| | 2775 | 15369 | 5333 | 6213 | 5358 | 6217 | 17628 | 17625 | 18439 | 16130 | 16132 | 6753 |
| | 5251 | 21776 | 6751 | 2354 | 25879 | 23170 | 5391 | 22896 | 17441 | 24539 | 26184 | 17715 |
| | 15866 | 16050 | 4846 | 11166 | 8132 | 24293 | 8769 | 25206 | 28037 | | | |
| 331: | 24465 | 21401 | 11218 | 19349 | 9644 | 15930 | 1235 | 8351 | 23088 | 10788 | 5765 | 5761 |
| | 5738 | 26337 | 7764 | 5228 | 23488 | 11190 | 11189 | 29202 | 12910 | 7661 | 27041 | 5745 |
| | 14084 | 14115 | 29789 | 28902 | 28922 | 27512 | 9542 | 7402 | 10727 | 6303 | 29079 | 716 |
| | 8930 | 24123 | 23841 | 1025 | 2086 | 2205 | 9419 | 7665 | 17363 | 11564 | 30184 | 30212 |
| | 19808 | 370 | 27115 | 23497 | | | | | | | | |
| 332: | 9181 | 25440 | 11322 | 10394 | 23194 | 10121 | 4183 | 13824 | 7065 | 8038 | 24714 | 10120 |
| | 11384 | 7161 | 23913 | 10483 | 2137 | 29194 | 28776 | 2787 | 24809 | 21173 | 6535 | 3144 |
| | 4366 | 9814 | 28454 | 25455 | 15353 | 2377 | 1885 | 27695 | 21552 | 9640 | 18639 | 27572 |
| | 20691 | 1325 | 13958 | 18343 | 26799 | 29048 | 2200 | 20277 | | | | |
| 333: | 26921 | 7592 | 26493 | 11706 | 14645 | 6556 | 17968 | 10624 | 17587 | 25908 | 2924 | 17103 |
| | 13861 | 10511 | 27191 | 24114 | 5142 | 29172 | 28080 | 11050 | 10690 | 1510 | 4359 | 21319 |
| | 6781 | 8848 | 15538 | 19869 | 14896 | 29647 | 5668 | 19736 | 10237 | 20371 | 16072 | 24961 |
| | 24791 | 19941 | 12201 | 8982 | 17218 | 10782 | 10597 | 6729 | 11210 | 14810 | 18962 | 23027 |
| | 10203 | 13462 | 14488 | 9807 | 4423 | 12684 | 8425 | 8870 | 3915 | 21985 | 16768 | 8704 |
| | 1565 | 23789 | 23820 | 7418 | 9151 | 17139 | 10241 | 16395 | 28549 | 16696 | 26260 | 1956 |
| | 1703 | 9974 | 14018 | 11287 | 4189 | 8195 | 14013 | 13078 | 6214 | 7142 | 19515 | 15065 |
| | 19121 | 25225 | 16111 | 21188 | 22049 | 14688 | 8348 | 23070 | 7954 | 27039 | 22516 | 29328 |
| | 27544 | 4425 | 29377 | 21474 | 16358 | 19897 | 29844 | 22622 | 10011 | 25784 | 5095 | 29886 |
| | 10887 | 21494 | 1699 | 17405 | 6742 | 5555 | 7654 | 6372 | 20556 | 11433 | 18121 | 711 |
| | 28322 | 5144 | 26167 | 22414 | 16549 | 16597 | 15798 | 17840 | 25393 | 26386 | 13330 | 18534 |
| | 8148 | 28509 | 25713 | 12258 | 16300 | 6266 | 13692 | 9914 | 17936 | 11424 | 2357 | 1495 |
| | 24304 | 21624 | 17464 | 20510 | 27781 | 27048 | 20786 | 14629 | 25414 | 4338 | 23895 | 14753 |
| | 18215 | 6269 | 5292 | 20280 | 16964 | 15394 | 12038 | 24873 | 17753 | 29686 | 6533 | 2426 |
| | 1488 | 9811 | 15994 | 28936 | 8206 | 13312 | 20408 | 22408 | 29102 | 26302 | 1554 | 20563 |
| | 2819 | 22268 | 7694 | 26930 | 2121 | 28099 | 11690 | 1787 | 19364 | 26629 | 15073 | 5495 |
| | 4250 | 3598 | 15984 | 6688 | 6941 | 27400 | 25610 | 20744 | 21572 | 5473 | 26332 | 11258 |
| | 25472 | 20128 | 27341 | 8319 | 778 | 9788 | 13491 | 8473 | 9785 | 13060 | 2305 | 4534 |
| | 11432 | 7240 | 19025 | 6134 | 13537 | 23825 | 11385 | 13347 | 21546 | 2263 | 27192 | 14999 |
| | 11669 | 16530 | 10070 | 3837 | 26130 | 15679 | 11385 | 3071 | 7367 | 19028 | 15996 | 24811 |
| | 25231 | 18760 | 23302 | 2797 | 1180 | 30019 | 17130 | 18486 | 10099 | 4640 | 12422 | 2256 |
| | 28757 | 11972 | 10587 | 6380 | 15768 | 2288 | 28253 | 5920 | 24383 | 26272 | 6630 | 30366 |
| | 28281 | 2446 | 20384 | 8724 | 627 | 4476 | 29103 | 971 | 8313 | 3464 | 11450 | 30022 |
| | 8792 | 10444 | 3352 | 16722 | 6442 | 16727 | 30340 | 27469 | 22973 | 3264 | 26011 | 29776 |
| | 17287 | 15743 | 18432 | 17880 | 26952 | 13961 | 25018 | 18340 | 19202 | 15274 | 5435 | 21995 |
| | 15160 | 4212 | 943 | 29709 | 23128 | 8036 | 17273 | 18379 | 30305 | 28533 | 6803 | 3533 |
| | 26885 | 23893 | 6928 | 28065 | 24832 | 21918 | 2499 | 23892 | 18660 | 6839 | 28562 | 12495 |
| | 25452 | 23372 | 951 | 8972 | 22734 | 12787 | 20346 | 28751 | 14496 | 6087 | 8910 | 8697 |
| | 11602 | 18658 | 28451 | 26909 | 4399 | 6778 | 28644 | 7020 | 24981 | 22402 | 17087 | 29329 |
| | 23420 | 28028 | 26733 | 8106 | 21509 | 19461 | 15474 | 16610 | 10594 | 29838 | 23279 | 23544 |
| | 16578 | 19700 | 28770 | 27715 | 26058 | 23037 | 15867 | 30376 | 22462 | 18967 | 29967 | 27622 |
| | 2882 | 11130 | 28361 | 5759 | 15942 | 18029 | 24677 | 19079 | 21622 | 29035 | 17723 | 25854 |
| | 3944 | 6911 | 1013 | 1285 | 3866 | 15522 | 21141 | 9022 | 21237 | 8516 | 25349 | 10774 |
| | 23023 | 28634 | 29555 | 4833 | 25567 | 30236 | 21630 | 680 | 9494 | 15257 | 10339 | 5379 |
| | 30394 | 2868 | 5681 | 30347 | 2708 | 10852 | 12986 | 15666 | 14674 | 6885 | 18610 | 11485 |
| | 20890 | 22892 | 11785 | 5290 | 25687 | 14615 | 13909 | 17379 | 22873 | 22179 | 29449 | 5512 |
| | 11968 | 8969 | 21497 | 22024 | 13845 | 29869 | 28636 | 18910 | 1183 | 17646 | 24431 | 22296 |
| | 16313 | 4458 | 27105 | 5773 | 11788 | 26122 | 16133 | 29980 | 17375 | 28439 | 27195 | 23332 |
| | 11211 | 11001 | 15279 | 27997 | 27141 | 20862 | 27769 | 2151 | 20194 | 4217 | 24493 | 25932 |
| | 13065 | 14864 | 7786 | 7203 | 14865 | 7369 | 11416 | 1823 | 28111 | 17268 | 19952 | 20225 |
| | 11929 | 28655 | 23398 | 10698 | 16723 | 21172 | 14799 | 29547 | 2688 | 5893 | 25328 | 24057 |
| | 13650 | 29820 | 21343 | 812 | 1264 | 1169 | 23732 | 14946 | 10923 | 7611 | 13311 | 8602 |
| | 10777 | 20238 | 23184 | 29626 | 23392 | 7238 | 29288 | 3263 | 21728 | 18312 | 12521 | 7257 |
| | 26520 | 5819 | 2658 | 23965 | 18360 | 14324 | 15376 | 11178 | 9599 | 13503 | 22746 | 17189 |
| | 26221 | 2958 | 11993 | 15128 | 16521 | 22064 | 17401 | | | | | |
| 334: | 17584 | 24839 | 25351 | 25790 | 5253 | 27882 | 27330 | 1284 | 24348 | 7347 | 21775 | 6413 |
| | 3799 | 16219 | 22068 | 15991 | 22211 | 25843 | 19950 | 28434 | 29905 | 17960 | 29644 | 26172 |
| | 9257 | 3803 | 12421 | 1767 | 27864 | 19783 | 18725 | 23501 | 21744 | 1328 | 25808 | |
| 335: | 1205 | 1202 | 8703 | 21335 | 24048 | 24042 | 18376 | 12899 | 18378 | 20455 | 6551 | 19940 |
| | 19978 | 19981 | 12825 | 2128 | 18413 | 18415 | 16198 | 3185 | 15855 | 2967 | 2960 | 2966 |
| | 4462 | 28501 | 25905 | 11227 | 28186 | 984 | 986 | 13539 | 20789 | 20758 | 25229 | 24103 |
| | 19988 | 25087 | 21788 | 19912 | 21275 | 19982 | 19909 | 24881 | 18852 | 12055 | 16381 | 12191 |
| | 3089 | 27641 | 10110 | 28531 | 23127 | 14065 | 24960 | 8966 | 11153 | 12488 | 28405 | 19321 |

TABLE 8-continued

| PEP SEQ ID NO: | homolog SEQ ID NOs | | | | | | | | | | |
|---|---|---|---|---|---|---|---|---|---|---|---|
| | 21051 | 17845 | 1936 | 23577 | 27609 | 28429 | 27692 | 27667 | 28424 | 28432 | 27698 | 27637 |
| | 19872 | 18303 | 18438 | 18412 | 11878 | 10396 | 18013 | 9203 | 29169 | 12043 | 6503 | 1965 |
| | 22532 | 14756 | 2898 | 29469 | 15871 | 4778 | 25660 | 29924 | 3826 | 16729 | 20884 | 2141 |
| | 19907 | 14255 | 22922 | 2063 | 26239 | 19936 | 19119 | 21272 | 19915 | 19985 | 19916 | 18368 |
| | 18306 | 18331 | 18333 | 18338 | 17515 | 18481 | 24335 | 19056 | 8109 | 10257 | 21481 | |
| 336: | 27850 | 28787 | 28026 | 26562 | 17207 | 29605 | 25076 | 7242 | 9198 | 9200 | 424 | 17118 |
| | 13373 | 22737 | 1153 | | | | | | | | | |
| 337: | 3810 | 8611 | 17523 | 26405 | 19789 | 12546 | 11748 | 24669 | 1234 | 10024 | 16888 | 15528 |
| | 17235 | 25214 | 4644 | 8485 | 29178 | 11567 | 18815 | 24974 | 12957 | 27030 | 735 | 8786 |
| | 23475 | 21423 | 14874 | 21982 | 4004 | 29719 | 6724 | 10758 | 15025 | 5033 | 1540 | 15117 |
| | 16450 | 9585 | 7687 | 22955 | 18744 | 16796 | 2152 | 2153 | 4039 | 25006 | 25631 | 4196 |
| | 5802 | 2614 | 2033 | 1607 | 18080 | 29921 | 28076 | 18341 | 13401 | 8330 | 23494 | 20841 |
| | 17362 | 1450 | 22986 | 28262 | 11117 | 11357 | 20471 | 9486 | 15543 | 9266 | 8762 | 24787 |
| | 23218 | 29190 | 12248 | 26945 | 29898 | 8006 | 648 | 27416 | 27859 | | | |
| 338: | 1532 | 17999 | 20660 | 20852 | 2298 | 11954 | 13776 | 7351 | 9240 | 11237 | 1902 | 864 |
| | 7458 | 11352 | 5771 | 28801 | 14059 | 8736 | 8763 | 25084 | 15687 | 2005 | 5926 | 12347 |
| | 7054 | 29550 | 23007 | 7315 | 24549 | 14285 | 16812 | 10419 | 11288 | 14847 | 13984 | 3285 |
| | 6329 | 18622 | 1233 | 16886 | 3999 | 18800 | 7680 | 6033 | 17549 | 8031 | 8417 | 15471 |
| | 21865 | 7551 | 5627 | 8229 | 7599 | 16228 | 23341 | 1224 | 26016 | 2100 | 24000 | |
| | 7902 | 3115 | 9357 | 6047 | 8165 | 11186 | 14852 | 20690 | 19002 | 14878 | 14193 | 2130 |
| | 24486 | 24658 | 29371 | 16354 | 13148 | 13299 | 4197 | 23441 | 8614 | 29835 | 6385 | 8661 |
| | 11329 | 2232 | 30390 | 13377 | 4586 | 30292 | 26684 | 4155 | 3368 | 27633 | 9221 | 25619 |
| | 29523 | 9722 | 8015 | 11400 | 20624 | 17918 | 27236 | 25542 | 29054 | 8443 | 8830 | 20507 |
| | 20511 | 9288 | 7810 | 12224 | 23122 | 25274 | 11300 | 16731 | 18057 | 1353 | 28241 | 19257 |
| | 21965 | 24765 | 21694 | 1125 | 7717 | 6791 | 22020 | 1148 | 14224 | 22733 | 24951 | 21649 |
| | 6241 | 9518 | 13158 | 14875 | 24858 | 5084 | 22366 | 7028 | 12202 | 24920 | 17082 | 9127 |
| | 11254 | 30391 | 20015 | 26069 | 24302 | 29448 | 5980 | 26014 | 26315 | 14699 | 2622 | |
| | 18394 | 11319 | 6101 | 27921 | 13860 | 3498 | 1678 | 3084 | 17471 | 29396 | 3095 | 14274 |
| | 17931 | 22106 | 23225 | 9855 | 11936 | 13479 | 19400 | 7777 | 12383 | 17970 | 3162 | 4433 |
| | 22192 | 8713 | 12616 | 17948 | 28288 | 24165 | 15515 | 18838 | 21889 | 7556 | 23834 | 7107 |
| | 11092 | 1129 | 17601 | 9007 | 9789 | 12689 | 14835 | 3141 | 25715 | 2855 | 29595 | 29933 |
| | 15120 | 26443 | 11783 | 11324 | 11522 | 12743 | 25470 | 16063 | 15036 | 3347 | 19495 | 16854 |
| | 18899 | 24201 | 12320 | 22765 | 6488 | 5574 | 26350 | 7078 | 26001 | 13400 | 2218 | 14264 |
| | 7682 | 30017 | 9445 | 12342 | 12203 | 4006 | 29826 | 29693 | 30395 | 10395 | 4382 | 27177 |
| | 23868 | 12291 | 4450 | 15691 | 12714 | 17241 | 23071 | 18444 | 14129 | 22357 | 15241 | 17237 |
| | 19249 | 15343 | 29028 | 21072 | 6097 | 23904 | 4970 | 1907 | 6635 | 4853 | 21640 | 5489 |
| | 1954 | 17033 | 8213 | 22620 | 10867 | 7407 | 25023 | 12557 | 15733 | 27841 | 29063 | 8359 |
| | 11768 | 8523 | 10794 | 7199 | 27601 | 11344 | 15698 | 15562 | 18313 | 25350 | 7109 | 15847 |
| | 16754 | 24819 | 8270 | 29851 | 17635 | 5781 | 25211 | 4572 | 602 | 5629 | 26726 | 21733 |
| | 27410 | 25749 | 17944 | 20520 | 24876 | 14501 | 10115 | 10755 | 7998 | 19299 | 16232 | 13097 |
| | 16748 | 8979 | 7952 | 14568 | 24480 | 29273 | 5197 | 26225 | 27768 | 12870 | 18503 | 28013 |
| | 26560 | 12219 | 11508 | 13068 | 25354 | 6146 | 7354 | 3044 | 8777 | 6995 | 8302 | 9965 |
| | 17333 | 14357 | 15939 | 19984 | 18700 | 16989 | 17416 | 22345 | 4461 | 25893 | 10943 | 30285 |
| | 2135 | 1165 | 5209 | 10901 | 15915 | 11482 | 10549 | 28528 | 3250 | 24130 | 6957 | |
| | 11591 | 11622 | 26697 | 25532 | 8580 | 9770 | 12812 | 22831 | 19560 | 17766 | 11391 | 21678 |
| | 20871 | 8932 | 10629 | 12754 | 18823 | 19085 | 29701 | 3430 | 1588 | 1283 | 7080 | 7660 |
| | 11436 | 13176 | 6315 | 18768 | 28840 | 1822 | 23115 | 16121 | 20995 | 4376 | 16306 | 4524 |
| | 6782 | 15389 | 14317 | 15764 | 15155 | 5082 | 21232 | 16190 | 18907 | 12297 | 14962 | 13933 |
| | 2791 | 13699 | 25215 | 20587 | 14328 | 4661 | 16129 | 25195 | 25196 | 23200 | 8201 | 22384 |
| | 7619 | 11403 | 9694 | 12362 | 18675 | 19398 | 5522 | 29356 | 5552 | 2465 | 8000 | 872 |
| | 26812 | 21277 | 22087 | 20308 | 28842 | 19047 | 14693 | 636 | 13442 | 27334 | 24007 | 23210 |
| | 25337 | 11334 | 29623 | 15011 | 8539 | 12304 | 29752 | 12121 | 28087 | 12117 | 8338 | 29567 |
| | 1465 | 12886 | 28608 | 1938 | 22510 | 964 | 22511 | 23166 | 30028 | 26098 | 26125 | 11479 |
| | 27876 | 734 | 7265 | 17623 | 17621 | 10566 | 11401 | 13938 | 9224 | 6160 | 8933 | 8766 |
| | 16366 | 26385 | 1888 | 10126 | 15926 | 4281 | 9004 | 15702 | 7480 | 20553 | 1549 | 4910 |
| | 19455 | 4245 | 6617 | 8566 | 27120 | 8429 | 29942 | 8400 | 28926 | 17282 | 3874 | 4898 |
| 339: | 26090 | 24906 | 7328 | 13640 | 3987 | 14369 | 14201 | 29751 | 23972 | 19048 | 19124 | 19518 |
| | 16929 | 12836 | 10980 | 5385 | 12514 | 14006 | 11639 | 9621 | 29755 | 9131 | 13564 | 783 |
| | 18177 | 14122 | 16367 | 18197 | 16067 | 10484 | 27976 | 27790 | 10726 | 28360 | 7845 | 26641 |
| | 12573 | 11417 | 1937 | 8810 | 11764 | 27199 | 26491 | 7149 | 27631 | 850 | 24218 | 22409 |
| | 30220 | 23301 | 604 | 12792 | 28356 | 12273 | 24682 | 21304 | 19627 | 21743 | 5612 | 19043 |
| | 5266 | 6456 | 8388 | 22771 | 8450 | 17154 | 17655 | 21229 | 17981 | 24666 | 29419 | 13898 |
| | 2927 | 968 | 25866 | 11437 | 11556 | 29559 | 28036 | 22558 | 28576 | 18030 | 20487 | 13123 |
| | 6229 | 21755 | 4019 | 14826 | 8138 | 13751 | 26764 | 8521 | 15037 | 12464 | 15103 | 18931 |
| | 1990 | 16594 | 2573 | 20483 | 23359 | 14747 | 4684 | 21853 | 9108 | 9107 | 22021 | 22025 |
| | 24031 | 21991 | 26569 | 29011 | 3328 | 15130 | 15099 | 21719 | 26251 | 13720 | 2076 | 26107 |
| | 29685 | 2456 | 2459 | 2455 | 27370 | 27372 | 13269 | 13267 | 451 | 450 | 9730 | 9757 |
| | 7464 | 2859 | 18689 | 21426 | 14657 | 11572 | 11571 | 20099 | 21999 | 21996 | 14338 | 14342 |
| | 14140 | 14363 | 14341 | 5549 | 14372 | 14882 | 14890 | 14886 | 30442 | 10628 | 10627 | 13868 |
| | 14633 | 10603 | 18761 | 17083 | 26475 | 9727 | 16866 | 26608 | 8550 | 21992 | 24316 | 24297 |
| | 2970 | 22223 | 16540 | 16890 | 3910 | 16235 | 4535 | 4961 | 11545 | 28378 | 28077 | 2309 |
| | 14104 | 27167 | 10780 | 13561 | 10432 | 24018 | 30465 | 23865 | 12964 | 12659 | 15841 | 19746 |
| | 26552 | 28337 | 28331 | 28342 | 28339 | | | | | | | |
| 340: | 21770 | 28720 | 10863 | 27545 | 9178 | 26787 | 6519 | 23297 | 20095 | 29341 | 9143 | 13894 |
| | 10082 | 4256 | 17653 | 20883 | 24135 | 13621 | 21762 | 6232 | 3608 | 11358 | 11361 | 1942 |
| | 28197 | 10439 | 21415 | 1254 | 24609 | 25586 | 30150 | 14516 | 8798 | 19201 | 14538 | 15248 |
| | 5015 | 12220 | 11853 | 23977 | 6054 | 29227 | 6328 | 18661 | 3429 | 10058 | 10062 | 22266 |
| | 1003 | 7877 | 1102 | 7303 | 26430 | 26433 | 5031 | 6486 | 24905 | 22466 | 20061 | 18161 |

TABLE 8-continued

| PEP SEQ ID NO: | homolog SEQ ID NOs | | | | | | | | | | |
|---|---|---|---|---|---|---|---|---|---|---|---|
| | 23748 | 28575 | 13516 | 13519 | 1247 | 7513 | 23296 | 25872 | 28950 | 20096 | 12419 | 25604 |
| | 10881 | 10835 | 12150 | 3049 | 28826 | 1057 | 11975 | 11976 | 12001 | 14156 | 28285 | 22231 |
| | 2118 | 3482 | 7434 | 29857 | 28541 | 16535 | 22078 | | | | | |
| 341: | 26090 | 24906 | 7328 | 16079 | 13640 | 1998 | 3987 | 14369 | 10118 | 24547 | 10168 | 19534 |
| | 14201 | 29751 | 23972 | 19048 | 19124 | 19518 | 16929 | 12836 | 10980 | 5385 | 12514 | 8603 |
| | 21615 | 14006 | 9621 | 29755 | 3278 | 9131 | 13564 | 783 | 18177 | 14122 | 16367 | 18197 |
| | 10484 | 27976 | 27790 | 10726 | 28360 | 7845 | 8361 | 7214 | 3978 | 10445 | 26641 | 12573 |
| | 11417 | 1937 | 8810 | 18305 | 17353 | 26604 | 11764 | 14422 | 27199 | 13341 | 7149 | 27631 |
| | 850 | 24218 | 22409 | 8455 | 30360 | 3313 | 24294 | 14091 | 12152 | 23301 | 604 | 28356 |
| | 12273 | 17439 | 23202 | 5642 | 24682 | 21304 | 19627 | 21743 | 5612 | 2420 | 8426 | 27392 |
| | 19043 | 29067 | 5266 | 8170 | 5679 | 6456 | 10383 | 22771 | 8450 | 17154 | 17655 | 21229 |
| | 10695 | 22850 | 20714 | 3703 | 17981 | 27996 | 24666 | 29419 | 13898 | 25251 | 2927 | 968 |
| | 25866 | 11823 | 11437 | 11556 | 29559 | 28036 | 22558 | 28576 | 18030 | 644 | 20487 | 13123 |
| | 6229 | 21755 | 4019 | 11073 | 14826 | 8138 | 4868 | 5476 | 13751 | 26764 | 24215 | 21989 |
| | 8521 | 23457 | 15037 | 29764 | 12464 | 17472 | 1453 | 3416 | 1990 | 16594 | 2573 | 20483 |
| | 22565 | 23359 | 4684 | 14747 | 21853 | 9107 | 9108 | 22028 | 22025 | 22021 | 24031 | 21991 |
| | 26569 | 29011 | 5830 | 3328 | 15099 | 15130 | 21719 | 26251 | 13720 | 2076 | 22740 | 19986 |
| | 24231 | 21220 | 18601 | 26295 | 4537 | 15313 | 1807 | 11247 | 9328 | 2456 | 2455 | 2459 |
| | 27366 | 27372 | 27370 | 13267 | 13269 | 451 | 450 | 9730 | 9757 | 9762 | 588 | 27732 |
| | 10917 | 1804 | 21426 | 14657 | 11572 | 11571 | 15508 | 10874 | 22276 | 21996 | 21999 | 14338 |
| | 14342 | 14140 | 14363 | 14341 | 15131 | 6669 | 14372 | 14890 | 14882 | 14886 | 14908 | 30442 |
| | 13868 | 14633 | 10627 | 10628 | 10603 | 9996 | 18761 | 17083 | 26475 | 9727 | 16415 | 22604 |
| | 16765 | 21893 | 21349 | 21992 | 24297 | 24316 | 13140 | 2970 | 22223 | 16540 | 763 | 16890 |
| | 3910 | 16235 | 11545 | 28378 | 28077 | 2792 | 23797 | 2309 | 14104 | 7723 | 27167 | 10108 |
| | 12589 | 10780 | 13561 | 10432 | 24018 | 30465 | 23865 | 12964 | 15841 | 26552 | 3311 | |
| 342: | 18131 | 3643 | 22334 | 10822 | 30209 | 15630 | 21810 | 27026 | 11320 | 29856 | 23622 | 29187 |
| | 27221 | 8547 | 14689 | 5603 | | | | | | | | |
| 343: | 4916 | 6512 | 345 | 2099 | 26590 | 29097 | 7276 | 21156 | 11819 | 9423 | 11182 | 10242 |
| | 5366 | 29351 | 25711 | 2772 | 18527 | 8710 | 4915 | 11402 | 11843 | 12538 | 3981 | 12632 |
| | 13769 | 9753 | 20717 | 23105 | 611 | 27849 | 16602 | 13617 | 4590 | 11101 | 15611 | 26384 |
| | 29416 | 21142 | 17846 | 14279 | 9447 | 15785 | 3589 | 10641 | 3749 | 6668 | 18679 | 29123 |
| | 29078 | | | | | | | | | | | |
| 344: | 18538 | 5825 | 13713 | 17120 | 16141 | 18556 | 24151 | 1677 | 23605 | 29721 | 20155 | 17125 |
| | 5796 | 25356 | 18349 | 741 | 21058 | 23633 | 21577 | 28180 | 28596 | 24025 | 25564 | 5408 |
| | 12806 | 15740 | 13408 | 27067 | 4436 | 19652 | 26285 | 27529 | 7639 | 5954 | | |
| 345: | 11988 | 10714 | 23912 | 14861 | 5911 | 2052 | 5344 | 27421 | 5258 | 13297 | 7301 | 14114 |
| | 4493 | 8572 | 11229 | 16497 | 6319 | 15022 | 2066 | 13925 | 11919 | 9928 | 7922 | 794 |
| | 17978 | 6386 | 8649 | 4916 | 6512 | 11182 | 10242 | 29351 | 29078 | 343 | 7164 | 17921 |
| | 7227 | 9612 | 21317 | 11922 | 26878 | 2772 | 18527 | 8710 | 7789 | 4915 | 11402 | 11843 |
| | 13769 | 12538 | 3981 | 12632 | 20717 | 9753 | 23105 | 13617 | 11101 | 4590 | 29416 | 26384 |
| | 15611 | 17846 | 14279 | 21142 | 9447 | 15785 | 10641 | 6668 | 11800 | 25436 | 11027 | 7276 |
| | 11819 | 26590 | | | | | | | | | | |
| 346: | 7938 | 7964 | 7962 | 19565 | 11649 | 1841 | 24052 | 25942 | 28102 | 21218 | 21222 | 21226 |
| | 25813 | 8989 | 13495 | 2802 | 17982 | 11467 | 19113 | 4583 | 3706 | 3705 | 5387 | 4585 |
| | 5393 | 5465 | 5445 | 5501 | 5472 | 5471 | 5448 | 5444 | 5469 | 14414 | 5998 | 20172 |
| | 13331 | 27590 | 7516 | 10486 | 24909 | 14569 | 18186 | 27256 | 29588 | 7905 | 7870 | 9487 |
| | 7775 | 5987 | 8194 | 2774 | 20986 | 6870 | 3660 | 11002 | 22398 | 15468 | | |
| 347: | 7938 | 7964 | 7962 | 19565 | 11649 | 1841 | 24052 | 25942 | 28102 | 21218 | 21222 | 21226 |
| | 25813 | 8989 | 13495 | 2802 | 17982 | 11467 | 19113 | 4583 | 3706 | 3705 | 5387 | 4585 |
| | 5393 | 5465 | 5445 | 5501 | 5472 | 5471 | 5448 | 5444 | 5469 | 14414 | 5998 | 20172 |
| | 13331 | 27590 | 7516 | 10486 | 24909 | 14569 | 18186 | 27256 | 29588 | 7905 | 7870 | 9487 |
| | 7775 | 5987 | 8194 | 2774 | 20986 | 3779 | 6870 | 3660 | 11002 | 22398 | 15468 | |
| 348: | 29418 | 22857 | 9311 | 17119 | 2104 | 25847 | 13088 | 3752 | 23347 | 15078 | 5810 | 13222 |
| | 3310 | | | | | | | | | | | |
| 349: | 614 | 724 | 3578 | 22853 | 3894 | 14408 | 17617 | 16005 | 5028 | 4994 | 6144 | 18942 |
| | 1739 | 19146 | 19006 | 21205 | 19955 | 18334 | 1836 | 688 | 8318 | 8309 | 8009 | 18573 |
| | 12586 | 2590 | 2565 | 2467 | 10589 | 12733 | 15544 | 27685 | 16097 | 11960 | 8314 | 8418 |
| | 30026 | 13264 | 25960 | 20279 | 28604 | 9168 | 9102 | 4334 | 18164 | 22788 | 19095 | 19662 |
| | 19042 | 19049 | 24125 | 27121 | 19723 | 2837 | | | | | | |
| 350: | 25920 | 24644 | 1529 | 23814 | 24344 | 15084 | 14227 | 18006 | 14646 | 23448 | 24200 | 9536 |
| | 18059 | 16068 | 8120 | 12166 | 1157 | 9942 | 23891 | 19467 | 18975 | 17571 | 13916 | 17062 |
| | 13954 | 30032 | 30072 | 21873 | 22881 | 22429 | 22033 | 14744 | 17913 | 8446 | 21245 | 13213 |
| | 11202 | 2023 | 21284 | 6453 | 13606 | 28247 | 18363 | 16827 | 7499 | 10306 | 2885 | 7034 |
| | 15748 | 18795 | 7135 | 2826 | 14349 | 26534 | 10017 | 9581 | 18077 | 16809 | 20911 | 1848 |
| | 1845 | 959 | 4109 | 6111 | 11844 | 17914 | 14967 | 21673 | 22031 | 7359 | 28409 | 10418 |
| | 22205 | 27228 | 15974 | 5704 | 793 | 8850 | 1706 | 29890 | 23956 | 11944 | 17184 | 1355 |
| | 27378 | 12341 | 6759 | 28306 | 28653 | 18936 | 29307 | 17520 | 27607 | 5304 | 17259 | 26939 |
| | 26965 | 29799 | 2845 | 2062 | 2070 | 15520 | 12492 | 15827 | 1192 | 30408 | 1139 | 15665 |
| | 19538 | 9816 | 13901 | 7716 | 19422 | 15897 | 12124 | 21262 | 15110 | 25363 | 7683 | 28049 |
| | 27480 | 18637 | 24637 | 26219 | 19136 | 7204 | 22563 | 15505 | 24643 | 5121 | 4350 | 4408 |
| | 3906 | 23597 | 8160 | 8131 | 2297 | 2304 | 25927 | 7095 | 17066 | 29209 | 25772 | 29350 |
| | 29562 | 5066 | 3637 | 28920 | 3057 | 6612 | 7770 | 20393 | 27662 | 28290 | 24705 | 16499 |
| | 19142 | 30186 | 3253 | 4552 | 27648 | 23462 | 16787 | 28442 | 22697 | 23321 | 3065 |
| | 10292 | 26395 | 22899 | 19141 | 6948 | 12559 | 19278 | 5533 | 27315 | 9016 | 7324 | 4683 |
| | 6113 | 15854 | 18924 | 20234 | 22655 | 26469 | 17177 | 14622 | 22318 | 755 | 7895 | 5074 |
| | 7569 | 19265 | 1098 | 2571 | 12840 | 10817 | 25634 | 3112 | 3358 | 28513 | 21346 | 21320 |
| | 29139 | 22925 | 18545 | 11825 | 12196 | 7530 | 24976 | 17397 | 10164 | 15770 | 30252 | 5196 |
| | 23259 | 1359 | 25426 | 3667 | 26115 | 19548 | 8687 | 6627 | 26061 | 21214 | 4028 | 3534 |

TABLE 8-continued

| PEP SEQ ID NO: | homolog SEQ ID NOs | | | | | | | | | | |
|---|---|---|---|---|---|---|---|---|---|---|---|
| | | 1345 | 23886 | 6923 | 11242 | 23901 | 4165 | 17152 | 9868 | 14083 | 20806 | 18263 | 25213 |
| | | 28694 | 21031 | 27059 | 24261 | 20030 | 13360 | 10494 | 22152 | 7226 | 27863 | 16168 | 17204 |
| | | 3394 | 26821 | 9744 | 19873 | 18837 | 941 | 28538 | 3543 | 9582 | 30164 | 22864 | 24540 |
| | | 15680 | 14586 | 22420 | 25280 | 29030 | 21767 | 23702 | 28314 | 12167 | 20702 | 16527 | 10572 |
| | | 4802 | 27738 | 3757 | 15681 | 19454 | 22509 | 25425 | 27457 | 2671 | 4541 | 2977 | 6184 |
| | | 27539 | 21872 | 28762 | 22278 | 19735 | 29493 | 29520 | 893 | 25366 | 16876 | 6305 | 25875 |
| | | 8993 | 28377 | 2624 | 2609 | 4566 | 21103 | 21943 | 17451 | 1319 | 29185 | 21139 | 28390 |
| | | 28171 | 6402 | 9696 | 14677 | 27369 | 26819 | 27805 | 22984 | 14700 | 11887 | 8472 | 14831 |
| | | 26049 | 7746 | 20854 | 7394 | 3365 | 3485 | 27032 | 3326 | 26432 | 23857 | 9779 | 26282 |
| | | 30359 | 22798 | 10974 | 10979 | 18841 | 11792 | 4797 | 2799 | 30300 | 5683 | 21944 | 30343 |
| | | 23272 | 23277 | 10554 | 22580 | 11539 | 11511 | 9920 | 2608 | 9023 | 14336 | 22381 | 14360 |
| | | 28647 | 10025 | 28641 | 28668 | 2851 | 7776 | 22358 | 20703 | 18665 | 697 | 26328 | 10907 |
| | | 5004 | 27589 | 25190 | 29584 | 24187 | 12314 | 3043 | 6989 | 14709 | 14830 | 14402 | 14008 |
| | | 4431 | 13366 | 16410 | 10783 | 22185 | 2470 | 25841 | 8458 | 24608 | 27170 | 30062 | 18922 |
| | | 21399 | 827 | 2011 | 5154 | 14132 | 11928 | 12070 | 30309 | 3467 | 30274 | 5877 | 25132 |
| | | 17987 | 7023 | 6872 | 2268 | 19346 | 10853 | 24176 | 19904 | 22368 | 19309 | 27844 | 25995 |
| | | 10199 | 13501 | 30377 | 10737 | 11418 | 8376 | 10584 | 8674 | 2911 | 12275 | 9547 | 21566 |
| | | 22643 | 9313 | 3260 | 13786 | 3783 | 26800 | 4169 | 21924 | 12461 | 11937 | 6408 | 19340 |
| | | 26860 | 9768 | 12050 | 14552 | 11573 | 3100 | 22475 | 2668 | 29923 | 19381 | | |
| 351: | | 27554 | 18984 | 16422 | 1088 | 21669 | 8135 | 26926 | 13594 | 10710 | 26801 | 21191 | 25806 |
| | | 19067 | 13318 | 26155 | 21968 | 14870 | 30140 | 13350 | 29241 | 8402 | 15374 | 8222 | 6863 |
| | | 4123 | 22839 | 6073 | 18370 | 28847 | 26587 | 25126 | 16326 | 26809 | 14380 | 29148 | 26255 |
| | | 23674 | 10803 | 28685 | 13691 | 17933 | 7223 | 25533 | 8619 | 22779 | 7749 | 11265 | 21339 |
| | | 22750 | 5454 | 17264 | 15289 | 1974 | 12428 | 29460 | 2817 | 29727 | 25125 | 1463 | 26610 |
| | | 11994 | 23682 | 25519 | 24067 | 14043 | 664 | 4760 | 13668 | 15516 | 4680 | 9993 | 5301 |
| | | 8221 | 863 | 25180 | 10815 | 13635 | 18926 | 10248 | 27340 | 26253 | 17205 | 5052 | 24731 |
| | | 3006 | 22102 | 24591 | 10529 | 11102 | 29117 | 17395 | 26634 | 21754 | 6987 | 6542 | 9467 |
| | | 9217 | 22531 | 19097 | 14241 | 13334 | 18834 | 16236 | 25886 | 24311 | 1160 | 22903 | 27329 |
| | | 26308 | 10311 | 8833 | 21593 | 25617 | 17687 | 24914 | 4346 | 23671 | 21206 | 1309 | 20939 |
| | | 12229 | 1669 | 27028 | 11980 | 12133 | 6357 | 9205 | 9991 | 1562 | 16106 | 28483 | 8149 |
| | | 2711 | 3792 | 19632 | 26474 | 7977 | 20623 | 7684 | 13424 | 19673 | 19421 | 18576 | 22127 |
| | | 29532 | 5384 | 8604 | 11038 | 24779 | 704 | 27058 | 22603 | 26792 | 11899 | 21119 | 22498 |
| | | 14504 | 20023 | 7267 | 24872 | 21452 | 24455 | 3454 | 9355 | 24853 | 2569 | 4671 | 1000 |
| | | 13281 | 1626 | 12768 | 18743 | 5214 | 2570 | 27862 | 15145 | 1812 | 28364 | 30374 | 27113 |
| | | 26507 | 709 | 20394 | 3836 | 11121 | 7396 | 3423 | 3421 | 795 | 12040 | 28488 | 29630 |
| | | 3405 | 2732 | 25092 | 14244 | 22841 | 629 | 30123 | 9528 | 23288 | 17596 | 8300 | 24721 |
| | | 26374 | 24739 | 2497 | 3304 | 30420 | 14660 | 13548 | 24948 | 20419 | 29868 | 6943 | 20416 |
| | | 22894 | 22859 | 27337 | 14992 | 14571 | 23208 | 25793 | 2678 | 6112 | 7622 | 13744 | 13286 |
| | | 25052 | 26379 | 7041 | 3766 | 17142 | 18468 | 3360 | 11148 | 27763 | 9737 | 3538 | 22901 |
| | | 21811 | 26786 | 1972 | 19313 | 21553 | 30449 | 8816 | 27617 | 5788 | 7097 | 20050 | 14214 |
| | | 4551 | 9042 | 7331 | 9689 | 17354 | 24391 | 29154 | 16347 | 22964 | 7835 | 6178 | 13509 |
| | | 28079 | | | | | | | | | | | |
| 352: | | 13149 | 13153 | 13126 | 30250 | 1216 | 10749 | 2895 | 19399 | 17847 | 24949 | 15664 | 6429 |
| | | 12123 | 15763 | 12183 | 17890 | 20990 | 5779 | 19020 | 9916 | 29404 | 16096 | 7457 | 17135 |
| | | 20086 | 19385 | 6032 | 19796 | 1721 | 18771 | 4608 | 1976 | 22526 | 4362 | 10279 | 29199 |
| | | 1925 | 29177 | 6255 | 18462 | 7822 | 27052 | 9938 | 23807 | 18227 | 15448 | 29130 | 8747 |
| 353: | | 2103 | 25480 | 1928 | 18714 | 20436 | 28906 | 29484 | 3073 | 13735 | 7476 | 27824 | 19963 |
| | | 3221 | 23291 | 5213 | 17979 | 16388 | 29603 | 10312 | 18230 | 8127 | 3934 | 18173 | 7813 |
| | | 9068 | 15259 | 5109 | 26784 | 12473 | 24998 | 2334 | 4049 | | | | |
| 354: | | 5363 | 22299 | 22301 | 18169 | 7872 | 29363 | 11251 | 27268 | 21532 | 6371 | 13796 | 15408 |
| | | 27858 | 1452 | 12799 | 20799 | 26602 | 10254 | 27046 | 18892 | 27064 | 15196 | 836 | 29137 |
| | | 2170 | 20807 | 16073 | 6012 | 4356 | 2303 | 2144 | 2301 | 7982 | 7959 | 3510 | 3537 |
| | | 3540 | 16997 | 11960 | 20516 | 1023 | 21047 | 18627 | 13264 | 25960 | 20817 | 19883 | 9992 |
| | | 13216 | 21440 | 18164 | 22230 | 2196 | 10569 | | | | | | |
| 355: | | 8451 | 16682 | 1584 | 27346 | 18635 | 8003 | 19163 | 12457 | 7316 | 6045 | 6044 | 17900 |
| | | 22128 | 8570 | 23399 | 30100 | 25277 | 12720 | 6355 | 26292 | 16567 | 1079 | 8261 | 25412 |
| | | 9771 | 29428 | 23374 | 22050 | 2217 | 1444 | 29813 | 17572 | 13343 | 28131 | 29052 | 27403 |
| | | 23936 | 20663 | 16582 | 7543 | 29769 | 19223 | 789 | 13517 | 26690 | 13362 | 4302 | 3466 |
| | | 5327 | 12303 | 6407 | 5508 | 16712 | 15042 | 2939 | 14381 | 14524 | 9050 | 20655 | 21318 |
| | | 4880 | 23357 | 21527 | 11747 | 3488 | 9924 | 4579 | 769 | 7405 | 25601 | 19728 | 28790 |
| | | 8577 | 8448 | 2136 | 3087 | 2120 | 26757 | 24202 | 8662 | 13752 | 13506 | 28251 | 15837 |
| | | 24079 | 6461 | 17052 | 30227 | 1404 | 13525 | 13831 | 26920 | 26744 | 26741 | 12815 | 7548 |
| | | 25652 | 20404 | 13389 | 29841 | 13200 | 13244 | | | | | | |
| 356: | | 21248 | 17257 | 15761 | 6077 | 10470 | 21419 | 28104 | 30402 | 17958 | 18501 | 29763 | 26183 |
| | | 17591 | 24404 | | | | | | | | | | |
| 357: | | 3118 | 4379 | 29540 | 25003 | 3912 | 2230 | 27094 | 5259 | 6746 | 23092 | 21097 | 2178 |
| | | 303 | 11912 | 22040 | 13730 | 19057 | 8657 | 6085 | 7368 | 837 | 22651 | 24494 | 29662 |
| | | 25823 | 24934 | 6049 | 13521 | 17683 | 12327 | 11243 | 15290 | 5880 | 16826 | 27443 | 10119 |
| | | 22886 | 23408 | 13219 | | | | | | | | | |
| 358: | | 9617 | 28607 | 25085 | 11495 | 9739 | 27311 | 12711 | 5185 | 9235 | 13544 | 13808 | 9009 |
| | | 27602 | 8237 | 4455 | 11195 | 2458 | 15832 | 1788 | 21739 | 23423 | 17693 | 12584 | 20756 |
| | | 756 | 22343 | 4327 | 1640 | 7725 | 7574 | 21227 | 13293 | | | | |
| 359: | | 28684 | 4984 | 832 | 5070 | 2944 | 20878 | 5124 | 1682 | 28846 | 11289 | 28431 | 1786 |
| | | 12260 | 12483 | 6765 | 22494 | 24751 | 7648 | 6170 | 19016 | 15428 | 12071 | 3106 | 23678 |
| | | 4676 | 2425 | 23478 | 15882 | 4252 | 25154 | 22484 | 16505 | 16511 | 6634 | 22008 | 16947 |
| | | 17749 | 14952 | 11908 | 6956 | 6530 | 10997 | 12539 | 10459 | 10823 | 19254 | 29444 | 22729 |
| | | 22727 | 22758 | 22327 | 1828 | 22257 | 29992 | 27891 | 22718 | 19452 | 19045 | 1825 | 1826 |

TABLE 8-continued

| PEP SEQ ID NO: | homolog SEQ ID NOs | | | | | | | | | | |
|---|---|---|---|---|---|---|---|---|---|---|---|
| | 15341 | 15298 | 15303 | 15262 | 15306 | 15271 | 15265 | 15268 | 15311 | 15309 | 15336 | 25966 |
| | 28410 | 14218 | 18529 | 22756 | 6300 | 11942 | 22731 | 18512 | 29862 | 27836 | | |
| 360: | 28688 | 17211 | 26128 | 17387 | 23775 | 5365 | 26559 | 10961 | 18822 | 10503 | 22874 | 29796 |
| | 14123 | 7003 | 21340 | 11377 | 5264 | 4239 | 18505 | 2866 | 20538 | 21900 | 7647 | 9387 |
| | 18205 | 26100 | 7093 | 15997 | 12852 | 18902 | 8422 | 22844 | 30200 | 17155 | 5287 | 19410 |
| | 26763 | 20062 | 7400 | 6080 | 9861 | 16848 | 25160 | 18543 | 15870 | 18615 | 23353 | 19198 |
| | 16391 | 28108 | 9713 | 24307 | 17164 | 23894 | 6206 | 3507 | 1631 | 2286 | 28040 | 30068 |
| | 12264 | 13732 | 29215 | 24056 | 23390 | 30206 | 28355 | 29773 | 21662 | 28161 | 2281 | 26370 |
| | 14301 | 23849 | 30240 | 12305 | 29871 | 15094 | 3700 | 10428 | 17841 | 9963 | 29073 | 16907 |
| | 16972 | 8905 | 3869 | 29354 | 27448 | 27478 | 9010 | 12163 | 7974 | 5888 | 7928 | 10870 |
| | 15645 | 17121 | 16716 | 25487 | 24456 | 2828 | 3557 | 14315 | 20357 | 14439 | 22800 | 18117 |
| | 1779 | 7914 | 1064 | 9183 | 20763 | 16844 | 4515 | 15386 | 9097 | 29839 | 13999 | 18441 |
| | 13092 | 18142 | 8838 | 9939 | 26169 | 20545 | 25488 | 10152 | 2093 | 15314 | 8718 | 21581 |
| | 2227 | 26903 | 20611 | 19297 | 20761 | 15531 | 9829 | 17574 | 5586 | 14373 | 10366 | 29285 |
| | 25386 | 30014 | 27087 | 22645 | 17679 | 18245 | 25448 | 3081 | 28033 | 24084 | 5192 | 6132 |
| | 9367 | 764 | 787 | 1636 | 1627 | 16919 | 15377 | 10883 | 10983 | 4309 | 5256 | 6796 |
| | 18974 | 30205 | 6832 | 24492 | 14656 | 14765 | 29798 | 3769 | 22805 | 5516 | 17371 | 17317 |
| | 11940 | 21083 | 29120 | 24185 | 1692 | 27644 | 11970 | 1802 | 23371 | 21941 | 17992 | 7532 |
| | 3424 | 29397 | 8878 | 22232 | 16936 | 13554 | 2872 | 11041 | 27470 | 10993 | 20650 | |
| | 27939 | 13950 | 11472 | 28305 | 6423 | 24864 | 23555 | 25522 | 24614 | 11793 | 3644 | 6286 |
| | 19468 | 27503 | 22255 | 25915 | 18081 | 650 | 12010 | 20661 | 27286 | 27001 | 29762 | 8647 |
| | 9237 | 10195 | 22777 | 9220 | 18437 | 18530 | 2266 | 12075 | 7366 | 28968 | 10244 | 14170 |
| | 21723 | | | | | | | | | | | |
| 361: | 20823 | 2065 | 3740 | 29754 | 27616 | 16665 | 3258 | 29600 | 23203 | 5289 | 8232 | 9063 |
| | 13002 | 29519 | 5947 | 19480 | 13551 | 12956 | 13622 | 16014 | 10672 | 2626 | 1050 | 19251 |
| | 29655 | 20406 | 9443 | 10553 | 29333 | 6383 | 1522 | 23646 | 16011 | 30464 | 18467 | 27376 |
| | 24258 | 15734 | 21223 | 811 | 1519 | 19496 | 26946 | 21837 | 5538 | 29836 | 26932 | 27468 |
| | 23870 | 27575 | 20557 | 2174 | 23926 | 9038 | 7620 | 20397 | 22248 | 22851 | 5602 | 22100 |
| | 6652 | 7388 | 7409 | 16957 | 23824 | 5434 | 5440 | 868 | 19270 | 20395 | 8343 | 1605 |
| | 18399 | 10105 | 2846 | 15337 | 19186 | 4373 | 28413 | 11503 | 27576 | 9876 | 24770 | 16314 |
| | 12067 | 29458 | 29558 | 26762 | 26758 | 28098 | 28094 | 4443 | 14685 | 2818 | 19017 | 10523 |
| | 26823 | 14859 | 700 | 9279 | 22665 | 7808 | 16000 | 965 | 23839 | 20428 | 19429 | 23065 |
| | 903 | 3801 | 19241 | 27786 | 6527 | 1164 | 1824 | 2840 | 22056 | 25554 | 9345 | 8675 |
| | 13300 | 24757 | 5814 | 10436 | 17186 | 8522 | 2572 | 22682 | 16438 | 25061 | 6301 | 14085 |
| | 18137 | 21354 | 26564 | 7491 | 24235 | | | | | | | |
| 362: | 25116 | 20229 | 16730 | 22738 | 8586 | 26303 | 20226 | 13995 | 15707 | 1726 | 11759 | 8532 |
| | 13981 | 13998 | 27885 | 26299 | 8534 | 28938 | 17481 | 11321 | 25163 | 21157 | 2971 | 16512 |
| | 3778 | 2602 | 19898 | 16631 | 6841 | 25316 | 27754 | 16884 | 5747 | 29427 | 23158 | 3708 |
| | 4679 | 10307 | 1145 | 1141 | 29694 | 6698 | 23809 | 15972 | 15251 | 29720 | 28672 | 2165 |
| | 11791 | 658 | 11787 | 25801 | 6900 | 8911 | 25947 | 3997 | 7019 | 6926 | 28841 | 24822 |
| | 29695 | 21328 | 10194 | 13178 | 29171 | 4182 | 1487 | 2710 | 16708 | 11397 | 2160 | 25082 |
| | 19944 | 12238 | 11755 | 28934 | 12376 | 1469 | 28249 | 19059 | 23089 | 22728 | 23922 | 23662 |
| | 23471 | 26428 | 1408 | 13990 | 26052 | 28932 | 13985 | 963 | 11250 | 13791 | 26321 | 29119 |
| | 8525 | 9308 | 12348 | 22463 | | | | | | | | |
| 363: | 15667 | 15776 | 22048 | 25867 | 17058 | 9020 | 7889 | 10022 | 18296 | 18319 | 12699 | 12695 |
| | 12694 | 25226 | 12728 | 30056 | 6650 | 3103 | 14968 | 10608 | 18148 | 18528 | 18524 | 18552 |
| | 19492 | 19418 | 15886 | 3386 | 807 | 17060 | 6797 | 25166 | 7038 | 15150 | 11717 | 9681 |
| | 18850 | 18174 | 6173 | 6712 | 29925 | 11786 | 1834 | 11518 | 30333 | 12530 | 17034 | |
| | 25336 | 7174 | 3863 | 7544 | 14005 | 24497 | 4940 | 16038 | 17380 | 21409 | 30142 | 21841 |
| | 29278 | 26033 | 29682 | 21293 | 4840 | 28067 | 6183 | 27778 | 23352 | 17951 | 21724 | 14579 |
| | 9563 | 6096 | 30288 | 27610 | 27694 | 21571 | 10653 | 26224 | 28712 | 8784 | 8496 | 14222 |
| | 11163 | 6525 | 27216 | 7812 | 8898 | 6843 | 20097 | 29008 | 20982 | 19178 | 12819 | 22895 |
| | 28642 | 25585 | 16520 | 4262 | 24359 | 20068 | 14181 | 12388 | 20657 | 17858 | 2269 | 26336 |
| | 26367 | 16777 | 25776 | 6318 | 8010 | 16987 | 5653 | 13632 | 12818 | 21521 | 17193 | 20965 |
| | 9383 | 18372 | 9808 | 14077 | 17063 | 7742 | 11557 | 1339 | 28816 | 15224 | 27290 | 3204 |
| | 8760 | 28905 | 28652 | 10278 | 4532 | 26722 | 11212 | 14889 | 21758 | 22755 | 14932 | 19394 |
| | 17448 | 29998 | 24340 | 27705 | 14497 | 25437 | 8285 | 26905 | 21137 | 9334 | 10649 | 6848 |
| | 14466 | 15626 | 19031 | 13549 | 21786 | 18681 | 14609 | 22115 | 21015 | 25885 | 18914 | 6131 |
| | 1455 | 5386 | 17446 | 26557 | 23061 | 1493 | 28497 | 28584 | 29041 | 24654 | 2156 | 5383 |
| | 18842 | 6373 | 19824 | 3455 | 26912 | 1490 | 21675 | 23514 | 26648 | 29447 | 28503 | 10441 |
| | 12732 | 16897 | 8507 | 9798 | 11583 | 30154 | 13257 | 10074 | 23974 | 11860 | 1799 | 26872 |
| | 23840 | 17313 | 16112 | 11678 | 11316 | 19613 | 7092 | 25376 | 25691 | 25616 | 25612 | 26421 |
| | 14665 | 9085 | 7134 | 8896 | 2989 | 2982 | 3018 | 2986 | 20461 | 9745 | 18327 | 19918 |
| | 5316 | 25580 | 23692 | 26322 | 2890 | 15963 | 27494 | 19237 | 4479 | 30042 | 3330 | 8748 |
| | 15124 | 8210 | 9098 | 29359 | 9092 | 9090 | 9094 | 1085 | 29959 | 10995 | 28851 | 26542 |
| | 1616 | 5906 | 20434 | 18154 | 9408 | 23004 | 30122 | 17973 | 9119 | 9121 | 10525 | 7876 |
| | 17415 | 2025 | 29336 | 5914 | 24606 | 10971 | 28989 | 20207 | 8265 | 10446 | 17494 | 27213 |
| | 8943 | 29723 | 1853 | 21594 | 22689 | 24233 | 23030 | 18934 | 3418 | 5128 | 5127 | 27418 |
| | 15304 | 9543 | 19187 | 7190 | 5712 | 29111 | 13759 | 16651 | 25827 | 3856 | 25514 | 9252 |
| | 12225 | 17196 | 23786 | 11120 | 22759 | 9241 | 19663 | 1331 | | | | |
| 364: | 572 | 22726 | 21868 | 23521 | 25117 | 27051 | 5777 | 25600 | 16565 | 22552 | 25832 | 16503 |
| | 21817 | 14728 | 10501 | 20312 | 1922 | 26143 | | | | | | |
| 365: | 2785 | 19798 | 21971 | 22501 | 8026 | 7044 | 7049 | 7046 | 18750 | 13666 | 3024 | 3038 |
| | 11039 | 14074 | 1429 | 8606 | 24553 | 1757 | 17726 | 17774 | 14618 | 22129 | 28723 | 16336 |
| | 19191 | 22207 | 23370 | 9532 | 17297 | 9218 | 2923 | 24024 | 18932 | 4361 | 17829 | 15456 |
| | 2364 | 6363 | 12612 | 6922 | 19498 | 13030 | 8341 | 28164 | 4258 | 13106 | 1811 | 16122 |
| | 1051 | 744 | 6529 | 5135 | 8908 | 4810 | 30047 | 13016 | 20550 | 6474 | 30079 | 4836 |
| | 14390 | 5894 | 15952 | 25952 | 16984 | 20565 | 22999 | 1037 | 1906 | 20526 | 30247 | 27474 |

TABLE 8-continued

| PEP SEQ ID NO: | homolog SEQ ID NOs | | | | | | | | | | |
|---|---|---|---|---|---|---|---|---|---|---|---|
| | 6834 | 24461 | 14477 | 26589 | 30015 | 9849 | 1281 | 29262 | 13270 | 27735 | 10808 | 20109 |
| | 6263 | 20296 | 23246 | 9911 | 1792 | 21541 | 2813 | 23854 | 22660 | 13873 | 6244 | 10328 |
| | 20192 | 17484 | 5593 | 28954 | 9444 | 11167 | 11388 | 30348 | 4972 | 20561 | 7018 | 16985 |
| | 24560 | 27578 | 2880 | 22305 | 16973 | 25664 | 19344 | 25467 | 10696 | 27992 | 6966 | 22703 |
| | 1278 | 30261 | 1231 | 22393 | 13639 | 2521 | 29348 | 12061 | 16655 | 25510 | 6733 | 6732 |
| | 11771 | 6758 | 6444 | 14367 | 16745 | 24525 | 22445 | 22666 | 28946 | 15182 | 3933 | 11820 |
| | 13952 | 14634 | 30178 | 2943 | 15060 | 9260 | 28357 | 13601 | 11022 | 28236 | 10389 | 16217 |
| | 3746 | 26696 | 24173 | 4154 | 1411 | 22141 | 21833 | 19331 | 10144 | 13294 | 20437 | 17754 |
| | 26947 | 19779 | 14906 | 15100 | 2107 | 21251 | 21025 | 5624 | 20001 | 1696 | 20726 | 10463 |
| | 8705 | 22313 | 3107 | 9503 | 10905 | 26121 | 1864 | 16828 | 19196 | 2247 | 22768 | 6517 |
| | 26490 | 26065 | 7392 | 14197 | 12658 | 3963 | 3966 | 14009 | 16539 | 22561 | 21947 | 24506 |
| | 26284 | 28532 | 22833 | 29368 | 16464 | 1131 | 10026 | 22163 | 3111 | 20784 | 27389 | 17201 |
| | 2905 | 2904 | 11350 | 9206 | 3509 | 18221 | 5579 | 11463 | 15132 | 28420 | 3182 | 4791 |
| | 29620 | 26713 | 3292 | 22543 | 20897 | 28545 | 18113 | 10753 | 23273 | 9930 | 16623 | 12945 |
| | 4291 | 7077 | 12747 | 14095 | 24406 | 16041 | 26991 | 27952 | 28566 | 1376 | 18300 | 8551 |
| | 6522 | 6532 | 14836 | 23677 | 3289 | 23409 | 28366 | 23851 | 10686 | 22521 | 6218 | 24927 |
| | 18916 | 24313 | 28124 | 5915 | 5547 | 11080 | 17068 | 1558 | 18371 | 8407 | 28877 | 9854 |
| | 9856 | 11911 | 3309 | 18232 | 21621 | 21105 | 17867 | 5002 | 16760 | 26441 | 6986 | 621 |
| | 11013 | 4343 | 12443 | 27133 | 11221 | 3252 | 9012 | 18375 | 25497 | 1413 | 24252 | 20195 |
| | 29884 | 15905 | 24567 | 21424 | 30284 | 11730 | 20007 | 9492 | 4599 | 28904 | 6016 | 25147 |
| | 18784 | 26867 | 7588 | 29200 | 30025 | 11149 | 1917 | 16252 | 17539 | 18416 | 5001 | 7760 |
| | 1275 | 2959 | 12722 | 12808 | 10813 | 14056 | 9706 | 28730 | 27579 | | | |
| 366: | 17662 | 23368 | 19260 | 953 | 2080 | 23266 | 11645 | 1187 | 23379 | 25541 | 3060 |
| | 30258 | 23236 | 15985 | 23812 | 18038 | 15864 | 23014 | 24985 | 23250 | 23331 | 7256 | 29218 |
| | 6537 | 8282 | 6825 | 16290 | 25482 | 5950 | 2607 | 10789 | 10812 | 1498 | 1122 | 26002 |
| | 16188 | 19194 | 21599 | 29031 | 11984 | 20400 | 13964 | 4133 | 25096 | 30080 | 24402 | 6338 |
| | 7573 | 18596 | 30323 | 16553 | 29248 | 30191 | 3818 | 16246 | 13336 | 15485 | 9429 | 7547 |
| | 2333 | 25054 | 20670 | 27775 | 8648 | 5878 | 21125 | | | | | |
| 367: | 12532 | 1185 | 15693 | 12627 | 19292 | 28786 | 14537 | 28010 | 20382 | 18294 | 18887 | 18885 |
| | 5808 | 17684 | 768 | 26489 | 30213 | | | | | | | |
| 368: | 16906 | 20559 | 21806 | 5055 | 9056 | 13559 | 14510 | 4167 | 13364 | 13441 | 11165 | 3862 |
| | 1913 | 6572 | 9353 | 29885 | 5672 | 23667 | 20433 | 11405 | 26215 | 8142 | 13983 | 9317 |
| | 1831 | 16167 | 26355 | 11049 | 12454 | 607 | 20163 | 21550 | 8941 | 3691 | 19336 | 8960 |
| | 11635 | 2500 | 12784 | 9832 | 13853 | 14431 | 6891 | 25892 | 24022 | 8074 | 10050 | 6314 |
| | 15883 | 23231 | 829 | 4758 | 4754 | 28646 | 4717 | 20464 | 9858 | 7971 | 12622 | 20501 |
| | 4271 | 12195 | 9291 | 19503 | 21548 | 4124 | 10854 | 6713 | 26029 | 12272 | 1775 | 25590 |
| | 22837 | 22812 | 22556 | 10678 | 16223 | 25625 | 21334 | 8456 | 22176 | 14327 | 14302 | 17822 |
| | 17624 | 16859 | 16850 | 17780 | 17619 | 17629 | 16852 | 10588 | 10650 | 1001 | 29219 | 15690 |
| | 20293 | 25766 | 12151 | 21485 | 14320 | 17504 | 15478 | 15477 | 15066 | 15835 | 30365 | 30421 |
| | 2696 | 20311 | 3417 | 19744 | 18488 | 3839 | 8782 | 17965 | 3743 | 3775 | 17509 | 17514 |
| | 7891 | 6457 | 12394 | 12411 | 4075 | 4077 | 17590 | 21909 | 28286 | 3388 | 16788 | 15982 |
| | 7848 | 29135 | 20349 | 19157 | 14248 | 29979 | 17396 | 17358 | 17398 | 17407 | 17410 | 17366 |
| | 17324 | 17403 | 17357 | 17368 | 17360 | 19996 | 19846 | 11904 | 23714 | 2173 | 22814 | 22809 |
| | 20197 | 29687 | 3983 | 24318 | 21492 | 20319 | 26103 | 28858 | 6802 | 20161 | 3448 | 4055 |
| | 12112 | 10358 | 7750 | 12606 | 13406 | 12501 | 6292 | 9527 | 13807 | 3896 | 12598 | 5152 |
| | 5149 | 5155 | 26816 | 300 | | | | | | | | |
| 369: | 12105 | 25662 | 9969 | 17226 | 25561 | 19375 | 19137 | 18295 | 18861 | 19386 | 13836 | 2279 |
| | 4873 | 4876 | 3820 | 3091 | 17868 | 23434 | 19125 | 27453 | 13210 | 8946 | 6913 |
| | 24880 | 24875 | 10855 | 10851 | 11632 | 4175 | 1889 | 28068 | 16417 | 3807 | 24970 | 19547 |
| | 25083 | 28222 | 27062 | 1397 | 28093 | 20514 | 1934 | 17351 | 5340 | 17475 | 6651 | 6628 |
| | 23848 | 21516 | 6717 | 11419 | 11421 | 6570 | 4635 | 11278 | 2641 | 27197 | 4386 | 12120 |
| | 12982 | 8875 | 9649 | 9303 | 29572 | 20558 | 24896 | 25979 | | | | |
| 370: | 24465 | 21401 | 11218 | 19349 | 9644 | 15930 | 1235 | 8351 | 23088 | 10788 | 5765 | 5761 |
| | 5738 | 26337 | 7764 | 5228 | 23488 | 11190 | 11189 | 29202 | 12910 | 7661 | 27041 | 5745 |
| | 14084 | 14115 | 29789 | 28902 | 28922 | 27512 | 9542 | 7402 | 10727 | 6303 | 29079 | 716 |
| | 8930 | 24123 | 23841 | 1025 | 2086 | 2205 | 9419 | 7665 | 11564 | 30212 | 17363 | 30184 |
| | 19808 | 23497 | 331 | | | | | | | | | |
| 371: | 20828 | 2018 | 29819 | 22216 | 5134 | 18043 | 29124 | 3400 | 30311 | 10221 | 10919 | 3008 |
| | 15824 | 27737 | 18632 | 30109 | 912 | 9609 | 19414 | 27547 | 13910 | 2325 | 30046 | 16563 |
| | 11184 | 12474 | 23560 | 19933 | 9705 | 23325 | 15597 | 24532 | 13595 | 18630 | 3813 | 21147 |
| | 23666 | 18452 | 8173 | 5530 | 10225 | 29269 | 26847 | 28198 | 27549 | 5423 | 8517 | 14755 |
| | 13305 | 17340 | 6951 | 17444 | 21075 | 19610 | 11191 | 9314 | 3484 | 5919 | 26028 | 27327 |
| | 16925 | 19302 | 23459 | 8937 | 18660 | 4087 | 21301 | 13146 | 5106 | 7307 | 9531 | 3669 |
| | 6992 | 21099 | 926 | 9546 | 25033 | 11143 | 7866 | 18849 | 25639 | 4131 | 14731 | 12666 |
| | 24674 | 21956 | 22772 | 10908 | 1840 | 26236 | 9375 | 8676 | 28261 | 29411 | 21699 | 8916 |
| | 6548 | 15637 | 14791 | 14919 | 1712 | 24713 | 27435 | 27895 | 13310 | 25971 | 13333 | 25998 |
| | 25969 | 25973 | 28430 | 17161 | 28170 | 24203 | 9153 | 3761 | 29294 | 4059 | 14595 | 5098 |
| | 16330 | 17529 | 26472 | 26351 | 22799 | 1837 | 898 | 10563 | 10556 | 16982 | 23987 | 28072 |
| | 3664 | 25730 | 13500 | 8168 | 18229 | 24508 | 7542 | 27295 | 25549 | | | |
| 372: | 29272 | 16408 | 7305 | 25504 | 30120 | 18562 | 6104 | 429 | 23539 | 19011 | 28591 | 13463 |
| | 16590 | 20339 | 29410 | 30183 | 4993 | 7120 | 6985 | 5112 | 26266 | 18260 | 4678 | 8552 |
| | 19030 | 28248 | 7679 | 4918 | 16318 | 21717 | 24060 | 21344 | 25297 | 22138 | 25346 | 22012 |
| | 5650 | 27496 | 21794 | | | | | | | | | |
| 373: | 11083 | 30232 | 9501 | 9499 | 14909 | 18574 | 1318 | 8956 | 22144 | 11445 | 7700 | 20469 |
| | 12900 | 25243 | 11836 | 6695 | 6670 | 17570 | 5294 | 27600 | 14930 | 2838 | 28257 | 7119 |
| | 28769 | 26445 | 3685 | 25444 | 20074 | 27152 | 929 | 27785 | 16606 | 2132 | 18223 | 15995 |
| | 2915 | 11331 | 21100 | 28868 | 26048 | 11852 | 12981 | 18993 | 5507 | 29666 | 15787 | 3078 |
| | 12343 | 3108 | 25390 | 25081 | 11565 | 11953 | 9652 | 19597 | 10514 | 29625 | | |

TABLE 8-continued

| PEP SEQ ID NO: | homolog SEQ ID NOs | | | | | | | | | | |
|---|---|---|---|---|---|---|---|---|---|---|---|
| 374: | 29995 | 13858 | 16799 | 15409 | 7506 | 3900 | 25479 | 27924 | 27233 | 26714 | 5749 | 2520 |
| | 7621 | 16752 | 5140 | 22422 | 2229 | 7907 | 2887 | 8548 | 27352 | 15383 | 9281 | 7088 |
| | 26440 | 22113 | 14246 | 8179 | 8157 | 4779 | 4777 | 2392 | 4396 | 19826 | 6526 | 22480 |
| | 5338 | 3048 | 26281 | 15964 | 17212 | 8814 | 2324 | 18317 | 15694 | 19860 | 6349 | 13128 |
| | 5556 | 1251 | 21951 | 28755 | 29722 | 2879 | 20185 | 13869 | 21210 | 23806 | 6702 | 4543 |
| | 4405 | 15007 | 2089 | 16413 | 24264 | 14941 | 14247 | 10125 | 9932 | 20980 | 20977 | 18088 |
| | 10848 | 15567 | 24471 | 1084 | 19325 | 23594 | 11486 | 16253 | 16264 | 9590 | 14117 | 17223 |
| | 10557 | 5623 | 2088 | 14385 | 1561 | 21395 | 6327 | 16898 | 29226 | 4670 | 18933 | 27066 |
| | 13458 | 18355 | 21569 | 9407 | 15436 | 21510 | 20305 | 14741 | 21830 | 24223 | 20078 | 20082 |
| | 20752 | 27132 | 21671 | 14238 | 13121 | 18767 | 19238 | 23101 | 9162 | 9163 | 5194 | 20027 |
| | 6622 | 19420 | 11795 | 9430 | 21095 | 15669 | 15672 | 15675 | 18014 | 18012 | 20048 | 20045 |
| | 28705 | 3175 | 25584 | 28625 | 27436 | 3545 | 10450 | 1515 | 13631 | 10778 | 16642 | 8141 |
| | 26233 | 14215 | 1191 | 23002 | 8096 | 27240 | 27799 | 2057 | 15673 | 29892 | 11139 | |
| 375: | 20858 | 26142 | 10809 | 14612 | 16454 | 19545 | 19537 | 19540 | 8482 | 24371 | 4160 | 20283 |
| | 14553 | 6799 | 25202 | 9659 | 14445 | 24224 | 19737 | 19738 | 8866 | 7937 | 25944 | 25059 |
| | 10155 | 21478 | 7852 | 7102 | 14451 | 6950 | 5026 | 14406 | 28090 | 5094 | 21421 | 13411 |
| | 27424 | 6366 | 22169 | 26988 | 24801 | 13224 | 14409 | 14494 | 14517 | 14518 | 14520 | 14521 |
| | 7173 | 19631 | 19633 | 29864 | 19674 | 19669 | 22743 | 15525 | 12661 | 4381 | 8374 | 12058 |
| | 12037 | 27740 | 24959 | 11750 | 1665 | 14092 | 11686 | 12278 | 12798 | 15327 | 29534 | 9738 |
| | 4989 | 7115 | 25912 | 26228 | 24830 | 26620 | 23068 | 23086 | 1638 | 4563 | 4496 | 15519 |
| | 1197 | 14710 | 5891 | 27244 | 7083 | 26941 | 26940 | 26894 | 26897 | 26904 | 26938 | 26888 |
| | 26891 | 4320 | 28614 | 15349 | 2396 | 5649 | 3734 | 7833 | 7900 | 2208 | 22821 | 15320 |
| | 29934 | 11345 | 22535 | 1531 | 14482 | 8469 | 14454 | 29548 | 28635 | 9987 | 2543 | 10952 |
| | 12764 | 20540 | 23787 | 21038 | 27498 | 21551 | 15465 | 9285 | 17855 | 5288 | 27678 | 14444 |
| | 14239 | 19778 | 7222 | 9980 | 3724 | 6735 | 17248 | 12325 | 8355 | 5396 | 7572 | 4642 |
| | 26594 | 30266 | 12513 | 15663 | 1676 | 1570 | 5326 | 30229 | 25028 | 13712 | 25204 | 15030 |
| | 8967 | 9847 | 17346 | 22369 | 24433 | 3228 | 1492 | 21919 | 3457 | 18490 | 16560 | 16356 |
| | 20957 | 8669 | 8556 | 27349 | 22593 | 19181 | 14071 | 26913 | 23223 | 19740 | 19741 | 19702 |
| | 6424 | 12427 | 3756 | 19528 | 28651 | 26436 | 23695 | 9106 | 18680 | 25651 | 29778 | 3385 |
| | 25547 | 16465 | 29957 | 23660 | 28119 | 25123 | 23161 | 12673 | 10341 | 10337 | 17877 | 16926 |
| | 5335 | 6313 | 27126 | 12985 | 8913 | 19166 | 26170 | 15524 | 3225 | 25803 | 17431 | 19242 |
| | 22221 | 19232 | 21302 | 5455 | 21808 | 25987 | 3306 | 21033 | 5949 | 12951 | 11207 | 26677 |
| | 5377 | 3154 | 4237 | 10277 | 10464 | 21397 | 26222 | 22976 | 24026 | 16432 | 14172 | 24505 |
| | 5159 | 8923 | 20766 | 30063 | 22214 | 8234 | 27929 | 29711 | 2824 | 13307 | 1027 | 2055 |
| | 10073 | 17104 | 8541 | 15113 | 10000 | 24419 | 9110 | 10493 | 28628 | 22247 | 5404 | 29270 |
| | 16863 | 3428 | 28997 | 21506 | 14549 | 25281 | 11006 | 28867 | 17838 | 27771 | 12933 | 20692 |
| | 19733 | 19704 | 27251 | 2386 | 19598 | 10663 | 23428 | 2637 | 27711 | 19997 | 18774 | 25727 |
| | 27718 | 9402 | 24817 | 6666 | 9647 | 13556 | 5248 | 11562 | 16054 | 13064 | 20698 | 15992 |
| | 23836 | 26766 | 12367 | 9376 | 25609 | 21567 | 12837 | 15575 | 19584 | 14844 | 25156 | 21026 |
| | 3140 | 25275 | 24917 | 17394 | 24748 | 18515 | 8565 | 28120 | 13593 | 17015 | 26924 | 4610 |
| | 13573 | 23412 | 6478 | 10079 | 7860 | 12653 | 7702 | 19415 | 11774 | 6562 | 10481 | 11804 |
| | 6051 | 18624 | 18909 | 8442 | 14265 | 17929 | 12311 | 22061 | 17975 | 11180 | 3404 | 6618 |
| | 3733 | 12950 | 9766 | 5493 | 3980 | 23627 | 23968 | 14205 | 26388 | 16017 | 19226 | 30230 |
| | 22394 | 8620 | 15956 | 19582 | 19549 | 19585 | 19666 | 19638 | 19635 | 29483 | 23233 | 4151 |
| | 18853 | 16248 | 21296 | 24366 | 10967 | 7110 | 2896 | 26390 | 27580 | 16446 | 16451 | 17612 |
| | 28143 | 14479 | 5845 | 17298 | 8885 | 14415 | 14487 | 14489 | 14491 | 14465 | 13581 | 13609 |
| | 14378 | 14371 | 13583 | 14374 | 13608 | 13616 | 13572 | 14384 | 14389 | 13612 | 14449 | 13619 |
| | 13577 | 13570 | 14523 | 14419 | 15849 | 542 | 17911 | 14411 | 16057 | 19767 | 23470 | 27608 |
| | 15894 | 16817 | 25786 | 11375 | 29808 | 2582 | 28328 | 20366 | 22975 | 16439 | 22295 | 21402 |
| | 19862 | 28494 | 14459 | 1199 | 24733 | 4349 | 14073 | 5733 | 23439 | 29533 | 4372 | 13627 |
| | 8409 | 28221 | 27151 | 25982 | 25978 | 25981 | 26080 | 25984 | 26010 | 25976 | 26106 | 26083 |
| | 25956 | 25959 | 26017 | 26055 | 26133 | 26026 | 26060 | 26822 | 26852 | 26132 | 26109 | |
| | 26820 | 26022 | 26850 | 26131 | 26825 | 26859 | 26085 | 26104 | 26102 | 26135 | 26053 | 26015 |
| | 26054 | 26827 | 26057 | 26076 | 26159 | 20846 | 26818 | 26136 | 26160 | 26163 | 20849 | 20842 |
| | 20808 | 20838 | 26156 | 20885 | 21828 | 20850 | 20891 | 26161 | 20886 | 25951 | 20718 | 26078 |
| | 25955 | 19799 | 20687 | 19772 | 21981 | 19794 | 19833 | 19803 | 21976 | 21960 | 19770 | 21983 |
| | 20719 | 19805 | 20686 | 20689 | 26854 | 19842 | 16456 | 21980 | 19839 | 19832 | 21803 | 19797 |
| | 26858 | 16489 | 20895 | 20804 | 21012 | 20767 | 20754 | 20923 | 20972 | 20970 | 16491 | 21010 |
| | 20926 | 20759 | 21004 | 20925 | 20721 | 16486 | 21908 | 21847 | 21953 | 20973 | 20723 | 21003 |
| | 20966 | 20930 | 20796 | 21946 | 21044 | 21948 | 21911 | 21880 | 21838 | 21050 | 20927 | 21844 |
| | 20969 | 21879 | 21014 | 21915 | 21055 | 21884 | 21048 | 21916 | 21882 | 21957 | 20893 | |
| | 21845 | 21877 | 2162 | 1916 | 5079 | 2116 | 14186 | 4604 | 4553 | 4521 | 13195 | 24012 |
| | 20562 | 18518 | 6546 | 13095 | 2878 | 25070 | 5498 | 20329 | 27871 | | | |
| 376: | 9514 | 18208 | 27699 | 24672 | 695 | 19688 | 17787 | 10946 | 18811 | 24157 | 17433 | 18211 |
| | 27587 | 29573 | 11124 | 574 | 576 | 16146 | 13361 | 26217 | 825 | 17239 | 428 | 13932 |
| | 5348 | | | | | | | | | | | |
| 377: | 26286 | 15828 | 29381 | 13729 | 9463 | 1447 | 21905 | 14853 | 28599 | 29214 | 29216 | 20781 |
| | 27729 | 18418 | 27603 | 25716 | 25707 | 12847 | 2534 | 2531 | 5406 | 28031 | 304 | 13896 |
| | 16751 | 5158 | 2533 | 10046 | 13689 | 22774 | 1911 | 1796 | 5545 | 10252 | 13315 | 6191 |
| | 13314 | 17203 | 23729 | 2537 | 6202 | 11849 | 11846 | 6193 | 27557 | 1797 | 10397 | 9442 |
| | 9470 | 2568 | 9471 | 9441 | 1789 | 6233 | 19634 | 2753 | 6222 | 6227 | 2751 | 26484 |
| | 2526 | 2523 | 10548 | 1794 | 6151 | 4931 | 4935 | 5392 | 10581 | 10578 | 28003 | 18285 |
| | 19177 | 10078 | 18805 | 25642 | 25644 | 9834 | 9293 | 12912 | 12907 | 633 | 4120 | 25781 |
| | 15640 | 18808 | 18210 | 19601 | 21903 | 25270 | 24910 | 10083 | 10084 | 10113 | 14947 | |
| 378: | 25474 | 14771 | 4723 | 2695 | 18286 | 1459 | 29180 | 29184 | 29182 | 29179 | 19650 | 6427 |
| | 4021 | 24424 | 19821 | 5833 | 15452 | 23315 | 26642 | 29704 | 7761 | 21612 | 25030 | 2327 |
| | 22167 | 2330 | 29528 | 5148 | 2361 | 26318 | 19158 | 12389 | | | | |

TABLE 8-continued

| PEP SEQ ID NO: | homolog SEQ ID NOs | | | | | | | | | | |
|---|---|---|---|---|---|---|---|---|---|---|---|
| 379: | 8336 | 407 | 28490 | 22527 | 23461 | 681 | 14155 | 24237 | 27107 | 21443 | 2665 | 27172 |
| | 24706 | 20420 | 5892 | 8105 | 6246 | 22041 | 16218 | 457 | 12930 | 14021 | 5230 | 9685 |
| | 2316 | 4924 | 22112 | 26146 | 19293 | 8274 | 19356 | 14025 | 3477 | 18809 | 753 | 18266 |
| | 26407 | 21926 | 380 | 25408 | 9209 | 8783 | 19607 | 25045 | 5143 | 16074 | 18650 | |
| 380: | 8336 | 28490 | 6567 | 22527 | 14155 | 27107 | 27172 | 5892 | 6246 | 16218 | 457 | 12930 |
| | 14021 | 5230 | 9685 | 2316 | 4924 | 22112 | 26146 | 19293 | 8274 | 19356 | 379 | 10900 |
| | 3477 | 18809 | 753 | 18266 | 26407 | 19607 | 25045 | 21926 | | | | |
| 381: | 16800 | 8883 | 21392 | 15014 | 12994 | 30175 | 24358 | 9344 | 16428 | 17993 | 26003 | 11292 |
| | 4948 | 4270 | 7148 | 7144 | 11585 | 29803 | 7628 | 23978 | 14719 | 15713 | 26051 | 23186 |
| | 21364 | 21363 | 12313 | 19211 | 12293 | 3184 | 21361 | 4251 | 29309 | 11106 | 8601 | 3656 |
| | 16575 | 10384 | 2231 | 6272 | 4440 | 25890 | 14003 | 23017 | 26886 | 10116 | 11138 | 3058 |
| | 29575 | 12636 | 14228 | 16945 | 13960 | 28481 | 24804 | 18612 | 23683 | 1560 | 30210 | 18531 |
| | 30124 | 14051 | 2951 | 28691 | 12583 | 14895 | 20570 | 29295 | 29014 | 15159 | 12881 | 19438 |
| | 17037 | 23643 | 18407 | 22380 | 13761 | 21280 | 30267 | 2114 | 20769 | 10123 | 3437 | 6949 |
| | 16125 | 22314 | 4257 | 7538 | 22317 | 29065 | 671 | 22201 | 19766 | 21568 | 7030 | |
| | 26970 | 24582 | 18078 | 23130 | 26658 | 19377 | 18835 | 4249 | 2051 | 3595 | 7527 | 7053 |
| | 6212 | 24385 | 17648 | 24821 | 22780 | 1333 | 6654 | 11266 | 21602 | 8339 | 27388 | 13866 |
| | 29872 | 6882 | 17417 | 1384 | 15154 | 16018 | 21174 | 17763 | 10140 | 15398 | 24041 | 661 |
| | 1818 | 16244 | 22194 | 810 | 28619 | 11611 | 9962 | 3017 | 19246 | 28744 | 7208 | 12671 |
| | 672 | 23171 | 27081 | 12060 | 14764 | 17741 | 19417 | 19866 | 4641 | 10040 | 3665 | 9316 |
| | 1443 | 4097 | 19724 | 7171 | 27471 | 4065 | 17292 | 620 | 19967 | 27285 | 16254 | 10426 |
| | 1031 | 3059 | 5751 | 26298 | 13298 | 14103 | 25415 | 17608 | 13073 | 19838 | 27082 | 22416 |
| | 19471 | 15554 | 10375 | 23326 | 21373 | 13529 | 6175 | 9427 | 27649 | 27791 | 23281 | 26347 |
| | 29100 | 20879 | 4801 | 4447 | 20578 | 6231 | 3817 | 23863 | 19942 | 2207 | 2783 | 15650 |
| | 15652 | 28992 | 2875 | 2749 | 29286 | 28367 | 9937 | 10318 | 13071 | 5030 | 20791 | 13306 |
| | 4353 | 5500 | 16715 | 20116 | 9338 | 11613 | 17692 | 17546 | 17543 | 17784 | 17742 | 17699 |
| | 17737 | 17696 | 17656 | 17533 | 17750 | 17649 | 17618 | 17581 | 17746 | 17578 | 17776 | |
| | 17611 | 17771 | 17576 | 17575 | 17541 | 17781 | 17580 | 28563 | 28525 | 17689 | 29296 | 28524 |
| | 29338 | 28567 | 28522 | 29382 | 29305 | 28486 | 29334 | 29299 | 28530 | 28485 | 28589 | 28586 |
| | 28588 | 28487 | 29292 | 29379 | 28491 | 28592 | 28571 | 29302 | 29344 | 28569 | 29383 | 28526 |
| | 29342 | 29335 | 28590 | 28564 | 11658 | 19964 | 2715 | 3367 | 5854 | 12104 | 13405 | 24584 |
| | 12771 | 4129 | 14512 | 13409 | 15647 | 27015 | 7234 | 8595 | 4345 | 7033 | 16467 | 23527 |
| | 26124 | 22096 | 14235 | 8758 | 13036 | 17632 | 2019 | 3016 | 687 | 30211 | 23375 | 4883 |
| | 27225 | 1110 | 27730 | 19218 | 25296 | 15643 | 4998 | 13345 | 11303 | 28411 | 17555 | 10819 |
| | 9658 | 20264 | 9656 | 16736 | 17026 | 13302 | 27306 | 27308 | 26348 | 16197 | 12340 | 21834 |
| | 15619 | 5295 | 5325 | 5349 | 5319 | 8477 | 29481 | 2737 | 2740 | 2743 | 25884 | 28722 |
| | 12157 | 18095 | 21273 | 982 | 21276 | 8514 | 21387 | 2038 | 9428 | 9426 | 9406 | 2039 |
| | 28482 | 4030 | 1407 | 22661 | 22664 | 22626 | 1244 | 2512 | 25499 | 18163 | 2228 | 1267 |
| | 2486 | 2513 | 2472 | 23931 | 7782 | 1424 | 2482 | 1430 | 1393 | 1241 | 1427 | 1273 |
| | 1431 | 25534 | 1323 | 9583 | 29887 | 26073 | 1270 | 1390 | 17236 | 6763 | 9490 | 9404 |
| | 9433 | 9458 | 17758 | 17797 | 17793 | 17680 | 9436 | 17721 | 17762 | 17716 | 9469 | 9464 |
| | 9460 | 9466 | 9498 | 17799 | 9495 | 17710 | 9489 | 17764 | 17705 | 9055 | 693 | 27326 |
| | 7084 | 2475 | 2479 | 17801 | 2042 | 29402 | 8012 | 14509 | 7859 | 17826 | 17505 | 13261 |
| | 7957 | 17507 | 2045 | 2047 | 10364 | 11896 | 27150 | 13110 | 1341 | 6977 | 2048 | |
| | 28835 | 19388 | 16841 | 28869 | 28890 | 28779 | 2075 | 19681 | 17476 | 2077 | 29442 | 14157 |
| | 19919 | 22184 | 27747 | 28149 | 25245 | 21260 | 21257 | 21303 | 13243 | 5590 | 10785 | 11128 |
| | 18281 | 9736 | 10648 | 12566 | 10739 | 10616 | 10472 | 11621 | 11554 | 10467 | 11661 | 10517 |
| | 9731 | 10518 | 10519 | 8358 | 7079 | 21804 | 27252 | 20822 | 28597 | 21562 | 8288 | 6342 |
| | 16743 | 21832 | 2502 | 12234 | 25288 | 26621 | 26623 | 26625 | 22586 | 22585 | 22611 | 22583 |
| | 22617 | 22590 | 22581 | 22614 | 22658 | 11770 | 23025 | 18987 | 4575 | 10505 | 26256 | 29981 |
| 382: | 1205 | 1202 | 23043 | 19105 | 13208 | 6551 | 6559 | 19940 | 19978 | 19981 | 4490 | 16198 |
| | 1306 | 1301 | 1305 | 14162 | 22654 | 23684 | 22719 | 28186 | 984 | 28534 | 25229 | |
| | 27701 | 17690 | 19988 | 21788 | 25087 | 19912 | 21275 | 19982 | 19909 | 18852 | 1894 | 7697 |
| | 1981 | 27932 | 27807 | 17275 | 17258 | 26144 | 8753 | 10153 | 2234 | 20381 | 10110 | 28531 |
| | 20355 | 28470 | 5936 | 14511 | 15482 | 19230 | 2975 | 29138 | 8877 | 5395 | 18703 | 5364 |
| | 19321 | 21051 | 17845 | 28539 | 28536 | 28429 | 27692 | 25933 | 28424 | 27698 | 27667 | 28432 |
| | 27637 | 19792 | 18013 | 13358 | 27690 | 9342 | 6730 | 28714 | 11798 | 8785 | 17920 | 25660 |
| | 16729 | 26290 | 19907 | 14255 | 26258 | 26234 | 26261 | 19936 | 19119 | 21272 | 19915 | 19985 |
| | 13259 | 19916 | 6608 | 29643 | 20900 | 5842 | | | | | | |
| 383: | 0 | | | | | | | | | | | |
| 384: | 29743 | 28452 | 28384 | 7106 | 15703 | 29461 | 18893 | 6003 | 3086 | 4606 | 25491 | 17772 |
| | 6933 | 10268 | 14470 | 14190 | 3145 | 9692 | 7299 | 5291 | 28343 | 28601 | 930 | 15288 |
| | 26611 | 1829 | 7925 | 17355 | 15633 | 7031 | 28578 | 30033 | 4956 | 8779 | 16006 | 17318 |
| | 2748 | 18821 | 21598 | 27933 | 16171 | 6850 | 25460 | 12668 | 24351 | 24345 | 24349 | 14361 |
| | 24867 | 22348 | 21002 | 29297 | 9784 | 10736 | 26297 | 27736 | 30295 | 23749 | 16572 | 16124 |
| 385: | 25583 | 25602 | 25606 | 25629 | 25635 | 25666 | 25668 | 25671 | 25675 | 25704 | 25708 | 30450 |
| | 19353 | 2616 | 2612 | 11581 | 2606 | 3607 | 2652 | 2656 | 4666 | 4562 | 4595 | 10715 |
| | 10757 | 10723 | 15148 | 7011 | 10145 | 10555 | 10562 | 10885 | 4615 | 4614 | 10592 | 11306 |
| | 11308 | 10950 | 11366 | 10981 | 11484 | 11491 | 11066 | 11524 | 11067 | 11589 | 11559 | |
| | 10940 | 11337 | 4867 | 15696 | 4771 | 15762 | 9196 | 16637 | 16636 | 9226 | 9230 | 16803 |
| | 4936 | 17828 | 5784 | 11301 | 10012 | 29367 | 10763 | 11274 | 11399 | 11435 | 10139 | 10137 |
| | 10135 | 11305 | 11363 | 11368 | 11409 | 11440 | 13737 | 22631 | 22635 | 14535 | 22638 | 14593 |
| | 14597 | 22671 | 22673 | 21171 | 21028 | 21175 | 20934 | 2618 | 10795 | 10798 | | |
| | 2619 | 2676 | 2675 | 2677 | 2679 | 5524 | 2681 | 2780 | 4637 | 3564 | 3605 | 29322 |
| | 29325 | 4600 | 4598 | 10792 | 10790 | 5599 | 5600 | 29374 | 21064 | 20944 | 20940 | 20937 |
| | 21061 | 20981 | 11767 | 21126 | 21092 | 21020 | 21069 | 22000 | 22029 | 22032 | 24069 | 24083 |
| | 24120 | 24194 | 24086 | 24122 | 24117 | 24119 | 24158 | 24182 | 24186 | 24188 | 24153 | 24216 |
| | 24219 | 24126 | 24244 | 24246 | 24249 | 24251 | 4774 | 4701 | 19529 | 19581 | 19532 | 3151 |

TABLE 8-continued

| PEP SEQ ID NO: | homolog SEQ ID NOs | | | | | | | | | | |
|---|---|---|---|---|---|---|---|---|---|---|---|
| | 19583 | 19617 | 19573 | 19536 | 19576 | 19621 | 19661 | 19578 | 26326 | 26323 | 5703 | 19524 |
| | 9634 | 14630 | 11338 | 10945 | 10937 | 10933 | 11094 | 11535 | 22003 | 16871 | 23011 | 13888 |
| | 10687 | 10759 | 10725 | 10691 | 10751 | 23322 | 15023 | 16600 | 24154 | 24080 | 30427 | 19348 |
| | 30456 | 25633 | 14773 | 7124 | 7178 | 7157 | 7150 | 7246 | 7182 | 7255 | 7101 | 7245 |
| | 7215 | 7094 | 7118 | 7210 | 7156 | 7153 | 7286 | 7220 | 7186 | 7293 | 7249 | 7125 |
| | 7151 | 7288 | 7326 | 7294 | 7296 | 7329 | 7333 | 8052 | 5631 | 3602 | 3600 | 4390 |
| | 4392 | 4393 | 4385 | 4446 | 4452 | 4449 | 4422 | 4491 | 4492 | 4495 | 4517 | 4518 |
| | 4547 | 4559 | 4555 | 4550 | 5523 | 5520 | 4718 | 5529 | 5560 | 5619 | 5626 | 5622 |
| | 5601 | 11610 | 5667 | 5673 | 5669 | 5635 | 4457 | 4454 | 10732 | 5675 | 5678 | 7123 |
| | 4852 | 4693 | 15678 | 4735 | 4821 | 15700 | 4736 | 4737 | 4741 | 4770 | 4773 | 4776 |
| | 4806 | 15757 | 15786 | 15788 | 15791 | 15812 | 15817 | 15840 | 15842 | 4825 | 16603 | 16634 |
| | 4856 | 16647 | 4860 | 16669 | 4863 | 16737 | 4894 | 4899 | 4900 | 4903 | 16778 | 16801 |
| | 16807 | 4929 | 16832 | 4932 | 16867 | 4939 | 17668 | 4969 | 4973 | 4976 | 4977 | 17722 |
| | 17725 | 5746 | 9982 | 10007 | 17788 | 17794 | 17800 | 5753 | 5757 | 5783 | 16703 | 10014 |
| | 17832 | 17757 | 16772 | 16706 | 9973 | 9976 | 16739 | 17708 | 11576 | 11608 | 29646 | 19212 |
| | 29648 | 29650 | 19215 | 29652 | 29668 | 19219 | 29669 | 29673 | 19240 | 29674 | 29676 | 19243 |
| | 29697 | 19247 | 29699 | 19252 | 690 | 20263 | 29702 | 19256 | 29703 | 652 | 19284 | 642 |
| | 20220 | 29734 | 19285 | 19287 | 29736 | 29737 | 30422 | 19322 | 30424 | 30426 | 19329 | 20265 |
| | 19350 | 30446 | 19351 | 19352 | 686 | 20223 | 20169 | 30457 | 20173 | 647 | 20228 | |
| | 605 | 608 | 16891 | 9952 | 10009 | 17765 | 9177 | 16643 | 9979 | 9983 | 14045 | 14016 |
| | 14039 | 14040 | 13976 | 13974 | 13980 | 14012 | 14993 | 1358 | 4588 | 4584 | 4571 | 4574 |
| | 4578 | 13670 | 13711 | 22598 | 22601 | 14564 | 14562 | 22667 | 16664 | 9182 | 9188 | 9223 |
| | 9950 | 9954 | 10004 | 10761 | 10667 | 10688 | 10717 | 11500 | 11507 | 11505 | 14991 | 17532 |
| | 1647 | 14787 | 14781 | 10730 | 13599 | 20410 | 2756 | 4380 | 3612 | 29364 | 29331 | 4522 |
| | 4519 | 11579 | 11601 | 26325 | 4631 | 4630 | 4633 | 10824 | 2657 | 29369 | 29372 | 10693 |
| | 4542 | 4540 | 4690 | 11333 | 11224 | 4733 | 4612 | 1900 | 10729 | 1898 | 1893 | 1896 |
| | 11599 | 2714 | 5565 | 5563 | 5564 | 2721 | 2752 | 2723 | 2747 | 3571 | 3573 | 3569 |
| | 4413 | 4411 | 4416 | 4420 | 4489 | 4485 | 4629 | 4603 | 4605 | 4660 | 4663 | 4702 |
| | 4674 | 4669 | 4710 | 4714 | 11582 | 4704 | 5526 | 5597 | 5567 | 5596 | 13979 | 21993 |
| | 13987 | 13992 | 13996 | 12409 | 13942 | 14015 | 1360 | 21231 | 14017 | 14782 | 14841 | 26664 |
| | 11552 | 18066 | 18134 | 18070 | 18101 | 18206 | 2768 | 20087 | 7036 | 18946 | 18255 | |
| | 18945 | 18264 | 13982 | 4581 | 4582 | 4908 | 11244 | 4616 | 4621 | 28178 | 4815 | 9947 |
| | 9192 | 16893 | 18369 | 17217 | 14632 | 29645 | 19209 | 13830 | 14636 | 14637 | 13919 | 13914 |
| | 13920 | 13917 | 13944 | 13945 | 13893 | 10689 | 21093 | 13854 | 13841 | 13847 | 17547 | 17545 |
| | 20904 | 20906 | 20899 | 19127 | 19155 | 19150 | 27482 | 15098 | 726 | 2332 | 10069 | 17569 |
| | 22026 | 14028 | 4404 | 4544 | 2336 | 13885 | 24342 | 9373 | 5634 | 19773 | 9371 | 16355 |
| | 12698 | 14876 | 2402 | 22790 | 17017 | 940 | 939 | 10096 | 12386 | 14050 | 14053 | 12408 |
| | 13921 | 750 | 749 | 782 | 745 | 747 | 23094 | 13889 | 1437 | 9150 | 15701 | 15718 |
| | 16604 | 16769 | 4942 | 9955 | 17675 | 17719 | 5750 | 10034 | 15754 | 15676 | 14020 | 14046 |
| | 24075 | 21228 | 13946 | 13951 | 14044 | 21225 | 21215 | 21221 | 14024 | 21178 | 21130 | 14818 |
| | 13135 | 14805 | 14808 | 4966 | 15784 | 7918 | 1366 | 1369 | 1505 | 1403 | 1396 | 1475 |
| | 1514 | 1389 | 1436 | 20903 | 14048 | 11618 | 10831 | 10827 | 10832 | 11612 | 20983 | 4694 |
| | 11282 | 15719 | 15838 | 16670 | 9229 | 5754 | 8876 | 25306 | 19624 | 11594 | 21987 | 21997 |
| | 14640 | 8051 | 649 | 610 | 20183 | 19318 | 715 | 20268 | 19159 | 10713 | 19358 | 19475 |
| | 2718 | 2719 | 23072 | 23044 | 23046 | 23077 | 13891 | 6915 | 6774 | 6817 | 6790 | 19354 |
| | 19357 | 13705 | 13708 | 13710 | 13714 | 13716 | 13747 | 13739 | 13741 | 13743 | 13745 | 13781 |
| | 13782 | 13785 | 13789 | 14809 | 14784 | 13828 | 13833 | 14817 | 14777 | 13835 | 13840 | 4611 |
| | 7376 | 7096 | 7374 | 7373 | 936 | 934 | 21135 | 20975 | 21169 | 21087 | 20978 | 10586 |
| | 21134 | 20935 | 14270 | 13778 | 17534 | 17537 | 9633 | 20901 | 4832 | 10134 | 21098 | 27949 |
| | 514 | 28711 | 16920 | | | | | | | | | |
| 386: | 7882 | 12624 | 24648 | 7567 | 20731 | 29246 | 13557 | 24299 | 11349 | 26482 | 23197 | 30121 |
| | 11007 | 18272 | 6064 | 28273 | 8156 | 23323 | 18696 | 2199 | 21366 | 18611 | 817 | 13520 |
| | 29728 | 24844 | 25005 | 12000 | 7747 | 11457 | 4078 | 4318 | 2050 | 17518 | 9735 | 11098 |
| | 6203 | 22233 | 10599 | 7752 | 15287 | 23469 | 26750 | 24405 | 1630 | 26154 | 26137 | 14899 |
| | 25769 | 7610 | 7037 | 10086 | 27409 | 27407 | 17049 | 17151 | 20444 | 7523 | 25492 | 28406 |
| | 15590 | 10197 | 23316 | 3750 | 9054 | 28523 | 4158 | 13211 | 28948 | 26806 | 30382 | 9535 |
| | 25501 | 13533 | 15796 | 29318 | 26382 | 14370 | 12937 | 14574 | 9931 | 5799 | 11078 | 13746 |
| | 10020 | 20282 | 6416 | 25298 | 5849 | 29006 | 22869 | 17306 | 26462 | 14226 | 16058 | 14263 |
| | 17573 | 14786 | 26451 | 28923 | 9374 | 4429 | 25618 | 22773 | 28275 | 12865 | 20976 | 27294 |
| | 828 | 8708 | 26360 | 9275 | 22574 | 22262 | 30310 | 4283 | 18068 | 4968 | 24285 | 25256 |
| | 28977 | 5519 | 15217 | 5412 | 10884 | 24397 | 17694 | 25575 | 30088 | 23404 | 24081 | 16839 |
| | 5107 | 8862 | 20079 | 17553 | 6918 | 7696 | 12535 | 17038 | 8997 | 20832 | 10223 | 9073 |
| | 18132 | 29509 | 5478 | 11312 | 1409 | 21181 | 26012 | 23113 | 10978 | 5297 | 11298 | 4964 |
| | 17101 | 16605 | 20370 | 24570 | 22259 | 6108 | 10236 | 12212 | 7445 | 18469 | 27353 | 5467 |
| | 1077 | 7762 | 21239 | 26187 | 16131 | 29514 | 23591 | 11815 | 18999 | 8501 | 12139 | 5767 |
| | 21383 | 2686 | 29757 | 11839 | 4301 | 3462 | 11447 | 16522 | 11623 | 28752 | 3179 | 14591 |
| | 6976 | 3373 | 20987 | 29125 | 7401 | 10219 | 7317 | 17818 | 15097 | 26598 | 26704 | 20088 |
| | 23312 | 10793 | 18246 | 17592 | 14273 | 4691 | 1993 | 14136 | 27321 | 20931 | 13690 | 10369 |
| | 26931 | 9853 | 28138 | 26603 | 11477 | 15496 | 13725 | 14514 | 13407 | 10283 | 29222 | 11832 |
| | 26502 | 26670 | 9114 | 1924 | 1412 | 28350 | 5281 | 16091 | 19855 | 17086 | 27176 | 27611 |
| | 25357 | 21603 | 30077 | 26906 | 8350 | 22679 | 18673 | 9140 | 18666 | 28921 | 23251 | 23519 |
| | 20361 | 20770 | 25453 | 20837 | 29966 | 27231 | 15403 | 28609 | 11201 | 11848 | 25518 | 16868 |
| | 22889 | 29735 | 17124 | 8175 | 20739 | 20369 | 12154 | 28580 | 8190 | 15884 | 15044 | 21154 |
| | 9315 | 9642 | 19788 | 4835 | 6578 | 1253 | 8773 | 15685 | 10431 | 5352 | 6871 | 25767 |
| | 14950 | 19775 | 5114 | 5589 | 17452 | 8608 | 27854 | 10987 | 21757 | 29392 | 8503 | 8481 |
| | 12839 | 19718 | 22926 | 9040 | 14900 | 7830 | 29421 | 9537 | 6500 | 16012 | 23512 | 25104 |
| | 656 | 17645 | 27804 | 15352 | 9712 | 5913 | 29582 | 26892 | 13949 | 15176 | 11476 | 25094 |
| | 2764 | 7380 | 6284 | 23799 | 18323 | 27153 | 25398 | 3341 | 11241 | 18735 | 1521 | 22016 |

TABLE 8-continued

| PEP SEQ ID NO: | homolog SEQ ID NOs | | | | | | | | | | |
|---|---|---|---|---|---|---|---|---|---|---|---|
| | 19647 | 18401 | 21554 | 20513 | 2805 | 17878 | 1940 | 26070 | 7663 | 3610 | 6563 | 24008 |
| | 6643 | 12824 | 29049 | 5076 | 5078 | 13223 | 6440 | 16674 | 2417 | 22702 | 14743 | 14797 |
| | 25787 | 24474 | 25771 | 15181 | 25271 | 28750 | 639 | 20190 | 18757 | 991 | 24602 | 11311 |
| | 21751 | 18315 | 23688 | 2908 | 26458 | 26270 | 5283 | 3627 | 25101 | 15350 | 12381 | 25545 |
| | 12033 | 9795 | 16156 | 15164 | 19152 | 1170 | 3238 | 4739 | 15254 | 9262 | 8304 | 27537 |
| | 30349 | 25524 | 30092 | 11304 | | | | | | | | |
| 387: | 4558 | 11893 | 13421 | 5582 | 23804 | 26468 | 26466 | 20275 | 14838 | 14839 | 17735 | 29084 |
| | 18188 | 29076 | 15600 | 30039 | 919 | 11408 | 901 | 8685 | 2371 | 9440 | 3547 | 7111 |
| | 8276 | 25471 | 17939 | 30262 | 29401 | 11076 | 10207 | 16596 | 21431 | 13490 | 7553 | 11422 |
| | 21043 | 4627 | 5438 | 17143 | 3476 | 4884 | 20375 | 14672 | 3777 | 11489 | 5053 | 24683 |
| | 24466 | 17525 | 8594 | 9714 | 24798 | 16490 | 28159 | 28437 | 27535 | 23196 | 23263 | 28941 |
| | 29147 | 3370 | 17964 | 11414 | 23349 | 27411 | 29195 | 20137 | 21695 | 21637 | 20399 | 20446 |
| | 12487 | 29234 | 6701 | 28295 | 3357 | 26876 | 13268 | 12016 | 1402 | 25239 | 27993 | 9006 |
| | 26508 | 24009 | 9842 | 27164 | 9843 | 8093 | 14174 | 14907 | 14180 | 8251 | 11223 | 29131 |
| | 14904 | 6743 | 26915 | 26914 | 12587 | 11766 | 3977 | 27351 | 13842 | 13838 | 17934 | 10791 |
| | 11651 | 21246 | 17945 | 17022 | 10818 | 13428 | 9709 | 24623 | 16581 | 22949 | 7546 | 19064 |
| | 23636 | 27599 | 24670 | 29538 | 26358 | 26361 | 16328 | 6121 | 1030 | 7784 | 4435 | 20083 |
| | 5003 | 4716 | 791 | 3702 | 7029 | 9167 | 28702 | 14596 | 14556 | 11538 | 24982 | 21152 |
| | 9549 | 15247 | 17111 | 16632 | 17709 | 21966 | 17305 | 16424 | 28354 | 28724 | 27364 | 24574 |
| | 16426 | 6348 | 6280 | 15221 | 1997 | 12742 | 22001 | 15753 | 7248 | 12877 | 12875 | 24109 |
| | 22403 | 5450 | 6999 | 22405 | 1130 | 17140 | 29251 | 7185 | 1810 | 3076 | 28353 | 26874 |
| | 24295 | 29943 | 10644 | 1049 | 12979 | 14037 | 21570 | 18712 | 15540 | 8936 | 3161 | 4570 |
| | 4539 | 4465 | 27883 | 12020 | 25071 | 28733 | 9892 | 29788 | 1819 | 29812 | 11598 | 3410 |
| | 9138 | 2585 | 23556 | 28874 | 2934 | 12374 | 1664 | 29691 | 29088 | 3921 | | |
| 388: | 16278 | 11063 | 25422 | 1816 | 11982 | 26099 | 6004 | 16365 | 28692 | 20122 | 20303 | 26654 |
| | 786 | 10182 | 4508 | 1343 | 20478 | 7988 | 24286 | 24386 | 3094 | 25259 | 20056 | 18347 |
| | 19690 | 23376 | 6317 | 27472 | 10522 | 30317 | 30020 | 22656 | 12232 | 4531 | 12165 | 28455 |
| | 10913 | 19443 | 4173 | 9125 | 24324 | 30454 | 2037 | 9909 | 15010 | 15153 | 25931 | |
| 389: | 21076 | 21074 | 24054 | 19303 | 4397 | 8433 | 9597 | 13681 | 25701 | 8529 | 13682 | 29417 |
| | 3329 | 6368 | 1930 | 18796 | 23129 | 8137 | 27913 | 27943 | 3570 | 15220 | 1921 | 23484 |
| | 26097 | 10322 | 15273 | 21458 | 24501 | 30004 | 1058 | 17126 | 20178 | 13780 | 27821 | 21499 |
| | 11343 | 2474 | 2429 | 23148 | 14120 | 1136 | 28029 | 5188 | 8301 | 2074 | 28682 | 23207 |
| | 25234 | 4592 | 6577 | 15018 | 25183 | 20104 | 25311 | 27014 | 28022 | 2407 | 29658 | 27137 |
| | 21835 | 22946 | 4286 | 2453 | 23771 | 1121 | 15152 | 7508 | 18125 | 14815 | 1806 | 16918 |
| | 22338 | 8216 | 27934 | 28665 | 22072 | 14984 | 16297 | 19962 | 20824 | 5496 | 16107 | 10178 |
| | 28394 | 3392 | 3438 | 3668 | 29062 | 28435 | 7617 | 14723 | 26147 | 15111 | 6330 | 5903 |
| | 5261 | 12168 | 13265 | 20572 | 669 | 29113 | 8533 | 12630 | 12759 | 5382 | 29134 | 603 |
| | 14259 | 15218 | 11176 | 19111 | 16904 | 4137 | 30155 | 22315 | 26211 | 5171 | 4474 | 13423 |
| | 699 | 26857 | 25889 | 15695 | 5656 | 13452 | 16624 | 24229 | 19905 | 19885 | 12708 | 13922 |
| | 18917 | 26895 | 14843 | 14806 | 24003 | 20069 | 6597 | 4337 | 21353 | 24639 | 8520 | 9720 |
| | 4430 | 1118 | 20387 | 24437 | 3181 | 3281 | 28201 | 2323 | 28358 | 10379 | 28321 | 7579 |
| | 2307 | 2278 | 15208 | 2901 | 8613 | 21511 | 5811 | 10636 | 18192 | 13404 | 28598 | 1556 |
| | 616 | 30406 | 655 | 29004 | 28129 | 3850 | 9148 | 20126 | 5502 | 2166 | 3650 | 16685 |
| | 26728 | 11100 | 9014 | 20231 | 843 | 845 | 23137 | 7834 | 6945 | 5583 | 30396 | |
| | 28421 | 1577 | 27492 | 11302 | 1987 | 30225 | 6290 | 11946 | 14973 | 840 | 13085 | 13054 |
| | 27292 | 9981 | 9959 | 28958 | 3716 | 14277 | 2285 | 24091 | 11256 | 28742 | 28741 | 15833 |
| | 21106 | 24036 | 26077 | 23993 | 20117 | 30096 | 10683 | 21582 | 21738 | 23681 | 21984 | 21885 |
| | 13678 | 25157 | 20887 | 19948 | 24070 | 27527 | 23997 | 16961 | 8064 | 29845 | 1884 | 9986 |
| | 7187 | 9957 | 7894 | 21587 | 13384 | 7772 | 26614 | 12745 | 27838 | 22022 | 22147 | 15901 |
| | 18009 | 8985 | 7805 | 29129 | 23495 | 20727 | 8101 | 8067 | 6335 | 6333 | 22062 | 24049 |
| | 3494 | 2983 | 19995 | 18749 | 3037 | 18015 | 5211 | 29352 | 9366 | 29282 | 9452 | 1093 |
| | 28291 | 24425 | 17497 | 29099 | 14986 | 7133 | 29551 | 12227 | 12228 | 24624 | 24420 | 22559 |
| | 13301 | 8373 | 9341 | 25695 | 24780 | 13044 | 6000 | 18736 | 24773 | 15831 | 26257 | 24398 |
| | 2928 | 18271 | 19938 | 8219 | 18147 | 28191 | 26595 | 18550 | 19355 | 26346 | 2776 | 12184 |
| | 28768 | 23707 | 9255 | 28548 | 7459 | 22182 | 17454 | 5995 | 16136 | 9213 | 8471 | 2315 |
| | 17099 | 29529 | 3898 | 12065 | 3718 | 1743 | 10595 | 28519 | 25835 | 28283 | 13197 | 17310 |
| | 21045 | 8375 | 25339 | 21500 | 24781 | 21655 | 1200 | 23953 | 28006 | 6543 | 9145 | 22710 |
| | 20132 | 12235 | 16370 | 19810 | | | | | | | | |
| 390: | 22423 | 29361 | 12542 | 16648 | 24697 | 17759 | 12099 | 3299 | 2596 | 1967 | | |
| 391: | 16278 | 11063 | 25422 | 1816 | 11982 | 21406 | 6004 | 24783 | 16365 | 20122 | 20303 | 26654 |
| | 3249 | 786 | 10182 | 26408 | 1343 | 20478 | 7988 | 3094 | 25259 | 20056 | 18347 | 19690 |
| | 23376 | 6317 | 27472 | 10522 | 30317 | 30020 | 22656 | 12232 | 4531 | 8668 | 14561 | 14464 |
| | 29649 | 11699 | 25874 | 12165 | 15149 | 26411 | 28455 | 10913 | 26414 | 4173 | 9125 | 24324 |
| | 30454 | 2037 | 9909 | 15010 | 15153 | 25931 | | | | | | |
| 392: | 12517 | 6596 | 26601 | 26683 | 5868 | 17245 | 28699 | 13374 | 16403 | 20008 | 26900 | 25162 |
| | 14567 | | | | | | | | | | | |
| 393: | 28605 | 4248 | 3296 | 29412 | 1544 | 4971 | 25372 | 29811 | 1043 | 22936 | 29875 | 15017 |
| | 12913 | 14832 | 11897 | 7444 | 7783 | 1580 | 1575 | 7449 | 27975 | 1736 | 10963 | 18607 |
| | 5012 | 4790 | 19491 | 26181 | 26164 | 26179 | 6084 | 22822 | 22119 | 11926 | 6143 | |
| | 18802 | 24675 | 1642 | 22297 | 12158 | 18339 | 19224 | 8729 | 8745 | 12629 | 14650 | 1776 |
| | 1741 | 1707 | 1778 | 12954 | 12140 | 17986 | 7486 | 14323 | 29298 | 6358 | 30249 | 7435 |
| | 16020 | 7899 | 28663 | 18034 | 27243 | 3117 | 16040 | 5952 | 12823 | 8778 | 27116 | 22716 |
| | 5812 | 26114 | 12292 | 27504 | 14526 | 25559 | 15865 | 2010 | 25596 | 8728 | 28654 | |
| | 24775 | 1378 | 24778 | 14306 | 24842 | 12932 | 25247 | 10314 | 18165 | 7012 | 28721 | 21714 |
| | 19012 | 6704 | 25342 | 19555 | 29166 | 25312 | 20859 | 13168 | 20643 | 10542 | 7494 | 20348 |
| | 24013 | 29672 | 30463 | 1523 | 9707 | 25278 | 30341 | 26500 | 17219 | 28319 | 7490 | 8545 |
| | 29013 | 27753 | 9225 | 26782 | 21073 | 23700 | 23703 | 6862 | 18520 | 30018 | 12861 | 4577 |
| | 15163 | 6845 | 3397 | 13969 | 1984 | 1624 | 4624 | 26478 | 30397 | 28565 | 17213 | 12054 |

TABLE 8-continued

| PEP SEQ ID NO: | homolog SEQ ID NOs | | | | | | | | | | |
|---|---|---|---|---|---|---|---|---|---|---|---|
| | 12089 | 10866 | 17773 | 23206 | 29565 | 21514 | 1401 | 11549 | 28292 | 23164 | 4926 | 23911 |
| | 4949 | 11088 | 10104 | 16644 | 1094 | 13688 | 6671 | 27258 | 3303 | 15049 | 2352 | 2991 |
| | 11713 | 19314 | 23318 | 8230 | 24947 | 27463 | 5484 | 30384 | 1163 | 17893 | 1416 | 9330 |
| | 12405 | 9333 | 15391 | 2936 | 8998 | 19519 | 19525 | 12156 | 7757 | 28818 | 30141 | 8398 |
| | 10740 | 15295 | 20325 | 17325 | 5730 | 18713 | 25031 | 2365 | 22116 | 25257 | 22657 | 29389 |
| | 28650 | 19315 | 17650 | 30443 | 20699 | 7510 | 7155 | 6448 | 1112 | 12915 | 6331 | 29239 |
| | 17760 | 17835 | 14733 | 25882 | 3979 | 21962 | 17861 | 18807 | 6030 | 23278 | 24272 | 29330 |
| | 27365 | 17805 | 8719 | 13173 | 12233 | 22827 | 19739 | 18618 | 18706 | 13658 | 4700 | 23121 |
| | 24243 | 12467 | 11326 | 26575 | 26573 | 20560 | 4045 | 10190 | 25319 | 26814 | 27915 | 23651 |
| | 707 | 12290 | 9084 | 9682 | 6494 | 3914 | 15760 | 5693 | 20537 | 26901 | 24888 | 6684 |
| | 22797 | 22636 | 11814 | 19188 | 29380 | 8147 | 19574 | 30403 | 20874 | 10580 | 21715 | 16700 |
| | 1474 | 26695 | 24247 | 25000 | 9657 | 18453 | 30101 | 23513 | 19849 | 24716 | 23516 | 1946 |
| | 1947 | 19018 | 26271 | 25477 | 25484 | 26363 | 25473 | 25441 | 25410 | 25409 | 26442 | 26406 |
| | 26437 | 26435 | 25385 | 15727 | 15923 | 20963 | 17949 | 17789 | 17795 | 26324 | 29456 | 30066 |
| | 26418 | 4838 | 18314 | 19403 | 15957 | 29036 | 6998 | 8654 | 6240 | 26356 | 28440 | 9269 |
| | 17028 | 10474 | 26202 | 10677 | 2087 | 2800 | 28132 | 22715 | 6476 | 20654 | 4987 | 15578 |
| | 6289 | 3621 | 2930 | 28144 | 27716 | 21519 | 21613 | 14654 | 25403 | 7163 | 6716 | 28476 |
| | 10944 | 1063 | 17188 | 5320 | 17158 | 26089 | 22149 | 5983 | 8791 | 8789 | 8788 | 28070 |
| | 13263 | 6861 | 19701 | 30278 | 19126 | 15936 | 18120 | 20620 | 4222 | 729 | 12941 | 18345 |
| | 10382 | 12252 | 9624 | 23119 | 14949 | 12867 | 907 | 911 | 13144 | 12938 | 730 | 14135 |
| | 3636 | 11786 | 23990 | 27897 | 10675 | 7456 | 12498 | 1820 | 28552 | 10722 | 11720 | 19506 |
| | 20979 | 774 | 24722 | 22877 | 7362 | 18911 | 10471 | 28039 | 23542 | 22349 | 3768 | 13202 |
| | 16598 | 6715 | 6484 | 4027 | 11381 | 2468 | 20475 | 8622 | 9998 | 25324 | 14855 | |
| | 27500 | 10138 | 26954 | 8111 | 10504 | 13274 | 8108 | 22554 | 26174 | 6009 | 12944 | 12936 |
| | 19730 | 12943 | 22572 | 23515 | 6827 | 10166 | 28974 | 24489 | 20584 | 21430 | 19541 | 26962 |
| | 25404 | 1595 | 9869 | 18282 | 24908 | 23226 | 20984 | 27679 | 25034 | 30447 | 9096 | 16204 |
| | 4650 | 8044 | 7260 | 17195 | 12935 | 21446 | 19526 | 20129 | 3842 | 17736 | 15276 | 2794 |
| | 22503 | 3051 | 5227 | 11362 | 4113 | 17220 | 15966 | 7488 | 28369 | | | |
| 394: | 13283 | 26673 | 13372 | 15811 | 26338 | 10282 | 13817 | 6554 | 14047 | 11667 | 10532 | 2214 |
| | 1074 | 7236 | 16820 | 12807 | 3295 | 23864 | 2601 | 24596 | 16280 | 17983 | 25511 | 29357 |
| | 25240 | 26751 | 12803 | 12244 | 7105 | 11527 | 20080 | 23916 | 10142 | 938 | 16901 | |
| | 25535 | 19825 | 15340 | 7736 | 7452 | 27777 | 19857 | 3690 | 18820 | 16411 | 29415 | 6075 |
| | 13087 | 15907 | 4322 | 4242 | 17935 | 4377 | 30307 | | | | | |
| 395: | 5925 | 5923 | 30049 | 5276 | 646 | 3497 | 16821 | 4682 | 4024 | 4026 | 3989 | 4022 |
| | 4201 | 3419 | 4089 | 11871 | 21479 | 11456 | 22786 | 12064 | 16900 | 7864 | 7137 | 27519 |
| | 23009 | 22962 | 27386 | 5910 | 9782 | 13669 | 5022 | 5922 | 28232 | 28240 | 28245 | 14945 |
| | 2384 | 26153 | 9863 | 17122 | 9701 | 4513 | 24276 | 24303 | 14985 | 11226 | 19391 | 7568 |
| | 7623 | 1468 | 5050 | 5147 | 22361 | 8683 | 16205 | 16243 | 16210 | 16234 | 16200 | 16272 |
| | 16237 | 16201 | 16178 | 22362 | 16267 | 16266 | 8681 | 16202 | 16269 | 16288 | 16274 | 16263 |
| | 16207 | 16241 | 16295 | 20101 | 18903 | 18977 | 3714 | 2312 | 18880 | 3684 | 18869 | 18905 |
| | 3713 | 30399 | 28299 | 18939 | 18972 | 18846 | 27074 | 17528 | 18898 | 18848 | 30321 | 23708 |
| | 19003 | 3689 | 3662 | 19026 | 18935 | 27273 | 19602 | 2620 | 27279 | 28024 | 18645 | 18667 |
| | 18669 | 928 | 20551 | 19019 | 14467 | 18251 | 3846 | 1656 | 20430 | 4364 | 30027 | 20555 |
| | 11096 | 24440 | 21580 | 25207 | 29141 | 10133 | 5354 | 7744 | 7942 | 17790 | 2061 | |
| | 18662 | 8642 | 23923 | 27214 | 15651 | 23078 | 14362 | 7927 | 10619 | 1018 | 14617 | 25685 |
| | 12777 | 22187 | 11042 | 18732 | 12198 | 29306 | 5504 | 15836 | 9171 | 30044 | 6414 | 25669 |
| | 13863 | 24429 | 11873 | 18064 | 27521 | 4646 | 10130 | 20051 | 3139 | 25845 | 30336 | 10377 |
| | 9691 | 5577 | 30414 | 1012 | 24812 | 5492 | 4428 | 1204 | 26650 | 18168 | 18283 | 4355 |
| | 21394 | 5462 | 4099 | 4071 | 4122 | 9325 | 15857 | 4125 | 4127 | 10368 | 816 | 814 |
| | 833 | 8020 | 12594 | 11867 | 25573 | 27585 | 27146 | 16588 | | | | |
| 396: | 10985 | 24465 | 5389 | 21752 | 27373 | 11218 | 19349 | 8484 | 27565 | 9644 | 15930 | 18320 |
| | 10788 | 1620 | 7764 | 5228 | 20488 | 8231 | 3344 | 26554 | 18643 | 8540 | 22162 | 6528 |
| | 5847 | 14377 | 7956 | 11564 | 7665 | 30212 | 26544 | 19808 | 27823 | | | |
| 397: | 10015 | 28467 | 9949 | 16910 | | | | | | | | |
| 398: | 14943 | 7938 | 7964 | 7962 | 19565 | 11649 | 1841 | 3138 | 18175 | 16084 | 28102 | 25813 |
| | 4265 | 27430 | 11048 | 5711 | 13120 | 2802 | 8841 | 19091 | 28086 | 27114 | 3741 | 21369 |
| | 19052 | 1394 | 21023 | 927 | 20385 | 28263 | 19113 | 7946 | 7941 | 28293 | 4583 | 3706 |
| | 3705 | 5387 | 4585 | 5998 | 1847 | 1844 | 18466 | 16361 | 28638 | 27344 | 7934 | 11733 |
| | 20519 | 14569 | 22469 | 24958 | 7905 | 7870 | 14980 | 580 | 6150 | 9513 | 28956 | 12098 |
| | 18280 | 9800 | 24457 | | | | | | | | | |
| 399: | 26644 | 4656 | 6625 | | | | | | | | | |
| 400: | 13109 | 6571 | 9398 | 6996 | 22385 | 12637 | 8380 | 28556 | 20052 | 30329 | 13485 | 10400 |
| | 27196 | 27193 | 15191 | 20656 | 10460 | 13771 | 3445 | 16498 | 12884 | 12318 | 3470 | 16845 |
| | 20269 | 5461 | 20330 | 20335 | 24308 | 4110 | 931 | 20492 | 19564 | 5770 | 24535 | 4499 |
| | 1881 | 9120 | 7450 | 18506 | 18374 | | | | | | | |
| 401: | 19639 | 6086 | 22364 | 24585 | 25042 | 23621 | 30345 | 28252 | 17067 | 23995 | 9310 | 22994 |
| | 5072 | 16172 | 25659 | 1771 | 16962 | 16937 | 8287 | 28032 | 28064 | 24087 | 25025 | 24400 |
| | 24269 | 970 | 14519 | 18442 | 9210 | 7765 | 21881 | 1530 | 26626 | 3698 | 12231 | 18434 |
| | 12830 | 13547 | 3947 | 11008 | 3887 | 4234 | 4319 | 9555 | 18366 | 17971 | 28689 | 20851 |
| | 19953 | 6180 | 28096 | 29797 | 13032 | 25388 | 3829 | 12069 | 11806 | 16075 | 26665 | 12135 |
| | 3790 | 11742 | 25940 | 28091 | 9662 | 28734 | 21963 | 29545 | 21722 | 7781 | 12477 | 7536 |
| | 29955 | 25777 | 5118 | 9304 | 15780 | 23706 | 14555 | 13156 | 18084 | 11085 | 25550 | 28520 |
| | 26030 | 15158 | 16126 | 9147 | 14340 | 25656 | 30430 | 27229 | 6216 | 18028 | 10276 | 6531 |
| | 25120 | 4464 | 28347 | 25326 | 5415 | 5702 | 2194 | 22060 | 25588 | 17643 | 24707 | 21709 |
| | 1406 | 19556 | 12441 | 11544 | 2972 | 18250 | 7310 | 18048 | 3005 | 5805 | 29963 | 9130 |
| | 27259 | 10371 | 19075 | 7197 | 10797 | 28371 | 6145 | 7878 | 14446 | 25400 | 29587 | 13473 |
| | 9117 | 7469 | 8935 | 28237 | 1268 | 5108 | 27560 | 30429 | 25279 | 29310 | 1971 | 9953 |
| | 27476 | 6140 | 2328 | 3186 | 1062 | 7447 | 28183 | 24438 | 1880 | 29932 | 28813 | 7346 |

TABLE 8-continued

| PEP SEQ ID NO: | homolog SEQ ID NOs | | | | | | | | | | |
|---|---|---|---|---|---|---|---|---|---|---|---|
| | 3575 | 23091 | 4502 | 10351 | 11558 | 27380 | 26117 | 24357 | 16376 | 18325 | 12600 | 30196 |
| | 11062 | 26767 | 17070 | 8022 | 28167 | 29891 | 16350 | 16423 | 23738 | 14399 | 17149 | 11103 |
| | 18776 | 4471 | 29877 | 2963 | 22453 | 23060 | 5677 | 19269 | 27154 | 22938 | 9041 | 21540 |
| | 16319 | 10029 | 7970 | 17888 | 22885 | 23452 | 18578 | 22148 | 6455 | 27794 | 5238 | 26759 |
| | 14078 | 28332 | 6196 | 3954 | 9208 | 7314 | 28148 | 5595 | 8962 | 26277 | 19037 | 2014 |
| | 10201 | 8980 | 7269 | 17510 | 17508 | 11702 | 1422 | 27709 | 9030 | 11694 | 14189 | 2206 |
| | 29095 | 15026 | 21970 | 28753 | 18638 | 12949 | 15782 | 23500 | 29566 | 19561 | 8922 | 18888 |
| | 8635 | 27031 | 7730 | 22273 | 26855 | 7802 | 29170 | 28338 | 12192 | 1857 | 20955 | 651 |
| | 22972 | 24396 | 11729 | 22455 | 22464 | 18763 | 22460 | 18762 | 22487 | 18739 | 22467 | 22485 |
| | 7470 | 7471 | 11693 | 18710 | 3193 | 13348 | 28870 | 15039 | 9841 | 5648 | 20114 | 7565 |
| | 12240 | 9101 | 5901 | 20829 | 13698 | 14604 | 10081 | 20528 | 2863 | 8077 | 2416 | 4156 |
| | 2415 | 27851 | 5551 | 28791 | 17075 | 30460 | 4848 | 2262 | 19771 | 25640 | 23109 | 12887 |
| | 6142 | 23733 | 3666 | 27756 | 6285 | 26283 | 21176 | 935 | 19132 | 4843 | 30126 | 22186 |
| | 4284 | 25896 | 18049 | 8295 | 19156 | 15981 | 1011 | 22968 | 22088 | 9857 | 14290 | 23049 |
| | 26397 | 13284 | 14418 | 4602 | 24020 | 6118 | 1395 | 23400 | 23507 | 21706 | 5367 | 19834 |
| | 8873 | 2302 | 8667 | 15171 | 22085 | 5729 | 16959 | 23940 | 5011 | 26616 | 18548 | 14054 |
| | 10262 | 5150 | 12512 | 25370 | 15464 | 13513 | 18053 | 17598 | 13448 | 14364 | 11233 | 11270 |
| | 21656 | 11011 | 22908 | 30151 | 8955 | 22425 | 17923 | 3380 | 1438 | 17594 | 19013 | 27621 |
| | 28389 | 28913 | 7821 | 28912 | 2786 | 11164 | 6678 | 15747 | 27497 | 20266 | 26776 | 29512 |
| | 28226 | 11971 | 28017 | 4008 | 20628 | 24450 | 3536 | 13603 | 8954 | 15550 | 17185 | 24310 |
| | 28797 | 23569 | 4473 | 20625 | 25921 | 3147 | 21089 | 14413 | 27638 | 5831 | 28480 | 1539 |
| | 27117 | 14704 | 3725 | 24113 | 28453 | 24936 | 18521 | 22134 | 4546 | 1552 | 12470 | 30034 |
| | 27520 | 23954 | 16139 | 16135 | 21623 | 24776 | 21357 | 28055 | 28940 | 10264 | 27628 | 12480 |
| | 27627 | 27654 | 25661 | 2259 | 25343 | 16930 | 7393 | 19140 | 13385 | 20057 | 8377 | 8740 |
| | 20298 | 23308 | 29768 | 12802 | 17381 | 1340 | 3519 | 24380 | 15106 | 23114 | 10043 | 17563 |
| | 665 | 11696 | 28774 | 3712 | 28052 | 28795 | 3710 | 28803 | 28004 | 1100 | 1745 | 6823 |
| | 28059 | 28007 | 28821 | 28831 | 28828 | 28011 | 1056 | 27973 | 7917 | 20110 | 20111 | 11689 |
| | 11735 | 11660 | 11691 | 11688 | 11656 | 11734 | 28885 | 28886 | 15549 | 12475 | 8397 | 11726 |
| | 11727 | 25525 | 28802 | 28800 | 28050 | 20013 | 7169 | 889 | 22332 | 15319 | 15635 | 19445 |
| | 8489 | 2563 | 5224 | 21062 | 14388 | 4477 | 8449 | 13099 | 25576 | 21311 | 13238 | 12634 |
| | 18024 | 8959 | 23255 | 13076 | 815 | 27247 | 3102 | 19128 | 16024 | 15512 | 6801 | 16846 |
| | 18133 | 28443 | 20053 | 8193 | 10003 | 3852 | 29972 | 24550 | 17915 | 23552 | 4315 | 4280 |
| | 4387 | 4277 | 11738 | 4275 | 4360 | 4233 | 4358 | 4229 | 26798 | 12704 | 8354 | 22489 |
| | 25836 | 5697 | 7788 | 23578 | 24327 | 24329 | 3364 | 3402 | 3399 | 3396 | 28914 | 7718 |
| | 7713 | 29806 | 15542 | 15541 | 17839 | 28097 | 11663 | 11455 | 11459 | 11454 | 11499 | 11496 |
| | 11664 | 11654 | 11509 | 11652 | 27004 | 28725 | 11740 | 18772 | 22365 | 16071 | 5570 | 15151 |
| | 6005 | 25563 | 15361 | 414 | 2505 | 20554 | 4205 | 4202 | 4162 | 4199 | 4164 | 15024 |
| 402: | 21731 | 19306 | 27634 | 10169 | 11204 | 28554 | 2003 | 8294 | 19828 | 26964 | 17294 | 22015 |
| | 26278 | 28659 | 19087 | 9113 | 12024 | 13846 | 12988 | 10512 | 22492 | 11099 | 10957 | 5104 |
| | 6103 | 7321 | 15346 | 2280 | 2464 | 29656 | 18958 | | | | | |
| 403: | 23201 | 8902 | 17383 | 26008 | 26005 | 9941 | 5941 | 28758 | 17348 | 25230 | 22478 | 22649 |
| | 5636 | 21104 | 21891 | 6072 | 16847 | 13755 | 10088 | 8809 | 14343 | 2411 | 23363 | 20102 |
| | 2593 | 10779 | 26745 | 24719 | 2096 | 19888 | 862 | 5398 | 2646 | 28899 | 17727 | 8324 |
| | 7614 | 24127 | | | | | | | | | | |
| 404: | 22505 | 17330 | 17332 | 3832 | 26661 | 24604 | 24601 | 26617 | 26553 | 26585 | 26591 | 26640 |
| | 26582 | 26471 | 26635 | 26572 | 26576 | 26556 | 26609 | 26423 | 25650 | 26551 | 2373 | 2405 |
| | 24690 | 25446 | 25450 | 26422 | 26473 | 25340 | 10489 | 21242 | 21238 | 21241 | 21279 | 24723 |
| | 24725 | 25494 | 25690 | 25164 | 16529 | 7978 | 10037 | 16615 | 16621 | 11055 | 12923 | 6955 |
| | 7874 | 7948 | 7839 | 8664 | 12144 | 14757 | 17096 | 14796 | 14828 | 26829 | 12171 | 21124 |
| | 23048 | 20000 | 23191 | 22333 | 20933 | 15625 | 22212 | 19851 | 28192 | 27896 | 22998 | 22992 |
| | 15629 | 28137 | 24133 | 22151 | 29931 | 985 | 2060 | 944 | 28955 | 28930 | 28990 | 29965 |
| | 15058 | 21486 | 21255 | 20071 | 19073 | 19014 | 18158 | 18127 | 18109 | 15620 | 2239 | 2233 |
| | 16398 | 14851 | 11657 | 12588 | 11744 | 14570 | 13748 | 13790 | 12143 | 12170 | 12173 | 12919 |
| | 15622 | 15628 | 15656 | 15604 | 16393 | 16394 | 16392 | 12916 | 11037 | 22432 | 8701 | 24656 |
| | 19135 | 19853 | 7817 | 18495 | 2869 | 8263 | 29437 | 29438 | 22440 | 22435 | 21711 | 22465 |
| | 21146 | 17031 | 19010 | 21907 | 27742 | 22415 | 5429 | 1188 | 5421 | 18365 | 23435 | 12382 |
| | 12090 | 12087 | 10571 | 18362 | 23640 | 15382 | 987 | 6445 | 6417 | 5413 | 8888 | 2538 |
| | 24892 | 15423 | 1089 | 1127 | 5417 | 21701 | 24630 | 24633 | 21702 | 21705 | 25589 | 25558 |
| | 21697 | 7438 | 22989 | 17339 | 1478 | 1506 | 1479 | 9199 | 25171 | 26307 | 1472 | 25424 |
| | 25418 | 5394 | 23942 | 8884 | 8887 | 12914 | 23541 | | | | | |
| 405: | 17859 | 1238 | 22054 | 28433 | 14522 | 12713 | 2265 | 30161 | 7453 | 4765 | 16339 | 3623 |
| | 16249 | 30466 | 23897 | 24523 | 18199 | 12780 | 12018 | 8775 | 20575 | 9860 | 9828 | 17997 |
| | 22323 | 12760 | 6777 | 25696 | 8048 | 7233 | 7159 | 10567 | 11570 | 5422 | 13420 | 743 |
| | 20960 | 20777 | 13662 | 6471 | 6450 | 722 | 1999 | 22130 | 15016 | 24746 | 17989 | 21018 |
| | 18525 | 29549 | 4744 | 4911 | 15417 | 16008 | 14299 | 4655 | 18309 | 20204 | 13162 | 27357 |
| | 28445 | 29670 | 12438 | 2514 | 2700 | 25507 | 27408 | 21700 | 6258 | 15916 | 23219 | 8612 |
| | 21584 | 7769 | 21090 | 21432 | 24336 | 2356 | 30137 | 4195 | 24837 | 12189 | 4171 | 20221 |
| | 23536 | 26716 | 7664 | 11285 | 23505 | 6454 | 21901 | 13438 | 27127 | 6046 | 28726 | 23456 |
| | 15186 | 1641 | 24978 | 18008 | 19271 | 13956 | 24528 | 17271 | 1119 | 18682 | 4177 | 14894 |
| | 2489 | 29476 | 22053 | 1277 | 2172 | 26999 | 13676 | 22871 | 16889 | 8678 | 12883 | 23881 |
| | 9761 | 20677 | 12855 | 3738 | 22399 | 20134 | 18998 | 18171 | 2684 | 15899 | 7332 | 29308 |
| | 9846 | 23454 | 17170 | 1559 | 28849 | 2839 | 27226 | 11010 | 10112 | 1021 | 29279 | 19520 |
| | 19722 | 26879 | 28081 | 15983 | 17146 | 15924 | 5208 | 2143 | 4634 | 16484 | 3406 | 25815 |
| | 25097 | 16791 | 9830 | 25112 | 1379 | 28559 | 28606 | 16292 | 16260 | 16208 | 16320 | 8188 |
| | 28196 | 5518 | 5513 | 11332 | 7484 | 24098 | 25192 | 11722 | 7295 | 4070 | 3808 | 20017 |
| | 21780 | 1418 | 3680 | 9910 | 7166 | 23057 | 22218 | 23084 | 16029 | 9268 | 11075 | 26038 |
| | 12485 | 7431 | 18804 | 6947 | 8806 | 3674 | 28046 | 5006 | 28297 | 7847 | 24808 | 19618 |
| | 22706 | 21561 | 4782 | 24417 | 3843 | 24691 | 11449 | 9680 | 30005 | 10365 | 4403 | 14746 |

TABLE 8-continued

| PEP SEQ ID NO: | homolog SEQ ID NOs | | | | | | | | | | |
|---|---|---|---|---|---|---|---|---|---|---|---|
| | 20774 | 4849 | 29201 | 28648 | 20671 | 18342 | 23463 | 29918 | 24863 | 14394 | 9080 | 25560 |
| | 8423 | 7517 | 27591 | 30030 | 7571 | 29151 | 7460 | 3064 | 8500 | 8416 | 18919 | 15655 |
| | 22879 | 22882 | 14872 | 2032 | 28860 | 21021 | 11112 | 2577 | 10386 | 7462 | 7356 | 9905 |
| | 21034 | 29197 | 8891 | 6388 | 15308 | 29956 | 25999 | 24693 | 19760 | 18166 | 14979 | 10427 |
| | 18403 | 23159 | 5100 | 26531 | 26168 | 9132 | 29747 | 26986 | 7010 | 6925 | 9803 | 26555 |
| | 30057 | 7883 | 20362 | 13923 | 21199 | 17720 | 10375 | 13693 | 28462 | 5696 | 15243 | 4681 |
| | 11036 | 28713 | 23116 | 22490 | 18697 | 15953 | 16090 | 8882 | 29422 | 26513 | 10652 | 10658 |
| | 14981 | 6819 | 823 | 19664 | 14931 | 2181 | 15988 | 17595 | 11629 | 10661 | 12706 | 6147 |
| | 6518 | 28422 | 8191 | 15040 | 11675 | 3972 | 3697 | 28043 | 5953 | 21288 | 17280 | 10246 |
| | 18586 | 18588 | 19908 | 19910 | 15765 | 26810 | 19134 | 17663 | 17697 | 3638 | 21052 | 16371 |
| | 15495 | 20728 | 421 | 2409 | 22097 | 3355 | 11327 | 6847 | 1500 | 24226 | 15048 | 13579 |
| | 1887 | 8939 | 8964 | 13794 | 9157 | 24816 | 21858 | 5885 | 22336 | 3805 | 3802 | 24169 |
| | 2292 | 26734 | 26770 | 6657 | 13127 | 26043 | 12384 | 16093 | 3544 | 14897 | 2567 | 27765 |
| | 27766 | 27677 | 15125 | 20964 | 23705 | 23066 | 24145 | 25943 | 24093 | 17443 | 7635 | 1827 |
| | 22760 | 29245 | 18346 | 14261 | 16514 | 16482 | 16233 | 16542 | 18557 | 9646 | 13061 | 28991 |
| | 23979 | 2413 | 30304 | 24393 | 6062 | 867 | 1186 | 8879 | 3327 | 2945 | 11059 | 22618 |
| 406: | 20907 | 20913 | 3191 | 25797 | 8462 | 1879 | 4652 | 24363 | 24360 | 10871 | 12810 | 10583 |
| | 10437 | 19450 | 18493 | 11510 | 27173 | 15212 | 15214 | 8588 | 8590 | 9632 | 24462 | 24484 |
| | 28260 | 23999 | 14749 | 8029 | 12739 | 14780 | 18654 | 18652 | 2625 | 8464 | 5633 | 5628 |
| | 27588 | 16686 | 3828 | 21787 | 21790 | 3125 | 13953 | 3308 | 4204 | 18019 | 7272 | 7273 |
| | 15636 | 28388 | 5136 | 17046 | 12262 | 11394 | 8268 | 3615 | 21005 | 16635 | 4983 | 7531 |
| | 30344 | 1135 | 10374 | 5166 | 10372 | 18447 | 18445 | 24095 | 21224 | 10039 | 10660 | 13773 |
| | 13775 | 2682 | 15088 | 15091 | 17289 | 28854 | 4389 | 6838 | 18118 | 25300 | 25284 |
| | 3909 | 19553 | 19550 | 9896 | 30410 | 6350 | 6352 | 21644 | 4235 | 14421 | 1655 | 1687 |
| | 11225 | 4512 | 25728 | 4126 | 13936 | 2284 | 9577 | 2434 | 9351 | 19189 | 736 | 738 |
| | 19080 | 19078 | 11886 | 14543 | 12731 | 5616 | 945 | 24661 | 29479 | 29477 | 19310 | 15449 |
| | 7264 | 7262 | 16117 | 8641 | 9679 | 13198 | 23382 | 16013 | 13897 | 21305 | 9361 | 26329 |
| | 25272 | 13326 | 6626 | 25686 | 24764 | 25861 | 11330 | 20684 | 25383 | 25380 | 19817 | 25252 |
| | 15330 | 15329 | 15599 | 19590 | 19588 | 8432 | 8434 | 6633 | 6636 | 7787 | 8665 | 22993 |
| | 14957 | 24628 | 15222 | 24197 | 24196 | 10768 | 12515 | 9666 | 21632 | 21629 | 29385 | 7904 |
| | 24043 | 27042 | 4463 | 8488 | 7594 | 18889 | 8468 | 7705 | 16095 | 15379 | 25365 | 1105 |
| | 1256 | 9781 | 9756 | 24514 | 13875 | 13877 | 29068 | 29070 | 25581 | 26936 | 641 | 18655 |
| | 13276 | 17422 | 6035 | 3456 | 10575 | 10285 | 22383 | 18810 | 27581 | 24301 | 19856 | 23293 |
| | 19774 | 14585 | 13837 | 18045 | 12415 | 28809 | 1719 | 6283 | 3275 | 5721 | 18107 | 18138 |
| | 14770 | 4010 | 29287 | 28310 | 24971 | 19974 | 19972 | 25303 | 12114 | 23538 | 19092 | 18207 |
| | 3401 | 8653 | 18020 | 28233 | 10290 | 27800 | 13497 | 12795 | 21143 | 24208 | 10362 | 14358 |
| | 30035 | 26498 | 26480 | 2579 | 2581 | 25553 | 30468 | 19029 | 11898 | 4098 | 14169 | 15514 |
| | 7910 | 7526 | 13171 | 27054 | 12790 | 1986 | 12789 | 23005 | 19231 | 2976 | 15569 | 20232 |
| | 15921 | 15922 | 23759 | 23842 | 28666 | 18692 | 18690 | 23244 | 23407 | 17423 | 17427 | 2897 |
| | 27714 | 25824 | 25996 | 7047 | 2917 | 12909 | 4107 | 4108 | 21136 | 12211 | 2611 | 3592 |
| | 10480 | 18755 | 1028 | 1083 | 1963 | 22608 | 22456 | 29314 | 12417 | 28403 | 1979 | 17156 |
| | 17153 | 13292 | 26514 | 19436 | 12547 | 19440 | 9160 | 14472 | 23872 | 23739 | 29989 | 1335 |
| | 14762 | 15717 | 8060 | 8059 | 23117 | 29375 | 29376 | 26898 | 26902 | 18701 | 18704 | 29253 |
| | 7320 | 30440 | 30441 | 20734 | 23837 | 10657 | 27536 | 27533 | 24001 | 20961 | 23981 | 24460 | 19850 |
| | 3286 | 25065 | 23832 | 17487 | 28157 | 27536 | 27533 | 4371 | 15156 | 17678 | 22952 | 16046 |
| | 5165 | 5370 | 8837 | 21890 | 19970 | 29406 | 8021 | 23986 | 28783 | 28553 | 5644 | 5641 |
| | 21285 | 22940 | 22969 | 13328 | 28250 | 4134 | 28550 | 3444 | 26567 | 21414 | 958 | 8881 |
| | 12551 | 1716 | 17811 | 17812 | 12712 | 13880 | 22545 | 22546 | 3504 | 3506 | 11188 | 11214 |
| | 17887 | 4937 | 3552 | 3551 | 17399 | 17402 | 10773 | 8411 | 5793 | 5318 | 16770 | 9716 |
| | 17927 | 8463 | 27561 | 29358 | 11998 | 27717 | 14721 | 14058 | 11597 | 28740 | 2871 | 26354 |
| | 25451 | 20098 | 7924 | 12550 | 6100 | 24279 | 24277 | 20396 | 2049 | 1065 | 11232 | 21892 |
| | 28207 | 25149 | 27734 | 6497 | 9417 | 26597 | 14974 | 20985 | 12570 | 20521 | 18886 | 17886 |
| | 23304 | 18904 | 19175 | 1387 | 29485 | 3384 | 16225 | 11238 | 9062 | 13183 | 17080 | 2487 |
| | 2491 | 27726 | 29848 | 3609 | 5598 | 22808 | 19182 | 24278 | 16173 | 8744 | 28044 | 1695 |
| | 3387 | 15194 | 27618 | 7048 | 3389 | 29713 | 5176 | 27037 | 9625 | 20426 | 29634 | 29188 |
| | 18873 | 18872 | 25945 | 27822 | 16344 | 11957 | 28964 | 17260 | 18190 | 24580 | 5580 | 6177 |
| | 17614 | 29315 | 23000 | 29323 | 23763 | 27598 | 26802 | 2068 | 8800 | 27178 | 22450 | 20363 |
| | 19397 | 16749 | 24564 | 22557 | 24273 | 24092 | 11197 | 13251 | 5525 | 11883 | 12610 | 8401 |
| | 5939 | 3180 | 17437 | 8733 | 19094 | 16076 | 16080 | 13482 | 15213 | 25017 | 14352 | 13469 |
| | 24642 | 29487 | 23655 | 19380 | 5916 | 10810 | 21784 | 3872 | 21783 | 10211 | 14168 | 20997 |
| | 3827 | | | | | | | | | | | |
| 407: | 21969 | 3426 | 23405 | 5511 | 8336 | 7035 | 21611 | 12774 | 12091 | 28615 | 20024 | 28014 |
| | 12005 | 3736 | 28490 | 17277 | 6567 | 2642 | 5615 | 22527 | 23461 | 23548 | 2510 | 16657 |
| | 14727 | 18948 | 681 | 14155 | 24237 | 9719 | 27107 | 2157 | 12368 | 4881 | 21443 | 3211 |
| | 6740 | 29290 | 12934 | 12791 | 15334 | 6320 | 12678 | 2665 | 7340 | 27172 | 25880 | 13369 |
| | 18111 | 20334 | 20201 | 24004 | 17227 | 1996 | 25095 | 15305 | 2617 | 8320 | 14635 | 5475 |
| | 24706 | 20420 | 5892 | 20894 | 8105 | 9553 | 6246 | 22041 | 14153 | 27670 | 20341 | 10564 |
| | 27658 | 2795 | 4144 | 6083 | 17408 | 6067 | 23247 | 16218 | 457 | 14021 | 12930 | 5230 |
| | 2316 | 26146 | 22112 | 8274 | 19356 | 14025 | 379 | 10900 | 3477 | 11849 | 25408 | 19607 |
| | 21727 | 2858 | 24353 | 25045 | 28887 | 5143 | 16074 | 9958 | 11336 | 4365 | 18650 | |
| 408: | 8062 | 25546 | 1621 | 1614 | 3009 | 3717 | 29164 | 16148 | 12892 | 13560 | 16717 | 22076 |
| | 27209 | 9526 | 29022 | 8028 | 19060 | 6866 | 9859 | 9521 | 7039 | 26735 | 8846 | 1715 |
| | 1672 | 28893 | 13883 | 2631 | 6794 | 16995 | 1850 | 14668 | 6858 | 28859 | 4514 | 23601 |
| | 16164 | 6975 | 12533 | 9365 | 9172 | 4159 | 21035 | 10240 | 18547 | 5671 | 11514 | 11548 |
| | 5676 | 11550 | 5680 | 5674 | 6470 | 6468 | 7842 | 12045 | 5223 | 8553 | 3704 | 24541 |
| | 4607 | 10019 | 18105 | 29082 | 29077 | 1410 | 15795 | 28994 | 29007 | 28915 | 29042 | 28911 |
| | 28939 | 28963 | 29040 | 28907 | 28213 | 28212 | 29071 | 29037 | 30138 | 29832 | 8948 | 2225 |
| | 5778 | 20322 | 28399 | 16532 | 28220 | 2469 | 4696 | 15116 | 16142 | 27979 | 3696 | 2867 |

TABLE 8-continued

| PEP SEQ ID NO: | homolog SEQ ID NOs | | | | | | | | | | |
|---|---|---|---|---|---|---|---|---|---|---|---|
| | 12965 | 28477 | 3280 | 12359 | 27750 | 22948 | 1258 | 5427 | 5460 | 18149 | 28362 | 4902 |
| | 17917 | 13498 | 14814 | 28150 | 24160 | 15483 | 12750 | 17479 | 1662 | 6433 | 9794 | 1592 |
| | 15146 | 9280 | 3088 | 12015 | 4354 | 20546 | 24902 | 11555 | 4335 | 22457 | 16123 | 17558 |
| | 17717 | 910 | 10438 | 28145 | 6908 | 10708 | 28408 | 5252 | 16374 | 26917 | 9238 | 8861 |
| | 24620 | 23131 | 22834 | 26229 | 28302 | 6235 | 26899 | 7779 | 4266 | 29616 | 1606 | 1609 |
| | 1467 | 1691 | 1659 | 1689 | 1661 | 1694 | 1501 | 1476 | 2647 | 2750 | 2746 | 1727 |
| | 1761 | 1734 | 1728 | 1725 | 1473 | 803 | 1587 | 10610 | 1574 | 1579 | 1572 | 2811 |
| | 1541 | 2561 | 2586 | 2589 | 2604 | 3580 | 10615 | 1509 | 2651 | 2742 | 2739 | 1768 |
| | 1763 | 1612 | 1651 | 1613 | 1618 | 1654 | 1583 | 1543 | 1537 | 2527 | 2530 | 2524 |
| | 1582 | 23525 | 19216 | 29085 | 7774 | 2331 | 23154 | 29609 | 25022 | 25381 | 23955 | 30244 |
| | 11367 | 9700 | 22351 | 15912 | 2551 | 3728 | 13514 | 17240 | 7818 | 21759 | 10429 | 19954 |
| | 10825 | 21007 | 15393 | 21331 | 25505 | 7916 | 9568 | 25938 | 11553 | 10131 | 3137 | 9322 |
| | 9027 | 3962 | 21216 | 11719 | 27112 | 30197 | 20407 | 2703 | 30094 | 10217 | 14312 | 23485 |
| | 10245 | 3529 | 12563 | 27224 | 10266 | 28943 | 23369 | 9552 | 22613 | 18513 | 21022 | 5606 |
| | 1546 | 1548 | 1573 | 1578 | 1586 | 1590 | 1608 | 1611 | 1617 | 1653 | 1657 | 1658 |
| | 6919 | 11797 | 11827 | 4451 | 19065 | 29618 | 5285 | 3288 | 7613 | 660 | 8693 | 27839 |
| | 2810 | 2553 | 18726 | 7901 | 24270 | 9299 | 2519 | 16420 | 6984 | 15297 | 18483 | 25174 |
| | 26789 | 23155 | 22686 | 14076 | 11152 | 16256 | 23295 | 20948 | 28788 | 22250 | 5411 | 3126 |
| | 25705 | 25265 | 6921 | 28113 | 5057 | 8743 | 14281 | 6158 | 9273 | 19478 | 10433 | 6792 |
| | 17640 | 27860 | 27003 | 9451 | 12592 | 28271 | 29712 | 22575 | 28981 | 27857 | 4096 | 24847 |
| | 12257 | 27013 | 8199 | 18182 | 20431 | 15357 | 7763 | 3491 | 24846 | 6182 | 18010 | 25888 |
| | 25407 | 25088 | 21588 | 16819 | 28637 | 24389 | 11216 | 5543 | 4135 | 7475 | 8609 | 22226 |
| | 24673 | 27255 | 1489 | 15644 | 21618 | 13285 | 6198 | 12085 | 18071 | 14682 | 13139 | 1415 |
| | 17807 | 17061 | 13474 | 13119 | 22434 | 6677 | 16352 | 23720 | 8083 | 6895 | 18930 | 28697 |
| | 24175 | 21438 | 5025 | 13598 | 6340 | 30086 | 17974 | 12976 | 25371 | 28537 | 22086 | 10711 |
| | 5962 | 18451 | 3617 | 1645 | 16773 | 18011 | 7668 | 8086 | 8075 | 8073 | 8445 | 11782 |
| | 19317 | 25997 | 25060 | 20401 | 23914 | 23917 | 23120 | 14111 | 3590 | 15442 | 9295 | 27636 |
| | 11966 | 7992 | 8095 | 14960 | 27986 | 24824 | 1538 | 25046 | 30318 | 28351 | 15917 | 9687 |
| | 10435 | 9187 | 20535 | 1599 | 24522 | 2542 | 19104 | 16153 | 2680 | 23937 | 14540 | 15961 |
| | 12126 | 2020 | 20693 | 26760 | 11857 | 1513 | 11794 | 4643 | 16921 | 21899 | 17288 | 2017 |
| | 7349 | 8476 | 19382 | 17169 | 13154 | 10448 | 913 | 11040 | 20243 | 13186 | 13142 | 13116 |
| | 13151 | 1753 | 14453 | 6037 | 6586 | 21167 | 17127 | 7728 | 14141 | 9472 | 14953 | 15731 |
| | 20138 | 20246 | 20354 | 13399 | 981 | 20198 | 796 | 1710 | 7487 | 1596 | 20288 | 723 |
| | 1471 | 11035 | 28184 | 28181 | 28156 | 28190 | 28189 | 28844 | 27928 | 17042 | 4772 | 1151 |
| | 24320 | 18465 | 13396 | 9570 | 20364 | 21253 | 20359 | 21250 | 20323 | 20157 | 20202 | 20153 |
| | 20158 | 20240 | 20356 | 20260 | 20257 | 20162 | 20255 | 20326 | 20367 | 20331 | 20208 | 20317 |
| | 20320 | 2605 | 2709 | 2716 | 2713 | 2615 | 2610 | 3587 | 3586 | 20193 | 797 | 20196 |
| | 20290 | 20164 | 2550 | 30289 | 13056 | 28817 | 10607 | 29043 | 26783 | 29075 | 28947 | 28944 |
| | 29964 | 26807 | 29192 | 1681 | 13082 | 7027 | 14335 | 25964 | 11058 | 4240 | 18756 | 14942 |
| | 12023 | 15451 | 27741 | 17482 | 27091 | 12350 | 25793 | 5974 | 1126 | 25128 | 13028 | 27746 |
| | 22847 | 22159 | 1639 | 13191 | 1751 | 13053 | 13124 | 13184 | 1643 | 20287 | 27063 | 7593 |
| | 15102 | 29000 | 8297 | 7129 | 12975 | 20523 | 17084 | 22500 | 3163 | 1310 | 13081 | 1504 |
| | 18430 | 25198 | 25679 | 25678 | 25106 | 25248 | 25175 | 25169 | 25255 | 25181 | 18459 | 18461 |
| | 18435 | 25396 | 25394 | 25329 | 25362 | 25335 | 25320 | 25282 | 25263 | 25325 | 28975 | 14262 |
| | 4747 | 28996 | 28999 | 16645 | 22944 | 8114 | 27237 | 13113 | 13084 | 13115 | 28318 | 13059 |
| | 13194 | 13147 | 13187 | 13145 | 13033 | 13086 | 13031 | 13189 | 1809 | 25865 | 14139 | 15466 |
| | 4851 | 1603 | 1633 | 1635 | 20284 | 20292 | 1747 | 1670 | 1748 | 1674 | 11704 | 14332 |
| | 15281 | 28967 | 29044 | 12730 | 29730 | 7399 | 1708 | 9253 | | | | |
| 409: | 13427 | 23058 | 5243 | 11587 | 23453 | 12652 | 21459 | 6252 | 7672 | 2947 | 5347 | 2102 |
| | 5688 | 25571 | 26365 | 10626 | 27508 | 18241 | 12440 | 12814 | 19050 | 23328 | 2423 | 8167 |
| | 4061 | 29223 | 10487 | 30179 | 8917 | 30231 | 2636 | 26203 | 18152 | 10949 | 28873 | 5376 |
| | 3157 | 16589 | 21681 | 25670 | 30177 | 16958 | 8840 | 18876 | 19876 | 12650 | 29394 | 16675 |
| | 15087 | 25201 | 4368 | 12753 | 6475 | 7056 | 17215 | 24280 | 20601 | 22335 | 8505 | 25901 |
| | 21973 | 4263 | 28089 | 16284 | 24470 | 19929 | 22991 | 17198 | 8765 | 21482 | 13324 | 3652 |
| | 17262 | 5517 | 4750 | 15168 | 2054 | 9507 | 4111 | 27757 | 20646 | 14592 | 19951 | 27118 |
| | 11142 | 15189 | 9637 | 14837 | 20735 | 12436 | 4064 | 30293 | 18039 | 24028 | 1259 | 3440 |
| | 10545 | 7446 | 25216 | 4415 | 11879 | 27148 | 26516 | | | | | |
| 410: | 17488 | 14670 | 25907 | 13589 | 14392 | 28308 | 12688 | 3967 | 27108 | 3325 | 11903 | 27253 |
| | 24850 | 14090 | 16633 | 5804 | 8233 | 11276 | | | | | | |
| 411: | 23960 | 23994 | 23991 | 24179 | 24180 | 24076 | 24118 | 24146 | 24149 | 24030 | 24181 | 24184 |
| | 24209 | 24210 | 24213 | 24217 | 24110 | 24232 | 24034 | 24105 | 24236 | 24238 | 23998 | 24071 |
| | 23989 | 24241 | 23996 | 24178 | 24037 | 24027 | 19800 | 24996 | 29453 | 11999 | 10858 | 30053 |
| | 28316 | 7212 | 16755 | 20729 | 22270 | 7627 | 11355 | 12504 | 27348 | 20733 | 28622 | 3242 |
| | 5744 | 13159 | 7477 | 4347 | 10410 | 10411 | 11339 | 10413 | 18220 | 15424 | 23615 | 717 |
| | 719 | 19472 | 26754 | 20123 | 11575 | 29990 | 17924 | 26612 | 26213 | 26212 | 26210 | 14807 |
| 412: | 14671 | 15692 | 15987 | 22073 | 5813 | 23395 | 3235 | 19033 | 861 | 4626 | 2988 | 10228 |
| | 766 | 6195 | 16805 | 18479 | | | | | | | | |
| 413: | 12549 | 18187 | 6723 | 6893 | 30215 | 24496 | 11543 | 17447 | 19279 | 30095 | 26452 | 14203 |
| | 8981 | 10294 | 25217 | 11910 | 25862 | 23600 | 25330 | 18729 | 1209 | 22132 | 7771 | 19809 |
| | 19840 | 1324 | 7421 | 28894 | 24897 | 15572 | 10412 | 10385 | 4017 | 10179 | 7291 | 7330 |
| | 15721 | 3227 | 9290 | 4031 | 22627 | 22621 | 1295 | 23614 | 16939 | 1294 | 13096 | 14594 |
| | 10826 | 23830 | 9875 | 14458 | 6600 | 11620 | 4115 | 7279 | 29579 | 6250 | 14102 | 12301 |
| | 24256 | 18504 | 3243 | 18239 | 21132 | 24871 | 24482 | 9462 | 30400 | 27319 | 12028 | 23195 |
| | 2195 | 2112 | 19258 | 27367 | 11902 | 1380 | 4207 | 1377 | 28739 | 28780 | 2560 | 2251 |
| | 8457 | 30203 | 20391 | 27431 | 2912 | 11442 | 14775 | 24603 | 20302 | 20411 | 25165 | 16179 |
| | 11959 | 10309 | 22529 | 14726 | 13772 | 6477 | 20236 | 5695 | 5369 | 19255 | 25035 | 28140 |
| | 25754 | 13122 | 17090 | 17088 | 19199 | 21934 | 19434 | 16556 | 7415 | 27702 | 23319 | 8854 |
| | 16044 | 22249 | 28264 | 10440 | 27671 | 28727 | 1022 | 26381 | 29304 | 1004 | 23153 | 27331 |

TABLE 8-continued

| PEP SEQ ID NO: | homolog SEQ ID NOs | | | | | | | | | | |
|---|---|---|---|---|---|---|---|---|---|---|---|
| | 14795 | 14064 | 30180 | 5439 | 7076 | 20788 | 2578 | 20541 | 6750 | 7219 | 17952 | 17206 |
| | 2016 | 29825 | 10673 | 2098 | 19307 | 28535 | 16396 | 19692 | 29355 | 23257 | 11756 | 8181 |
| | 25454 | 3487 | 3490 | 7146 | 4986 | 21626 | 17743 | 17657 | 4306 | 30116 | 15904 | 22714 |
| | 20998 | 23432 | 15302 | 14276 | 17895 | 11156 | 12032 | 30445 | 29816 | 989 | 26655 | 26656 |
| | 24099 | 24101 | 4219 | 4218 | 28402 | 28336 | 2249 | 23351 | 961 | 3797 | 24100 | 1464 |
| | 28397 | 24921 | 20495 | 25816 | 3359 | 13439 | 28969 | 9704 | 19131 | 19554 | 28472 | 19193 |
| | 6493 | 3128 | 24287 | 29398 | 8945 | 29802 | 23794 | 9455 | 8508 | 6576 | 6785 | 21286 |
| | 8869 | 9559 | 8824 | 8823 | 6225 | 1015 | 9878 | 30412 | 29319 | 16475 | 21186 | 13968 |
| | 10743 | 12132 | 10002 | 14558 | 15461 | 11653 | 11655 | 27592 | 8987 | 9015 | 26600 | 22337 |
| | 29254 | 16672 | 5661 | 23871 | 27946 | 8717 | 16536 | 2729 | 7175 | 6458 | 2730 | 19886 |
| | 19884 | 26668 | 26666 | 3562 | 28005 | 27490 | 27944 | 22845 | 6463 | 4095 | 3000 | 14154 |
| | 9000 | 3542 | 3458 | 17748 | 7558 | 5488 | 12500 | 8528 | 15560 | 7439 | 6739 | 3611 |
| | 19323 | 25663 | 28683 | 6590 | 776 | 21017 | 21203 | 12649 | 14927 | 12693 | 14937 | 23123 |
| | 15889 | 27918 | 14923 | 24230 | 11753 | 4148 | 19106 | 20058 | 6880 | 12738 | 10316 | 10405 |
| | 28971 | 11945 | 21707 | 8901 | 17579 | 11315 | 15603 | 14965 | 11951 | 15789 | 27908 | 11068 |
| | 25881 | 15610 | 8857 | 28019 | 30319 | 22677 | 9164 | 26279 | 23628 | 22792 | 12255 | 11290 |
| | 20508 | 27661 | 13605 | 10261 | 22573 | 22577 | 22576 | 23487 | 16010 | 10061 | 24578 | 9544 |
| | 26041 | 13967 | 27940 | 22051 | 7263 | 9033 | 29592 | 6788 | 16551 | 16002 | 10443 | 15858 |
| | 15862 | 10300 | 15860 | 28315 | 8379 | 15207 | 15170 | 15140 | 15137 | 15173 | 26987 |
| | 16524 | 14204 | 14211 | 12261 | 18209 | 977 | 30115 | 10746 | 17054 | 11609 | 10585 | 22918 |
| | 22916 | 22982 | 23033 | 28626 | 24555 | 25261 | 25520 | 9166 | 10297 | 30131 | 9872 | 8915 |
| | 9272 | 5608 | 22842 | 11082 | 13193 | 1660 | 11466 | 13161 | 10196 | 10255 | 8292 | 24977 |
| | 19456 | 24387 | 16983 | 25788 | 17307 | 14298 | 23921 | 24520 | 11546 | 15021 | 3035 | 19122 |
| | 22397 | 8387 | 30428 | 12614 | 18816 | 29994 | 29186 | 22807 | 27437 | 26000 | 24509 | 24477 |
| | 24511 | 24515 | 24517 | 8909 | 9968 | 19447 | 10561 | 19507 | 16661 | 12928 | 29264 | 5409 |
| | 15284 | 8889 | 19268 | 27219 | 27217 | 26835 | 27423 | 26663 | 25782 | 8129 | 26565 | 7796 |
| | 19841 | 28880 | 20239 | 27075 | | | | | | | | |
| 414: | 28852 | 15638 | 17009 | 6683 | 16039 | 5647 | 28427 | 890 | 18228 | 6105 | 16172 | 1771 |
| | 7145 | 10622 | 6022 | 2613 | 28259 | 29515 | 4357 | 8326 | 19653 | 12830 | 12478 | 401 |
| | 8441 | 9141 | 18198 | 4527 | 17869 | 26532 | 24923 | 21211 | 976 | 17092 | 7122 | 1167 |
| | 4885 | 8002 | 20762 | 23274 | 20547 | 25649 | 19161 | 10754 | 5179 | 6465 | 25364 | 3395 |
| | 27640 | 24980 | 7840 | 29738 | 12477 | 17516 | 9474 | 3936 | 16980 | 19557 | 13703 | 16878 |
| | 22607 | 25235 | 13904 | 13250 | 1047 | 13392 | 6129 | 30257 | 6509 | 24453 | 23187 | 26194 |
| | 21355 | 11222 | 26605 | 6397 | 13313 | 10666 | 3577 | 8479 | 14823 | 11666 | 18856 | 30297 |
| | 14116 | 7827 | 22359 | 7791 | 20046 | 25765 | 1385 | 26631 | 19200 | 21539 | 19116 | 28056 |
| | 23396 | 16713 | 5651 | 23317 | 14513 | 25124 | 16180 | 15307 | 17556 | 27259 | 14768 | 8865 |
| | 13696 | 18699 | 19395 | 11033 | 12605 | 28945 | 17006 | 16032 | 9880 | 24412 | 28474 | 25974 |
| | 22541 | 22540 | 30368 | 30401 | 19370 | 14995 | 2369 | 13973 | 18212 | 11309 | 9695 | 9324 |
| | 22518 | 23300 | 4831 | 3345 | 2257 | 9702 | 21449 | 18968 | 3503 | 24702 | 1266 | 12286 |
| | 11393 | 21501 | 6804 | 25638 | 15689 | 21091 | 28116 | 20314 | 13050 | 13353 | 12953 | 19169 |
| | 27681 | 25991 | 3553 | 27783 | 8863 | 21558 | 6432 | 3585 | 19009 | 8984 | 22488 | 28425 |
| | 28372 | 20493 | 14706 | 15432 | 28301 | 15697 | 7947 | 22520 | 22749 | 20146 | 29086 | 25985 |
| | 2650 | 29707 | 21537 | 20350 | 20618 | 16287 | 14042 | 7804 | 18046 | 6176 | 14412 | 27806 |
| | 22536 | 22090 | 4038 | 16872 | 2541 | 6592 | 15938 | 11702 | 17508 | 17510 | 1422 | 3635 |
| | 11694 | 14189 | 10388 | 2142 | 27706 | 23269 | 4150 | 9767 | 6994 | 9838 | 24831 | 1730 |
| | 11855 | 4622 | 16400 | 4426 | 4456 | 18745 | 20869 | 24274 | 21316 | 5871 | 27263 | 25036 |
| | 7801 | 14267 | 16965 | 24586 | 22741 | 28908 | 11729 | 22455 | 18739 | 22464 | 18763 | 22467 |
| | 22487 | 22460 | 18762 | 22485 | 11693 | 18710 | 3193 | 13348 | 28870 | 15039 | 5551 | 7913 |
| | 29439 | 9149 | 17075 | 30460 | 4848 | 2262 | 19771 | 25640 | 23109 | 12887 | 6142 | 23733 |
| | 3666 | 27756 | 935 | 4843 | 28791 | 4284 | 30126 | 10081 | 15981 | 2415 | 2416 | 27851 |
| | 7565 | 5901 | 20829 | 13698 | 14604 | 21706 | 23400 | 14418 | 24020 | 25799 | 14956 | 20528 |
| | 26397 | 9627 | 20378 | 14290 | 1395 | 21176 | 19132 | 19806 | 6002 | 24924 | 8295 | 26523 |
| | 1011 | 22939 | 22968 | 4602 | 13284 | 18049 | 22528 | 6267 | 9857 | 4757 | 6118 | 6053 |
| | 19156 | 17418 | 617 | 10776 | 27467 | 18329 | 24475 | 12655 | 22088 | 13133 | 6137 | 5743 |
| | 27955 | 11718 | 15232 | 14150 | 11737 | 12375 | 11728 | 11641 | 27323 | 4620 | 2147 | 4967 |
| | 23049 | 25416 | 5541 | 15260 | 11047 | 13972 | 13504 | 1010 | 21041 | 4417 | 29749 | 5930 |
| | 15783 | 7966 | 3003 | 29823 | 14759 | 19481 | 2779 | 27454 | 11537 | 22341 | 2883 | 5343 |
| | 22493 | 22883 | 2906 | 6396 | 13663 | 1168 | 5729 | 5011 | 15171 | 22085 | 10262 | 16959 |
| | 5150 | 12512 | 23940 | 15464 | 18548 | 14054 | 26616 | 19834 | 18053 | 8873 | 13448 | 25370 |
| | 2302 | 14364 | 11270 | 11233 | 13513 | 17598 | 22425 | 8667 | 17594 | 22908 | 30151 | 17923 |
| | 19013 | 8955 | 27899 | 5428 | 27481 | 4282 | 14393 | 25953 | 8707 | 1438 | 11011 | 2360 |
| | 28214 | 3380 | 14004 | 21652 | 12442 | 9823 | 14608 | 16151 | 11314 | 7692 | 14481 | 9809 |
| | 27621 | 28389 | 28913 | 7821 | 28912 | 11698 | 2786 | 16182 | 30108 | 28226 | 24310 | 8954 |
| | 15550 | 28017 | 4008 | 20628 | 24450 | 3536 | 13603 | 28797 | 25921 | 4473 | 20625 | 3147 |
| | 14413 | 21089 | 1539 | 23569 | 18521 | 14704 | 5831 | 22134 | 24936 | 18035 | 28480 | 4546 |
| | 799 | 27117 | 11365 | 4143 | 8899 | 30102 | 4689 | 18234 | 15735 | 3232 | 7395 | 27043 |
| | 14845 | 3725 | 12816 | 20902 | 25355 | 16212 | 16823 | 17436 | 25565 | 29860 | 3294 | 21972 |
| | 20025 | 11084 | 27638 | 24113 | 3434 | 28595 | 12042 | 3002 | 14802 | 8280 | 22114 | 13288 |
| | 7247 | 4188 | 30324 | 18791 | 1552 | 23915 | 25341 | 12470 | 16139 | 16135 | 21623 | 24776 |
| | 28775 | 28055 | 25677 | 28940 | 10264 | 27627 | 12480 | 27628 | 27654 | 28416 | 27817 | 3098 |
| | 3450 | 17563 | 11696 | 665 | 3712 | 28774 | 28052 | 28795 | 3710 | 19046 | 28803 | 28004 |
| | 6823 | 1100 | 1745 | 28059 | 28007 | 28831 | 28821 | 28828 | 1056 | 27973 | 28011 | 7917 |
| | 20110 | 20111 | 11689 | 11660 | 11735 | 11688 | 11691 | 11734 | 28885 | 28886 | 15549 |
| | 12475 | 8397 | 11726 | 11727 | 25525 | 28800 | 28802 | 28050 | 28794 | 27983 | 28773 | 10507 |
| | 889 | 7932 | 9202 | 9772 | 25449 | 6644 | 9821 | 21194 | 13207 | 13099 | 16098 | 13238 |
| | 15967 | 1671 | 26108 | 27788 | 26849 | 28704 | 24124 | 16660 | 25348 | 3363 | 1759 | 8750 |
| | 22058 | 17197 | 12031 | 19854 | 4329 | 8752 | 12335 | 8926 | 14096 | 3870 | 2640 | 22222 |
| | 21042 | 12635 | 6801 | 13076 | 815 | 3102 | 19128 | 28443 | 23255 | 10003 | 24550 | 8193 |

TABLE 8-continued

| PEP SEQ ID NO: | | | | homolog SEQ ID NOs | | | | | | |
|---|---|---|---|---|---|---|---|---|---|---|
| | 18024 | 18913 | 10475 | 20706 | 29365 | 8732 | 25064 | 7381 | 7862 | 4280 | 4387 | 4315 |
| | 4275 | 4360 | 4233 | 4358 | 4229 | 4277 | 11738 | 22193 | 18443 | 28274 | 3364 | 3396 |
| | 3402 | 3399 | 28914 | 4375 | 12215 | 4677 | 12631 | 11664 | 11654 | 11663 | 11652 | 11499 |
| | 11496 | 11455 | 11509 | 11459 | 11454 | 16704 | 19282 | 16740 | 27227 | 11740 | 6436 | 10899 |
| | 19172 | 8486 | 5666 | 21822 | 29680 | 23925 | 30438 | 26094 | 23888 | 23957 | 21627 | 4202 |
| | 4162 | 4205 | 4199 | 4164 | 9176 | 2146 | 12300 | | | | | |
| 415: | 15090 | 9360 | 19558 | 17391 | 10057 | 17102 | 15552 | 29057 | 1555 | 15910 | 6334 | |
| 416: | 23286 | 11758 | 1274 | 8225 | 27981 | 25684 | 25757 | 16457 | 16452 | 1391 | 12214 | 23260 |
| | 23289 | 1744 | 11105 | 11360 | 5199 | 25720 | 25688 | 14705 | 6709 | 6649 | 16261 | 22979 |
| | 22977 | 16994 | 16270 | 2059 | 2009 | 16265 | 20642 | 23803 | 20644 | 15180 | 15175 | 4941 |
| | 4914 | 3758 | 4703 | 4713 | 16785 | 10080 | 16509 | 27451 | 6582 | 12093 | 3831 | 1155 |
| | 9438 | 17429 | 4505 | 9638 | 12510 | 11369 | 12332 | 11407 | 12298 | 12366 | 12270 | 11488 |
| | 11530 | 12277 | 12432 | 12339 | 12269 | 17458 | 17460 | 19786 | 19822 | 21082 | 19790 | 19696 |
| | 19761 | 19793 | 19758 | 19719 | 19935 | 19903 | 19827 | 19930 | 19868 | 21151 | 21148 | 21112 |
| | 19763 | 21144 | 19928 | 3788 | 4668 | 4665 | 4699 | 4673 | 16783 | 4824 | 16782 | 6878 |
| | 6991 | 6910 | 6932 | 6936 | 6940 | 5992 | 4628 | 3791 | 4740 | 4743 | 26710 | 23228 |
| | 28484 | 14653 | 14703 | 17093 | 15617 | 15646 | 15668 | 15641 | 15642 | 15670 | 15639 | 22762 |
| | 13093 | 20149 | 2079 | 4751 | 4775 | 4982 | 6024 | 6061 | 6868 | 16810 | 4978 | 6837 |
| | 5982 | 6907 | 26794 | 25144 | 24355 | 5247 | 3727 | 3754 | 16757 | 3755 | 3784 | 3787 |
| | 4632 | 4659 | 4662 | 4707 | 4746 | 4749 | 4830 | 4834 | 4879 | 4909 | 4907 | 4912 |
| | 4944 | 4945 | 4980 | 5768 | 5792 | 5829 | 5862 | 5899 | 5895 | 5938 | 5942 | 5975 |
| | 5986 | 6059 | 6091 | 6093 | 6099 | 6869 | 6897 | 6902 | 6942 | 6961 | 6964 | 6969 |
| | 3748 | 3751 | 25626 | 18897 | 18900 | 11659 | 3110 | 1332 | 23097 | 27977 | 1190 | 15240 |
| | 5284 | 5204 | 5307 | 5306 | 5310 | 5201 | 5331 | 5329 | 5234 | 5232 | 5226 | 5278 |
| | 5236 | 5239 | 5277 | 10149 | 2306 | 12349 | 27947 | 19479 | 19484 | 25020 | 24994 | 14113 |
| | 14253 | 14109 | 14251 | 14282 | 15069 | 14138 | 30160 | 14321 | 14278 | 19566 | 14326 | 14195 |
| | 19682 | 14068 | 14161 | 29739 | 10181 | 17666 | 10210 | 17706 | 17711 | 17670 | 17681 | 23292 |
| | 16447 | 13249 | 28736 | 13813 | 4269 | 8971 | 24172 | 10784 | 6621 | 6581 | 21799 | 28030 |
| | 14647 | 5282 | 27990 | 28015 | 16419 | 5909 | 5945 | 6619 | 6614 | 14800 | 17524 | 28146 |
| | 21825 | 21826 | 8124 | 8126 | 8159 | 8214 | 28025 | 28023 | 28020 | 8218 | 8196 | 30192 |
| | 4794 | 15242 | 2511 | 14452 | 25359 | 13419 | 1836 | 2576 | 16666 | 1428 | 1423 | 19836 |
| | 1910 | 7820 | 10218 | 20683 | 29045 | 6026 | 6025 | 16449 | 4481 | 14869 | 10745 | 11813 |
| | 20059 | 22400 | 11648 | 7691 | 16414 | 8183 | 16455 | 16412 | 16460 | 13181 | 2994 | 2965 |
| | 26527 | 16462 | 11863 | 7168 | 20675 | 16443 | 20678 | 967 | 17461 | 2509 | 11502 | 7375 |
| | 17492 | 28280 | 6553 | 17455 | 2264 | 16409 | 16416 | 16418 | 16407 | 16444 | 4844 | 14779 |
| | 20794 | 12379 | 7963 | 19990 | 15714 | 670 | 11705 | 25327 | 26672 | 28323 | 23256 | 17560 |
| | 18542 | 22080 | 13354 | 13352 | 21460 | 21463 | 3023 | 16390 | 14532 | 29577 | 29581 | 29580 |
| | 29552 | 29576 | 29541 | 8329 | 6616 | 6645 | 6642 | 16406 | 5279 | 20860 | 3939 | 8558 |
| | 3973 | 4297 | 17449 | 19743 | 8597 | 25495 | 25466 | 23522 | 22778 | 809 | 27528 | 1300 |
| | 23760 | 29578 | 25760 | 25761 | 20932 | 11894 | 20864 | 9396 | 3800 | 15568 | 9826 | 11866 |
| | 20815 | 26007 | 7525 | 8113 | 8080 | 19979 | 20833 | 20882 | 19973 | 20991 | 20988 | 21040 |
| | 20992 | 20962 | 20958 | 20922 | 20875 | 7061 | 20135 | 14531 | 6555 | 3548 | 3465 | 3461 |
| | 21597 | 21821 | 7008 | 19716 | 7001 | 19725 | 13816 | 19729 | 19765 | 25693 | 21823 | 15215 |
| | 4827 | 5081 | 20680 | 8119 | 12128 | 7002 | 25110 | 5305 | 16506 | 4866 | 4872 |
| | 4875 | 4869 | 1977 | 15074 | 15072 | 15105 | 23221 | 23227 | 18915 | 6585 | 4781 | 15238 |
| | 28000 | 27811 | 27816 | 27832 | 27962 | 27900 | 27901 | 27903 | 27966 | 27969 | 27994 | 27907 |
| | 27909 | 27835 | 27840 | 27842 | 27865 | 27870 | 27873 | 27877 | 27808 | 27809 | 27810 | 27999 |
| | 27925 | 27926 | 27879 | 27930 | 28002 | 27935 | 27938 | 27998 | 27958 | 27959 | 9095 | 3804 |
| | 22867 | 17450 | 483 | 482 | 417 | 4731 | | | | | | |
| 417: | 23286 | 11758 | 1274 | 8225 | 27981 | 25684 | 25757 | 16457 | 16452 | 1391 | 12214 | 23260 |
| | 23289 | 1744 | 11105 | 11360 | 5199 | 25720 | 25688 | 14705 | 6709 | 6649 | 16261 | 22979 |
| | 22977 | 16994 | 16270 | 2059 | 2009 | 16265 | 20642 | 23803 | 20644 | 15180 | 15175 | 4941 |
| | 4914 | 3758 | 4703 | 4713 | 16785 | 10080 | 16509 | 27451 | 6582 | 12093 | 3831 | 1155 |
| | 9438 | 17429 | 4505 | 9638 | 12510 | 11369 | 12332 | 11407 | 12298 | 12366 | 12270 | 11488 |
| | 11530 | 12277 | 12432 | 12339 | 12269 | 17458 | 17460 | 19786 | 19822 | 21082 | 19790 | 19696 |
| | 19761 | 19793 | 19758 | 19719 | 19935 | 19903 | 19827 | 19930 | 19868 | 21151 | 21148 | 21112 |
| | 19763 | 21144 | 19928 | 3788 | 4668 | 4665 | 4699 | 4673 | 16783 | 4824 | 16782 | 6878 |
| | 6991 | 6910 | 6932 | 6936 | 6940 | 5992 | 4628 | 3791 | 4740 | 4743 | 26710 | 23228 |
| | 28484 | 14653 | 14703 | 17093 | 15617 | 15646 | 15668 | 15641 | 15642 | 15670 | 15639 | 22762 |
| | 13093 | 20149 | 2079 | 4751 | 4775 | 4982 | 6024 | 6061 | 6868 | 16810 | 4978 | 6837 |
| | 5982 | 6907 | 26794 | 25144 | 24355 | 5247 | 3727 | 3754 | 16757 | 3755 | 3784 | 3787 |
| | 4632 | 4659 | 4662 | 4707 | 4746 | 4749 | 4830 | 4834 | 4879 | 4909 | 4907 | 4912 |
| | 4944 | 4945 | 4980 | 5768 | 5792 | 5829 | 5862 | 5899 | 5895 | 5938 | 5942 | 5975 |
| | 5986 | 6059 | 6091 | 6093 | 6099 | 6869 | 6897 | 6902 | 6942 | 6961 | 6964 | 6969 |
| | 3748 | 3751 | 25626 | 18897 | 18900 | 11659 | 3110 | 1332 | 23097 | 27977 | 1190 | 15240 |
| | 5284 | 5204 | 5307 | 5306 | 5310 | 5201 | 5331 | 5329 | 5234 | 5232 | 5226 | 5278 |
| | 5236 | 5239 | 5277 | 10149 | 2306 | 12349 | 27947 | 19479 | 19484 | 25020 | 24994 | 14113 |
| | 14253 | 14109 | 14251 | 14282 | 15069 | 14138 | 30160 | 14321 | 14278 | 19566 | 14326 | 14195 |
| | 19682 | 14068 | 14161 | 29739 | 10181 | 17666 | 10210 | 17706 | 17711 | 17670 | 17681 | 23292 |
| | 16447 | 13249 | 28736 | 13813 | 4269 | 8971 | 24172 | 10784 | 6621 | 6581 | 21799 | 28030 |
| | 14647 | 5282 | 27990 | 28015 | 16419 | 5909 | 5945 | 6619 | 6614 | 14800 | 17524 | 28146 |
| | 21825 | 21826 | 8124 | 8126 | 8159 | 8214 | 28025 | 28023 | 28020 | 8218 | 8196 | 30192 |
| | 4794 | 15242 | 2511 | 14452 | 25359 | 13419 | 1836 | 2576 | 16666 | 1428 | 1423 | 19836 |
| | 1910 | 7820 | 10218 | 20683 | 29045 | 6026 | 6025 | 16449 | 4481 | 14869 | 10745 | 11813 |
| | 20059 | 22400 | 11648 | 7691 | 16414 | 8183 | 16455 | 16412 | 16460 | 13181 | 2994 | 2965 |
| | 26527 | 16462 | 11863 | 7168 | 20675 | 16443 | 20678 | 967 | 17461 | 2509 | 11502 | 7375 |
| | 17492 | 28280 | 6553 | 17455 | 2264 | 16409 | 16416 | 16418 | 16407 | 16444 | 4844 | 14779 |
| | 20794 | 12379 | 7963 | 19990 | 15714 | 670 | 11705 | 25327 | 26672 | 28323 | 23256 | 17560 |

TABLE 8-continued

| PEP SEQ ID NO: | homolog SEQ ID NOs | | | | | | | | | | |
|---|---|---|---|---|---|---|---|---|---|---|---|
| | 18542 | 22080 | 13354 | 13352 | 21460 | 21463 | 3023 | 16390 | 14532 | 29577 | 29581 | 29580 |
| | 29552 | 29576 | 29541 | 8329 | 6616 | 6645 | 6642 | 16406 | 5279 | 20860 | 3939 | 8558 |
| | 3973 | 4297 | 17449 | 19743 | 8597 | 25495 | 25466 | 23522 | 22778 | 809 | 27528 | 1300 |
| | 23760 | 29578 | 25760 | 25761 | 20932 | 11894 | 20864 | 9396 | 3800 | 15568 | 9826 | 11866 |
| | 20815 | 26007 | 7525 | 8113 | 8080 | 19979 | 20833 | 20882 | 19973 | 20991 | 20988 | 21040 |
| | 20992 | 20962 | 20958 | 20922 | 20875 | 7061 | 20135 | 14531 | 6555 | 3548 | 3465 | 3461 |
| | 21597 | 21821 | 7008 | 19716 | 7001 | 19725 | 13816 | 19729 | 19765 | 25693 | 21823 | 15215 |
| | 4827 | 5081 | 20680 | 8119 | 12128 | 7002 | 5206 | 25110 | 5305 | 16506 | 4866 | 4872 |
| | 4875 | 4869 | 1977 | 15074 | 15072 | 15105 | 23221 | 23227 | 18915 | 6585 | 4781 | 15238 |
| | 28000 | 27811 | 27816 | 27832 | 27962 | 27900 | 27901 | 27903 | 27966 | 27969 | 27994 | 27907 |
| | 27909 | 27835 | 27840 | 27842 | 27865 | 27870 | 27873 | 27877 | 27808 | 27809 | 27810 | 27999 |
| | 27925 | 27926 | 27879 | 27930 | 28002 | 27935 | 27938 | 27998 | 27958 | 27959 | 9095 | 3804 |
| | 22867 | 17450 | 483 | 482 | 416 | 4731 | | | | | | |
| 418: | 23286 | 11758 | 1274 | 8225 | 27981 | 25684 | 25757 | 16457 | 16452 | 1391 | 12214 | 23260 |
| | 23289 | 1744 | 11105 | 11360 | 5199 | 25720 | 14705 | 6709 | 6649 | 16261 | 22979 |
| | 22977 | 16994 | 16270 | 2059 | 2009 | 16265 | 20642 | 23803 | 20644 | 15180 | 15175 | 4941 |
| | 4914 | 3758 | 4703 | 4713 | 16785 | 15326 | 16509 | 6582 | 9011 | 8975 | 12093 | 3831 |
| | 1155 | 17429 | 4505 | 9638 | 12510 | 11369 | 12332 | 11407 | 12298 | 12366 | 12270 | 11488 |
| | 11530 | 12277 | 12432 | 12339 | 12269 | 17458 | 17540 | 19786 | 19822 | 21082 | 19790 | 19696 |
| | 19761 | 19793 | 19758 | 19719 | 19935 | 19903 | 19827 | 19930 | 19868 | 21151 | 21148 | 21112 |
| | 19763 | 21144 | 19928 | 3788 | 4665 | 4668 | 4699 | 4673 | 16783 | 4824 | 16782 | 6878 |
| | 6991 | 6910 | 6932 | 6936 | 6940 | 5992 | 4628 | 3791 | 4740 | 4743 | 26710 | 23228 |
| | 28484 | 17093 | 15617 | 15646 | 15668 | 15641 | 15642 | 22762 | 13093 | 20149 | 2079 | 4751 |
| | 4775 | 4982 | 6024 | 6061 | 6868 | 16810 | 6837 | 5982 | 6907 | 26794 | 25144 | 24355 |
| | 5247 | 3727 | 3754 | 16757 | 3784 | 3787 | 4632 | 4659 | 4662 | 4707 | 4746 | 4749 |
| | 4830 | 4834 | 4879 | 4909 | 4907 | 4912 | 4944 | 4945 | 4980 | 5768 | 5792 | 5829 |
| | 5862 | 5899 | 5938 | 5942 | 5975 | 5986 | 6059 | 6091 | 6093 | 6099 | 6869 | 6897 |
| | 6902 | 6942 | 6961 | 6964 | 6969 | 3748 | 3751 | 25626 | 18897 | 18900 | 11659 | 3110 |
| | 1332 | 23097 | 27977 | 1190 | 15240 | 5284 | 5204 | 5307 | 5306 | 5310 | 5201 | 5331 |
| | 5329 | 5234 | 5232 | 5226 | 5278 | 5236 | 5239 | 5277 | 10149 | 2306 | 12349 | 27947 |
| | 19479 | 19484 | 25020 | 24994 | 14113 | 14253 | 14251 | 14282 | 15069 | 14138 | 30160 |
| | 14321 | 14278 | 19566 | 14326 | 14195 | 19682 | 14068 | 14161 | 29739 | 10181 | 17666 | 10210 |
| | 17706 | 17711 | 17670 | 17681 | 23292 | 16447 | 13249 | 28736 | 13813 | 4269 | 8971 | 24172 |
| | 10784 | 6621 | 6581 | 21799 | 28030 | 27428 | 5282 | 27990 | 28015 | 16419 | 2481 | 2473 |
| | 28172 | 6619 | 6614 | 14800 | 17524 | 28146 | 21825 | 21826 | 8124 | 8126 | 8159 | 8214 |
| | 28025 | 28023 | 28020 | 8218 | 8196 | 30192 | 4794 | 15242 | 14452 | 2511 | 25359 | 13419 |
| | 1836 | 22347 | 8504 | 29236 | 1910 | 7825 | 10218 | 20683 | 29045 | 6026 | 6025 | 16449 |
| | 4481 | 4203 | 8291 | 16087 | 7549 | 23421 | 5273 | 5270 | 29657 | 25948 | 5275 | 6968 |
| | 15722 | 21480 | 14769 | 12074 | 6737 | 3041 | 3986 | 11648 | 5607 | 7691 | 16414 | 8183 |
| | 16455 | 16412 | 16460 | 13181 | 2994 | 2965 | 12670 | 27234 | 6265 | 14420 | 3760 | 17424 |
| | 8749 | 12663 | 29710 | 9123 | 11863 | 7168 | 20675 | 16443 | 20678 | 967 | 17461 | 2509 |
| | 12471 | 4719 | 17457 | 17421 | 17489 | 6553 | 17419 | 2745 | 26006 | 16409 | 16416 | 16418 |
| | 23189 | 16407 | 16444 | 4844 | 14779 | 20115 | 23570 | 19989 | 15714 | 670 | 11705 | 26672 |
| | 25327 | 28323 | 23256 | 17560 | 18542 | 22080 | 13354 | 13352 | 21463 | 21460 | 3023 | 16390 |
| | 14532 | 29552 | 29541 | 29576 | 13203 | 8329 | 6616 | 6645 | 6642 | 16406 | 5279 | 20860 |
| | 3939 | 8558 | 3973 | 4297 | 26020 | 4934 | 16268 | 6700 | 5817 | 7285 | 24569 | 30389 |
| | 25857 | 27134 | 25760 | 25761 | 20932 | 11894 | 20864 | 9396 | 3800 | 15568 | 9826 | 11866 |
| | 20815 | 26007 | 7525 | 8113 | 8076 | 19979 | 20992 | 19973 | 20991 | 20988 | 20833 | 21040 |
| | 20882 | 20962 | 20958 | 20922 | 20875 | 7061 | 20135 | 14531 | 6555 | 3548 | 3465 | 3461 |
| | 21597 | 21821 | 7008 | 19716 | 7001 | 19725 | 13816 | 19729 | 19765 | 25693 | 21823 | 15215 |
| | 4827 | 5081 | 20680 | 8119 | 12128 | 7002 | 5206 | 25110 | 5305 | 16506 | 4866 | 4872 |
| | 4875 | 4869 | 1977 | 15074 | 15072 | 15105 | 4732 | 13465 | 23221 | 23227 | 18915 | 6585 |
| | 4781 | 15238 | 28000 | 27811 | 27816 | 27832 | 27962 | 27900 | 27901 | 27903 | 27966 | 27969 |
| | 27994 | 27907 | 27909 | 27835 | 27840 | 27842 | 27865 | 27870 | 27873 | 27877 | 27808 | 27809 |
| | 27810 | 27999 | 27925 | 27926 | 27879 | 27930 | 28002 | 27935 | 27938 | 27998 | 27958 | 27959 |
| | 9095 | 3804 | 22436 | 16838 | 20688 | 4511 | 25167 | | | | | |
| 419: | 14198 | 870 | 17932 | 16069 | 13851 | 13461 | 12701 | 18143 | 19044 | 9845 | 28935 | 12911 |
| | 9746 | 12378 | 26844 | 6279 | 3256 | 6492 | 1927 | 14725 | 5210 | 16911 | 19053 | 15107 |
| | 10053 | 10052 | 17902 | 18728 | 14921 | 21008 | 27672 | 15861 | 22004 | 25826 | 27570 | 30385 |
| | 24545 | 7602 | 11773 | 2106 | 25012 | 29882 | 5639 | 8632 | 19341 | 3676 | 13801 | 17969 |
| | 18455 | 7576 | 29000 | 30010 | 25127 | 8356 | 9350 | 10154 | 5237 | 9923 | 12796 | 8187 |
| | 29896 | 5402 | 643 | 24362 | 15888 | 14391 | 3369 | 3240 | 19906 | 23740 | 26063 | 12643 |
| | 4304 | 13273 | 11196 | 13304 | 30067 | 3274 | 7355 | 14440 | 5431 | 27525 | 12373 | 26674 |
| | 13025 | 10728 | 19975 | 19976 | 13989 | 13166 | 13167 | 28931 | 27390 | 2736 | 27297 | 485 |
| | 28745 | 7015 | 29168 | 3670 | 5562 | 12710 | 9729 | 16719 | 17020 | 1225 | 28194 | 28348 |
| | 22794 | 9021 | 15530 | 5874 | 9984 | 11413 | 1550 | 422 | 19877 | 19878 | 26951 | 17946 |
| | 2877 | 17097 | 18956 | 15056 | 21779 | 18201 | 2127 | 713 | 5162 | 15588 | 18293 | 7479 |
| | 10639 | 7629 | 27675 | 7385 | 23019 | 8438 | 20405 | 25592 | 15584 | 9862 | 19958 |
| 420: | 1766 | 25623 | 2634 | 8567 | 8546 | 8030 | 8035 | 28060 | 8033 | 13487 | 12426 | 12425 |
| | 27566 | 16382 | 13471 | 13472 | 27829 | 21056 | 7641 | 5010 | 7722 | 17728 | 13546 | 9391 |
| | 8454 | 11625 | 8039 | 26982 | 2216 | 28645 | 19396 | 6428 | 12857 | 6029 | 8927 | 26241 |
| | 28882 | 2058 | 17137 | 23307 | 23313 | 14163 | 30357 | 1758 | 1762 | 1765 | 22795 | 1007 |
| | 12696 | 20720 | 20722 | 21606 | 21600 | 20724 | 9877 | 8100 | 8623 | 9032 | 26511 | 15887 |
| | 17511 | 19373 | 11822 | 19998 | 25957 | 20063 | 20812 | 20816 | 20818 | 24166 | 23982 | 8056 |
| | 30201 | 2731 | 26481 | 8640 | 22623 | 518 | 24795 | | | | | |
| 421: | 17859 | 1238 | 22054 | 28433 | 14522 | 12713 | 2265 | 30161 | 7453 | 4765 | 16339 | 3623 |
| | 16249 | 30466 | 23897 | 24523 | 18199 | 12780 | 12018 | 8775 | 20575 | 9860 | 9828 | 17997 |
| | 22323 | 12760 | 6777 | 25696 | 8048 | 7233 | 7159 | 10567 | 11570 | 5422 | 13420 | 743 |

TABLE 8-continued

| PEP SEQ ID NO: | homolog SEQ ID NOs | | | | | | | | | | |
|---|---|---|---|---|---|---|---|---|---|---|---|
| | 20960 | 20777 | 13662 | 6471 | 6450 | 722 | 1999 | 22130 | 15016 | 24746 | 17989 | 21018 |
| | 18525 | 16321 | 25778 | 29549 | 4744 | 4911 | 15147 | 16008 | 14299 | 4655 | 18309 | 20204 |
| | 13162 | 27357 | 28445 | 29670 | 12438 | 2514 | 2700 | 25507 | 27408 | 21700 | 6258 | 15916 |
| | 23219 | 8612 | 21584 | 7769 | 21090 | 21432 | 24336 | 2356 | 30137 | 4195 | 24837 | 12189 |
| | 4171 | 20221 | 23536 | 26716 | 7664 | 11285 | 23505 | 6454 | 21901 | 13438 | 27127 | 6046 |
| | 28726 | 23456 | 15186 | 1641 | 24978 | 18008 | 19271 | 13956 | 24528 | 17271 | 1119 | 18682 |
| | 4177 | 14894 | 2489 | 29476 | 22053 | 1277 | 2172 | 26999 | 13676 | 22871 | 16889 | 8678 |
| | 12883 | 23881 | 9761 | 12855 | 20677 | 3738 | 22399 | 20134 | 18998 | 18171 | 2684 | 15899 |
| | 7332 | 29308 | 9846 | 23454 | 17170 | 1559 | 28849 | 2839 | 27226 | 11010 | 10112 | 1021 |
| | 29279 | 19520 | 19722 | 26879 | 28081 | 15983 | 17146 | 15924 | 5208 | 2143 | 4634 | 16484 |
| | 3406 | 25815 | 25097 | 16791 | 22937 | 9830 | 25112 | 1379 | 28559 | 28606 | 16292 | 16260 |
| | 16208 | 16320 | 8188 | 28196 | 5518 | 5513 | 11332 | 7484 | 24098 | 25192 | 11722 | 7295 |
| | 4070 | 3808 | 20017 | 21780 | 1418 | 3680 | 9910 | 7166 | 23057 | 22218 | 23084 | 9268 |
| | 11075 | 26038 | 12485 | 7431 | 18804 | 6947 | 8806 | 3674 | 28046 | 5006 | 28297 | 7847 |
| | 24808 | 19618 | 22706 | 21561 | 4782 | 24417 | 3843 | 24691 | 11449 | 9680 | 30005 | 10365 |
| | 4403 | 14746 | 20774 | 4849 | 29201 | 28648 | 20671 | 18342 | 23463 | 29918 | 24863 | 14394 |
| | 9080 | 25560 | 8423 | 7517 | 27591 | 30030 | 7571 | 29151 | 7460 | 3064 | 8500 | 8416 |
| | 18919 | 15655 | 22879 | 22882 | 14872 | 2032 | 28860 | 21021 | 11112 | 2577 | 10386 | 7462 |
| | 7356 | 9905 | 21034 | 29197 | 8891 | 6388 | 15308 | 29956 | 25999 | 24693 | 19760 | 18166 |
| | 14979 | 10427 | 18403 | 23159 | 5100 | 26531 | 26168 | 9132 | 29747 | 26986 | 7010 | 6925 |
| | 9803 | 26555 | 30057 | 7883 | 20362 | 13923 | 21199 | 17720 | 10376 | 13693 | 28462 | 5696 |
| | 15243 | 4681 | 11036 | 28713 | 23116 | 22490 | 18697 | 15953 | 16090 | 8882 | 29422 | 26513 |
| | 10652 | 10658 | 12898 | 14981 | 6819 | 823 | 17872 | 2674 | 19462 | 20810 | 2655 |
| | 17278 | 17299 | 29880 | 9890 | 17589 | 14931 | 19664 | 2181 | 15988 | 17595 | 11629 | 10661 |
| | 7177 | 12706 | 6147 | 6518 | 8191 | 28422 | 15040 | 11675 | 3972 | 3697 | 28043 | 5019 |
| | 689 | 19234 | 10006 | 7229 | 7695 | 3574 | 29895 | 19441 | 28177 | 28498 | 18428 | 15614 |
| | 3789 | 15573 | 29663 | 7406 | 22093 | 3093 | 27495 | 16461 | 8817 | 19093 | 18724 | 25322 |
| | 6607 | 14736 | 5953 | 21288 | 17280 | 10246 | 18588 | 18586 | 19908 | 19910 | 15765 | 26810 |
| | 19134 | 17663 | 17697 | 3638 | 21052 | 16371 | 21054 | 2935 | 15495 | 20728 | 22097 | 813 |
| | 5137 | 9972 | 18986 | 10167 | 27136 | 14751 | 15479 | 22618 | 405 | 27122 | 29583 | 15609 |
| | 7933 | 3355 | 24226 | 15048 | 13579 | 1887 | 8939 | 8964 | 13794 | 9157 | 24816 | 21858 |
| | 5885 | 22336 | 3805 | 3802 | 24169 | 2292 | 26734 | 26770 | 6657 | 13127 | 26043 | 12384 |
| | 16093 | 3544 | 14897 | 2567 | 27765 | 27766 | 27677 | 15125 | 20964 | 23705 | 23066 | 24145 |
| | 25943 | 24093 | 17443 | 7635 | 1827 | 22760 | 29245 | 18346 | 14261 | 16514 | 16482 | 16233 |
| | 16542 | 18557 | 9646 | 13061 | 28991 | 23979 | 2413 | 30304 | 24393 | 6062 | 867 | 1186 |
| | 8879 | 3327 | 2945 | 11059 | | | | | | | | |
| 422: | 866 | 7071 | 17930 | 870 | 17932 | 7072 | 16069 | 13851 | 13381 | 13461 | 13464 | 12701 |
| | 12702 | 8312 | 13470 | 8308 | 419 | 19755 | 18143 | 19044 | 9845 | 28935 | 27346 | 12911 |
| | 12908 | 9746 | 6906 | 12378 | 12755 | 26844 | 6279 | 3256 | 29096 | 6492 | 6491 | 1927 |
| | 1926 | 14725 | 14724 | 5210 | 5182 | 19053 | 16911 | 15107 | 10053 | 10052 | 17902 | 18728 |
| | 15861 | 21008 | 27672 | 14921 | 25826 | 22004 | 27570 | 30385 | 24545 | 17631 | 11773 | 2106 |
| | 29882 | 25012 | 8632 | 5639 | 19341 | 3676 | 8591 | 5630 | 13801 | 18455 | 17969 | 12282 |
| | 7576 | 29080 | 10256 | 30010 | 25127 | 9350 | 10154 | 5237 | 8356 | 9923 | 12796 | 8187 |
| | 29896 | 5402 | 643 | 678 | 24362 | 24361 | 15888 | 14391 | 15244 | 3240 | 19906 | 23741 |
| | 25136 | 23740 | 26062 | 26063 | 25138 | 12643 | 4304 | 3209 | 13273 | 13304 | 11196 | 13277 |
| | 13296 | 30067 | 3274 | 7355 | 1871 | 5431 | 5433 | 10593 | 12373 | 26674 | 13025 | 10728 |
| | 19975 | 19976 | 19969 | 18860 | 13989 | 13166 | 13167 | 28931 | 28928 | 2736 | 27390 | 27297 |
| | 26448 | 485 | 7015 | 28745 | 29168 | 3670 | 5562 | 12710 | 21159 | 25904 | 16719 | 28194 |
| | 1225 | 28348 | 22794 | 9021 | 15530 | 5874 | 9984 | 1486 | 11413 | 1550 | 26951 | 26948 |
| | 17946 | 17941 | 2877 | 2996 | 17097 | 17095 | 18956 | 818 | 15055 | 18335 | 21779 | 15056 |
| | 24735 | 24579 | 18201 | 2127 | 25041 | 713 | 5162 | 5181 | 15588 | 15582 | 18293 | 7479 |
| | 7474 | 10639 | 10640 | 7629 | 27675 | 7385 | 23019 | 23020 | 12990 | 8438 | 25592 | 20405 |
| | 15584 | 15585 | 9862 | 19958 | | | | | | | | |
| 423: | 15029 | 25307 | 9676 | 8311 | 26916 | 23959 | 11677 | 23081 | 2694 | 13387 | 5447 | 10573 |
| | 11670 | 13978 | 11123 | 26839 | 27158 | 3619 | 28393 | 16399 | 14284 | 11420 | 30182 | 18878 |
| | 10160 | 16007 | 26522 | 15577 | 10156 | 24813 | 10771 | 10742 | 26803 | 2343 | 2380 | 2382 |
| | 1591 | 2460 | 2383 | 2353 | 2462 | 2053 | 27103 | 26865 | 22418 | 18140 | 8068 | 27942 |
| | 26009 | 29347 | 26834 | 8774 | 15488 | 13383 | 15874 | 8921 | 12705 | 14118 | 14258 | 21153 |
| | 24198 | 28012 | 5588 | 16861 | 10216 | 23576 | 3923 | 6699 | 3918 | 3926 | 3920 | 20836 |
| | 22849 | 892 | 16183 | 27978 | 26550 | 9488 | 20021 | 16915 | 6824 | 30294 | 16762 | 8804 |
| | 7419 | 23008 | 25744 | 29149 | 14295 | 30146 | 25107 | 16558 | 19890 | 14319 | 4639 | 20402 |
| | 8947 | 5643 | 1147 | 11395 | 728 | 5293 | 4510 | 26624 | 12288 | 27309 | 15368 | 17961 |
| | 15252 | 23928 | 24860 | 11838 | 29987 | 14792 | 3414 | 11679 | 19671 | 2183 | 14230 | 13870 |
| | 13912 | 27989 | 7587 | 26711 | 14106 | 3481 | 14124 | 24519 | 26046 | 6594 | 30393 | 22818 |
| 424: | 28787 | 28026 | 26562 | 27850 | 3993 | 21457 | 13373 | 22737 | 25673 | 336 | 13510 | 1153 |
| | 27040 | 13055 | 17285 | | | | | | | | | |
| 425: | 14715 | 27077 | 7091 | 8238 | 15342 | 28311 | 28335 | 29231 | 9534 | 4494 | 13615 | 18789 |
| | 27725 | 1230 | 10455 | 804 | 9254 | 10865 | 12623 | 18172 | 22589 | 640 | 26535 | 13575 |
| | 8164 | 6881 | 25375 | 27163 | 27466 | 27305 | 29441 | 9966 | 628 | 26476 | 23339 | 23425 |
| | 23698 | 14548 | 21310 | 12160 | 5898 | 30372 | 17110 | 2245 | 22497 | 22275 | 20136 | 29114 |
| | 3433 | 19544 | 22006 | 16128 | 16917 | 10830 | 10600 | 18991 | 28811 | 1336 | 25859 | 8919 |
| | 13541 | 13587 | 27186 | 4947 | 3845 | 11723 | 27086 | 3520 | 15911 | 14958 | 14920 | 13075 |
| | 25073 | 24384 | 24215 | 8424 | 26449 | 23782 | 7578 | 24615 | 5515 | 12565 | 1052 | 20622 |
| | 9144 | 9083 | 30107 | 24035 | 11692 | 4715 | 26578 | 10028 | 19100 | 15396 | 12004 | 2277 |
| | 26427 | 22150 | 4990 | 17320 | 14898 | 4014 | 11890 | 10187 | 2273 | 19281 | 17315 | 1602 |
| | 25789 | 12947 | 23230 | 20113 | 8781 | 3902 | 3335 | 8931 | 22254 | 23950 | 15881 | 16378 |
| | 21068 | 18992 | 28385 | 24260 | 21185 | 10953 | 17209 | 4756 | 23880 | 12048 | 2515 | 6473 |
| | 2545 | 26896 | 667 | 13227 | 19734 | 29717 | 17470 | 5067 | 17620 | 1371 | 29876 | 5086 |

TABLE 8-continued

| PEP SEQ ID NO: | homolog SEQ ID NOs | | | | | | | | | | |
|---|---|---|---|---|---|---|---|---|---|---|---|
| | 29140 | 12846 | 11469 | 8066 | 16701 | 15123 | 17065 | 16699 | 19711 | 23152 | 28749 | 28891 |
| | 897 | 20121 | 27569 | 5843 | 22595 | 22600 | 26841 | 4709 | 4712 | 12337 | 22378 | 22374 |
| | 24033 | 2913 | 24701 | 14475 | 23715 | 26245 | 19991 | 7584 | 10643 | 15179 | 18396 | 7609 |
| | 23792 | 13602 | 7586 | 11956 | 19021 | 26545 | 15237 | 29474 | 19066 | 22629 | 22597 | 15821 |
| | 1174 | 1175 | 21504 | 21692 | 27022 | 27441 | 10473 | 24973 | 12482 | 20713 | 6929 | 10056 |
| | 2246 | 19651 | 27645 | 10303 | 24352 | 4478 | 17176 | 3654 | 2540 | 29431 | 22009 | 15070 |
| | 1261 | 25439 | 5968 | 7887 | 7727 | 12448 | 24300 | 15193 | 18608 | 30313 | 6505 | 613 |
| | 22166 | 17182 | 15820 | 23530 | 721 | 24333 | 10326 | 5506 | 9091 | 1357 | 3649 | 24309 |
| | 9988 | 19229 | 13908 | 24866 | 1512 | 2914 | 20798 | 20262 | 13907 | 13447 | 12842 | 13566 |
| | 6367 | 21312 | 19637 | 6549 | 5840 | 25058 | 18097 | 18571 | 15246 | 11060 | 27827 | 25710 |
| | 1091 | 21748 | 21747 | 3653 | 17000 | 12027 | 29642 | 30144 | 22522 | 15275 | 11882 | 9236 |
| | 28312 | 15527 | 18156 | 27362 | 22428 | 24687 | 5611 | 15499 | 19435 | 16504 | 7875 | 20945 |
| | 15534 | 24214 | 28466 | 28436 | 28715 | 21448 | 28469 | 22921 | 27957 | 10454 | 20564 | 1417 |
| | 15157 | 29858 | 20076 | 22634 | 25089 | 27558 | 8378 | 16523 | 4289 | 7819 | 22253 | 28208 |
| | 5308 | 18162 | 18114 | 14939 | 801 | 19072 | 7646 | 9780 | 29973 | 5857 | 5882 | 26190 |
| | 14988 | 17199 | 25151 | 28781 | 28804 | 24016 | 11569 | 13634 | 8363 | 10492 | 22387 | 13363 |
| | 17138 | 14970 | 25926 | | | | | | | | | |
| 426: | 30316 | 28341 | 20440 | 21403 | 28460 | 8764 | 5483 | 10239 | 21294 | 3625 | 20041 | 25161 |
| | 16037 | 29671 | 15602 | 15738 | 13680 | 4919 | 6243 | 23006 | 3034 | 752 | 8677 | 14314 |
| | 13422 | 1619 | 6262 | 6521 | 23305 | 17002 | 18373 | 1173 | 1149 | 11674 | 28125 | 22571 |
| | 22569 | 1752 | 28123 | 21437 | 1073 | 1072 | 5748 | 2955 | 27548 | 8337 | 6584 | 6580 |
| | 4722 | 6764 | 20583 | 706 | 8627 | 3362 | 14034 | 10533 | 10535 | 15608 | 16784 | 6496 |
| | 9194 | 29947 | 16882 | 29432 | 11684 | 1245 | 25870 | 1652 | 28681 | 7191 | 27632 | 29345 |
| | 3908 | 26214 | 18387 | 6769 | 6400 | 20414 | 26269 | 17674 | 16459 | 8262 | 15546 | 9173 |
| | 12354 | 29426 | 15949 | 5362 | 24788 | 8630 | 26833 | 19714 | 1878 | 16103 | 26526 | 14486 |
| | 10208 | 24594 | 20180 | 13753 | 3056 | 6467 | 20070 | 26719 | 13574 | 28110 | 11845 | 29110 |
| | 12541 | 29814 | | | | | | | | | | |
| 427: | 1205 | 1202 | 23043 | 18478 | 21335 | 24048 | 24042 | 12899 | 18378 | 18376 | 20455 | 6551 |
| | 19940 | 19978 | 19981 | 2128 | 18413 | 18415 | 16198 | 16668 | 3185 | 15855 | 9352 | 14616 |
| | 2960 | 2967 | 2966 | 4462 | 25905 | 11227 | 28186 | 984 | 13539 | 20758 | 20789 | 20750 |
| | 20753 | 20749 | 28534 | 25229 | 27701 | 17690 | 22452 | 24103 | 19988 | 21788 | 25087 | 19912 |
| | 21275 | 19982 | 19909 | 24881 | 24899 | 26679 | 18852 | 27639 | 12055 | 16381 | 1897 | 1894 |
| | 1892 | 20060 | 7377 | 10185 | 27612 | 27664 | 3919 | 27641 | 10110 | 28531 | 28470 | 2758 |
| | 4227 | 10669 | 24960 | 23679 | 11153 | 19321 | 30078 | 21051 | 17845 | 17557 | 1936 | 23577 |
| | 27609 | 28429 | 27692 | 20186 | 20188 | 20182 | 20177 | 20222 | 20179 | 20174 | 20216 | 20218 |
| | 27667 | 19872 | 26730 | 18303 | 18438 | 18412 | 22954 | 10396 | 9203 | 29169 | 12043 | 1965 |
| | 24374 | 25660 | 17724 | 29924 | 16729 | 20884 | 2141 | 19907 | 22922 | 27089 | 2063 | 26239 |
| | 19936 | 19119 | 21272 | 19915 | 19985 | 13259 | 19916 | 18368 | 18306 | 18331 | 18333 | 18338 |
| | 17515 | 18481 | 17665 | 16401 | 13021 | 7850 | 570 | | | | | |
| 428: | 9514 | 18208 | 27699 | 24672 | 695 | 1581 | 17502 | 19870 | 19688 | 17787 | 10946 | 18811 |
| | 24157 | 19726 | 17433 | 18211 | 27587 | 29573 | 574 | 576 | 11124 | 19880 | 5553 | 16146 |
| | 13361 | 825 | 17239 | 5348 | 376 | 9975 | | | | | | |
| 429: | 29272 | 16408 | 24394 | 21534 | 7305 | 25504 | 8552 | 18079 | 18052 | 19030 | 28248 | 16816 |
| | 24060 | 21344 | 372 | 1466 | 29462 | 29423 | 29420 | 29457 | 5650 | 27496 | | |
| 430: | 17468 | 17393 | 17389 | 17390 | 16815 | 13067 | 12931 | 11325 | 16679 | 8328 | 9249 | 3824 |
| | 11932 | 29725 | 21677 | 28810 | 13568 | 16519 | 17018 | 13170 | 24756 | 8004 | 30147 | 28329 |
| | 23718 | 13963 | 27073 | 2452 | 16177 | 27300 | 14029 | 30291 | 19914 | 14387 | 21586 | 30281 |
| | 21049 | 14678 | 4088 | 11967 | | | | | | | | |
| 431: | 6307 | 3233 | 20896 | 9887 | 26622 | 4960 | 4658 | 27322 | 28670 | 6575 | 7676 | 25783 |
| | 1426 | 12035 | 27335 | 14401 | 16385 | 27296 | 16425 | 13199 | 19424 | 11348 | 10680 | |
| 432: | 14667 | 22888 | 17013 | 13915 | 2925 | 12977 | 12675 | 17605 | 26291 | 5000 | 11907 | 1511 |
| | 27830 | 18555 | 7284 | 15187 | 10929 | 24838 | 8371 | 15946 | 8322 | 19594 | 4424 | 21192 |
| | 12206 | 20285 | 16940 | 24995 | 16946 | 29622 | 25643 | 29160 | 2942 | 13884 | 17117 | 20604 |
| | 22279 | 23664 | 10325 | 29846 | 15526 | 4557 | 7795 | 10008 | 23496 | 21495 | 11465 | 8089 |
| | 23533 | 8128 | 22340 | 27131 | 22562 | 2632 | 20012 | 2852 | 2822 | 23026 | 16348 | 10038 |
| | 20496 | 10775 | 21267 | 6404 | 6276 | 11703 | 3535 | 4554 | 5180 | 19347 | 854 | 22228 |
| | 21030 | 18594 | 23540 | 18642 | 16640 | 7007 | 21219 | 12820 | 20795 | 28225 | 12596 | 23093 |
| | 7052 | 10939 | 17912 | 4720 | 7729 | 1132 | 11961 | 16203 | 2290 | 21596 | 8725 | 12481 |
| | 13527 | 24777 | 20996 | 18559 | 1078 | 16928 | 11870 | 24078 | 25941 | 13975 | 13410 | 16065 |
| | 26929 | 28457 | 14649 | 24650 | 10198 | 29393 | 30143 | 20951 | 28853 | 3493 | 21315 | 18940 |
| | 23811 | 12737 | 26959 | 25378 | 5760 | 24588 | 7309 | 27680 | 23118 | 28100 | 26837 | 1288 |
| | 8754 | 16609 | 6974 | 19882 | 950 | 10136 | 13906 | 20299 | 2222 | 6219 | 4225 | 20616 |
| | 10333 | 3582 | 13413 | 28193 | 22074 | 20491 | 25961 | 16797 | 25977 | 12162 | 26811 | 10251 |
| | 21670 | 5907 | 8757 | 15621 | 15814 | 30089 | 18491 | 25493 | 25232 | 28527 | 9940 | 15033 |
| | 6789 | 19362 | 26832 | 29018 | 16333 | 25608 | 18330 | 4363 | 15127 | 13991 | 24467 | 16550 |
| 433: | 13586 | 26653 | 1211 | 21651 | 12022 | 7022 | 19757 | 29569 | 2997 | 3218 | 4850 | 5039 |
| | 28662 | 23364 | 9454 | 21001 | 26643 | 2073 | 2485 | 5532 | 25152 | 2326 | 3026 | 17909 |
| | 12902 | 6337 | 6395 | 25729 | 3630 | 17316 | 20626 | 25864 | 20141 | 8996 | 11264 | 18844 |
| | 2439 | 12006 | 20392 | 19335 | 10528 | 18253 | 29753 | 29029 | 7141 | 12472 | 22829 | 22392 |
| | 24916 | 25044 | 10577 | 25658 | 7656 | 23543 | 19748 | 15439 | 3460 | 16429 | 25244 | 11383 |
| | 3178 | 9684 | 8024 | 13697 | 12969 | 1800 | 17370 | 15570 | 26846 | 15654 | 6727 | 13647 |
| | 18740 | 2031 | 24059 | 15716 | 13114 | 22413 | 11257 | 29809 | 3525 | 26064 | 17001 | 11260 |
| | 5474 | 9100 | 18705 | 7045 | 25582 | 12968 | 13934 | 7045 | 16229 | 8102 | 2539 | 14525 |
| | 12334 | 29021 | 8155 | 27787 | 2430 | 28510 | 23504 | 2444 | 6502 | 19509 | 14681 | 12036 |
| | 21356 | 22862 | 29732 | 7184 | 16331 | 25968 | 1291 | 1269 | 20206 | 10897 | 13715 | 23473 |
| | 27212 | 27582 | 30392 | 7950 | 10490 | 8383 | 28561 | 28767 | 14041 | 7504 | 956 | 28731 |
| | 8392 | 29317 | 15261 | 13079 | 18879 | 18877 | 29327 | 3215 | 11731 | 11640 | 3881 | 3877 |
| | 3873 | 26505 | 18966 | 20107 | 24144 | 10349 | 17179 | 3512 | 3505 | 4812 | 20783 | 4742 |

TABLE 8-continued

| PEP SEQ ID NO: | homolog SEQ ID NOs | | | | | | | | | | |
|---|---|---|---|---|---|---|---|---|---|---|---|
| | 10253 | 12927 | 23474 | 15809 | 11004 | 21372 | 22045 | 9573 | 5245 | 27101 | 12822 | 13675 |
| | 13339 | 29874 | 4348 | 18265 | 25189 | 14287 | 13515 | 5969 | 24595 | 21046 | 2836 | 29639 |
| | 19902 | 18322 | 16979 | 22451 | 22391 | 10157 | 3223 | 17108 | 13403 | 7951 | 28632 | 3890 |
| | 10280 | 13736 | 26628 | 26963 | 14499 | 27812 | 15935 | 5122 | | | | |
| 434: | 14858 | 8871 | 2388 | 29193 | 23611 | 29343 | 15969 | 3408 | 5093 | 26787 | 9002 | 6519 |
| | 9143 | 17653 | 27755 | 29466 | 6232 | 3608 | 11358 | 11361 | 1254 | 15971 | 25586 | 30150 |
| | 28671 | 30162 | 1856 | 6784 | 8680 | 6054 | 12435 | 25468 | 24267 | 6090 | 17810 | 29384 |
| | 25428 | 24820 | 7303 | 19932 | 5951 | 11255 | 18631 | 21360 | 2946 | 21362 | 4654 | 28107 |
| | 6605 | 19931 | 23748 | 28575 | 13516 | 13519 | 1247 | 7513 | 12271 | 5985 | 5453 | 9951 |
| | 23296 | 25872 | 28950 | 20096 | 26412 | 12419 | 22978 | 27642 | 23608 | 28276 | 674 | 11249 |
| | 23350 | 11976 | 12001 | 14156 | 28285 | 29661 | 8658 | 25191 | 6043 | 7432 | 2118 | 3482 |
| | 11935 | 11939 | 28718 | 26871 | | | | | | | | |
| 435: | 15751 | 12169 | 15239 | 15929 | 26189 | 15900 | 23906 | 16887 | 12540 | 20889 | 14441 | 21704 |
| | 21676 | 13545 | 13492 | 27980 | 15688 | 23036 | 4892 | 12295 | 20500 | 3991 | 3945 | 29238 |
| | 2237 | 29105 | 28374 | 17908 | 14292 | 15115 | 15732 | 10955 | 23971 | 7986 | 22459 | 17962 |
| | 20020 | 22328 | 13357 | 3594 | 16689 | 22346 | 21444 | 18354 | 16734 | 6074 | 6816 | 6620 |
| | 8267 | 8178 | 5244 | 25917 | 29414 | 24598 | 824 | 24242 | 11712 | 25712 | 24715 | 22599 |
| | 14137 | 1053 | 4244 | 19514 | 2978 | 10289 | 29087 | 28834 | 9109 | 18405 | 23656 | 2850 |
| | 20632 | 20853 | 14621 | 7225 | 16586 | 4231 | 22270 | 2784 | 20857 | 21716 | 16695 | 28188 |
| | 14495 | 24469 | 16671 | 17896 | 25055 | 1375 | 21390 | 16442 | 8600 | 17234 | 15699 | 18742 |
| | 26263 | 26398 | 28320 | 29127 | 26400 | 21029 | 9971 | 21645 | 27577 | 26419 | 7025 | 10796 |
| | 11992 | 4326 | 10214 | 2221 | 24451 | 9329 | 15797 | 13644 | 16721 | 15943 | 21150 | 27748 |
| | 9850 | 12756 | 26739 | 9013 | 18025 | 9579 | 3723 | 2525 | 7944 | 15545 | 27260 | 762 |
| | 10551 | 11851 | 25402 | 5816 | 5959 | 5963 | 11441 | 7858 | 14233 | 9186 | 19677 | 2108 |
| | 20171 | 25345 | 1008 | 28748 | 28073 | 25902 | 6516 | 5265 | 16835 | 7259 | 27489 | 27484 |
| | 26410 | 2544 | 1668 | 9478 | 28876 | 9416 | 8991 | 15898 | 15807 | 30362 | 18777 | 19596 |
| | 10802 | 27691 | 17911 | 29983 | 1252 | 29903 | 15359 | 17051 | 24096 | 10904 | 4052 | 19449 |
| | 28227 | 24046 | 30332 | 20549 | 5103 | 12103 | 18923 | 22957 | 9111 | 14917 | 24695 | 18894 |
| | 1680 | 19563 | 19709 | 28772 | 17862 | 5036 | 6133 | 19859 | 18950 | 25894 | 22091 | 16880 |
| | 23175 | 6946 | 24953 | 26197 | 16245 | 30312 | 1742 | 21807 | 3593 | 18707 | 10847 | 29922 |
| | 17586 | 22427 | 3131 | 17609 | 4243 | 21802 | 13346 | 17538 | 27169 | 21393 | 21393 | 10263 |
| | 6930 | 11342 | 14500 | 17328 | 14503 | 17326 | 19129 | 8860 | 23051 | 23053 | 19595 | 6899 |
| | 14063 | 9994 | 16599 | 8079 | 9386 | 3626 | 6011 | 1901 | 10005 | 2508 | 3833 | 2727 |
| | 22316 | 22439 | 25992 | 23112 | 4523 | 3865 | 17168 | 28152 | 16258 | 30052 | 14089 | 23833 |
| | 966 | 5414 | 13058 | 16496 | 30350 | 15440 | 6125 | 21778 | 25751 | 7583 | 4067 | 14007 |
| | 23808 | 3291 | 6813 | | | | | | | | | |
| 436: | 28743 | 16580 | 16834 | 8593 | 9933 | 3230 | 27502 | 12572 | 12452 | 7671 | 30301 | 30190 |
| | 20166 | 10222 | 5692 | 9903 | 12874 | 30037 | 20309 | 11529 | 20004 | 21371 | 26141 | 22217 |
| | 21455 | 12017 | 3239 | 4147 | 3374 | 29961 | 10409 | 15819 | 22560 | 909 | 24291 | 27198 |
| | 28843 | 9248 | 15121 | 14344 | 5035 | 21019 | 15096 | 28579 | 7985 | 7631 | 20586 | 6973 |
| | 10171 | 7070 | 26342 | 24979 | 612 | 11600 | 1087 | 28446 | 22111 | 10434 | 27911 | 1686 |
| | 10892 | 15085 | 12829 | 16500 | 7633 | 10962 | 6095 | 27281 | 24640 | 13480 | 6844 | 7181 |
| 437: | 27723 | 4530 | 4561 | 5996 | 6561 | 27265 | 3876 | 5881 | 17755 | 18096 | 8944 | 19900 |
| | 18971 | 18960 | 18994 | 2864 | 2862 | 5061 | 17682 | 14938 | 14940 | 14944 | 26943 | 26861 |
| | 19086 | 4597 | 3083 | 8858 | 14023 | 19466 | 8886 | 17367 | 29465 | 7832 | 19071 | 9894 |
| | 28471 | 20261 | 15954 | 22612 | 22610 | 22653 | | | | | | |
| 438: | 16231 | 8527 | 24427 | 16494 | 23245 | 23271 | 12322 | 14082 | 12321 | 23243 | 6257 | 16309 |
| | 9449 | 4003 | 11697 | 11141 | 1172 | 18278 | 8801 | 28324 | 13460 | 19497 | 18891 | 21306 |
| | 10064 | 3661 | 29176 | 12129 | 28789 | 7632 | 22164 | 30327 | 5170 | 2321 | 23701 | 19543 |
| | 30045 | 9256 | 2894 | | | | | | | | | |
| 439: | 10346 | 18603 | 23885 | 13652 | 9175 | 18536 | 13700 | 6245 | 22789 | 19622 | 14498 | 24408 |
| | 22191 | 14417 | 22910 | 23910 | 2072 | 16138 | 14112 | 25002 | 22454 | 25878 | 8444 | 25302 |
| | 21271 | 4988 | 25900 | 1601 | 24221 | 27057 | 9216 | 10965 | 3383 | 26732 | 27190 | 3116 |
| | 11200 | 27744 | 13335 | 18970 | 12918 | 3012 | 15494 | 22942 | 30223 | 22293 | 28246 | 28244 |
| | 1265 | 17327 | 1421 | 10302 | 14910 | 6065 | 12687 | 17866 | 17957 | 22396 | 27972 | 5764 |
| | 4238 | 6979 | 4468 | 10259 | 23150 | 5405 | 28344 | 19453 | 3581 | 24255 | 8934 | 30181 |
| | 3198 | 22810 | 9827 | 23415 | 4925 | 8386 | 20191 | 1777 | 29750 | 29952 | 5195 | 25155 |
| | 27222 | 25791 | | | | | | | | | | |
| 440: | 12773 | 10744 | 27007 | 24376 | 14280 | 27625 | 17836 | 23138 | 27078 | 14316 | 12218 | 25743 |
| | 18082 | 4788 | 6886 | | | | | | | | | |
| 441: | 4509 | 26259 | 29760 | 23472 | 11198 | 27076 | 3262 | 6507 | 15178 | 16996 | 21932 | 12251 |
| | 8372 | 24476 | 19290 | 5080 | 15711 | 29081 | 25694 | 29597 | 3354 | 23050 | 16758 | 29935 |
| | 6107 | 2900 | 15219 | 1960 | 24898 | 28176 | 22447 | 5585 | 26079 | 16049 | 22377 | 29574 |
| | 24681 | 29289 | 11294 | 14961 | 22642 | 24789 | 15211 | 18091 | 22605 | | | |
| 442: | 8367 | 6864 | 12524 | 20258 | 2547 | 30153 | 14333 | 6312 | 5797 | 14892 | 12811 | 3222 |
| | 4007 | 28352 | 15723 | 8465 | 19840 | 20803 | 24946 | 3331 | 22830 | 4472 | 8957 | 22970 |
| | 26158 | 3251 | 9292 | 10270 | 2480 | 1321 | 18185 | 16968 | 6298 | 19777 | 4959 | 5834 |
| | 18110 | 7965 | 14822 | 18240 | 19154 | 13821 | 16977 | 4206 | 28210 | 15355 | 9517 | 16060 |
| | 26755 | 27815 | 6034 | 23493 | 4200 | 826 | 25552 | 4105 | 27433 | 28392 | 13728 | 18554 |
| | 13734 | 30455 | 30452 | 13731 | 20476 | 20411 | 21515 | 27155 | 9956 | 15002 | 6480 | 6362 |
| | 20227 | 26521 | 28901 | 24447 | 24986 | 13091 | 13072 | 17565 | 14590 | 23862 | 12052 | 2002 |
| | 9380 | 1899 | 11464 | 17311 | 27666 | 3502 | 3880 | 30334 | 29240 | 8511 | 7060 | 18584 |
| | 2755 | 17985 | 10141 | 11821 | 12465 | 10738 | 6254 | 24904 | 2639 | 28985 | 29136 |
| | 25807 | 22711 | 3439 | 10513 | 1250 | 23823 | 26967 | 4299 | 26218 | 30125 | 22784 | 15188 |
| | 6648 | 5359 | 12680 | 12088 | 26702 | 26701 | 26639 | 4221 | 2244 | 3899 | 22988 | 28951 |
| | 23620 | 27540 | 21636 | 27324 | 13874 | 6489 | 24288 | 3333 | 29400 | 9364 | 6638 | 6798 |
| | 5535 | 21283 | 8864 | 11272 | 15682 | 9557 | 8827 | 6223 | 29321 | 15771 | 25975 | 11631 |
| | 21357 | 23503 | 16608 | 25936 | 23575 | 5709 | 8692 | 9082 | 8690 | 11913 | 2726 | 4264 |

TABLE 8-continued

| PEP SEQ ID NO: | homolog SEQ ID NOs | | | | | | | | | | |
|---|---|---|---|---|---|---|---|---|---|---|---|
| | 17585 | 2351 | 676 | 23242 | 12174 | 17019 | 6360 | 10976 | 22461 | 4228 | 17644 | 17751 |
| | 18677 | 5490 | 10327 | 28657 | 22256 | 8143 | 23747 | 1904 | 29771 | 24665 | 8223 | 25399 |
| | 15704 | 27065 | 21382 | 2348 | 29390 | 12948 | 5682 | 22699 | 10408 | 19222 | 24698 | 24885 |
| | 14398 | 8544 | 21707 | 8901 | 18093 | 11520 | 21854 | 15853 | 8974 | 8391 | 23652 | 6637 |
| | 9047 | 28062 | 5315 | 23486 | 26636 | 28105 | 25555 | 26657 | 18509 | 11091 | 7075 | 17996 |
| | 1791 | 3859 | 22197 | 2691 | 15475 | 17854 | 16639 | 30356 | 18798 | 18770 | 18765 | 11805 |
| | 3174 | 11751 | 11406 | 684 | 12736 | 18606 | 10095 | 19895 | 18781 | 5482 | 4410 | 20156 |
| | 27217 | 9641 | 25562 | 29866 | 5145 | 4241 | 18691 | 10393 | 28993 | | | |
| 443: | 15900 | 15751 | 15929 | 26189 | 16887 | 20889 | 7980 | 13017 | 24338 | 24315 | 12585 | 13524 |
| | 23036 | 12295 | 3991 | 2237 | 29105 | 17908 | 11425 | 8460 | 8123 | 9031 | 20801 | 21161 |
| | 4787 | 5900 | 22459 | 17962 | 20020 | 13357 | 3594 | 21444 | 16734 | 6816 | 6620 | 5244 |
| | 8267 | 8178 | 29414 | 24598 | 6965 | 4922 | 29122 | 28155 | 1053 | 14137 | 18085 | 29087 |
| | 14621 | 2784 | 16695 | 20853 | 1260 | 17896 | 25055 | 16442 | 18742 | 15699 | 26263 | 9971 |
| | 26417 | 11992 | 26419 | 24451 | 15797 | 9850 | 16721 | 27748 | 21150 | 9579 | 18025 | 2525 |
| | 3723 | 7944 | 21545 | 27260 | 762 | 10551 | 11851 | 11441 | 6398 | 9186 | 2108 | 5265 |
| | 27489 | 9478 | 15898 | 15807 | 30362 | 18777 | 19596 | 27691 | 1252 | 15359 | 17051 | 4839 |
| | 4842 | 24695 | 1680 | 19563 | 2957 | 2962 | 27985 | 16880 | 6946 | 24953 | 26197 | 16245 |
| | 20502 | 20499 | 20470 | 30312 | 27948 | 12885 | 3379 | 6810 | 5540 | 20456 | 18124 | 5060 |
| | 18003 | 13201 | 7969 | 4342 | 24884 | 30103 | 30082 | 23051 | 23053 | 19595 | 14966 | |
| | 27988 | 5426 | 9422 | 8079 | 29927 | 25173 | 4523 | 27982 | 25080 | 26093 | 23156 | 17194 |
| | 25140 | 24032 | 11230 | 18381 | 23833 | 19925 | 26095 | 3237 | 28206 | 12469 | 7251 | 7059 |
| | 3629 | 25751 | 21778 | 6446 | 16561 | 16775 | 3291 | 10423 | 8415 | 8365 | 16557 | 11016 |
| 444: | 703 | 16986 | 10530 | 24696 | 29631 | 15216 | 19465 | 12205 | 2111 | 13009 | 733 | 3123 |
| | 5782 | 12717 | 22838 | 3301 | 7207 | 3177 | 1650 | 10162 | 12118 | 18359 | 22793 | 12486 |
| | 27776 | 663 | 5452 | 9594 | 21011 | 29500 | 24292 | 10637 | 19035 | 23055 | 9212 | 25016 |
| | 7139 | 24727 | 26715 | 26740 | 17536 | 11580 | 16466 | 28242 | 9045 | 14101 | 16469 | 13665 |
| | 26392 | 7824 | 27393 | 10521 | 20413 | 15589 | 19636 | 23467 | 5187 | 5184 | 27095 | 19483 |
| | 25993 | 3806 | 20544 | 4580 | 3739 | 23095 | 6653 | 9945 | 27764 | 6115 | 18456 | 13215 |
| | 14893 | 4321 | 16612 | 11020 | 25876 | 24618 | 20971 | 30299 | 27399 | 24167 | 24220 | 27674 |
| | 23909 | 29116 | 2454 | 22725 | 10075 | 6722 | 27143 | | | | | |
| 445: | 30054 | 9562 | 9529 | 9525 | 9566 | 9603 | 23232 | 9751 | 11028 | 6117 | 14648 | 4395 |
| | 22884 | 24631 | 21491 | 21653 | 4029 | 13588 | 30436 | 17233 | 11596 | 11194 | 9508 | 8431 |
| | 4484 | 12640 | 25503 | 18864 | 21979 | 11634 | 22280 | 6114 | 27302 | 3729 | 19968 | 20580 |
| | 22038 | 18324 | 18326 | 761 | 9516 | 15020 | 14996 | 17577 | 27784 | 19686 | 20530 | 29949 |
| | 13558 | 13626 | 20254 | 26352 | 20100 | 22776 | 21270 | 2907 | 19221 | 25572 | 29976 | 28066 |
| | 28112 | 28114 | 25506 | 25483 | 8868 | 13129 | 1944 | 25485 | 9569 | 7868 | 21107 | 4955 |
| | 14457 | 15310 | 17238 | 7103 | 21488 | 21487 | 7104 | 7108 | 14471 | 15941 | | |
| 446: | 24743 | 18890 | 20338 | 15579 | 24945 | 3403 | 11390 | 7926 | 3786 | | | |
| 447: | 13827 | 24653 | 2760 | 21851 | 26157 | 25150 | 12111 | 2562 | 20140 | 26647 | 15801 | 2390 |
| | 3532 | 9193 | 23744 | 25253 | 21177 | 3080 | 11263 | 452 | 13134 | 23306 | 9258 | 22014 |
| | 15200 | 15385 | 14210 | 2432 | 1137 | 20189 | 7975 | 21708 | 8011 | 12963 | 29490 | 18633 |
| | 28799 | 1182 | 5174 | 25735 | 25459 | 5789 | 30130 | 15317 | | | | |
| 448: | 2789 | 15523 | 18289 | 30198 | 24495 | 6772 | 654 | 15067 | 13394 | 28473 | 7794 | 12180 |
| | 5835 | 28884 | 3735 | 14624 | 10296 | 15431 | 21816 | 2139 | 13105 | | | |
| 449: | 20866 | 29212 | 14854 | 9418 | 29467 | 18050 | 11000 | 15581 | 6435 | 25384 | 19947 | 27875 |
| | 18498 | 13045 | | | | | | | | | | |
| 450: | 26090 | 24906 | 7328 | 16079 | 13640 | 1998 | 3987 | 14369 | 24547 | 10118 | 10168 | 19534 |
| | 14201 | 4351 | 29751 | 23972 | 19048 | 19124 | 19518 | 16929 | 12836 | 10980 | 5385 | 12514 |
| | 8603 | 21615 | 14006 | 11639 | 9621 | 29755 | 3278 | 9131 | 13564 | 783 | 18177 | 14122 |
| | 16367 | 23248 | 18197 | 16067 | 10484 | 27976 | 27790 | 10726 | 28360 | 7845 | 8361 | 7214 |
| | 7541 | 3978 | 10445 | 26641 | 12573 | 11417 | 1937 | 8810 | 18305 | 17353 | 26604 | 11764 |
| | 14422 | 27199 | 26491 | 13341 | 8502 | 7149 | 22354 | 27631 | 850 | 24218 | 22409 | |
| | 8455 | 30360 | 3313 | 24294 | 14091 | 12152 | 30220 | 23301 | 604 | 12792 | 28356 | 12273 |
| | 17439 | 5642 | 24682 | 2394 | 781 | 21304 | 19627 | 7391 | 21743 | 5612 | 2420 | 8426 |
| | 27392 | 19043 | 22515 | 29067 | 5266 | 8170 | 5679 | 6456 | 11093 | 8388 | 22771 | 8450 |
| | 17154 | 17655 | 21229 | 10695 | 22850 | 20714 | 3703 | 17981 | 27996 | 24666 | 29419 | 13898 |
| | 25251 | 2927 | 968 | 25866 | 11823 | 11437 | 11556 | 29559 | 28036 | 22558 | 28576 | 18030 |
| | 644 | 20487 | 13123 | 6229 | 21755 | 4019 | 11073 | 14826 | 8138 | 4868 | 5476 | 13751 |
| | 26764 | 24215 | 21989 | 8521 | 23457 | 22084 | 15037 | 29764 | 12464 | 14383 | 27005 | 11776 |
| | 28824 | 9025 | 18016 | 15103 | 18931 | 28602 | 8158 | 17472 | 1453 | 3416 | 1990 | 16594 |
| | 2573 | 20483 | 22565 | 23359 | 4684 | 14747 | 21853 | 24807 | 9107 | 9108 | 22028 | 22025 |
| | 22021 | 24031 | 21991 | 26569 | 29011 | 5830 | 3328 | 15130 | 15099 | 21719 | 26251 | 26252 |
| | 13720 | 2076 | 22740 | 24231 | 19986 | 21220 | 18601 | 2781 | 11918 | 4664 | 8250 | 28676 |
| | 18541 | 28331 | 28337 | 339 | 4767 | 28342 | 28339 | 5219 | 26295 | 4537 | 1807 | 15313 |
| | 11247 | 25153 | 12268 | 2308 | 4168 | 2771 | 29692 | 26107 | 29685 | 28833 | 9328 | 2456 |
| | 2455 | 2459 | 27366 | 2459 | 27370 | 13267 | 19730 | 9757 | 9762 | 1804 | 588 | |
| | 10917 | 27732 | 21183 | 2693 | 16543 | 21668 | 16222 | 29162 | 22592 | 7464 | 26199 | 15576 |
| | 6058 | 2248 | 16943 | 6613 | 18400 | 6406 | 28875 | 30169 | 21426 | 14657 | 11572 | 11571 |
| | 10874 | 15508 | 22276 | 22496 | 21391 | 21149 | 20099 | 21996 | 21999 | 14338 | 14342 | 14140 |
| | 14363 | 14341 | 15131 | 6669 | 995 | 21986 | 5549 | 14372 | 14890 | 14882 | 14886 | 14908 |
| | 30442 | 10627 | 13868 | 14633 | 10628 | 10603 | 9996 | 18761 | 17083 | 26475 | 9727 | 16415 |
| | 17048 | 28330 | 24234 | 25184 | 7849 | 29233 | 12077 | 18458 | 16866 | 6253 | 15009 | 21468 |
| | 22604 | 21893 | 16765 | 21349 | 10996 | 2998 | 16618 | 22757 | 11069 | 29828 | 10308 | 16323 |
| | 20432 | 26608 | 11347 | 18818 | 2720 | 22764 | 341 | 3311 | 28703 | 1361 | 548 | 8249 |
| | 30246 | 14879 | 25683 | 1195 | 26838 | 21940 | 16856 | 12346 | 24829 | 21523 | 8831 | 29982 |
| | 18688 | 11159 | 10760 | 21202 | 8264 | 28303 | 22043 | 25091 | 21992 | 8269 | 28346 | 13382 |
| | 24297 | 24316 | 13140 | 2970 | 22223 | 16540 | 763 | 16890 | 3910 | 16235 | 4535 | 4961 |

TABLE 8-continued

| PEP SEQ ID NO: | homolog SEQ ID NOs | | | | | | | | | | |
|---|---|---|---|---|---|---|---|---|---|---|---|
| | 11545 | 28378 | 28077 | 2792 | 23797 | 2309 | 14104 | 7723 | 27167 | 10108 | 12589 | 10780 |
| | 13561 | 10432 | 24018 | 30465 | 23985 | 23865 | 12964 | 15841 | 26552 | 12280 | | |
| 451: | 26090 | 24906 | 7328 | 16079 | 13640 | 1998 | 3987 | 14369 | 24547 | 10118 | 10168 | 19534 |
| | 14201 | 4351 | 29751 | 23972 | 19048 | 19124 | 19518 | 16929 | 12836 | 10980 | 5385 | 12514 |
| | 8603 | 21615 | 14006 | 11639 | 9621 | 29755 | 3278 | 9131 | 13564 | 783 | 18177 | 14122 |
| | 16367 | 23248 | 18197 | 16067 | 10484 | 27976 | 27790 | 10726 | 28360 | 7845 | 8361 | 7214 |
| | 7541 | 3978 | 10445 | 26641 | 12573 | 11417 | 1937 | 8810 | 18305 | 17353 | 26604 | 11764 |
| | 14422 | 27199 | 26491 | 13341 | 8502 | 7149 | 14121 | 22354 | 27631 | 850 | 24218 | 22409 |
| | 8455 | 30360 | 3313 | 24294 | 14091 | 12152 | 30220 | 23301 | 604 | 12792 | 28356 | 12273 |
| | 17439 | 5642 | 24682 | 2394 | 781 | 21304 | 19627 | 7391 | 21743 | 5612 | 2420 | 8426 |
| | 27392 | 19043 | 22515 | 29067 | 5266 | 8170 | 5679 | 6456 | 11093 | 8388 | 22771 | 8450 |
| | 17154 | 17655 | 21229 | 10695 | 22850 | 20714 | 3703 | 17981 | 27996 | 24666 | 29419 | 13898 |
| | 25251 | 2927 | 968 | 25866 | 11823 | 11437 | 11556 | 29559 | 28036 | 22558 | 28576 | 18030 |
| | 644 | 20487 | 13123 | 6229 | 21755 | 4019 | 11073 | 14826 | 8138 | 4868 | 5476 | 13751 |
| | 26764 | 24215 | 21989 | 8521 | 23457 | 22084 | 15037 | 29764 | 12464 | 14383 | 27005 | 11776 |
| | 28824 | 9025 | 18016 | 15103 | 18931 | 28602 | 8158 | 17472 | 1453 | 3416 | 1990 | 16594 |
| | 2573 | 20483 | 22565 | 23359 | 4684 | 14747 | 21853 | 24807 | 9107 | 9108 | 22028 | 22025 |
| | 22021 | 24031 | 21991 | 26569 | 29011 | 5830 | 3328 | 15130 | 15099 | 21719 | 26251 | 26252 |
| | 13720 | 2076 | 22740 | 24231 | 19986 | 21220 | 18601 | 2781 | 11918 | 4664 | 8250 | 28676 |
| | 18541 | 28331 | 28337 | 339 | 4767 | 28342 | 28339 | 5219 | 26295 | 4537 | 1807 | 15313 |
| | 11247 | 25153 | 12268 | 2308 | 4168 | 2771 | 29692 | 26107 | 29685 | 28833 | 9328 | 2456 |
| | 2455 | 2459 | 27366 | 27372 | 27370 | 13267 | 13269 | 9730 | 9757 | 9762 | 1804 | 588 |
| | 10917 | 27732 | 21183 | 2693 | 16543 | 21668 | 16222 | 29162 | 22592 | 7464 | 26199 | 15576 |
| | 6058 | 2248 | 16943 | 6613 | 18400 | 6406 | 28875 | 30169 | 21426 | 14657 | 11572 | 11571 |
| | 10874 | 15508 | 22276 | 22496 | 21391 | 21149 | 20099 | 21996 | 21999 | 14338 | 14342 | 14140 |
| | 14363 | 14341 | 15131 | 6669 | 995 | 21986 | 5549 | 14372 | 14890 | 14882 | 14886 | 14908 |
| | 30442 | 10627 | 13868 | 14633 | 10628 | 10603 | 9996 | 18761 | 17083 | 26475 | 9727 | 16415 |
| | 17048 | 28330 | 24234 | 25184 | 7849 | 29233 | 12077 | 18458 | 16866 | 6253 | 15009 | 21468 |
| | 22604 | 21893 | 16765 | 21349 | 10996 | 2998 | 16618 | 22757 | 11069 | 29828 | 10308 | 16323 |
| | 20432 | 26608 | 11347 | 18818 | 2720 | 22764 | 341 | 3311 | 28703 | 1361 | 548 | 8249 |
| | 30426 | 14879 | 25683 | 1195 | 26838 | 21940 | 16856 | 12346 | 24829 | 21523 | 8831 | 29982 |
| | 18688 | 11159 | 10760 | 21202 | 8264 | 28303 | 22043 | 25091 | 21992 | 8269 | 28346 | 13382 |
| | 24297 | 24316 | 13140 | 2970 | 22223 | 16540 | 763 | 16890 | 3910 | 16235 | 4535 | 4961 |
| | 11545 | 28378 | 28077 | 2792 | 23797 | 2309 | 14104 | 7723 | 27167 | 10108 | 12589 | 10780 |
| | 13561 | 10432 | 24018 | 30465 | 23985 | 23865 | 12964 | 15841 | 26552 | 12280 | | |
| 452: | 13827 | 24794 | 24653 | 2760 | 21851 | 26157 | 12111 | 25150 | 2562 | 16927 | 20140 | 2390 |
| | 15801 | 26647 | 11245 | 3532 | 9193 | 23744 | 25253 | 21177 | 3080 | 11263 | 15317 | 447 |
| | 21560 | 23306 | 9258 | 17954 | 22014 | 15200 | 25970 | 12414 | 8034 | 19378 | 21298 | 15385 |
| | 15384 | 14210 | 26968 | 8346 | 2432 | 1137 | 20189 | 7975 | 25141 | 8011 | 18633 | 28799 |
| | 12963 | 29490 | 1182 | 5174 | 25735 | 22547 | 13204 | 6963 | 18646 | 25459 | 5789 | 23252 |
| | 30130 | | | | | | | | | | | |
| 453: | 22309 | 16508 | | | | | | | | | | |
| 454: | 20066 | 8631 | 6983 | 6988 | 7348 | 17302 | 7353 | 2347 | 9889 | 23658 | 24193 | 16953 |
| | 19830 | 25103 | 21473 | 26882 | 28832 | 22567 | 14661 | 23064 | 4384 | 2368 | 20595 | 27093 |
| | 5979 | 23062 | 6031 | 14031 | 21060 | 15345 | 17493 | 13555 | 16552 | 6038 | 22502 | 19406 |
| | 11005 | 29928 | 13879 | 6299 | 9551 | 30298 | 12283 | 13468 | | | | |
| 455: | 12197 | 5083 | 22748 | 25233 | 21145 | 4018 | 2633 | 16102 | 12779 | 29833 | 11193 | 8821 |
| | 8822 | 5591 | 5978 | 7241 | 27069 | 19493 | 10625 | 6544 | 21805 | 23685 | 23663 |
| | 27510 | 27513 | 27515 | 25379 | 29072 | 846 | 1262 | 16659 | 23446 | 23314 | 2834 | 25292 |
| | 22709 | 8169 | 20003 | 21182 | 18200 | 2067 | 28820 | 18356 | 27543 | 19791 | 7792 | 12744 |
| | 4194 | 18884 | 2842 | 29496 | 8027 | 18247 | 19024 | 4805 | 8531 | 18422 | 20244 | 20210 |
| | 19630 | 27242 | 25821 | 6050 | 20022 | 17852 | 21434 | 19090 | | | | |
| 456: | 5713 | 5731 | 7666 | 23694 | 22911 | 18150 | 26649 | 2034 | 8001 | 30006 | 10177 | 4692 |
| | 14395 | 29033 | 29544 | 15443 | 10544 | 24797 | 10873 | 7935 | 29003 | 15255 | 4236 | 3050 |
| | 13865 | 21949 | 14356 | 1329 | 28334 | 11607 | 21180 | 26293 | 21077 | 16585 | 5701 | 3709 |
| | 27462 | 13332 | 14583 | 25043 | | | | | | | | |
| 457: | 21969 | 407 | 6567 | 2642 | 681 | 24237 | 27172 | 24706 | 5892 | 8105 | 22041 | 16218 |
| | 2316 | 4924 | 22112 | 26146 | 19293 | 8274 | 19356 | 14025 | 379 | 10900 | 18809 | 3477 |
| | 753 | 18266 | 26407 | 25408 | 380 | 21926 | 9209 | 19607 | 25045 | 14021 | | |
| 458: | 16744 | 4407 | 25100 | 21084 | 25750 | 22690 | 20467 | 9787 | 22694 | 20474 | 19088 | 14913 |
| | 14914 | 24851 | 21000 | 1213 | 16158 | 30234 | 4889 | 30041 | 30040 | 18311 | 6589 | 2008 |
| | 2276 | 29636 | 10560 | 16082 | 12880 | 12882 | 27184 | 3985 | 10180 | 12256 | 15752 | 3953 |
| | 22588 | 2670 | 5009 | 17129 | 8599 | 3657 | 11624 | 14128 | 727 | 11869 | 18500 | 14209 |
| | 19819 | 22815 | 20307 | 17323 | 25048 | 18179 | 1414 | 24660 | 24638 | 22963 | 17432 | 26842 |
| | 22880 | 2592 | 19847 | 20451 | 3055 | 10336 | 2910 | 22753 | 22754 | 13718 | 24605 | 2358 |
| | 4981 | 1851 | 12081 | 25037 | 17222 | 17221 | 19195 | 21936 | 16573 | 7414 | 9623 | 23310 |
| | 5178 | 29027 | 16016 | 25544 | 10442 | 21658 | 21659 | 28729 | 7026 | 26969 | 29301 | 26753 |
| | 12164 | 18602 | 1243 | 29091 | 3701 | 15406 | 8344 | 28267 | 6135 | 3561 | 10671 | 15878 |
| | 10750 | 10970 | 6970 | 23035 | 8118 | 17491 | 5018 | 12726 | 12942 | 14767 | 29257 | 27629 |
| | 25172 | 25170 | 7283 | 12727 | 24619 | 27552 | 16255 | 29256 | 28279 | 25594 | 876 | 27774 |
| | 17636 | 30055 | 4952 | 6912 | 6914 | 4950 | 26688 | 3371 | 3356 | 27012 | 15203 | 12615 |
| | 21483 | 11271 | 20441 | 29061 | 23791 | 1564 | 16732 | 8867 | 6163 | 28544 | 26455 | 17744 |
| | 12012 | 2253 | 26349 | 4803 | 4804 | 27446 | 17956 | 17091 | 17955 | 26563 | 25681 | 5047 |
| | 2835 | 16537 | 6565 | 7807 | 7176 | 6483 | 18151 | 3560 | 28942 | 27493 | 668 | 14152 |
| | 8834 | 29598 | 29340 | 6273 | 4878 | 1909 | 11746 | 11745 | 14903 | 26071 | 26700 | 13493 |
| | 27961 | 11683 | 21235 | 28009 | 11760 | 13876 | 17809 | 12752 | 10315 | 8005 | 12860 | 16240 |
| | 24121 | 19108 | 14075 | 27793 | 1494 | 30050 | 22237 | 732 | 6109 | 27507 | 16471 | 15948 |
| | 13484 | 9708 | 10477 | 19339 | 22137 | 18287 | 14289 | 25145 | 14303 | 22047 | 19644 | 2391 |

TABLE 8-continued

| PEP SEQ ID NO: | homolog SEQ ID NOs | | | | | | | | | | |
|---|---|---|---|---|---|---|---|---|---|---|---|
| | 23284 | 26180 | 1201 | 17522 | 7880 | 15095 | 23874 | 16577 | 2294 | 20130 | 14936 | 14915 |
| | 8994 | 25135 | 21336 | 29920 | 10839 | 11346 | 2350 | 14108 | 13633 | 15851 | 24552 | 27770 |
| | 27149 | 13108 | 25406 | 30425 | 27387 | 19343 | 18819 | 7131 | 24769 | 19476 | 21522 | 17365 |
| | 12929 | 12621 | 7081 | 19263 | 14881 | 9813 | 7973 | 9239 | 25883 | 11769 | 28879 | 27072 |
| 459: | 1392 | 27440 | 952 | 11231 | 20435 | 16441 | 9264 | 8684 | 20316 | 3765 | 21565 | 22449 |
| | 14297 | 27098 | 21009 | 26075 | 13940 | 15745 | 18825 | 24720 | 3267 | 20672 | 20701 | 3772 |
| | 29912 | 5984 | 21895 | 18957 | 22067 | 1830 | 18410 | 17473 | 3764 | 21358 | 24490 | 16843 |
| | 3480 | 8815 | 4317 | 10147 | 28888 | 21736 | 16935 | 17136 | 10010 | 13924 | 3604 | 23429 |
| | 14793 | 20512 | 13262 | 12013 | 12007 | 3937 | 11715 | 9034 | 24957 | 20209 | 23672 | 21633 |
| | 29710 | 10153 | 10301 | 1298 | 30398 | 1600 | 17050 | 23327 | 25040 | 4042 | 3785 | 6154 |
| | 9882 | 4288 | 17796 | 14231 | 23134 | 15162 | 22444 | 19275 | 11523 | 11779 | 9051 | 2667 |
| | 4649 | 4648 | 1499 | 20517 | 19837 | 12567 | 16221 | 6806 | 6472 | 773 | 27635 | 11542 |
| | 6829 | 29280 | 22140 | 11949 | 11952 | | | | | | | |
| 460: | 23201 | 17383 | 23224 | 26008 | 26005 | 9941 | 5941 | 17348 | 25254 | 25230 | 4414 | 5687 |
| | 10674 | 1801 | 2767 | 19184 | 19713 | 8809 | 601 | 25137 | 10779 | 26745 | 24818 | 8897 |
| | 1368 | 27623 | 30093 | 19413 | 28690 | 18037 | | | | | | |
| 461: | 2488 | 2490 | 2492 | 16114 | 16109 | 1842 | 2374 | 7721 | 16119 | 1863 | 25039 | 2379 |
| | 2376 | 16118 | 1861 | 2372 | 1843 | 1868 | 16155 | 16157 | 16159 | 2457 | 2461 | 28195 |
| | 28216 | 24571 | 24556 | 11512 | 9497 | 9502 | 9278 | 21661 | 10042 | 13872 | 1959 | 5069 |
| | 30433 | 3795 | 24649 | 23526 | 17615 | 13518 | 29873 | 26193 | 6169 | 7274 | 4943 | 9750 |
| | 17943 | 27097 | 11513 | 11965 | 11516 | 18895 | 12284 | 10013 | 10941 | 615 | 26596 | 24685 |
| | 3883 | 16089 | 27100 | 5943 | 21917 | 20253 | 13576 | 7539 | 20582 | 698 | 16187 | 2401 |
| | 2400 | 4092 | 16152 | 2337 | 2340 | 1866 | 16149 | 2342 | 2345 | 11604 | 19568 | 22680 |
| | 2889 | 21674 | | | | | | | | | | |
| 462: | 28452 | 28384 | 7106 | 11134 | 20318 | 6599 | 18866 | 24932 | 26345 | 16954 | 25858 | 26047 |
| | 6501 | 8305 | 13871 | 28850 | 25122 | 24370 | 8396 | 30331 | 28333 | 25796 | 6640 | 12891 |
| | 17285 | 6631 | 9286 | 5090 | 29297 | 1218 | 18883 | 1344 | 5464 | | | |
| 463: | 26045 | 30127 | 29320 | 26289 | 12924 | 11235 | 5935 | 10527 | 17821 | 630 | 29473 | 12869 |
| | 11451 | 5618 | 10027 | 14888 | 11990 | 24259 | 5720 | 780 | 9122 | 27531 | 18352 | 14061 |
| | 14010 | 13206 | 17734 | 13867 | 14560 | 17261 | 17144 | 11790 | 29913 | 9244 | 11170 | 24312 |
| | 4819 | 23638 | 12648 | 26815 | 19921 | 17384 | 7194 | 1019 | 1017 | 25228 | 25224 | 17767 |
| | 29602 | 5818 | 13327 | 1950 | 21814 | 6787 | 25734 | 26586 | 14652 | 25785 | 27175 | 14530 |
| | 30381 | 7252 | 14959 | 30282 | 4979 | 23724 | 6001 | 11024 | 7290 | | | |
| 464: | 15367 | 24282 | 29815 | 8366 | 819 | 4826 | 9906 | 8903 | 15845 | 24726 | 12243 | 13433 |
| | 2043 | 20438 | 18051 | 3857 | 2660 | 8084 | 15539 | 17178 | 14718 | 2092 | 3558 | 9493 |
| | 24848 | 7892 | 15086 | 25526 | 23930 | 30058 | | | | | | |
| 465: | 20805 | 12922 | 14821 | 25099 | 16808 | 23561 | 25115 | 19924 | 19858 | 30036 | 10807 | 17562 |
| | 17559 | 13375 | 13378 | 19173 | 19143 | 19138 | 19170 | 13380 | 19109 | 16611 | 28475 | 16515 |
| | 11072 | 13792 | 4888 | 7308 | 7306 | 7339 | 7337 | 6325 | 6321 | 7239 | 9620 | 5776 |
| | 18454 | 8853 | 18492 | 13237 | 6359 | 27246 | 5222 | 17478 | 16250 | 14573 | 14576 | 14602 |
| | 14599 | 14607 | 14614 | 14611 | 16303 | 7130 | 3624 | 2938 | 24066 | 1364 | 10344 | 8055 |
| | 11763 | 12901 | 26566 | 22412 | 19923 | 4023 | 25159 | 4893 | 3213 | 23466 | 27085 | 14216 |
| | 14507 | 25168 | 8796 | 5832 | 8091 | 27991 | 26781 | 17266 | 10209 | 1347 | 7032 | 27523 |
| | 19861 | 19863 | 19926 | 25579 | 15446 | 30369 | 2973 | 18544 | 24922 | 21575 | 30296 | 11175 |
| | 11752 | 28465 | 6888 | 11296 | 18715 | 27288 | 16176 | 29939 | 2236 | 27166 | 20256 | 1533 |
| | 29617 | 8182 | 4467 | 1441 | 28304 | 1107 | 10964 | 10352 | 19316 | 15371 | 25916 | 17254 |
| | 13035 | 15081 | 12315 | 25001 | 26950 | 25641 | 18276 | 3069 | 21746 | 27359 | 13083 | 25323 |
| | 8988 | 17953 | 705 | 17263 | 29051 | 25622 | 30273 | 21798 | 9886 | 18577 | 29842 | 29346 |
| | 9571 | 16738 | 8098 | 13661 | 23941 | 28640 | 8842 | 5528 | 1458 | 15064 | 2712 | 8598 |
| | 12718 | 22843 | 3848 | 19776 | 19901 | 19899 | 25119 | 18720 | 14060 | 21819 | 1461 | 24111 |
| | 8925 | 19891 | 19894 | 16276 | 1446 | 6854 | 21398 | 24699 | 24222 | 23460 | 20936 | 4995 |
| | 14002 | 26439 | 19176 | 17864 | 9545 | 7929 | 4591 | 14774 | 25731 | 17634 | 7345 | 7350 |
| | 26023 | 26027 | 15925 | 9411 | 14829 | 10453 | 29997 | 14801 | 5479 | 5477 | 14857 | 25218 |
| | 9564 | 12476 | 20797 | 5125 | 6667 | 28570 | 22388 | 16525 | 25779 | 12682 | 17030 | 26024 |
| | 25988 | 26019 | 17486 | 25989 | 25990 | 26021 | 26056 | 25986 | 18092 | 13750 | 1705 | 30145 |
| | 9421 | 28825 | 13043 | 10654 | 25972 | 13240 | 22075 | 27963 | 12518 | 2179 | 29108 | 27888 |
| | 17849 | 17820 | 17851 | 17816 | 17844 | 11955 | 17848 | 17814 | 4789 | 15859 | 4784 | 4753 |
| | 4783 | 4785 | 28898 | 11378 | 9600 | 13882 | 15012 | 14989 | 14987 | 15013 | 14983 | 10193 |
| | 9453 | 9409 | 8209 | 23604 | 15400 | 10184 | 18398 | 10206 | 17942 | 13948 | 26377 | 6187 |
| | 6664 | 6574 | 10958 | | | | | | | | | |
| 466: | 9833 | 10948 | 27731 | 11438 | 8716 | 8587 | 20505 | 29173 | 12404 | 17922 | 9506 | 8836 |
| | 26632 | 12107 | 26223 | 1941 | | | | | | | | |
| 467: | 3744 | 2450 | 26907 | 24268 | 6387 | 21543 | 27201 | 3273 | 475 | 25458 | 8487 | 4208 |
| | 17673 | 26773 | 23524 | 5099 | 1386 | 5956 | 3486 | 23059 | 30021 | 20480 | 18160 | 18918 |
| | 18033 | 25273 | | | | | | | | | | |
| 468: | 29430 | 14714 | 28230 | 1782 | 14011 | 27396 | 5339 | | | | | |
| 469: | 16873 | 25672 | 15458 | 2920 | 2728 | 1220 | 8483 | 17024 | 20028 | 11789 | 14581 | 6962 |
| | 14566 | 6780 | 10497 | 18752 | 15596 | 7590 | 14877 | 24206 | 3031 | 9852 | 8813 | 25593 |
| | 2133 | 21408 | 5993 | 7816 | 1485 | 23125 | 17967 | 19580 | 11617 | 29950 | 1964 | 13535 |
| | 7873 | 1700 | 25906 | 27047 | 3109 | 21870 | 22860 | 3951 | 13040 | 16584 | 14426 | 18304 |
| | 13505 | 14575 | 3047 | 26072 | 13607 | 6818 | 2339 | 15046 | 13231 | 11155 | 8634 | 21648 |
| | 19697 | 14033 | 3695 | 19659 | 7790 | 10350 | 30202 | 30173 | 15759 | 21307 | 16088 | 15050 |
| | 29904 | 4276 | 14093 | 11685 | 9214 | 857 | 10093 | 8047 | 11053 | 1895 | 4951 | 9337 |
| | 25914 | 11817 | 11203 | 24772 | 24834 | 20533 | 6853 | 14954 | 19965 | 25009 | 20267 | 7919 |
| | 6720 | 28669 | 10416 | 4564 | 4548 | 22203 | 22633 | 22630 | 14275 | 15521 | 9359 | 14354 |
| | 5860 | 11606 | 5856 | 12897 | 999 | 24729 | 12418 | 27660 | 5646 | 4764 | 18470 | 30417 |
| | 1189 | 1688 | 9661 | 30170 | 24583 | 24527 | 20152 | 8115 | 16262 | 25419 | 26123 | 15518 |
| | 22544 | 16437 | 12809 | 6172 | 10896 | 29571 | 5756 | 15816 | 10947 | 13903 | 25047 | 12762 |

TABLE 8-continued

| PEP SEQ ID NO: | homolog SEQ ID NOs | | | | | | | | | | |
|---|---|---|---|---|---|---|---|---|---|---|---|
| | 1419 | 8259 | 18553 | 16718 | 29881 | 12446 | 14386 | 18195 | 9265 | 15463 | 14948 | 19151 |
| | 26404 | 26568 | 5361 | 8368 | 26541 | 8689 | 5994 | 10932 | 16196 | 7218 | 22411 | 7126 |
| | 4340 | 16226 | 15830 | 17244 | 18927 | 11252 | 4651 | 1527 | 29455 | 29211 | 1718 | 29888 |
| | 23402 | 27203 | 1140 | 17025 | 29313 | 25203 | 27384 | 11267 | 14067 | 15004 | 18433 | 28130 |
| | 21635 | 1457 | 19207 | 10986 | 14070 | 13770 | 19606 | 27889 | 29378 | 29163 | 30302 | 17445 |
| | 3879 | 6439 | 5119 | 25676 | 2554 | 9067 | 6426 | 3320 | 858 | 19522 | 23558 | 25517 |
| | 25543 | 3398 | 17672 | 17588 | 18395 | 18393 | 17554 | 17622 | 17659 | 17551 | 28516 | 8929 |
| | 11986 | 20844 | 28512 | 3782 | 24943 | 10076 | 1249 | 30461 | 5451 | 25647 | 16875 | 4259 |
| | 1156 | 9135 | 15348 | 29495 | 21381 | 30038 | 30133 | 26467 | 2180 | 3897 | 8197 | 9243 |
| | 12254 | 23856 | 3634 | 10356 | 13042 | 10165 | 5990 | 11909 | 22525 | 5883 | 12983 | 24350 |
| | 19164 | 4224 | 7398 | 6610 | 7726 | 29557 | 20165 | 1257 | 1221 | 22579 | 9510 | 6560 |
| | 27739 | 10111 | 20005 | 11991 | 9437 | 16683 | 9431 | 701 | 7408 | 18332 | 19698 | 19474 |
| | 22934 | 23815 | 24314 | 19083 | 24047 | 13962 | 16440 | 17202 | 17175 | 16541 | 9468 | 27887 |
| | 988 | 29910 | 22209 | 13074 | 4047 | 6656 | 13329 | 22189 | 26333 | 13077 | 5151 | 8562 |
| | 11947 | 12765 | 13008 | 1045 | 29454 | 21234 | 27837 | 25093 | 22281 | 5399 | 24382 | 25352 |
| | 23626 | 16851 | 3427 | 7600 | 3518 | 2777 | 10977 | 23551 | 15202 | 27262 | 18511 | 20454 |
| | 26958 | 2990 | 25620 | 8561 | 17718 | 17761 | 8331 | 29962 | 7603 | 8538 | 25241 | 18032 |
| | 18042 | 2329 | 19041 | 11662 | 29586 | 28661 | 18523 | 18497 | 18056 | 7497 | 758 | 6311 |
| | 3195 | 16630 | 15553 | 21809 | 28814 | 11392 | 28345 | 17873 | 22891 | 3413 | 5446 | 21187 |
| | 21059 | 17392 | 13230 | 14310 | 25442 | 17453 | 29069 | 6194 | 18181 | 24627 | 24597 | 12030 |
| | 27412 | 10536 | 6692 | 22997 | 5101 | 29651 | 16078 | 21617 | 14348 | 9403 | 25722 | 25013 |
| | 24988 | 6236 | 28169 | 29641 | 4623 | 25258 | 26524 | 8968 | 14651 | 18839 | 5130 | 5690 |
| | 24709 | 10506 | 11668 | 19887 | 14443 | 18623 | 19994 | 9066 | 11064 | 28970 | 10838 | 27657 |
| | 29353 | 8576 | 4060 | 12604 | 9332 | 14088 | 15142 | 23625 | 13684 | 29167 | 14208 | 17255 |
| | 16837 | 23853 | 22395 | 22373 | 8621 | 1194 | 16942 | 20696 | 23619 | 9410 | 17440 | 22288 |
| | 24562 | 15990 | 2435 | 27045 | 19807 | 21524 | 25176 | 25597 | 26483 | 19055 | 26599 | 29954 |
| | 1733 | 3453 | 8942 | 19139 | 25262 | 28205 | 13959 | 2466 | 23563 | 23535 | 23938 | 1106 |
| | 26394 | 27432 | 15335 | 23743 | 30073 | 25540 | 25509 | 788 | 16908 | 22285 | 4058 | 23356 |
| | 16019 | 9448 | 13342 | 13320 | 4398 | 5838 | 808 | 16813 | 11977 | 30287 | 2318 | 29144 |
| | 25946 | 26119 | 29817 | 21184 | 22289 | 18170 | 4310 | 5324 | 17550 | 1349 | 12618 | 11468 |
| | 11595 | 8061 | 15325 | 9505 | 22350 | 16335 | 20449 | 2163 | 852 | 2733 | 18301 | 17686 |
| | 13850 | 12974 | 4897 | 5048 | 15813 | 10685 | 15928 | 12455 | 29570 | 20665 | 15052 | 26244 |
| 470: | 12633 | 22272 | 6939 | 5436 | 6903 | 19289 | 12073 | 4246 | 11239 | 11220 | 5207 | 17109 |
| | 24162 | 21590 | 19286 | 5425 | 5430 | 28756 | 5610 | 28547 | 30375 | 21508 | 15517 | 23879 |
| | 24168 | 15269 | 22766 | 30444 | 5774 | 2159 | 22995 | 14625 | 22961 | 27546 | 16625 | 25748 |
| | 3774 | 23778 | 18896 | 29115 | 22848 | 6662 | 15338 | 18141 | 14813 | 4311 | 12188 | 4186 |
| | 17651 | 16654 | 22596 | 24543 | 24139 | 24171 | 13070 | 14145 | 15047 | 9867 | 22339 | 6261 |
| | 7342 | 29017 | 8122 | 25903 | 12863 | 29221 | 7811 | 21016 | 20259 | 12960 | 24163 | 23831 |
| | 24134 | 3722 | 25962 | 3343 | 17871 | 18224 | 24138 | 13856 | 9840 | 17246 | 18426 | 5864 |
| | 29945 | 28973 | 9848 | 5133 | 10174 | 26116 | 16948 | 21378 | 855 | 19993 | 30218 | 11003 |
| | 8090 | 28428 | 12644 | 14159 | 4657 | 7703 | 7704 | 24137 | 16308 | 14049 | 13022 | 13027 |
| | 12177 | 2556 | 7496 | 13569 | 884 | 18847 | 16724 | 13023 | 2419 | 28613 | 14144 | 3276 |
| | 26725 | 23143 | 23690 | 23691 | 10724 | 2410 | 20847 | 6017 | 26851 | 16062 | 19848 | 10284 |
| | 16302 | 7117 | 15902 | 16224 | 27646 | 13245 | 16310 | 5202 | 15607 | 19751 | 10030 | 16301 |
| | 16282 | 5225 | 7893 | 7921 | 7923 | 1983 | 17040 | 12399 | 12402 | 12401 | 12397 | 12398 |
| | 9089 | 9591 | 11778 | 30113 | 13024 | 16120 | 6482 | 13019 | 13004 | 26633 | 6479 | 26162 |
| | 20447 | 21352 | 23855 | 993 | 14542 | 2101 | 992 | 13020 | 5205 | 6181 | 11536 | 13905 |
| | 14825 | 24913 | 24331 | 16312 | 9484 | 20036 | 24913 | 14812 | 20073 | 1039 | 2389 | 2274 |
| | 16607 | 29034 | 16307 | 21350 | 29213 | 7738 | 9401 | 30222 | 7652 | 19703 | 24790 | 21351 |
| | 1082 | 3958 | 5534 | 20602 | 16304 | 4223 | 29001 | 16931 | 24164 | 9476 | 19512 | 19513 |
| | 5233 | 8163 | 28865 | 27974 | 13483 | 9874 | 13645 | 27614 | 15344 | 28778 | 10055 | 10085 |
| | 908 | 23139 | 26856 | 14272 | 27905 | 28728 | 13538 | 5203 | 5175 | 9222 | | |
| 471: | 22195 | 30152 | 6215 | 18310 | 30176 | 15008 | 9053 | 20909 | 11090 | 13937 | 29492 | 23498 |
| | 9540 | 22473 | 7063 | 15879 | 22002 | 1784 | 26042 | 21862 | 22104 | 20425 | 18226 | 17435 |
| | 17496 | 6569 | 19294 | 13823 | 4369 | 21849 | 9672 | 23557 | 13834 | 9321 | 5013 | 17783 |
| | 23639 | 30253 | 21258 | 18100 | 18203 | 23366 | 1867 | 29161 | 7090 | 8065 | 5912 | 21906 |
| | 27553 | 20415 | 22173 | 9336 | 3393 | 597 | 2428 | 19220 | 28235 | 23451 | 8008 | 20477 |
| | 8963 | 4593 | 10304 | 28707 | 16373 | 1451 | 1649 | 24524 | 23177 | 2929 | 27941 | 19444 |
| | 18785 | 19253 | 16493 | 19416 | 20332 | 6876 | 13131 | 10202 | 8699 | 24504 | 10090 | 15533 |
| | 7826 | 16346 | 22825 | 3442 | 12372 | 6892 | 7068 | 29938 | 13101 | 29032 | 15744 | 24108 |
| | 24491 | 8940 | 20067 | 7670 | 16960 | 6558 | 20509 | 5537 | 30330 | 16325 | 11892 | 900 |
| | 24379 | 18788 | 18563 | 29104 | 4890 | 9327 | 8618 | 3255 | 16033 | 25747 | 3633 | 17301 |
| | 28400 | 8097 | 24192 | 2272 | 5220 | 7448 | 24170 | 6248 | 1783 | 10060 | 22564 | 5407 |
| | 16030 | 6997 | 2224 | 12460 | 21439 | 23198 | 2414 | 18351 | 30061 | 3603 | 21954 | 26188 |
| | 2015 | 4725 | 18641 | 6042 | 26953 | 16528 | 1292 | 23424 | 30419 | 915 | 14133 | 16667 |
| | 13532 | 9233 | 23431 | 14659 | 29349 | 13674 | 998 | 3220 | 29610 | 22704 | 21923 | 27232 |
| | 16230 | 17364 | 14469 | 28827 | 26985 | 7838 | 20249 | 13966 | 13272 | 7911 | 4800 | 22133 |
| | 26192 | 24647 | 27313 | 13818 | 25557 | 13638 | 17495 | 15507 | 26227 | 19646 | 24766 | 8950 |
| | 16865 | 27760 | 28258 | 26805 | 25529 | 25465 | 22945 | 6063 | 6587 | 28808 | 6247 | 16538 |
| | 6524 | 12656 | 2663 | 25855 | 21840 | 29993 | 27653 | 21451 | 28266 | 8983 | 1299 | 10274 |
| | 4886 | 11987 | 3436 | 18214 | 29516 | 7231 | 24843 | 19829 | 21657 | 20943 | 2763 | 28674 |
| | 29403 | 8032 | 20989 | 7748 | 19920 | 4818 | 1439 | 13349 | 10552 | 13489 | 26254 | 19708 |
| | 15937 | 19611 | 18759 | 19661 | 30448 | 2504 | 1855 | 14304 | 16161 | 14794 | 27687 | 918 | 22692 |
| | 20085 | 5459 | 10458 | 18793 | 7582 | 4992 | 7411 | 12999 | 20450 | 1903 | 23661 | 23637 |
| | 9363 | 26777 | 4504 | 9414 | 19764 | 12316 | 24423 | 20929 | 26737 | 6860 | 29546 | 9742 |
| | 8220 | 4128 | 28979 | 28018 | 17279 | 19419 | 8050 | 6749 | 26314 | 23455 | 21876 | 22644 |
| | 20424 | 23606 | 8564 | 23299 | 23267 | 23362 | 23336 | 10269 | 22675 | 23589 | 26780 | 23610 |
| | 26749 | 26752 | 19407 | 26778 | 16533 | 18291 | 3340 | 22005 | 20418 | 29511 | 16025 | 26731 |

TABLE 8-continued

| PEP SEQ ID NO: | homolog SEQ ID NOs | | | | | | | | | | |
|---|---|---|---|---|---|---|---|---|---|---|---|
| | 28962 | 20199 | 29688 | 8236 | 27950 | 27465 | 11943 | 11493 | 28696 | 9754 | 13165 | 25873 |
| | 28209 | 835 | 24845 | 3447 | 5559 | 10898 | 9504 | 7751 | 5357 | 26525 | 29818 | 13252 |
| | 13804 | 25753 | 16100 | 4034 | 12595 | 24263 | 14146 | 18949 | 7005 | 7898 | 25294 | 6499 |
| 472: | 27556 | 7298 | 2699 | 2702 | 21764 | 26703 | 28272 | 933 | 25223 | 20176 | 2115 | 8738 |
| | 7560 | 22098 | 12859 | 26875 | 27530 | 30084 | 12326 | | | | | |
| 473: | 1966 | 1962 | 19645 | 2659 | 22951 | 7955 | 17023 | 3046 | 15490 | 23268 | 7909 | 10931 |
| | 9358 | 24015 | 7511 | 24796 | 28896 | 3334 | 20294 | 29399 | 9729 | 1315 | 12080 | 12690 |
| | 18145 | 6120 | 14300 | 5798 | 24062 | 15082 | 18474 | 10392 | 20038 | 28782 | 27211 | 27210 |
| | 16534 | 23675 | 25578 | 25574 | 11754 | 11501 | 13393 | 5742 | 6310 | 17106 | 2424 | 22017 |
| | 6611 | 28211 | 17544 | 28373 | 1932 | 8904 | 28621 | 9362 | 8894 | 18421 | 2186 | 8390 |
| | 11593 | 23976 | | | | | | | | | | |
| 474: | 7357 | 21359 | 8847 | 14322 | 27450 | 6412 | 18367 | 3895 | 23298 | 1735 | 9395 | 790 |
| | 1632 | 5157 | 10982 | 7522 | 5934 | 6755 | 15043 | 702 | 5707 | 16981 | | |
| 475: | 3744 | 2450 | 26907 | 24268 | 6387 | 21543 | 27201 | 25458 | 8487 | 4208 | 17673 | 6162 |
| | 467 | 21400 | 10103 | 26773 | 23524 | 1386 | 5099 | 3486 | 23059 | 30021 | 20480 | 18160 |
| | 18918 | 18033 | 25273 | 3273 | | | | | | | | |
| 476: | 27272 | 12345 | 3614 | 29499 | 10273 | 17627 | 27894 | 21679 | 19957 | 25636 | 14105 | 23973 |
| | 22438 | 23520 | 3033 | 29083 | 24228 | 7931 | 2119 | 28793 | 7454 | 666 | 13512 | 16877 |
| | 29640 | 24014 | 15267 | 17919 | 18018 | 8307 | 1348 | 5027 | 7278 | 26242 | 27881 | 17269 |
| | 10091 | 15877 | 20047 | 3998 | 11519 | 27820 | 11364 | 9296 | 30371 | 28924 | 7745 | 28515 |
| | 16257 | 6234 | 4854 | 23517 | 4861 | 4858 | 27270 | 27266 | 9307 | 27264 | 12149 | |
| 477: | 21573 | 6136 | 6726 | 1002 | 14014 | 24915 | 6875 | 17885 | 17296 | 1780 | 14580 | 21574 |
| | 5809 | 23106 | 15893 | 28179 | 28204 | 28200 | 23235 | 28239 | 8085 | | | |
| 478: | 19911 | 2933 | 12176 | 5732 | 5566 | 22181 | 894 | 19342 | 4738 | 27202 | 8172 | 20527 |
| | 20835 | 13886 | 18863 | 10895 | 30148 | 6550 | 16993 | 17604 | 10705 | 12703 | 25457 | 26504 |
| | 20609 | 14506 | 16453 | 25435 | 22687 | 22745 | 15565 | 28365 | 8246 | 26226 | 22781 | 22609 |
| | 28074 | 10378 | 25187 | 20593 | 10975 | 29843 | 28154 | 30166 | 25360 | 29090 | 25810 | 24964 |
| | 7645 | 29316 | 7379 | 11901 | 25060 | 20120 | 25382 | 22811 | 19983 | 25469 | 12906 | 16564 |
| | 16601 | 15729 | 5105 | 13643 | 8303 | 25194 | 9769 | 15291 | 17892 | 16383 | 3415 | 22356 |
| | 21682 | 4193 | 18106 | 7989 | 22804 | 19305 | 28115 | 25199 | 13138 | 27283 | 26870 | 12445 |
| | 2451 | 14975 | 12959 | 23717 | | | | | | | | |
| 479: | 23860 | 12429 | 3776 | 14164 | 24870 | 10068 | 13531 | 9524 | 10508 | 16691 | 13768 | 10861 |
| | 26460 | 17256 | 27208 | 13814 | 16726 | 26667 | 10023 | 10054 | 9078 | 18969 | 9074 | 18965 |
| | 9043 | 18963 | 9039 | 19494 | 13757 | 17613 | 13758 | 13798 | 13763 | 27205 | 27206 | 26682 |
| | 10233 | 13810 | 27848 | 15447 | 13806 | 6552 | 17603 | 16684 | 15856 | 15986 | 11356 | 9077 |
| | 1929 | 7466 | 1069 | 28585 | 29621 | 740 | 12011 | 14644 | 14666 | 12083 | 3261 | 14690 |
| | 10918 | 24952 | 9964 | 11423 | 4560 | 6851 | 4501 | 17463 | 28611 | 657 | 10879 | 2083 |
| | 26235 | 1171 | 10878 | 29468 | 10910 | 20924 | 10909 | 25250 | 2827 | 6201 | 26981 | 1290 |
| | 16544 | 12724 | 4260 | 8092 | 15444 | 11269 | 23635 | 18854 | 21138 | 8537 | 7555 | 9139 |
| | 27937 | 11964 | 10614 | 1006 | 8279 | 2557 | 19791 | 18694 | 27789 | 11132 | 15363 | 4333 |
| | 13764 | 13803 | 7681 | 9512 | 10355 | 15473 | 27183 | 13848 | 28837 | 15511 | 13229 | 13417 |
| | 22242 | 10321 | 15312 | 12102 | 1589 | 28737 | 10288 | 15365 | 15293 | 24826 | 17630 | 23146 |
| | 26660 | 10361 | 15509 | 27350 | 10295 | 22669 | 6293 | 5558 | 15294 | 15366 | 15296 | 15370 |
| | 10291 | 12562 | 28309 | 17928 | 17925 | 13679 | 15321 | 17966 | 15397 | 20092 | 15324 | 15399 |
| | 26662 | 15332 | 24590 | 15405 | 28957 | 13849 | 3248 | 13812 | 13809 | 15413 | 13105 | 25405 |
| | 19835 | 20576 | 2226 | 10293 | 10298 | 2149 | 18471 | 15318 | 16277 | 10882 | 18022 | 11840 |
| | 23758 | 23761 | 28953 | 12536 | 12537 | 12207 | 26681 | 12204 | 2922 | 4891 | 22854 | 10880 |
| | 10886 | 25924 | 16591 | 25423 | 1729 | 1732 | 12857 | 28984 | 10359 | 15481 | 1536 | 15118 |
| | 8737 | 8735 | 29936 | 15551 | 10859 | 3924 | 23016 | 3459 | 10911 | 30283 | 10363 | 15256 |
| | 18628 | 3841 | 28560 | 19197 | 17400 | 7515 | 18058 | 16349 | 19235 | 30238 | 30024 | 26335 |
| | 2069 | 29915 | 1134 | 13811 | 13802 | 13797 | 25698 | 3007 | 8289 | 30023 | 18238 | 15388 |
| | 16397 | 9379 | 8995 | 12328 | 18477 | 10491 | 6603 | 12468 | 4769 | 5317 | 10602 | 18836 |
| | 10482 | 7711 | 6508 | 11646 | 24479 | 2203 | 3075 | | | | | |
| 480: | 6859 | 12279 | 15737 | 28496 | 21769 | 14969 | 27180 | 9733 | 24403 | 11636 | 10570 | 1070 |
| | 2798 | 9970 | 10415 | 11236 | 8470 | 8345 | 19642 | 22539 | 22512 | 25445 | 29247 | 26768 |
| | 20252 | 21978 | 15292 | 30404 | 30111 | 29999 | 11284 | 13291 | 16756 | 1193 | 1646 | 19831 |
| | 14916 | 19300 | 9340 | 30226 | 5046 | 13014 | 22101 | 14185 | 12066 | 2705 | 7024 | 24882 |
| | 9683 | 27483 | 29883 | 11174 | 19960 | 14502 | 13090 | 12155 | 15071 | 23104 | 19917 | 10129 |
| | 12646 | 6199 | 13887 | 20888 | 21538 | 29787 | 23970 | 23967 | 21684 | 21683 | 21688 | 30159 |
| | 30185 | 24444 | 2588 | 2255 | 12746 | 23378 | 3834 | 3815 | 3819 | 25318 | 18870 | 3821 |
| | 20089 | 19266 | 20090 | 20084 | 6102 | 4127 | 6128 | 20093 | 12645 | 6092 | 14127 | |
| | 12905 | 23180 | 12647 | 12611 | 10868 | 26743 | 29974 | 6070 | 15868 | 8589 | 29181 | 20707 |
| | 18074 | 18072 | 20031 | 9895 | 9891 | 9893 | 19280 | 22865 | 17827 | 21935 | 20386 | 22156 |
| | 17976 | 18076 | 23593 | 11032 | 3679 | 9611 | 9614 | 26018 | 25179 | 25756 | | |
| 481: | 5332 | 23342 | 24029 | 27571 | 23765 | 18921 | 3620 | 17462 | 13455 | 17803 | 24364 | 6672 |
| | 2289 | 23193 | 5356 | 10089 | 21592 | 28489 | 26479 | 29205 | 21994 | 22730 | 22035 | 22858 |
| | 25290 | 17216 | 12721 | 9211 | 5605 | 20033 | 20032 | 9069 | 11834 | 29638 | 22246 | 11158 |
| | 26998 | 13971 | 11387 | 21456 | 5539 | 11547 | 9354 | 13365 | 19987 | 17274 | 25427 | 24426 |
| | 20383 | 27342 | 22310 | 29745 | 25026 | 23952 | 26499 | 9378 | 5368 | 12997 | | |
| 482: | 23286 | 1274 | 8225 | 27981 | 25684 | 25757 | 16457 | 16452 | 1391 | 12214 | 23260 | 23289 |
| | 1744 | 11105 | 11360 | 5199 | 25720 | 25688 | 14705 | 6709 | 6649 | 16261 | 22979 | 22977 |
| | 16994 | 16270 | 2059 | 2009 | 16265 | 20642 | 23803 | 20644 | 15180 | 15175 | 4941 | 4914 |
| | 3758 | 4703 | 4713 | 16785 | 10080 | 16509 | 12093 | 6582 | 12093 | 3831 | 1155 | 9438 |
| | 17429 | 4505 | 9638 | 12510 | 11369 | 12332 | 11407 | 12298 | 12366 | 12270 | 11488 | 11530 |
| | 12277 | 12432 | 12339 | 12269 | 17458 | 17460 | 19786 | 19822 | 21082 | 19790 | 19696 | 19761 |
| | 19793 | 19758 | 19719 | 19935 | 19903 | 19827 | 19930 | 19868 | 21151 | 21148 | 19763 | 19928 |
| | 3788 | 4668 | 4665 | 4699 | 4673 | 16783 | 4824 | 16782 | 6878 | 6991 | 6910 | 6932 |
| | 6936 | 6940 | 5992 | 4628 | 3791 | 4740 | 4743 | 26710 | 23228 | 28484 | 14653 | 14703 |

TABLE 8-continued

| PEP SEQ ID NO: | homolog SEQ ID NOs | | | | | | | | | | |
|---|---|---|---|---|---|---|---|---|---|---|---|
| | 17093 | 15617 | 15646 | 15668 | 15641 | 15642 | 15670 | 15639 | 22762 | 13093 | 20149 | 2079 |
| | 4751 | 4775 | 4982 | 6024 | 6061 | 6868 | 16810 | 6837 | 5982 | 6907 | 26794 | 25144 |
| | 24355 | 5247 | 3727 | 3754 | 16757 | 3755 | 3784 | 3787 | 4632 | 4659 | 4662 | 4707 |
| | 4746 | 4749 | 4830 | 4034 | 4079 | 4909 | 4907 | 4912 | 4944 | 4945 | 4980 | 5768 |
| | 5792 | 5862 | 5899 | 5938 | 5942 | 5975 | 5986 | 6059 | 6091 | 6093 | 6099 | 6869 |
| | 6897 | 6902 | 6942 | 6961 | 6964 | 6969 | 3748 | 25626 | 18897 | 18900 | 11659 | 3110 |
| | 1332 | 23097 | 27977 | 1190 | 15240 | 5284 | 5204 | 5307 | 5306 | 5310 | 5201 | 5331 |
| | 5329 | 5234 | 5232 | 5226 | 5278 | 5236 | 5239 | 5277 | 10149 | 2306 | 12349 | 27947 |
| | 19479 | 19484 | 25020 | 24994 | 14113 | 14253 | 14109 | 14251 | 14282 | 15069 | 14138 | 30160 |
| | 14321 | 14278 | 19566 | 14326 | 14195 | 19682 | 14068 | 14161 | 29739 | 10181 | 17666 | 10210 |
| | 17706 | 17711 | 17670 | 17681 | 23292 | 16447 | 28736 | 13813 | 4269 | 8971 | 24172 | 10784 |
| | 6581 | 21799 | 28030 | 14647 | 5282 | 27990 | 28015 | 16419 | 5909 | 5945 | 6619 | 14800 |
| | 17524 | 28146 | 21825 | 21826 | 8124 | 8126 | 8159 | 8214 | 28025 | 28023 | 28020 | 8218 |
| | 8196 | 30192 | 4794 | 15242 | 14452 | 2511 | 25359 | 13419 | 1836 | 2576 | 16666 | 1428 |
| | 1423 | 19836 | 1910 | 7820 | 10218 | 20683 | 29045 | 6026 | 6025 | 16449 | 4481 | 14869 |
| | 10745 | 11813 | 20059 | 22400 | 11648 | 7691 | 16414 | 8183 | 16455 | 16412 | 16460 | 13181 |
| | 2994 | 2965 | 26527 | 16462 | 11863 | 7168 | 20675 | 16443 | 20678 | 967 | 17461 | 2509 |
| | 11502 | 7375 | 17492 | 28280 | 6553 | 17455 | 2264 | 16409 | 16416 | 16418 | 16407 | 16444 |
| | 4844 | 14779 | 20794 | 12379 | 7963 | 19990 | 15714 | 670 | 11705 | 25327 | 26672 | 28323 |
| | 23256 | 17560 | 18542 | 22080 | 13354 | 13352 | 21460 | 21463 | 14532 | 29577 | 29581 | 29580 |
| | 29552 | 29576 | 29541 | 8329 | 6616 | 6645 | 6642 | 16406 | 5279 | 20860 | 3939 | 8558 |
| | 3973 | 4297 | 17449 | 19743 | 8597 | 25495 | 25466 | 23522 | 22778 | 809 | 27528 | 1300 |
| | 23760 | 29578 | 25760 | 25761 | 20932 | 11894 | 20864 | 9396 | 3800 | 15568 | 9826 | 11866 |
| | 20815 | 26007 | 7525 | 8113 | 8080 | 19979 | 20833 | 20882 | 19973 | 20991 | 20988 | 21040 |
| | 20992 | 20962 | 20958 | 20922 | 20875 | 7061 | 20135 | 14531 | 6555 | 21597 | 21821 | 7008 |
| | 19716 | 7001 | 19725 | 13816 | 19729 | 19765 | 25693 | 21823 | 15215 | 5081 | 20680 | 8119 |
| | 12128 | 7002 | 5206 | 25110 | 5305 | 16506 | 4866 | 4872 | 4875 | 4869 | 1977 | 15074 |
| | 15072 | 15105 | 23221 | 23227 | 18915 | 6585 | 4781 | 15238 | 28000 | 27811 | 27816 | 27832 |
| | 27962 | 27900 | 27901 | 27903 | 27966 | 27969 | 27994 | 27907 | 27909 | 27835 | 27840 | 27842 |
| | 27865 | 27870 | 27873 | 27877 | 27808 | 27809 | 27810 | 27999 | 27925 | 27926 | 27879 | 27930 |
| | 28002 | 27935 | 27938 | 27998 | 27958 | 27959 | 9095 | 3804 | 417 | 416 | 22867 | 17450 |
| | 4731 | | | | | | | | | | | |
| 483: | 23286 | 11758 | 1274 | 8225 | 27981 | 25684 | 25757 | 16457 | 16452 | 1391 | 12214 | 23260 |
| | 23289 | 1744 | 11105 | 11360 | 5199 | 25720 | 25688 | 14705 | 6709 | 6649 | 16261 | 22979 |
| | 22977 | 16994 | 16270 | 2059 | 2009 | 16265 | 20642 | 23803 | 20644 | 15180 | 15175 | 4941 |
| | 4914 | 3758 | 4703 | 4713 | 16785 | 10080 | 16509 | 27451 | 6582 | 12093 | 3831 | 1155 |
| | 9438 | 17429 | 4505 | 9638 | 12510 | 11369 | 12332 | 11407 | 12298 | 12366 | 12270 | 11488 |
| | 11530 | 12277 | 12432 | 12339 | 12269 | 17458 | 17460 | 19786 | 19822 | 21082 | 19790 | 19696 |
| | 19761 | 19793 | 19758 | 19719 | 19935 | 19903 | 19827 | 19930 | 19868 | 21151 | 21148 | 21112 |
| | 19763 | 21144 | 19928 | 3788 | 4668 | 4665 | 4699 | 4673 | 16783 | 4824 | 16782 | 6878 |
| | 6991 | 6910 | 6932 | 6936 | 6940 | 5992 | 4628 | 3791 | 4740 | 4743 | 26710 | 23228 |
| | 28484 | 14653 | 14703 | 17093 | 15617 | 15646 | 15668 | 15641 | 15642 | 15670 | 15639 | 22762 |
| | 13093 | 20149 | 2079 | 4751 | 4775 | 4982 | 6024 | 6061 | 6868 | 16810 | 4978 | 6837 |
| | 5982 | 6907 | 26794 | 25144 | 24355 | 5247 | 3727 | 3754 | 16757 | 3755 | 3784 | 3787 |
| | 4632 | 4659 | 4662 | 4707 | 4746 | 4749 | 4830 | 4834 | 4879 | 4909 | 4907 | 4912 |
| | 4944 | 4945 | 4980 | 5768 | 5792 | 5829 | 5862 | 5899 | 5895 | 5938 | 5942 | 5975 |
| | 5986 | 6059 | 6091 | 6093 | 6099 | 6869 | 6897 | 6902 | 6942 | 6961 | 6964 | 6969 |
| | 3748 | 3751 | 25626 | 18897 | 18900 | 11659 | 3110 | 1332 | 23097 | 27977 | 1190 | 15240 |
| | 5284 | 5204 | 5307 | 5306 | 5310 | 5201 | 5331 | 5329 | 5234 | 5232 | 5226 | 5278 |
| | 5236 | 5239 | 5277 | 10149 | 2306 | 12349 | 27947 | 19479 | 19484 | 25020 | 24994 | 14113 |
| | 14253 | 14109 | 14251 | 14282 | 15069 | 14138 | 30160 | 14321 | 14278 | 19566 | 14326 | 14195 |
| | 19682 | 14068 | 14161 | 29739 | 10181 | 17666 | 10210 | 17706 | 17711 | 17670 | 17681 | 23292 |
| | 16447 | 13249 | 28736 | 13813 | 4269 | 8971 | 24172 | 10784 | 6621 | 6581 | 21799 | 28030 |
| | 14647 | 5282 | 27990 | 28015 | 16419 | 5909 | 5945 | 6619 | 6614 | 14800 | 17524 | 28146 |
| | 21825 | 21826 | 8124 | 8126 | 8159 | 8214 | 28025 | 28023 | 28020 | 8218 | 8196 | 30192 |
| | 4794 | 15242 | 14452 | 2511 | 25359 | 13419 | 1836 | 2576 | 16666 | 1428 | 1423 | 19836 |
| | 1910 | 7820 | 10218 | 20683 | 29045 | 6026 | 6025 | 16449 | 4481 | 14869 | 10745 | 11813 |
| | 20059 | 22400 | 11648 | 7691 | 16414 | 8183 | 16455 | 16412 | 16460 | 13181 | 2994 | 2965 |
| | 26527 | 16462 | 11863 | 7168 | 20675 | 16443 | 20678 | 967 | 17461 | 2509 | 11502 | 7375 |
| | 17492 | 28280 | 6553 | 17455 | 2264 | 16409 | 16416 | 16418 | 16407 | 16444 | 4844 | 14779 |
| | 20794 | 12379 | 7963 | 19990 | 15714 | 670 | 11705 | 25327 | 26672 | 28323 | 23256 | 17560 |
| | 18542 | 22080 | 13354 | 13352 | 21460 | 21463 | 3023 | 16390 | 14532 | 29577 | 29581 | 29580 |
| | 29552 | 29576 | 29541 | 8329 | 6616 | 6645 | 6642 | 16406 | 5279 | 20860 | 3939 | 8558 |
| | 3973 | 4297 | 17449 | 19743 | 8597 | 25495 | 25466 | 23522 | 22778 | 809 | 27528 | 1300 |
| | 23760 | 29578 | 25760 | 25761 | 20932 | 11894 | 20864 | 9396 | 3800 | 15568 | 9826 | 11866 |
| | 20815 | 26007 | 7525 | 8113 | 8080 | 19979 | 20833 | 20882 | 19973 | 20991 | 20988 | 21040 |
| | 20992 | 20962 | 20958 | 20922 | 20875 | 7061 | 20135 | 14531 | 6555 | 3548 | 3465 | 3461 |
| | 21597 | 21821 | 7008 | 19716 | 7001 | 19725 | 13816 | 19729 | 19765 | 25693 | 21823 | 15215 |
| | 4827 | 5081 | 20680 | 8119 | 12128 | 7002 | 5206 | 25110 | 5305 | 16506 | 4866 | 4872 |
| | 4875 | 4869 | 1977 | 15074 | 15072 | 15105 | 23221 | 23227 | 18915 | 6585 | 4781 | 15238 |
| | 28000 | 27811 | 27816 | 27832 | 27962 | 27900 | 27901 | 27903 | 27966 | 27969 | 27994 | 27907 |
| | 27909 | 27835 | 27840 | 27842 | 27865 | 27870 | 27873 | 27877 | 27808 | 27809 | 27810 | 27999 |
| | 27925 | 27926 | 27879 | 27930 | 28002 | 27935 | 27938 | 27998 | 27958 | 27959 | 9095 | 3804 |
| | 417 | 416 | 22867 | 17450 | 4731 | | | | | | | |
| 484: | 12506 | 14885 | 13628 | 27161 | 9283 | 29508 | 5274 | 16688 | 18995 | 18075 | 26869 | 21530 |
| | 18055 | 626 | 4352 | 28798 | 14098 | 8518 | 22602 | 1223 | 14754 | 29635 | 15057 | 13180 |
| | 22594 | 13466 | 12497 | 14620 | 27130 | 5420 | 28117 | 26031 | 821 | 18817 | 2441 | 9541 |
| | 19961 | 17159 | 22190 | 22154 | 28078 | 22441 | | | | | | |

TABLE 8-continued

| PEP SEQ ID NO: | homolog SEQ ID NOs | | | | | | | | | | |
|---|---|---|---|---|---|---|---|---|---|---|---|
| 485: | 14198 | 16733 | 17932 | 870 | 7072 | 866 | 17930 | 7071 | 16069 | 13851 | 13461 | 13464 |
| | 14055 | 12701 | 12702 | 419 | 19755 | 8312 | 13470 | 8308 | 18143 | 19044 | 9845 | 28935 |
| | 12911 | 12908 | 9746 | 12378 | 26844 | 6279 | 3256 | 29096 | 6492 | 6491 | 10340 | 1927 |
| | 1926 | 14725 | 14724 | 5210 | 5182 | 16911 | 19053 | 10053 | 15107 | 10052 | 17902 | 18728 |
| | 15861 | 21008 | 27672 | 14921 | 22004 | 25826 | 27570 | 30385 | 24545 | 7602 | 11773 | 25012 |
| | 2106 | 29882 | 5639 | 8632 | 19341 | 3676 | 5630 | 8591 | 13801 | 17969 | 18455 | 7576 |
| | 12282 | 29080 | 30010 | 25127 | 8356 | 9350 | 10154 | 5237 | 9923 | 12796 | 8187 | 29896 |
| | 5402 | 643 | 678 | 24362 | 24361 | 15888 | 14391 | 3369 | 3240 | 19906 | 26063 | 23740 |
| | 25138 | 23741 | 26062 | 25136 | 12643 | 4304 | 13273 | 13304 | 11196 | 30067 | 3274 | 7355 |
| | 14440 | 5431 | 5433 | 12373 | 26674 | 13025 | 10728 | 19975 | 19976 | 9320 | 6309 | 13989 |
| | 13167 | 13166 | 28931 | 28928 | 27390 | 2736 | 27297 | 28745 | 7015 | 29168 | 3670 | 5562 |
| | 12710 | 21159 | 16719 | 1225 | 28194 | 28348 | 22794 | 9021 | 15530 | 5874 | 9984 | 11413 |
| | 1550 | 422 | 19877 | 19878 | 26951 | 26948 | 17946 | 17941 | 13047 | 2877 | 2996 | 17097 |
| | 17095 | 12242 | 18956 | 15056 | 21779 | 24579 | 15055 | 18335 | 24735 | 18201 | 2127 | 25041 |
| | 1128 | 713 | 5162 | 5181 | 15588 | 15582 | 7479 | 7474 | 15585 | 10639 | 10640 | 7629 |
| | 27675 | 7385 | 23019 | 23020 | 8438 | 25592 | 20405 | 15584 | 15585 | 6639 | 9862 | 19958 |
| 486: | 14551 | 23240 | 12125 | 29926 | 21428 | 10051 | 10049 | 16359 | 17521 | 1303 | 1304 | 14480 |
| | 4855 | 23766 | 21027 | 1673 | 16070 | 3990 | 16377 | 24434 | 2164 | 15264 | 21647 | 7979 |
| | 1576 | 19535 | 6020 | 25742 | 30458 | 26519 | 7968 | 4483 | 5371 | 8892 | 23905 | 10500 |
| | 5400 | 12858 | 16857 | 14546 | 19747 | 11568 | 13536 | 27245 | 19603 | 18653 | 14485 | 25726 |
| | 4041 | 3096 | 24513 | 24510 | 24516 | 11995 | 4870 | 23214 | 5717 | 17916 | 18617 | 18851 |
| | 9961 | 15421 | 22688 | 22691 | 9793 | 23634 | 17356 | 15933 | 29805 | 18191 | 10215 | 3190 |
| | 4287 | 13779 | 22930 | 15197 | 26185 | 23217 | 24874 | 10212 | 12489 | 12493 | 17035 | 3884 |
| | 21643 | 21639 | 2122 | 8139 | 28008 | 30099 | 16747 | 14130 | 7655 | 26274 | 16059 | 2597 |
| | 28325 | 2041 | 3099 | 9480 | 17079 | 24011 | 24010 | 3576 | | | | |
| 487: | 17778 | 10938 | 18908 | 15653 | 17688 | 13066 | 20725 | 13107 | 15112 | 13722 | 27140 | 14271 |
| | 20967 | 11905 | 9749 | 5780 | 24679 | 13585 | 22476 | 9385 | 9674 | 21773 | 28461 | 25983 |
| | 6602 | 18801 | 7941 | 7946 | 1594 | 5716 | 29759 | 26813 | 14884 | 17561 | 22668 | 25577 |
| | 21619 | 12686 | 6466 | 26619 | | | | | | | | |
| 488: | 6934 | 5852 | 24700 | 13371 | 8459 | 3747 | 4220 | 18103 | 30243 | 17039 | 9865 | 20065 |
| | 12317 | 27021 | 27008 | 15166 | 7906 | 9349 | 10894 | 15908 | 16759 | 16761 | 23777 | 15799 |
| | 6271 | 10631 | 13844 | 25051 | 29405 | 26935 | 19945 | 15114 | 8013 | 12127 | 4033 | 17959 |
| | 13939 | 2886 | 14702 | 12707 | 5269 | 9267 | 4958 | 17664 | 1724 | 12344 | 6415 | 6807 |
| | 3257 | 7598 | 10613 | 19411 | 26748 | 1992 | 7040 | 27803 | 16343 | 5065 | 12921 | 10829 |
| | 5021 | 10016 | 17191 | 23742 | 3992 | 27542 | 15109 | 17148 | 2046 | 15557 | 12552 | 11673 |
| | 28667 | 6381 | 11784 | 25877 | 2496 | 3337 | 27363 | 11872 | 9602 | 8203 | 24744 | 5064 |
| | 3835 | 13654 | 17071 | 18386 | 28277 | 16239 | 14763 | 19665 | 7258 | 12051 | 5718 | 22306 |
| | 25102 | 20081 | 29020 | 25347 | 18098 | 27391 | 22157 | 27398 | 19579 | 27053 | 27866 | 9775 |
| | 16206 | 10692 | 25358 | 15063 | 17503 | 29653 | 26785 | 10424 | 3339 | 2406 | 11831 | 10224 |
| | 24533 | 5120 | 13130 | 21595 | 12025 | 3353 | 6405 | 7519 | 9734 | 28998 | 23813 | 19217 |
| | 9783 | 28678 | 1286 | 838 | 5887 | 5691 | 18558 | 15504 | 12079 | 4498 | 7653 | 3528 |
| | 7642 | 28459 | 25809 | 25548 | 19298 | 17459 | 13182 | 26486 | 29795 | 23090 | 17891 | 18954 |
| | 4645 | 18236 | 19204 | 5487 | 8283 | 11812 | 21660 | 1117 | 17055 | 29716 | 14442 | 10496 |
| | 21065 | 5503 | 9298 | 25967 | 1280 | 7920 | 9741 | 13660 | 16199 | 25963 | 6316 | 30277 |
| | 12213 | 27036 | 28375 | 20106 | 2717 | 30214 | 27299 | 24886 | 26991 | 29531 | 29271 | 22861 |
| | 8625 | 7468 | 8255 | 14243 | 6351 | 14811 | 22713 | 29527 | 2919 | 22390 | 8698 | 19330 |
| | 6632 | 19192 | 710 | 3907 | 26984 | 15169 | 12444 | 29263 | 14484 | 28593 | 29506 | 7879 |
| | 13416 | 12267 | 1217 | 9851 | 22900 | 18698 | 26583 | 7958 | 24239 | 9331 | 11515 | 5257 |
| | 13793 | 18597 | 20619 | 29615 | 27843 | 24944 | 20205 | 16174 | 24378 | 8293 | 13370 | 29840 |
| | 17228 | 904 | 26067 | 19551 | 7384 | 25432 | 29810 | 17732 | 21533 | 26359 | 24928 | 4619 |
| | 9825 | 25056 | 14541 | 18499 | 7473 | 11627 | 25774 | 13496 | 30437 | 15774 | 16279 | 1756 |
| | 955 | 29175 | 24856 | 23657 | 21726 | 16327 | 23687 | 25692 | 12364 | 14610 | 10922 | 12781 |
| | 18832 | 4928 | 17112 | 28449 | 23898 | 19296 | 25621 | 24240 | 27574 | 3781 | 21380 | 19463 |
| | 13012 | 11969 | 30407 | 12672 | 10097 | 22219 | 25764 | 22342 | 25852 | 15736 | 2000 | 29637 |
| | 10127 | 30271 | 15993 | 13062 | 22971 | 14468 | 22662 | 10390 | 12082 | 4963 | 3646 | 27034 |
| | 1442 | 9686 | 21140 | 5218 | 24956 | 9764 | 13049 | 17064 | 1760 | 15712 | 24825 | 2363 |
| | 27050 | 11796 | 22872 | 8970 | 2404 | 25310 | 6023 | 11475 | 4253 | 3054 | 8771 | 7930 |
| | 27405 | 28680 | 16015 | 12716 | 3618 | 13826 | 18616 | 12845 | 5865 | 20843 | 1048 | 25315 |
| | 15144 | 13425 | 18780 | 19288 | 28088 | 27434 | 4470 | 29946 | 7863 | 11116 | 10260 | 18709 |
| | 28499 | 822 | 26230 | 23951 | 15108 | 10756 | 23572 | 23571 | 29153 | 13941 | 5801 | 20856 |
| | 7689 | 10398 | 25699 | 28956 | 19040 | 25842 | 22135 | 29606 | 25475 | 23445 | 6495 | 14739 |
| | 2594 | 2600 | 12307 | 12310 | 969 | 18583 | 24045 | 18005 | 7132 | 10960 | 25818 | 24481 |
| | 20581 | 24190 | 27395 | 6275 | 12591 | 23422 | 29543 | 22312 | 7404 | 27708 | 27710 | 11837 |
| | 17583 | 28903 | 20133 | 28862 | 8117 | 10574 | 26353 | 8071 | 22965 | 5897 | 24749 | 25079 |
| | 25069 | 2687 | 10452 | 19679 | 25844 | 15015 | 9439 | 7669 | 9765 | 21477 | 6421 | 24068 |
| | 15381 | 30105 | 30328 | 26862 | 20374 | 4069 | 5424 | 25846 | 13929 | 7370 | 20412 | 1372 |
| | 18112 | 8200 | 12667 | 29930 | 11161 | 27707 | 1440 | | | | | |
| 489: | 20634 | 28717 | 28716 | 21425 | 8439 | 6534 | 2346 | 2341 | 2344 | 2293 | 15778 | 9185 |
| | 23756 | 17947 | 12827 | 25538 | 12433 | 20855 | 29677 | 8406 | 26074 | 21476 | 7021 | 4549 |
| | 29681 | 23174 | 28456 | 25965 | 24156 | 1279 | 27655 | 3825 | 18526 | 21883 | 7426 | 6057 |
| | 23419 | 21753 | 784 | 18605 | 6809 | 6812 | 6814 | 12657 | 22628 | 3324 | 15750 | 21556 |
| | 23728 | 27188 | 24044 | 23711 | 30241 | 21654 | | | | | | |
| 490: | 22876 | 17843 | 24061 | 23547 | 9277 | 1484 | 8780 | 8333 | 20353 | 7228 | 3622 | 21977 |
| | 21710 | 30060 | 29991 | 27220 | 23136 | 4216 | 22981 | 26646 | 27541 | 15497 | 20462 | 3290 |
| | 16144 | 8335 | 24931 | | | | | | | | | |
| 491: | 6855 | 23827 | 6260 | 10531 | 9711 | 3036 | 11396 | 16702 | 22401 | 12385 | 17132 | 25508 |
| 492: | 4073 | 4074 | 23394 | 2844 | 26262 | 26265 | 4274 | 22555 | 4100 | 28493 | 28492 | 18874 |
| | 21520 | 2408 | 2403 | 23481 | 22482 | 5544 | 23403 | 29897 | 28529 | 10837 | 23686 | 10611 |

TABLE 8-continued

| PEP SEQ ID NO: | homolog SEQ ID NOs | | | | | | | | | | |
|---|---|---|---|---|---|---|---|---|---|---|---|
| | | 4063 | 19971 | 20002 | 7073 | 13723 | 13721 | 19412 | 29019 | 23907 | 8695 | 10864 | 10862 |
| | 25433 | 5314 | 29590 | 13618 | 5736 | 15587 | 2366 | 15756 | 18027 | 18644 | 25869 | 13478 |
| | 6691 | 17779 | 8272 | 28495 | 24521 | 28573 | 21337 | 18951 | 18989 | 16902 | 18985 | 18980 |
| | 1933 | 26747 | 29391 | 14309 | 1994 | 8624 | 13325 | 25476 | 12360 | 15080 | 16289 | 9817 |
| 493: | 26288 | 10403 | 17815 | 27594 | 1569 | 20525 | 6783 | 7521 | 15205 | 4292 | 8103 | 8104 |
| | 19076 | 12966 | 10380 | 17314 | 26092 | 23329 | 24319 | 21471 | 27171 | 14184 | 24840 | 10915 |
| | 25210 | 10612 | 26989 | 16694 | 10183 | 24937 | 3284 | 19533 | 14871 | 4215 | 5097 | 6378 |
| | 7437 | | | | | | | | | | | |
| 494: | 8146 | 26918 | 16137 | 14667 | 22888 | 2925 | 12977 | 12675 | 17605 | 11907 | 10816 | 1511 |
| | 8686 | 18555 | 8371 | 15387 | 15980 | 15946 | 19594 | 4424 | 21192 | 12206 | 20285 | 25643 |
| | 16094 | 9631 | 1060 | 29094 | 13890 | 20604 | 9287 | 29846 | 15526 | 23496 | 21495 | 11465 |
| | 12889 | 23533 | 8128 | 27131 | 24321 | 9105 | 2632 | 20012 | 8756 | 24369 | 20496 | 19096 |
| | 10775 | 11703 | 9598 | 3535 | 5180 | 12894 | 11708 | 22228 | 21030 | 18594 | 11453 | 23069 |
| | 2643 | 5685 | 1293 | 12820 | 20795 | 28225 | 12437 | 7052 | 4066 | 10939 | 18748 | 4720 |
| | 19338 | 16483 | 16203 | 5024 | 4488 | 21596 | 1367 | 13527 | 20996 | 1078 | 29159 | 16928 |
| | 24078 | 25941 | 16065 | 14834 | 21133 | 8722 | 28457 | 14649 | 24650 | 23373 | 22767 | 10198 |
| | 26501 | 29393 | 22158 | 27479 | 18609 | 20951 | 3493 | 21315 | 18940 | 12737 | 26959 | 8053 |
| | 26928 | 5760 | 1288 | 16609 | 19882 | 5569 | 950 | 10136 | 14613 | 13906 | 2222 | 10576 |
| | 3452 | 6219 | 4225 | 11561 | 16022 | 22121 | 10333 | 3582 | 19168 | 18619 | 19785 | 432 |
| | 21894 | 16650 | 13413 | 683 | 22074 | 20491 | 28193 | 25961 | 25977 | 15634 | 12162 | 15814 |
| | 18491 | 21190 | 25232 | 28527 | 6789 | 19362 | 26832 | 29018 | 7067 | 22568 | 18361 | 13991 |
| | 15127 | 14165 | | | | | | | | | | |
| 495: | 15510 | 23745 | 869 | 9643 | 25537 | 5240 | 19233 | 21470 | 18859 | 19426 | 13254 | 15595 |
| | 24634 | 19005 | 14331 | 653 | 7732 | 27035 | 14662 | 4170 | 24736 | 5337 | 21591 | 28042 |
| | 22227 | 7428 | 8805 | 8731 | 19101 | 16690 | 4016 | 25800 | 22905 | | | |
| 496: | 19486 | 25309 | 25317 | 22542 | 9999 | 22071 | 883 | 5638 | 3062 | 28160 | 16341 | 15955 |
| | 24747 | 9805 | 14528 | 8069 | 760 | 7165 | 16988 | 8557 | 11439 | 24893 | 22650 | 26721 |
| | 25863 | 1985 | 17347 | 11317 | 23596 | 25314 | 7739 | 25313 | 12725 | 20274 | 6438 | 20401 |
| | 23762 | 15395 | 15054 | 4255 | 27514 | 14867 | 2154 | 26627 | 19008 | 17483 | 7844 | 13878 |
| | 29451 | 26459 | 10762 | 5531 | 26974 | 19145 | 17027 | 8316 | 24676 | 9076 | 9129 | 22796 |
| | 14785 | 28284 | | | | | | | | | | |
| 497: | 30239 | 18561 | 14887 | 24891 | 22826 | 14478 | 18533 | 18532 | 17376 | 17344 | 17582 | 17329 |
| | 25301 | 3737 | 17338 | 23847 | 16831 | 25930 | 14584 | 11924 | 26712 | 20144 | 12700 | 5186 |
| | 26320 | 19185 | 6655 | 21737 | 2191 | 25804 | 6123 | 10800 | 6615 | 17331 | 16315 | 7441 |
| | 12516 | 6706 | 30268 | 14663 | 8306 | 7017 | 3322 | 3317 | 28649 | 17345 | 17343 | 11428 |
| | 11431 | 1923 | 18510 | 24667 | 18508 | 25114 | 28417 | 20343 | 1750 | 13368 | 27910 | 17731 |
| | 24664 | 12147 | 28463 | 15891 | 8025 | 7493 | 27000 | 11916 | 18119 | 18123 | 18069 | 18031 |
| | 18104 | 18062 | 18129 | 17938 | 17907 | 18026 | 11917 | 18065 | 2558 | 20664 | 21108 | 19670 |
| | 19675 | 19668 | 5494 | 21110 | 19727 | 6159 | 9900 | 12046 | 8215 | 14188 | 23583 | 23587 |
| | 23586 | 23588 | 27477 | 10150 | 21536 | 13003 | 23199 | 10146 | 24950 | 12276 | 21852 | 9943 |
| | 10122 | 885 | 7266 | 27079 | 9759 | 12664 | 5851 | 4962 | 25528 | 17777 | 29865 | 26434 |
| | 26431 | 29863 | 22893 | 18572 | 806 | 2260 | 6156 | 21650 | 4130 | 24563 | 6186 | 6185 |
| | 842 | 24330 | 839 | 24694 | 10227 | 6161 | 6164 | 24692 | 21616 | 4132 | 1666 | 6189 |
| | 24281 | 834 | 24659 | 20802 | 24657 | 7550 | 27555 | 27461 | 3566 | 27461 | 7976 | 5684 |
| | 18463 | 22676 | 18830 | 18827 | 18792 | 18826 | 17884 | 5351 | 5132 | 21888 | 14842 | 8107 |
| | 3297 | 26178 | 10161 | 10065 | 6762 | 11095 | 9619 | 3164 | 23438 | 26911 | 23249 | 23411 |
| | 18794 | 17906 | 18803 | 18799 | 18806 | 17905 | 5828 | 26450 | 2627 | 13443 | 4439 | 5581 |
| | 18831 | 22897 | 3640 | 5587 | 27055 | 17059 | 27312 | 11862 | 3882 | 3917 | 3851 | 3886 |
| | 3878 | 3854 | 3893 | 3913 | 3847 | 13402 | 19939 | 21583 | 21322 | 13820 | 1604 | 28218 |
| | 8042 | 17341 | 1207 | 21475 | 30187 | 23361 | | | | | | |
| 498: | 12651 | 27676 | 16874 | 28937 | 28103 | 27096 | 6937 | 8281 | 25899 | 16470 | 20876 | 19505 |
| | 1535 | 20819 | 17014 | 22996 | 13260 | 29855 | 12078 | 29568 | 28910 | 8811 | 12735 | 22292 |
| | 3226 | 14027 | 3224 | 14589 | 14588 | 8393 | 1526 | 1563 | 25703 | 22950 | 21732 | 25276 |
| | 10367 | 14086 | 17499 | 6711 | 27501 | 23532 | 5853 | 7098 | 30157 | 6852 | 10875 | 2857 |
| | 14202 | | | | | | | | | | | |
| 499: | 24678 | 24901 | 2909 | 24878 | 27828 | 10766 | 18202 | 27168 | 24561 | 28398 | 10999 | 19658 |
| | 22042 | 16881 | 5846 | 2027 | 23338 | 27825 | 7667 | 11643 | 22204 | 8174 | 12879 | 19312 |
| | 25910 | 30439 | 29607 | 23632 | 29585 | 29613 | 14738 | 27767 | 23975 | 14683 | 30467 | 17756 |
| | 18041 | 24199 | 12034 | 8930 | 25146 | 23162 | 26992 | 9540 | 22124 | 17337 | 2395 | 1351 |
| | 18222 | 20577 | 2645 | 12926 | 25752 | 14926 | 12719 | 12962 | 8723 | 18964 | 10682 | 16372 |
| | 22803 | 24343 | 13390 | 13190 | 11927 | 10094 | 11981 | 10100 | 10092 | 10018 | 11934 | 18269 |
| | 11087 | 6728 | 5117 | 10021 | 13926 | 19521 | 16790 | 12607 | 16794 | 16795 | 21942 | 16792 |
| | 29599 | 14334 | 22507 | 23021 | 22161 | 18485 | 28919 | 6721 | 28631 | 6308 | 22701 | 25478 |
| | 22553 | 2349 | 22695 | 22663 | 29089 | 1154 | 14925 | 23534 | 1033 | 21547 | 23649 | 17047 |
| | 24711 | 1215 | 11404 | 6106 | 17984 | 856 | 17980 | 6324 | 22985 | 21129 | 820 | 7300 |
| | 23309 | 7042 | 12817 | 8347 | 2271 | 4688 | 12972 | 27652 | 1425 | 19508 | 18569 | 24684 |
| | 29435 | 25489 | 24680 | 23876 | 24655 | 24651 | 6752 | 18482 | 9035 | 13590 | 9523 | 1873 |
| | 6874 | 26068 | 2870 | 25332 | 11743 | 27596 | 9088 | 8428 | 9072 | 9086 | 28298 | 7686 |
| | 2548 | 7575 | 23391 | 28294 | 11150 | 23767 | 10281 | 25353 | 16357 | 7994 | 29948 | 23712 |
| | 24940 | 21067 | 19517 | 25831 | 18925 | 20908 | 28458 | 27573 | 26558 | 26529 | 7690 | 16502 |
| | 16507 | 13795 | 16510 | 25078 | 26294 | 13221 | 28698 | 16026 | 20142 | 15378 | 5345 | 24428 |
| | 24395 | 10286 | 12062 | 12059 | 12063 | 1179 | 13013 | 1176 | 7180 | 2385 | 7154 | |
| 500: | 12633 | 5576 | 26464 | 6939 | 5436 | 6903 | 19289 | 12073 | 11239 | 11220 | 5207 | 17109 |
| | 24162 | 21590 | 19286 | 5425 | 5430 | 27381 | 19320 | 5610 | 30375 | 28547 | 21508 | 15517 |
| | 694 | 24168 | 15269 | 30444 | 22766 | 5774 | 2159 | 22995 | 14625 | 27546 | 16625 | 25748 |
| | 18896 | 29115 | 2211 | 22848 | 6662 | 15338 | 18141 | 14813 | 12188 | 4186 | 17651 | 16654 |
| | 22596 | 24543 | 24139 | 24171 | 13070 | 14145 | 9867 | 22339 | 6261 | 7342 | 29017 | 8122 |
| | 12863 | 7811 | 20259 | 12960 | 24163 | 15890 | 24933 | 16181 | 844 | 23831 | 24134 | 3722 |

TABLE 8-continued

| PEP SEQ ID NO: | homolog SEQ ID NOs | | | | | | | | | | |
|---|---|---|---|---|---|---|---|---|---|---|---|
| | 25962 | 3343 | 17871 | 18224 | 24138 | 13856 | 9840 | 17246 | 5864 | 29945 | 28973 | 9848 |
| | 5133 | 10174 | 26116 | 16948 | 21378 | 855 | 19993 | 11003 | 30218 | 8090 | 28428 | 12644 |
| | 14159 | 4657 | 7704 | 7703 | 24137 | 16308 | 14049 | 13022 | 13027 | 12177 | 2556 | 7496 |
| | 13569 | 884 | 18847 | 16724 | 13023 | 14144 | 26725 | 23143 | 3276 | 2419 | 28613 | 23690 |
| | 23691 | 10724 | 2410 | 20847 | 6017 | 26851 | 16062 | 19848 | 10284 | 16302 | 7117 | 15902 |
| | 16224 | 27646 | 13245 | 16310 | 5202 | 15607 | 19751 | 10030 | 16301 | 16282 | 5225 | 7893 |
| | 7923 | 7921 | 1983 | 12399 | 12402 | 12401 | 12398 | 12397 | 17040 | 9339 | 8652 | 29039 |
| | 11778 | 13024 | 16120 | 6482 | 13004 | 13019 | 26633 | 6479 | 26162 | 20447 | 21352 | 23855 |
| | 993 | 14542 | 2101 | 992 | 25595 | 13001 | 13007 | 5205 | 6181 | 11536 | 13905 | 17769 |
| | 22987 | 26761 | 9483 | 24331 | 16312 | 9484 | 20036 | 20039 | 20073 | 1039 | 2389 | 29034 |
| | 21350 | 7738 | 9401 | 24790 | 21351 | 1082 | 3958 | 5534 | 20602 | 7626 | 18581 | 29001 |
| | 9368 | 24164 | 9476 | 5233 | 28865 | 8163 | 27974 | 13483 | 9874 | 13645 | 27614 | 15344 |
| | 10055 | 28778 | 10085 | 908 | 26856 | 14272 | 27905 | 23139 | 28728 | 13538 | 5203 | 5175 |
| 501: | 22063 | 26045 | 16912 | 30127 | 29320 | 29303 | 3541 | 26289 | 19539 | 21860 | 11235 | 5935 |
| | 12869 | 17821 | 10527 | 11451 | 8244 | 9118 | 1287 | 12226 | 5618 | 25068 | 10889 | |
| | 2056 | 16966 | 10027 | 11990 | 14888 | 18855 | 14742 | 24259 | 5720 | 9122 | 27531 | 18352 |
| | 14061 | 13206 | 17734 | 5040 | 13026 | 12003 | 14560 | 17261 | 17144 | 11790 | 3651 | 17116 |
| | 11170 | 6990 | 5807 | 27796 | 18507 | 16941 | 19250 | 22019 | 2438 | 5374 | 17384 | 7194 |
| | 25109 | 21461 | 5102 | 30370 | 3332 | 5229 | 8370 | 1950 | 21814 | 6787 | 25734 | 26586 |
| | 14652 | 25785 | 14530 | 30381 | 7252 | 27175 | 2028 | 22652 | 29101 | 14959 | 17276 | 4979 |
| | 30282 | 23724 | 8395 | 508 | 22852 | 29157 | | | | | | |
| 502: | 13141 | 24663 | 5432 | 4653 | 22175 | 1044 | 12194 | 7412 | 19489 | 2082 | 25029 | 9904 |
| | 18731 | 18122 | 14783 | 6856 | 4391 | 23499 | 15960 | 18126 | 14229 | 6166 | 17114 | 10579 |
| | 29459 | 23550 | 16448 | 19706 | 25118 | 28479 | 9093 | 14062 | 29804 | 30189 | 13089 | 16932 |
| | 26848 | 29521 | 29522 | 29526 | 11199 | 25321 | 26944 | 19367 | 4460 | 19368 | 26955 | 26979 |
| | 5715 | 8189 | 10936 | 16430 | 10232 | 11989 | 10845 | 30364 | 18875 | 27814 | 19118 | 1717 |
| | 5766 | 19577 | 20055 | 26454 | 13098 | 27931 | 2418 | 5803 | 28217 | 2766 | | |
| 503: | 25958 | 21576 | 13591 | 25389 | 20630 | 3483 | 22382 | 12692 | 10229 | 11434 | 6540 | 15815 |
| | 12873 | 5034 | 17995 | 9790 | 6967 | 28265 | 2830 | 21768 | 9648 | 3858 | 16066 | 18411 |
| | 2300 | 2126 | 18598 | 5073 | 25603 | 24984 | 19699 | 23754 | 29387 | 7972 | 7378 | 27782 |
| | 28686 | 14100 | 20872 | 4178 | 14658 | 25949 | | | | | | |
| 504: | 15660 | 8610 | 3591 | 26937 | 28126 | 14474 | 5858 | 18044 | 14032 | 29395 | 24710 | 9902 |
| | 15749 | 12526 | 3271 | 4975 | 25111 | 27049 | 2193 | 13784 | 29244 | 29594 | 11386 | 1623 |
| | 6768 | 5328 | 13226 | 24129 | 22632 | 2427 | | | | | | |
| 505: | 18237 | 23960 | 23994 | 23991 | 24179 | 24180 | 24076 | 24118 | 24146 | 24149 | 24030 | 24181 |
| | 24184 | 24209 | 24210 | 24213 | 24217 | 24110 | 24232 | 24034 | 24105 | 24236 | 24238 | 23998 |
| | 24071 | 23989 | 24241 | 23996 | 24178 | 24037 | 24027 | 19800 | 29453 | 11999 | 15201 | 18953 |
| | 30110 | 7915 | 24337 | 23241 | 30053 | 20316 | 3763 | 12309 | 2522 | 21405 | 7212 | 5850 |
| | 23549 | 623 | 30338 | 24161 | 22828 | 20729 | 17637 | 3270 | 7313 | 6659 | 5092 | 6952 |
| | 4347 | 26191 | 1042 | 9629 | 19472 | 26754 | 4273 | 13112 | | | | |
| 506: | 26977 | 2097 | 28521 | 6741 | 15677 | 8890 | 26152 | 6354 | 2916 | 26592 | 8078 | 7651 |
| | 2399 | 5735 | 895 | 14151 | 10748 | 1302 | 12141 | 9457 | 10877 | 20297 | 17304 | 30352 |
| | 17639 | 19667 | 21703 | 24800 | 18865 | 30149 | 6282 | 23510 | 25032 | 28508 | 15914 | 21931 |
| | 13957 | 962 | 15356 | 12958 | 4817 | 27144 | 25222 | 26503 | 26593 | 10679 | 30007 | 25456 |
| | 20427 | 14505 | 20490 | 5443 | 18592 | 25401 | 2854 | 22437 | 22685 | 22037 | 21088 | 28656 |
| | 14978 | 26195 | 22751 | 18797 | 6460 | 25369 | 13440 | 19144 | 5499 | 5573 | 26606 | 24983 |
| | 23850 | 21698 | 3319 | 14701 | 21713 | 24422 | 13029 | 22785 | 14283 | 11353 | 21563 | 24006 |
| | 8150 | 1263 | 2765 | 24262 | 16099 | 2029 | 1975 | 7552 | 28441 | 15323 | 10935 | 5160 |
| | 28101 | 5861 | 21800 | 18259 | 24392 | 27733 | 27620 | 8037 | 25834 | 30194 | 25637 | 12199 |
| | 3192 | 2814 | 2314 | 16707 | 24266 | 712 | 5948 | 15772 | 10721 | 25413 | 19780 | 4500 |
| | 10647 | 16680 | 5863 | 16892 | 24799 | 10806 | 18073 | 5725 | 18316 | 7158 | 23032 | 23819 |
| | 21839 | 21691 | 12086 | 27923 | 1875 | 29050 | 24051 | 15808 | 7277 | 18233 | 20830 | 12116 |
| | 6296 | 6757 | 11411 | 23523 | 13225 | 30259 | 24347 | 23380 | 13451 | 15503 | 18219 | 13214 |
| | 12800 | 24183 | 14291 | | | | | | | | | |
| 507: | 20779 | 24939 | 5311 | 15671 | 2296 | 20652 | 29109 | 28620 | 3206 | 3200 | 28629 | 4589 |
| | 24485 | 948 | 15172 | 7128 | 3922 | 17466 | 17990 | 21375 | 3142 | 1846 | 28139 | 7341 |
| | 21244 | 21287 | 21295 | 21297 | 22145 | 22180 | 22178 | 21254 | 21332 | 26081 | 3066 | 3105 |
| | 4117 | 4005 | 3965 | 4002 | 3971 | 4040 | 4079 | 4083 | 4112 | 4037 | 4013 | 4051 |
| | 4085 | 4114 | 4086 | 3968 | 4009 | 4044 | 4048 | 4011 | 4091 | 4118 | 3169 | 26086 |
| | 3101 | 2953 | 16273 | 3143 | 4119 | 4140 | 4179 | 4141 | 4149 | 4176 | 4181 | 4142 |
| | 15489 | 3165 | 4185 | 3130 | 4146 | 2949 | 2980 | 2981 | 2985 | 3203 | 3025 | 3067 |
| | 23283 | 3092 | 3167 | 3028 | 3090 | 3132 | 3172 | 18566 | 5161 | 28978 | 21102 | 15354 |
| | 23047 | 15472 | 18591 | 21291 | 12821 | 21164 | 21198 | 22103 | 22083 | 22143 | 22110 | 3021 |
| | 3020 | 3068 | 21252 | 2690 | 13702 | 21330 | 2517 | 9247 | 19405 | 11833 | 20755 | 12527 |
| | 7417 | 23149 | 3888 | 8162 | 10621 | 27724 | 9473 | 27459 | 2829 | 9059 | 3318 | 14598 |
| | 6399 | 1832 | 14639 | 5075 | 20574 | 7540 | 3254 | 6498 | 15079 | 25237 | 25717 | 18738 |
| | 27099 | 2094 | 14428 | 27712 | 5129 | 8845 | 16967 | 20466 | 19980 | 15767 | 14977 | 23713 |
| | 5820 | 16186 | 9309 | 3216 | 3940 | 24473 | 10630 | 29434 | 849 | 5322 | 17378 | 772 |
| | 28623 | 22245 | 11137 | 3523 | 8751 | 17963 | 24926 | 2367 | 4290 | 21608 | 16227 | 25630 |
| | 3812 | 16692 | 29235 | 14220 | 10781 | 15605 | 15245 | 4837 | 8579 | 13179 | 17910 | 19812 |
| | 3127 | 14425 | 2549 | 17607 | 19705 | 16842 | 23437 | 27174 | 11157 | 20352 | 12148 | 18582 |
| | 13552 | 19628 | 28927 | 11275 | 8650 | 28754 | 21601 | 21605 | 18537 | 12838 | 8054 | 25377 |
| | 20187 | 10814 | 27375 | 21086 | 14376 | 26151 | 2335 | 1920 | 23181 | 3568 | 11054 | |
| | 26826 | 4974 | 4438 | 15277 | 12940 | 1980 | 29047 | 6511 | 6690 | 11979 | 29984 | 24503 |
| | 15358 | 19823 | 22832 | 9415 | 27615 | 21329 | 27853 | 23178 | 28845 | 8706 | 1212 | 19502 |
| | 9820 | 9726 | 10243 | 15903 | 4921 | 24963 | 19457 | 12330 | 28572 | 19685 | 26339 | 29786 |
| | 917 | 21450 | 14732 | 22089 | 923 | 14536 | 6343 | 3663 | 17098 | 10720 | 20472 | 29471 |
| | 8023 | 19291 | 1835 | 1124 | 28988 | 13271 | 21913 | 5017 | 6297 | 12797 | 10767 | 17295 |

TABLE 8-continued

| PEP SEQ ID NO: | homolog SEQ ID NOs | | | | | | | | | | |
|---|---|---|---|---|---|---|---|---|---|---|---|
| | 13111 | 3431 | 21493 | 21247 | 13672 | 29339 | 17698 | 20044 | 4482 | 18358 | 5822 | 21385 |
| | 1709 | 5937 | 1330 | 23764 | 8382 | 3231 | 8583 | 12115 | 19190 | 17480 | 5614 | 8467 |
| | 26165 | 7280 | 14035 | 4957 | 25733 | 2168 | 4261 | 28085 | 19259 | 7793 | 12844 | 19678 |
| | 20592 | 25443 | 28577 | 18775 | 14964 | 12904 | 20324 | 12253 | 11299 | 16242 | 2064 | 21929 |
| | 21544 | 18318 | 25219 | 1545 | 19720 | 24063 | 9881 | 26788 | 15537 | 12998 | 3693 | 7888 |
| | 30188 | 12424 | 12363 | 16914 | 5342 | 8474 | 13659 | 24546 | 960 | 14126 | 1740 | 22524 |
| | 29899 | 24833 | 21975 | 8271 | 1931 | 7069 | 18183 | 19392 | 13338 | 9699 | 18568 | 14080 |
| | 19020 | 20524 | 20974 | 9116 | 24390 | 25530 | 15480 | 4211 | 24148 | 8207 | 21327 | 3097 |
| | 4214 | 4187 | 3928 | 3960 | 3956 | 3932 | 3930 | 3925 | 26618 | 15185 | 27318 | 16698 |
| | 22055 | 28710 | 28706 | 1114 | 25182 | 17940 | 22641 | 10226 | 11018 | 4497 | 22234 | 20826 |
| | 5594 | 29126 | 10805 | 28558 | 26651 | 21427 | 6126 | 9791 | 6278 | 1229 | 21117 | 21155 |
| | 21163 | 20666 | 21321 | 22927 | 11026 | 11741 | 14905 | 9728 | 13522 | 26927 | 21896 | 24147 |
| | 1629 | 14177 | 30195 | 10510 | 18812 | 18546 | 23087 | 30245 | 27802 | 4459 | 1046 | 15919 |
| | 7624 | 5334 | 12548 | 27606 | 3816 | 24969 | 11126 | 16924 | 5632 | 20968 | 22081 | 19036 |
| | 18590 | 11125 | 6110 | 3546 | 1041 | 6377 | 28952 | 29794 | 11921 | 23034 | 12741 | 14655 |
| | 4538 | 21490 | 18565 | 3556 | 5419 | 18579 | 19922 | 2707 | 1491 | 1497 | 21323 | 11154 |
| | 26574 | 29960 | 13760 | 2987 | 23801 | 22077 | 21200 | 21249 | 21122 | 25421 | 19768 | 21836 |
| | 30337 | 22105 | 3030 | 3061 | 942 | 3171 | 9485 | 26196 | 17053 | 23416 | 15062 | 25260 |
| | 22146 | 17950 | 15199 | 23867 | 28735 | 10559 | 23054 | 23147 | 3136 | 3072 | 6566 | 21207 |
| | 9274 | 22079 | 25293 | 11881 | 7338 | 21160 | 21121 | 7420 | 891 | 21201 | 22107 | 22241 |
| | 13174 | 11127 | 3199 | 3197 | 29237 | 18539 | 17286 | 9115 | 1483 | 27826 | 24785 | 15035 |
| | 22974 | 11803 | 12237 | 25289 | 26718 | 26453 | 1870 | 15674 | 11151 | 21791 | 21204 | 937 |
| | 2992 | 24040 | 16384 | | | | | | | | | |
| 508: | 26045 | 16912 | 30127 | 29320 | 29303 | 3541 | 26289 | 19539 | 21860 | 11235 | 5935 | 12869 |
| | 17821 | 10527 | 11451 | 8244 | 9118 | 24250 | 1287 | 12226 | 5618 | 25068 | 10889 | 2056 |
| | 16966 | 10027 | 11990 | 14888 | 18855 | 14742 | 24259 | 5720 | 9122 | 27531 | 18352 | 14061 |
| | 13206 | 17734 | 5040 | 13026 | 12003 | 14560 | 17261 | 17144 | 3651 | 11170 | 6990 | 5807 |
| | 27796 | 18507 | 16941 | 19250 | 22019 | 2438 | 5374 | 17384 | 7194 | 25109 | 21461 | 5102 |
| | 30370 | 3332 | 5229 | 29593 | 8370 | 1950 | 21814 | 6787 | 25734 | 26586 | 14652 | 25785 |
| | 14530 | 30381 | 7252 | 27175 | 2028 | 22652 | 29101 | 14959 | 17276 | 4979 | 30282 | 23724 |
| | 8395 | 22852 | 501 | | | | | | | | | |
| 509: | 24805 | 6339 | 29491 | 7984 | 17081 | 2370 | 13507 | 12097 | 20345 | 20830 | 15927 | 6296 |
| | 26465 | 24548 | 11566 | | | | | | | | | |
| 510: | 23567 | 15328 | 22917 | 10973 | 28600 | 1066 | 18353 | 14143 | 13169 | 18901 | 23209 | 26996 |
| | 6647 | | | | | | | | | | | |
| 511: | 23773 | 16720 | 20388 | 16728 | 12602 | 14397 | 18489 | 25591 | 21502 | 27456 | 7172 | 9936 |
| | 18128 | 1038 | 18270 | 12642 | 29770 | 13323 | 6027 | 2757 | 26790 | 20536 | 15896 | 4247 |
| | 2291 | 1798 | 23805 | 6374 | 24459 | 27464 | 13913 | 23529 | 8440 | 15263 | 9459 | |
| 512: | 27904 | 25431 | 14789 | 14183 | 22929 | 27218 | 4526 | 6673 | 9061 | 23949 | 17881 | 1080 |
| | 25209 | 2770 | 23334 | 20251 | 27328 | 21578 | 12878 | 28058 | 22801 | 17685 | 30119 | |
| | 7443 | 28228 | 28916 | 18235 | 29133 | 19893 | 21663 | 24150 | 2673 | 11043 | 27772 | |
| 513: | 4331 | 23464 | 11950 | 28889 | 3508 | 9715 | 5921 | 5029 | 5212 | 17167 | 6776 | 14171 |
| | 26980 | 4402 | 19061 | 6538 | 19039 | 8820 | 12841 | | | | | |
| 514: | 25583 | 25602 | 25606 | 25629 | 25635 | 25666 | 25668 | 25671 | 25675 | 25704 | 25708 | 30450 |
| | 19353 | 2616 | 2612 | 11581 | 2606 | 3607 | 2652 | 2656 | 4666 | 4562 | 4595 | 10715 |
| | 10757 | 10723 | 15148 | 7011 | 10145 | 10555 | 10562 | 10885 | 4615 | 4614 | 10592 | 11306 |
| | 11308 | 10950 | 11366 | 10981 | 11484 | 11491 | 11061 | 11066 | 11524 | 11067 | 11589 | 11559 |
| | 10940 | 11337 | 17802 | 4867 | 15696 | 4771 | 15762 | 9196 | 16637 | 16636 | 9226 | 9230 |
| | 16803 | 4936 | 17828 | 5784 | 11301 | 10012 | 29367 | 10763 | 11274 | 11399 | 11435 | 10139 |
| | 10137 | 10135 | 11305 | 11363 | 11368 | 11409 | 11440 | 13737 | 22631 | 22635 | 14535 | 22638 |
| | 14593 | 14597 | 22671 | 22673 | 21171 | 21127 | 21028 | 21175 | 20934 | 2618 | 2648 | 10795 |
| | 10798 | 2619 | 2676 | 2675 | 2677 | 2679 | 5524 | 2681 | 2780 | 4637 | 3564 | 3605 |
| | 29322 | 29325 | 4600 | 4598 | 10792 | 10790 | 5599 | 5600 | 29374 | 21064 | 20944 | 20940 |
| | 20937 | 21061 | 20981 | 21126 | 21092 | 11767 | 21020 | 21069 | 22000 | 22029 | 22032 | 24069 |
| | 24083 | 24120 | 24194 | 24086 | 24122 | 24117 | 24119 | 24158 | 24182 | 24186 | 24188 | 24153 |
| | 24216 | 24219 | 24126 | 24244 | 24246 | 24249 | 24251 | 4774 | 4701 | 19529 | 19581 | 19532 |
| | 3151 | 19583 | 19617 | 19573 | 19536 | 19576 | 19621 | 19661 | 19578 | 26326 | 26323 | 5703 |
| | 19524 | 9634 | 14630 | 11338 | 10945 | 10937 | 10933 | 11094 | 11535 | 22003 | 16871 | 23011 |
| | 13888 | 10687 | 10759 | 10725 | 10691 | 10751 | 23322 | 15023 | 16600 | 24154 | 24080 | 30427 |
| | 19348 | 30456 | 25633 | 14773 | 7124 | 7178 | 7157 | 7150 | 7246 | 7182 | 7255 | 7101 |
| | 7245 | 7215 | 7094 | 7118 | 7210 | 7156 | 7286 | 7220 | 7186 | 7293 | 7249 | |
| | 7125 | 7151 | 7288 | 7326 | 7294 | 7296 | 7329 | 7333 | 8052 | 5631 | 3602 | 3600 |
| | 4390 | 4392 | 4393 | 4385 | 4446 | 4452 | 4449 | 4422 | 4491 | 4492 | 4495 | 4517 |
| | 4518 | 4547 | 4559 | 4555 | 4550 | 5523 | 5520 | 4718 | 5529 | 5560 | 5619 | 5626 |
| | 5622 | 5601 | 11610 | 5667 | 5673 | 5669 | 5635 | 4457 | 4454 | 10732 | 5675 | 5678 |
| | 7123 | 4852 | 4693 | 15678 | 4735 | 4821 | 15700 | 4736 | 4737 | 4741 | 4770 | 4773 |
| | 4776 | 4806 | 15757 | 15786 | 15788 | 15791 | 15812 | 15817 | 15840 | 15842 | 4825 | 16603 |
| | 16634 | 4856 | 16647 | 4860 | 16669 | 4863 | 16737 | 4894 | 4899 | 4900 | 4903 | 16778 |
| | 16801 | 16807 | 4929 | 16832 | 4932 | 16867 | 4939 | 17668 | 4969 | 4973 | 4976 | 4977 |
| | 17722 | 17725 | 5746 | 9982 | 10007 | 17788 | 17794 | 17800 | 5753 | 5757 | 5783 | 16703 |
| | 10014 | 17832 | 17757 | 16772 | 16706 | 9973 | 9976 | 16739 | 17708 | 11576 | 11608 | 29646 |
| | 19212 | 29648 | 29650 | 19215 | 29652 | 29668 | 19219 | 29669 | 29673 | 19240 | 29674 | 29676 |
| | 19243 | 29697 | 19247 | 29699 | 19252 | 690 | 20263 | 29702 | 19256 | 29703 | 652 | 19284 |
| | 642 | 20220 | 29734 | 19285 | 19287 | 29736 | 29737 | 30422 | 19322 | 30424 | 30426 | 19329 |
| | 20265 | 19350 | 30446 | 19351 | 19352 | 686 | 20223 | 30453 | 20169 | 30457 | 20173 | 647 |
| | 20228 | 605 | 608 | 16891 | 9952 | 10009 | 17765 | 9177 | 16643 | 9979 | 9983 | 14045 |
| | 14016 | 14039 | 14040 | 13976 | 13974 | 13980 | 14012 | 14993 | 1358 | 4588 | 4584 | 4571 |
| | 4574 | 4578 | 13670 | 13711 | 22598 | 22601 | 14564 | 14562 | 22667 | 16664 | 9182 | 9188 |

TABLE 8-continued

| PEP SEQ ID NO: | homolog SEQ ID NOs | | | | | | | | | | |
|---|---|---|---|---|---|---|---|---|---|---|---|
| | 9223 | 9950 | 9954 | 10004 | 10761 | 10667 | 10688 | 10717 | 11500 | 11507 | 11505 | 14991 |
| | 17532 | 1647 | 14787 | 14781 | 10730 | 13599 | 20410 | 2756 | 4380 | 29364 | 3612 | 29331 |
| | 4522 | 4519 | 11579 | 11601 | 26325 | 4631 | 4630 | 4633 | 10824 | 2657 | 29369 | 29372 |
| | 10693 | 4542 | 4540 | 4690 | 11333 | 11224 | 4733 | 4612 | 1900 | 10729 | 1898 | 1893 |
| | 1896 | 11599 | 2714 | 5565 | 5563 | 5564 | 2721 | 2723 | 2752 | 2747 | 3571 | 3573 |
| | 3569 | 4413 | 4411 | 4416 | 4420 | 4489 | 4485 | 4629 | 4603 | 4605 | 4660 | 4663 |
| | 4702 | 4674 | 4669 | 4710 | 4714 | 11582 | 4704 | 5526 | 5597 | 5567 | 5596 | 13979 |
| | 13987 | 21993 | 13992 | 13996 | 12409 | 13942 | 14015 | 1360 | 21231 | 14017 | 14782 | 14841 |
| | 7853 | 26652 | 26664 | 11552 | 18066 | 18134 | 18070 | 18101 | 18206 | 13236 | 2768 | 20087 |
| | 7036 | 18946 | 18255 | 18945 | 18264 | 13982 | 4581 | 4582 | 4908 | 11244 | 4616 | 4621 |
| | 28178 | 4815 | 9947 | 9192 | 16893 | 18369 | 17217 | 14632 | 29645 | 19209 | 13830 | 14636 |
| | 14637 | 13919 | 13914 | 13920 | 13917 | 13944 | 13945 | 13893 | 10689 | 21093 | 13841 | 13854 |
| | 13847 | 17547 | 17545 | 20904 | 20906 | 20899 | 19127 | 19155 | 19150 | 27482 | 15098 | 726 |
| | 2332 | 10069 | 17569 | 22026 | 14028 | 4404 | 4544 | 2336 | 9373 | 5634 | 19773 | 16355 |
| | 9371 | 12698 | 14876 | 22790 | 2402 | 17017 | 940 | 939 | 10096 | 12386 | 14050 | 14053 |
| | 12408 | 13921 | 750 | 749 | 747 | 782 | 745 | 13889 | 23094 | 1437 | 9150 | 15701 |
| | 15718 | 16604 | 16769 | 4942 | 9955 | 17675 | 17719 | 5750 | 10034 | 15754 | 15676 | 14020 |
| | 14046 | 24075 | 21228 | 13946 | 13951 | 14044 | 14024 | 21225 | 21215 | 21221 | 21178 | 21130 |
| | 14818 | 13135 | 14805 | 14808 | 4966 | 15784 | 1369 | 1366 | 1505 | 1403 | 1475 |
| | 1396 | 1514 | 1389 | 1436 | 20903 | 14048 | 11618 | 10831 | 10827 | 10832 | 11612 | 20983 |
| | 4694 | 11282 | 15719 | 15838 | 16670 | 9229 | 5754 | 8876 | 25306 | 19624 | 11594 | 21987 |
| | 21997 | 14640 | 8051 | 649 | 610 | 20183 | 19318 | 715 | 20268 | 19159 | 10713 | 19358 |
| | 19475 | 2718 | 2719 | 13891 | 23044 | 23072 | 23046 | 23077 | 6817 | 6915 | 6790 | 6774 |
| | 19354 | 19357 | 13705 | 13708 | 13710 | 13714 | 13716 | 13747 | 13739 | 13741 | 13743 | 13745 |
| | 13781 | 13782 | 13785 | 13789 | 14809 | 14784 | 13828 | 13833 | 14817 | 14777 | 13835 | 13840 |
| | 4611 | 7376 | 7096 | 7374 | 7373 | 936 | 934 | 21135 | 20975 | 21169 | 21087 | 20978 |
| | 10586 | 20935 | 21134 | 14270 | 13778 | 17534 | 17537 | 9633 | 20901 | 28711 | 27949 | 21098 |
| | 4832 | 385 | 10134 | | | | | | | | | |
| 515: | 21290 | 5113 | 10834 | 24810 | 4054 | 3176 | 24225 | 12009 | 21368 | 7302 | 8961 | 6157 |
| | 3943 | 9934 | 26831 | 10132 | 15895 | 7282 | 20949 | 16473 | 27284 | 8644 | 5550 | 15133 |
| | 18257 | 24023 | 2317 | 6190 | 8953 | 20344 | 13069 | 2192 | 28175 | 12896 | 13677 | 1143 |
| | 4793 | 10109 | 7604 | 3381 | 18047 | 3245 | 23727 | 30248 | 16113 | 23595 | 7606 | 6573 |
| | 19236 | 21032 | 9806 | 28383 | 19431 | 980 | 16998 | 7275 | 2198 | 1289 | 23562 | 13235 |
| | 720 | 26429 | 1312 | 7580 | 16923 | | | | | | | |
| 516: | 17638 | 29775 | 19546 | 7100 | 21078 | 29472 | 26206 | 14606 | 5866 | 21542 | 10893 | 23028 |
| | 28069 | 9435 | 27011 | 4314 | 20175 | 18297 | 12978 | 2762 | 20143 | 6089 | 27189 | 27017 |
| | 23784 | 23697 | 24689 | 6779 | 23568 | 16806 | 2628 | 19337 | 27084 | 30085 | 8185 | 16480 |
| | 5557 | 1961 | 2421 | 18364 | 24072 | 10205 | 19813 | 12996 | 13094 | 7636 | 29267 | 15739 |
| | 10609 | 16763 | 26659 | 2575 | 17702 | 15594 | 12665 | 29225 | 8278 | 9180 | 28016 | 29556 |
| | 25090 | 24005 | 9907 | 28287 | 21642 | 24941 | 24942 | 5491 | 2270 | 16971 | 5215 | 5062 |
| | 5059 | 5054 | 16969 | 22674 | 10175 | 10170 | 10172 | 10072 | 29929 | 10173 | 14928 | 20423 |
| | 14922 | 8299 | 26409 | 3588 | 7503 | 26584 | 8043 | 28658 | 1029 | 12685 | 17300 | 9165 |
| | 30326 | 7436 | 23962 | 28830 | 25587 | 12369 | 23509 | 9475 | 27204 | 8176 | 29489 | 23188 |
| | 18480 | 2148 | 19133 | 24058 | 4847 | 582 | 800 | 10954 | 11217 | | | |
| 517: | 21770 | 30011 | 30013 | 5855 | 4865 | 5700 | 5706 | 5859 | 5791 | 5752 | 5728 | 5724 |
| | 5658 | 4862 | 4829 | 5824 | 5795 | 4859 | 5786 | 5848 | 5821 | 5698 | 5670 | 5699 |
| | 5664 | 22816 | 29343 | 15969 | 15231 | 3408 | 12434 | 6846 | 18881 | 5093 | 3559 | 26787 |
| | 17007 | 6775 | 6773 | 9005 | 9002 | 8310 | 8317 | 6519 | 19404 | 21689 | 19427 | 7861 |
| | 10335 | 10332 | 6295 | 5905 | 14072 | 9143 | 17653 | 20883 | 27755 | 15198 | 27238 | 27235 |
| | 13829 | 13621 | 15190 | 11997 | 6232 | 3608 | 7261 | 28197 | 1254 | 12545 | 15825 | 15823 |
| | 9461 | 9465 | 24609 | 15683 | 12603 | 29951 | 9133 | 5839 | 6831 | 17073 | 16192 | 11603 |
| | 15973 | 15725 | 11616 | 6056 | 6054 | 18067 | 7608 | 29384 | 25428 | 983 | 9576 | 9578 |
| | 7050 | 9539 | 17232 | 26208 | 6738 | 7303 | 9533 | 28961 | 9530 | 17883 | 15373 | 4706 |
| | 15028 | 26207 | 8829 | 17171 | 6877 | 18002 | 6391 | 6390 | 23748 | 23746 | 23721 | 15226 |
| | 28575 | 13516 | 13519 | 7513 | 1247 | 16864 | 16869 | 16860 | 15236 | 21128 | 21162 | 8369 |
| | 4809 | 15959 | 4813 | 14803 | 23564 | 15975 | 23296 | 25872 | 28950 | 20617 | 20612 | 20585 |
| | 20589 | 20591 | 1955 | 12092 | 29243 | 6887 | 23508 | 24581 | 26412 | 25814 | 25817 | 15223 |
| | 24577 | 17336 | 17342 | 10786 | 10820 | 17335 | 9678 | 12419 | 6805 | 11847 | 11874 | 11868 |
| | 11877 | 25604 | 14313 | 14673 | 25291 | 13488 | 12989 | 14149 | 18651 | 1448 | 21435 | 17469 |
| | 15415 | 1104 | 12544 | 14219 | 6226 | 1162 | 12479 | 527 | 23565 | 8755 | 731 | 17150 |
| | 23607 | 23609 | 1057 | 11976 | 12001 | 14156 | 13164 | 30387 | 15233 | 28285 | 20615 | 29661 |
| | 8658 | 9723 | 22231 | 2124 | 5200 | 6043 | 7432 | 2118 | 3482 | 7434 | 3868 | 11931 |
| | 11939 | 11935 | 23750 | 15806 | 15810 | 19068 | 17420 | 12769 | 12770 | 5300 | 5299 | 5303 |
| | 23770 | 12285 | 25513 | 15834 | 13977 | 25515 | 23648 | 25516 | | | | |
| 518: | 1766 | 25623 | 2634 | 8567 | 8546 | 8035 | 8030 | 28060 | 8033 | 13487 | 12426 | 12425 |
| | 27566 | 16382 | 13471 | 13472 | 27829 | 21056 | 5010 | 7641 | 7722 | 17728 | 13546 | 9391 |
| | 8454 | 11625 | 8039 | 26982 | 28645 | 2216 | 19396 | 12857 | 6428 | 6029 | 8927 | 26241 |
| | 28882 | 2058 | 17137 | 23307 | 23313 | 14163 | 30357 | 1765 | 1758 | 22795 | 1762 | 1007 |
| | 12696 | 20720 | 20722 | 21606 | 21600 | 20724 | 9877 | 8100 | 8623 | 9032 | 26511 | 15887 |
| | 17511 | 19373 | 19998 | 11822 | 25957 | 20063 | 20812 | 20816 | 20818 | 24166 | 23982 | 8056 |
| | 26481 | 24795 | 8640 | 22623 | 30201 | 420 | 14318 | 2731 | | | | |
| 519: | 25197 | 11884 | 10001 | 9801 | 25850 | 3323 | 3196 | 26301 | 11122 | 19333 | 25689 | 27968 |
| | 6238 | 2621 | 26736 | 12639 | 4174 | 23354 | 17388 | 27426 | 27427 | 10406 | 21116 | 23213 |
| | 21243 | 29059 | 8253 | 8171 | 5008 | 4506 | 8673 | 5592 | 22265 | 8826 | 22303 | 618 |
| | 16976 | 29729 | 2320 | 27010 | 3688 | 26173 | 14160 | 3350 | 14293 | 18290 | 15945 | 13015 |
| | 4325 | 17647 | 17610 | 21529 | 27333 | 18279 | 29919 | 12396 | 609 | 6953 | 24793 | 9668 |
| | 30204 | 3889 | 3892 | 18054 | 25062 | 20543 | 23442 | 16638 | 28168 | 28173 | 28174 | 5350 |
| | 1914 | 11930 | 24089 | | | | | | | | | |

TABLE 8-continued

| PEP SEQ ID NO: | homolog SEQ ID NOs | | | | | | | | | | |
|---|---|---|---|---|---|---|---|---|---|---|---|
| 520: | 2689 | 14849 | 20863 | 7612 | 25755 | 3539 | 14404 | 22824 | 4568 | 24464 | 6490 | 16629 |
| | 25849 | 20730 | 17593 | 26509 | 6459 | 5167 | 8574 | 8626 | 19464 | 14601 | 11531 | 8491 |
| | 22866 | 26306 | 21750 | 18256 | 12236 | 11056 | 24205 | 15793 | 2311 | 4917 | 10189 | 18004 |
| | 29165 | 15726 | 29715 | 26447 | 12181 | 13562 | 24328 | 6504 | 6665 | 22011 | 22044 | 20372 |
| | 15347 | 14990 | 11045 | 5260 | 17373 | 20928 | 23859 | 3305 | 1833 | 3152 | 8720 | 1113 |
| | 20291 | 22615 | 15019 | 21326 | 11382 | 11389 | 7281 | 24857 | 12221 | 26840 | 26877 | 26883 |
| | 29907 | 19228 | 2630 | 28574 | 3931 | 22277 | 3011 | 12778 | 10598 | 7566 | 18722 | 20915 |
| | 26581 | 19117 | 5375 | 28215 | 22769 | 1891 | 22538 | 20306 | 11808 | 17633 | 19319 | 9819 |
| | 6884 | 16389 | 30016 | 23358 | 25759 | 5468 | 18990 | 18978 | 18976 | 10902 | 10903 | 4755 |
| | 6211 | 24576 | 10925 | 22835 | 27922 | 1663 | 2816 | 27656 | 10912 | 22920 | 16952 | 15822 |
| | 12193 | 15885 | 3916 | 16481 | 2090 | 5235 | 23752 | 17700 | 22846 | 22648 | 25430 | 15548 |
| | 21672 | 9837 | 16822 | 10843 | 14758 | 23165 | 13578 | 15613 | 29761 | 18686 | 23160 | 24538 |
| | 25011 | 28960 | 26247 | 22287 | 25246 | 3205 | 28109 | 19999 | 6434 | 5183 | 18813 | 25027 |
| | 2793 | 28805 | 7455 | 15092 | 24341 | 24919 | 9394 | 26036 | 17100 | 16104 | 5255 | 17147 |
| | 5620 | 10331 | 26139 | 11859 | 18267 | 20614 | 27524 | 22924 | 15741 | 21386 | 14368 | 18695 |
| | 19625 | 21559 | 22647 | 12356 | 12450 | 10772 | 9946 | 24686 | 23039 | 18741 | 13749 | 19442 |
| | 29388 | 1308 | 8573 | 23890 | 23397 | 25108 | 30435 | 6430 | 23944 | 8419 | 30418 | 29445 |
| | 11313 | 21066 | 4729 | 16658 | 28771 | 17865 | 25008 | 17695 | 26533 | 24074 | 8734 | 12776 |
| | 12772 | 1862 | 22372 | 25624 | 25628 | 21945 | 5561 | 10520 | 11880 | 9565 | 17739 | 24912 |
| | 12352 | 18912 | 8247 | 11192 | 19227 | 1203 | 21625 | 2664 | 15404 | 15372 | 2035 | 30315 |
| | 27995 | 2185 | 1860 | 15792 | 15794 | 28925 | 2471 | 27024 | 3479 | 7806 | 27673 | 10067 |
| | 22566 | 3811 | 1026 | 5138 | 4466 | 4569 | 3659 | 7221 | 6890 | 10684 | 14880 | 11619 |
| | 5480 | 14429 | 26775 | 6239 | 15506 | 11172 | 9263 | 4139 | 15183 | 906 | 23440 | |
| 521: | 24439 | 16617 | 16614 | 24792 | 25067 | 26220 | 22153 | 29830 | 15351 | 4278 | 9607 | 5481 |
| | 8057 | 29705 | 18225 | 15593 | 16311 | 7831 | 20757 | 22578 | 11948 | 16905 | 6302 | 9978 |
| | 21179 | 3762 | 13100 | 1232 | 8659 | 10956 | 10849 | 10707 | 16405 | 22360 | 17386 | 7766 |
| | 29684 | 15545 | 23939 | 17526 | 23477 | 23696 | 26536 | | | | | |
| 522: | 1839 | 30065 | 26828 | 30001 | 23943 | 8081 | 3984 | 18730 | 8542 | 30087 | 20248 | 24377 |
| | 21974 | 14359 | | | | | | | | | | |
| 523: | 10402 | 30128 | 746 | 3584 | 9667 | 18721 | 18723 | 29525 | 27516 | 9370 | 4121 | 10700 |
| | 1296 | 13641 | 9927 | 27125 | 23124 | 19608 | 25386 | 27538 | 9922 | 24112 | 13624 | 10702 |
| | 27797 | 10324 | 23709 | 14911 | 3420 | 7361 | 28407 | 13623 | 26488 | 26461 | 20793 | 11323 |
| | 14423 | 14337 | 25741 | 17677 | 25768 | 17701 | 25702 | 17704 | 17671 | 25775 | 25738 | 25770 |
| | 25739 | 25732 | 25700 | 17713 | 17707 | 25737 | 17667 | 25227 | 11372 | 27567 | 3349 | 17768 |
| | 5190 | 11340 | 12888 | 28511 | 2422 | 22136 | 22168 | 22126 | 22131 | 20529 | 20532 | 20498 |
| | 8436 | 15800 | 27619 | 28163 | 28185 | 28153 | 10420 | 22213 | 22215 | 24436 | 22239 | 22308 |
| | 22331 | 16975 | 18672 | 8807 | 22244 | 6725 | 26424 | 22206 | 22208 | 12134 | 12217 | 975 |
| 524: | 17281 | 10048 | 1061 | 27298 | 12259 | 26864 | 1886 | 23852 | 20315 | 17733 | 7467 | 3875 |
| | 11978 | 9586 | 14416 | 7416 | 28871 | 1882 | 659 | 21549 | 22329 | 25113 | 13687 | 17284 |
| | 1383 | 18299 | 19371 | 21742 | 6152 | 29208 | 15547 | 6139 | 30322 | 19120 | 19782 | 19160 |
| | 14435 | 26456 | 6188 | 25334 | 27145 | 19843 | 905 | 9424 | 3425 | 9195 | 25098 | 6204 |
| | 3146 | 14405 | 28133 | 6982 | 4434 | 21377 | 21342 | 4419 | 20571 | 7344 | 26444 | 21696 |
| | 22269 | 9663 | 17145 | 19473 | 2552 | 2832 | 8430 | 9879 | 14432 | 19683 | 14572 | 15648 |
| | 8334 | 1239 | 13248 | 29497 | 2804 | 6376 | 15258 | 19501 | 13997 | 24414 | 9232 | 23983 |
| | 12654 | 11371 | 22407 | 2084 | 8536 | 23598 | 9561 | 7507 | 4985 | 4409 | 27856 | 28041 |
| | 19409 | 16741 | 21812 | 23098 | 15059 | 24965 | 25063 | 26082 | 21256 | 28959 | 8058 | 26692 |
| | 8578 | 6745 | 14232 | 28084 | 2449 | 12813 | 17676 | 10804 | 27586 | 1953 | 13218 | 8651 |
| | 27647 | 15493 | 6119 | 18920 | 20458 | 11219 | 22417 | 21848 | 13037 | 17669 | 22931 | 13993 |
| | 3104 | 1081 | 14038 | 14557 | 18514 | 2788 | 2704 | 18017 | 19063 | 8770 | 8192 | 29482 |
| | 21347 | 1781 | 10370 | 1138 | 4296 | 12660 | 10550 | 23699 | 12569 | 17901 | 24806 | 4573 |
| | 8965 | 21557 | 24755 | 3840 | 9381 | 4636 | 9065 | 17542 | 9276 | 9017 | 10769 | 17242 |
| | 11297 | 10547 | 24762 | 2961 | 5571 | 1158 | 2242 | 16293 | 23330 | 29902 | 17312 | 15931 |
| | 16322 | 1032 | 17813 | 27249 | 23918 | 7162 | 11373 | 25463 | 7147 | 21268 | 11034 | 25050 |
| | 1242 | 12854 | 13232 | 29259 | 13911 | 15250 | 29143 | 9703 | 22736 | 10087 | 24373 | |
| 525: | 23537 | 16291 | 16296 | 16251 | 2956 | 21230 | 14256 | 8499 | 12509 | 14266 | 16518 | |
| 526: | 17830 | 9810 | 13683 | 16742 | 14698 | 29777 | 8999 | 23264 | 12153 | 2738 | 23387 | 15161 |
| | 23239 | 30139 | 27491 | 23265 | 30221 | 30219 | 30199 | 30167 | 30075 | 30031 | 30000 | 29975 |
| | 30193 | 30081 | 30002 | 30106 | 30071 | 30104 | 2584 | 29675 | 14437 | 3246 | 29708 | 9081 |
| | 3432 | 29413 | 5096 | 22761 | 8240 | 10515 | 10516 | 20479 | 11146 | 19360 | 28594 | 26990 |
| | 5263 | 2477 | 22075 | 3549 | 11113 | 12361 | 14473 | 5884 | 7559 | 16166 | 3517 | 7701 |
| | 16380 | 10828 | 6425 | 3522 | 8180 | 24430 | 2669 | 8851 | 23845 | 27485 | 4613 | 2378 |
| | 3794 | 2741 | 2744 | 9921 | 19795 | 29025 | 28243 | 24346 | 7179 | 18979 | 9251 | 5665 |
| | 29266 | 19614 | 4587 | 24441 | 1055 | 2362 | 2546 | 22856 | 13815 | 17041 | 12019 | 4841 |
| | 24704 | 9885 | 15165 | 28995 | 17535 | 13542 | 11551 | 3234 | 13011 | 757 | 3501 | 12835 |
| | 8633 | 8421 | 18328 | 15210 | 26966 | 24559 | 14125 | 2761 | 27861 | 13155 | 3039 | 7089 |
| | 10430 | 27124 | 8859 | 15486 | 15462 | 14410 | 18061 | 29996 | 28883 | 5867 | 5873 | 5876 |
| | 15484 | 7625 | 17291 | 23716 | 21341 | 25840 | 2881 | 21436 | 27316 | 25822 | 5844 | 25607 |
| | 3550 | 22514 | 27847 | 28918 | 10920 | 5353 | 22284 | 14544 | 26995 | 5837 | 5841 | 25266 |
| | 15457 | 15454 | 5870 | 3471 | 20865 | 15407 | 15412 | 28760 | 9839 | 15450 | 15418 | 15414 |
| | 15420 | 25853 | 25264 | 20594 | 1637 | 13580 | 9812 | 5360 | 3463 | 2013 | 3472 | 23788 |
| | 9748 | | | | | | | | | | | |
| 527: | 24446 | 29343 | 21407 | 1978 | 1970 | 15969 | 15231 | 9802 | 18390 | 18389 | 14680 | 19082 |
| | 18391 | 11540 | 5093 | 3559 | 26787 | 9005 | 9002 | 8310 | 6519 | 20095 | 14072 | 9143 |
| | 17653 | 20883 | 27755 | 15198 | 3721 | 29466 | 13621 | 6232 | 3608 | 11358 | 11361 | 7261 |
| | 14788 | 30358 | 1254 | 2190 | 7520 | 24136 | 7731 | 25586 | 3524 | 17782 | 2201 | 15973 |
| | 19038 | 12628 | 19001 | 2796 | 29384 | 25428 | 7050 | 7303 | 634 | 8672 | 20732 | 28961 |
| | 17883 | 26207 | 15028 | 8829 | 17171 | 18002 | 13614 | 19852 | 15226 | 28575 | 13516 | 13519 |
| | 1247 | 7513 | 15236 | 14803 | 23564 | 15975 | 23296 | 25872 | 28950 | 16711 | 29243 | 20096 |

TABLE 8-continued

| PEP SEQ ID NO: | homolog SEQ ID NOs | | | | | | | | | | |
|---|---|---|---|---|---|---|---|---|---|---|---|
| | 26412 | 18845 | 10786 | 17335 | 9678 | 25604 | 13488 | 14149 | 3283 | 17045 | 21435 | 14219 |
| | 12544 | 1057 | 11976 | 11975 | 12001 | 14156 | 13164 | 15233 | 28285 | 8658 | 14918 | 5200 |
| | 2118 | 7434 | 23750 | 15810 | 28718 | 29857 | 17420 | 25851 | 8755 | | | |
| 528: | 16492 | 6409 | 2252 | 1593 | 19867 | 28929 | 30208 | 13118 | 21413 | 12266 | 21411 | 28238 |
| | 9482 | 6938 | 27956 | 30367 | 4687 | 9664 | 18377 | 6766 | 6719 | 24296 | 17192 | 14935 |
| | 16375 | 3675 | 14099 | 4268 | 530 | | | | | | | |
| 529: | 22898 | 22919 | 4748 | 22980 | 30423 | 15119 | 24626 | 932 | 10860 | 16283 | 12991 | 20127 |
| 530: | 16492 | 6409 | 1593 | 19867 | 2252 | 28929 | 30208 | 13118 | 21413 | 12266 | 21411 | 28238 |
| | 9482 | 6938 | 27956 | 30367 | 4687 | 9664 | 18377 | 6766 | 6719 | 24296 | 17192 | 14935 |
| | 16375 | 3675 | 14099 | 4268 | 528 | 24265 | | | | | | |
| 531: | 1675 | 6747 | 9024 | 20653 | 21604 | 15192 | 16195 | 30132 | 8696 | 9651 | 10734 | 18036 |
| | 10373 | 7230 | 20184 | 7055 | 14708 | 2071 | 16818 | 9305 | 18261 | 10313 | 9104 | 10846 |
| | 15498 | 10811 | 10836 | 6197 | 6676 | 6675 | 6748 | 28327 | 3822 | 25411 | 22070 | 27551 |
| | 26669 | 30270 | 5153 | 20247 | 2823 | 10651 | 21365 | 24415 | 20606 | 13317 | 16566 | 22225 |
| | 18828 | 21467 | 18664 | 6674 | 21325 | 6680 | 18734 | 8153 | 27563 | 25667 | 29627 | 4344 |
| | 29742 | 3648 | 2841 | 26738 | 11273 | 11248 | 15844 | 13246 | 13282 | 22458 | 8466 | 29937 |
| | 19600 | 16194 | 29276 | 21189 | 24558 | 24568 | 23654 | 20112 | 30156 | 26176 | 954 | 18522 |
| | 24967 | 25531 | 16036 | 27834 | 19239 | 6710 | 26317 | 18659 | 13733 | 12973 | 20870 | 19262 |
| | 24907 | 26091 | 27855 | 27872 | 25795 | 15417 | 4882 | 22678 | 14382 | 30339 | 2155 | 18657 |
| | 6681 | 6685 | 17903 | 17894 | 17898 | 28166 | 1755 | 3114 | 30029 | 6714 | 30415 | 30416 |
| | 30136 | 3010 | 14351 | 14347 | 18663 | 3085 | 26884 | 25919 | 25627 | 27129 | 23585 | 16697 |
| | 24254 | 22311 | 1805 | 4618 | 29326 | 12209 | 8145 | 7712 | 13051 | 18626 | 27207 | 15402 |
| | 28900 | 9215 | 17833 | 26035 | 19110 | 8394 | 25682 | 1973 | 17372 | 19332 | 7535 | 9804 |
| | 4896 | 8040 | 10235 | 10407 | 29660 | 22707 | 8266 | 22906 | 23726 | 14107 | 11376 | 5068 |
| | 3753 | 13316 | 13653 | 5032 | 25221 | 2310 | 6694 | 23479 | 23270 | 24930 | 20214 | 20704 |
| | 17506 | 12834 | 7512 | 21667 | 27720 | 2463 | 3970 | 1738 | 18275 | 19022 | 24566 | 18747 |
| | 12306 | 22142 | 15316 | 12971 | 6069 | 9071 | 16992 | 7489 | 3063 | 21740 | 1400 | 29941 |
| | 7403 | 6464 | 11415 | 16092 | 4254 | 1222 | 6822 | 1684 | 1720 | 18021 | 8323 | 22224 |
| 532: | 7364 | 29443 | 860 | 12274 | 4596 | 25725 | 30280 | 12581 | 7597 | 26675 | 12353 | 16673 |
| | 13436 | 1092 | 5023 | 22887 | 1097 | 24622 | 7524 | 3315 | 14207 | 8563 | 22909 | 9610 |
| | 25598 | 14994 | 3885 | 19801 | 9273 | 11933 | 12775 | 20422 | | | | |
| 533: | 28376 | 13430 | 9755 | 29312 | 6924 | 16479 | 18829 | 21115 | 11828 | 13457 | 24688 | 16663 |
| | 22717 | 10343 | 15684 | 28381 | 23673 | 17085 | 21309 | 24356 | 28514 | 25283 | 4923 | 22990 |
| | 8490 | 8880 | 10422 | 12749 | 18007 | 5763 | 8581 | 21433 | 5689 | 21120 | 16299 | 26580 |
| | 1685 | 20921 | 29093 | | | | | | | | | |
| 534: | 11865 | 5762 | 26893 | 29386 | 28054 | 28057 | 28051 | 28053 | 19402 | 18298 | 18321 | 20379 |
| | 30260 | 20170 | 26373 | 28700 | 28701 | 18746 | 11370 | 11286 | 11412 | 16021 | 15038 | 9660 |
| | 9697 | 9721 | 9693 | 12599 | 24997 | 21866 | 21417 | 2876 | 21418 | 15790 | 21869 | 30165 |
| | 12850 | 12849 | 12856 | 12848 | 12853 | 10934 | 18040 | 12715 | 8243 | 1096 | 18754 | 11923 |
| | 5388 | 6595 | 21842 | 14955 | 12331 | 20861 | 14547 | 23644 | 26004 | 2001 | 11490 | 14934 |
| | 6066 | 6208 | 3375 | 6663 | 15126 | 15715 | 28092 | 14463 | 17166 | 2313 | 20148 | |
| 535: | 14286 | 3849 | 11781 | 26893 | 29386 | 28054 | 28057 | 28053 | 28051 | 19402 | 18298 | 18321 |
| | 21864 | 1838 | 23932 | 30158 | 20379 | 30260 | 20170 | 26373 | 28700 | 28701 | 18746 | 11370 |
| | 11412 | 11286 | 9721 | 9697 | 9693 | 12599 | 21866 | 21417 | 2876 | 21418 | | |
| | 15790 | 21869 | 3120 | 30165 | 12850 | 12849 | 12856 | 12848 | 12853 | 8243 | 1096 | 18754 |
| | 12715 | 5388 | 18040 | 11923 | 10934 | 6595 | 21842 | 21109 | 14955 | 12331 | 20861 | 14547 |
| | 23644 | 26004 | 2001 | 11490 | 14934 | 6066 | 6208 | 3375 | 6663 | | | |
| 536: | 11584 | 13724 | 9554 | 16616 | 11861 | 29446 | 2685 | 2666 | 2692 | 1388 | 2697 | 1585 |
| | 14288 | 1255 | 23869 | 7127 | 24502 | 19874 | 27071 | 12831 | 23261 | 4734 | 874 | 23045 |
| | 23769 | 7502 | 28061 | 18457 | 15556 | 15559 | 15561 | 15555 | 15529 | 21912 | 15390 | 8535 |
| | 8958 | 22252 | 24498 | 13117 | 25178 | 30459 | 15583 | 4752 | 23038 | 18254 | 7244 | 10345 |
| | 20327 | 23212 | 5007 | 30091 | 7554 | 22684 | 5719 | 606 | 20333 | 15301 | 14483 | 792 |
| | 29861 | 15027 | 18648 | 7016 | 13651 | 1770 | 16899 | 16855 | 28048 | 662 | 18404 | 15455 |
| | 14827 | 22321 | 11701 | 24050 | 10538 | 15416 | 15419 | 15425 | 15460 | 15427 | 15380 | 15459 |
| | 2809 | 13727 | 17094 | 9390 | 1327 | 6658 | 9556 | 6697 | 577 | | | |
| 537: | 27487 | 26588 | 15322 | 6441 | 22352 | 19102 | 27509 | 1210 | 26463 | 25898 | 5441 | 27945 |
| 538: | 25121 | 21384 | 7121 | 8414 | 12357 | 27953 | 13398 | 29440 | 4857 | 16974 | 11487 | 18184 |
| | 3613 | 539 | | | | | | | | | | |
| 539: | 25121 | 21384 | 7121 | 8414 | 12357 | 27953 | 13398 | 29440 | 4857 | 16974 | 11487 | 18184 |
| | 3613 | 538 | 11807 | | | | | | | | | |
| 540: | 26182 | 23506 | 4721 | 3407 | 5510 | 28141 | 20289 | 2375 | 19707 | 8478 | 20026 | 20281 |
| | 24204 | 25568 | 13565 | 7885 | 9747 | 12804 | 30409 | 27044 | 26268 | 3082 | 26845 | 25021 |
| | 13039 | 21422 | 20711 | 14460 | 28379 | 6369 | 22171 | 9400 | 14912 | 802 | 24802 | 24771 |
| | 8224 | 1502 | 13255 | 9710 | 8498 | 15184 | 15051 | 4279 | 14087 | 11687 | 5051 | 14366 |
| | 16922 | 10833 | 5999 | 9792 | 11044 | 25909 | 13239 | 13275 | 30135 | 20448 | 13220 | 26919 |
| | 4711 | 23144 | 24827 | 20648 | 21039 | 13567 | 26113 | 26111 | 28444 | 1311 | 29092 | 4556 |
| | 15492 | 23079 | 2536 | 5889 | 23731 | 14554 | 14550 | 17606 | 16023 | 2106 | 26804 | 29756 |
| | 4313 | 8632 | 7678 | 5806 | 20421 | 2398 | 2397 | 27397 | 23276 | 27338 | 4768 | 5609 |
| | 3677 | 11920 | 4686 | 13177 | 8526 | 24531 | 24738 | 13805 | 8112 | 21930 | 11695 | |
| | 22198 | 26120 | 22534 | 6274 | 29542 | 11876 | 14833 | 10972 | 22036 | 12767 | 3160 | 19374 |
| | 20342 | 23781 | 23785 | 20993 | 27499 | 15470 | 9818 | 18102 | 9948 | 9496 | 26547 | 4383 |
| | 10770 | 14240 | 9152 | 7152 | 7188 | 9925 | 6382 | 23444 | 17250 | 21693 | 8186 | 13000 |
| | 11279 | 5403 | 10662 | 27406 | 30083 | 10558 | 28370 | 25205 | 7637 | 14097 | 14998 | 13965 |
| | 21638 | 22371 | 1454 | 29332 | 16216 | 10914 | 19058 | 10891 | 21898 | 21990 | 7195 | 23665 |
| | 28500 | 30320 | 29260 | 2161 | 28836 | 28872 | 18217 | 7183 | 21782 | 4672 | 7865 | 2807 |
| | 6422 | 11110 | 17642 | 19531 | 8184 | 6205 | 26438 | 28401 | 5989 | 22023 | 25740 | 30012 |
| | 7495 | 20566 | 6287 | 29783 | 25646 | 28764 | 28507 | 28368 | 12876 | 28396 | 26416 | 4190 |
| | 28307 | 12312 | 29953 | 26577 | 23693 | 8130 | 24972 | 23063 | 26305 | 26248 | 30064 | 12578 |

TABLE 8-continued

| PEP SEQ ID NO: | homolog SEQ ID NOs | | | | | | | | | | |
|---|---|---|---|---|---|---|---|---|---|---|---|
| | 4576 | 2528 | 24869 | 15032 | 27371 | 12697 | 11650 | 26296 | 12987 | 1871 | 19446 | 25420 |
| | 2484 | 29690 | 19648 | 14582 | 23482 | 17442 | 23413 | 23216 | 3489 | 16477 | 3378 | 10348 |
| | 6138 | 26364 | 4192 | 8154 | 11757 | 7232 | 23920 | 1542 | 22099 | 5372 | 5373 | 12265 |
| | 1068 | 4102 | 21878 | 21348 | 19892 | 19977 | 21412 | 16436 | 16433 | 20230 | 8918 | 8920 |
| | 22210 | 5330 | 9026 | 10213 | 8952 | 9259 | 29706 | 13303 | 21389 | 10071 | 13931 | 8560 |
| | 14982 | 10498 | 10495 | 17994 | 5401 | 16858 | 8768 | 9509 | 20814 | 17937 | 7058 | 22326 |
| | 29480 | 21749 | 14578 | 14549 | 29370 | 27230 | 24836 | 18516 | 2993 | 23324 | 5787 | 22836 |
| | 5723 | 8582 | 7719 | 27248 | 1568 | 19599 | 2387 | 23790 | 26678 | 22983 | 7013 | 29168 |
| | 15058 | 1150 | 27458 | 4374 | 29230 | 29228 | 6520 | 21564 | 9671 | 11335 | 11057 | 11637 |
| | 24752 | 23041 | 3411 | 29513 | 21057 | 21024 | 17434 | 19365 | 16579 | 10330 | 29074 | 24593 |
| | 6689 | 17303 | 25838 | 22875 | 14716 | 13596 | 19206 | 14325 | 21526 | 28194 | 1382 | 2941 |
| | 1109 | 23948 | 7856 | 7884 | 7993 | 5686 | 5875 | 12179 | 10478 | 23287 | 18636 | 18621 |
| | 14476 | 14438 | 11410 | 22059 | 5037 | 18708 | 6815 | 6411 | 4820 | 17808 | 4072 | 23969 |
| | 27659 | 1547 | 12788 | 29619 | 26791 | 9760 | 4675 | 23624 | 23629 | 14213 | 22376 | 21266 |
| | 8617 | 8615 | 2769 | 4406 | 29450 | 23238 | 27234 | 17190 | 19530 | 29629 | 19814 | 18473 |
| | 19369 | 28542 | 4823 | 19881 | 20715 | 19875 | 16404 | 15253 | 14816 | 14131 | 7741 | 23111 |
| | 16329 | 26383 | 5163 | 5886 | 12961 | 15592 | 27761 | 19879 | 22640 | 7217 | 14628 | 1248 |
| | 18929 | 16814 | 26863 | 24767 | 2595 | 2583 | 6079 | 22291 | 22294 | 25697 | 765 | 1356 |
| | 15204 | 12895 | 28219 | 11277 | 18540 | 28892 | 5125 | 2158 | 1919 | 2932 | 12172 | 23725 |
| | 22155 | 5485 | 9908 | 10329 | 7268 | 7386 | 5378 | 11875 | 20489 | 16154 | 26344 | 1991 |
| | 15586 | 12459 | 9866 | 5442 | 12096 | 26240 | 19959 | 20139 | | | | |
| 541: | 22243 | 22240 | 26949 | 26774 | 29683 | 23772 | 17552 | 29740 | 9778 | 2873 | 22325 | 7529 |
| | 19007 | 11351 | 13667 | 14798 | 14772 | 16896 | 17729 | 8513 | 7501 | 26528 | 25615 | 24929 |
| | 15979 | 15977 | 26249 | 6954 | 14735 | 22375 | 2091 | 2095 | 27749 | 12131 | 24367 | 23704 |
| | 17863 | 19615 | 20629 | 12939 | 17501 | 16781 | 19684 | 21815 | 12638 | 12466 | 17498 | 21314 |
| | 7505 | 7500 | 7482 | 7478 | 7472 | 7509 | 21278 | 20224 | 9137 | 4082 | 20639 | 18719 |
| | 18718 | 18716 | 9036 | 3732 | 10733 | 18116 | 2287 | 8712 | 24065 | 21209 | 12250 | 19361 |
| | 1405 | 7693 | 3342 | 8585 | 14052 | 18176 | 13379 | 26334 | 17183 | 27452 | 21264 | 25368 |
| | 26540 | 22791 | 18496 | 7202 | 16662 | 7709 | 8412 | 4184 | 3904 | 7099 | 24703 | 16027 |
| | 27455 | 27486 | 27374 | 26793 | 22065 | 27056 | 29553 | 10267 | 28673 | 4312 | 28128 | 23355 |
| | 25487 | 22549 | 30363 | 3300 | 16696 | 8688 | 7382 | 16950 | 1795 | 4152 | 22188 | 2790 |
| | 3302 | 23083 | 18446 | 1610 | 19171 | 10417 | 14619 | 1067 | 10645 | 10299 | 22958 | 16083 |
| | 16622 | 22863 | 27719 | 29767 | 19818 | 20006 | 27261 | 27241 | 11614 | 11588 | 11647 | 27762 |
| | 22120 | 14245 | 1071 | 12970 | 18409 | 27276 | 6326 | 2447 | 14057 | 17251 | 23173 | 5268 |
| | 5272 | 7657 | 8298 | 7780 | 3599 | 15364 | 29591 | 29503 | 17641 | 22582 | 18858 | 28395 |
| | 20159 | 12662 | 19081 | 16368 | 23618 | 11114 | 15437 | 1679 | 4012 | 6344 | 23108 | 23085 |
| | 23082 | 23080 | 23103 | 14066 | 7803 | 24918 | 15433 | 9008 | 6879 | 19641 | 15435 | 19032 |
| | 11136 | 3314 | 19051 | 25287 | 18258 | 1814 | 15532 | 15536 | 15802 | 23603 | 24372 | 24211 |
| | 15438 | 15430 | 11291 | 1865 | 7570 | 28732 | 632 | 15426 | 14712 | 14711 | 14713 | 11429 |
| | 18952 | 24537 | 12400 | 12462 | 9297 | 9294 | 798 | 30272 | 30269 | 15758 | 28047 | 3077 |
| | 22570 | 27250 | 6443 | 8290 | 2926 | 11586 | 20772 | 20776 | 20775 | 25367 | 7673 | 7659 |
| | 11307 | 7710 | 7715 | 7708 | 6014 | 5973 | 5970 | 5967 | 5964 | 20151 | 6021 | 5977 |
| | 14752 | 9944 | 29498 | 23222 | 23211 | 23254 | 22474 | 23367 | 16955 | 16753 | 6873 | 28254 |
| | 20645 | 22646 | 25158 | 23132 | 23135 | 5694 | 27562 | 12106 | 21555 | 5221 | 27356 | 27354 |
| | 27358 | 27360 | 27383 | 9917 | 2241 | 11710 | 15476 | | | | | |
| 542: | 20858 | 10809 | 26142 | 14612 | 16454 | 19545 | 19537 | 19540 | 8482 | 24371 | 4160 | 20283 |
| | 14553 | 6799 | 25202 | 9659 | 14445 | 24224 | 27194 | 8364 | 19737 | 19738 | 8866 | 7937 |
| | 25944 | 25059 | 10155 | 21478 | 7852 | 7102 | 14451 | 6950 | 5026 | 14406 | 28090 | 5094 |
| | 21421 | 13411 | 27424 | 6366 | 14790 | 22169 | 26988 | 24801 | 2483 | 13224 | 14147 | 14409 |
| | 14494 | 14517 | 14518 | 14520 | 14521 | 7173 | 19631 | 19633 | 29864 | 19669 | 19674 | 22743 |
| | 4381 | 12661 | 8374 | 12058 | 12037 | 27740 | 24959 | 11750 | 14092 | 11686 | 12278 | 12798 |
| | 4989 | 7115 | 11906 | 25912 | 26228 | 24830 | 26620 | 20613 | 23068 | 23086 | 1638 | 4563 |
| | 4496 | 15519 | 1197 | 14710 | 5891 | 26941 | 26940 | 26894 | 26897 | 26904 | 26938 | 26888 |
| | 26891 | 4320 | 28614 | 2396 | 15349 | 5649 | 3734 | 19586 | 7900 | 2208 | 22821 | 15320 |
| | 29934 | 11345 | 22535 | 1531 | 21396 | 14482 | 8469 | 29548 | 28635 | 9987 | 2543 | 21166 |
| | 10952 | 12764 | 20540 | 23787 | 21038 | 27498 | 15465 | 17855 | 5288 | 27678 | 14444 | 14239 |
| | 19778 | 7222 | 9980 | 3241 | 6735 | 17248 | 8355 | 5396 | 7572 | 4642 | 26594 | 30266 |
| | 12513 | 15663 | 1676 | 1570 | 13712 | 25028 | 25204 | 15030 | 8967 | 9847 | 17346 | 22369 |
| | 24433 | 3228 | 1492 | 21919 | 16560 | 18490 | 3457 | 29822 | 16356 | 20957 | 8669 | 27349 |
| | 8556 | 22593 | 19181 | 14071 | 2338 | 26913 | 23223 | 19740 | 19741 | 19702 | 6424 | 12427 |
| | 19528 | 28651 | 26436 | 23695 | 9106 | 18680 | 25651 | 29778 | 3385 | 25547 | 23653 | 16465 |
| | 29957 | 23660 | 28119 | 25123 | 23161 | 10341 | 10337 | 17877 | 16926 | 6313 | 5335 | 27126 |
| | 12985 | 8913 | 19166 | 26170 | 15524 | 3225 | 17431 | 25803 | 19232 | 22221 | 21808 | 25987 |
| | 3306 | 21033 | 12951 | 5949 | 12101 | 11207 | 26677 | 5377 | 3154 | 10277 | 4237 | 10464 |
| | 21397 | 26222 | 24026 | 22976 | 16432 | 14172 | 24505 | 8923 | 20766 | 7372 | 30063 | 22214 |
| | 27929 | 8234 | 29711 | 2824 | 2892 | 13307 | 1027 | 2055 | 10073 | 17104 | 8541 | 15113 |
| | 10000 | 24419 | 9110 | 10493 | 28628 | 22247 | 5404 | 29270 | 16863 | 3428 | 28997 | 21506 |
| | 14549 | 25281 | 28269 | 28867 | 11006 | 17838 | 27771 | 12933 | 20692 | 19733 | 19704 | 27251 |
| | 2386 | 19598 | 10663 | 23428 | 2637 | 27711 | 19997 | 18774 | 25727 | 27718 | 9402 | 6666 |
| | 24817 | 13556 | 9647 | 5248 | 11562 | 13064 | 16054 | 20698 | 15992 | 23836 | 26766 | 12367 |
| | 9376 | 25609 | 21567 | 12837 | 15575 | 19584 | 14844 | 25156 | 21026 | 3140 | 24917 | 25275 |
| | 17394 | 24748 | 18515 | 8565 | 28120 | 13593 | 4610 | 26924 | 13573 | 23412 | 6478 | 10079 |
| | 7860 | 12653 | 7702 | 19415 | 11774 | 6562 | 10481 | 11804 | 6051 | 18624 | 18909 | 8442 |
| | 12311 | 22061 | 17975 | 11180 | 17334 | 3404 | 6618 | 3733 | 12950 | 9766 | 5493 | 3980 |
| | 23627 | 23968 | 14205 | 26388 | 16017 | 19226 | 30230 | 22394 | 8620 | 15956 | 19582 | 19549 |
| | 19585 | 29807 | 19635 | 19638 | 19666 | 29483 | 23233 | 375 | 21589 | 4151 | 18853 | 16248 |
| | 21296 | 24366 | 16526 | 10967 | 7110 | 2896 | 26390 | 27580 | 28419 | 16446 | 16451 | 17612 |
| | 28143 | 14479 | 8885 | 17298 | 5845 | 14415 | 14487 | 14465 | 14491 | 13609 | 14489 | 14378 |

TABLE 8-continued

| PEP SEQ ID NO: | homolog SEQ ID NOs | | | | | | | | | | |
|---|---|---|---|---|---|---|---|---|---|---|---|
| | 13581 | 14371 | 13583 | 14374 | 13616 | 13608 | 13572 | 14389 | 13612 | 14384 | 13577 | 13619 |
| | 14449 | 13570 | 14523 | 21910 | 14411 | 16057 | 19767 | 23470 | 15894 | 16817 | 25786 | 2582 |
| | 28328 | 20366 | 22975 | 16439 | 22295 | 21402 | 19862 | 28494 | 14459 | 1199 | 24733 | 4349 |
| | 14073 | 5733 | 23439 | 4372 | 13627 | 8409 | 28221 | 27151 | 26080 | 26055 | 25984 | 25982 |
| | 26010 | 25976 | 26083 | 26822 | 26852 | 25978 | 26017 | 25959 | 26132 | 26133 | 26850 | 26859 |
| | 26820 | 26825 | 26106 | 26109 | 26105 | 26022 | 26026 | 26827 | 25956 | 26085 | 25981 | 26135 |
| | 26131 | 26104 | 26102 | 26076 | 26057 | 26015 | 26159 | 26818 | 26156 | 26053 | 26054 | 26161 |
| | 26060 | 26136 | 26163 | 26160 | 20849 | 20846 | 25951 | 25955 | 20885 | 20842 | 26078 | 20891 |
| | 20886 | 20850 | 20808 | 20838 | 20718 | 19833 | 20686 | 21980 | 19803 | 19799 | 20687 | 19794 |
| | 19772 | 19797 | 21983 | 19770 | 21981 | 19842 | 19839 | 21960 | 20689 | 20719 | 19832 | 19805 |
| | 21976 | 16489 | 16456 | 21012 | 20804 | 20767 | 20754 | 16486 | 20973 | 20970 | 21908 | 20969 |
| | 21880 | 21010 | 20759 | 20930 | 20895 | 20923 | 21879 | 20966 | 21847 | 21911 | 21044 | 21948 |
| | 21838 | 21004 | 20972 | 21882 | 21844 | 21050 | 21055 | 21014 | 21003 | 21843 | 21916 | 16491 |
| | 21957 | 21915 | 20893 | 20723 | 20796 | 21845 | 21953 | 21877 | 21946 | 20721 | 21048 | 20927 |
| | 20925 | 26854 | 20926 | 21884 | 26858 | 21828 | 21803 | 2162 | 1916 | 5079 | 2116 | 14186 |
| | 4604 | 4553 | 4521 | 13195 | 24012 | 20562 | 18518 | 6546 | 957 | 13095 | 2878 | 25070 |
| | 5498 | 20329 | 27871 | 15849 | | | | | | | | |
| 543: | 15285 | 20482 | 26613 | 13010 | 14587 | 23348 | 17517 | 1915 | 30335 | 17540 | 18023 | 13902 |
| | 2215 | 19384 | 5020 | 18425 | 13592 | 17005 | 27801 | 12620 | 13102 | 14308 | 12370 | 25212 |
| | 18833 | 13754 | 16338 | 24536 | 17029 | 28412 | 23157 | 6821 | 12613 | 5346 | 28829 | 3443 |
| | 14707 | 14529 | 24381 | 10928 | 26280 | 16516 | | | | | | |
| 544: | 4536 | 25496 | 28709 | 6661 | 25923 | 19605 | 8730 | 26387 | 24734 | 27819 | 26391 | 24458 |
| | 1276 | 27415 | 13295 | 21712 | 2654 | 9901 | 28582 | 3974 | 9593 | 12761 | 5972 | 17010 |
| | 17012 | 18764 | 18766 | 26843 | 11762 | 5896 | 25057 | 22202 | 7424 | 8694 | 18683 | 12734 |
| | 28761 | 13476 | 15235 | 18427 | 27902 | 26887 | | | | | | |
| 545: | 12056 | 13356 | 8152 | 11079 | 6304 | 8906 | 15970 | 12431 | 25131 | 7138 | 7325 | 29624 |
| | 4272 | 19148 | 22274 | 20301 | 11681 | 23992 | 20167 | 12503 | 12758 | 20453 | 21517 |
| | 9990 | 20365 | 8227 | 12406 | 24019 | 2884 | 1943 | 26426 | 21282 | 16574 | 10447 | 28071 |
| | 23258 | 25792 | 23010 | 4308 | 8045 | 16351 | 6883 | 6696 | 15209 | 3194 | 8198 | 15469 |
| | 16547 | 30383 | 5262 | 29564 | 30255 | 25461 | 17243 | 27291 | 13943 | 23751 | 21208 | 26238 |
| | 8332 | 27345 | 22817 | 17321 | 27526 | 25049 | 23169 | 8088 | 22673 | 28856 | 8990 |
| | 22046 | 4267 | 8099 | 8700 | 6867 | 3156 | 17467 | 29726 | 11140 | 24478 | 14750 | 625 |
| | 6451 | 8709 | 28679 | 28038 | 28001 | 24064 | 14675 | 20054 | 7000 | 3451 | 6116 | 6082 |
| | 6076 | 22932 | 15566 | 15563 | 21665 | 21666 | 11642 | 12287 | 6557 | 3864 | 2918 | 21850 |
| | 3189 | 20742 | 3187 | 19334 | 26824 | 996 | 19103 | 19430 | 8381 | 12625 | 16081 | 16825 |
| | 6972 | 12801 | 26676 | 22290 | 12917 | 21013 | 9589 | 24625 | 29608 | 6071 | 23377 | 23980 |
| | 12412 | 1989 | 27630 | 28363 | 11724 | 4814 | 23346 | 25177 | 831 | 16951 | | |
| 546: | 16231 | 8527 | 24427 | 23271 | 23243 | 25551 | 18288 | 7869 | 11697 | 11141 | 13630 | 14901 |
| | 28300 | 12403 | 15034 | 2921 | 27414 | 5640 | 3475 | 28127 | 22446 | 21874 | 21875 | 26216 |
| | 17530 | 27795 | 8524 | 2321 | 8493 | 8530 | 28494 | 23701 | 30045 | 30432 | 27595 |
| 547: | 22240 | 22243 | 26774 | 29683 | 26949 | 9732 | 16548 | 17552 | 29740 | 24038 | 7529 | 11351 |
| | 19007 | 14772 | 14798 | 27139 | 30265 | 17691 | 26528 | 25615 | 1769 | 7501 | 15977 | 24929 |
| | 15979 | 26249 | 6954 | 6081 | 4811 | 22375 | 2091 | 2095 | 17501 | 19593 | 16053 | 9137 |
| | 4082 | 10703 | 20639 | 18719 | 18718 | 3732 | 10733 | 9036 | 8712 | 2287 | 26795 | 21209 |
| | 3361 | 19361 | 7693 | 3342 | 18176 | 13379 | 23433 | 27452 | 16662 | 9601 | 4184 | 28719 |
| | 14891 | 23285 | 27401 | 27056 | 21680 | 28083 | 30363 | 3300 | 20716 | 10231 | 17069 | 29023 |
| | 1610 | 19171 | 10417 | 14619 | 27669 | 29767 | 27261 | 27241 | 27762 | 22120 | 12970 | 1071 |
| | 14245 | 2874 | 6019 | 5268 | 5272 | 7545 | 27088 | 28278 | 14365 | 12561 | 28395 | 20159 |
| | 12662 | 19081 | 20880 | 16368 | 23618 | 11114 | 8208 | 29667 | 18517 | 21904 | 4520 | 18090 |
| | 20800 | 5908 | 4172 | 16285 | 6944 | 14066 | 25462 | 6898 | 5734 | 5737 | 19034 | 15089 |
| | 6828 | 14820 | 10334 | 5790 | 5254 | 5014 | 6836 | 6840 | 10524 | 11295 | 28438 | 6345 |
| | 11461 | 12400 | 12462 | 9297 | 9294 | 798 | 30276 | 30279 | 3639 | 10399 | 2937 | 20776 |
| | 20775 | 25367 | 20772 | 7673 | 7659 | 14752 | 29498 | 23222 | 23211 | 23254 | 22474 | 16955 |
| | 28254 | 25158 | 23132 | 23135 | 5694 | 12106 | 27356 | 27354 | 27358 | 27383 | 27360 | 7564 |
| | 2258 | | | | | | | | | | | |
| 548: | 26090 | 24906 | 7328 | 16079 | 13640 | 1998 | 3987 | 24547 | 10118 | 10168 | 19534 | 29751 |
| | 23972 | 19048 | 19518 | 16929 | 12836 | 10980 | 5385 | 12514 | 8603 | 21615 | 14006 | 9621 |
| | 29755 | 3278 | 9131 | 13564 | 783 | 18177 | 14122 | 16367 | 18197 | 10484 | 27976 | 27790 |
| | 10726 | 28360 | 7845 | 8361 | 7214 | 3978 | 10445 | 26641 | 12573 | 11417 | 1937 | 8810 |
| | 18305 | 17353 | 26604 | 11764 | 14422 | 27199 | 13341 | 7149 | 27631 | 850 | 24218 | 22409 |
| | 8455 | 30360 | 3313 | 24294 | 14091 | 12152 | 23301 | 604 | 28356 | 12273 | 17439 | 5642 |
| | 24682 | 21304 | 19627 | 21743 | 5612 | 8426 | 27392 | 19043 | 29067 | 5266 | 8170 | 5679 |
| | 6456 | 10383 | 22771 | 8450 | 17154 | 17655 | 21229 | 10695 | 22850 | 20714 | 3703 | 17981 |
| | 27996 | 24666 | 29419 | 13898 | 25251 | 2927 | 968 | 25866 | 11823 | 11437 | 11556 | 29559 |
| | 28036 | 22558 | 28576 | 18030 | 644 | 20487 | 13123 | 6229 | 21755 | 4019 | 11073 | 14826 |
| | 8138 | 4868 | 5476 | 13751 | 26764 | 24215 | 21989 | 8521 | 23457 | 22775 | 15037 | 29764 |
| | 12464 | 17472 | 1453 | 3416 | 1990 | 16594 | 2573 | 20483 | 23359 | 4684 | 14747 | 21853 |
| | 9108 | 9107 | 22028 | 22025 | 22021 | 24031 | 21991 | 26569 | 29011 | 5830 | 3328 | 15099 |
| | 15130 | 21719 | 26252 | 13720 | 2076 | 11918 | 4664 | 8250 | 28676 | 18541 | 9328 | 2455 |
| | 2456 | 2459 | 27366 | 27372 | 27370 | 13269 | 13267 | 9730 | 9757 | 9762 | 21183 | 21426 |
| | 14657 | 11572 | 11571 | 15508 | 22496 | 21996 | 21999 | 995 | 14372 | 14890 | 14882 | 14886 |
| | 14908 | 30442 | 13868 | 14633 | 10627 | 10628 | 10603 | 9996 | 18761 | 17083 | 26475 | 9727 |
| | 28330 | 16618 | 2998 | 21992 | 24297 | 24316 | 2970 | 22223 | 16540 | 763 | 16890 |
| | 3910 | 16235 | 11545 | 28378 | 28077 | 2792 | 23797 | 2309 | 14104 | 7723 | 27167 | 10108 |
| | 12589 | 10780 | 13561 | 10432 | 24018 | 30465 | 23865 | 12964 | 15841 | 26552 | 1195 | 25683 |
| | 8249 | 30246 | 26838 | | | | | | | | | |
| 549: | 1877 | 11478 | 12729 | 25130 | 1968 | 1905 | 22481 | 10656 | 10659 | 29731 | 29801 | 27643 |
| | 17021 | 714 | 21585 | 8258 | 9099 | 4230 | 29698 | 29696 | 26561 | 4191 | 1099 | 29827 |

TABLE 8-continued

| PEP SEQ ID NO: | homolog SEQ ID NOs | | | | | | | | | | |
|---|---|---|---|---|---|---|---|---|---|---|---|
| | 29854 | 7534 | 3244 | 29821 | 29850 | 29824 | 29852 | 10968 | 10966 | 631 | 13526 | 5890 |
| | 3446 | 6703 | 13508 | 3492 | 3495 | 10876 | 13337 | 6008 | 6006 | 6013 | 6015 | 6041 |
| | 6018 | 25925 | 29829 | 29800 | 29831 | 8497 | 7953 | 26401 | 1095 | 1969 | 5740 | 11097 |
| | 11671 | 12568 | 11672 | 13453 | 24895 | 12520 | 11494 | 11458 | 11498 | 15061 | 27293 | 7843 |
| | 6148 | 6153 | 26487 | 878 | 9774 | 22442 | 22471 | 22472 | 22445 | 23110 | 22479 | 3053 |
| | 3019 | 25794 | 3527 | 11473 | 25486 | 25512 | 10716 | 10694 | 10719 | 1101 | 21420 | 20389 |
| 550: | 1877 | 11478 | 12729 | 25130 | 1968 | 1905 | 22481 | 10656 | 10659 | 29731 | 29801 | 27643 |
| | 21585 | 8258 | 9099 | 4230 | 29698 | 29696 | 26561 | 4191 | 1099 | 29827 | 29854 | 7534 |
| | 3244 | 29821 | 29850 | 29824 | 29852 | 10968 | 10966 | 631 | 13526 | 5890 | 3492 | 3446 |
| | 6703 | 13508 | 3495 | 10876 | 13337 | 6008 | 6006 | 6015 | 6013 | 6041 | 6018 | 25925 |
| | 29829 | 29800 | 29831 | 8497 | 7953 | 26401 | 1095 | 1969 | 5740 | 11097 | 11671 | 12568 |
| | 11672 | 13453 | 24895 | 12520 | 11494 | 11458 | 11498 | 15061 | 27293 | 7843 | 6148 | 6153 |
| | 26487 | 878 | 9774 | 22442 | 22471 | 22472 | 22445 | 23110 | 22479 | 3019 | 3053 | 25794 |
| | 3527 | 11473 | 25486 | 25512 | 10716 | 10694 | 10719 | 1101 | 21420 | 20389 | | |
| 551: | 12056 | 13356 | 8152 | 11079 | 24868 | 11081 | 6304 | 8906 | 15970 | 7699 | 12431 | 25131 |
| | 7138 | 7325 | 29624 | 4272 | 19148 | 22274 | 20301 | 11681 | 9560 | 23992 | 21196 | 20167 |
| | 12503 | 12758 | 12507 | 20453 | 21517 | 9990 | 20365 | 12406 | 8227 | 2884 | 1943 | 24019 |
| | 26426 | 21282 | 16574 | 10447 | 28071 | 23258 | 23010 | 25792 | 4308 | 8045 | 6696 | 15209 |
| | 3194 | 8198 | 15469 | 16547 | 30383 | 5262 | 29564 | 17243 | 25461 | 27291 | 13943 |
| | 23751 | 21208 | 12723 | 8360 | 27345 | 22817 | 17321 | 4145 | 27526 | 25049 | 23169 | 28856 |
| | 8990 | 22046 | 4267 | 8099 | 17467 | 14750 | 24478 | 28679 | 8709 | 6451 | 625 | 14675 |
| | 17465 | 17089 | 7006 | 14679 | 3759 | 24990 | 3451 | 6082 | 6116 | 10676 | 6078 | 22932 |
| | 9844 | 15564 | 21687 | 23511 | 12287 | 2918 | 21850 | 3189 | 4533 | 9356 | 12014 | 7981 |
| | 19327 | 26824 | 996 | 19103 | 7585 | 8381 | 12625 | 16081 | 25374 | 6972 | 12801 | 12917 |
| | 9377 | 25188 | 1307 | 879 | 25200 | 17548 | 9926 | 21013 | 9589 | 24625 | 29608 | 6071 |
| | 22139 | 25295 | 25185 | 25344 | 23377 | 23980 | 12412 | 1989 | 27630 | 28363 | 11724 | 4814 |
| | 23346 | 25177 | 1342 | 27275 | 16879 | 6418 | 9242 | 4795 | 1399 | 12175 | 8327 | 8296 |
| 552: | 19781 | 24742 | 27550 | 17602 | 13205 | 15958 | 18307 | 16764 | 3929 | 17477 | 21928 | 14400 |
| | 21933 | 27006 | 916 | 18115 | 6993 | 25331 | 4503 | 4507 | 15940 | 682 | 25053 | 14192 |
| | 24761 | 23031 | 20685 | 11089 | 7209 | 9758 | 10534 | 11206 | 4427 | 9159 | 17658 | 11938 |
| | 3124 | 10347 | 12049 | 9558 | 15502 | 3366 | 27361 | 27355 | 6040 | 3911 | 9985 | 2893 |
| | 9207 | 9103 | 9995 | 26691 | 14148 | 20147 | 20181 | 29859 | 27613 | 12782 | 12786 | 26910 |
| | 16035 | 28693 | 10485 | 28340 | 27984 | 17004 | 14462 | 16386 | 17597 | 29867 | 27179 | 14346 |
| | 18593 | 18567 | 11888 | 9191 | 6960 | 12451 | 28617 | 24925 | 1350 | 30251 | 12302 | 22551 |
| | 22548 | 18216 | 21525 | 9960 | 28505 | 26680 | 18460 | 19054 | 26420 | 2184 | 28630 | 28660 |
| | 15705 | 15724 | 8893 | 14296 | 27310 | 24443 | 15659 | 4093 | 6389 | 2478 | 26983 | 25010 |
| | 13132 | 4295 | 2529 | 2495 | 25236 | 20124 | 2507 | 1152 | 28282 | 645 | 2825 | 1005 |
| | 28518 | 19167 | 21466 | 7537 | 599 | 18087 | 16298 | 18089 | 24852 | 11775 | 11749 | 26204 |
| | 22018 | 27920 | 16003 | 9786 | 18867 | 17703 | 19448 | 25939 | 21338 | 28627 | 2171 | 3726 |
| | 12641 | 16435 | 11830 | 18711 | 9190 | 20376 | 16247 | 3938 | 12903 | 9822 | 2412 |
| | 23436 | 29142 | 28502 | 6323 | 13150 | 28551 | 27425 | 27016 | 2853 | 26310 | 23414 | 19425 |
| | 9079 | 16055 | 5625 | 16085 | 16999 | 15000 | 23468 | 3658 | 3655 | 22468 | 11497 | 11504 |
| | 2129 | 30286 | 25392 | 30355 | 10317 | 10421 | 15053 | 25299 | 16571 | 16554 | 12626 | 11521 |
| | 27936 | 4845 | 9201 | 3312 | 6579 | 9500 | 17290 | 12355 | 10927 | 17798 | 16824 | 14684 |
| | 20018 | 20105 | 26393 | 17519 | 16804 | 21988 | 16061 | 14242 | 29971 | 4816 | 23345 | 3015 |
| | 2322 | 14182 | 7352 | 9049 | 9052 | 9075 | 28540 | 20892 | 24955 | 22823 | 27287 | 11526 |
| | 4828 | 925 | 1159 | 1462 | 20485 | 29252 | 20515 | 28349 | 21472 | 10456 | 24784 | 20662 |
| | 20700 | 17775 | 21939 | 7768 | 1374 | 1120 | 25719 | 29293 | 23096 | 22813 | 8592 | 15249 |
| | 5391 | 1354 | 24887 | 10031 | 11029 | 20019 | 18824 | 18337 | 5546 | 7498 | 8616 | 28777 |
| | 22506 | 24617 | 16583 | 24760 | 3188 | 7237 | 29337 | 23884 | 21937 | 21938 | 27713 | 23133 |
| | 29373 | 3013 | 19023 | 25645 | 29183 | 5089 | 28861 | 8217 | 8794 | 29210 | 10457 | 6835 |
| | 27792 | 1774 | 13788 | 18773 | 27759 | 22960 | 7483 | 3513 | 5800 | 28583 | 11996 | 8087 |
| | 15913 | 4796 | 11215 | 8205 | 23783 | 24712 | 20834 | 22914 | 26209 | 15278 | 29766 | 5769 |
| | 9871 | 11801 | 14191 | 4161 | 21690 | 21721 | 21725 | 9665 | 27460 | 17474 | 25268 | 22523 |
| | 17600 | 21528 | 19363 | 8212 | 27682 | 14221 | 23190 | 24326 | 24128 | 9189 | 8795 | 23067 |
| | 23908 | 23822 | 23843 | 23947 | 23882 | 23846 | 23838 | 23817 | 23878 | 24021 | 23818 |
| | 29053 | 27160 | 7596 | 30008 | 16281 | 24613 | 22747 | 24572 | 28587 | 20237 | 21376 | 7451 |
| | 4727 | 6917 | 4763 | 21170 | 25724 | 9343 | 29782 | 6155 | 29792 | 598 | 3247 | 10391 |
| | 3122 | 3052 | 9087 | 30207 | 16468 | 9873 | 20241 | 10159 | 16271 | 3867 | 13217 | 14330 |
| | 15999 | 1849 | 28546 | 18193 | 6959 | 2022 | 2861 | 4341 | 4298 | 4336 | 12393 | 2559 |
| | 7213 | 6281 | 6306 |
| 553: | 26182 | 26171 | 26138 | 9717 | 23506 | 4721 | 3407 | 5510 | 28141 | 20289 | 2375 | 19707 |
| | 8478 | 20026 | 20281 | 24204 | 25568 | 29196 | 28839 | 29900 | 5917 | 13565 | 7885 | 9747 |
| | 12804 | 30409 | 27044 | 26268 | 3082 | 26845 | 25021 | 13039 | 21422 | 20711 | 14460 | 28379 |
| | 6369 | 22171 | 9400 | 14912 | 8666 | 9592 | 9670 | 802 | 24802 | 24771 | 8224 | 1502 |
| | 13255 | 9710 | 8498 | 15184 | 15051 | 4279 | 14087 | 11687 | 5051 | 14366 | 16922 | 10833 |
| | 5999 | 9792 | 11044 | 25909 | 13239 | 12371 | 13275 | 30135 | 20448 | 13220 | 26919 | 4711 |
| | 23144 | 24827 | 20648 | 21039 | 13567 | 26113 | 26111 | 28444 | 1311 | 29092 | 4556 | 15492 |
| | 26276 | 23079 | 2536 | 5889 | 23731 | 14554 | 14550 | 17606 | 16023 | 2106 | 26804 | 29756 |
| | 4313 | 8632 | 7678 | 5806 | 20421 | 2398 | 2397 | 27397 | 23276 | 27338 | 24306 | 4768 |
| | 5609 | 3677 | 11920 | 4686 | 13177 | 8526 | 24531 | 24738 | 13805 | 8112 | 29518 | 21930 |
| | 11695 | 22198 | 26120 | 22534 | 6274 | 29542 | 11876 | 14833 | 10972 | 22036 | 12767 | 3160 |
| | 19374 | 20342 | 23781 | 23785 | 20993 | 27499 | 15470 | 18102 | 9818 | 29948 | 9496 | 26547 |
| | 4383 | 10770 | 14240 | 9152 | 7152 | 7188 | 9925 | 6382 | 23444 | 17250 | 21693 | 8186 |
| | 13000 | 11279 | 5403 | 10662 | 27406 | 30083 | 10558 | 28370 | 25205 | 7637 | 14097 | 14998 |
| | 13965 | 21638 | 22371 | 1454 | 29332 | 16216 | 10914 | 19058 | 10891 | 21898 | 21990 | 7195 |
| | 23665 | 28500 | 30320 | 29260 | 2161 | 28836 | 28872 | 18217 | 7183 | 21782 | 4672 | 7865 |
| | 2807 | 6422 | 11110 | 17642 | 19531 | 8184 | 6205 | 26438 | 28401 | 5989 | 22023 | 25740 |

TABLE 8-continued

| PEP SEQ ID NO: | homolog SEQ ID NOs | | | | | | | | | | |
|---|---|---|---|---|---|---|---|---|---|---|---|
| | 30012 | 7495 | 20566 | 6287 | 29783 | 25646 | 28764 | 28507 | 28368 | 12876 | 28396 | 26416 |
| | 4190 | 28307 | 12312 | 29953 | 26577 | 23693 | 8130 | 24972 | 23063 | 26305 | 26248 | 30064 |
| | 12578 | 12560 | 4324 | 4576 | 2528 | 24869 | 15032 | 27371 | 12697 | 11650 | 26296 | 12987 |
| | 1871 | 19180 | 23167 | 27165 | 19446 | 25420 | 2484 | 29690 | 19648 | 14582 | 23482 | 17442 |
| | 23413 | 23216 | 3489 | 16477 | 3378 | 10348 | 13228 | 6138 | 26364 | 4192 | 8154 | 11757 |
| | 7232 | 23920 | 1542 | 22099 | 5372 | 5373 | 12265 | 1068 | 4102 | 21878 | 26956 | 30275 |
| | 21348 | 19892 | 19977 | 21412 | 16436 | 16433 | 20230 | 8918 | 8920 | 22210 | 5330 | 9026 |
| | 10213 | 8952 | 9259 | 29706 | 13303 | 21389 | 10071 | 13931 | 18857 | 8560 | 14982 | 10498 |
| | 10495 | 17994 | 5401 | 16858 | 8768 | 9509 | 20814 | 17937 | 7058 | 22326 | 29480 | 21749 |
| | 14578 | 14549 | 29370 | 27230 | 24836 | 18516 | 2993 | 23324 | 5787 | 22836 | 5723 | 8582 |
| | 7719 | 27248 | 1568 | 19599 | 2387 | 23790 | 26678 | 22983 | 7013 | 29168 | 15058 | 1150 |
| | 22530 | 17837 | 26771 | 27458 | 4374 | 29230 | 29228 | 6520 | 21564 | 9671 | 11335 | 11057 |
| | 11637 | 23873 | 24752 | 23041 | 3411 | 29513 | 21057 | 21024 | 17434 | 19365 | 16579 | 10330 |
| | 29074 | 24593 | 6689 | 17303 | 25838 | 22875 | 14716 | 13596 | 19206 | 14325 | 21526 | 28194 |
| | 1382 | 2941 | 1109 | 23948 | 7856 | 7884 | 7993 | 5686 | 5875 | 12179 | 10478 | 23287 |
| | 18636 | 18621 | 14476 | 14438 | 11410 | 22059 | 5037 | 18708 | 6815 | 6411 | 4820 | 17808 |
| | 4072 | 23969 | 27659 | 1547 | 12788 | 29619 | 26791 | 9760 | 4675 | 23624 | 23629 | 14213 |
| | 22376 | 21266 | 8617 | 8615 | 2769 | 25811 | 4406 | 29450 | 23238 | 23234 | 17190 | 19530 |
| | 29629 | 19814 | 18473 | 19369 | 28542 | 4823 | 29640 | 19981 | 20715 | 19875 | 16404 | 15253 |
| | 14816 | 14131 | 7741 | 23111 | 16329 | 26383 | 5163 | 5886 | 12961 | 15592 | 27761 | 19879 |
| | 22640 | 7217 | 14628 | 1248 | 18929 | 16814 | 26863 | 24767 | 2595 | 2583 | 6079 | 22291 |
| | 22294 | 25697 | 765 | 1356 | 15204 | 4401 | 20610 | 17157 | 7629 | 14311 | 9146 | 12895 |
| | 28219 | 11277 | 18540 | 28892 | 11025 | 2158 | 1919 | 2932 | 12172 | 23725 | 22155 | 5485 |
| | 9908 | 10329 | 7268 | 7386 | 5378 | 11875 | 20489 | 16154 | 26344 | 1991 | 15586 | 12459 |
| | 9866 | 5442 | 12096 | 26240 | 19959 | 20139 | | | | | | |
| 554: | 26708 | 26727 | 26707 | 12532 | 13832 | 28786 | 23554 | 3996 | 3961 | 3964 | 3949 | 23584 |
| | 3950 | 23553 | 23574 | 23581 | 23573 | 23582 | 23580 | 3952 | 3994 | 3959 | 3946 | 3955 |
| | 3948 | 28010 | 8799 | 18294 | 5808 | 17684 | 10249 | 768 | | | | |
| 555: | 16550 | 16134 | 23003 | 20840 | 13449 | 2662 | 23631 | 14173 | 12029 | 1116 | 19485 | 27743 |
| | 13656 | 7996 | 8349 | 6481 | 10989 | 9388 | 26088 | 12925 | 21513 | 2843 | 27683 | 5410 |
| | 16798 | 26686 | 23450 | 6237 | 6341 | 27505 | 15031 | 5944 | 17208 | 21831 | 21831 | 7433 |
| | 25746 | 23877 | 23430 | 16379 | 27758 | 4871 | 27605 | 4946 | 7706 | 24786 | 6179 | 23013 |
| | 23502 | 22094 | 7336 | 9048 | 26957 | 2202 | 1754 | 29911 | 5726 | 3468 | 6786 | 24530 |
| | 8257 | 3382 | 5016 | 21265 | 13625 | 4394 | 26084 | 27833 | 718 | 25361 | 27506 | 7591 |
| | 3942 | 6693 | 10984 | 15234 | 25994 | 13459 | 27404 | 12200 | 17174 | 557 | 25015 | |
| 556: | 18237 | 23960 | 23994 | 23991 | 24179 | 24180 | 24076 | 24118 | 24146 | 24149 | 24030 | 24181 |
| | 24184 | 24209 | 24210 | 24213 | 24217 | 24110 | 24232 | 24034 | 24105 | 24236 | 24238 | 23998 |
| | 24071 | 23989 | 24241 | 23996 | 24178 | 24037 | 24027 | 19800 | 29453 | 11999 | 10858 | 12309 |
| | 3763 | 5918 | 20729 | 17637 | 6952 | 6641 | 26191 | 9629 | 19472 | 26754 | 505 | 13319 |
| | 6060 | 4273 | 7915 | 30110 | 23241 | 24337 | | | | | | |
| 557: | 16550 | 16134 | 23003 | 20840 | 13449 | 2662 | 23631 | 14173 | 12029 | 1116 | 19485 | 27743 |
| | 13656 | 7996 | 8349 | 6481 | 10989 | 9388 | 26088 | 12925 | 21513 | 2843 | 27683 | 5410 |
| | 16798 | 26686 | 23450 | 6237 | 6341 | 27505 | 15031 | 5944 | 17208 | 3129 | 21831 | 7433 |
| | 25746 | 23877 | 23430 | 16379 | 27758 | 4871 | 27605 | 4946 | 7706 | 24786 | 6179 | 23013 |
| | 23502 | 22094 | 7336 | 9048 | 26957 | 2202 | 1754 | 29911 | 5726 | 3468 | 6786 | 24530 |
| | 8257 | 3382 | 5016 | 21265 | 13625 | 4394 | 26084 | 27833 | 718 | 25361 | 27506 | 7591 |
| | 3942 | 6693 | 10984 | 15234 | 25994 | 13459 | 27404 | 12200 | 17174 | 555 | 10258 | 25015 |
| 558: | 11865 | 14286 | 1773 | 14694 | 9046 | 10926 | 2603 | 9799 | 5762 | 22591 | 8702 | 14134 |
| | 19345 | 3849 | 11781 | 26893 | 29386 | 28051 | 28057 | 28054 | 28053 | 19402 | 18298 | 18321 |
| | 21864 | 4487 | 11071 | 1036 | 30260 | 5652 | 6536 | 28700 | 28701 | 18746 | 11412 | 11370 |
| | 11286 | 9697 | 9721 | 9693 | 24997 | 9660 | 15038 | 12599 | 22363 | 19623 | 21866 | 21417 |
| | 21418 | 2876 | 15790 | 21869 | 3120 | 30165 | 7567 | 12850 | 12849 | 12856 | 12848 | 11923 |
| | 1096 | 8243 | 12715 | 18754 | 5388 | 18040 | 6595 | 11983 | 21842 | 10934 | 26685 | 14329 |
| | 26134 | 7114 | 6547 | 13437 | 14955 | 12331 | 20861 | 2706 | 14547 | 15411 | 22324 | 19562 |
| | 21801 | 7211 | 20912 | 23644 | 19326 | 26004 | 2001 | 11490 | 14934 | 6208 | 3375 | 6663 |
| | 12294 | | | | | | | | | | | |
| 559: | 21053 | 5637 | 13367 | 30097 | 30098 | 1714 | 4293 | 13481 | 14355 | 1206 | 1181 | 7897 |
| | 14745 | 9179 | 2803 | 2806 | 19460 | 10635 | 28838 | 25830 | 16687 | 19459 | 23427 | 9319 |
| | 15848 | 15846 | 12390 | 12391 | 10033 | 21274 | 8353 | 18944 | 2176 | 14748 | 9271 | 11074 |
| | 12439 | 7936 | 20697 | 13928 | 20737 | 15591 | 1381 | 1363 | 5045 | 5043 | 23810 | 15873 |
| | 18769 | 26971 | 26972 | 9219 | 3214 | 3212 | 2831 | 2833 | 16064 | 6039 | 24993 | 24991 |
| | 27439 | 27438 | 29207 | 1634 | 19383 | 24416 | 24418 | 16903 | 11802 | 13429 | 2494 | 28555 |
| | 28557 | 4328 | 3269 | 3272 | 14997 | 1597 | 27111 | 25193 | 9655 | 13046 | 13048 | 6270 |
| | 7198 | 27215 | 1146 | 26515 | 26517 | 21921 | 15283 | 27402 | 27868 | 9639 | 16209 | 8679 |
| | 15709 | 27332 | 20494 | 13930 | 5116 | 6353 | 7756 | 7601 | 8986 | 9515 | 1362 | 1365 |
| | 685 | 24332 | 25918 | 25928 | 20497 | 12076 | 973 | 974 | 7589 | 1314 | 2849 | 7200 |
| | 21813 | 9155 | 9156 | 10841 | 19587 | 19589 | 6171 | 8235 | 16570 | 3531 | 3526 | 8286 |
| | 3377 | 5657 | 22868 | 22870 | 1551 | 1553 | 26201 | 26375 | 6394 | 14686 | 14687 | 26817 |
| | 2903 | 10287 | 16363 | 11145 | 5246 | 5250 | 14737 | 23734 | 23730 | 21861 | 21859 | 26687 |
| | 29894 | 30434 | 30431 | 2899 | 2902 | 16334 | 5302 | 5298 | 9888 | 4303 | 10265 | 22367 |
| | 18580 | 14695 | 27846 | 17626 | 2109 | 6052 | 16127 | 30216 | 4367 | 6687 | 26267 | 24728 |
| | 24730 | 14722 | 14720 | 1445 | 27700 | 27697 | 1322 | 18938 | 17173 | 17172 | 14492 | 24191 |
| | 26309 | 26311 | 18431 | 18429 | 22637 | 22639 | 841 | 19542 | 25007 | 23073 | 921 | |
| | 8727 | 22508 | 11259 | 2295 | 28478 | 17819 | 26866 | 29146 | 1507 | 7960 | 7961 | 11492 |
| | 26369 | 26371 | 18436 | 5241 | 24911 | 10101 | 10102 | 7319 | 7323 | 10634 | 18983 | 29268 |
| | 29265 | 26149 | 26150 | 21925 | 21927 | 17972 | 18001 | 20748 | 20747 | 23042 | 30325 | 19845 |
| | 24599 | 4808 | 29229 | 14641 | 14643 | 6370 | 15708 | 15710 | 29633 | 29632 | 21113 | 21114 |
| | 11209 | 11213 | 22426 | 22424 | 29203 | 29204 | 29502 | 29488 | 4378 | 26546 | 26549 | 4062 |

TABLE 8-continued

| PEP SEQ ID NO: | homolog SEQ ID NOs | | | | | | | | | |
|---|---|---|---|---|---|---|---|---|---|---|
| | 18589 | 26724 | 6332 | 23821 | 27135 | 22196 | 16034 | 11065 | 11709 | 23015 | 18600 | 2580 |
| | 29261 | 27119 | 27964 | 27971 | 11480 | 11481 | 9572 | 17430 | 17428 | 9575 | 7945 | 14729 |
| | 8825 | 26717 | 26720 | 9302 | 9326 | 18620 | 924 | 27200 | 20233 | 10699 | 27257 | 26880 |
| | 26881 | 12995 | 17825 | 17823 | 24741 | 22069 | 19432 | 19359 | 13970 | 3496 | 1711 | 23383 |
| | 21158 | 12866 | 30263 | 18787 | 26538 | 14868 | 4035 | 4388 | 10801 | 10632 | 25632 | 23963 |
| | 28612 | 23253 | 27927 | 1178 | 29132 | 20213 | 1016 | 14461 | 24758 | 23386 | 21388 | 5313 |
| | 5058 | 28289 | 4759 | 4761 | 4762 | 2437 | 12185 | 12187 | 18988 | 1713 | 28792 | 18380 |
| | 15839 | 14194 | 18840 | 4330 | 4864 | 8121 | 9335 | 10310 | 10638 | 18392 | 21281 | 20942 |
| | 20443 | 26148 | 20072 | 21300 | 12484 | 2275 | 25950 | 3671 | 29507 | 16628 | 10059 | 2250 |
| | 1723 | 882 | 29614 | 22890 | 7292 | 3148 | 16143 | 24227 | 8787 | 10741 | 1326 | 5613 |
| | 9289 | 9306 | 865 | 6419 | 4798 | 13777 | 13774 | 17747 | 17712 | 708 | 16833 | 3004 |
| | 17056 | 6800 | 2653 | 20042 | 17162 | 26198 | 26200 | 27852 | 24966 | 24968 | 11426 | 30306 |
| | 30308 | 5191 | 6541 | 20215 | 20217 | 1772 | 3268 | 4046 | 4053 | 4050 | 3207 | 3027 |
| | 3022 | 4057 | 3074 | 3029 | 3173 | 3168 | 12543 | 10664 | 21634 | 17128 | 6401 | 12365 |
| | 8519 | 13988 | 13986 | 30242 | 15429 | 9261 | 23736 | 7773 | 12871 | 20211 | 20212 | 2210 |
| | 10272 | 16332 | 16353 | 5091 | 25709 | 22283 | 592 | 2498 | 2518 | 3861 | 19815 | 28848 |
| | 16627 | 1790 | 20457 | | | | | | | | | |
| 560: | 16185 | 25895 | 4001 | 30373 | 8413 | 24865 | 7113 | 11532 | 12890 | 18385 | 12053 | 4807 |
| | 8506 | 17850 | 16626 | 27185 | 8569 | 12416 | 19408 | | | | | |
| 561: | 23793 | 18790 | 29098 | 21734 | 13819 | 24140 | 18727 | 8559 | 785 | 19511 | 16337 | 27278 |
| | 1226 | 20337 | 1398 | 2189 | 29255 | 9913 | 972 | 8849 | 20168 | 11234 | 17738 | 9477 |
| | 28987 | 15076 | 25762 | 8410 | 23602 | 11310 | 9650 | 4780 | 13397 | 24565 | 16656 | 23229 |
| | 26118 | 24815 | 15206 | 19896 | 6288 | 13671 | 896 | 30168 | 26836 | 24841 | 24102 | 16849 |
| | 3941 | 562 | 13157 | 14350 | 16990 | 10451 | 11525 | 26264 | 29121 | 8019 | 18656 | 20809 |
| | 26496 | 13454 | 15045 | 4528 | 20271 | 17831 | 600 | 24452 | 12828 | 6707 | 26769 | 638 |
| | 13386 | 29429 | 20627 | 20839 | 28624 | 12407 | 3134 | 16709 | 563 | 637 | 24275 | 24542 |
| | 7836 | 27684 | 13611 | 18144 | 29774 | 12757 | 29174 | 5497 | 7397 | 25897 | 19074 | 5958 |
| | 4432 | 4647 | 10526 | 5714 | 20064 | 13499 | 9446 | 27604 | 19261 | 27314 | 23489 | 15876 |
| | 20588 | 1701 | 10200 | 26101 | 8656 | 7051 | 11891 | 7136 | 5827 | 18060 | 8242 | 12109 |
| | 21489 | 8385 | 29785 | 8389 | 3731 | 29847 | 20504 | 29916 | 16445 | 11086 | 24284 | 14179 |
| | 24668 | 24107 | 24106 | 9456 | 4469 | 9743 | 3153 | 4103 | 1313 | 24756 | 26756 | 18494 |
| | 14533 | 16275 | 15083 | 17043 | 3645 | 28897 | 6403 | 7837 | 23029 | 11293 | 20956 | 12145 |
| | 14434 | 25871 | 5971 | 19784 | 17500 | 22386 | 28165 | 13955 | 8924 | 16793 | 22370 | 12281 |
| | 24468 | 2821 | 3905 | 17904 | 9915 | 22744 | 26446 | 14856 | 11630 | 21379 | 24611 | 13726 |
| | 20506 | 3830 | 25891 | 29537 | 9372 | 11185 | 18947 | 18702 | 19469 | 6365 | 1988 | 28035 |
| | 1228 | 7358 | 3014 | 1690 | 2393 | 26723 | 26830 | 22513 | 775 | 2282 | 13540 | 770 |
| | 23142 | 15615 | 27092 | 23883 | 922 | 24454 | 20351 | 2725 | 12230 | 11676 | 2815 | 9204 |
| | 18941 | 4116 | 27727 | 16147 | 15624 | 24212 | 6251 | 4480 | 13344 | 23040 | 24055 | 19070 |
| | 21441 | 5663 | 25714 | 30134 | 1184 | 24989 | 4728 | 29452 | 22470 | 26402 | 11398 | 11262 |
| | 12130 | 2044 | 12505 | 11829 | 8671 | 20459 | 14527 | 7871 | 2587 | 26994 | 15300 | 18248 |
| | 2979 | 14490 | 1808 | 8094 | 9346 | 22495 | 17804 | 2722 | 4594 | 27317 | 27593 | 23670 |
| | 28675 | 12119 | 15392 | 17875 | 7057 | 13063 | 23126 | 23579 | 20651 | 27745 | 27584 | 26925 |
| | 20778 | 1598 | 14158 | 14079 | | | | | | | | |
| 562: | 23793 | 18790 | 29098 | 29530 | 21734 | 13819 | 24140 | 18727 | 8559 | 785 | 19511 | 16337 |
| | 27278 | 1226 | 20337 | 1398 | 2189 | 29255 | 9913 | 972 | 8849 | 20168 | 11234 | 17738 |
| | 9477 | 28987 | 15076 | 25762 | 8410 | 23602 | 11310 | 9650 | 4780 | 13397 | 24565 | 16656 |
| | 23229 | 26118 | 24815 | 15206 | 19896 | 13671 | 6288 | 896 | 30168 | 26836 | 24841 | 24102 |
| | 16849 | 26769 | 12828 | 638 | 16709 | 24275 | 637 | 563 | 27684 | 7836 | 24542 | 18144 |
| | 12757 | 18060 | 8242 | 12109 | 21489 | 8385 | 8389 | 29785 | 29847 | 3731 | 20504 | 29916 |
| | 16445 | 11086 | 24284 | 14179 | 24668 | 24107 | 24106 | 9456 | 4469 | 9743 | 26756 | 18494 |
| | 14533 | 16275 | 17500 | 13955 | 28165 | 8924 | 22386 | 22370 | 2821 | 16793 | 19784 | 17904 |
| | 26446 | 9915 | 14856 | 15615 | 27092 | 922 | 23883 | 24454 | 20351 | 18941 | 12230 | 2725 |
| | 9204 | 11676 | 4116 | 27727 | 16147 | 15624 | 24212 | 23579 | 20651 | 561 | 28151 | 9630 |
| | 27745 | 27584 | 26925 | 20778 | 1598 | 14158 | 14079 | 14350 | | | | |
| 563: | 23793 | 18790 | 29530 | 13819 | 24140 | 18727 | 8559 | 785 | 19511 | 27278 | 1226 | 20337 |
| | 1398 | 2189 | 29255 | 9913 | 972 | 8849 | 11234 | 9477 | 28987 | 15076 | 25762 | 8410 |
| | 23602 | 11310 | 9650 | 4780 | 13397 | 24565 | 16656 | 23229 | 26118 | 15206 | 19896 | 896 |
| | 30168 | 26836 | 24841 | 24102 | 16849 | 16990 | 10451 | 11525 | 562 | 13157 | 14350 | 26264 |
| | 3941 | 29121 | 18656 | 26496 | 29429 | 13386 | 6707 | 20627 | 12828 | 26769 | 638 | 20839 |
| | 28624 | 18060 | 12109 | 21489 | 8385 | 8389 | 29785 | 3731 | 29847 | 20504 | 29916 | 11086 |
| | 16445 | 24284 | 14179 | 24668 | 24107 | 24106 | 4469 | 9743 | 9456 | 26756 | 18494 | 14533 |
| | 16275 | 1313 | 20351 | 23579 | 561 | 28151 | 27584 | 26925 | 20778 | 1598 | 14158 | 14079 |
| | 24275 | 637 | 16709 | | | | | | | | | |
| 564: | 25129 | 27368 | 25249 | 29970 | 4685 | 4766 | 10275 | 29055 | 21313 | 10701 | 19680 | 9935 |
| | 16488 | 8177 | 4015 | 27951 | 25825 | 21512 | 20368 | 27128 | 9690 | 12146 | 27413 | 15195 |
| | 23828 | 11841 | 5189 | 14776 | 9064 | 21233 | 26231 | 12002 | 11133 | 9018 | 15501 | 26127 |
| | 12008 | 11129 | 7116 | 16009 | 27954 | 10924 | 12108 | 21081 | 12026 | 22330 | 27916 | 24283 |
| | 7140 | 27779 | 24073 | 4136 | 30112 | 11168 | 1115 | 22933 | 22672 | 19676 | 21195 | 1111 |
| | 11985 | 28917 | 22696 | 16189 | 13287 | 3293 | 12420 | 30163 | 6141 | 3686 | 20573 | 16193 |
| | 23458 | 4617 | 4625 | 24189 | 11578 | 9003 | 13450 | 11577 | 11574 | 12862 | 21165 | 16191 |
| | 11772 | 16870 | 29589 | 7318 | 7287 | 7322 | 27518 | 12423 | 6771 | 29765 | 18959 | 18928 |
| | 6767 | 18139 | 771 | 6718 | 10234 | 14176 | 7640 | 29596 | 7371 | 15272 | 14212 | 10238 |
| | 5355 | 23723 | 23465 | 10565 | 7485 | 1227 | 16546 | 24889 | 29958 | 25556 | 5655 |
| | 8828 | 28823 | 28380 | 2635 | 12575 | 21856 | 6971 | 17870 | 15410 | 13234 | 11015 | 22504 |
| | 8340 | 8342 | 9158 | 18685 | 29258 | 8072 | 29470 | 19267 | 18350 | 2117 | 14539 | 725 |
| | 3730 | 13289 | 14559 | 10188 | 15006 | 7581 | 22282 | 5390 | 2261 | 10220 | 2021 | 22170 |
| | 22174 | 22172 | 16620 | 6756 | 12246 | 18575 | 17265 | 21720 | 17791 | 3742 | 25238 | 7440 |
| | 19956 | 1764 | 19482 | 23779 | | | | | | | | |

TABLE 8-continued

| PEP SEQ ID NO: | homolog SEQ ID NOs | | | | | | | | | | |
|---|---|---|---|---|---|---|---|---|---|---|---|
| 565: | 13444 | 29969 | 14565 | 8761 | 4609 | 27488 | 15129 | 21484 | 10063 | 3692 | 15266 | 13584 |
|  | 9606 | 3133 | 29198 | 12289 | 29118 | 4198 | 3469 | 1246 | 9029 | 22236 |  |  |
| 566: | 12946 | 14206 | 6593 | 6591 | 25758 | 19731 | 19754 | 23642 |  |  |  |  |
| 567: | 13038 | 4724 | 16883 | 8660 | 7271 | 2574 | 7312 | 7307 | 19099 | 16463 | 22752 | 16786 |
|  | 24534 | 1935 | 18448 | 8772 | 9405 | 12044 | 16340 | 27473 |  |  |  |  |
| 568: | 20417 | 27886 | 19619 | 7800 | 1272 | 3823 | 7082 | 27564 | 15616 | 24116 | 14223 | 27721 |
|  | 8014 | 22783 | 8325 | 24621 | 17123 | 20009 | 29665 | 28581 | 24641 | 24616 | 24828 | 13057 |
|  | 16913 | 9997 | 29744 | 10107 | 29748 | 29746 | 22723 | 14234 | 2110 | 8575 | 10591 | 9773 |
|  | 9777 | 8670 | 11915 | 18424 | 9511 | 18564 | 20764 | 13787 | 18423 | 11187 | 18604 | 3516 |
|  | 20154 | 14600 | 14603 | 19437 | 26638 | 27689 | 27696 | 27693 | 22261 | 12113 | 10921 | 9824 |
|  | 7009 | 7004 | 8973 | 8978 | 6447 | 1337 | 1352 | 16043 | 21920 | 21961 | 8161 | 8211 |
|  | 26300 | 13172 | 13843 | 20552 | 12458 | 14142 | 9797 | 19787 | 3606 | 25773 | 16317 | 23816 |
|  | 3673 | 899 | 13278 | 22264 | 22235 | 22260 | 22267 | 17224 | 14236 | 10840 | 11111 | 11109 |
|  | 11107 | 19732 | 3976 | 5933 | 6842 | 28949 | 20695 | 9231 | 2267 | 22271 | 9587 | 27307 |
|  | 19107 | 21070 | 15001 | 21236 | 14427 | 27038 | 20250 | 12766 | 12763 | 6036 | 12377 | 9763 |
|  | 12793 | 507 | 14396 |  |  |  |  |  |  |  |  |  |
| 569: | 1581 | 16146 | 11925 | 5139 | 11665 | 14692 | 30172 |  |  |  |  |  |
| 570: | 1205 | 1202 | 23043 | 18478 | 21335 | 24048 | 24042 | 12899 | 18378 | 18376 | 6551 | 9413 |
|  | 9412 | 19940 | 19978 | 19981 | 2128 | 18413 | 16198 | 16668 | 3185 | 15855 | 9352 |
|  | 14616 | 2960 | 2967 | 2966 | 4462 | 25905 | 11227 | 28186 | 984 | 13539 | 20758 | 20789 |
|  | 20750 | 20753 | 20749 | 25229 | 28534 | 17690 | 22452 | 24103 | 19988 | 21788 | 25087 | 19912 |
|  | 21275 | 19982 | 19909 | 24881 | 24899 | 26679 | 18852 | 27639 | 12055 | 16381 | 1897 | 1894 |
|  | 1892 | 20060 | 7377 | 10185 | 12191 | 13610 | 6686 | 27612 | 27664 | 3919 | 27641 | 10110 |
|  | 28531 | 28470 | 2758 | 4227 | 10669 | 8133 | 24960 | 23679 | 11153 | 19321 | 30078 | 21051 |
|  | 17845 | 17557 | 1936 | 23577 | 27609 | 28429 | 27692 | 28464 | 27698 | 27667 | 28432 | 28424 |
|  | 27637 | 19872 | 26730 | 18303 | 18438 | 18412 | 10396 | 9203 | 29169 | 12043 | 1965 | 24374 |
|  | 25660 | 17724 | 16729 | 20884 | 2141 | 19907 | 22922 | 27089 | 2063 | 26239 | 19936 | 19119 |
|  | 21272 | 19915 | 19985 | 19916 | 18368 | 18306 | 18331 | 18333 | 18338 | 17515 | 18481 | 17665 |
|  | 16401 | 13021 | 427 | 23518 | 7850 |  |  |  |  |  |  |  |
| 571: | 15818 | 24500 | 6249 | 24365 | 21416 | 9058 | 5044 | 3647 | 14963 | 14493 | 20694 | 7254 |
|  | 20765 |  |  |  |  |  |  |  |  |  |  |  |
| 572: | 28807 | 27051 | 3150 | 20358 | 5777 | 13209 | 5111 | 9645 | 17113 | 16565 | 22552 | 16503 |
|  | 25832 | 29107 | 1460 | 14728 | 21817 | 17382 | 20312 | 10501 | 20673 | 3346 | 1922 | 10077 |
|  | 6744 | 26143 | 7881 | 8571 | 364 | 26287 | 15280 | 26997 | 9989 | 27429 | 4294 | 26013 |
|  | 754 | 22726 | 25117 |  |  |  |  |  |  |  |  |  |
| 573: | 8315 | 18414 | 30224 | 15804 | 2638 | 19500 | 17309 | 12992 | 30378 | 9019 | 1704 | 6981 |
|  | 7658 | 9420 | 23401 |  |  |  |  |  |  |  |  |  |
| 574: | 19688 | 10946 | 17787 | 18811 | 24157 | 19726 | 16146 | 16140 | 13361 | 26217 | 825 | 17239 |
|  | 11925 | 5139 | 1815 | 428 | 13932 | 5348 | 14692 | 376 | 9975 | 30172 | 569 | 19165 |
|  | 576 | 29573 |  |  |  |  |  |  |  |  |  |  |
| 575: | 4786 | 9635 | 22533 | 22517 | 6361 | 6393 | 742 | 9918 | 3287 | 10618 | 13765 | 22118 |
|  | 15728 | 12502 | 26571 | 17426 | 25481 | 6770 | 9626 | 2081 | 11885 | 24724 | 2078 | 13738 |
|  | 28822 | 8819 |  |  |  |  |  |  |  |  |  |  |
| 576: | 19688 | 10946 | 17787 | 18811 | 24157 | 19726 | 16146 | 16140 | 13361 | 26217 | 825 | 17239 |
|  | 11925 | 5139 | 1815 | 428 | 13932 | 5348 | 14692 | 376 | 9975 | 30172 | 569 | 19165 |
|  | 574 | 29573 |  |  |  |  |  |  |  |  |  |  |
| 577: | 11584 | 13724 | 29524 | 9554 | 16616 | 11861 | 29446 | 29504 | 29601 | 2685 | 2666 | 2692 |
|  | 1388 | 2697 | 1585 | 14288 | 1255 | 23869 | 7127 | 24502 | 19874 | 27071 | 12831 | 23261 |
|  | 4734 | 874 | 23045 | 23769 | 7502 | 28061 | 18457 | 15556 | 15559 | 15561 | 15555 | 15529 |
|  | 21912 | 15390 | 8535 | 8958 | 22252 | 24498 | 13117 | 25178 | 30459 | 15583 | 4752 | 23038 |
|  | 18254 | 7244 | 10345 | 20327 | 23212 | 5007 | 30091 | 7554 | 22684 | 5719 | 606 | 15301 |
|  | 14483 | 792 | 29861 | 15027 | 18648 | 7016 | 13651 | 1770 | 16899 | 16855 | 28048 | 662 |
|  | 18404 | 15455 | 14827 | 22321 | 11701 | 24050 | 10538 | 15416 | 15419 | 15425 | 15460 | 15427 |
|  | 15380 | 15459 | 2809 | 13727 | 17094 | 9390 | 1327 | 6658 | 9556 | 6697 |  |  |
| 578: | 11761 | 19089 | 16165 | 8711 | 2759 | 12674 | 13415 | 29879 | 7066 |  |  |  |
| 579: | 22555 | 27884 | 11448 | 8273 | 27880 | 8275 | 11446 | 27878 | 27874 | 3478 | 15805 | 11443 |
|  | 23102 | 23280 | 14976 | 1219 | 13309 | 22763 |  |  |  |  |  |  |
| 580: | 7938 | 7964 | 1841 | 14824 | 14760 | 24052 | 3138 | 28102 | 21222 | 21218 | 21226 | 13120 |
|  | 4265 | 5711 | 11048 | 27430 | 17350 | 25395 | 9698 | 14345 | 25391 | 19114 | 11354 | 25539 |
|  | 2802 | 28086 | 19052 | 1394 | 4583 | 3706 | 3705 | 5387 | 4585 | 14414 | 5998 | 1847 |
|  | 27344 | 16676 | 16678 | 22469 | 24958 | 7905 | 7870 | 3660 | 12098 | 9513 | 6150 |  |
| 581: | 12041 | 23443 | 2888 | 28895 | 11471 | 11483 | 11474 | 21745 | 12751 | 8116 | 16160 | 16162 |
|  | 17998 | 4000 | 27970 | 9384 | 5381 | 3441 | 24737 | 859 | 26362 | 24708 | 6811 | 6754 |
|  | 18178 | 22419 | 15989 | 15143 | 14642 | 1282 | 27419 | 18937 | 18587 | 23984 | 7343 | 15826 |
|  | 15863 | 17425 | 1009 | 8802 | 9588 | 17485 | 1240 | 10670 | 10668 | 20548 | 27277 |
|  | 9613 | 19477 | 15631 | 11051 | 11046 | 11023 | 10988 | 10990 | 11021 | 11017 | 10994 | 10992 |
|  | 11019 | 11052 | 11014 | 9124 | 29772 | 24903 | 30361 | 12677 | 12681 | 17414 | 12679 | 21760 |
|  | 22304 | 26366 | 7605 | 27534 | 6568 |  |  |  |  |  |  |  |
| 582: | 19546 | 7100 | 21078 | 29472 | 26206 | 14606 | 8808 | 9347 | 21542 | 10893 | 23028 | 28069 |
|  | 9435 | 27011 | 4314 | 15686 | 20175 | 18297 | 20143 | 6089 | 6122 | 27189 | 27017 | 26037 |
|  | 25820 | 24689 | 6779 | 23568 | 2628 | 19337 | 27084 | 30085 | 8185 | 3032 | 16480 | 5557 |
|  | 2421 | 18364 | 24072 | 19813 | 12996 | 10951 | 13094 | 7636 | 15739 | 29267 | 10609 | 16613 |
|  | 16763 | 26659 | 2575 | 17702 | 15594 | 12665 | 29225 | 8278 | 9180 | 28016 | 29556 | 25090 |
|  | 24005 | 9907 | 28287 | 24942 | 24941 | 5491 | 2270 | 16971 | 5215 | 5054 | 5062 | 5059 |
|  | 16969 | 22674 | 10175 | 10170 | 10172 | 10072 | 29929 | 10173 | 20423 | 14928 | 14922 | 8299 |
|  | 8043 | 26409 | 7503 | 3588 | 26584 | 28658 | 1029 | 12685 | 28830 | 25587 | 9165 | 17300 |
|  | 30326 | 23962 | 7436 | 12369 | 23509 | 16214 | 8176 | 29489 | 18480 | 2148 | 4847 | 19133 |
|  | 516 | 24058 | 10954 | 800 | 11217 |  |  |  |  |  |  |  |

TABLE 8-continued

| PEP SEQ ID NO: | homolog SEQ ID NOs | | | | | | | | | | |
|---|---|---|---|---|---|---|---|---|---|---|---|
| 583: | 25129 | 27368 | 25249 | 29970 | 4685 | 30235 | 4766 | 10275 | 29055 | 24740 | 20607 | 21313 |
| | 10701 | 19680 | 16488 | 9935 | 4015 | 8177 | 27951 | 25825 | 21512 | 20368 | 27128 | 9690 |
| | 4877 | 27413 | 15195 | 23828 | 20916 | 28202 | 14776 | 9064 | 21233 | 26231 | 20077 | 25077 |
| | 12008 | 9018 | 15501 | 12108 | 12002 | 11133 | 16009 | 26127 | 12026 | 11129 | 28917 | 7116 |
| | 30112 | 24073 | 16189 | 22672 | 22330 | 10924 | 27779 | 27954 | 1115 | 22933 | 1111 | 21195 |
| | 27916 | 24283 | 21081 | 30163 | 11168 | 19676 | 11985 | 4136 | 22696 | 7140 | 13287 | 24189 |
| | 3293 | 11578 | 16193 | 20573 | 23458 | 4617 | 4625 | 9003 | 3686 | 12420 | 6141 | 13450 |
| | 11577 | 11574 | 12862 | 11772 | 16870 | 29589 | 7287 | 7318 | 7322 | 27518 | 12423 | 6771 |
| | 29765 | 18959 | 771 | 6718 | 10234 | 29596 | 14176 | 7371 | 7640 | 14212 | 15272 | 23723 |
| | 10238 | 23465 | 1227 | 22251 | 16546 | 24889 | 29958 | 28823 | 8828 | 5655 | 25556 | 28380 |
| | 2635 | 12575 | 6971 | 15410 | 21856 | 22504 | 8340 | 18685 | 29258 | 9158 | 8072 | 29470 |
| | 18350 | 19267 | 2117 | 14539 | 725 | 3730 | 14559 | 10188 | 13289 | 15006 | 7581 | 5390 |
| | 22282 | 2261 | 10220 | 2021 | 22170 | 22172 | 22174 | 16620 | 13494 | 14407 | 21902 | 17265 |
| | 6756 | 12246 | 18575 | 21720 | 17791 | 3742 | 25238 | 7440 | 19956 | 4913 | 1764 | 19482 |
| | 23676 | 564 | 28187 | 21453 | 11680 | | | | | | | |
| 584: | 2555 | 25500 | 14030 | 22659 | 25613 | 8260 | 27377 | 29793 | 1177 | 23381 | 14036 | 15968 |
| | 21609 | 6826 | 5584 | 2182 | 28639 | 5929 | 1090 | 9967 | 16653 | 19423 | 6909 | 27061 |
| | 805 | 16595 | 11380 | 27033 | | | | | | | | |
| 585: | 16495 | 15818 | 18613 | 27890 | 10799 | 11700 | 27624 | 27254 | 9740 | 5044 | 6485 | 14963 |
| | 14493 | 4453 | 8639 | 8663 | 8638 | 8637 | 9491 | 30129 | 23337 | 20765 | 19015 | 16487 |
| 586: | 7759 | 1528 | 23333 | 853 | 16894 | 13376 | 11592 | 18242 | 15920 | 8992 | | |
| 587: | 20417 | 27886 | 19619 | 7800 | 1272 | 3823 | 7082 | 27564 | 15616 | 24116 | 14223 | 27721 |
| | 8014 | 22783 | 8325 | 24621 | 17123 | 20009 | 29665 | 28581 | 24641 | 24616 | 24828 | 13057 |
| | 16913 | 9997 | 29744 | 10107 | 29748 | 29746 | 22723 | 14234 | 2110 | 8575 | 10591 | 9773 |
| | 9777 | 8670 | 11915 | 18424 | 9511 | 18564 | 20764 | 13787 | 18423 | 11187 | 18604 | 3516 |
| | 20154 | 14600 | 14603 | 19437 | 26638 | 27689 | 27696 | 27693 | 22261 | 12113 | 10921 | 9824 |
| | 7009 | 7004 | 8973 | 8978 | 6447 | 1337 | 1352 | 16043 | 21920 | 21961 | 8161 | 8211 |
| | 26300 | 13172 | 13843 | 20552 | 12458 | 14142 | 9797 | 19787 | 3606 | 25773 | 16317 | 23816 |
| | 3673 | 899 | 13278 | 22264 | 22235 | 22260 | 22267 | 17224 | 14236 | 10840 | 11111 | 11109 |
| | 11107 | 19732 | 3976 | 5933 | 6842 | 28949 | 20695 | 9231 | 2267 | 22271 | 9587 | 27307 |
| | 19107 | 21070 | 15001 | 21236 | 14427 | 27038 | 20250 | 12766 | 12763 | 6036 | 12377 | 27914 |
| | 9763 | 12793 | 568 | | | | | | | | | |
| 588: | 26090 | 24906 | 7328 | 16079 | 13640 | 1998 | 3987 | 14369 | 10118 | 24547 | 10168 | 19534 |
| | 14201 | 4351 | 29751 | 23972 | 19048 | 19518 | 16929 | 12836 | 10980 | 5385 | 12514 | 8603 |
| | 21615 | 14006 | 9621 | 29755 | 3278 | 9131 | 13564 | 783 | 18177 | 14122 | 16367 | 23240 |
| | 18197 | 10484 | 27976 | 27790 | 10726 | 28360 | 7845 | 8361 | 7541 | 3978 | 10445 | 26641 |
| | 1937 | 8810 | 18305 | 17353 | 26604 | 14422 | 26491 | 13341 | 8502 | 7149 | 14121 | 22354 |
| | 27631 | 850 | 24218 | 22409 | 8455 | 30360 | 24294 | 14091 | 30220 | 23301 | 12792 | 17439 |
| | 5642 | 24682 | 2394 | 781 | 21304 | 19627 | 7391 | 21743 | 2420 | 8426 | 27392 | 19043 |
| | 22515 | 29067 | 5266 | 5679 | 8170 | 6456 | 10383 | 8388 | 22771 | 8450 | 17154 | 17655 |
| | 21229 | 10695 | 22850 | 20714 | 3703 | 27996 | 24666 | 29419 | 13898 | 25251 | 2927 | 968 |
| | 25866 | 11823 | 11437 | 11556 | 29559 | 28036 | 22558 | 28576 | 18030 | 644 | 20487 | 13123 |
| | 21755 | 11073 | 8138 | 4868 | 5476 | 24215 | 8521 | 23457 | 22084 | 29764 | 12464 | 14383 |
| | 27005 | 11776 | 28824 | 9025 | 18016 | 15103 | 18931 | 28602 | 8158 | 17472 | 1453 | 1990 |
| | 16594 | 2573 | 20483 | 22565 | 23359 | 4684 | 14747 | 21853 | 24807 | 9107 | 9108 | 22028 |
| | 24031 | 21991 | 26569 | 29011 | 5830 | 3328 | 15099 | 15130 | 21719 | 26251 | 13720 | 2076 |
| | 22740 | 19986 | 24231 | 21220 | 18601 | 2781 | 26295 | 4537 | 1807 | 15313 | 11247 | 9328 |
| | 2456 | 2455 | 2459 | 13267 | 13269 | 451 | 4730 | 9730 | 9757 | 9762 | 21426 | 14657 |
| | 11571 | 10874 | 15508 | 22276 | 22496 | 21391 | 21149 | 21996 | 21999 | 14338 | 14342 | 14140 |
| | 14341 | 14363 | 15131 | 6669 | 14372 | 14890 | 14882 | 14886 | 14908 | 30442 | 13868 | 10627 |
| | 14633 | 10628 | 10603 | 9996 | 18761 | 17083 | 26475 | 9727 | 16415 | 22604 | 16765 | 21893 |
| | 21349 | 22764 | 341 | 3311 | 21992 | 8269 | 18346 | 13382 | 24297 | 24316 | 13140 | 2970 |
| | 22223 | 763 | 16890 | 3910 | 16235 | 11545 | 28077 | 2792 | 23797 | 2309 | 7723 | 10108 |
| | 12589 | 10780 | 13561 | 10432 | 24018 | 30465 | 23985 | 23865 | 12964 | 15841 | 26552 | 12280 |
| | 10917 | | | | | | | | | | | |
| 589: | 21641 | 11914 | 23866 | 8645 | 13613 | 9312 | 23237 | 9134 | 23388 | 20043 | 2701 | 16767 |
| | 28224 | 13756 | 18982 | 19274 | 23559 | 11811 | 2974 | 2235 | 28082 | 19162 | 8555 | 18862 |
| | 24954 | 8256 | 20898 | 18136 | 10706 | 4529 | 15333 | 26671 | 4930 | 16619 | 29659 | 25935 |
| | 24554 | 12329 | 15453 | 22322 | 9282 | 7014 | 23385 | 24862 | 14339 | 14577 | 13104 | 29724 |
| | 6660 | | | | | | | | | | | |
| 590: | 1370 | 1803 | 10479 | 6604 | 11379 | 22320 | 2150 | 19084 | 8835 | 21367 | 3715 | 27142 |
| | 28468 | 16052 | 29977 | 20304 | 15104 | 17160 | 22606 | 11506 | 10642 | 20938 | 19470 | 5997 |
| | 2431 | 12142 | 10998 | 8140 | 2012 | 692 | | | | | | |
| 591: | 20634 | 29046 | 27023 | 27018 | 27020 | 15445 | 17319 | 8384 | 8435 | 8439 | 4475 | 26372 |
| | 26378 | 20484 | 17008 | 21911 | 1826 | 2381 | 27301 | 16213 | 17011 | 3572 | 27818 |
| | 17652 | 27668 | 7815 | 11633 | 10323 | 7206 | 6849 | 28423 | 21614 | 28759 | 10404 | 11171 |
| | 1722 | 14717 | 6437 | 5521 | 13143 | 26232 | 22628 | 28738 | 15781 | 15775 | 15777 | 23480 |
| | 13052 | 16215 | 17016 | 22902 | 27289 | 27188 | 24044 | 24290 | | | | |
| 592: | 21053 | 5637 | 13367 | 30097 | 30098 | 1714 | 4293 | 13481 | 14355 | 1206 | 1181 | 7897 |
| | 14745 | 9179 | 2803 | 2806 | 19460 | 10635 | 28838 | 25830 | 16687 | 19459 | 23427 | 9319 |
| | 15848 | 15846 | 12390 | 12391 | 10033 | 21274 | 8353 | 18944 | 2176 | 14748 | 9271 | 11074 |
| | 12439 | 7936 | 20697 | 13928 | 20737 | 15591 | 1381 | 1363 | 5045 | 5043 | 23810 | 15873 |
| | 18769 | 26971 | 26972 | 2831 | 9219 | 3214 | 3212 | 2833 | 16064 | 6039 | 24993 | 24991 |
| | 27439 | 27438 | 29207 | 1634 | 19383 | 24416 | 24418 | 16903 | 11802 | 13429 | 2494 | 28555 |
| | 28557 | 4328 | 3269 | 3272 | 14997 | 1597 | 27111 | 25193 | 9655 | 13046 | 13048 | 6270 |
| | 7198 | 27215 | 1146 | 26515 | 26517 | 21921 | 15283 | 27402 | 27868 | 9639 | 16209 | 8679 |
| | 15709 | 27332 | 20494 | 13930 | 5116 | 6353 | 7756 | 7601 | 8986 | 9515 | 1362 | 1365 |
| | 685 | 24332 | 25918 | 25928 | 20497 | 12076 | 973 | 974 | 7589 | 1314 | 2849 | 7200 |

TABLE 8-continued

| PEP SEQ ID NO: | homolog SEQ ID NOs | | | | | | | | | | |
|---|---|---|---|---|---|---|---|---|---|---|---|
| | 21813 | 9155 | 9156 | 10841 | 19587 | 19589 | 6171 | 8235 | 16570 | 3531 | 3526 | 8286 |
| | 3377 | 5657 | 22868 | 22870 | 1551 | 1553 | 26201 | 26375 | 6394 | 14686 | 14687 | 26817 |
| | 2903 | 10287 | 16363 | 11145 | 5246 | 5250 | 14737 | 23734 | 23730 | 21861 | 21859 | 26687 |
| | 29894 | 30434 | 30431 | 2899 | 2902 | 16334 | 5302 | 5298 | 9888 | 4303 | 10265 | 22367 |
| | 18580 | 14695 | 27846 | 17626 | 2109 | 6052 | 16127 | 30216 | 4367 | 6687 | 26267 | 24728 |
| | 24730 | 14722 | 14720 | 1445 | 27700 | 27697 | 1322 | 18938 | 17173 | 17172 | 14492 | 24191 |
| | 26309 | 26311 | 18431 | 18429 | 22637 | 22639 | 1746 | 841 | 19542 | 25007 | 23073 | 921 |
| | 8727 | 22508 | 11259 | 2295 | 28478 | 17819 | 26866 | 29146 | 1507 | 7960 | 7961 | 11492 |
| | 26369 | 26371 | 18436 | 5241 | 24911 | 10101 | 10102 | 7319 | 7323 | 10634 | 18983 | 29268 |
| | 29265 | 26149 | 26150 | 21925 | 21927 | 17972 | 18001 | 20748 | 20747 | 23042 | 30325 | 19845 |
| | 24599 | 4808 | 29229 | 14641 | 14643 | 6370 | 15708 | 15710 | 29633 | 29632 | 21113 | 21114 |
| | 11209 | 11213 | 22426 | 22424 | 29203 | 29204 | 29502 | 29488 | 4378 | 26546 | 26549 | 4062 |
| | 18589 | 26724 | 6332 | 23821 | 27135 | 22196 | 16034 | 11065 | 11709 | 23015 | 18600 | 2580 |
| | 29261 | 27119 | 27964 | 27971 | 11480 | 11481 | 9572 | 17430 | 17428 | 9575 | 7945 | 14729 |
| | 8825 | 26717 | 26720 | 9302 | 9326 | 18620 | 924 | 27200 | 20233 | 10699 | 27257 | 26880 |
| | 26881 | 12995 | 17825 | 17823 | 24741 | 22069 | 19432 | 19359 | 13970 | 3496 | 1711 | 23383 |
| | 21158 | 12866 | 30263 | 18787 | 26538 | 14868 | 4035 | 4388 | 10801 | 10632 | 25632 | 23963 |
| | 28612 | 23253 | 27927 | 1178 | 29132 | 20213 | 1016 | 14461 | 24758 | 23386 | 21388 | 5313 |
| | 5058 | 28289 | 4759 | 4761 | 4762 | 2437 | 12185 | 12187 | 18988 | 1713 | 28792 | 18380 |
| | 15839 | 14194 | 18840 | 4330 | 4864 | 8121 | 9335 | 10310 | 10638 | 18392 | 21281 | 20942 |
| | 20443 | 26148 | 20072 | 21300 | 12484 | 2275 | 25950 | 3671 | 29507 | 16628 | 10059 | 2250 |
| | 1723 | 882 | 29614 | 22890 | 7292 | 3148 | 16143 | 24227 | 8787 | 10741 | 1326 | 5613 |
| | 9289 | 9306 | 865 | 6419 | 4798 | 13774 | 17747 | 17712 | 708 | 16833 | 3004 | |
| | 17056 | 6800 | 2653 | 20042 | 17162 | 26198 | 26200 | 27852 | 24966 | 24968 | 11426 | 30306 |
| | 30308 | 5191 | 6541 | 20215 | 20217 | 1772 | 3268 | 4046 | 4053 | 4050 | 3207 | 3027 |
| | 3022 | 4057 | 3074 | 3029 | 3173 | 3168 | 12543 | 10664 | 21634 | 17128 | 6401 | 12365 |
| | 8519 | 13988 | 13986 | 30242 | 15429 | 9261 | 23736 | 7773 | 12871 | 20211 | 20212 | 2210 |
| | 10272 | 16332 | 16353 | 5091 | 25709 | 22283 | 2518 | 559 | 3861 | 19815 | 28848 | 16627 |
| | 1790 | 20457 | | | | | | | | | | |
| 593: | 23100 | 8437 | 16789 | 9184 | 9170 | 14972 | 26126 | 2782 | 2808 | 8912 | 12593 | 5659 |
| | 27751 | 17249 | 847 | 16077 | 17003 | 17564 | 19748 | 9675 | 16458 | 25308 | 11810 | 6462 |
| | 19004 | 23303 | 25333 | 8046 | 1432 | 22200 | 23141 | 1516 | 3596 | 26032 | 1858 | 3259 |
| | 28746 | 25829 | 23426 | 25373 | 17115 | 18882 | 24257 | 4938 | 22448 | 11228 | 22286 | 22389 |
| | 18549 | 21796 | 28404 | 16829 | 23612 | 23617 | 23616 | 23645 | 23590 | 25680 | 25614 | 3975 |
| | 18943 | 21410 | 15360 | 23410 | 8549 | 26330 | 4056 | 30346 | 24472 | 24445 | 15829 | 27029 |
| | 27626 | 7896 | 28162 | 7743 | 11962 | 15101 | 26380 | 30303 | 26492 | 1890 | 15003 | 15005 |
| | 17406 | 17853 | 5309 | 7867 | 3683 | 23220 | 12178 | 1817 | 12021 | 3159 | 5110 | 21308 |
| | 29714 | 30354 | 28815 | 2223 | 12072 | 23205 | 2188 | 19401 | 16746 | 23172 | 5164 | 19927 |
| | 20771 | 7518 | 23417 | 13391 | 12324 | 29494 | 4043 | 27813 | 29038 | 29780 | 28610 | 19153 |
| | 7533 | 13762 | 4157 | 16421 | 4895 | 27867 | 17568 | 17567 | 21063 | 16780 | 13258 | |
| | 11850 | 1334 | 24652 | 24325 | 18753 | 5836 | 16750 | 11824 | 20390 | 3170 | 13418 | 12249 |
| | 20037 | 15769 | 5466 | 11682 | 25338 | 15918 | 9169 | 14001 | 3135 | 16677 | 18384 | 2213 |
| | 9831 | 9001 | 2847 | 20465 | 14307 | 20286 | 10381 | 14305 | 30233 | 20568 | 24612 | 28359 |
| | 13523 | 11725 | 13899 | 677 | 3809 | 24421 | 12358 | 12047 | 11941 | 29944 | 10425 | 20270 |
| | 7425 | 12223 | 22959 | 25148 | 9300 | 8277 | 29986 | 21518 | 16545 | 25208 | 26145 | |
| 594: | 14081 | 8646 | 19510 | 3201 | 2969 | 21123 | 15598 | 14545 | 3412 | 24368 | 6958 | 8607 |
| | 10353 | | | | | | | | | | | |
| 595: | 3687 | 13637 | 6857 | 13434 | 15892 | 15230 | 25954 | 18782 | 18783 | 18779 | 26319 | 3515 |
| | 1014 | 21404 | 29758 | 1644 | 27147 | 15850 | 24399 | 9128 | 9154 | 16774 | 3773 | 27893 |
| | 20486 | 12084 | 13600 | 29024 | 13597 | 29026 | 12676 | 4516 | 12392 | 10606 | 3631 | 16048 |
| | 10151 | 20647 | 7798 | 14866 | 22177 | 6793 | 19027 | 4906 | 27511 | 7809 | 25075 | 26399 |
| | 26044 | 1108 | 21212 | 3720 | 19569 | 14929 | 10537 | 11077 | 24782 | 21269 | 13233 | 23192 |
| | 10539 | 24375 | 28382 | 7724 | 29220 | 7674 | 24131 | 28806 | 6795 | 28135 | 6830 | 26699 |
| | 14196 | 28182 | 7465 | 6291 | 15138 | 29628 | 1123 | 15229 | 14863 | 15755 | 2030 | 14862 |
| | 14269 | 17078 | 9228 | 4792 | 13137 | 8362 | 6931 | 8252 | 3767 | 14734 | 2995 | 13859 |
| | 1957 | 3616 | 12222 | 2724 | 8691 | 15141 | 20150 | 4991 | 22712 | 22160 | 13892 | 14933 |
| | 18671 | 18647 | 3672 | 8714 | 21442 | 25038 | 11854 | 6682 | 26742 | 6623 | 12833 | 1237 |
| | 10466 | 10469 | 886 | 26275 | 17293 | 25839 | 20091 | 13855 | 18348 | 5981 | 13646 | 12691 |
| | 10633 | 15139 | | | | | | | | | | |
| 596: | 11135 | 17513 | 29853 | 2950 | 5458 | 29779 | 20336 | 13241 | 4799 | 29016 | 17076 | 11780 |
| | 4104 | 12952 | 11732 | 12095 | 4999 | 16170 | 5457 | 3045 | 25718 | 6165 | 16051 | 8403 |
| | 18273 | 6347 | 3040 | 24142 | 6392 | 3814 | 4226 | 20621 | 13649 | 27722 | 19640 | 9479 |
| | 26129 | 15632 | 8041 | 25934 | 21263 | 12094 | 3514 | 30043 | 15134 | 24774 | 25723 | 29058 |
| | 14294 | 10387 | 22923 | 13706 | 8226 | 14883 | 18231 | | | | | |

Example 7. Selection of Transgenic Plants with Enhanced Agronomic Trait(s)

This example illustrates identification of plant cells of the invention by screening derived plants and seeds for enhanced trait. Transgenic seed and plants in corn, soybean, cotton or canola with recombinant DNA constructs identified in Table 2 are prepared by plant cells transformed with DNA that is stably integrated into the genome of the corn cell. Progeny transgenic plants and seed of the transformed plant cells are screened for enhanced water use efficiency, enhanced cold tolerance, increased yield, enhanced nitrogen use efficiency, enhanced seed protein and enhanced seed oil as compared to control plants A. Selection for Enhanced Nitrogen Use Efficiency Transgenic corn seeds provided by the present invention are planted in fields with three levels of nitrogen (N) fertilizer being applied, i.e. low level (0 N), medium level (80 lb/ac) and high level (180 lb/ac). A variety of physiological traits are monitored. Plants with enhanced NUE provide higher yield as compared to control plants.

B. Selection for Increased Yield

Effective selection of enhanced yielding transgenic plants uses hybrid progeny of the transgenic plants for corn, cotton, and canola, or inbred progeny of transgenic plants for soybeanplants plant such as corn, cotton, canola, or inbred plant such as soy, canola and cottoncotton over multiple locations with plants grown under optimal production management practices, and maximum pest control. A useful target for improved yield is a 5% to 10% increase in yield as compared to yield produced by plants grown from seed for a control plant. Selection methods may be applied in multiple and diverse geographic locations, for example up to 16 or more locations, over one or more planting seasons, for example at least two planting seasons, to statistically distinguish yield improvement from natural environmental effects.

In one field trial, transgenic corn plants comprising corn G1543 like 2 transgene as set forth in NUC SEQ ID NO: 74 under a tissue preferred promoter, such as green tissue promoter, have been shown to have an increased yield.

C. Selection for Enhanced Water Use Efficiency (WUE)

The selection process imposes a water withholding period to induce stress drought followed by watering. For example, for corn, a useful selection process imposes 3 drought/rewater cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

D. Selection for Growth Under Cold Stress (1) Cold germination assay—Trays of transgenic and control seeds are placed in a growth chamber at 9.7° C. for 24 days (no light). Seeds having higher germination rates as compared to the control are identified.

(2) Cold field efficacy trial—A cold field efficacy trial is used to identify gene constructs that confer enhanced cold vigor at germination and early seedling growth under early spring planting field conditions in conventional-till and simulated no-till environments. Seeds are planted into the ground around two weeks before local farmers begin to plant corn so that a significant cold stress is exerted onto the crop, named as cold treatment. Seeds also are planted under local optimal planting conditions such that the crop has little or no exposure to cold condition, named as normal treatment. At each location, seeds are planted under both cold and normal conditions with 3 repetitions per treatment. Two temperature monitors are set up at each location to monitor both air and soil temperature daily.

Seed emergence is defined as the point when the growing shoot breaks the soil surface. The number of emerged seedlings in each plot is counted everyday from the day the earliest plot begins to emerge until no significant changes in emergence occur. In addition, for each planting date, the latest date when emergence is 0 in all plots is also recorded. Seedling vigor is also rated at V3-V4 stage before the average of corn plant height reaches 10 inches, with 1=excellent early growth, 5=Average growth and 9=poor growth. Days to 50% emergence, maximum percent emergence and seedling vigor are used to determine plants with enhanced cold tolerance.

E. Screens for Transgenic Plant Seeds with Increased Protein and/or Oil Levels

This example sets forth a high-throughput selection for identifying plant seeds with improvement in seed composition using the Infratec 1200 series Grain Analyzer, which is a near-infrared transmittance spectrometer used to determine the composition of a bulk seed sample (Table 9). Near infrared analysis is a non-destructive, high-throughput method that can analyze multiple traits in a single sample scan. An NIR calibration for the analytes of interest is used to predict the values of an unknown sample. The NIR spectrum is obtained for the sample and compared to the calibration using a complex chemometric software package that provides predicted values as well as information on how well the sample fits in the calibration.

Infratec Model 1221, 1225, or 1227 with transport module by Foss North America is used with cuvette, item #1000-4033, Foss North America or for small samples with small cell cuvette, Foss standard cuvette modified by Leon Girard Co. Corn and soy check samples of varying composition maintained in check cell cuvettes are supplied by Leon Girard Co. NIT collection software is provided by Maximum Consulting Inc. Software. Calculations are performed automatically by the software. Seed samples are received in packets or containers with barcode labels from the customer. The seed is poured into the cuvettes and analyzed as received.

TABLE 9

| | |
|---|---|
| Typical sample(s): | Whole grain corn and soybean seeds |
| Analytical time to run method: | Less than 0.75 min per sample |
| Total elapsed time per run: | 1.5 minute per sample |
| Typical and minimum sample size: | Corn typical: 50 cc; minimum 30 cc<br>Soybean typical: 50 cc; minimum 5 cc |
| Typical analytical range: | Determined in part by the specific calibration.<br>Corn - moisture 5-15%, oil 5-20%, protein 5-30%, starch 50-75%, and density 1.0-1.3%.<br>Soybean - moisture 5-15%, oil 15-25%, and protein 35-50%. |

Example 8. Consensus Sequence

This example illustrates the identification of consensus amino acid sequence for the proteins and homologs encoded by DNA that is used to prepare the transgenic seed and plants of this invention having enhanced agronomic traits.

ClustalW program was selected for multiple sequence alignments of the amino acid sequence of SEQ ID NO: 301 and its 20 homologs. Three major factors affecting the sequence alignments dramatically are (1) protein weight matrices; (2) gap open penalty; (3) gap extension penalty. Protein weight matrices available for ClustalW program include Blosum, Pam and Gonnet series. Those parameters with gap open penalty and gap extension penalty were extensively tested. On the basis of the test results, Blosum weight matrix, gap open penalty of 10 and gap extension penalty of 1 were chosen for multiple sequence alignment. FIG. 1 shows the sequences of SEQ ID NO: 301, its homologs and the consensus sequence (SEQ ID NO: 30526) at the end. The symbols for consensus sequence are (1) uppercase letters for 100% identity in all positions of multiple sequence alignment output; (2) lowercase letters for >=70% identity; symbol; (3) "X" indicated <70% identity; (4) dashes "-" meaning that gaps were in >=70% sequences.

The consensus amino acid sequence can be used to identify DNA corresponding to the full scope of this invention that is useful in providing transgenic plants, for example corn and soybean plants with enhanced agronomic traits, for example improved nitrogen use efficiency, improved yield, improved water use efficiency and/or improved growth under cold stress, due to the expression in the plants of DNA encoding a protein with amino acid sequence identical to the consensus amino acid sequence.

Example 9. Identification of Amino Acid Domain by Pfam Analysis

This example illustrates the identification of domain and domain module by Pfam analysis.

The amino acid sequence of the expressed proteins that are shown to be associated with an enhanced trait are analyzed for Pfam protein family against the current Pfam collection of multiple sequence alignments and hidden Markov models using the HMMER software in the appended computer listing. The Pfam protein domains and modules for the proteins of SEQ ID NO: 299 through 596 are shown in Tables 10, 11 and 12. The Hidden Markov model databases for the identified patent families are also in the appended computer listing allowing identification of other homologous proteins and their cognate encoding DNA to enable the full breadth of the invention for a person of ordinary skill in the art. Certain proteins are identified by a single Pfam domain and others by multiple Pfam domains. For instance, the protein with amino acids of SEQ ID NO: 299 is characterized by three Pfam domains, i.e. KNOX1, KNOX2 and ELK.

TABLE 10

Pfam annotation

| PEP SEQ ID NO | Gene ID | Pfam domain name | Begin | Stop | Score | E-value |
|---|---|---|---|---|---|---|
| 299 | PHE0007721__18998.pep | KNOX1 | 102 | 146 | 90.4 | 5.50E−24 |
| 299 | PHE0007721__18998.pep | KNOX2 | 153 | 204 | 101.2 | 3.10E−27 |
| 299 | PHE0007721__18998.pep | ELK | 242 | 263 | 37 | 6.50E−08 |
| 300 | PHE0007756__18009.pep | RPE65 | 105 | 591 | 864 | 7.30E−257 |
| 302 | PHE0004988__15925.pep | F-box | 4 | 52 | 23.7 | 0.00064 |
| 302 | PHE0004988__15925.pep | LRR_1 | 157 | 179 | 9.7 | 4.4 |
| 302 | PHE0004988__15925.pep | LRR_2 | 290 | 314 | 14.1 | 0.19 |
| 303 | PHE0007140__21771.pep | MtN3_slv | 9 | 98 | 98.2 | 2.50E−26 |
| 303 | PHE0007140__21771.pep | MtN3_slv | 134 | 221 | 73.6 | 6.20E−19 |
| 304 | PHE0006823__16403.pep | Globin | 10 | 149 | 102.6 | 1.10E−27 |
| 305 | PHE0007440__22555.pep | Miro | 14 | 128 | 88.4 | 2.20E−23 |
| 305 | PHE0007440__22555.pep | Ras | 14 | 175 | 332.3 | 8.40E−97 |
| 306 | PHE0000206__22432.pep | Pkinase | 79 | 337 | 342.2 | 8.80E−100 |
| 306 | PHE0000206__22432.pep | efhand | 384 | 412 | 25 | 0.00026 |
| 306 | PHE0000206__22432.pep | efhand | 456 | 484 | 24.9 | 0.00028 |
| 306 | PHE0000206__22432.pep | efhand | 490 | 518 | 35.1 | 2.40E−07 |
| 307 | PHE0000598__16824.pep | HLH | 385 | 434 | 54.6 | 3.30E−13 |
| 308 | PHE0007590__17883.pep | S1 | 2 | 70 | 92.7 | 1.10E−24 |
| 309 | PHE0007588__17881.pep | S1 | 2 | 86 | 73.5 | 6.50E−19 |
| 310 | PHE0007592__17885.pep | S1 | 1 | 75 | 48 | 3.20E−11 |
| 311 | PHE0007587__17880.pep | S1 | 3 | 75 | 106.6 | 7.10E−29 |
| 312 | PHE0007624__17923.pep | S1 | 2 | 72 | 45.6 | 1.70E−10 |
| 312 | PHE0007624__17923.pep | eIf-1a | 5 | 70 | 134.9 | 2.20E−37 |
| 313 | PHE0007591__17884.pep | S1 | 2 | 68 | 63.9 | 5.20E−16 |
| 314 | PHE0007623__17922.pep | CN_hydrolase | 11 | 184 | 166.3 | 7.50E−47 |
| 315 | PHE0007583__17871.pep | MtN3_slv | 9 | 98 | 102.2 | 1.50E−27 |
| 315 | PHE0007583__17871.pep | MtN3_slv | 132 | 218 | 112.8 | 1.00E−30 |
| 316 | PHE0006618__16146.pep | S10_plectin | 3 | 98 | 240.6 | 3.40E−69 |
| 317 | PHE0006791__16374.pep | GUN4 | 84 | 227 | 308.7 | 1.00E−89 |
| 318 | PHE0007620__17918.pep | peroxidase | 89 | 321 | 192.4 | 1.10E−54 |
| 319 | PHE0006659__16195.pep | MFS_1 | 10 | 391 | 111.5 | 2.50E−30 |
| 321 | PHE0006274__15867.pep | E2F_TDP | 130 | 195 | 135.8 | 1.10E−37 |
| 322 | PHE0006637__16166.pep | PP2C | 7 | 305 | 255.6 | 1.00E−73 |
| 323 | PHE0006926__16815.pep | VPS28 | 18 | 209 | 281.8 | 1.40E−81 |
| 324 | PHE0006821__16402.pep | PALP | 49 | 358 | −65.8 | 0.00015 |
| 325 | PHE0007687__18057.pep | p450 | 35 | 462 | 124 | 4.20E−34 |
| 326 | PHE0007642__17999.pep | PAS | 186 | 300 | 15.6 | 0.014 |
| 326 | PHE0007642__17999.pep | PAS_3 | 211 | 303 | 25.3 | 0.00022 |
| 326 | PHE0007642__17999.pep | PAS | 464 | 578 | 17.8 | 0.0089 |
| 326 | PHE0007642__17999.pep | PAS_3 | 489 | 581 | 23.5 | 0.00052 |
| 326 | PHE0007642__17999.pep | Pkinase | 663 | 952 | 269.7 | 5.80E−78 |
| 327 | PHE0007677__18052.pep | FAD_binding_3 | 5 | 372 | −96.1 | 4.10E−05 |
| 328 | PHE0007644__18001.pep | LRRNT_2 | 23 | 64 | 49.2 | 1.40E−11 |
| 328 | PHE0007644__18001.pep | LRR_1 | 97 | 119 | 10.5 | 3.1 |
| 328 | PHE0007644__18001.pep | LRR_1 | 121 | 143 | 14.4 | 0.42 |
| 328 | PHE0007644__18001.pep | LRR_1 | 145 | 167 | 12.1 | 1.5 |
| 328 | PHE0007644__18001.pep | LRR_1 | 169 | 192 | 13 | 1.1 |
| 328 | PHE0007644__18001.pep | LRR_1 | 194 | 216 | 14.1 | 0.52 |
| 328 | PHE0007644__18001.pep | Pkinase | 414 | 716 | 57.1 | 5.60E−14 |
| 329 | PHE0007640__17992.pep | CorA | 66 | 448 | 438.4 | 9.30E−129 |
| 330 | PHE0007678__18053.pep | 4HBT | 66 | 151 | 56.4 | 9.40E−14 |
| 331 | PHE0007649__18006.pep | Ank | 108 | 140 | 50.4 | 6.20E−12 |
| 331 | PHE0007649__18006.pep | Pkinase | 196 | 455 | 113 | 8.80E−31 |

TABLE 10-continued

Pfam annotation

| PEP SEQ ID NO | Gene ID | Pfam domain name | Begin | Stop | Score | E-value |
|---|---|---|---|---|---|---|
| 331 | PHE0007649__18006.pep | Pkinase_Tyr | 196 | 455 | 94.9 | 2.40E−25 |
| 332 | PHE0006726__16298.pep | WD40 | 45 | 83 | 30.2 | 7.30E−06 |
| 332 | PHE0006726__16298.pep | WD40 | 135 | 173 | 38.6 | 2.10E−08 |
| 333 | PHE0006218__8776.pep | Pyr_redox_2 | 85 | 370 | 163.7 | 4.70E−46 |
| 333 | PHE0006218__8776.pep | Pyr_redox | 231 | 325 | 93.9 | 4.80E−25 |
| 333 | PHE0006218__8776.pep | Thioredoxin | 423 | 528 | 25 | 1.50E−06 |
| 333 | PHE0006218__8776.pep | Glutaredoxin | 446 | 508 | 27.6 | 4.30E−05 |
| 335 | PHE0002554__17876.pep | Chloroa_b-bind | 63 | 261 | 263.3 | 5.00E−76 |
| 336 | PHE0006807__16388.pep | CCT | 352 | 390 | 76 | 1.20E−19 |
| 337 | PHE0003359__8487.pep | p450 | 51 | 489 | 120.5 | 4.90E−33 |
| 338 | PHE0006542__15765.pep | PMSR | 92 | 245 | 271 | 2.30E−78 |
| 339 | PHE0007622__17921.pep | Spermine_synth | 34 | 279 | 249.7 | 6.10E−72 |
| 340 | PHE0007630__17956.pep | 2OG-FeII_Oxy | 190 | 291 | 149.7 | 7.90E−42 |
| 341 | PHE0007593__17886.pep | Spermine_synth | 28 | 273 | 503.6 | 2.20E−148 |
| 342 | PHE0006475__15588.pep | PsbQ | 3 | 162 | 209.5 | 7.60E−60 |
| 343 | PHE0007619__17915.pep | MBD | 11 | 84 | 65.4 | 1.80E−16 |
| 344 | PHE0006846__16447.pep | Sterol_desat | 1 | 186 | 76.3 | 9.30E−20 |
| 345 | PHE0007584__17874.pep | MBD | 4 | 77 | 81.3 | 3.00E−21 |
| 346 | PHE0003695__17913.pep | LRRNT_2 | 23 | 64 | 41.6 | 2.80E−09 |
| 346 | PHE0003695__17913.pep | LRR_1 | 93 | 115 | 14.3 | 0.45 |
| 346 | PHE0003695__17913.pep | LRR_1 | 117 | 139 | 18.3 | 0.028 |
| 346 | PHE0003695__17913.pep | LRR_1 | 141 | 163 | 9.2 | 5.5 |
| 346 | PHE0003695__17913.pep | LRR_1 | 165 | 186 | 12.7 | 1.2 |
| 346 | PHE0003695__17913.pep | LRR_1 | 189 | 211 | 10.1 | 3.6 |
| 346 | PHE0003695__17913.pep | LRR_1 | 213 | 235 | 9.8 | 4.3 |
| 346 | PHE0003695__17913.pep | LRR_1 | 237 | 259 | 14.8 | 0.32 |
| 346 | PHE0003695__17913.pep | LRR_1 | 260 | 281 | 10.6 | 2.9 |
| 346 | PHE0003695__17913.pep | LRR_1 | 284 | 306 | 17.4 | 0.053 |
| 346 | PHE0003695__17913.pep | LRR_1 | 308 | 330 | 13.8 | 0.65 |
| 346 | PHE0003695__17913.pep | LRR_1 | 332 | 354 | 19.3 | 0.014 |
| 346 | PHE0003695__17913.pep | LRR_1 | 356 | 378 | 9 | 5.8 |
| 346 | PHE0003695__17913.pep | LRR_1 | 380 | 402 | 15.7 | 0.17 |
| 346 | PHE0003695__17913.pep | LRR_1 | 404 | 426 | 11.8 | 1.8 |
| 346 | PHE0003695__17913.pep | LRR_1 | 428 | 450 | 18.8 | 0.02 |
| 346 | PHE0003695__17913.pep | LRR_1 | 452 | 474 | 13.2 | 0.93 |
| 346 | PHE0003695__17913.pep | LRR_1 | 476 | 498 | 13.1 | 1 |
| 346 | PHE0003695__17913.pep | LRR_1 | 500 | 521 | 10.4 | 3.3 |
| 346 | PHE0003695__17913.pep | LRR_1 | 523 | 542 | 14.4 | 0.42 |
| 346 | PHE0003695__17913.pep | Pkinase | 648 | 917 | 111.8 | 2.00E−30 |
| 346 | PHE0003695__17913.pep | Pkinase_Tyr | 648 | 914 | 90.4 | 5.40E−24 |
| 347 | PHE0003695__17879.pep | LRRNT_2 | 23 | 64 | 41.6 | 2.80E−09 |
| 347 | PHE0003695__17879.pep | LRR_1 | 93 | 115 | 14.3 | 0.45 |
| 347 | PHE0003695__17879.pep | LRR_1 | 117 | 139 | 18.3 | 0.028 |
| 347 | PHE0003695__17879.pep | LRR_1 | 141 | 163 | 9.2 | 5.5 |
| 347 | PHE0003695__17879.pep | LRR_1 | 165 | 186 | 12.7 | 1.2 |
| 347 | PHE0003695__17879.pep | LRR_1 | 189 | 211 | 10.1 | 3.6 |
| 347 | PHE0003695__17879.pep | LRR_1 | 213 | 235 | 9.8 | 4.3 |
| 347 | PHE0003695__17879.pep | LRR_1 | 237 | 259 | 14.8 | 0.32 |
| 347 | PHE0003695__17879.pep | LRR_1 | 260 | 281 | 10.6 | 2.9 |
| 347 | PHE0003695__17879.pep | LRR_1 | 284 | 306 | 17.4 | 0.053 |
| 347 | PHE0003695__17879.pep | LRR_1 | 308 | 330 | 13.8 | 0.65 |
| 347 | PHE0003695__17879.pep | LRR_1 | 332 | 354 | 19.3 | 0.014 |
| 347 | PHE0003695__17879.pep | LRR_1 | 356 | 378 | 9 | 5.8 |
| 347 | PHE0003695__17879.pep | LRR_1 | 380 | 402 | 15.7 | 0.17 |
| 347 | PHE0003695__17879.pep | LRR_1 | 404 | 426 | 11.8 | 1.8 |
| 347 | PHE0003695__17879.pep | LRR_1 | 428 | 450 | 18.8 | 0.02 |
| 347 | PHE0003695__17879.pep | LRR_1 | 452 | 474 | 13.2 | 0.93 |
| 347 | PHE0003695__17879.pep | LRR_1 | 476 | 498 | 13.1 | 1 |
| 347 | PHE0003695__17879.pep | LRR_1 | 500 | 521 | 10.4 | 3.3 |
| 347 | PHE0003695__17879.pep | LRR_1 | 523 | 542 | 14.4 | 0.42 |
| 347 | PHE0003695__17879.pep | Pkinase | 648 | 917 | 111.8 | 2.00E−30 |
| 347 | PHE0003695__17879.pep | Pkinase_Tyr | 648 | 914 | 90.4 | 5.40E−24 |
| 349 | PHE0007645__18002.pep | AP2 | 115 | 180 | 156.4 | 7.20E−44 |
| 350 | PHE0006784__16366.pep | PALP | 12 | 301 | 453.6 | 2.50E−133 |
| 351 | PHE0006171__16491.pep | Glyoxalase | 70 | 214 | 136.8 | 5.90E−38 |
| 353 | PHE0006906__16796.pep | Proteasome | 10 | 206 | 145.9 | 1.00E−40 |
| 354 | PHE0006649__16180.pep | AP2 | 46 | 110 | 149.5 | 8.60E−42 |
| 355 | PHE0006809__16390.pep | Prismane | 1 | 548 | 886.8 | 9.80E−264 |
| 356 | PHE0006918__16808.pep | SWIM | 321 | 353 | 42.8 | 1.10E−09 |
| 357 | PHE0007813__18219.pep | MtN3_slv | 9 | 98 | 79.8 | 8.50E−21 |
| 357 | PHE0007813__18219.pep | MtN3_slv | 132 | 218 | 125.3 | 1.80E−34 |
| 359 | PHE0006825__16405.pep | Cytochrom_C552 | 27 | 476 | 1333.6 | 0 |
| 360 | PHE0006964__16864.pep | tRNA_anti | 43 | 122 | 55.2 | 2.10E−13 |
| 360 | PHE0006964__16864.pep | tRNA-synt_2 | 140 | 557 | 208.2 | 1.90E−59 |

TABLE 10-continued

Pfam annotation

| PEP SEQ ID NO | Gene ID | Pfam domain name | Begin | Stop | Score | E-value |
|---|---|---|---|---|---|---|
| 361 | PHE0008105_18407.pep | Histone | 152 | 225 | 69.9 | 8.40E−18 |
| 361 | PHE0008105_18407.pep | CBFD_NFYB_HMF | 158 | 222 | 77.9 | 3.10E−20 |
| 362 | PHE0006630_16159.pep | Ldh_1_N | 90 | 239 | 202 | 1.30E−57 |
| 362 | PHE0006630_16159.pep | Ldh_1_C | 241 | 413 | 258.1 | 1.80E−74 |
| 363 | PHE0006966_16868.pep | DNA_photolyase | 12 | 183 | 298.7 | 1.10E−86 |
| 363 | PHE0006966_16868.pep | FAD_binding_7 | 214 | 492 | 536.3 | 3.30E−158 |
| 365 | PHE0006608_16123.pep | GSHPx | 42 | 150 | 237.8 | 2.30E−68 |
| 366 | PHE0010462_21459.pep | NUDIX | 17 | 159 | 111.7 | 2.20E−30 |
| 366 | PHE0010462_21459.pep | NUDIX | 190 | 322 | 100.5 | 4.90E−27 |
| 367 | PHE0009211_21774.pep | Auxin_inducible | 1 | 106 | 149.5 | 8.80E−42 |
| 368 | PHE0006256_8775.pep | RPE65 | 105 | 591 | 864.5 | 5.10E−257 |
| 369 | PHE0006989_16918.pep | Pkinase | 88 | 396 | 224.8 | 1.90E−64 |
| 370 | PHE0007649_18166.pep | Ank | 108 | 140 | 50.4 | 6.20E−12 |
| 370 | PHE0007649_18166.pep | Pkinase | 196 | 455 | 115.1 | 2.00E−31 |
| 370 | PHE0007649_18166.pep | Pkinase_Tyr | 196 | 455 | 98.9 | 1.50E−26 |
| 371 | PHE0006708_16264.pep | DEAD | 57 | 223 | 202.7 | 8.40E−58 |
| 371 | PHE0006708_16264.pep | Helicase_C | 291 | 367 | 127.8 | 3.10E−35 |
| 372 | PHE0001117_19094.pep | Homeobox | 79 | 133 | 68.2 | 2.70E−17 |
| 372 | PHE0001117_19094.pep | HALZ | 134 | 178 | 66.7 | 7.20E−17 |
| 373 | PHE0006266_8814.pep | Fe_bilin_red | 16 | 244 | 209.5 | 7.50E−60 |
| 374 | PHE0006795_16378.pep | Na_H_antiport_1 | 4 | 380 | 875.9 | 1.90E−260 |
| 375 | PHE0006956_16853.pep | Molybdop_Fe4S4 | 2 | 56 | 92 | 1.90E−24 |
| 375 | PHE0006956_16853.pep | Molybdopterin | 59 | 482 | 377.8 | 1.60E−110 |
| 375 | PHE0006956_16853.pep | Molydop_binding | 578 | 689 | 159.8 | 7.10E−45 |
| 375 | PHE0006956_16853.pep | Fer2_BFD | 825 | 877 | 62 | 2.00E−15 |
| 377 | PHE0006824_16404.pep | Globin | 14 | 154 | 93.4 | 7.00E−25 |
| 378 | PHE0006812_16393.pep | Bac_globin | 3 | 118 | 188.4 | 1.70E−53 |
| 379 | PHE0006815_16396.pep | Bac_globin | 26 | 146 | 191.4 | 2.10E−54 |
| 380 | PHE0006806_16387.pep | Bac_globin | 26 | 146 | 196.8 | 5.10E−56 |
| 381 | PHE0006624_16153.pep | NAD_binding_2 | 3 | 178 | 282.5 | 7.90E−82 |
| 381 | PHE0006624_16153.pep | 6PGD | 182 | 473 | 713.8 | 1.20E−211 |
| 382 | PHE0005006_15823.pep | Chloroa_b-bind | 63 | 242 | 241.4 | 1.90E−69 |
| 384 | PHE0006683_16229.pep | Response_reg | 10 | 151 | 73.8 | 5.40E−19 |
| 385 | PHE0006884_16703.pep | Glyco_transf_5 | 83 | 344 | 462.7 | 4.80E−136 |
| 385 | PHE0006884_16703.pep | Glycos_transf_1 | 384 | 567 | 40.2 | 7.10E−09 |
| 386 | PHE0006691_16237.pep | NAD_Gly3P_dh_N | 6 | 165 | 285 | 1.40E−82 |
| 386 | PHE0006691_16237.pep | ApbA | 8 | 169 | 6.6 | 0.00011 |
| 386 | PHE0006691_16237.pep | NAD_Gly3P_dh_C | 183 | 327 | 289.1 | 8.20E−84 |
| 387 | PHE0006790_16372.pep | Rieske | 220 | 317 | 96.7 | 7.10E−26 |
| 387 | PHE0006790_16372.pep | PaO | 408 | 507 | 180.7 | 3.60E−51 |
| 388 | PHE0009143_19932.pep | Histone_HNS | 21 | 129 | 170.1 | 5.70E−48 |
| 389 | PHE0008406_18830.pep | AA_permease | 57 | 511 | 619.8 | 2.40E−183 |
| 390 | PHE0008279_18708.pep | Mit_rib_S27 | 14 | 93 | 135.3 | 1.70E−37 |
| 391 | PHE0009142_19931.pep | Histone_HNS | 21 | 130 | 175.1 | 1.70E−49 |
| 393 | PHE0007639_17991.pep | ELFV_dehydrog_N | 84 | 214 | 298.9 | 9.20E−87 |
| 393 | PHE0007639_17991.pep | ELFV_dehydrog | 229 | 474 | 469.7 | 3.60E−138 |
| 394 | PHE0007646_18170.pep | F-box | 36 | 83 | 51.8 | 2.20E−12 |
| 394 | PHE0007646_18170.pep | Kelch_1 | 131 | 185 | 25.1 | 0.00026 |
| 394 | PHE0007646_18170.pep | Kelch_1 | 187 | 233 | 44.2 | 4.40E−10 |
| 394 | PHE0007646_18170.pep | Kelch_2 | 187 | 233 | 26.1 | 0.00012 |
| 395 | PHE0007765_18182.pep | GST_N | 5 | 79 | 69.6 | 1.00E−17 |
| 395 | PHE0007765_18182.pep | GST_C | 101 | 204 | 28.8 | 1.90E−05 |
| 396 | PHE0008167_18465.pep | Pkinase | 8 | 262 | 210 | 5.60E−60 |
| 396 | PHE0008167_18465.pep | Pkinase_Tyr | 8 | 262 | 247.9 | 2.10E−71 |
| 398 | PHE0008183_18479.pep | LRRNT_2 | 23 | 66 | 49.3 | 1.30E−11 |
| 398 | PHE0008183_18479.pep | LRR_1 | 71 | 93 | 12.1 | 1.6 |
| 398 | PHE0008183_18479.pep | LRR_1 | 95 | 117 | 10.3 | 3.3 |
| 398 | PHE0008183_18479.pep | LRR_1 | 119 | 142 | 13 | 1 |
| 398 | PHE0008183_18479.pep | LRR_1 | 144 | 166 | 19.5 | 0.012 |
| 398 | PHE0008183_18479.pep | LRR_1 | 168 | 190 | 10.6 | 3 |
| 398 | PHE0008183_18479.pep | LRR_1 | 192 | 214 | 8.8 | 6.4 |
| 398 | PHE0008183_18479.pep | LRR_1 | 289 | 311 | 17.3 | 0.055 |
| 398 | PHE0008183_18479.pep | LRR_1 | 313 | 335 | 10.6 | 2.9 |
| 398 | PHE0008183_18479.pep | LRR_1 | 337 | 359 | 10.8 | 2.8 |
| 398 | PHE0008183_18479.pep | LRR_1 | 361 | 384 | 12 | 1.6 |
| 398 | PHE0008183_18479.pep | LRR_1 | 409 | 431 | 10.4 | 3.2 |
| 398 | PHE0008183_18479.pep | LRR_1 | 457 | 479 | 11.9 | 1.7 |
| 398 | PHE0008183_18479.pep | LRR_1 | 481 | 503 | 10.2 | 3.4 |
| 398 | PHE0008183_18479.pep | LRR_1 | 505 | 527 | 10.4 | 3.3 |
| 398 | PHE0008183_18479.pep | LRR_1 | 529 | 551 | 10.9 | 2.6 |
| 398 | PHE0008183_18479.pep | LRR_1 | 553 | 575 | 9.3 | 5.2 |
| 398 | PHE0008183_18479.pep | LRR_1 | 577 | 598 | 11 | 2.4 |
| 398 | PHE0008183_18479.pep | Pkinase | 695 | 966 | 133.8 | 4.80E−37 |
| 398 | PHE0008183_18479.pep | Pkinase_Tyr | 695 | 966 | 134.8 | 2.30E−37 |

TABLE 10-continued

| PEP SEQ ID NO | Gene ID | Pfam domain name | Begin | Stop | Score | E-value |
|---|---|---|---|---|---|---|
| 399 | PHE0007585__17875.pep | LEA_3 | 2 | 98 | 138.9 | 1.30E−38 |
| 400 | PHE0006804__16385.pep | zf-CCCH | 13 | 39 | 35.4 | 1.90E−07 |
| 400 | PHE0006804__16385.pep | zf-CCCH | 149 | 174 | 24.3 | 0.00045 |
| 401 | PHE0006703__15751.pep | PFK | 72 | 347 | 650.2 | 1.70E−192 |
| 402 | PHE0007410__17653.pep | Acyltransferase | 27 | 249 | 29.2 | 1.00E−05 |
| 403 | PHE0006854__16456.pep | YABBY | 40 | 278 | 249.1 | 9.30E−72 |
| 404 | PHE0007721__21293.pep | KNOX1 | 102 | 146 | 90.4 | 5.50E−24 |
| 404 | PHE0007721__21293.pep | KNOX2 | 153 | 204 | 101.2 | 3.10E−27 |
| 404 | PHE0007721__21293.pep | ELK | 242 | 263 | 37 | 6.50E−08 |
| 405 | PHE0006563__15990.pep | GATase_2 | 2 | 161 | 103.9 | 4.70E−28 |
| 405 | PHE0006563__15990.pep | Asn_synthase | 209 | 450 | 328.7 | 9.80E−96 |
| 406 | PHE0006619__16147.pep | AA_kinase | 15 | 261 | 192.3 | 1.20E−54 |
| 407 | PHE0006813__16394.pep | Bac_globin | 7 | 124 | 123 | 8.50E−34 |
| 408 | PHE0006688__16234.pep | Ribosomal_S2 | 13 | 229 | 448.6 | 8.00E−132 |
| 409 | PHE0006635__16164.pep | MGS | 28 | 121 | 99.4 | 1.10E−26 |
| 411 | PHE0008416__18838.pep | PTR2 | 115 | 504 | 350.4 | 3.00E−102 |
| 413 | PHE0008599__19166.pep | Isoamylase_N | 24 | 115 | 93.4 | 6.60E−25 |
| 413 | PHE0008599__19166.pep | Alpha-amylase | 164 | 578 | 75.8 | 1.40E−19 |
| 414 | PHE0008375__18732.pep | Pribosyltran | 93 | 237 | 141.8 | 1.80E−39 |
| 416 | PHE0008394__18763.pep | Gln-synt_N | 68 | 148 | 147.3 | 4.20E−41 |
| 416 | PHE0008394__18763.pep | Gln-synt_C | 154 | 406 | 287.7 | 2.20E−83 |
| 417 | PHE0008395__18764.pep | Gln-synt_N | 68 | 148 | 147.3 | 4.20E−41 |
| 417 | PHE0008395__18764.pep | Gln-synt_C | 154 | 406 | 285 | 1.50E−82 |
| 418 | PHE0008444__18846.pep | Gln-synt_N | 17 | 97 | 150.4 | 4.70E−42 |
| 418 | PHE0008444__18846.pep | Gln-synt_C | 103 | 355 | 283.9 | 3.00E−82 |
| 419 | PHE0006819__16400.pep | Lactamase_B | 47 | 236 | 77.1 | 5.60E−20 |
| 419 | PHE0006819__16400.pep | Flavodoxin_1 | 267 | 397 | 8.1 | 0.0041 |
| 419 | PHE0006819__16400.pep | Flavin_Reduct | 424 | 573 | 254.7 | 1.90E−73 |
| 420 | PHE0007417__17663.pep | EIN3 | 60 | 467 | 777.5 | 7.80E−231 |
| 421 | PHE0008443__18845.pep | GATase_2 | 2 | 161 | 98.7 | 1.70E−26 |
| 421 | PHE0008443__18845.pep | Asn_synthase | 209 | 450 | 331 | 2.00E−96 |
| 422 | PHE0006818__16399.pep | Lactamase_B | 34 | 227 | 105.3 | 1.80E−28 |
| 422 | PHE0006818__16399.pep | Flavodoxin_1 | 256 | 389 | 86.4 | 8.80E−23 |
| 422 | PHE0006818__16399.pep | Rubredoxin | 423 | 471 | 89.8 | 8.10E−24 |
| 423 | PHE0006579__16031.pep | Thi4 | 63 | 306 | 552.2 | 5.40E−163 |
| 423 | PHE0006579__16031.pep | DAO | 91 | 319 | −9 | 1.90E−05 |
| 424 | PHE0006808__16389.pep | CCT | 354 | 392 | 75.3 | 1.90E−19 |
| 425 | PHE0008160__18460.pep | TPP_enzyme_N | 45 | 221 | 286.5 | 5.20E−83 |
| 425 | PHE0008160__18460.pep | TPP_enzyme_M | 243 | 376 | 82.1 | 1.70E−21 |
| 425 | PHE0008160__18460.pep | TPP_enzyme_C | 431 | 578 | 34.8 | 2.80E−09 |
| 426 | PHE0007571__17834.pep | GSH_synth_ATP | 29 | 499 | 836.5 | 1.30E−248 |
| 426 | PHE0007571__17834.pep | GSH_synthase | 229 | 331 | 200 | 5.50E−57 |
| 427 | PHE0007586__17877.pep | Chloroa_b-bind | 64 | 261 | 255.3 | 1.20E−73 |
| 429 | PHE0009729__21717.pep | Homeobox | 67 | 123 | 68.9 | 1.60E−17 |
| 429 | PHE0009729__21717.pep | HALZ | 124 | 168 | 53.4 | 7.60E−13 |
| 430 | PHE0006424__15520.pep | PsbW_2 | 1 | 133 | 382.1 | 8.60E−112 |
| 431 | PHE0006392__15480.pep | PsbP | 106 | 322 | 252.9 | 6.50E−73 |
| 432 | PHE0006589__16093.pep | Thioredoxin | 64 | 167 | 130.3 | 5.20E−36 |
| 433 | PHE0009258__21487.pep | Na_H_Exchanger | 22 | 441 | 181.7 | 1.70E−51 |
| 434 | PHE0006680__16226.pep | 2OG-FeII_Oxy | 187 | 287 | 158 | 2.40E−44 |
| 435 | PHE0006481__16072.pep | adh_short | 33 | 181 | 28.8 | 7.00E−08 |
| 436 | PHE0006269__8820.pep | TPR_1 | 74 | 107 | 21.3 | 0.0035 |
| 436 | PHE0006269__8820.pep | TPR_2 | 74 | 107 | 24.7 | 0.00034 |
| 436 | PHE0006269__8820.pep | TPR_1 | 108 | 141 | 37.4 | 4.80E−08 |
| 436 | PHE0006269__8820.pep | TPR_2 | 108 | 141 | 35.3 | 2.10E−07 |
| 436 | PHE0006269__8820.pep | TPR_1 | 142 | 175 | 15 | 0.086 |
| 436 | PHE0006269__8820.pep | TPR_2 | 142 | 175 | 23.8 | 0.00063 |
| 436 | PHE0006269__8820.pep | TPR_1 | 179 | 212 | 7.9 | 0.61 |
| 436 | PHE0006269__8820.pep | TPR_4 | 247 | 272 | 23.6 | 0.00069 |
| 436 | PHE0006269__8820.pep | TPR_1 | 281 | 314 | 16.2 | 0.063 |
| 436 | PHE0006269__8820.pep | TPR_2 | 281 | 314 | 26 | 0.00014 |
| 436 | PHE0006269__8820.pep | TPR_1 | 349 | 382 | 13.6 | 0.13 |
| 437 | PHE0006783__16365.pep | Aa_trans | 32 | 469 | 574.9 | 7.90E−170 |
| 438 | PHE0003151__18392.pep | AP2 | 318 | 391 | 149.5 | 8.70E−42 |
| 438 | PHE0003151__18392.pep | AP2 | 420 | 485 | 125.8 | 1.20E−34 |
| 439 | PHE0008272__18723.pep | HSF_DNA-bind | 18 | 188 | 213.9 | 3.50E−61 |
| 440 | PHE0008277__18706.pep | SNF5 | 172 | 400 | 471.8 | 8.60E−139 |
| 441 | PHE0008109__18411.pep | Sad1_UNC | 203 | 330 | 195.6 | 1.10E−55 |
| 442 | PHE0008280__18826.pep | Alpha-amylase | 14 | 452 | 198.9 | 1.20E−56 |
| 443 | PHE0002424__15825.pep | adh_short | 43 | 215 | 24.9 | 1.30E−07 |
| 443 | PHE0002424__15825.pep | KR | 43 | 200 | −69.1 | 0.0024 |
| 444 | PHE0006914__16804.pep | AAA | 204 | 391 | 298.6 | 1.10E−86 |
| 445 | PHE0006642__16172.pep | p450 | 42 | 496 | 213.5 | 4.80E−61 |
| 447 | PHE0009926__21079.pep | DSPc | 24 | 152 | 137.5 | 3.60E−38 |

TABLE 10-continued

Pfam annotation

| PEP SEQ ID NO | Gene ID | Pfam domain name | Begin | Stop | Score | E-value |
|---|---|---|---|---|---|---|
| 448 | PHE0006206_19159.pep | Sina | 106 | 305 | 426.4 | 4.00E−125 |
| 449 | PHE0008274_18705.pep | BURP | 56 | 280 | 380 | 3.60E−111 |
| 450 | PHE0009510_20526.pep | Spermine_synth | 38 | 283 | 500.4 | 2.10E−147 |
| 451 | PHE0009937_21097.pep | Spermine_synth | 38 | 283 | 500.4 | 2.10E−147 |
| 452 | PHE0009927_21080.pep | DSPc | 24 | 162 | 146.6 | 6.60E−41 |
| 454 | PHE0006445_15956.pep | Allene_ox_cyc | 74 | 253 | 401.6 | 1.20E−117 |
| 455 | PHE0006987_16893.pep | efhand | 86 | 114 | 25 | 0.00026 |
| 455 | PHE0006987_16893.pep | efhand | 167 | 195 | 27.6 | 4.30E−05 |
| 456 | PHE0004230_15865.pep | E2F_TDP | 146 | 211 | 133.8 | 4.60E−37 |
| 457 | PHE0006814_16395.pep | Bac_globin | 26 | 144 | 206 | 8.80E−59 |
| 458 | PHE0002773_15881.pep | NTP_transferase | 88 | 366 | 415.4 | 8.30E−122 |
| 459 | PHE0006060_15842.pep | ubiquitin | 5 | 73 | 138 | 2.50E−38 |
| 459 | PHE0006060_15842.pep | ubiquitin | 81 | 149 | 138 | 2.50E−38 |
| 459 | PHE0006060_15842.pep | ubiquitin | 157 | 225 | 138 | 2.50E−38 |
| 459 | PHE0006060_15842.pep | ubiquitin | 233 | 301 | 138 | 2.50E−38 |
| 460 | PHE0006850_16451.pep | YABBY | 6 | 166 | 342.9 | 5.20E−100 |
| 461 | PHE0008043_18199.pep | Homeobox | 25 | 85 | 64.6 | 3.20E−16 |
| 461 | PHE0008043_18199.pep | START | 164 | 374 | 198.3 | 1.80E−56 |
| 461 | PHE0008043_18199.pep | MEKHLA | 693 | 840 | 296.7 | 4.40E−86 |
| 462 | PHE0000125_18852.pep | Response_reg | 28 | 153 | 25.4 | 3.80E−05 |
| 462 | PHE0000125_18852.pep | CCT | 457 | 495 | 70.6 | 5.10E−18 |
| 463 | PHE0008269_18720.pep | Pkinase | 23 | 279 | 234 | 3.30E−67 |
| 464 | PHE0008264_18712.pep | zf-UBR | 40 | 109 | 73.4 | 7.10E−19 |
| 465 | PHE0002782_20059.pep | PGI | 2 | 457 | 172.8 | 8.80E−49 |
| 466 | PHE0009438_20404.pep | GATA | 191 | 226 | 72.7 | 1.10E−18 |
| 467 | PHE0009429_20392.pep | ParBc | 70 | 151 | 47.5 | 4.50E−11 |
| 468 | PHE0009440_20406.pep | ParBc | 11 | 126 | 55.3 | 2.00E−13 |
| 469 | PHE0008543_18945.pep | TP_methylase | 222 | 435 | 272.6 | 7.70E−79 |
| 470 | PHE0006960_16857.pep | Oxidored_molyb | 116 | 301 | 289.2 | 7.70E−84 |
| 470 | PHE0006960_16857.pep | Mo-co_dimer | 326 | 459 | 300.9 | 2.30E−87 |
| 470 | PHE0006960_16857.pep | Cyt-b5 | 515 | 588 | 93.3 | 7.20E−25 |
| 470 | PHE0006960_16857.pep | FAD_binding_6 | 633 | 740 | 212.6 | 9.20E−61 |
| 470 | PHE0006960_16857.pep | NAD_binding_1 | 759 | 872 | 169.6 | 8.00E−48 |
| 471 | PHE0009427_20389.pep | IGPD | 103 | 247 | 372.6 | 6.20E−109 |
| 472 | PHE0006437_15906.pep | Pkinase | 39 | 307 | 15.8 | 1.70E−09 |
| 473 | PHE0007409_17652.pep | DAGAT | 64 | 340 | 278.2 | 1.60E−80 |
| 474 | PHE0009426_20387.pep | PHP | 2 | 281 | 104.4 | 3.30E−28 |
| 475 | PHE0009430_20393.pep | ParBc | 44 | 128 | 45.7 | 1.60E−10 |
| 476 | PHE0007003_16906.pep | PTPA | 96 | 396 | 524 | 1.60E−154 |
| 477 | PHE0008378_18741.pep | bZIP_1 | 223 | 280 | 76.5 | 8.20E−20 |
| 477 | PHE0008378_18741.pep | bZIP_2 | 224 | 277 | 47.5 | 4.40E−11 |
| 478 | PHE0008273_18725.pep | zf-CCCH | 80 | 106 | 39.3 | 1.30E−08 |
| 479 | PHE0008547_18953.pep | Fer2 | 20 | 95 | 95 | 2.20E−25 |
| 480 | PHE0006922_16812.pep | Hexokinase_1 | 44 | 251 | 260.7 | 2.90E−75 |
| 480 | PHE0006922_16812.pep | Hexokinase_2 | 258 | 501 | 261.2 | 2.10E−75 |
| 481 | PHE0006920_16810.pep | AAA | 267 | 458 | 270 | 4.60E−78 |
| 481 | PHE0006920_16810.pep | Vps4_C | 464 | 514 | 4.5 | 0.00031 |
| 482 | PHE0008396_18765.pep | Gln-synt_N | 68 | 148 | 147.3 | 4.20E−41 |
| 482 | PHE0008396_18765.pep | Gln-synt_C | 154 | 406 | 285.4 | 1.10E−82 |
| 483 | PHE0006957_16854.pep | Gln-synt_N | 68 | 148 | 147.3 | 4.20E−41 |
| 483 | PHE0006957_16854.pep | Gln-synt_C | 154 | 406 | 285.4 | 1.10E−82 |
| 484 | PHE0006404_15936.pep | RRM_1 | 8 | 77 | 81.4 | 2.80E−21 |
| 484 | PHE0006404_15936.pep | RRM_1 | 112 | 182 | 81.8 | 2.10E−21 |
| 485 | PHE0006820_16401.pep | Lactamase_B | 47 | 236 | 82.8 | 1.10E−21 |
| 485 | PHE0006820_16401.pep | Flavin_Reduct | 423 | 572 | 222.8 | 7.90E−64 |
| 486 | PHE0006690_16236.pep | MFS_1 | 57 | 421 | 44.3 | 4.30E−10 |
| 487 | PHE0006395_15932.pep | LRR_1 | 185 | 206 | 11.9 | 1.7 |
| 487 | PHE0006395_15932.pep | LRR_1 | 208 | 229 | 17.1 | 0.065 |
| 487 | PHE0006395_15932.pep | LRR_1 | 231 | 252 | 13.5 | 0.77 |
| 487 | PHE0006395_15932.pep | LRR_1 | 254 | 272 | 12.6 | 1.2 |
| 487 | PHE0006395_15932.pep | LRR_1 | 278 | 299 | 8.4 | 7.8 |
| 487 | PHE0006395_15932.pep | LRR_1 | 349 | 370 | 20.8 | 0.0049 |
| 487 | PHE0006395_15932.pep | LRR_1 | 372 | 394 | 7.8 | 9.8 |
| 488 | PHE0006759_16384.pep | SHMT | 55 | 453 | 1032.6 | 0 |
| 489 | PHE0006576_16028.pep | Myb_DNA-binding | 11 | 57 | 59.3 | 1.30E−14 |
| 489 | PHE0006576_16028.pep | Myb_DNA-binding | 63 | 108 | 48.9 | 1.70E−11 |
| 490 | PHE0006979_16885.pep | Tryp_alpha_amyl | 33 | 111 | 55.3 | 2.00E−13 |
| 491 | PHE0009786_21754.pep | HLH | 33 | 80 | 30 | 8.20E−06 |
| 492 | PHE0006572_16007.pep | Pkinase | 11 | 269 | 317 | 3.30E−92 |
| 494 | PHE0006588_16092.pep | Thioredoxin | 56 | 161 | 128.8 | 1.50E−35 |
| 495 | PHE0006985_16891.pep | DUF1716 | 13 | 118 | 159.3 | 1.00E−44 |
| 496 | PHE0006875_16688.pep | PSI_PSAK | 44 | 138 | 191.6 | 1.90E−54 |
| 497 | PHE0006626_16155.pep | Glyco_hydro_17 | 30 | 335 | 587.5 | 1.20E−173 |
| 498 | PHE0006689_16235.pep | Aa_trans | 165 | 548 | 224.1 | 3.20E−64 |

TABLE 10-continued

| Pfam annotation | | | | | | |
|---|---|---|---|---|---|---|
| PEP SEQ ID NO | Gene ID | Pfam domain name | Begin | Stop | Score | E-value |
| 499 | PHE0006799__16382.pep | B12-binding | 10 | 135 | 104.3 | 3.70E−28 |
| 499 | PHE0006799__16382.pep | Radical_SAM | 202 | 368 | 91.2 | 3.10E−24 |
| 500 | PHE0006959__16856.pep | Oxidored_molyb | 143 | 328 | 286.7 | 4.40E−83 |
| 500 | PHE0006959__16856.pep | Mo-co_dimer | 353 | 486 | 297.6 | 2.40E−86 |
| 500 | PHE0006959__16856.pep | Cyt-b5 | 543 | 616 | 90.4 | 5.60E−24 |
| 500 | PHE0006959__16856.pep | FAD_binding_6 | 660 | 767 | 231.6 | 1.70E−66 |
| 500 | PHE0006959__16856.pep | NAD_binding_1 | 786 | 899 | 186.4 | 7.00E−53 |
| 501 | PHE0011615__23861.pep | Pkinase | 267 | 523 | 297.5 | 2.50E−86 |
| 501 | PHE0011615__23861.pep | Pkinase_Tyr | 267 | 523 | 127.5 | 3.70E−35 |
| 502 | PHE0006925__16814.pep | Tim17 | 4 | 133 | 198.1 | 2.10E−56 |
| 503 | PHE0006713__16274.pep | APC8 | 1 | 161 | 401.5 | 1.20E−117 |
| 503 | PHE0006713__16274.pep | TPR_1 | 339 | 372 | 34.7 | 3.20E−07 |
| 503 | PHE0006713__16274.pep | TPR_2 | 339 | 372 | 23.7 | 0.00066 |
| 503 | PHE0006713__16274.pep | TPR_2 | 373 | 406 | 23.7 | 0.00068 |
| 503 | PHE0006713__16274.pep | TPR_1 | 373 | 406 | 34.1 | 4.80E−07 |
| 503 | PHE0006713__16274.pep | TPR_2 | 407 | 440 | 22.1 | 0.002 |
| 503 | PHE0006713__16274.pep | TPR_1 | 407 | 440 | 24.3 | 0.00043 |
| 504 | PHE0008447__18848.pep | Lir1 | 1 | 126 | 178.6 | 1.60E−50 |
| 505 | PHE0006674__16221.pep | PTR2 | 96 | 505 | 222.7 | 8.20E−64 |
| 506 | PHE0010613__22398.pep | DAGK_cat | 43 | 184 | 106.4 | 8.50E−29 |
| 507 | PHE0002720__22558.pep | DnaJ | 90 | 151 | 137.6 | 3.40E−38 |
| 507 | PHE0002720__22558.pep | DnaJ_CXXCXGXG | 218 | 301 | 100.5 | 5.20E−27 |
| 507 | PHE0002720__22558.pep | DnaJ_C | 314 | 436 | 210.6 | 3.60E−60 |
| 508 | PHE0011760__24005.pep | Pkinase | 400 | 656 | 297.5 | 2.50E−86 |
| 508 | PHE0011760__24005.pep | Pkinase_Tyr | 400 | 656 | 127.5 | 3.70E−35 |
| 509 | PHE0010612__22397.pep | G-patch | 15 | 59 | 62 | 1.90E−15 |
| 511 | PHE0007411__17654.pep | Acyltransferase | 136 | 283 | 86.4 | 8.50E−23 |
| 512 | PHE0010617__22402.pep | Isochorismatase | 27 | 210 | −41 | 0.0027 |
| 513 | PHE0010610__22395.pep | zf-C3HC4 | 103 | 144 | 36.3 | 1.10E−07 |
| 514 | PHE0006883__16702.pep | Glyco_transf_5 | 78 | 339 | 461.4 | 1.10E−135 |
| 514 | PHE0006883__16702.pep | Glycos_transf_1 | 379 | 562 | 40.5 | 5.80E−09 |
| 515 | PHE0010636__22408.pep | UAA | 96 | 387 | −125.2 | 0.00037 |
| 515 | PHE0010636__22408.pep | DUF6 | 105 | 230 | 32.1 | 2.00E−06 |
| 515 | PHE0010636__22408.pep | TPT | 239 | 384 | 188.8 | 1.30E−53 |
| 516 | PHE0011082__23038.pep | adh_short | 19 | 187 | 111.5 | 2.50E−30 |
| 516 | PHE0011082__23038.pep | KR | 19 | 202 | −67.5 | 0.0019 |
| 517 | PHE0009475__20462.pep | 2OG-FeII_Oxy | 223 | 322 | 166.9 | 5.20E−47 |
| 518 | PHE0007415__17661.pep | EIN3 | 60 | 467 | 781.6 | 4.80E−232 |
| 519 | PHE0006614__16129.pep | Cellulase | 19 | 358 | −25.9 | 1.00E−05 |
| 520 | PHE0010611__22396.pep | FMO-like | 25 | 424 | −364.7 | 5.40E−07 |
| 521 | PHE0011719__23946.pep | Acyltransferase | 69 | 222 | 30 | 8.30E−06 |
| 522 | PHE0006861__16463.pep | NPH3 | 166 | 409 | 387.6 | 1.80E−113 |
| 523 | PHE0006568__16005.pep | DUF26 | 80 | 134 | 56.9 | 6.70E−14 |
| 523 | PHE0006568__16005.pep | DUF26 | 199 | 253 | 62.1 | 1.80E−15 |
| 523 | PHE0006568__16005.pep | Pkinase_Tyr | 346 | 615 | 114 | 4.20E−31 |
| 523 | PHE0006568__16005.pep | Pkinase | 346 | 615 | 163.2 | 6.70E−46 |
| 524 | PHE0010652__22429.pep | FtsJ | 21 | 211 | 282.4 | 8.80E−82 |
| 525 | PHE0008158__18448.pep | PLATZ | 22 | 144 | 232.3 | 1.00E−66 |
| 526 | PHE0003316__20755.pep | Glyco_hydro_2_N | 9 | 180 | 238.7 | 1.30E−68 |
| 526 | PHE0003316__20755.pep | Glyco_hydro_2 | 182 | 272 | 129.9 | 7.00E−36 |
| 526 | PHE0003316__20755.pep | Glyco_hydro_2_C | 274 | 593 | 612.1 | 5.00E−181 |
| 527 | PHE0009478__20470.pep | 2OG-FeII_Oxy | 229 | 328 | 171.2 | 2.50E−48 |
| 528 | PHE0010395__21760.pep | DUF716 | 109 | 266 | 180.5 | 4.10E−51 |
| 529 | PHE0010391__21753.pep | DUF640 | 28 | 160 | 296.6 | 4.70E−86 |
| 530 | PHE0010396__21761.pep | DUF716 | 109 | 265 | 175.2 | 1.60E−49 |
| 531 | PHE0009511__22422.pep | SAM_decarbox | 5 | 337 | 710.3 | 1.30E−210 |
| 532 | PHE0010614__22399.pep | SOUL | 28 | 211 | 330.7 | 2.50E−96 |
| 534 | PHE0011454__23667.pep | Histone | 56 | 126 | 103.3 | 7.20E−28 |
| 535 | PHE0011443__24001.pep | Histone | 61 | 131 | 103.3 | 7.20E−28 |
| 536 | PHE0011452__23665.pep | Histone | 58 | 132 | 142.7 | 9.80E−40 |
| 537 | PHE0010394__21758.pep | SAP18 | 29 | 150 | 260.5 | 3.30E−75 |
| 540 | PHE0010100__21467.pep | Pyr_redox_2 | 5 | 285 | 134.4 | 3.10E−37 |
| 540 | PHE0010100__21467.pep | Pyr_redox | 147 | 240 | 91 | 3.50E−24 |
| 540 | PHE0010100__21467.pep | Fer2_BFD | 420 | 472 | 81.5 | 2.60E−21 |
| 540 | PHE0010100__21467.pep | NIR_SIR_ferr | 554 | 621 | 89.9 | 7.80E−24 |
| 540 | PHE0010100__21467.pep | NIR_SIR | 629 | 775 | 176.5 | 6.70E−50 |
| 541 | PHE0011503__23734.pep | GAF | 158 | 307 | 91.9 | 1.90E−24 |
| 541 | PHE0011503__23734.pep | HisKA | 343 | 408 | 87.5 | 4.10E−23 |
| 541 | PHE0011503__23734.pep | HATPase_c | 455 | 586 | 123.9 | 4.50E−34 |
| 542 | PHE0010099__21319.pep | Molybdop_Fe4S4 | 1 | 55 | 91.2 | 3.30E−24 |
| 542 | PHE0010099__21319.pep | Molybdopterin | 58 | 475 | 479.9 | 3.00E−141 |
| 542 | PHE0010099__21319.pep | Molydop_binding | 570 | 681 | 140 | 6.60E−39 |
| 542 | PHE0010099__21319.pep | Fer2_BFD | 811 | 863 | 74.8 | 2.70E−19 |
| 543 | PHE0011269__23400.pep | Homeobox | 21 | 78 | 70.4 | 5.80E−18 |

TABLE 10-continued

Pfam annotation

| PEP SEQ ID NO | Gene ID | Pfam domain name | Begin | Stop | Score | E-value |
|---|---|---|---|---|---|---|
| 543 | PHE0011269__23400.pep | START | 215 | 437 | 167.3 | 3.90E−47 |
| 546 | PHE0011613__23858.pep | AP2 | 62 | 136 | 129.6 | 8.70E−36 |
| 546 | PHE0011613__23858.pep | AP2 | 165 | 230 | 109.9 | 7.50E−30 |
| 547 | PHE0001582__22064.pep | GAF | 195 | 344 | 57.2 | 5.30E−14 |
| 547 | PHE0001582__22064.pep | HisKA | 380 | 445 | 22.2 | 0.00068 |
| 547 | PHE0001582__22064.pep | Response_reg | 645 | 761 | 69.4 | 1.20E−17 |
| 548 | PHE0007444__22314.pep | Spermine_synth | 90 | 349 | 414.5 | 1.50E−121 |
| 549 | PHE0010543__22298.pep | PBP | 19 | 165 | 216.7 | 5.30E−62 |
| 550 | PHE0010543__22323.pep | PBP | 19 | 157 | 186 | 9.30E−53 |
| 551 | PHE0011081__23033.pep | Sugar_tr | 33 | 465 | −7.2 | 1.20E−06 |
| 552 | PHE0011075__23026.pep | P-II | 73 | 175 | 181.5 | 2.10E−51 |
| 553 | PHE0010100__21462.pep | Pyr_redox_2 | 5 | 285 | 134.4 | 3.10E−37 |
| 553 | PHE0010100__21462.pep | Pyr_redox | 147 | 240 | 91 | 3.50E−24 |
| 553 | PHE0010100__21462.pep | Fer2_BFD | 420 | 472 | 81.5 | 2.60E−21 |
| 553 | PHE0010100__21462.pep | NIR_SIR_ferr | 554 | 621 | 89.9 | 7.80E−24 |
| 553 | PHE0010100__21462.pep | NIR_SIR | 629 | 775 | 176.5 | 6.70E−50 |
| 554 | PHE0009640__21775.pep | Auxin_inducible | 1 | 102 | 151.5 | 2.10E−42 |
| 555 | PHE0010092__21307.pep | S1 | 13 | 88 | 51.4 | 3.00E−12 |
| 555 | PHE0010092__21307.pep | EIF_2_alpha | 125 | 256 | 217.3 | 3.50E−62 |
| 556 | PHE0004611__24123.pep | PTR2 | 13 | 406 | 283.1 | 5.40E−82 |
| 557 | PHE0010093__21308.pep | S1 | 13 | 88 | 50 | 8.10E−12 |
| 557 | PHE0010093__21308.pep | EIF_2_alpha | 125 | 256 | 217.3 | 3.50E−62 |
| 558 | PHE0008605__23084.pep | Histone | 58 | 128 | 105.5 | 1.60E−28 |
| 559 | PHE0009939__21100.pep | GDC-P | 81 | 508 | 1024.4 | 0 |
| 560 | PHE0009941__21105.pep | mTERF | 2 | 262 | 117.5 | 3.70E−32 |
| 561 | PHE0009951__21135.pep | Ribosomal_L10e | 1 | 176 | 487.9 | 1.20E−143 |
| 562 | PHE0009943__21127.pep | Ribosomal_L10e | 1 | 176 | 460.5 | 2.20E−135 |
| 563 | PHE0009948__21132.pep | Ribosomal_L10e | 1 | 176 | 476.4 | 3.40E−140 |
| 564 | PHE0011084__23040.pep | Peptidase_S10 | 54 | 482 | 561 | 1.20E−165 |
| 565 | PHE0008233__23042.pep | Phi_1 | 40 | 314 | 616.9 | 1.80E−182 |
| 566 | PHE0010854__22730.pep | RGS | 294 | 412 | 23.2 | 2.80E−06 |
| 567 | PHE0003797__23051.pep | zf-Dof | 34 | 96 | 127 | 5.20E−35 |
| 568 | PHE0010194__21769.pep | Glyco_hydro_9 | 52 | 509 | 1007.2 | 5.70E−300 |
| 570 | PHE0011665__23899.pep | Chloroa_b-bind | 63 | 260 | 255.3 | 1.20E−73 |
| 571 | PHE0012178__24443.pep | Whirly | 53 | 191 | 263.2 | 5.30E−76 |
| 573 | PHE0011064__22994.pep | TPR_1 | 73 | 106 | 33.7 | 6.50E−07 |
| 573 | PHE0011064__22994.pep | TPR_2 | 73 | 106 | 33.4 | 7.80E−07 |
| 577 | PHE0011446__23659.pep | Histone | 58 | 132 | 142.9 | 8.50E−40 |
| 578 | PHE0001424__22077.pep | Agglutinin | 55 | 193 | 46.9 | 6.30E−12 |
| 579 | PHE0011445__23658.pep | C2 | 6 | 87 | 74.9 | 2.50E−19 |
| 580 | PHE0010090__21297.pep | LRRNT_2 | 33 | 73 | 34.2 | 4.60E−07 |
| 580 | PHE0010090__21297.pep | LRR_1 | 78 | 101 | 11.5 | 2 |
| 580 | PHE0010090__21297.pep | LRR_1 | 103 | 127 | 11.2 | 2.3 |
| 580 | PHE0010090__21297.pep | LRR_1 | 129 | 151 | 21.9 | 0.0024 |
| 580 | PHE0010090__21297.pep | LRR_1 | 177 | 199 | 16 | 0.14 |
| 580 | PHE0010090__21297.pep | LRR_1 | 226 | 248 | 10.3 | 3.3 |
| 580 | PHE0010090__21297.pep | LRR_1 | 274 | 296 | 18.9 | 0.018 |
| 580 | PHE0010090__21297.pep | LRR_1 | 298 | 320 | 12.1 | 1.6 |
| 580 | PHE0010090__21297.pep | LRR_1 | 322 | 341 | 11.2 | 2.3 |
| 580 | PHE0010090__21297.pep | LRR_1 | 395 | 417 | 9.8 | 4.1 |
| 580 | PHE0010090__21297.pep | LRR_1 | 444 | 466 | 8.2 | 8.3 |
| 580 | PHE0010090__21297.pep | LRR_1 | 468 | 490 | 12.8 | 1.1 |
| 580 | PHE0010090__21297.pep | LRR_1 | 492 | 514 | 7.7 | 10 |
| 580 | PHE0010090__21297.pep | LRR_1 | 516 | 538 | 15.7 | 0.17 |
| 580 | PHE0010090__21297.pep | LRR_1 | 540 | 562 | 7.8 | 10 |
| 580 | PHE0010090__21297.pep | LRR_1 | 564 | 585 | 8.5 | 7.4 |
| 580 | PHE0010090__21297.pep | Pkinase | 678 | 952 | 107.9 | 3.00E−29 |
| 580 | PHE0010090__21297.pep | Pkinase_Tyr | 678 | 952 | 110.4 | 5.10E−30 |
| 581 | PHE0012180__24445.pep | B3 | 516 | 619 | 90.3 | 6.00E−24 |
| 582 | PHE0011083__23039.pep | adh_short | 44 | 200 | 46.7 | 7.60E−11 |
| 583 | PHE0011085__23041.pep | Peptidase_S10 | 31 | 459 | 551.6 | 8.20E−163 |
| 584 | PHE0012175__24440.pep | CXC | 457 | 498 | 80.2 | 6.60E−21 |
| 584 | PHE0012175__24440.pep | CXC | 543 | 584 | 83.5 | 6.40E−22 |
| 585 | PHE0012177__24442.pep | Whirly | 91 | 229 | 325.2 | 1.10E−94 |
| 587 | PHE0010194__21426.pep | Glyco_hydro_9 | 52 | 509 | 1013.8 | 5.70E−302 |
| 588 | PHE0011666__23900.pep | Spermine_synth | 46 | 291 | 503.1 | 3.20E−148 |
| 589 | PHE0011448__24160.pep | Histone | 25 | 90 | 35.4 | 1.90E−07 |
| 590 | PHE0008324__18636.pep | DUF1005 | 256 | 460 | 524.8 | 9.30E−155 |
| 591 | PHE0006971__16875.pep | Myb_DNA-binding | 14 | 61 | 44.2 | 4.40E−10 |
| 591 | PHE0006971__16875.pep | Myb_DNA-binding | 67 | 112 | 51.3 | 3.20E−12 |
| 592 | PHE0009939__21147.pep | GDC-P | 81 | 508 | 1024.4 | 0 |
| 593 | PHE0009953__21137.pep | Na_sulph_symp | 110 | 578 | 831.2 | 5.40E−247 |
| 595 | PHE0008557__18970.pep | NAD_binding_1 | 234 | 350 | 138.6 | 1.60E−38 |
| 596 | PHE0006443__15955.pep | YDG_SRA | 360 | 519 | 403.5 | 3.00E−118 |

TABLE 10-continued

Pfam annotation

| PEP SEQ ID NO | Gene ID | Pfam domain name | Begin | Stop | Score | E-value |
|---|---|---|---|---|---|---|
| 596 | PHE0006443__15955.pep | Pre-SET | 543 | 639 | 156.7 | 6.00E−44 |
| 596 | PHE0006443__15955.pep | SET | 641 | 771 | 181.7 | 1.80E−51 |

TABLE 11 pfam module annotation

| PEP SEQ ID NO | Gene ID | Pfam domain module | Position |
|---|---|---|---|
| 299 | PHE0007721__18998.pep | KNOX1::KNOX2::ELK | 102-146::153-204::242-263 |
| 300 | PHE0007756__18009.pep | RPE65 | 105-591 |
| 302 | PHE0004988__15925.pep | F-box::LRR_1::LRR_2 | 4-52::157-179::290-314 |
| 303 | PHE0007140__21771.pep | MtN3_slv::MtN3_slv | 9-98::134-221 |
| 304 | PHE0006823__16403.pep | Globin | 10-149 |
| 305 | PHE0007440__22555.pep | Ras | 14-175 |
| 306 | PHE0000206__22432.pep | Pkinase::efhand::efhand::efhand | 79-337::384-412::456-484::490-518 |
| 307 | PHE0000598__16824.pep | HLH | 385-434 |
| 308 | PHE0007590__17883.pep | S1 | 2-70 |
| 309 | PHE0007588__17881.pep | S1 | 2-86 |
| 310 | PHE0007592__17885.pep | S1 | 1-75 |
| 311 | PHE0007587__17880.pep | S1 | 3-75 |
| 312 | PHE0007624__17923.pep | eIF-1a | 5-70 |
| 313 | PHE0007591__17884.pep | S1 | 2-68 |
| 314 | PHE0007623__17922.pep | CN_hydrolase | 11-184 |
| 315 | PHE0007583__17871.pep | MtN3_slv::MtN3_slv | 9-98::132-218 |
| 316 | PHE0006618__16146.pep | S10_plectin | 3-98 |
| 317 | PHE0006791__16374.pep | GUN4 | 84-227 |
| 318 | PHE0007620__17918.pep | peroxidase | 89-321 |
| 319 | PHE0006659__16195.pep | MFS_1 | 10-391 |
| 321 | PHE0006274__15867.pep | E2F_TDP | 130-195 |
| 322 | PHE0006637__16166.pep | PP2C | 7-305 |
| 323 | PHE0006926__16815.pep | VPS28 | 18-209 |
| 324 | PHE0006821__16402.pep | PALP | 49-358 |
| 325 | PHE0007687__18057.pep | p450 | 35-462 |
| 326 | PHE0007642__17999.pep | PAS_3::PAS_3::Pkinase | 211-303::489-581::663-952 |
| 327 | PHE0007677__18052.pep | FAD_binding_3 | 5-372 |
| 328 | PHE0007644__18001.pep | LRRNT_2::LRR_1::LRR_1::LRR_1::LRR_1::LRR_1::Pkinase | 23-64::97-119::121-143::145-167::169-192::194-216::414-716 |
| 329 | PHE0007640__17992.pep | CorA | 66-448 |
| 330 | PHE0007678__18053.pep | 4HBT | 66-151 |
| 331 | PHE0007649__18006.pep | Ank::Pkinase | 108-140::196-455 |
| 332 | PHE0006726__16298.pep | WD40::WD40 | 45-83::135-173 |
| 333 | PHE0006218__8776.pep | Pyr_redox_2::Thioredoxin | 85-370::423-528 |
| 335 | PHE0002554__17876.pep | Chloroa_b-bind | 63-261 |
| 336 | PHE0006807__16388.pep | CCT | 352-390 |
| 337 | PHE0003359__8487.pep | p450 | 51-489 |
| 338 | PHE0006542__15765.pep | PMSR | 92-245 |
| 339 | PHE0007622__17921.pep | Spermine_synth | 34-279 |
| 340 | PHE0007630__17956.pep | 2OG-FeII_Oxy | 190-291 |
| 341 | PHE0007593__17886.pep | Spermine_synth | 28-273 |
| 342 | PHE0006475__15588.pep | PsbQ | 3-162 |
| 343 | PHE0007619__17915.pep | MBD | 11-84 |
| 344 | PHE0006846__16447.pep | Sterol_desat | 1-186 |
| 345 | PHE0007584__17874.pep | MBD | 4-77 |
| 346 | PHE0003695__17913.pep | LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase | 23-64::93-115::117-139::141-163::165-186::189-211::213-235::237-259::260-281::284-306::308-330::332-354::356-378::380-402::404-426::428-450::452-474::476-498::500-521::523-542::648-917 |
| 347 | PHE0003695__17879.pep | LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase | 23-64::93-115::117-139::141-163::165-186::189-211::213-235::237-259::260-281::284-306::308-330::332-354::356-378::380-402::404-426::428-450::452-474::476-498::500-521::523-542::648-917 |

TABLE 11-continued pfam module annotation

| PEP SEQ ID NO | Gene ID | Pfam domain module | Position |
|---|---|---|---|
| 349 | PHE0007645__18002.pep | AP2 | 115-180 |
| 350 | PHE0006784__16366.pep | PALP | 12-301 |
| 351 | PHE0006171__16491.pep | Glyoxalase | 70-214 |
| 353 | PHE0006906__16796.pep | Proteasome | 10-206 |
| 354 | PHE0006649__16180.pep | AP2 | 46-110 |
| 355 | PHE0006809__16390.pep | Prismane | 1-548 |
| 356 | PHE0006918__16808.pep | SWIM | 321-353 |
| 357 | PHE0007813__18219.pep | MtN3_slv::MtN3_slv | 9-98::132-218 |
| 359 | PHE0006825__16405.pep | Cytochrom_C552 | 27-476 |
| 360 | PHE0006964__16864.pep | tRNA_anti::tRNA-synt_2 | 43-122::140-557 |
| 361 | PHE0008105__18407.pep | CBFD_NFYB_HMF | 158-222 |
| 362 | PHE0006630__16159.pep | Ldh_1_N::Ldh_1_C | 90-239::241-413 |
| 363 | PHE0006966__16868.pep | DNA_photolyase::FAD_binding_7 | 12-183::214-492 |
| 365 | PHE0006608__16123.pep | GSHPx | 42-150 |
| 366 | PHE0010462__21459.pep | NUDIX::NUDIX | 17-159::190-322 |
| 367 | PHE0009211__21774.pep | Auxin_inducible | 1-106 |
| 368 | PHE0006256__8775.pep | RPE65 | 105-591 |
| 369 | PHE0006989__16918.pep | Pkinase | 88-396 |
| 370 | PHE0007649__18166.pep | Ank::Pkinase | 108-140::196-455 |
| 371 | PHE0006708__16264.pep | DEAD::Helicase_C | 57-223::291-367 |
| 372 | PHE0001117__19094.pep | Homeobox::HALZ | 79-133::134-178 |
| 373 | PHE0006266__8814.pep | Fe_bilin_red | 16-244 |
| 374 | PHE0006795__16378.pep | Na_H_antiport_1 | 4-380 |
| 375 | PHE0006956__16853.pep | Molybdop_Fe4S4::Molybdopterin::Molydop_binding::Fer2_BFD | 2-56::59-482::578-689::825-877 |
| 377 | PHE0006824__16404.pep | Globin | 14-154 |
| 378 | PHE0006812__16393.pep | Bac_globin | 3-118 |
| 379 | PHE0006815__16396.pep | Bac_globin | 26-146 |
| 380 | PHE0006806__16387.pep | Bac_globin | 26-146 |
| 381 | PHE0006624__16153.pep | NAD_binding_2::6PGD | 3-178::182-473 |
| 382 | PHE0005006__15823.pep | Chloroa_b-bind | 63-242 |
| 384 | PHE0006683__16229.pep | Response_reg | 10-151 |
| 385 | PHE0006884__16703.pep | Glyco_transf_5::Glycos_transf_1 | 83-344::384-567 |
| 386 | PHE0006691__16237.pep | NAD_Gly3P_dh_N::NAD_Gly3P_dh_C | 6-165::183-327 |
| 387 | PHE0006790__16372.pep | Rieske::PaO | 220-317::408-507 |
| 388 | PHE0009143__19932.pep | Histone_HNS | 21-129 |
| 389 | PHE0008406__18830.pep | AA_permease | 57-511 |
| 390 | PHE0008279__18708.pep | Mit_rib_S27 | 14-93 |
| 391 | PHE0009142__19931.pep | Histone_HNS | 21-130 |
| 393 | PHE0007639__17991.pep | ELFV_dehydrog_N::ELFV_dehydrog | 84-214::229-474 |
| 394 | PHE0007646__18170.pep | F-box::Kelch_1::Kelch_1 | 36-83::131-185::187-233 |
| 395 | PHE0007765__18182.pep | GST_N::GST_C | 5-79::101-204 |
| 396 | PHE0008167__18465.pep | Pkinase_Tyr | 8-262 |
| 398 | PHE0008183__18479.pep | LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase_Tyr | 23-66::71-93::95-117::119-142::144-166::168-190::192-214::289-311::313-335::337-359::361-384::409-431::457-479::481-503::505-527::529-551::553-575::577-598::695-966 |
| 399 | PHE0007585__17875.pep | LEA_3 | 35827 |
| 400 | PHE0006804__16385.pep | zf-CCCH::zf-CCCH | 13-39::149-174 |
| 401 | PHE0006703__15751.pep | PFK | 72-347 |
| 402 | PHE0007410__17653.pep | Acyltransferase | 27-249 |
| 403 | PHE0006854__16456.pep | YABBY | 40-278 |
| 404 | PHE0007721__21293.pep | KNOX1::KNOX2::ELK | 102-146::153-204::242-263 |
| 405 | PHE0006563__15990.pep | GATase_2::Asn_synthase | 2-161::209-450 |
| 406 | PHE0006619__16147.pep | AA_kinase | 15-261 |
| 407 | PHE0006813__16394.pep | Bac_globin | 7-124 |
| 408 | PHE0006688__16234.pep | Ribosomal_S2 | 13-229 |
| 409 | PHE0006635__16164.pep | MGS | 28-121 |
| 411 | PHE0008416__18838.pep | PTR2 | 115-504 |
| 413 | PHE0008599__19166.pep | Isoamylase_N::Alpha-amylase | 24-115::164-578 |
| 414 | PHE0008375__18732.pep | Pribosyltran | 93-237 |
| 416 | PHE0008394__18763.pep | Gln-synt_N::Gln-synt_C | 68-148::154-406 |
| 417 | PHE0008395__18764.pep | Gln-synt_N::Gln-synt_C | 68-148::154-406 |
| 418 | PHE0008444__18846.pep | Gln-synt_N::Gln-synt_C | 17-97::103-355 |

TABLE 11-continued pfam module annotation

| PEP SEQ ID NO | Gene ID | Pfam domain module | Position |
|---|---|---|---|
| 419 | PHE0006819__16400.pep | Lactamase_B::Flavodoxin_1::Flavin_Reduct | 47-236::267-397::424-573 |
| 420 | PHE0007417__17663.pep | EIN3 | 60-467 |
| 421 | PHE0008443__18845.pep | GATase_2::Asn_synthase | 2-161::209-450 |
| 422 | PHE0006818__16399.pep | Lactamase_B::Flavodoxin_1::Rubredoxin | 34-227::256-389::423-471 |
| 423 | PHE0006579__16031.pep | Thi4 | 63-306 |
| 424 | PHE0006808__16389.pep | CCT | 354-392 |
| 425 | PHE0008160__18460.pep | TPP_enzyme_N::TPP_enzyme_M::TPP_enzyme_C | 45-221::243-376::431-578 |
| 426 | PHE0007571__17834.pep | GSH_synth_ATP | 29-499 |
| 427 | PHE0007586__17877.pep | Chloroa_b-bind | 64-261 |
| 429 | PHE0009729__21717.pep | Homeobox::HALZ | 67-123::124-168 |
| 430 | PHE0006424__15520.pep | PsbW_2 | 1-133 |
| 431 | PHE0006392__15480.pep | PsbP | 106-322 |
| 432 | PHE0006589__16093.pep | Thioredoxin | 64-167 |
| 433 | PHE0009258__21487.pep | Na_H_Exchanger | 22-441 |
| 434 | PHE0006680__16226.pep | 2OG-FeII_Oxy | 187-287 |
| 435 | PHE0006481__16072.pep | adh_short | 33-181 |
| 436 | PHE0006269__8820.pep | TPR_2::TPR_1::TPR_2::TPR_1::TPR_4::TPR_2::TPR_1 | 74-107::108-141::142-175::179-212::247-272::281-314::349-382 |
| 437 | PHE0006783__16365.pep | Aa_trans | 32-469 |
| 438 | PHE0003151__18392.pep | AP2::AP2 | 318-391::420-485 |
| 439 | PHE0008272__18723.pep | HSF_DNA-bind | 18-188 |
| 440 | PHE0008277__18706.pep | SNF5 | 172-400 |
| 441 | PHE0008109__18411.pep | Sad1_UNC | 203-330 |
| 442 | PHE0008280__18826.pep | Alpha-amylase | 14-452 |
| 443 | PHE0002424__15825.pep | adh_short | 43-215 |
| 444 | PHE0006914__16804.pep | AAA | 204-391 |
| 445 | PHE0006642__16172.pep | p450 | 42-496 |
| 447 | PHE0009926__21079.pep | DSPc | 24-152 |
| 448 | PHE0006206__19159.pep | Sina | 106-305 |
| 449 | PHE0008274__18705.pep | BURP | 56-280 |
| 450 | PHE0009510__20526.pep | Spermine_synth | 38-283 |
| 451 | PHE0009937__21097.pep | Spermine_synth | 38-283 |
| 452 | PHE0009927__21080.pep | DSPc | 24-162 |
| 454 | PHE0006445__15956.pep | Allene_ox_cyc | 74-253 |
| 455 | PHE0006987__16893.pep | efhand::efhand | 86-114::167-195 |
| 456 | PHE0004230__15865.pep | E2F_TDP | 146-211 |
| 457 | PHE0006814__16395.pep | Bac_globin | 26-144 |
| 458 | PHE0002773__15881.pep | NTP_transferase | 88-366 |
| 459 | PHE0006060__15842.pep | ubiquitin::ubiquitin::ubiquitin::ubiquitin | 5-73::81-149::157-225::233-301 |
| 460 | PHE0006850__16451.pep | YABBY | 6-166 |
| 461 | PHE0008043__18199.pep | Homeobox::START::MEKHLA | 25-85::164-374::693-840 |
| 462 | PHE0000125__18852.pep | Response_reg::CCT | 28-153::457-495 |
| 463 | PHE0008269__18720.pep | Pkinase | 23-279 |
| 464 | PHE0008264__18712.pep | zf-UBR | 40-109 |
| 465 | PHE0002782__20059.pep | PGI | 2-457 |
| 466 | PHE0009438__20404.pep | GATA | 191-226 |
| 467 | PHE0009429__20392.pep | ParBc | 70-151 |
| 468 | PHE0009440__20406.pep | ParBc | 11-126 |
| 469 | PHE0008543__18945.pep | TP_methylase | 222-435 |
| 470 | PHE0006960__16857.pep | Oxidored_molyb::Mo-co_dimer::Cyt-b5::FAD_binding_6::NAD_binding_1 | 116-301::326-459::515-588::633-740::759-872 |
| 471 | PHE0009427__20389.pep | IGPD | 103-247 |
| 472 | PHE0006437__15906.pep | Pkinase | 39-307 |
| 473 | PHE0007409__17652.pep | DAGAT | 64-340 |
| 474 | PHE0009426__20387.pep | PHP | 2-281 |
| 475 | PHE0009430__20393.pep | ParBc | 44-128 |
| 476 | PHE0007003__16906.pep | PTPA | 96-396 |
| 477 | PHE0008378__18741.pep | bZIP_1 | 223-280 |
| 478 | PHE0008273__18725.pep | zf-CCCH | 80-106 |
| 479 | PHE0008547__18953.pep | Fer2 | 20-95 |
| 480 | PHE0006922__16812.pep | Hexokinase_1::Hexokinase_2 | 44-251::258-501 |
| 481 | PHE0006920__16810.pep | AAA::Vps4_C | 267-458::464-514 |
| 482 | PHE0008396__18765.pep | Gln-synt_N::Gln-synt_C | 68-148::154-406 |
| 483 | PHE0006957__16854.pep | Gln-synt_N::Gln-synt_C | 68-148::154-406 |
| 484 | PHE0006404__15936.pep | RRM_1::RRM_1 | 8-77::112-182 |

TABLE 11-continued

| | | pfam module annotation | |
|---|---|---|---|
| PEP SEQ ID NO | Gene ID | Pfam domain module | Position |
| 485 | PHE0006820__16401.pep | Lactamase_B::Flavin_Reduct | 47-236::423-572 |
| 486 | PHE0006690__16236.pep | MFS_1 | 57-421 |
| 487 | PHE0006395__15932.pep | LRR_1::LRR_1::LRR_1::LRR_1::LRR_1::LRR_1::LRR_1 | 185-206::208-229::231-252::254-272::278-299::349-370::372-394 |
| 488 | PHE0006759__16384.pep | SHMT | 55-453 |
| 489 | PHE0006576__16028.pep | Myb_DNA-binding::Myb_DNA-binding | 11-57::63-108 |
| 490 | PHE0006979__16885.pep | Tryp_alpha_amyl | 33-111 |
| 491 | PHE0009786__21754.pep | HLH | 33-80 |
| 492 | PHE0006572__16007.pep | Pkinase | 11-269 |
| 494 | PHE0006588__16092.pep | Thioredoxin | 56-161 |
| 495 | PHE0006985__16891.pep | DUF1716 | 13-118 |
| 496 | PHE0006875__16688.pep | PSI_PSAK | 44-138 |
| 497 | PHE0006626__16155.pep | Glyco_hydro_17 | 30-335 |
| 498 | PHE0006689__16235.pep | Aa_trans | 165-548 |
| 499 | PHE0006799__16382.pep | B12-binding::Radical_SAM | 10-135::202-368 |
| 500 | PHE0006959__16856.pep | Oxidored_molyb::Mo-co_dimer::Cyt-b5::FAD_binding_6::NAD_binding_1 | 143-328::353-486::543-616::660-767::786-899 |
| 501 | PHE0011615__23861.pep | Pkinase | 267-523 |
| 502 | PHE0006925__16814.pep | Tim17 | 4-133 |
| 503 | PHE0006713__16274.pep | APC8::TPR_1::TPR_1::TPR_1 | 1-161::339-372::373-406::407-440 |
| 504 | PHE0008447__18848.pep | Lir1 | 1-126 |
| 505 | PHE0006674__16221.pep | PTR2 | 96-505 |
| 506 | PHE0010613__22398.pep | DAGK_cat | 43-184 |
| 507 | PHE0002720__22558.pep | DnaJ::DnaJ_CXXCXGXG::DnaJ_C | 90-151::218-301::314-436 |
| 508 | PHE0011760__24005.pep | Pkinase | 400-656 |
| 509 | PHE0010612__22397.pep | G-patch | 15-59 |
| 511 | PHE0007411__17654.pep | Acyltransferase | 136-283 |
| 512 | PHE0010617__22402.pep | Isochorismatase | 27-210 |
| 513 | PHE0010610__22395.pep | zf-C3HC4 | 103-144 |
| 514 | PHE0006883__16702.pep | Glyco_transf_5::Glycos_transf_1 | 78-339::379-562 |
| 515 | PHE0010636__22408.pep | DUF6::TPT | 105-230::239-384 |
| 516 | PHE0011082__23038.pep | adh_short | 19-187 |
| 517 | PHE0009475__20462.pep | 2OG-FeII_Oxy | 223-322 |
| 518 | PHE0007415__17661.pep | EIN3 | 60-467 |
| 519 | PHE0006614__16129.pep | Cellulase | 19-358 |
| 520 | PHE0010611__22396.pep | FMO-like | 25-424 |
| 521 | PHE0011719__23946.pep | Acyltransferase | 69-222 |
| 522 | PHE0006861__16463.pep | NPH3 | 166-409 |
| 523 | PHE0006568__16005.pep | DUF26::DUF26::Pkinase | 80-134::199-253::346-615 |
| 524 | PHE0010652__22429.pep | FtsJ | 21-211 |
| 525 | PHE0008158__18448.pep | PLATZ | 22-144 |
| 526 | PHE0003316__20755.pep | Glyco_hydro_2_N::Glyco_hydro_2::Glyco_hydro_2_C | 9-180::182-272::274-593 |
| 527 | PHE0009478__20470.pep | 2OG-FeII_Oxy | 229-328 |
| 528 | PHE0010395__21760.pep | DUF716 | 109-266 |
| 529 | PHE0010391__21753.pep | DUF640 | 28-160 |
| 530 | PHE0010396__21761.pep | DUF716 | 109-265 |
| 531 | PHE0009511__22422.pep | SAM_decarbox | 5-337 |
| 532 | PHE0010614__22399.pep | SOUL | 28-211 |
| 534 | PHE0011454__23667.pep | Histone | 56-126 |
| 535 | PHE0011443__24001.pep | Histone | 61-131 |
| 536 | PHE0011452__23665.pep | Histone | 58-132 |
| 537 | PHE0010394__21758.pep | SAP18 | 29-150 |
| 540 | PHE0010100__21467.pep | Pyr_redox_2::Fer2_BFD::NIR_SIR_ferr::NIR_SIR | 5-285::420-472::554-621::629-775 |
| 541 | PHE0011503__23734.pep | GAF::HisKA::HATPase_c | 158-307::343-408::455-586 |
| 542 | PHE0010099__21319.pep | Molybdop_Fe4S4::Molybdopterin::Molydop_binding::Fer2_BFD | 1-55::58-475::570-681::811-863 |
| 543 | PHE0011269__23400.pep | Homeobox::START | 21-78::215-437 |
| 546 | PHE0011613__23858.pep | AP2::AP2 | 62-136::165-230 |
| 547 | PHE0001582__22064.pep | GAF::HisKA::Response_reg | 195-344::380-445::645-761 |
| 548 | PHE0007444__22314.pep | Spermine_synth | 90-349 |
| 549 | PHE0010543__22298.pep | PBP | 19-165 |
| 550 | PHE0010543__22323.pep | PBP | 19-157 |

TABLE 11-continued pfam module annotation

| PEP SEQ ID NO | Gene ID | Pfam domain module | Position |
|---|---|---|---|
| 551 | PHE0011081__23033.pep | Sugar_tr | 33-465 |
| 552 | PHE0011075__23026.pep | P-II | 73-175 |
| 553 | PHE0010100__21462.pep | Pyr_redox_2::Fer2_BFD::NIR_SIR_ferr::NIR_SIR | 5-285::420-472::554-621::629-775 |
| 554 | PHE0009640__21775.pep | Auxin_inducible | 1-102 |
| 555 | PHE0010092__21307.pep | S1::EIF_2_alpha | 13-88::125-256 |
| 556 | PHE0004611__24123.pep | PTR2 | 13-406 |
| 557 | PHE0010093__21308.pep | S1::EIF_2_alpha | 13-88::125-256 |
| 558 | PHE0008605__23084.pep | Histone | 58-128 |
| 559 | PHE0009939__21100.pep | GDC-P | 81-508 |
| 560 | PHE0009941__21105.pep | mTERF | 2-262 |
| 561 | PHE0009951__21135.pep | Ribosomal_L10e | 1-176 |
| 562 | PHE0009943__21127.pep | Ribosomal_L10e | 1-176 |
| 563 | PHE0009948__21132.pep | Ribosomal_L10e | 1-176 |
| 564 | PHE0011084__23040.pep | Peptidase_S10 | 54-482 |
| 565 | PHE0008233__23042.pep | Phi_1 | 40-314 |
| 566 | PHE0010854__22730.pep | RGS | 294-412 |
| 567 | PHE0003797__23051.pep | zf-Dof | 34-96 |
| 568 | PHE0010194__21769.pep | Glyco_hydro_9 | 52-509 |
| 570 | PHE0011665__23899.pep | Chloroa_b-bind | 63-260 |
| 571 | PHE0012178__24443.pep | Whirly | 53-191 |
| 573 | PHE0011064__22994.pep | TPR_1 | 73-106 |
| 577 | PHE0011446__23659.pep | Histone | 58-132 |
| 578 | PHE0001424__22077.pep | Agglutinin | 55-193 |
| 579 | PHE0011445__23658.pep | C2 | 6-87 |
| 580 | PHE0010090__21297.pep | LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase_Tyr | 33-73::78-101::103-127::129-151::177-199::226-248::274-296::298-320::322-341::395-417::444-466::468-490::492-514::516-538::540-562::564-585::678-952 |
| 581 | PHE0012180__24445.pep | B3 | 516-619 |
| 582 | PHE0011083__23039.pep | adh_short | 44-200 |
| 583 | PHE0011085__23041.pep | Peptidase_S10 | 31-459 |
| 584 | PHE0012175__24440.pep | CXC::CXC | 457-498::543-584 |
| 585 | PHE0012177__24442.pep | Whirly | 91-229 |
| 587 | PHE0010194__21426.pep | Glyco_hydro_9 | 52-509 |
| 588 | PHE0011666__23900.pep | Spermine_synth | 46-291 |
| 589 | PHE0011448__24160.pep | Histone | 25-90 |
| 590 | PHE0008324__18636.pep | DUF1005 | 256-460 |
| 591 | PHE0006971__16875.pep | Myb_DNA-binding::Myb_DNA-binding | 14-61::67-112 |
| 592 | PHE0009939__21147.pep | GDC-P | 81-508 |
| 593 | PHE0009953__21137.pep | Na_sulph_symp | 110-578 |
| 595 | PHE0008557__18970.pep | NAD_binding_1 | 234-350 |
| 596 | PHE0006443__15955.pep | YDG_SRA::Pre-SET::SET | 360-519::543-639::641-771 |

TABLE 12

Description of pfam domains

| Pfam domain name | Accession number | Gathering cutoff | Domain description |
|---|---|---|---|
| 2OG-FeII_Oxy | PF03171.10 | 11.5 | 2OG-Fe(II) oxygenase superfamily |
| 4HBT | PF03061.12 | 20.6 | Thioesterase superfamily |
| 6PGD | PF00393.9 | −232.3 | 6-phosphogluconate dehydrogenase, C-terminal domain |
| AAA | PF00004.19 | 12.3 | ATPase family associated with various cellular activities (AAA) |
| AA_kinase | PF00696.18 | −40 | Amino acid kinase family |
| AA_permease | PF00324.11 | −120.8 | Amino acid permease |
| AP2 | PF00847.10 | 0 | AP2 domain |
| APC8 | PF04049.4 | −19.8 | Anaphase promoting complex subunit 8/Cdc23 |
| Aa_trans | PF01490.8 | −128.4 | Transmembrane amino acid transporter protein |
| Acyltransferase | PF01553.11 | −0.4 | Acyltransferase |
| Agglutinin | PF07468.2 | 25 | Agglutinin |
| Allene_ox_cyc | PF06351.2 | 25 | Allene oxide cyclase |
| Alpha-amylase | PF00128.14 | −92.6 | Alpha amylase, catalytic domain |

TABLE 12-continued

Description of pfam domains

| Pfam domain name | Accession number | Gathering cutoff | Domain description |
|---|---|---|---|
| Ank | PF00023.20 | 0 | Ankyrin repeat |
| ApbA | PF02558.6 | −16.2 | Ketopantoate reductase PanE/ApbA |
| Asn_synthase | PF00733.11 | −52.8 | Asparagine synthase |
| Auxin_inducible | PF02519.5 | −15 | Auxin responsive protein |
| B12-binding | PF02310.9 | 19.6 | B12 binding domain |
| B3 | PF02362.12 | 26.5 | B3 DNA binding domain |
| BURP | PF03181.6 | −52 | BURP domain |
| Bac_globin | PF01152.11 | −12.7 | Bacterial-like globin |
| C2 | PF00168.20 | 3.7 | C2 domain |
| CBFD_NFYB_HMF | PF00808.13 | 18.4 | Histone-like transcription factor (CBF/NF-Y) and archaeal histone |
| CCT | PF06203.4 | 25 | CCT motif |
| CN_hydrolase | PF00795.12 | −13.9 | Carbon-nitrogen hydrolase |
| CXC | PF03638.5 | 25 | Tesmin/TSO1-like CXC domain |
| Cellulase | PF00150.8 | −49.3 | Cellulase (glycosyl hydrolase family 5) |
| Chloroa_b-bind | PF00504.12 | −31.9 | Chlorophyll A-B binding protein |
| CorA | PF01544.9 | −61.3 | CorA-like Mg2+ transporter protein |
| Cyt-b5 | PF00173.18 | 4 | Cytochrome b5-like Heme/Steroid binding domain |
| Cytochrom_C552 | PF02335.6 | −166 | Cytochrome c552 |
| DAGAT | PF03982.3 | −151.7 | Diacylglycerol acyltransferase |
| DAGK_cat | PF00781.14 | −5.7 | Diacylglycerol kinase catalytic domain (presumed) |
| DAO | PF01266.14 | −35 | FAD dependent oxidoreductase |
| DEAD | PF00270.19 | 7.2 | DEAD/DEAH box helicase |
| DNA_photolyase | PF00875.8 | 26.1 | DNA photolyase |
| DSPc | PF00782.11 | −21.8 | Dual specificity phosphatase, catalytic domain |
| DUF1005 | PF06219.3 | 25 | Protein of unknown function (DUF1005) |
| DUF1716 | PF08216.2 | 25 | Eukaryotic domain of unknown function (DUF1716) |
| DUF26 | PF01657.8 | 0 | Domain of unknown function DUF26 |
| DUF6 | PF00892.11 | 20.8 | Integral membrane protein DUF6 |
| DUF640 | PF04852.3 | 2.4 | Protein of unknown function (DUF640) |
| DUF716 | PF04819.3 | −18.4 | Family of unknown function (DUF716) |
| DnaJ | PF00226.21 | −8 | DnaJ domain |
| DnaJ_C | PF01556.9 | −24 | DnaJ C terminal region |
| DnaJ_CXXCXGXG | PF00684.9 | 1 | DnaJ central domain (4 repeats) |
| E2F_TDP | PF02319.11 | 17 | E2F/DP family winged-helix DNA-binding domain |
| EIF_2_alpha | PF07541.2 | −4.2 | Eukaryotic translation initiation factor 2 alpha subunit |
| EIN3 | PF04873.4 | −137.6 | Ethylene insensitive 3 |
| ELFV_dehydrog | PF00208.11 | −27 | Glutamate/Leucine/Phenylalanine/Valine dehydrogenase |
| ELFV_dehydrog_N | PF02812.8 | 31.8 | Glu/Leu/Phe/Val dehydrogenase, dimerisation domain |
| ELK | PF03789.4 | 25 | ELK domain |
| F-box | PF00646.23 | 13.9 | F-box domain |
| FAD_binding_3 | PF01494.9 | −136.6 | FAD binding domain |
| FAD_binding_6 | PF00970.14 | −11.4 | Oxidoreductase FAD-binding domain |
| FAD_binding_7 | PF03441.4 | 25 | FAD binding domain of DNA photolyase |
| FMO-like | PF00743.9 | −381.6 | Flavin-binding monooxygenase-like |
| Fe_bilin_red | PF05996.3 | 25 | Ferredoxin-dependent bilin reductase |
| Fer2 | PF00111.17 | 7 | 2Fe—2S iron-sulfur cluster binding domain |
| Fer2_BFD | PF04324.5 | 25 | BFD-like [2Fe—2S] binding domain |
| Flavin_Reduct | PF01613.8 | −18 | Flavin reductase like domain |
| Flavodoxin_1 | PF00258.15 | 6.3 | Flavodoxin |
| FtsJ | PF01728.9 | −50.2 | FtsJ-like methyltransferase |
| G-patch | PF01585.13 | 18.3 | G-patch domain |
| GAF | PF01590.16 | 23 | GAF domain |
| GATA | PF00320.17 | 28.5 | GATA zinc finger |
| GATase_2 | PF00310.11 | −95.1 | Glutamine amidotransferases class-II |
| GDC-P | PF02347.6 | −306.2 | Glycine cleavage system P-protein |
| GSHPx | PF00255.10 | −16 | Glutathione peroxidase |
| GSH_synth_ATP | PF03917.8 | −129.9 | Eukaryotic glutathione synthase, ATP binding domain |
| GSH_synthase | PF03199.6 | 25 | Eukaryotic glutathione synthase |
| GST_C | PF00043.15 | 22.3 | Glutathione S-transferase, C-terminal domain |
| GST_N | PF02798.10 | 14.6 | Glutathione S-transferase, N-terminal domain |
| GUN4 | PF05419.3 | 25 | GUN4-like |
| Gln-synt_C | PF00120.14 | −124 | Glutamine synthetase, catalytic domain |

TABLE 12-continued

Description of pfam domains

| Pfam domain name | Accession number | Gathering cutoff | Domain description |
|---|---|---|---|
| Gln-synt_N | PF03951.9 | 9 | Glutamine synthetase, beta-Grasp domain |
| Globin | PF00042.12 | −8.8 | Globin |
| Glutaredoxin | PF00462.14 | 17.2 | Glutaredoxin |
| Glyco_hydro_17 | PF00332.9 | −152.3 | Glycosyl hydrolases family 17 |
| Glyco_hydro_2 | PF00703.11 | −19.3 | Glycosyl hydrolases family 2, immunoglobulin-like beta-sandwich domain |
| Glyco_hydro_2_C | PF02836.7 | −127.7 | Glycosyl hydrolases family 2, TIM barrel domain |
| Glyco_hydro_2_N | PF02837.8 | −46.9 | Glycosyl hydrolases family 2, sugar binding domain |
| Glyco_hydro_9 | PF00759.9 | −246.7 | Glycosyl hydrolase family 9 |
| Glyco_transf_5 | PF08323.2 | −114.9 | Starch synthase catalytic domain |
| Glycos_transf_1 | PF00534.10 | −7.3 | Glycosyl transferases group 1 |
| Glyoxalase | PF00903.15 | 12.1 | Glyoxalase/Bleomycin resistance protein/Dioxygenase superfamily |
| HALZ | PF02183.8 | 17 | Homeobox associated leucine zipper |
| HATPase_c | PF02518.16 | 22.4 | Histidine kinase-, DNA gyrase B-, and HSP90-like ATPase |
| HLH | PF00010.16 | 8.3 | Helix-loop-helix DNA-binding domain |
| HSF_DNA-bind | PF00447.8 | −70 | HSF-type DNA-binding |
| Helicase_C | PF00271.21 | 2.1 | Helicase conserved C-terminal domain |
| Hexokinase_1 | PF00349.11 | −110.3 | Hexokinase |
| Hexokinase_2 | PF03727.6 | −131.3 | Hexokinase |
| HisKA | PF00512.15 | 10.3 | His Kinase A (phosphoacceptor) domain |
| Histone | PF00125.14 | 17.4 | Core histone H2A/H2B/H3/H4 |
| Histone_HNS | PF00816.11 | 25 | H-NS histone family |
| Homeobox | PF00046.19 | −4.1 | Homeobox domain |
| IGPD | PF00475.9 | 25 | Imidazoleglycerol-phosphate dehydratase |
| Isoamylase_N | PF02922.8 | −6.5 | Isoamylase N-terminal domain |
| Isochorismatase | PF00857.11 | −46 | Isochorismatase family |
| KNOX1 | PF03790.4 | 25 | KNOX1 domain |
| KNOX2 | PF03791.4 | 25 | KNOX2 domain |
| KR | PF08659.1 | −74.3 | KR domain |
| Kelch_1 | PF01344.15 | 7.8 | Kelch motif |
| Kelch_2 | PF07646.5 | 14 | Kelch motif |
| LEA_3 | PF03242.4 | 25 | Late embryogenesis abundant protein |
| LRRNT_2 | PF08263.3 | 18.6 | Leucine rich repeat N-terminal domain |
| LRR_1 | PF00560.23 | 7.7 | Leucine Rich Repeat |
| LRR_2 | PF07723.3 | 6 | Leucine Rich Repeat |
| Lactamase_B | PF00753.17 | 24.6 | Metallo-beta-lactamase superfamily |
| Ldh_1_C | PF02866.8 | −13 | lactate/malate dehydrogenase, alpha/beta C-terminal domain |
| Ldh_1_N | PF00056.13 | −31.3 | lactate/malate dehydrogenase, NAD binding domain |
| Lir1 | PF07207.2 | 25 | Light regulated protein Lir1 |
| MBD | PF01429.10 | 12.9 | Methyl-CpG binding domain |
| MEKHLA | PF08670.1 | −59.7 | MEKHLA domain |
| MFS_1 | PF07690.6 | 23.5 | Major Facilitator Superfamily |
| MGS | PF02142.12 | 3 | MGS-like domain |
| Miro | PF08477.3 | 10.8 | Miro-like protein |
| Mit_rib_S27 | PF08293.2 | 25 | Mitochondrial ribosomal subunit S27 |
| Mo-co_dimer | PF03404.6 | 25 | Mo-co oxidoreductase dimerisation domain |
| Molybdop_Fe4S4 | PF04879.6 | 13.6 | Molybdopterin oxidoreductase Fe4S4 domain |
| Molybdopterin | PF00384.12 | −50 | Molybdopterin oxidoreductase |
| Molydop_binding | PF01568.11 | 1.1 | Molydopterin dinucleotide binding domain |
| MtN3_slv | PF03083.6 | 9.7 | MtN3/saliva family |
| Myb_DNA-binding | PF00249.21 | 14 | Myb-like DNA-binding domain |
| NAD_Gly3P_dh_C | PF07479.4 | −50.8 | NAD-dependent glycerol-3-phosphate dehydrogenase C-terminus |
| NAD_Gly3P_dh_N | PF01210.13 | −44 | NAD-dependent glycerol-3-phosphate dehydrogenase N-terminus |
| NAD_binding_1 | PF00175.11 | −3.9 | Oxidoreductase NAD-binding domain |
| NAD_binding_2 | PF03446.5 | −63.5 | NAD binding domain of 6-phosphogluconate dehydrogenase |
| NIR_SIR | PF01077.12 | −19.6 | Nitrite and sulphite reductase 4Fe—4S domain |
| NIR_SIR_ferr | PF03460.7 | 2.4 | Nitrite/Sulfite reductase ferredoxin-like half domain |
| NPH3 | PF03000.5 | 25 | NPH3 family |
| NTP_transferase | PF00483.13 | −90.5 | Nucleotidyl transferase |
| NUDIX | PF00293.18 | 0.2 | NUDIX domain |

TABLE 12-continued

Description of pfam domains

| Pfam domain name | Accession number | Gathering cutoff | Domain description |
|---|---|---|---|
| Na_H_Exchanger | PF00999.11 | −67.9 | Sodium/hydrogen exchanger family |
| Na_H_antiport_1 | PF06965.2 | −270.8 | Na+/H+ antiporter 1 |
| Na_sulph_symp | PF00939.9 | −259 | Sodium:sulfate symporter transmembrane region |
| Oxidored_molyb | PF00174.9 | −39.6 | Oxidoreductase molybdopterin binding domain |
| P-II | PF00543.12 | −29 | Nitrogen regulatory protein P-II |
| PALP | PF00291.15 | −70 | Pyridoxal-phosphate dependent enzyme |
| PAS | PF00989.14 | 0 | PAS fold |
| PAS_3 | PF08447.1 | 13.4 | PAS fold |
| PBP | PF01161.10 | −20.6 | Phosphatidylethanolamine-binding protein |
| PFK | PF00365.10 | −132 | Phosphofructokinase |
| PGI | PF00342.9 | −168.9 | Phosphoglucose isomerase |
| PHP | PF02811.9 | 13.8 | PHP domain |
| PLATZ | PF04640.4 | 20 | PLATZ transcription factor |
| PMSR | PF01625.11 | −62 | Peptide methionine sulfoxide reductase |
| PP2C | PF00481.12 | −44 | Protein phosphatase 2C |
| PSI_PSAK | PF01241.9 | 25 | Photosystem I psaG/psaK |
| PTPA | PF03095.5 | −106 | Phosphotyrosyl phosphate activator (PTPA) protein |
| PTR2 | PF00854.12 | −50 | POT family |
| PaO | PF08417.2 | 25 | Pheophorbide a oxygenase |
| ParBc | PF02195.8 | 25 | ParB-like nuclease domain |
| Peptidase_S10 | PF00450.12 | −198 | Serine carboxypeptidase |
| Phi_1 | PF04674.3 | 25 | Phosphate-induced protein 1 conserved region |
| Pkinase | PF00069.15 | −70.3 | Protein kinase domain |
| Pkinase_Tyr | PF07714.7 | 65 | Protein tyrosine kinase |
| Pre-SET | PF05033.6 | 3.9 | Pre-SET motif |
| Pribosyltran | PF00156.17 | 2 | Phosphoribosyl transferase domain |
| Prismane | PF03063.10 | −169.3 | Prismane/CO dehydrogenase family |
| Proteasome | PF00227.16 | −36.7 | Proteasome A-type and B-type |
| PsbP | PF01789.7 | 25 | PsbP |
| PsbQ | PF05757.2 | 25 | Oxygen evolving enhancer protein 3 (PsbQ) |
| PsbW_2 | PF07123.2 | −25.8 | Photosystem II reaction centre W protein (PsbW) |
| Pyr_redox | PF00070.17 | 5 | Pyridine nucleotide-disulphide oxidoreductase |
| Pyr_redox_2 | PF07992.4 | −20 | Pyridine nucleotide-disulphide oxidoreductase |
| RGS | PF00615.9 | 10 | Regulator of G protein signaling domain |
| RPE65 | PF03055.6 | −156.5 | Retinal pigment epithelial membrane protein |
| RRM_1 | PF00076.12 | 17.7 | RNA recognition motif. (a.k.a. RRM, RBD, or RNP domain) |
| Radical_SAM | PF04055.11 | 8.5 | Radical SAM superfamily |
| Ras | PF00071.12 | −69.9 | Ras family |
| Response_reg | PF00072.14 | 4 | Response regulator receiver domain |
| Ribosomal_L10e | PF00826.8 | 25 | Ribosomal L10 |
| Ribosomal_S2 | PF00318.10 | −22 | Ribosomal protein S2 |
| Rieske | PF00355.16 | −7 | Rieske [2Fe—2S] domain |
| Rubredoxin | PF00301.10 | 12.1 | Rubredoxin |
| S1 | PF00575.13 | 16.8 | S1 RNA binding domain |
| S10_plectin | PF03501.5 | 25 | Plectin/S10 domain |
| SAM_decarbox | PF01536.7 | −154 | Adenosylmethionine decarboxylase |
| SAP18 | PF06487.3 | −49.7 | Sin3 associated polypeptide p18 (SAP18) |
| SET | PF00856.18 | 23.5 | SET domain |
| SHMT | PF00464.10 | −238.5 | Serine hydroxymethyltransferase |
| SNF5 | PF04855.3 | 25 | SNF5/SMARCB1/INI1 |
| SOUL | PF04832.3 | 25 | SOUL heme-binding protein |
| START | PF01852.10 | −20.7 | START domain |
| SWIM | PF04434.8 | 11 | SWIM zinc finger |
| Sad1_UNC | PF07738.3 | −20.4 | Sad1/UNC-like C-terminal |
| Sina | PF03145.7 | −48.4 | Seven in absentia protein family |
| Spermine_synth | PF01564.7 | −93.8 | Spermine/spermidine synthase |
| Sterol_desat | PF01598.8 | −13 | Sterol desaturase |
| Sugar_tr | PF00083.14 | −85 | Sugar (and other) transporter |
| TPP_enzyme_C | PF02775.11 | 19.7 | Thiamine pyrophosphate enzyme, C-terminal TPP binding domain |
| TPP_enzyme_M | PF00205.12 | −8.1 | Thiamine pyrophosphate enzyme, central domain |
| TPP_enzyme_N | PF02776.8 | −70 | Thiamine pyrophosphate enzyme, N-terminal TPP binding domain |

TABLE 12-continued

Description of pfam domains

| Pfam domain name | Accession number | Gathering cutoff | Domain description |
| --- | --- | --- | --- |
| TPR_1 | PF00515.18 | 7.7 | Tetratricopeptide repeat |
| TPR_2 | PF07719.7 | 20.1 | Tetratricopeptide repeat |
| TPR_4 | PF07721.5 | 15 | Tetratricopeptide repeat |
| TPT | PF03151.7 | −15.3 | Triose-phosphate Transporter family |
| TP_methylase | PF00590.10 | −38 | Tetrapyrrole (Corrin/Porphyrin) Methylases |
| Thi4 | PF01946.7 | −65.1 | Thi4 family |
| Thioredoxin | PF00085.10 | −25.7 | Thioredoxin |
| Tim17 | PF02466.9 | 2.7 | Tim17/Tim22/Tim23 family |
| Tryp_alpha_amyl | PF00234.12 | −4 | Protease inhibitor/seed storage/LTP family |
| UAA | PF08449.2 | −146.2 | UAA transporter family |
| VPS28 | PF03997.3 | 25 | VPS28 protein |
| Vps4_C | PF09336.1 | −4.6 | Vps4 C terminal oligomerisation domain |
| WD40 | PF00400.22 | 21.5 | WD domain, G-beta repeat |
| Whirly | PF08536.2 | 25 | Whirly transcription factor |
| YABBY | PF04690.4 | 25 | YABBY protein |
| YDG_SRA | PF02182.8 | 25 | YDG/SRA domain |
| adh_short | PF00106.15 | −40.2 | short chain dehydrogenase |
| bZIP_1 | PF00170.11 | 24.5 | bZIP transcription factor |
| bZIP_2 | PF07716.5 | 15 | Basic region leucine zipper |
| eIF-1a | PF01176.9 | 20 | Translation initiation factor 1A/IF-1 |
| efhand | PF00036.22 | 21.7 | EF hand |
| mTERF | PF02536.5 | −60 | mTERF |
| p450 | PF00067.12 | −105 | Cytochrome P450 |
| peroxidase | PF00141.13 | −10 | Peroxidase |
| tRNA-synt_2 | PF00152.11 | −168.2 | tRNA synthetases class II (D, K and N) |
| tRNA_anti | PF01336.15 | 8 | OB-fold nucleic acid binding domain |
| ubiquitin | PF00240.13 | 19.4 | Ubiquitin family |
| zf-C3HC4 | PF00097.15 | 16 | Zinc finger, C3HC4 type (RING finger) |
| zf-CCCH | PF00642.15 | 0 | Zinc finger C-x8-C-x5-C-x3-H type (and similar) |
| zf-Dof | PF02701.6 | 25 | Dof domain, zinc finger |
| zf-UBR | PF02207.10 | 25 | Putative zinc finger in N-recognin (UBR box) |

Example 9. Selection of Transgenic Plants with Enhanced Agronomic Trait(s)

This example illustrates the preparation and identification by selection of transgenic seeds and plants derived from transgenic plant cells of this invention where the plants and seed are identified by screening for a transgenic plant having an enhanced agronomic trait imparted by expression of a protein selected from the group including the homologous proteins identified in Example 6. Transgenic plant cells of corn, soybean, cotton, canola, alfalfa, wheat and rice are transformed with recombinant DNA for expressing each of the homologs identified in Example 6. Plants are regenerated from the transformed plant cells and used to produce progeny plants and seed that are screened for enhanced water use efficiency, enhanced cold tolerance, increased yield, enhanced nitrogen use efficiency, enhanced seed protein and enhanced seed oil. Plants are identified exhibiting enhanced traits imparted by expression of the homologous proteins.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10570408B2). An electronic copy of the "Sequence Listing" will also be available from the USPTO upon request and payment of the fee set forth in 37 CFR 1.19(b)(3).

What is claimed is:

1. A method for manufacturing transgenic seeds that can be used to produce a crop of transgenic plants with an enhanced trait resulting from expression of a DNA segment in a plant cell nucleus comprising a stably integrated recombinant DNA construct comprising a promoter that is functional in a plant cell and that is operably linked to a DNA segment encoding a protein comprising an amino acid sequence having at least 90% amino acid sequence identity to SEQ ID NO: 373, or a homolog of SEQ ID NO:373 thereof, wherein said method comprises:

(a) screening a population of plants for said enhanced trait and said recombinant DNA construct, wherein said enhanced trait is increased yield;

(b) selecting from said population one or more plants that exhibit said trait at a level greater than the level that said trait is exhibited in control plants; and (c) collecting seeds from the selected plant.

2. The method of claim 1, wherein said method further comprises:

(a) verifying that said recombinant DNA construct is stably integrated in said selected plants; and (b) analyzing tissue of said selected plant to determine the expression of the protein.

3. The method of claim 2 wherein said seed is corn, soybean, cotton, alfalfa, canola wheat or rice seed.

4. The method of claim 1 wherein the selected plant is a herbicide tolerant corn plant.

5. The method of claim 2 wherein said transgenic plant cell is homozygous for said recombinant DNA construct.

6. The method of claim 2 wherein the transgenic plant cell further comprises DNA expressing a protein that provides tolerance from exposure to an herbicide applied at levels that are lethal to a wild type of said plant cell.

7. The method of claim 4 wherein said herbicide is a glyphosate, dicamba, or glufosinate compound.

8. The method of claim 1 wherein the protein has SEQ ID NO: 373.

9. The method of claim 3 wherein the yield is determined by measuring the number of kernels.

10. The method of claim 1 wherein the homolog has SEQ ID NO:29625.

* * * * *